United States Patent
Gigstad et al.

(10) Patent No.: US 10,144,742 B2
(45) Date of Patent: Dec. 4, 2018

(54) QUINOXALINE COMPOUNDS AND USES THEREOF

(71) Applicant: Millennium Pharmaceuticals, Inc., Cambridge, MA (US)

(72) Inventors: Kenneth M. Gigstad, Westford, MA (US); David P. Cardin, Wilmington, MA (US); Takaharu Hirayama, Kanagawa (JP); Masaaki Hirose, Tokyo (JP); Yongbo Hu, Winchester, MA (US); Hiroyuki Kakei, Kanagawa (JP); Hong Myung Lee, Cambridge, MA (US); Takashi Motoyaji, Kanagawa (JP); Noriyuki Nii, Kanagawa (JP); Zhan Shi, Concord, MA (US); Stepan Vyskocil, Arlington, MA (US); Hiroyuki Watanabe, Hyogo (JP)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/304,947

(22) PCT Filed: Apr. 17, 2015

(86) PCT No.: PCT/US2015/026275
§ 371 (c)(1),
(2) Date: Oct. 18, 2016

(87) PCT Pub. No.: WO2015/161142
PCT Pub. Date: Oct. 22, 2015

(65) Prior Publication Data
US 2017/0174704 A1  Jun. 22, 2017

Related U.S. Application Data

(60) Provisional application No. 61/981,273, filed on Apr. 18, 2014.

(30) Foreign Application Priority Data

Apr. 16, 2015  (JO) ........................... 74/2015

(51) Int. Cl.
| | | |
|---|---|---|
| *C07D 498/04* | (2006.01) | |
| *C07D 403/12* | (2006.01) | |
| *C07D 401/14* | (2006.01) | |
| *C07D 405/14* | (2006.01) | |
| *C07D 413/14* | (2006.01) | |
| *C07D 401/12* | (2006.01) | |
| *C07D 403/14* | (2006.01) | |
| *C07D 409/14* | (2006.01) | |

(Continued)

(52) U.S. Cl.
CPC .......... *C07D 498/04* (2013.01); *A61K 31/498* (2013.01); *A61K 31/4985* (2013.01); *A61K 31/501* (2013.01); *A61K 31/506* (2013.01); *A61K 31/5375* (2013.01); *A61K 31/541* (2013.01); *A61K 31/55* (2013.01); *A61K 31/553* (2013.01); *C07D 401/12* (2013.01); *C07D 401/14* (2013.01); *C07D 403/12* (2013.01); *C07D 403/14* (2013.01); *C07D 405/14* (2013.01); *C07D 409/14* (2013.01); *C07D 413/14* (2013.01); *C07D 417/12* (2013.01); *C07D 417/14* (2013.01); *C07D 471/04* (2013.01); *C07D 487/04* (2013.01); *C07D 491/08* (2013.01); *C07D 491/107* (2013.01); *C07D 491/113* (2013.01)

(58) Field of Classification Search
None
See application file for complete search history.

(56) References Cited

U.S. PATENT DOCUMENTS

| | | |
|---|---|---|
| 6,548,499 B1 | 4/2003 | Carson et al. |
| 7,189,724 B2 | 3/2007 | An et al. |

(Continued)

FOREIGN PATENT DOCUMENTS

| | | |
|---|---|---|
| JP | 2007 099641 | 4/2007 |
| WO | WO 2004/043950 | 5/2004 |

(Continued)

OTHER PUBLICATIONS

Pinedo et al. (2000).*

(Continued)

*Primary Examiner* — Paul V Ward
(74) *Attorney, Agent, or Firm* — McNeill Baur PLLC

(57) ABSTRACT

This invention provides compounds of formula I and subsets thereof: wherein T, J, R, $R^4$, $R^q$, o, $R^A$, and $R^B$ and subsets thereof are as described in the specification. The compounds are inhibitors of NAMPT and are thus useful for treating cancer, inflammatory conditions, or T-cell mediated autoimmune disease.

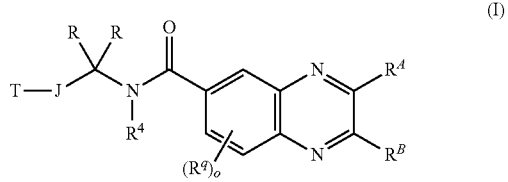

(I)

17 Claims, No Drawings

(51) Int. Cl.
| | |
|---|---|
| *C07D 417/12* | (2006.01) |
| *C07D 417/14* | (2006.01) |
| *C07D 471/04* | (2006.01) |
| *C07D 487/04* | (2006.01) |
| *C07D 491/107* | (2006.01) |
| *A61K 31/498* | (2006.01) |
| *A61K 31/4985* | (2006.01) |
| *A61K 31/501* | (2006.01) |
| *A61K 31/506* | (2006.01) |
| *A61K 31/5375* | (2006.01) |
| *A61K 31/541* | (2006.01) |
| *A61K 31/55* | (2006.01) |
| *A61K 31/553* | (2006.01) |
| *C07D 491/08* | (2006.01) |
| *C07D 491/113* | (2006.01) |

(56) References Cited

U.S. PATENT DOCUMENTS

| | | |
|---|---|---|
| 2009/0170840 A1 | 7/2009 | Roth et al. |
| 2012/0010172 A1 | 1/2012 | Christensen et al. |
| 2012/0122924 A1 | 5/2012 | Curtin et al. |
| 2012/0165318 A1 | 6/2012 | McCall et al. |
| 2012/0220589 A1 | 8/2012 | McCall et al. |
| 2012/0225846 A1 | 9/2012 | McCall et al. |
| 2012/0232056 A1 | 9/2012 | McCall et al. |
| 2012/0264755 A1 | 10/2012 | Christensen et al. |
| 2012/0277224 A1 | 11/2012 | McCall et al. |
| 2013/0273034 A1 | 10/2013 | Bair et al. |
| 2013/0274286 A1 | 10/2013 | Kumaravel et al. |
| 2013/0295051 A1 | 11/2013 | Bair et al. |
| 2013/0303508 A1 | 11/2013 | Clark et al. |
| 2013/0303509 A1 | 11/2013 | Hansen et al. |
| 2013/0303510 A1 | 11/2013 | Hansen et al. |
| 2013/0303511 A1 | 11/2013 | Clark et al. |
| 2013/0317027 A1 | 11/2013 | Willardsen et al. |
| 2014/0336167 A1 | 11/2014 | Sweis et al. |

FOREIGN PATENT DOCUMENTS

| | | |
|---|---|---|
| WO | WO 2004/089416 | 10/2004 |
| WO | WO 2005/007099 | 1/2005 |
| WO | WO 2010/023307 | 3/2010 |
| WO | WO 2010/142735 | 12/2010 |
| WO | WO 2011/109441 | 9/2011 |
| WO | WO 2011/121055 | 10/2011 |
| WO | WO 2011/121434 | 10/2011 |
| WO | WO 2012/031196 | 3/2012 |
| WO | WO 2012/031197 | 3/2012 |
| WO | WO 2012/031199 | 3/2012 |
| WO | WO 2012/087861 | 6/2012 |
| WO | WO 2012/150952 | 11/2012 |
| WO | WO 2012/154194 | 11/2012 |
| WO | WO 2012/177782 | 12/2012 |
| WO | WO 2013/067710 | 5/2013 |
| WO | WO 2013/082150 | 6/2013 |
| WO | WO 2013/127267 | 9/2013 |
| WO | WO 2013/127628 | 9/2013 |
| WO | WO 2013/130935 | 9/2013 |
| WO | WO 2013/130943 | 9/2013 |
| WO | WO 2013/158649 | 10/2013 |
| WO | WO 2013/170112 | 11/2013 |
| WO | WO 2013/170113 | 11/2013 |
| WO | WO 2013/170115 | 11/2013 |
| WO | WO 2013/170118 | 11/2013 |
| WO | WO 2013/170191 | 11/2013 |
| WO | WO 2014/004884 | 1/2014 |
| WO | WO 2015/100322 | 7/2015 |

OTHER PUBLICATIONS

McMahon et al. (2000).*
Bi et al., "Overexpression of Nampt in Gastric Cancer and Chemopotentiating Effects of the Nampt Inhibitor FK866 in Combination with Fluorouracil," Oncology Reports, 2011, 26:1251-1257.
Bowlby et al., "Nicotinamide Phosphoribosyl Transferase (Nampt) is Required for De Novo Lipogenesis in Tumor Cells," PLoS One, 2012, 7(6):e40195.
Chemical Abstracts Service, Online Database Registry, XP002772406, Aug. 21, 2006.
Chemical Abstracts Service, Online Database Registry, XP002772407, Aug. 21, 2006.
Chemical Abstracts Service, Online Database Registry, XP002772408, Jun. 25, 2009.
Christensen et al., "Nicotinamide Phosphoribosyltransferase Inhibitors, Design, Preparation and SAR," J. Med. Chem., 2013, 1-55.
Ekelund et al., "Interactions Between the New Cytotoxic Drug CHS 828 and Amiloride and Mitomycin C in a Human Tumour Cell Line and in Tumour Cells from Patients," Chemotherapy, 2002, 48:196-204.
Extended European Search Report received in European Patent Application No. 15779407.4, dated Aug. 9, 2017, 21 pages.
Galli et al., "Medicinal Chemistry of Nicotinamide Phosphoribosyltransferase (Nampt) Inhibitors," J. Med. Chem, 2013, Review, A-R.
Giannetti et al., "Fragment-Based Identification of Amides Derived from Trans-2-(Pyridin-3-yl)Cyclopropanecarboxylic Acid as Potent Inhibitors of Human Nicotinamide Phosphoribosyltransferase (NAMPT)," J. Med. Chem, 2014, 1-94.
Gunzer-Toste et al., "Discovery of Potent and Efficacious Urea-Containing Nicotinamide Phosphoribosyltransferase (NAMPT) Inhibitors with Reduced CYP2C9 Inhibition Properties," Bioorganic & Medicinal Chemistry Letters, 2013, 23:3531-3538.
Hajduk et al., "Privileged Molecules for Protein Binding Identified from NMR-Based Screening," J. Med. Chem., 2000, 43:3443-3447.
Hupkes et al., "Identification of Novel Bacterial M.Sssl DNA Methyltransferase Inhibitors," Journal of Biomolecular Screening, 2012, 18(3):348-355.
International Search Report for PCT/US2015/026275 dated Jul. 9, 2015, 8 pages.
Martinsson et al., "The Combination of the Antitumoural Pyridyl Cyanoguanidine CHS 828 and Etoposide in vitro—from Cytotoxic Synergy to Complete Inhibition of Apoptosis," British Journal of Pharmacology, 2002, 137:568-573.
Muruganandham et al, "Metabolic Signatures Associated with a NAD Synthesis Inhibitor-Induced Tumor Apoptosis Identified by $^1$H-Decoupled-$^{31}$P Magnetic Resonance Spectroscopy," Clin. Cancer Res., 2005, 11:3503-3513.
Pogrebniak et al., "Chemopotentiating Effects of a Novel NAD Biosynthesis Inhibitor, FK866, in Combination with Antineoplastic Agents," Eur. J. Med. Res., 2006, 11:313-321.
Rongvaux et al., "Nicotinamide Phosphoribosyl Transferase/Pre-B Cell Colony-Enhancing Factor/Visfatin is Required for Lymphocyte Development and Cellular Resistance to Genotoxic Stress," Jour. Immunol., 2008, 181:4685-4695.
Takeuchi et al., "Discovery of a Novel Nicotinamide Phosphoribosyl Transferase (NAMPT) Inhibitor via in Silico Screening," Biol. Pharm. Bull., 2014, 37(1):31-36.
Zak et al., "Identification of Nicotinamide Phosphoribosyltransferase (NAMPT) Inhibitors with no Evidence of CYP3A4 Time-Dependent Inhibition and Improved Aqueous Solubility," Bioorg. Med. Chem. Lett., 2015, 25:529-541.
Zheng et al., "Structure-Based Discovery of Novel Amide-Containing Nicotinamide Phosphoribosyltransferase (Nampt) Inhibitors," J. Med. Chem., 2013, 56:6413-6433.
Zheng et al., "Structure-Based Identification of Ureas as Novel Nicotinamide Phosphoribosyltransferase (Nampt) Inhibitors," J. Med. Chem, 2013, 56:4921-4937.
Zheng et al., "Identification of Amides Derived from 1H-Pyrazolo [3,4-b]Pyridine-5-Carboxylic Acid as Potent Inhibitors of Human Nicotinamide Phosphoribosyltransferase (NAMPT)," Bioorg. Med. Chem. Lett., 2013, 23:5488-5497.

(56) References Cited

OTHER PUBLICATIONS

Zheng et al., "Discovery of Potent and Efficacious Cyanoguanidine-Containing Nicotinamide Phosphoribosyltransferase (NAMPT) Inhibitors," Bioorg. Med. Chem. Lett., 2014, 24:337-343.
Zoppoli et al., "Potent Synergistic Interaction Between the Nampt Inhibitor APO866 and the Apoptosis Activator TRAIL in Human Leukemia Cells," Experimental Hematology, 2010, 38:979-988.

* cited by examiner

QUINOXALINE COMPOUNDS AND USES THEREOF

BACKGROUND OF THE INVENTION

Nicotinamide phosphoribosyltransferase (NAMPT; also known as visfatin and pre-B-cell colony-enhancing factor 1 (PBEF)) is an enzyme that catalyzes the condensation of nicotinamide (NaM) with 5-phosphoribosyl-1-pyrophosphate to yield nicotinamide mononucleotide. This is the first and rate-limiting step in one biosynthetic pathway that cells use to make nicotinamide adenine dinucleotide (NAD+). NAD+ is a critical cofactor for multiple enzymes involved in cell metabolism and homeostasis.

Inhibition of NAMPT results in the lowering of cellular concentrations of NAD+(Beauparlant et al (2007) AACR-NCI-EORTC International Conference on Molecular Targets and Cancer Therapeutics, 2007 Oct. 22-26 Abstract nr A82; and Roulson et al (2007) AACR-NCI-EORTC International Conference on Molecular Targets and Cancer Therapeutics, 2007 Oct. 22-26 Abstract nr A81). Cancer cells have a higher basal turnover of NAD+ and also display higher energy requirements compared with normal cells. Small-molecule inhibitors of NAMPT have been shown to cause depletion of intracellular NAD+ levels and ultimately induce tumor cell death (Hansen, C M et al. Anticancer Res. 20, 42111-4220, 2000) as well as inhibit tumor growth in xenograft models (Olese, U. H. et al. Mol Cancer Ther. 9, 1609-1617, 2010).

Compounds of the invention inhibit the activity of NAMPT, and therefore, may be useful for the treatment of cancer. Cases where NAMPT inhibition has been linked to cancer, a disease where the compounds of the invention may have a therapeutic benefit, include but are not limited to colorectal cancer (Van Beijnum, J. R. et al. Int. J. Cancer 101, 118-127, 2002) and NAMPT is involved in angiogenesis (Kim, S. R. et al. Biochem. Biophys. Res. Commun. 357, 150-156, 2007), multiple myeloma (Chauhan, D. et al., Blood, 2012, 120, 3519-3529), breast cancer (Lord, C. J. EMBO Mol. Med. 2012, 4, 1087-1096), leukemia (Thakur, B. K. et al. Int. J. Cancer 2013, 132, 766-774), non-small cell lung (NSCL) cancer (Okumura, S. J. Thorac. Oncol. 2012, 7, 49-56), gastric cancer (Bi, T. Q. et al. Oncol. Rep. 2011, 26, 1251-1257), neuroblastoma (Travelli, C. et al. J. Pharmacol. Exp. Ther. 2011, 338, 829-840), bladder cancer (Yang, H. J. Exp. Biol. Med. 2010, 235, 869-876), mammary carcinoma (Muruganandham, M. et al. Clin. Cancer Res. 2005, 11, 3503-3513), liver carcinoma (Hasmann, M. Cancer Res. 2003, 63, 7436-7442), renal carcinoma (Drevs, J. Anticancer Res. 2003, 23, 4853-4858, cervix adenocarcinoma (Pittelli, M. et al. J. Biol. Chem. 2010, 285, 34106-34114), glioma (Pitelli, N. et al), lymphoma (Le, A. et al. Proc. Natl. Acad. Sci. U.S.A. 2010, 107, 2037-2042), pancreatic cancer (Le, A. et al.), ovarian cancer (Olesen, U. H. et al. Mol. Cancer Ther. 2010, 9, 1609-1617), melanoma (Maldi, E. et al. Pigm. Cell Melanoma Res. 2013, 26, 144-146), prostate cancer (Zerp, S. F. et al. Radiother. and Oncol. 10, 2014, 110, 348).

Other cases, where a compound of the invention may have a therapeutic benefit as a NAMPT inhibitor, include inflammatory conditions such as rheumatoid arthritis, inflammatory bowel disease, asthma, COPD (chronic obstructive pulmonary disease), osteoarthritis, osteoporosis, sepsis, lupus, spinal cord injury and infection (Galli, M. et al Cancer Res. 70, 8-11, 2010). For example, NAMPT is the predominant enzyme in T and B lymphocytes. Selective inhibition of NAMPT leads to NAD+ depletion in lymphocytes blocking the expansion that accompanies autoimmune disease progression whereas cell types expressing the other NAD+ generating pathways might be spared. A small molecule NAMPT inhibitor (FK866) has been shown to selectively block proliferation and induce apoptosis of activated T cells and was efficacious in animal models of arthritis (collagen-induced arthritis) (Busso, N. et al. Plos One 3, e2267, 2008). FK866, a small molecule NAMPT inhibitor, ameliorated the manifestations of experimental autoimmune encephalomyelitis (EAE), a model of T-cell mediated autoimmune disorders. (Bruzzone, S et al. Plos One 4, e7897, 2009). NAMPT activity increases NF-kB transcriptional activity in human vascular endothelial cell, resulting in MMP-2 and MMP-9 activation, suggesting a role for NAMPT inhibitors in the prevention of inflammatory mediated complications of obesity and type 2 diabetes (Adya, R. et. Al. Diabetes Care, 31, 758-760, 2.

Clearly, it would be beneficial to provide novel NAMPT inhibitors that possess good therapeutic properties, especially for the treatment of cancer, inflammatory conditions, and T-cell mediated autoimmune disease.

1. General Description of Compounds of the Invention

This invention provides compounds that are inhibitors of NAMPT and accordingly are useful for the treatment of cancer, inflammatory conditions, and T-cell mediated autoimmune disease. The invention relates to the following:

Embodiment [1]

A compound of formula I:

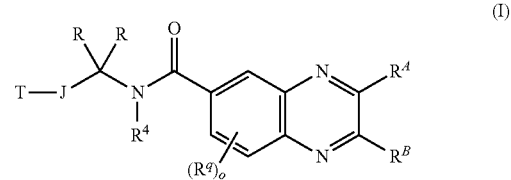

or a pharmaceutically acceptable salt thereof, wherein:
$R^A$ and $R^B$ are each independently selected from

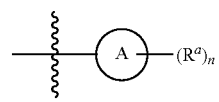

and $XR^1R^2R^3$, provided that one of $R^A$ and $R^B$ is

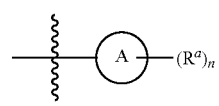

and the other is $XR^1R^2R^3$;
X is selected from CN, halogen, C, O, S, and N, provided that (1) when X is N, then one of $R^1$, $R^2$, and $R^3$ is absent, (2) when X is halogen or CN, then $R^1$, $R^2$, and $R^3$ are absent, and (3) when X is O or S, then two of $R^1$, $R^2$, and $R^3$ are absent;

$R^1$, $R^2$, and $R^3$ are each independently selected from hydrogen; $OR^{20}$; $N(R^{20})_2$; $C_{1-6}$ aliphatic, wherein 1 or 2 methylene units of the $C_{1-6}$ aliphatic are optionally and independently replaced by O, S, S(O), $S(O)_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl is optionally substituted with one or more $R^k$;

or wherein any two of $R^1$, $R^2$, and $R^3$ taken together with the atom X to which they are bound, when X is C or N, form a ring selected from a 4-10-membered heterocycle having 1-5 heteroatoms independently selected from nitrogen, oxygen and sulfur and a 3-10-membered cycloaliphatic, wherein the ring is optionally substituted with one or more $R^b$, or wherein any two of $R^1$, $R^2$, and $R^3$ taken together with the atom X to which they are bound, when X is N, form a 5-10-membered heteroaryl having 1-5 heteroatoms independently selected from nitrogen, oxygen, and sulfur, wherein the heteroaryl is optionally substituted with one or more $R^b$, or wherein $R^1$, $R^2$, and $R^3$ taken together with the atom X to which they are bound, when X is C, form a ring selected from a 5-10-membered heteroaryl having 1-4 heteroatoms independently selected from nitrogen, oxygen, and sulfur and a 6-10-membered aryl, wherein the ring is optionally substituted with one or more $R^b$;

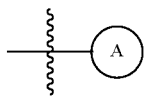

is a ring selected from a 3-7-membered saturated, partially unsaturated, and aromatic monocyclic ring having 0-3 heteroatoms independently selected from nitrogen, oxygen, and sulfur and an 8-10-membered saturated, partially unsaturated, and aromatic bicyclic ring having 0-5 heteroatoms independently selected from nitrogen, oxygen, and sulfur;

each occurrence of $R^a$ is independently selected from $C_{1-6}$ aliphatic and $Z_1$—$R^8$;

or wherein two $R^a$ taken together with the atom or atoms to which they are bound, form a ring selected from a 4-10-membered heterocycle having 1-5 heteroatoms independently selected from nitrogen, oxygen, and sulfur and a 3-6-membered cycloaliphatic, wherein the ring is optionally substituted with one or more $R^p$;

each occurrence of $R^p$ is independently selected from CN, $CH_3$, $CF_3$, $CH_2F$, $CF_2H$, $NH_2$, $NH(C_{1-3}$ aliphatic), $N(C_{1-3}$ aliphatic$)_2$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $Z_1$ is independently selected from a direct bond, $C_{1-3}$ alkylene chain, O, $N(R^{16})$, S, S(O), $S(O)_2$, C(O), $CO_2$, $C(O)NR^{16}$, $N(R^{16})C(O)$, $N(R^{16})CO_2$, $S(O)_2NR^{16}$, $N(R^{16})S(O)_2$, $OC(O)N(R^{16})$, $N(R^{16})C(O)NR^{16}$, $N(R^{16})S(O)_2N(R^{16})$, and OC(O), wherein the alkylene chain is optionally substituted with one or more $R^h$;

each occurrence of $R^h$ is independently selected from CN, $CH_3$, $CF_3$, $CH_2F$, $CF_2H$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^b$ is independently selected from $C_{1-6}$ aliphatic and $Z_2$—$R^6$;

or wherein two $R^b$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein the ring is optionally substituted with one or more $R^c$;

each occurrence of $R^c$ is independently selected from $C_{1-6}$ aliphatic, $CF_3$, $CF_2H$, $CH_2F$, halogen, $OR^{12}$, $(CH_2)_v$—C$(O)R^9$, and $(CH_2)_w$—$NR^{10}C(O)R^{11}$;

each occurrence of $Z_2$ is independently selected from direct bond, $C_{1-3}$ alkylene chain, O, $N(R^{17})$, S, S(O), $S(O)_2$, C(O), $CO_2$, $C(O)NR^{17}$, $N(R^{17})C(O)$, $N(R^{17})CO_2$, $S(O)_2NR^{17}$, $N(R^{17})S(O)_2$, $OC(O)NR^{17}$, $N(R^{17})C(O)NR^{17}$, $N(R^{17})S(O)_2N(R^{17})$, and OC(O), wherein the alkylene chain is optionally substituted with one or more $R^i$;

each occurrence of $R^i$ is independently selected from CN, $CH_3$, $CF_3$, $CH_2F$, $CF_2H$, halogen, OH, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^k$ is independently selected from $C_{1-6}$ aliphatic and $Z_3$—$R^{23}$;

or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and a 7-10-membered saturated, partially unsaturated, or aromatic bicyclic ring having 0-5 heteroatoms independently selected from nitrogen, oxygen, and sulfur, wherein the ring is optionally substituted with one or more $R^m$;

each occurrence of $R^m$ is independently selected from $C_{1-6}$ aliphatic, CN, $CF_3$, $CH_2F$, $CF_2H$, halogen, $OR^{25}$, $(CH_2)_q$—$C(O)R^{26}$, and $(CH_2)_r$—$NR^{27}C(O)R^{28}$;

each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and OC(O), wherein the alkylene chain is optionally substituted $N(R^{24})S(O)_2N(R^{24})$, with one or more $R^n$;

each occurrence of $R^n$ is independently selected from CN, $CH_3$, $CF_3$, $CH_2F$, $CF_2H$, halogen, OH, $OCH_3$, $OCF_3$, $OCH_2F$, $OCF_2H$, $O(C_{2-3}$ aliphatic), and $C_{2-3}$ aliphatic, wherein said $C_{2-3}$ aliphatic is optionally substituted with one or more F;

J is selected from a direct bond; a linear or branched $C_{1-6}$ aliphatic, wherein 1 or 2 methylene units of J are optionally and independently replaced by O, S, or $N(R^{13})$ and further wherein the $C_{1-6}$ aliphatic is optionally substituted with one or more $R^j$;

each occurrence of $R^j$ is independently selected from fluorine, $CH_3$, $CF_3$, $CH_2F$, $CF_2H$, OH, $OCH_3$, $OCF_3$, $OCH_2F$, $OCF_2H$, $O(C_{2-3}$ aliphatic), $NH_2$, $NH(C_{1-3}$ aliphatic), $N(C_{1-3}$ aliphatic$)_2$, and $C_{2-3}$ aliphatic, wherein said $C_{2-3}$ aliphatic is optionally substituted with one or more F;

or wherein two $R^j$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein the ring is optionally substituted with one or more $R^e$;

or wherein $R^j$ and one of R taken together with the atom or atoms to which they are bound form a ring selected from a 3-6-membered heterocycle having 1 heteroatom selected from nitrogen, oxygen, and sulfur and a 3-6-membered cycloaliphatic, wherein the ring is optionally substituted with one or more $R^e$;

each occurrence of R is independently selected from hydrogen and $C_{1-3}$ aliphatic, wherein the $C_{1-3}$ aliphatic is optionally substituted with one or more F;

$R^4$ is selected from hydrogen and $C_{1-6}$ aliphatic;

or wherein one of R and $R^4$ or $R^j$ and $R^4$ taken together with the atoms to which they are bound, form a 4-10-membered heterocycle having 1-5 heteroatoms independently selected from nitrogen, oxygen, and sulfur, wherein the heterocycle is optionally substituted with one or more $R^e$;

each occurrence of $R^e$ is independently selected from halogen, $CF_3$, $CF_2H$, $CH_2F$, $C_{1-6}$aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^h$;

or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^h$;

each occurrence of $R^h$ is independently selected from halogen, $CF_3$, $CF_2H$, $CH_2F$, $C_{1-6}$ aliphatic, $C(O)N(R^{18})_2$, OH, and $OC_{1-6}$ aliphatic;

each occurrence of $R^5$ is independently selected from hydrogen, $CF_3$, $CF_2H$, $CH_2F$, and $C_{1-6}$aliphatic;

each occurrence of $R^6$ is independently selected from CN, halogen, $OR^7$, $N(R^{19})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^c$;

each occurrence of $R^7$ is independently selected from hydrogen, $CF_3$, $CF_2H$, $CH_2F$, $C_{1-6}$aliphatic, and 6-10-membered aryl;

each occurrence of $R^8$ is independently selected from CN, halogen, $OR^5$, $N(R^{21})_2$, $C_{1-6}$aliphatic, 6-10-membered aryl, 3-10 membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein the aryl, cycloaliphatic, heteroaryl, and heterocycle is optionally substituted with one or more $R^g$;

each occurrence of $R^g$ is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^9$ is independently selected from OH, $OC_{1-6}$ aliphatic, $N(R^{15})_2$, and $C_{1-6}$ aliphatic;

each occurrence of $R^{10}$ is independently selected from hydrogen and $C_{1-6}$aliphatic;

each occurrence of $R^{11}$ is independently selected from OH, $OC_{1-6}$aliphatic, $N(R^{14})_2$, and $C_{1-6}$aliphatic;

each occurrence of $R^{12}$ is independently selected from hydrogen and $C_{1-6}$aliphatic;

each occurrence of $R^{13}$ is independently selected from hydrogen and $C_{1-6}$aliphatic;

each occurrence of $R^{14}$ is independently selected from hydrogen and $C_{1-6}$aliphatic;

each occurrence of $R^{15}$ is independently selected from hydrogen and $C_{1-6}$aliphatic;

each occurrence of $R^{16}$ is independently selected from hydrogen and $C_{1-6}$aliphatic;

each occurrence of $R^{17}$ is independently selected from hydrogen and $C_{1-6}$aliphatic;

each occurrence of $R^{18}$ is independently selected from hydrogen and $C_{1-6}$ aliphatic;

each occurrence of $R^{19}$ is independently selected from hydrogen and $C_{1-3}$ aliphatic;

each occurrence of $R^{20}$ is independently selected from hydrogen and $C_{1-6}$ aliphatic;

each occurrence of $R^{21}$ is independently selected from hydrogen and $C_{1-6}$aliphatic;

each occurrence of $R^{23}$ is independently selected from CN, halogen, $OR^{31}$, $N(R^{32})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^m$;

each occurrence of $R^{24}$ is independently selected from hydrogen and $C_{1-6}$aliphatic;

each occurrence of $R^{25}$ is independently selected from hydrogen and $C_{1-6}$aliphatic;

each occurrence of $R^{26}$ is independently selected from OH, $OC_{1-6}$ aliphatic, $N(R^{29})_2$, and $C_{1-6}$ aliphatic;

each occurrence of $R^{27}$ is independently selected from hydrogen and $C_{1-6}$aliphatic;

each occurrence of $R^{28}$ is independently selected from OH, $OC_{1-6}$aliphatic, $N(R^{30})_2$, and $C_{1-6}$aliphatic;

each occurrence of $R^{29}$ is independently selected from hydrogen and $C_{1-6}$aliphatic;

each occurrence of $R^{30}$ is independently selected from hydrogen and $C_{1-6}$aliphatic;

each occurrence of $R^{31}$ is independently selected from hydrogen, $CF_3$, $CF_2H$, $CH_2F$, $C_{1-6}$aliphatic, and 6-10-membered aryl;

each occurrence of $R^{32}$ is independently selected from hydrogen and $C_{1-3}$ aliphatic;

each occurrence of $R^{33}$ is independently selected from hydrogen and $C_{1-3}$ aliphatic;

T is hydrogen or $(CH_2)_z$-5-10-membered monocyclic or bicyclic heteroaryl having 1-5 heteroatoms independently selected from nitrogen, oxygen, and sulfur, wherein the heteroaryl is optionally substituted with one or more $R^d$, provided that T is hydrogen only when R and $R^4$ or $R^4$ and $R^j$ are taken together with the atoms to which they are bound to form a 4-10-membered heterocycle having 1-5 heteroatoms independently selected from nitrogen, oxygen, and sulfur;

each occurrence of $R^d$ is independently selected from halogen, $N(R^{33})_2$, and $C_{1-6}$aliphatic or wherein taken together two $R^d$ together with the atom or atoms to which they are bound, form a 4-10-membered heterocycle having 1-5 heteroatoms independently selected from nitrogen, oxygen, and sulfur;

each occurrence of $R^q$ is independently selected from CN, $CH_3$, $CF_3$, $CF_2H$, $CH_2F$, halogen, OH, $OCH_3$, $OCF_3$, OCH$_2$F, OCF$_2$H, O(C$_{2-3}$ aliphatic), and C$_{2-3}$ aliphatic, wherein said C$_{2-3}$ aliphatic is optionally substituted with one or more F;

n is 0, 1, 2, 3, 4, or 5; o is 0, 1, 2, or 3; p is 0, 1, 2, or 3; q is 0, 1, 2, or 3; r is 0, 1, 2, or 3; s is 0, 1, 2, or 3; t is 0, 1, 2, or 3; u is 0, 1, 2, or 3; v is 0, 1, 2, or 3; w is 0, 1, 2, or 3; x is 0, 1, 2, or 3; and z is 0, 1, 2, or 3;

provided that:

(a) when R$^A$ and R$^B$ are the same and selected from optionally substituted phenyl, unsubstituted 2-furan, unsubstituted 3-furan, unsubstituted 3-thiophene, 2-pyridine, and unsubstituted 2-thiophene;

o is 0;

R and R$^4$ are hydrogen; and

J is direct bond or unsubstituted C$_1$ aliphatic, then T is other than

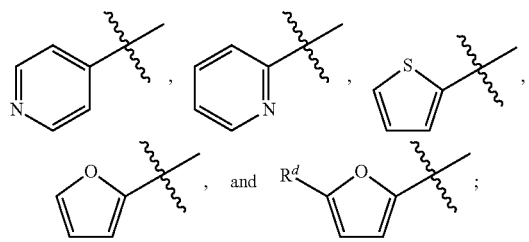

and b) the compound is other than:

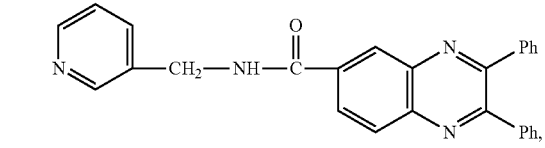

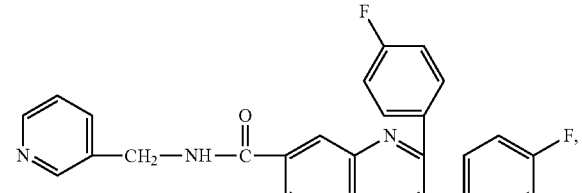

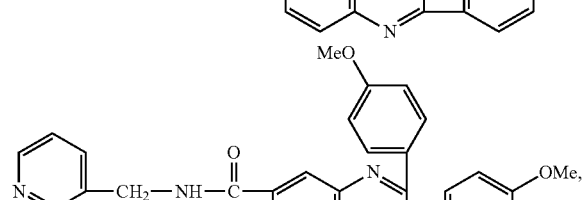

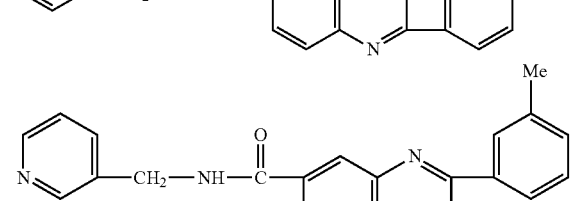

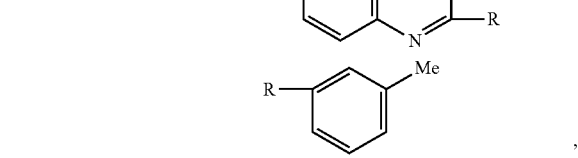

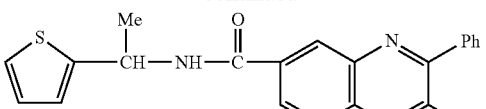

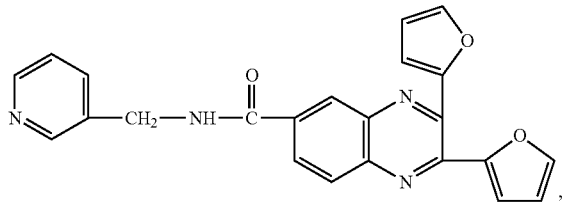

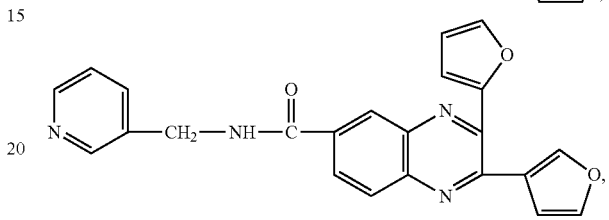

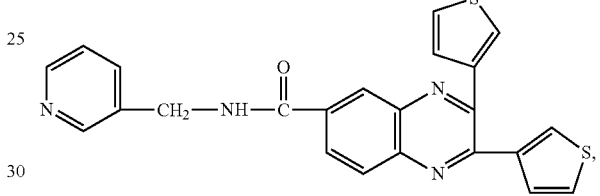

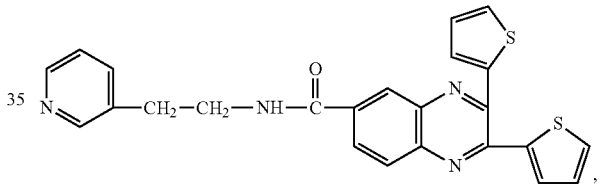

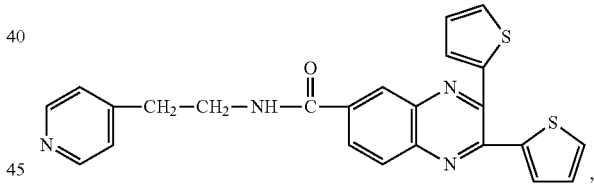

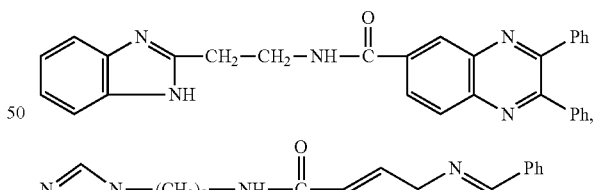

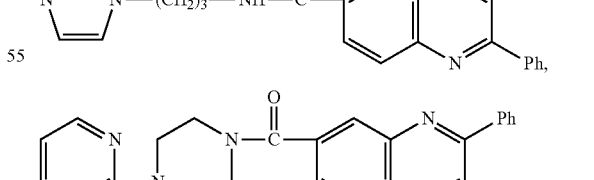

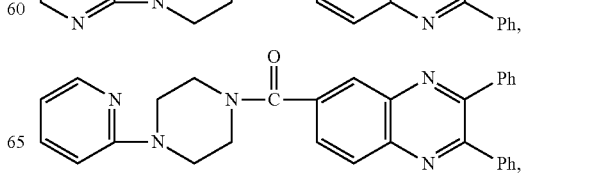

-continued

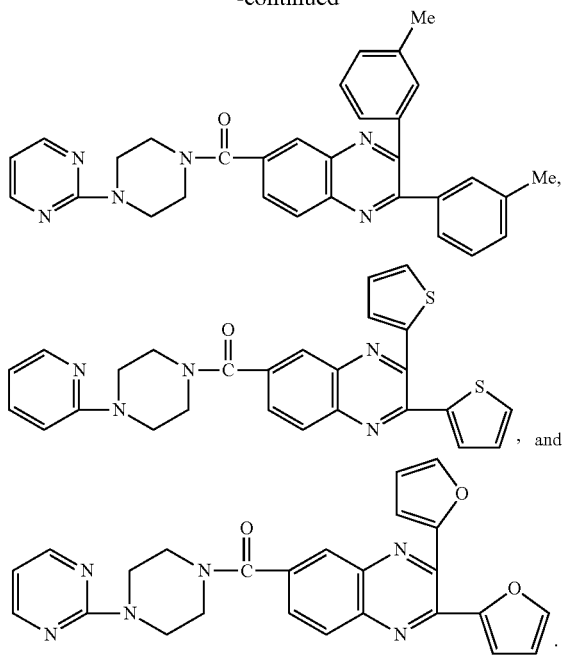

Embodiment [2]

A compound of formula I or a pharmaceutically acceptable salt thereof, wherein:
$R^A$ and $R^B$ are each independently selected from

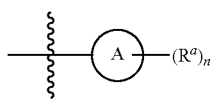

and $XR^1R^2R^3$, provided that one of $R^A$ and $R^B$ is

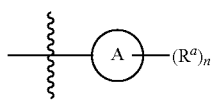

and the other is $XR^1R^2R^3$;

X is selected from CN, halogen, C, O, S, and N, provided that (1) when X is N, then one of $R^1$, $R^2$, and $R^3$ is absent, (2) when X is halogen or CN, then $R^1$, $R^2$, and $R^3$ are absent, and (3) when X is O or S, then two of $R^1$, $R^2$, and $R^3$ are absent;

$R^1$, $R^2$, and $R^3$ are each independently selected from hydrogen; $N(R^{20})_2$; $C_{1-6}$aliphatic, wherein 1 or 2 methylene units of the $C_{1-6}$ aliphatic are optionally and independently replaced by O, S, S(O), S(O)$_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl is optionally substituted with one or more $R^k$;

or wherein any two of $R^1$, $R^2$, and $R^3$ taken together with the atom X to which they are bound, when X is C or N, form a ring selected from a 4-10-membered heterocycle having 1-5 heteroatoms independently selected from nitrogen, oxygen and sulfur and a 3-10-membered cycloaliphatic, wherein the ring is optionally substituted with one or more $R^b$, or wherein $R^1$, $R^2$, and $R^3$ taken together with the atom X to which they are bound, when X is C, form a ring selected from a 5-10-membered heteroaryl having 1-4 heteroatoms independently selected from nitrogen, oxygen, and sulfur and a 6-10-membered aryl, wherein the ring is optionally substituted with one or more $R^b$;

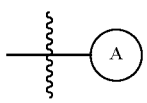

is a ring selected from a 3-7-membered saturated, partially unsaturated, and aromatic monocyclic ring having 0-3 heteroatoms independently selected from nitrogen, oxygen, and sulfur and an 8-10-membered saturated, partially unsaturated, and aromatic bicyclic ring having 0-5 heteroatoms independently selected from nitrogen, oxygen, and sulfur;

each occurrence of $R^a$ is independently selected from $C_{1-6}$ aliphatic and $Z_1$—$R^8$;

or wherein two $R^a$ taken together with the atom or atoms to which they are bound, form a ring selected from a 4-10-membered heterocycle having 1-5 heteroatoms independently selected from nitrogen, oxygen, and sulfur and a 3-6-membered cycloaliphatic, wherein the ring is optionally substituted with one or more $R^p$;

each occurrence of $R^p$ is independently selected from CN, $CH_3$, $CF_3$, $CH_2F$, $CF_2H$, $NH_2$, $NH(C_{1-3}$ aliphatic), $N(C_{1-3}$ aliphatic)$_2$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $Z_1$ is independently selected from a direct bond, $C_{1-3}$ alkylene chain, O, $N(R^{16})$, S, S(O), S(O)$_2$, C(O), $CO_2$, $C(O)NR^{16}$, $N(R^{16})C(O)$, $N(R^{16})CO_2$, $S(O)_2NR^{16}$, $N(R^{16})S(O)_2$, $OC(O)N(R^{16})$, $N(R^{16})C(O)NR^{16}$, $N(R^{16})S(O)_2N(R^{16})$, and OC(O), wherein the alkylene chain is optionally substituted with one or more $R^h$;

each occurrence of $R^h$ is independently selected from CN, $CH_3$, $CF_3$, $CH_2F$, $CF_2H$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^b$ is independently selected from $C_{1-6}$ aliphatic and $Z_2$—$R^6$;

or wherein two $R^b$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein the ring is optionally substituted with one or more $R^c$;

each occurrence of $R^c$ is independently selected from $C_{1-6}$ aliphatic, $CF_3$, $CF_2H$, $CH_2F$, halogen, $OR^{12}$, $(CH_2)_v$—C(O)$R^9$, and $(CH_2)_w$—$NR^{10}C(O)R^{11}$;

each occurrence of $Z_2$ is independently selected from direct bond, $C_{1-3}$ alkylene chain, O, $N(R^{17})$, S, S(O), S(O)$_2$, C(O), $CO_2$, $C(O)NR^{17}$, $N(R^{17})C(O)$, $N(R^{17})CO_2$, $S(O)_2NR^{17}$, N($R^{17}$)S(O)$_2$, OC(O)N($R^{17}$), N($R^{17}$)C(O)N$R^{17}$, N($R^{17}$)S(O)$_2$ N($R^{17}$), and OC(O), wherein the alkylene chain is optionally substituted with one or more $R^i$;

each occurrence of $R^i$ is independently selected from CN, CH$_3$, CF$_3$, CH$_2$F, CF$_2$H, halogen, OH, OCH$_3$, OCF$_3$, OCH$_2$F, OCF$_2$H, O(C$_{2-3}$ aliphatic) and C$_{2-3}$ aliphatic, wherein said C$_{2-3}$ aliphatic is optionally substituted with one or more F;

each occurrence of $R^k$ is independently selected from C$_{1-6}$ aliphatic and $Z_3$—$R^{23}$;

or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and a 7-10-membered saturated, partially unsaturated, or aromatic bicyclic ring having 0-5 heteroatoms independently selected from nitrogen, oxygen, and sulfur, wherein the ring is optionally substituted with one or more $R^m$;

each occurrence of $R^m$ is independently selected from C$_{1-6}$ aliphatic, CN, CF$_3$, CH$_2$F, CF$_2$H, halogen, O$R^{25}$, (CH$_2$)$_q$—C(O)$R^{26}$, and (CH$_2$)$_r$—N$R^{27}$C(O)$R^{28}$;

each occurrence of $Z_3$ is independently selected from direct bond, C$_{1-3}$ alkylene chain, O, N($R^{24}$), S, S(O), S(O)$_2$, C(O), CO$_2$, C(O)N$R^{24}$, N($R^{24}$)C(O), N($R^{24}$)CO$_2$, S(O)$_2$N$R^{24}$, N($R^{24}$)S(O)$^2$, OC(O)N($R^{24}$), N($R^{24}$)C(O)N$R^{24}$, N($R^{24}$)S(O)$_2$ N($R^{24}$), and OC(O), wherein the alkylene chain is optionally substituted with one or more $R^n$;

each occurrence of $R^n$ is independently selected from CN, CH$_3$, CF$_3$, CF$_2$H, CH$_2$F, halogen, OH, OCH$_3$, OCF$_3$, OCH$_2$F, OCF$_2$H, O(C$_{2-3}$ aliphatic), and C$_{2-3}$ aliphatic, wherein said C$_{2-3}$ aliphatic is optionally substituted with one or more F;

J is selected from a direct bond; a linear or branched C$_{1-6}$aliphatic, wherein 1 or 2 methylene units of J are optionally and independently replaced by O, S, or N($R^{13}$) and further wherein the C$_{1-6}$aliphatic is optionally substituted with one or more $R^j$;

each occurrence of $R^j$ is independently selected from fluorine, CH$_3$, CF$_3$, CH$_2$F, CF$_2$H, OH, OCH$_3$, OCF$_3$, OCH$_2$F, OCF$_2$H, O(C$_{2-3}$aliphatic), NH$_2$, NH(C$_{1-3}$aliphatic), N(C$_{1-3}$ aliphatic)$_2$, and C$_{2-3}$ aliphatic, wherein said C$_{2-3}$ aliphatic is optionally substituted with one or more F;

or wherein two $R^j$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein the ring is optionally substituted with one or more $R^e$;

or wherein W and one of R taken together with the atom or atoms to which they are bound form a ring selected from a 3-6-membered heterocycle having 1 heteroatom selected from nitrogen, oxygen, and sulfur and a 3-6-membered cycloaliphatic, wherein the ring is optionally substituted with one or more $R^e$;

each occurrence of R is independently selected from hydrogen and C$_{1-3}$ aliphatic, wherein the C$_{1-3}$ aliphatic is optionally substituted with one or more F;

$R^4$ is selected from hydrogen and C$_{1-6}$ aliphatic;

or wherein one of R and $R^4$ or $R^j$ and $R^4$ taken together with the atoms to which they are bound, form a 4-10-membered heterocycle having 1-5 heteroatoms independently selected from nitrogen, oxygen, and sulfur, wherein the heterocycle is optionally substituted with one or more $R^e$;

each occurrence of $R^e$ is independently selected from halogen, CF$_3$, CF$_2$H, CH$_2$F, C$_{1-6}$aliphatic, and (CH$_2$)$_x$-[3-7-membered saturated, partially unsaturated, or aromatic monocyclic ring having 1-3 heteroatoms independently selected from nitrogen, oxygen, and sulfur], wherein the ring is optionally substituted with one or more $R^h$;

or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^h$;

each occurrence of $R^h$ is independently selected from halogen, CF$_3$, CF$_2$H, CH$_2$F, C$_{1-6}$ aliphatic, C(O)N($R^{18}$)$_2$, OH, and OC$_{1-6}$ aliphatic;

each occurrence of $R^5$ is independently selected from hydrogen, CF$_3$, CF$_2$H, CH$_2$F, and C$_{1-6}$aliphatic;

each occurrence of $R^6$ is independently selected from CN, halogen, O$R^7$, N($R^{19}$)$_2$, C$_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^c$;

each occurrence of $R^7$ is independently selected from hydrogen, CF$_3$, CF$_2$H, CH$_2$F, C$_{1-6}$aliphatic, and 6-10-membered aryl;

each occurrence of $R^8$ is independently selected from CN, halogen, O$R^5$, N($R^{21}$)$_2$, C$_{1-6}$aliphatic, 6-10-membered aryl, 3-10 membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein the aryl, cycloaliphatic, heteroaryl, and heterocycle is optionally substituted with one or more $R^g$;

each occurrence of $R^g$ is independently selected from CN, CH$_3$, CF$_3$, CF$_2$H, CH$_2$F, halogen, OH, OCH$_3$, OCF$_3$, OCH$_2$F, OCF$_2$H, O(C$_{2-3}$ aliphatic) and C$_{2-3}$ aliphatic, wherein said C$_{2-3}$ aliphatic is optionally substituted with one or more F;

each occurrence of $R^9$ is independently selected from OH, OC$_{1-6}$ aliphatic, N($R^{15}$)$_2$, and C$_{1-6}$ aliphatic;

each occurrence of $R^{10}$ is independently selected from hydrogen and C$_{1-6}$aliphatic;

each occurrence of $R^{11}$ is independently selected from OH, OC$_{1-6}$aliphatic, N($R^{14}$)$_2$, and C$_{1-6}$aliphatic;

each occurrence of $R^{12}$ is independently selected from hydrogen and C$_{1-6}$aliphatic;

each occurrence of $R^{13}$ is independently selected from hydrogen and C$_{1-6}$aliphatic;

each occurrence of $R^{14}$ is independently selected from hydrogen and C$_{1-6}$aliphatic;

each occurrence of $R^{15}$ is independently selected from hydrogen and C$_{1-6}$aliphatic;

each occurrence of $R^{16}$ is independently selected from hydrogen and C$_{1-6}$aliphatic;

each occurrence of $R^{17}$ is independently selected from hydrogen and C$_{1-6}$aliphatic;

each occurrence of $R^{18}$ is independently selected from hydrogen and C$_{1-6}$ aliphatic;

each occurrence of $R^{19}$ is independently selected from hydrogen and C$_{1-3}$ aliphatic;

each occurrence of $R^{20}$ is independently selected from hydrogen and C$_{1-6}$ aliphatic;

each occurrence of $R^{21}$ is independently selected from hydrogen and C$_{1-6}$aliphatic;

each occurrence of R²³ is independently selected from CN, halogen, OR³¹, N(R³²)₂, C₁₋₆aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^m$;

each occurrence of R²⁴ is independently selected from hydrogen and C₁₋₆aliphatic;

each occurrence of R²⁵ is independently selected from hydrogen and C₁₋₆aliphatic;

each occurrence of R²⁶ is independently selected from OH, OC₁₋₆ aliphatic, N(R²⁹)₂, and C₁₋₆ aliphatic;

each occurrence of R²⁷ is independently selected from hydrogen and C₁₋₆aliphatic;

each occurrence of R²⁸ is independently selected from OH, OC₁₋₆aliphatic, N(R³⁰)₂, and C₁₋₆aliphatic;

each occurrence of R²⁹ is independently selected from hydrogen and C₁₋₆aliphatic;

each occurrence of R³⁰ is independently selected from hydrogen and C₁₋₆aliphatic;

each occurrence of R³¹ is independently selected from hydrogen, CF₃, CF₂H, CH₂F, C₁₋₆aliphatic, and 6-10-membered aryl;

each occurrence of R³² is independently selected from hydrogen and C₁₋₃ aliphatic;

T is hydrogen or (CH₂)$_z$-5-10-membered monocyclic or bicyclic heteroaryl having 1-5 heteroatoms independently selected from nitrogen, oxygen, and sulfur, wherein the heteroaryl is optionally substituted with one or more $R^d$, provided that T is hydrogen only when R and R⁴ or R⁴ and $R^j$ are taken together with the atoms to which they are bound to form a 4-10-membered heterocycle, having 1-5 heteroatoms independently selected from nitrogen, oxygen, and sulfur;

each occurrence of $R^d$ is independently selected from halogen, and C₁₋₆aliphatic or wherein taken together two $R^d$ together with the atom or atoms to which they are bound, form a 4-10-membered heterocycle having 1-5 heteroatoms independently selected from nitrogen, oxygen, and sulfur;

each occurrence of $R^q$ is independently selected from CN, CH₃, CF₃, CF₂H, CH₂F, halogen, OH, OCH₃, OCF₃, OCH₂F, OCF₂H, O(C₂₋₃ aliphatic), and C₂₋₃ aliphatic, wherein said C₂₋₃ aliphatic is optionally substituted with one or more F;

n is 0, 1, 2, 3, 4, or 5; o is 0, 1, 2, or 3; p is 0, 1, 2, or 3; q is 0, 1, 2, or 3; r is 0, 1, 2, or 3; s is 0, 1, 2, or 3; t is 0, 1, 2, or 3; u is 0, 1, 2, or 3; v is 0, 1, 2, or 3; w is 0, 1, 2, or 3; x is 0, 1, 2, or 3; and z is 0, 1, 2, or 3; provided a) and b) from Embodiment [1].

Embodiment [3]

A compound of formula II:

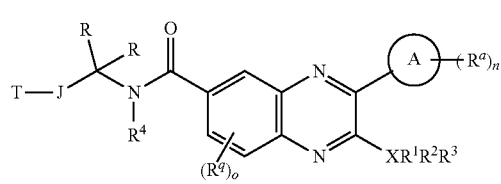

(II)

or a pharmaceutically acceptable salt thereof, wherein T, X, J, R, R¹, R², R³, R⁴, $R^a$, $R^q$, n, o, and

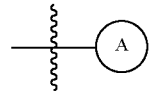

are as defined herein for formula I.

Embodiment [4]

A compound of formula III:

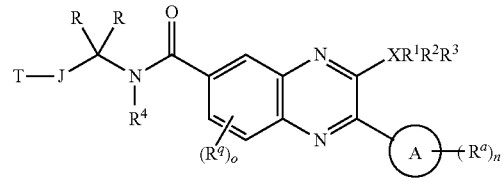

(III)

or a pharmaceutically acceptable salt thereof, wherein T, X, J, R, R¹, R², R³, R⁴, $R^a$, $R^q$, n, o, and

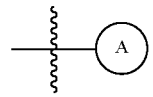

are as defined herein for formula I.

Embodiment [5]

The compound of any one of embodiments [1]-[4], wherein J is selected from a direct bond, C₁ aliphatic, and C₂ aliphatic and J is not substituted with one or more $R^j$.

Embodiment [6]

A compound of formula IV, V, VI or VII:

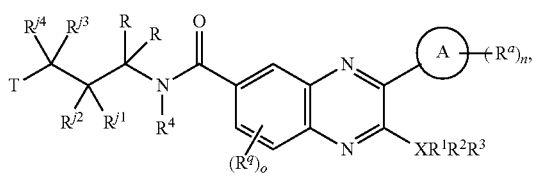

(IV)

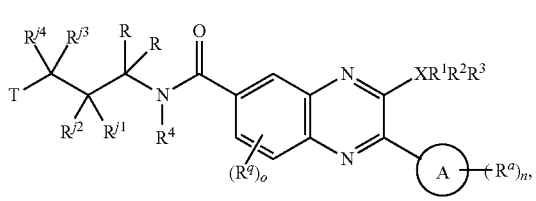

(V)

-continued

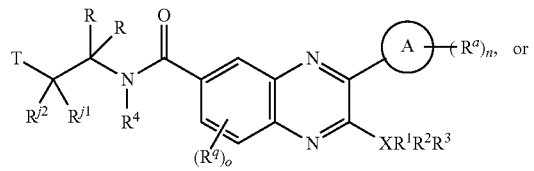

(VI)

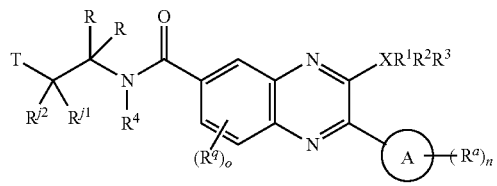

(VII)

or a pharmaceutically acceptable salt thereof, wherein T, X, R, $R^1$, $R^2$, $R^3$, $R^4$, $R^a$, $R^q$, n, o, and

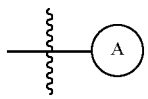

are as defined herein for formula I and $R^{j1}$, $R^{j2}$, $R^{j3}$, and $R^{j4}$ are each independently selected from hydrogen, fluorine, OH, O($C_{1-3}$aliphatic), $NH_2$, NH($C_{1-3}$aliphatic), N($C_{1-3}$aliphatic)$_2$, and $C_{1-3}$ aliphatic;

or wherein any two of $R^{j1}$, $R^{j2}$, $R^{j3}$, and $R^{j4}$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$;

or wherein any one of $R^{j1}$, $R^{j2}$, $R^{j3}$, and $R^{j4}$ and one of R taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$; and or wherein any one of $R^{j1}$, $R^{j2}$, $R^{j3}$, and $R^{j4}$ and one of R taken together with the atom or atoms to which they are bound form a ring selected from a 4-10-membered heterocycle having 1-5 heteroatoms independently selected from nitrogen, oxygen, and sulfur, wherein said heterocycle is optionally substituted with one or more $R^e$;

each occurrence of $R^e$ is independently selected from halogen, $CF_3$, $CF_2H$, $CH_2F$, $C_{1-6}$aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^h$;

or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^h$;

each occurrence of $R^h$ is independently selected from halogen, $CF_3$, $CF_2H$, $CH_2F$, $C_{1-6}$ aliphatic, C(O)N($R^{18}$)$_2$, OH, and $OC_{1-6}$aliphatic;

each occurrence of $R^{18}$ is independently selected from hydrogen and $C_{1-6}$ aliphatic;

and x is 0, 1, 2, or 3.

DETAILED DESCRIPTION OF THE INVENTION

2. Compounds and Definitions

Compounds of this invention include those described generally above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of 3 to 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having 3 to 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. In one aspect, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. In one aspect, the aralkyl group is $C_{6-10}$ aryl$C_{1-6}$ alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, for example 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, in one aspect, mono-, bi-, or tricyclic, in another aspect, mono- or bicyclic. The term "heteroatom" refers to nitrogen, oxygen, or sulfur, and includes any oxidized form of nitrogen or sulfur, and any quaternized form of a basic nitrogen atom. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Non-limiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen atom. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, in one aspect, mono-, bi-, or tricyclic, in another aspect, mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $-(CH_2)_n-$, wherein n is a positive integer, in one aspect from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, $-NO_2$, $-CN$, $-R^+$, $-C(R^+)=C(R^+)_2$, $-C\equiv C-R^+$, $-OR^+$, $-SR^o$, $-S(O)R^o$, $-SO_2R^o$, $-SO_3R^+$, $-SO_2N(R^+)_2$, $-N(R^+)_2$, $-NR^+C(O)R^+$, $-NR^+C(S)R^+$, $-NR^+C(O)N(R^+)_2$, $-NR^+C(S)N(R^+)_2$, $-N(R^+)C(=NR^+)-N(R^+)_2$, $-N(R^+)C(=NR^+)-R^o$, $-NR^+CO_2R^+$, $-NR^+SO_2R^o$, $-NR^+SO_2N(R^+)_2$, $-O-C(O)R^+$, $-O-CO_2R^+$, $-OC(O)N(R^+)_2$, $-C(O)R^+$, $-C(S)R^o$, $-CO_2R^+$, $-C(O)-C(O)R^+$, $-C(O)N(R^+)_2$, $-C(S)N(R^+)_2$, $-C(O)N(R^+)-OR^+$, $-C(O)N(R^+)C(=NR^+)-N(R^+)_2$, $-N(R^+)C(=NR^+)-N(R^+)-C(O)R^+$, $-C(=NR^+)-N(R^+)_2$, $-C(=NR^+)-OR^+$, $-N(R^+)-N(R^+)_2$, $-C(=NR^+)-N(R^+)-OR^+$, $-C(R^o)=N-OR^+$, $-P(O)(R^+)_2$, $-P(O)(OR^+)_2$, $-O-P(O)-OR^+$, and $-P(O)(NR^+)-N(R^+)_2$, wherein $R^+$, independently, is hydrogen or an optionally substituted aliphatic, aryl, heteroaryl, cycloaliphatic, or heterocyclyl group, or two independent occur-rences of $R^+$ are taken together with their intervening atom(s) to form an optionally substituted 5-7-membered aryl, heteroaryl, cycloaliphatic, or heterocyclyl ring. Each $R^o$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: $=O$, $=S$, $=C(R^*)_2$, $=N-N(R^*)_2$, $=N-OR^*$, $=N-NHC(O)R^*$, $=N-NHCO_2R^o$, $=N-NHSO_2R^o$ or $=N-R^*$ where $R^o$ is defined above, and each $R^*$ is independently selected from hydrogen or an optionally substituted $C_{1-6}$ aliphatic group.

In addition to the substituents defined above and herein, optional substituents on the nitrogen of a non-aromatic heterocyclic ring also include and are generally selected from $-R^+$, $-N(R^+)_2$, $-C(O)R^+$, $-C(O)OR^+$, $-C(O)C(O)R^+$, $-C(O)CH_2C(O)R^+$, $-S(O)_2R^+$, $-S(O)_2N(R^+)_2$, $-C(S)N(R^+)_2$, $-C(=NH)-N(R^+)_2$, or $-N(R^+)S(O)_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of $R^+$ (or any other variable similarly defined in the specification and claims herein), are taken together with their intervening atom(s) include, but are not limited to the following: a) two independent occurrences of $R^+$ (or any other variable similarly defined in the specification or claims herein) that are bound to the same atom and are taken together with that atom to form a ring, for example, $N(R^+)_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of $OR^+$

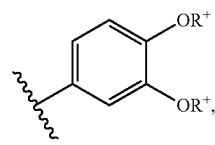

these two occurrences of $R^+$ are taken together with the oxygen atoms to which they are bound to form a fused 6-membered oxygen containing ring:

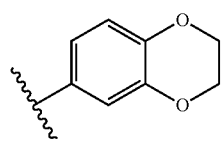

It will be appreciated that a variety of other rings (e.g., spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}C$- or $^{14}C$-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of compound free from the corresponding optical isomer, racemic mixture of the compound and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

Embodiment [7]

The compound of any one of embodiments [1]-[6], wherein $XR^1R^2R^3$ is selected from

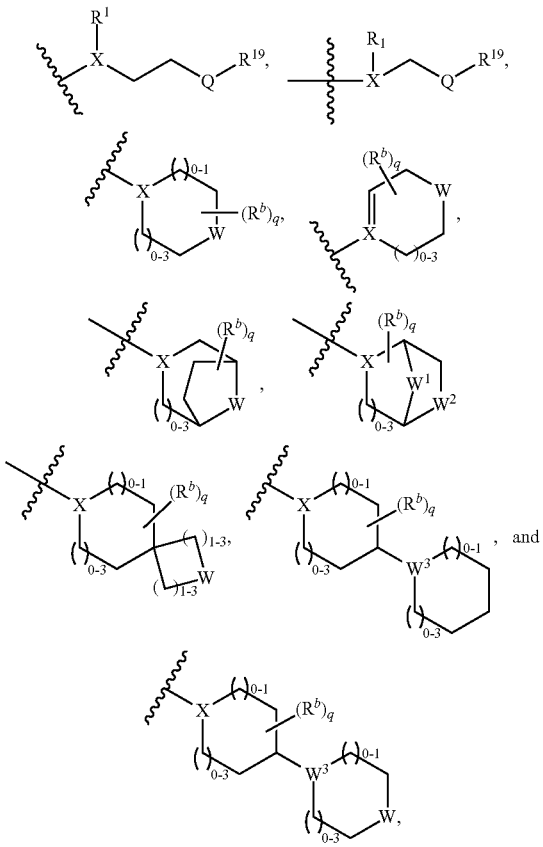

wherein
Q is selected from $CH_2$, O, S, and $N(R^{19})$;
W, $W^1$ and $W^2$ are each independently selected from $CH_2$, $CHR^b$, $CR^bR^b$, O, S, and $N(R^{22})$;
$W^3$ is selected from CH, $CR^b$, and N;
$R^{22}$ is independently selected from hydrogen and $C_{1-3}$aliphatic;

q is 0, 1, 2, 3, 4, 5, 6, 7, 8, 9, or 10 and
X, $R^1$, $R^{19}$, and $R^b$ are as defined herein for formula I.

Embodiment [8]

The compound of any one of any one of embodiments [1]-[6], wherein $XR^1R^2R^3$ is selected from:

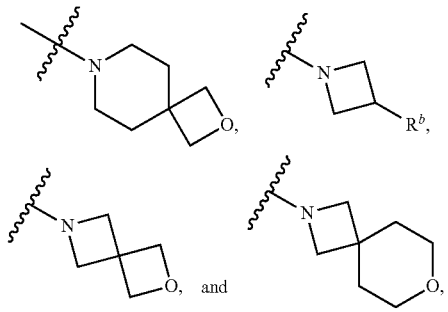

wherein $R^b$ is as defined herein for formula I.

Embodiment [9]

The compound of any one of any one of embodiments [1]-[6], wherein $XR^1R^2R^3$ is selected from:

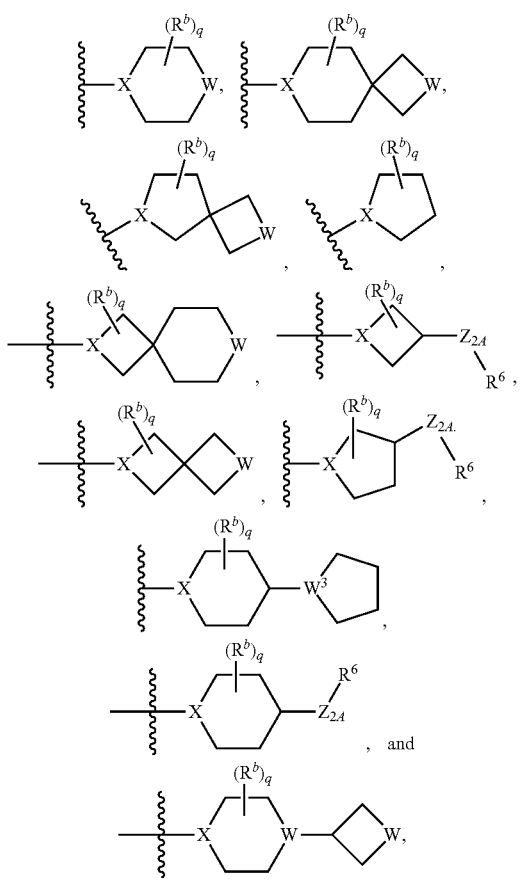

wherein
q is 0, 1, 2, 3, 4, 5, 6, 7, or 8;
$Z_{2A}$ is selected from $CH_2$, $CHR^i$, $CR^iR^i$, O, S, and $N(R^{17})$;
$R^i$ is selected from CN, $CF_3$, $CH_2F$, $CF_2H$, halogen, OH, $O(C_{1-3}$ aliphatic) and $C_{1-3}$ aliphatic;
W is selected from $CH_2$, $CHR^b$, $CR^bR^b$, O, S, and $N(R^{22})$;
$W^3$ is selected from CH, $CR^b$, and N;
$R^{22}$ is independently selected from hydrogen and $C_{1-3}$aliphatic;
and X, $R^6$, and $R^b$ are as defined herein for formula I.

Embodiment [10]

The compound of formula IX:

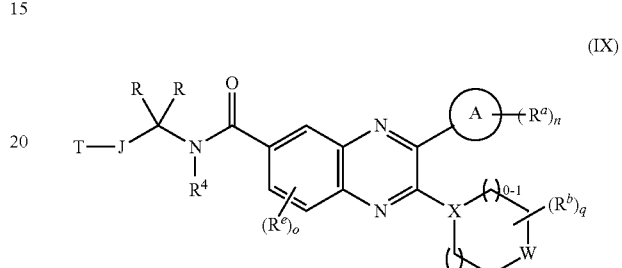

or a pharmaceutically acceptable salt thereof, wherein T, J, X, R, $R^4$, $R^a$, $R^e$, $R^b$, o, n, and

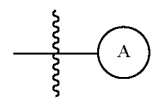

are as defined herein for formula I and W is selected from $CH_2$, $CHR^b$, $CR^bR^b$, O, S, and $N(R^{22})$;
q is 0, 1, 2, 3, 4, 5, 6, 7, 8, 9, or 10; and
$R^{22}$ is independently selected from hydrogen and $C_{1-3}$aliphatic;

Embodiment [11]

A compound of formula X, XI, XII, or XIII:

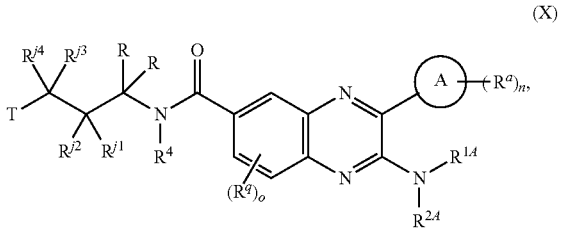

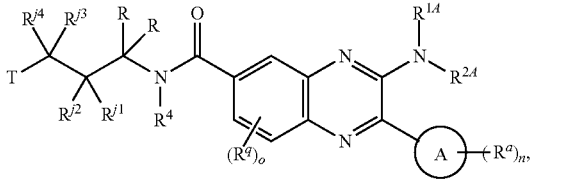

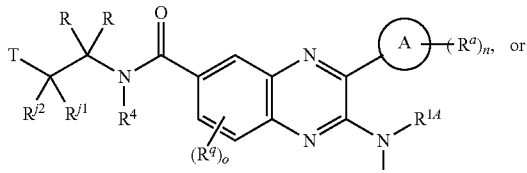

(XII)

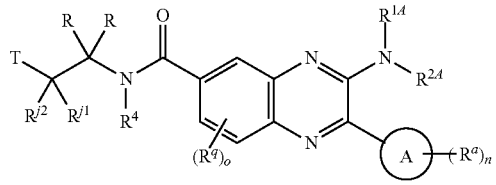

(XIII)

or a pharmaceutically acceptable salt thereof, wherein T, R, $R^a$, $R^q$, $R^4$, n, o, and

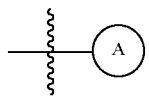

are as defined herein for formula I and wherein
$R^{1A}$ and $R^{2A}$ are each independently selected from hydrogen; $N(R^{20})_2$; $C_{1-6}$aliphatic, wherein 1 or 2 methylene units of said $C_{1-6}$ aliphatic are optionally and independently replaced by O, S, or $N(R^{19})$; $(CH_2)_s$-6-10-membered aryl; $(CH_2)^t$-3-10-membered cycloaliphatic; $(CH_2)^u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein said $C_{1-6}$ aliphatic, aryl, cycloaliphatic, heterocycle, and heteroaryl is optionally substituted with one or more $R^k$;
or wherein $R^{1A}$ and $R^{2A}$ taken together with the nitrogen atom to which they are bound, form a 4-10-membered heterocycle having 1-5 heteroatoms independently selected from nitrogen, oxygen and sulfur and a 3-10-membered cycloaliphatic, wherein the heterocycle is optionally substituted with one or more $R^b$,
or wherein $R^{1A}$ and $R^{2A}$ taken together with the nitrogen atom to which they are bound, form a 5-10-membered heteroaryl having 1-5 heteroatoms independently selected from nitrogen, oxygen, and sulfur, wherein the heteroaryl is optionally substituted with one or more $R^b$,
each occurrence of $R^b$ is independently selected from $C_{1-6}$ aliphatic and $Z_2$—$R^6$;
or wherein two $R^b$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein said ring is optionally substituted with one or more $R^c$;
each occurrence of $R^c$ is independently selected from $C_{1-6}$ aliphatic, $CF_3$, $CF_2H$, $CH_2F$, halogen, $OR^{12}$, $(CH_2)_v$—$C(O)R^9$, and $(CH_2)_w$—$NR^{10}C(O)R^{11}$;
each occurrence of $Z_2$ is independently selected from direct bond, $C_{1-3}$ alkylene chain, O, $N(R^{17})$, S, S(O), $S(O)_2$, C(O), $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2 N(R^{17})$, and OC(O), wherein said alkylene chain is optionally substituted with one or more $R^i$;
each occurrence of $R^i$ is independently selected from CN, $CF_3$, $CH_2F$, $CF_2H$, halogen, OH, $O(C_{1-3}$ aliphatic) and $C_{1-3}$ aliphatic;
each occurrence of $R^6$ is independently selected from CN, halogen, $OR^7$, $N(R^{19})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein said is aryl, heteroaryl, heterocycle, and cycloaliphatic is optionally substituted with one or more $R^c$;
each occurrence of $R^7$ is independently selected from hydrogen, $CF_3$, $CHCF_2$, $CH_2F$, $C_{1-6}$aliphatic, and 6-10-membered aryl;
each occurrence of $R^k$ is independently selected from $C_{1-6}$ aliphatic and $Z_3$—$R^{23}$;
or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein said ring is optionally substituted with one or more $R^m$;
each occurrence of $R^m$ is independently selected from $C_{1-6}$ aliphatic, $CF_3$, halogen, $OR^{25}$, $(CH_2)_q$—$C(O)R^{26}$, and $(CH_2)_r$—$NR^{27}C(O)R^{28}$;
each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2 N(R^{24})$, and OC(O), wherein said alkylene chain is optionally substituted with one or more $R^n$;
each occurrence of $R^n$ is independently selected from CN, $CF_3$, $CF_2H$, $CFH_2$, halogen, OH, $O(C_{1-3}$ aliphatic), and $C_{1-3}$ aliphatic;
each occurrence of $R^9$ is independently selected from OH, $OC_{1-6}$ aliphatic, $N(R^{15})_2$, and $C_{1-6}$ aliphatic;
each occurrence of $R^{10}$ is independently selected from hydrogen and $C_{1-6}$aliphatic;
each occurrence of $R^{11}$ is independently selected from OH, $OC_{1-6}$aliphatic, $N(R^{14})_2$, and $C_{1-6}$aliphatic;
each occurrence of $R^{12}$ is independently selected from hydrogen and $C_{1-6}$aliphatic;
each occurrence of $R^{14}$ is independently selected from hydrogen and $C_{1-6}$aliphatic;
each occurrence of $R^{15}$ is independently selected from hydrogen and $C_{1-6}$aliphatic;
each occurrence of $R^{17}$ is independently selected from hydrogen and $C_{1-6}$aliphatic;
each occurrence of $R^{19}$ is independently selected from hydrogen and $C_{1-3}$ aliphatic;
each occurrence of $R^{20}$ is independently selected from hydrogen and $C_{1-6}$ aliphatic;
each occurrence of $R^{23}$ is independently selected from CN, halogen, $OR^{31}$, $N(R^{32})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10- membered cycloaliphatic, wherein said is aryl, heteroaryl, heterocycle, and cycloaliphatic is optionally substituted with one or more $R^m$;
each occurrence of $R^{24}$ is independently selected from hydrogen and $C_{1-6}$aliphatic;
each occurrence of $R^{25}$ is independently selected from hydrogen and $C_{1-6}$aliphatic;
each occurrence of $R^{26}$ is independently selected from OH, $OC_{1-6}$ aliphatic, $N(R^{29})_2$, and $C_{1-6}$ aliphatic;
each occurrence of $R^{27}$ is independently selected from hydrogen and $C_{1-6}$aliphatic;
each occurrence of $R^{28}$ is independently selected from OH, $OC_{1-6}$aliphatic, $N(R^{30})_2$, and $C_{1-6}$aliphatic;
each occurrence of $R^{29}$ is independently selected from hydrogen and $C_{1-6}$aliphatic;
each occurrence of $R^{30}$ is independently selected from hydrogen and $C_{1-6}$aliphatic;
each occurrence of $R^{31}$ is independently selected from hydrogen, $CF_3$, $CHCF_2$, $CH_2F$, $C_{1-6}$aliphatic, and 6-10-membered aryl;
each occurrence of $R^{32}$ is independently selected from hydrogen and $C_{1-3}$ aliphatic;
p is 0, 1, 2, or 3; q is 0, 1, 2, or 3; r is 0, 1, 2, or 3; s is 0, 1, 2, or 3; t is 0, 1, 2, or 3; u is 0, 1, 2, or 3; v is 0, 1, 2, or 3; w is 0, 1, 2, or 3; and
$R^{j1}$, $R^{j2}$, $R^{j3}$, and $R^{j4}$ are each independently selected from hydrogen, fluorine, OH, $O(C_{1-3}$aliphatic), $NH_2$, $NH(C_{1-3}$ aliphatic), $N(C_{1-3}$aliphatic)$_2$, and $C_{1-3}$ aliphatic;
or wherein any two of $R^{j1}$, $R^{j2}$, $R^{j3}$, and $R^{j4}$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$ and
or wherein any one of $R^{j1}$, $R^{j2}$, $R^{j3}$, and $R^{j4}$ and one of R taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$;
or wherein any one of $R^{j1}$, $R^{j2}$, $R^{j3}$, and $R^{j4}$ and one of $R^4$ taken together with the atom or atoms to which they are bound form a 4-10-membered heterocycle having 1-5 heteroatoms independently selected from nitrogen, oxygen, and sulfur, wherein said heterocycle is optionally substituted with one or more $R^e$;
each occurrence of $R^e$ is independently selected from halogen, $CF_3$, $CF_2H$, $CH_2F$, $C_{1-6}$aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^h$;
or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^h$;
each occurrence of $R^h$ is independently selected from halogen, $CF_3$, $CF_2H$, $CH_2F$, $C_{1-6}$ aliphatic, $C(O)N(R^{18})_2$, OH, and $OC_{1-6}$aliphatic;
each occurrence of $R^{18}$ is independently selected from hydrogen and $C_{1-6}$ aliphatic;
and x is 0, 1, 2, or 3.

Embodiment [12]

A compound of formula X, XI, XII, or XIII or a pharmaceutically acceptable salt thereof, wherein T, R, $R^a$, $R^q$, $R^4$, n, o, and

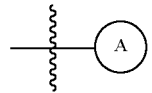

are as defined herein for formula I and wherein
$R^{1A}$ and $R^{2A}$ are each independently selected from hydrogen; $N(R^{20})_2$; $C_{1-6}$aliphatic, wherein 1 or 2 methylene units of said $C_{1-6}$ aliphatic are optionally and independently replaced by O, S, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein said $C_{1-6}$ aliphatic, aryl, cycloaliphatic, heterocycle, and heteroaryl is optionally substituted with one or more $R^k$;
or wherein $R^{1A}$ and $R^{2A}$ taken together with the nitrogen atom to which they are bound, form a 4-10-membered heterocycle having 1-5 heteroatoms independently selected from nitrogen, oxygen and sulfur and a 3-10-membered cycloaliphatic, wherein the heterocycle is optionally substituted with one or more $R^b$,
each occurrence of $R^b$ is independently selected from $C_{1-6}$ aliphatic and $Z_2$—$R^6$;
or wherein two $R^b$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein said ring is optionally substituted with one or more $R^c$;
each occurrence of $R^c$ is independently selected from $C_{1-6}$ aliphatic, $CF_3$, $CF_2H$, $CH_2F$, halogen, $OR^{12}$, $(CH_2)_v$—$C(O)R^9$, and $(CH_2)_w$—$NR^{10}C(O)R^{11}$;
each occurrence of $Z_2$ is independently selected from direct bond, $C_{1-3}$ alkylene chain, O, $N(R^{17})$, S, S(O), $S(O)_2$, C(O), $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2 N(R^{17})$, and OC(O), wherein said alkylene chain is optionally substituted with one or more $R^i$;
each occurrence of $R^i$ is independently selected from CN, $CF_3$, $CH_2F$, $CF_2H$, halogen, OH, $O(C_{1-3}$ aliphatic) and $C_{1-3}$ aliphatic;
each occurrence of $R^6$ is independently selected from CN, halogen, $OR^7$, $N(R^{19})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein said is aryl, heteroaryl, heterocycle, and cycloaliphatic is optionally substituted with one or more $R^c$;
each occurrence of $R^7$ is independently selected from hydrogen, $CF_3$, $CHCF_2$, $CH_2F$, $C_{1-6}$aliphatic, and 6-10-membered aryl;
each occurrence of $R^k$ is independently selected from $C_{1-6}$ aliphatic and $Z_3$—$R^{23}$;
or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10- membered saturated, partially unsaturated, or aromatic bicyclic ring having 0-5 heteroatoms independently selected from nitrogen, oxygen, and sulfur, wherein said ring is optionally substituted with one or more $R^m$;

each occurrence of $R^m$ is independently selected from $C_{1-6}$ aliphatic, $CF_3$, halogen, $OR^{25}$, $(CH_2)_q$—$C(O)R^{26}$, and $(CH_2)_r$—$NR^{27}C(O)R^{28}$;

each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)^2$, $OC(O)N(R^{24})$, $N(R^{24})C(O)NR^{24}$, $N(R^{24})S(O)_2$ $N(R^{24})$, and OC(O), wherein said alkylene chain is optionally substituted with one or more $R^n$;

each occurrence of $R^n$ is independently selected from CN, $CF_3$, $CF_2H$, $CFH_2$, halogen, OH, $O(C_{1-3}$ aliphatic), and $C_{1-3}$ aliphatic;

each occurrence of $R^9$ is independently selected from OH, $OC_{1-6}$ aliphatic, $N(R^{15})_2$, and $C_{1-6}$ aliphatic;

each occurrence of $R^{10}$ is independently selected from hydrogen and $C_{1-6}$aliphatic;

each occurrence of $R^{11}$ is independently selected from OH, $OC_{1-6}$aliphatic, $N(R^{14})_2$, and $C_{1-6}$aliphatic;

each occurrence of $R^{12}$ is independently selected from hydrogen and $C_{1-6}$aliphatic;

each occurrence of $R^{14}$ is independently selected from hydrogen and $C_{1-6}$aliphatic;

each occurrence of $R^{15}$ is independently selected from hydrogen and $C_{1-6}$aliphatic;

each occurrence of $R^{17}$ is independently selected from hydrogen and $C_{1-6}$aliphatic;

each occurrence of $R^{19}$ is independently selected from hydrogen and $C_{1-3}$ aliphatic;

each occurrence of $R^{20}$ is independently selected from hydrogen and $C_{1-6}$ aliphatic;

each occurrence of $R^{23}$ is independently selected from CN, halogen, $OR^{31}$, $N(R^{32})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein said is aryl, heteroaryl, heterocycle, and cycloaliphatic is optionally substituted with one or more $R^m$;

each occurrence of $R^{24}$ is independently selected from hydrogen and $C_{1-6}$aliphatic;

each occurrence of $R^{25}$ is independently selected from hydrogen and $C_{1-6}$aliphatic;

each occurrence of $R^{26}$ is independently selected from OH, $OC_{1-6}$ aliphatic, $N(R^{29})_2$, and $C_{1-6}$ aliphatic;

each occurrence of $R^{27}$ is independently selected from hydrogen and $C_{1-6}$aliphatic;

each occurrence of $R^{28}$ is independently selected from OH, $OC_{1-6}$aliphatic, $N(R^{30})_2$, and $C_{1-6}$aliphatic;

each occurrence of $R^{29}$ is independently selected from hydrogen and $C_{1-6}$aliphatic;

each occurrence of $R^{30}$ is independently selected from hydrogen and $C_{1-6}$aliphatic;

each occurrence of $R^{31}$ is independently selected from hydrogen, $CF_3$, $CHCF_2$, $CH_2F$, $C_{1-6}$aliphatic, and 6-10-membered aryl;

each occurrence of $R^{32}$ is independently selected from hydrogen and $C_{1-3}$ aliphatic;

p is 0, 1, 2, or 3; q is 0, 1, 2, or 3; r is 0, 1, 2, or 3; s is 0, 1, 2, or 3; t is 0, 1, 2, or 3; u is 0, 1, 2, or 3; v iso, 1, 2, or 3; w is 0, 1, 2, or 3; and $R^{j1}$, $R^{j2}$, $R^{j3}$, and $R^{j4}$ are each independently selected from hydrogen, fluorine, OH, $O(C_{1-3}$aliphatic), $NH_2$, $NH(C_{t-3}$aliphatic), $N(C_{1-3}$aliphatic$)_2$, and $C_{1-3}$ aliphatic;

or wherein any two of $R^{j1}$, $R^{j2}$, $R^{j3}$, and $R^{j4}$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$ and or wherein any one of $R^{j1}$, $R^{j2}$, $R^{j3}$, and $R^{j4}$ and one of R taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$;

or wherein any one of $R^{j1}$, $R^{j2}$, $R^{j3}$, and $R^{j4}$ and one of $R^4$ taken together with the atom or atoms to which they are bound form a 4-10-membered heterocycle having 1-5 heteroatoms independently selected from nitrogen, oxygen, and sulfur, wherein said heterocycle is optionally substituted with one or more $R^e$;

each occurrence of $R^e$ is independently selected from halogen, $CF_3$, $CF_2H$, $CH_2F$, $C_{1-6}$aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^h$;

or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^h$;

each occurrence of $R^h$ is independently selected from halogen, $CF_3$, $CF_2H$, $CH_2F$, $C_{1-6}$ aliphatic, $C(O)N(R^{18})_2$, OH, and $OC_{1-6}$ aliphatic;

each occurrence of $R^{18}$ is independently selected from hydrogen and $C_{1-6}$ aliphatic;

and x is 0, 1, 2, or 3.

Embodiment [13]

A compound of formula XIV, XV, XVI, or XVII:

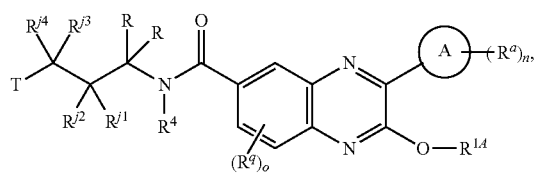

(XIV)

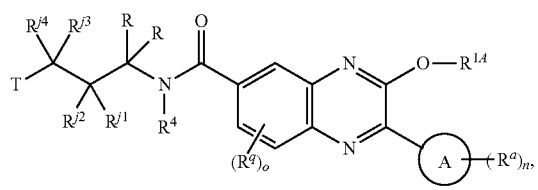

(XV)

-continued

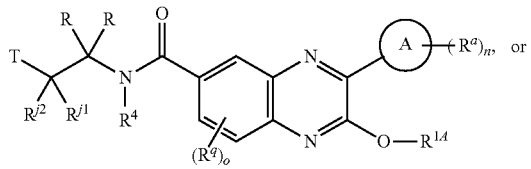

(XVI)

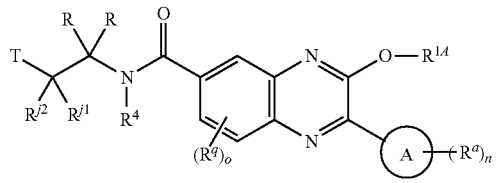

(XVII)

or a pharmaceutically acceptable salt thereof, wherein T, R, $R^4$, $R^q$, o, $R^a$, n and

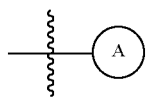

are as defined herein for formula I and wherein
$R^{1A}$ is selected from hydrogen; $C_{1-6}$aliphatic, wherein 1 or 2 methylene units of said $C_{1-6}$ aliphatic are optionally and independently replaced by O, S, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein said $C_{1-6}$ aliphatic, aryl, cycloaliphatic, heterocycle, and heteroaryl is optionally substituted with one or more $R^k$;
each occurrence of $R^k$ is independently selected from $C_{1-6}$ aliphatic and $Z_3$—$R^{23}$;
or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein said ring is optionally substituted with one or more $R^m$;
each occurrence of $R^m$ is independently selected from $C_{1-6}$ aliphatic, $CF_3$, halogen, $OR^{25}$, $(CH_2)_q$—$C(O)R^{26}$, and $(CH_2)_r$—$NR^{27}C(O)R^{28}$;
each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2 N(R^{24})$, and OC(O), wherein said alkylene chain is optionally substituted with one or more $R^n$;
each occurrence of $R^n$ is independently selected from CN, $CF_3$, $CF_2H$, $CFH_2$, halogen, OH, $O(C_{1-3}$ aliphatic), and $C_{1-3}$ aliphatic;
each occurrence of $R^{19}$ is independently selected from hydrogen and $C_{1-3}$ aliphatic;
each occurrence of $R^{23}$ is independently selected from CN, halogen, $OR^{31}$, $N(R^{32})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein said is aryl, heteroaryl, heterocycle, and cycloaliphatic is optionally substituted with one or more $R^m$;
each occurrence of $R^{24}$ is independently selected from hydrogen and $C_{1-6}$aliphatic;
each occurrence of $R^{25}$ is independently selected from hydrogen and $C_{1-6}$aliphatic;
each occurrence of $R^{26}$ is independently selected from OH, $OC_{1-6}$ aliphatic, $N(R^{29})_2$, and $C_{1-6}$ aliphatic;
each occurrence of $R^{27}$ is independently selected from hydrogen and $C_{1-6}$aliphatic;
each occurrence of $R^{28}$ is independently selected from OH, $OC_{1-6}$aliphatic, $N(R^{30})_2$, and $C_{1-6}$aliphatic;
each occurrence of $R^{29}$ is independently selected from hydrogen and $C_{1-6}$aliphatic;
each occurrence of $R^{30}$ is independently selected from hydrogen and $C_{1-6}$aliphatic;
each occurrence of $R^{31}$ is independently selected from hydrogen, $CF_3$, $CHCF_2$, $CH_2F$, $C_{1-6}$aliphatic, and 6-10-membered aryl;
each occurrence of $R^{32}$ is independently selected from hydrogen and $C_{1-3}$ aliphatic;
p is 0, 1, 2, or 3; q is 0, 1, 2, or 3; r is 0, 1, 2, or 3; s is 0, 1, 2, or 3; t is 0, 1, 2, or 3; u is 0, 1, 2, or 3; w is 0, 1, 2, or 3; and
$R^{j1}$, $R^{j2}$, $R^{j3}$, and $R^{j4}$ are each independently selected from hydrogen, fluorine, OH, $O(C_{1-3}$aliphatic), $NH_2$, $NH(C_{1-3}$aliphatic), $N(C_{1-3}$aliphatic$)_2$, and $C_{1-3}$ aliphatic;
or wherein any two of $R^{j1}$, $R^{j2}$, $R^{j3}$, and $R^{j4}$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$;
or wherein any one of $R^{j1}$, $R^{j2}$, $R^{j3}$, and $R^{j4}$ and one of R taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$;
or wherein any one of $R^{j1}$, $R^{j2}$, $R^{j3}$, and $R^{j4}$ and one of $R^4$ taken together with the atoms to which they are bound, form a 4-10-membered heterocycle having 1-5 heteroatoms independently selected from nitrogen, oxygen, and sulfur, wherein said heterocycle is optionally substituted with one or more $R^e$; and
each occurrence of $R^e$ is independently selected from halogen, $CF_3$, $CF_2H$, $CH_2F$, $C_{1-6}$aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^h$;
or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^h$;
each occurrence of $R^h$ is independently selected from halogen, $CF_3$, $CF_2H$, $CH_2F$, $C_{1-6}$ aliphatic, $C(O)N(R^{18})_2$, OH, and $OC_{1-6}$ aliphatic;
each occurrence of $R^{18}$ is independently selected from hydrogen and $C_{1-6}$ aliphatic;
and x is 0, 1, 2, or 3.

Embodiment [14]

A compound of formula XVIII, XIX, XX, or XXI:

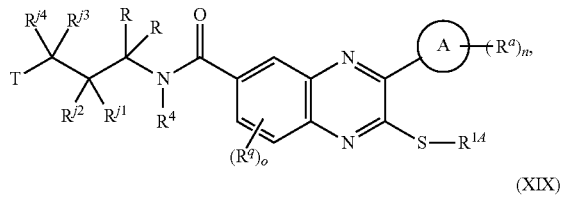
(XVIII)

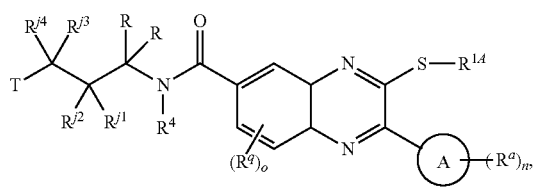
(XIX)

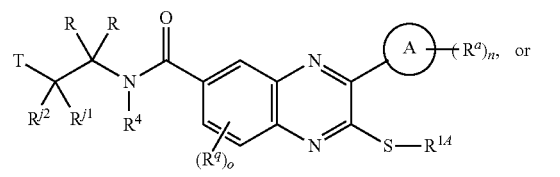
(XX)

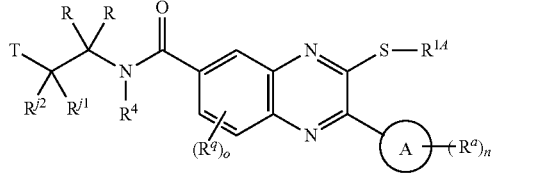
(XXI)

a pharmaceutically acceptable salt thereof, wherein T, R, $R^4$, $R^q$, o, $R^a$, n and

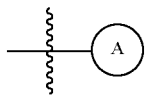

are as defined herein for formula I and wherein
$R^{14}$ is selected from hydrogen; $C_{1-6}$aliphatic, wherein 1 or 2 methylene units of said $C_{1-6}$ aliphatic are optionally and independently replaced by O, S, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein said $C_{1-6}$ aliphatic, aryl, cycloaliphatic, heterocycle, and heteroaryl is optionally substituted with one or more $R^k$;
each occurrence of $R^k$ is independently selected from $C_{1-6}$ aliphatic and $Z_3$—$R^{23}$;
or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein said ring is optionally substituted with one or more $R^m$;
each occurrence of $R^m$ is independently selected from $C_{1-6}$ aliphatic, $CF_3$, halogen, $OR^{25}$, $(CH_2)_q$—$C(O)R^{26}$, and $(CH_2)_r$—$NR^{27}C(O)R^{28}$;
each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)^2$, $OC(O)N(R^{24})$, $N(R^{24})C(O)NR^{24}$, $N(R^{24})S(O)_2 N(R^{24})$, and OC(O), wherein said alkylene chain is optionally substituted with one or more $R^n$;
each occurrence of $R^n$ is independently selected from CN, $CF_3$, $CF_2H$, $CFH_2$, halogen, OH, $O(C_{1-3}$ aliphatic), and $C_{1-3}$ aliphatic;
each occurrence of $R^{19}$ is independently selected from hydrogen and $C_{1-3}$ aliphatic;
each occurrence of $R^{23}$ is independently selected from CN, halogen, $OR^{31}$, $N(R^{32})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein said is aryl, heteroaryl, heterocycle, and cycloaliphatic is optionally substituted with one or more $R^m$;
each occurrence of $R^{24}$ is independently selected from hydrogen and $C_{1-6}$aliphatic;
each occurrence of $R^{25}$ is independently selected from hydrogen and $C_{1-6}$aliphatic;
each occurrence of $R^{26}$ is independently selected from OH, $OC_{1-6}$ aliphatic, $N(R^{29})_2$, and $C_{1-6}$ aliphatic;
each occurrence of $R^{27}$ is independently selected from hydrogen and $C_{1-6}$aliphatic;
each occurrence of $R^{28}$ is independently selected from OH, $OC_{1-6}$aliphatic, $N(R^{30})_2$, and $C_{1-6}$aliphatic;
each occurrence of $R^{29}$ is independently selected from hydrogen and $C_{1-6}$aliphatic;
each occurrence of $R^{30}$ is independently selected from hydrogen and $C_{1-6}$aliphatic;
each occurrence of $R^{31}$ is independently selected from hydrogen, $CF_3$, $CHCF_2$, $CH_2F$, $C_{1-6}$aliphatic, and 6-10-membered aryl;
each occurrence of $R^{32}$ is independently selected from hydrogen and $C_{1-3}$ aliphatic;
p is 0, 1, 2, or 3; q is 0, 1, 2, or 3; r is 0, 1, 2, or 3; s is 0, 1, 2, or 3; t is 0, 1, 2, or 3; u is 0, 1, 2, or 3;
$R^{j1}$, $R^{j2}$, $R^{j3}$, and $R^{j4}$ are each independently selected from hydrogen, fluorine, OH, $O(C_{1-3}$aliphatic), $NH_2$, $NH(C_{1-3}$aliphatic), $N(C_{1-3}$aliphatic$)_2$, and $C_{1-3}$ aliphatic;
or wherein any two of $R^{j1}$, $R^{j2}$, $R^{j3}$, and $R^{j4}$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$; and
or wherein any one of $R^{j1}$, $R^{j2}$, $R^{j3}$, and $R^{j4}$ and one of R taken together with the atom or atoms to which they are bound form a ring selected from a 3-6-membered heterocycle having 1 heteroatom selected from nitrogen, oxygen, and sulfur and a 3-6-membered cycloaliphatic ring, wherein said ring is optionally substituted with one or more $R^e$;
or wherein any one of $R^{j1}$, $R^{j2}$, $R^{j3}$, and $R^{j4}$ and $R^4$ taken together with the atom or atoms to which they are bound form a 4-10-membered heterocycle having 1-5 heteroatoms independently selected from nitrogen, oxygen, and sulfur, wherein said heterocycle is optionally substituted with one or more $R^e$ and each occurrence of $R^e$ is independently selected from halogen, $CF_3$, $CF_2H$, $CH_2F$, $C_{1-6}$aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^h$;

or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^h$;

each occurrence of $R^h$ is independently selected from halogen, $CF_3$, $CF_2H$, $CH_2F$, $C_{1-6}$aliphatic, $C(O)N(R^{18})_2$, OH, and $OC_{1-6}$aliphatic;

each occurrence of $R^{18}$ is independently selected from hydrogen and $C_{1-6}$ aliphatic;

and x is 0, 1, 2, or 3.

Embodiment [15]

The compound of any one of embodiments [1]-[6], wherein X is C and any two of $R^1$, $R^2$, and $R^3$ taken together with the carbon atom to which they are bound form a ring selected from 4-10-membered heterocycle having 1-5 heteroatoms independently selected from nitrogen, oxygen, and sulfur and a 3-10-membered cycloaliphatic, wherein said ring is optionally substituted with one or more $R^b$, wherein $R^b$ is as defined herein for formula I.

Embodiment [16]

The compound of any one of embodiments [1]-[6], wherein X is C and any two of $R^1$, $R^2$, and $R^3$ taken together with the carbon atom to which they are bound form a 6-membered cyclohexene ring optionally substituted with one or more $R^b$, wherein $R^b$ is as defined herein for formula I.

Embodiment [17]

The compound of any one of embodiments [1]-[16], wherein

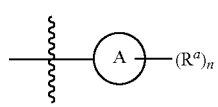

is selected from a 6 or 10-membered aryl and a 5-6 membered heteroaryl having 1-4 heteroatoms independently selected from nitrogen, oxygen, and sulfur, wherein said aryl and heteroaryl are optionally substituted with $R^a$, wherein $R^a$ is as defined herein for formula I and n=0, 1, 2, 3, 4, or 5.

Embodiment [18]

The compound of any one of embodiments [1]-[16], wherein

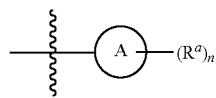

is selected from a 6-membered aryl and a 5-6 membered heteroaryl having 1-4 heteroatoms independently selected from nitrogen, oxygen, and sulfur, wherein said aryl and heteroaryl are optionally substituted with $R^a$, wherein $R^a$ is as defined herein for formula I and n=0, 1, 2, 3, 4, or 5.

Embodiment [19]

The compound of any one of embodiments [1]-[16], wherein

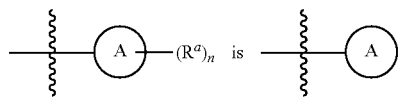

selected from phenyl, thiophene, pyrazole, furan, pyrrole, pyridine, pyrazine, thiazole, imidazole, imidazopyridine, indole, and benzoimidazole, wherein said

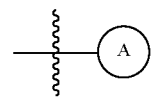

is optionally substituted with $R^a$, wherein $R^a$ is as defined herein for formula I and n=0, 1, 2, 3, 4, or 5.

Embodiment [20]

The compound of any one of embodiments [1]-[16], wherein

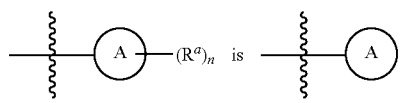

selected from phenyl, thiophene, pyrazole, furan, pyrrole, pyridine, pyrazine, thiazole, imidazole, imidazopyridine, indole, benzodioxole, dihydrobenzodioxine, benzothiophene, and benzoimidazole, wherein said

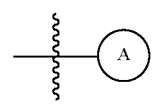

is optionally substituted with $R^a$, wherein $R^a$ is as defined herein for formula I and n=0, 1, 2, 3, 4, or 5.

Embodiment [21]

The compound of any one of embodiments [1]-[20], wherein n is 0.

Embodiment [22]

The compound of any one of embodiments [1]-[20], wherein n is 1 or 2.

Embodiment [23]

The compound of any one of embodiments [1]-[20], wherein n is 1.

Embodiment [24]

The compound of any one of embodiments [1]-[20], wherein n is 2.

Embodiment [25]

A compound of formula XXII, XXIII, XXIV, or XXV:

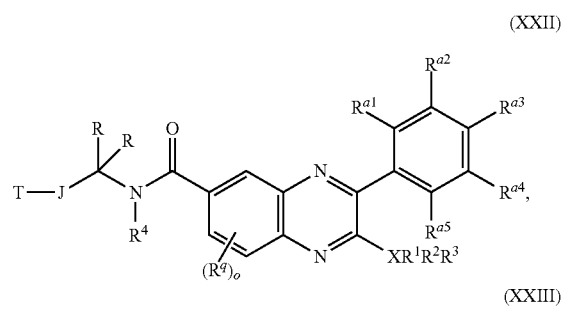

(XXII)

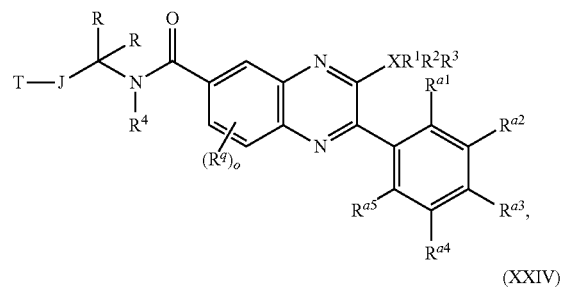

(XXIII)

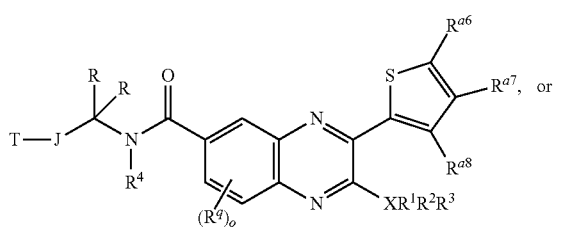

(XXIV)

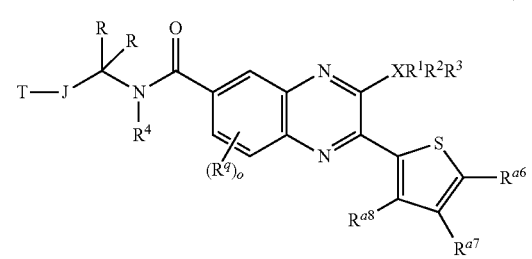

(XXV)

or a pharmaceutically acceptable salt thereof, wherein T, J, R, X, $R^1$, $R^2$, $R^3$, $R^4$, $R^q$, and o are as defined herein for formula I and wherein $R^{a1}$, $R^{a2}$, $R^{a3}$, $R^{a4}$, $R^{a5}$, $R^{a6}$, $R^{a7}$, and $R^{a8}$ are each independently selected from hydrogen, $C_{1-6}$ aliphatic and $Z_1$—$R^8$;

or wherein two adjacent $R^{a1}$, $R^{a2}$, $R^{a3}$, $R^{a4}$, and $R^{a5}$ or two adjacent $R^{a6}$, $R^{a7}$, and $R^{a8}$ taken together with the atoms to which they are bound, form a ring selected from a 4-10-membered heterocycle having 1-5 heteroatoms independently selected from nitrogen, oxygen, and sulfur and a 3-6-membered cycloaliphatic, wherein said ring is optionally substituted with one or more $R^p$;

each occurrence of $R^p$ is independently selected from CN, $CF_3$, $CH_2F$, $CF_2H$, $NH_2$, $NH(C_{1-3}aliphatic)$, $N(C_{1-3}$ aliphatic), OH, halogen, $O(C_{1-3}aliphatic)$ and $C_{1-3}$ aliphatic;

each occurrence of $Z_1$ is independently selected from a direct bond, $C_{1-3}$ alkylene chain, O, $N(R^{16})$, S, S(O), $S(O)_2$, C(O), $CO_2$, $C(O)NR^{16}$, $N(R^{16})C(O)$, $N(R^{16})CO_2$, $S(O)_2NR^{16}$, $N(R^{16})S(O)^2$, $OC(O)N(R^{16})$, $N(R^{16})C(O)NR^{16}$, $N(R^{16})S(O)_2N(R^{16})$, and OC(O), wherein said alkylene chain is optionally substituted with one or more $R^h$;

each occurrence of $R^{16}$ is independently selected from hydrogen and $C_{1-6}$aliphatic;

each occurrence of $R^h$ is independently selected from CN, $CF_3$, $CH_2F$, $CF_2H$, OH, halogen, $O(C_{1-3}$ aliphatic) and $C_{1-3}$ aliphatic;

each occurrence of $R^8$ is independently selected from CN, halogen, $OR^5$, $N(R^{21})_2$, $C_{1-6}$aliphatic, 6-10-membered aryl, 3-10 membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein said aryl, cycloaliphatic, heteroaryl, and heterocycle is optionally substituted with one or more $R^g$;

each occurrence of $R^g$ is independently selected from CN, $CF_3$, $CF_2H$, $CH_2F$, halogen, OH, $O(C_{1-3}$ aliphatic) and $C_{1-3}$ aliphatic;

each occurrence of $R^5$ is independently selected from hydrogen, $CF_3$, $CF_2H$, $CH_2F$, and $C_{1-6}$aliphatic and each occurrence of $R^{21}$ is independently selected from hydrogen and $C_{1-6}$aliphatic.

Embodiment [26]

A compound of formula XXIIA, XXIIIA, XXIVA:

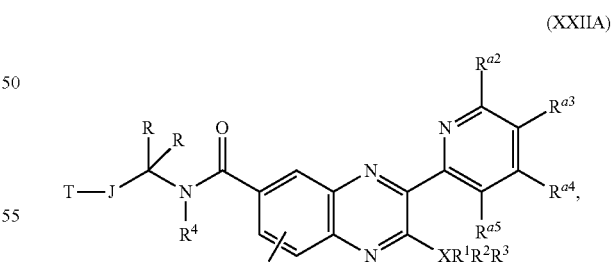

(XXIIA)

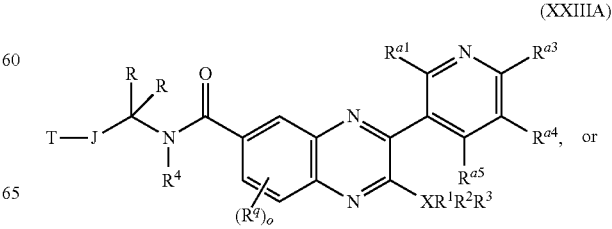

(XXIIIA)

(XXIVA)

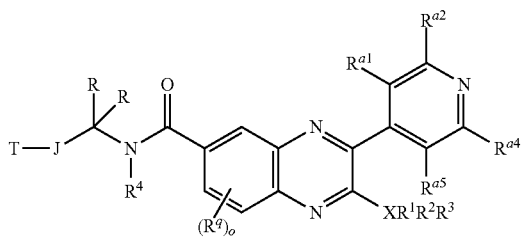

or a pharmaceutically acceptable salt thereof, wherein T, J, R, X, $R^1$, $R^2$, $R^3$, $R^4$, $R^q$, and o are as defined herein for formula I and wherein $R^{a1}$, $R^{a2}$, $R^{a3}$, $R^{a4}$, $R^{a5}$, $R^{a6}$, $R^{a7}$, and $R^{a8}$ are each independently selected from hydrogen, $C_{1-6}$ aliphatic and $Z_1$—$R^8$;
or wherein two adjacent $R^{a1}$, $R^{a2}$, $R^{a3}$, $R^{a4}$, and $R^{a5}$ or two adjacent $R^{a6}$, $R^{a7}$, and $R^{a8}$ taken together with the atoms to which they are bound, form a ring selected from a 4-10-membered heterocycle having 1-5 heteroatoms independently selected from nitrogen, oxygen, and sulfur and a 3-6-membered cycloaliphatic, wherein said ring is optionally substituted with one or more $R^p$;
each occurrence of $R^p$ is independently selected from CN, $CF_3$, $CH_2F$, $CF_2H$, $NH_2$, $NH(C_{1-3}$ aliphatic), $N(C_{1-3}$ aliphatic), OH, halogen, $O(C_{1-3}$ aliphatic) and $C_{1-3}$ aliphatic;
each occurrence of $Z_1$ is independently selected from a direct bond, $C_{1-3}$ alkylene chain, O, $N(R^{16})$, S, S(O), $S(O)_2$, C(O), $CO_2$, $C(O)NR^{16}$, $N(R^{16})C(O)$, $N(R^{16})CO_2$, $S(O)_2NR^{16}$, $N(R^{16})S(O)_2$, $OC(O)N(R^{16})$, $N(R^{16})C(O)NR^{16}$, $N(R^{16})S(O)_2N(R^{16})$, and OC(O), wherein said alkylene chain is optionally substituted with one or more $R^h$;
each occurrence of $R^{16}$ is independently selected from hydrogen and $C_{1-6}$aliphatic;
each occurrence of $R^h$ is independently selected from CN, $CF_3$, $CH_2F$, $CF_2H$, OH, halogen, $O(C_{1-3}$ aliphatic) and $C_{1-3}$ aliphatic;
each occurrence of $R^8$ is independently selected from CN, halogen, $OR^5$, $N(R^{21})_2$, $C_{1-6}$aliphatic, 6-10-membered aryl, 3-10 membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein said aryl, cycloaliphatic, heteroaryl, and heterocycle is optionally substituted with one or more $R^g$;
each occurrence of $R^g$ is independently selected from CN, $CF_3$, $CF_2H$, $CH_2F$, halogen, OH, $O(C_{1-3}$ aliphatic) and $C_{1-3}$ aliphatic;
each occurrence of $R^5$ is independently selected from hydrogen, $CF_3$, $CF_2H$, $CH_2F$, and $C_{1-6}$aliphatic and
each occurrence of $R^{21}$ is independently selected from hydrogen and $C_{1-6}$aliphatic.

Embodiment [27]

The compound of any one of embodiments [1]-[4], [7]-[10] or [15]-[26], wherein J is selected from direct bond, $C_1$ aliphatic, and $C_2$ aliphatic and J is not substituted with one or more $R^j$.

Embodiment [28]

The compound of any one of embodiments [1]-[4], [7]-[10] or [15]-[26], wherein J is a direct bond.

Embodiment [29]

The compound of any one of embodiments [1]-[4], [7]-[10] or [15]-[26], wherein J is $C_1$ aliphatic.

Embodiment [30]

The compound of any one of embodiments [1]-[4], [7]-[10] or [15]-[26], wherein J is $C_2$ aliphatic.

Embodiment [31]

The compound of any one of embodiments [1]-[4], [7]-[10] or [15]-[26], wherein J is a linear $C_{1-6}$ aliphatic, wherein 1-2 methylene units of J are optionally and independently replaced by O, S, or $N(R^{13})$.

Embodiment [32]

The compound of any one of embodiments [1]-[4], [7]-[10] or [15]-[26], wherein J is a linear $C_{1-6}$ aliphatic, wherein 1-2 methylene units of J are replaced by O.

Embodiment [33]

The compound of any one of embodiments [1]-[4], [7]-[10] or [15]-[26], wherein J is a linear $C_{1-6}$ aliphatic and two $R^j$ taken together with the atom or atoms to which they are bound form a ring selected from 3-4-membered cycloaliphatic ring.

Embodiment [34]

The compound of any one of embodiments [1]-[4], [7]-[10] or [15]-[26], wherein J is a linear $C_2$ aliphatic, wherein 1 methylene unit of J is replaced by O.

Embodiment [35]

The compound of any one of embodiments [1]-[6] or [17]-[34], wherein $XR^1R^2R^3$ is $NR^{1A}R^{2A}$ and $R^{1A}$ and $R^{2A}$ are as defined herein for formula X, XI, XII, or XIII.

Embodiment [36]

The compound of any one of embodiments [1]-[6] or [17]-[34], wherein $XR^1R^2R^3$ is $NR^{1A}R^{2A}$ and $R^{1A}$ and $R^{2A}$ are each independently selected from $C_{1-6}$ aliphatic.

Embodiment [37]

The compound of any one of embodiments [1]-[6] or [17]-[36], wherein $R^{1A}$ and $R^{2A}$ are each methyl.

Embodiment [38]

The compound of any one of embodiments [1]-[6] or [17]-[34], wherein $XR^1R^2R_3$ is $OR^{1A}$ and $R^{1A}$ is as defined herein for formula XIV, XV, XVI, or XVII.

Embodiment [39]

The compound of any one of embodiments [1]-[6] or [17]-[34], wherein $XR^1R^2R^3$ is $SR^{1A}$ and $R^{1A}$ is as defined herein for formula XVIII, XIX, XX, or XXI.

Embodiment [40]

The compound of any one of embodiments [1]-[6] or [17]-[39], wherein $R^{1A}$ is selected from $C_{1-6}$ aliphatic, $(CH_2)$ $_s$-6-10-membered aryl, $(CH_2)_t$-3-10-membered cycloaliphatic, $(CH_2)^u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the aliphatic, aryl, cycloaliphatic, heterocycle, and heteroaryl are optionally substituted with one or more $R^k$.

Embodiment [41]

The compound of any one of embodiments [1]-[6] or [17]-[40], wherein $R^{1A}$ is selected from $C_{1-6}$ aliphatic, 6-10-membered aryl, and 3-10-membered cycloaliphatic.

Embodiment [42]

The compound of any one of embodiments [1]-[6] or [17]-[40], wherein $R^{1A}$ is selected from $C_{1-4}$ aliphatic (e.g., methyl, ethyl, propyl, isopropyl, isobutyl), $(CH_2)_s$-6-membered aryl (e.g., phenyl $CH_2$phenyl, $(CH_2CH_2)$phenyl), $(CH_2)_t$-3-6-membered cycloaliphatic (e.g., cyclobutyl, cyclopentyl, cyclohexyl, $(CH_2)$cyclohexyl, $(CH_2)$cyclobutyl, $(CH_2)$cyclopentyl, $(CH_2)$cyclopropyl), $(CH_2)_u$-4-6-membered heterocycle having 1-5 heteroatoms independently selected from nitrogen, oxygen, and sulfur (e.g., oxetanyl, tetrahydrofuranyl, piperidinyl, $(CH_2)$oxetanyl, $(CH_2)$tetrahydropyranyl, $(CH_2)$piperidinyl, $(CH_2)$pyrrolidinyl), and $(CH_2)_p$-5-6-membered heteroaryl having 1-2 heteroatoms independently selected from nitrogen, oxygen, and sulfur (e.g., $(CH_2)$pyrazolyl, $(CH_2)$thienyl, $(CH_2)$thiazolyl, $(CH_2)$furanyl, $(CH_2)$imidazoyl, $(CH_2)$isoxazoyl, $(CH_2)$pyridinyl, $(CH_2CH_2)$pyrazolyl, $(CH_2CH_2)$pyridinyl, $(CH_2CH_2)$isoxazoyl, $(CH_2CH_2CH_2)$furanyl), wherein the aliphatic, aryl, cycloaliphatic, heterocycle, and heteroaryl is optionally substituted with one or more $R^k$; s is 0, 1, or 2; t is 0 or 1; u is 0 or 1; p is 1, 2, or 3.

Embodiment [43]

The compound of any one of embodiments [1]-[6] or [17]-[40], wherein $R^{1A}$ is selected from methyl, ethyl, propyl, isopropyl, phenyl, and cyclohexyl.

Embodiment [44]

The compound of any one of embodiments [1]-[6] or [17]-[40], wherein $R^{1A}$ is selected from methyl, ethyl, propyl, isopropyl, isobutyl, phenyl, cyclobutyl, cyclopentyl, cyclohexyl, oxetanyl, tetrahydrofuranyl, piperidinyl, $(CH_2)$cyclohexyl, $(CH_2)$cyclobutyl, $(CH_2)$cyclopentyl, $(CH_2)$cyclopropyl, $(CH_2)$phenyl, $(CH_2CH_2)$phenyl, $(CH_2)$oxetanyl, $(CH_2)$tetrahydropyranyl, $(CH_2)$piperidinyl, $(CH_2)$pyrrolidinyl, $(CH_2)$pyrazolyl, $(CH_2)$thienyl, $(CH_2)$thiazolyl, $(CH_2)$furanyl, $(CH_2)$imidazoyl, $(CH_2)$isoxazoyl, $(CH_2)$pyridinyl, $(CH_2CH_2)$pyrazolyl, $(CH_2CH_2)$pyridinyl, $(CH_2CH_2)$isoxazoyl, $(CH_2CH_2CH_2)$furanyl, wherein said $R^{1A}$ is optionally substituted with one or more $R^k$.

Embodiment [45]

The compound of any one of embodiments [25]-[44], wherein $R^{a1}$, $R^{a2}$, $R^{a3}$, $R^{a4}$, and $R^{a5}$ are hydrogen.

Embodiment [46]

The compound of any one of embodiments [25]-[44], wherein one of $R^{a1}$, $R^{a2}$, $R^{a3}$, $R^{a4}$, and $R^{a5}$ is not hydrogen.

Embodiment [47]

The compound of any one of embodiments [25]-[44] or [46], wherein $R^{a3}$ is not hydrogen.

Embodiment [48]

The compound of any one of embodiments [25]-[44] or [46], wherein $R^{a2}$ is not hydrogen.

Embodiment [49]

The compound of embodiment [47], wherein the remaining $R^{a1}$, $R^{a2}$, $R^{a4}$, and $R^{a5}$ are hydrogen.

Embodiment [50]

The compound of embodiment [48], wherein the remaining $R^{1a}$, $R^{3a}$, $R^{a4}$, and $R^{a5}$ are hydrogen.

Embodiment [51]

The compound of any one of embodiments [25]-[44], wherein one of $R^{a2}$ or $R^{a4}$ is not hydrogen.

Embodiment [52]

The compound of embodiment [51], wherein the remaining $R^{a1}$, $R^{a2}$, (or $R^{a4}$), $R^{a3}$, and $R^{a5}$ are hydrogen.

Embodiment [53]

The compound of any one of embodiments [25]-[44], wherein $R^{a2}$ and $R^{a4}$ are not hydrogen.

Embodiment [54]

The compound of any one of embodiments [25]-[44], wherein $R^{aa}$ and $R^{a2}$ are not hydrogen.

Embodiment [55]

The compound of any one of embodiments [25]-[44], wherein $R^{a1}$ and $R^{a3}$ are not hydrogen.

Embodiment [56]

The compound of any one of embodiments [25]-[44], wherein $R^{a2}$ and $R^{a3}$ are not hydrogen.

Embodiment [57]

The compound of any one of embodiments [25]-[44], wherein $R^{a1}$ and $R^{a4}$ are not hydrogen.

Embodiment [58]

The compound of any one of embodiments [25]-[44], wherein $R^{a1}$, $R^{a3}$, and $R^{a4}$ are not hydrogen.

Embodiment [59]

The compound of any one of embodiments [25]-[44], wherein $R^{a2}$, $R^{a3}$, and $R^{a4}$ are not hydrogen.

Embodiment [60]

The compound of any one of embodiments [53]-[59], wherein the remaining $R^{a1}$, $R^{a2}$, $R^{a3}$, $R^{a4}$, and $R^{a5}$ are hydrogen.

Embodiment [61]

The compound of any one of embodiments [26]-[44], wherein one of $R^{a2}$, $R^{a3}$, $R^{a4}$, and $R^{a5}$ is not hydrogen.

Embodiment [62]

The compound of any one of embodiments [26]-[44], wherein one of $R^{a1}$, $R^{a3}$, $R^{a4}$, and $R^{a5}$ is not hydrogen.

Embodiment [63]

The compound of any one of embodiments [26]-[44], wherein one of $R^{a1}$, $R^{a2}$, $R^{a4}$, and $R^{a5}$ is not hydrogen.

Embodiment [64]

The compound of any one of embodiments [26]-[44], wherein two of $R^{a2}$, $R^{a3}$, $R^{a4}$, and $R^{a5}$ are not hydrogen.

Embodiment [65]

The compound of any one of embodiments [26]-[44], wherein two of $R^{a1}$, $R^{a3}$, $R^{a4}$, and $R^{a5}$ are not hydrogen.

Embodiment [66]

The compound of any one of embodiments [26]-[44], wherein two of $R^{a1}$, $R^{a2}$, $R^{a4}$, and $R^{a5}$ are not hydrogen.

Embodiment [67]

The compound of any one of embodiments [25]-[44], wherein $R^{a1}$, $R^{a2}$, $R^{a3}$, $R^{a4}$, and $R^{a5}$ are each independently selected from hydrogen, halogen, $O(C_{1-3}$ aliphatic), $C_{1-3}$ aliphatic, ($C_{1-3}$ alkylene chain)-$N(R^{16})C(O)O(C_{1-6}$ aliphatic), ($C_{1-3}$ alkylene chain)-$N(R^{21})_2$, $OCF_3$, $N(R^{16})C(O)$ ($C_{1-6}$ aliphatic), $N(R^{16})S(O)_2(C_{1-6}$ aliphatic), CN, and $C(O)N(R^{21})_2$ or two adjacent $R^{a1}$, $R^{a2}$, $R^{a3}$, $R^{a4}$, and $R^{a5}$ taken together with the atoms to which they are bound, form a ring selected from a 5-10-membered heterocycle having 1-5 heteroatoms independently selected from nitrogen, oxygen, and sulfur and $R^{16}$ and $R^{21}$ are as defined herein for formula I.

Embodiment [68]

The compound of any one of embodiments [25]-[44], wherein $R^{a1}$, $R^{a2}$, $R^{a3}$, $R^{a4}$, and $R^{a5}$ are each independently selected from hydrogen, halogen, $O(C_{1-3}$ aliphatic), $C_{1-3}$ aliphatic, ($C_{1-3}$ alkylene chain)-$N(R^{16})C(O)O(C_{1-6}$aliphatic), ($C_{1-3}$ alkylene chain)-$N(R^{21})_2$, $OCF_3$, $N(R^{16})C(O)$ ($C_{1-6}$ aliphatic), $N(R^{16})S(O)_2(C_{1-6}$aliphatic), CN, $N(R^{21})_2$, $S(O)_2N(R^{21})_2$, $CF_3$, $SCF_3$, and $C(O)N(R^{21})_2$ or two adjacent $R^{a1}$, $R^{a2}$, $R^{a3}$, $R^{a4}$, and $R^{a5}$ taken together with the atoms to which they are bound, form a ring selected from a 4-10-membered heterocycle having 1-5 heteroatoms independently selected from nitrogen, oxygen, and sulfur and $R^{16}$ and $R^{21}$ are as defined herein for formula I.

Embodiment [69]

The compound of any one of embodiments [25]-[44], wherein $R^{a1}$, $R^{a2}$, $R^{a3}$, $R^{a4}$, and $R^{a5}$ are each independently selected from hydrogen, fluorine, chlorine, $OCH_3$, $OCF_3$, $CH_2NHC(O)O^tBu$, $CH_2NH_2$, $NHC(O)CH_3$, CN, and $C(O)NH_2$.

Embodiment [70]

The compound of any one of embodiments [25]-[44], wherein $R^{a1}$, $R^{a2}$, $R^{a3}$, $R^{a4}$, and $R^{a5}$ are each independently selected from hydrogen, fluorine, chlorine, $OCH_3$, $OCF_3$, $CH_2NHC(O)O^tBu$, $CH_2NH_2$, $NHC(O)CH_3$, CN, $NH_2$, $OCH_2CH_3$, $SCF_3$, $CH_3$, $CH_2CH_3$, and $C(O)NH_2$.

Embodiment [71]

The compound of any one of embodiments [26]-[44], wherein $R^{a2}$, $R^{a3}$, $R^{a4}$, and $R^{a5}$ are each independently selected from hydrogen, halogen, $O(C_{1-3}$aliphatic), $C_{1-3}$ aliphatic, ($C_{1-3}$ alkylene chain)-$N(R^{16})C(O)O(C_{1-6}$ aliphatic), ($C_{1-3}$ alkylene chain)-$N(R^{21})_2$, $OCF_3$, $N(R^{16})C(O)$ ($C_{1-6}$ aliphatic), $N(R^{16})S(O)_2(C_{1-6}$aliphatic), CN, $N(R^{21})_2$, $S(O)_2N(R^{21})_2$, $CF_3$, $S(C_{1-3}$aliphatic), $SCF_3$, and $C(O)N(R^{21})_2$ or two adjacent $R^{a1}$, $R^{a2}$, $R^{a3}$, $R^{a4}$, and $R^{a5}$ taken together with the atoms to which they are bound, form a ring selected from a 4-10-membered heterocycle having 1-5 heteroatoms independently selected from nitrogen, oxygen, and sulfur and $R^{16}$ and $R^{21}$ are as defined herein for formula I.

Embodiment [72]

The compound of any one of embodiments [26]-[44], wherein $R^{a2}$, $R^{a3}$, $R^{a4}$, and $R^{a5}$ are each independently selected from hydrogen, fluorine, chlorine, $OCH_3$, $OCF_3$, $CH_2NHC(O)O^tBu$, $CH_2NH_2$, $NHC(O)CH_3$, CN, $NH_2$, $OCH_2CH_3$, $SCF_3$, $CH_3$, $CH_2CH_3$, and $C(O)NH_2$.

Embodiment [73]

The compound of any one of embodiments [26]-[44], wherein $R^{a1}$, $R^{a3}$, $R^{a4}$, and $R^{a5}$ are each independently selected from hydrogen, halogen, $O(C_{1-3}$aliphatic), $C_{1-3}$ aliphatic, ($C_{1-3}$ alkylene chain)-$N(R^{16})C(O)O(C_{1-6}$aliphatic), ($C_{1-3}$ alkylene chain)-$N(R^{21})_2$, $OCF_3$, $N(R^{16})C(O)$ ($C_{1-6}$ aliphatic), $N(R^{16})S(O)_2(C_{1-6}$aliphatic), CN, $N(R^{21})_2$, $S(O)_2N(R^{21})_2$, $CF_3$, $S(C_{1-3}$aliphatic), $SCF_3$, and $C(O)N(R^{21})_2$ or two adjacent $R^{a1}$, $R^{a2}$, $R^{a3}$, $R^{a4}$, and $R^{a5}$ taken together with the atoms to which they are bound, form a ring selected from a 4-10-membered heterocycle having 1-5 heteroatoms independently selected from nitrogen, oxygen, and sulfur and $R^{16}$ and $R^{21}$ are as defined herein for formula I.

Embodiment [74]

The compound of any one of embodiments [26]-[44], wherein $R^{a1}$, $R^{a3}$, $R^{a4}$, and $R^{a5}$ are each independently selected from hydrogen, fluorine, chlorine, $OCH_3$, $OCF_3$, CH$_2$NHC(O)O$^t$Bu, CH$_2$NH$_2$, NHC(O)CH$_3$, CN, NH$_2$, OCH$_2$CH$_3$, SCF$_3$, CH$_3$, CH$_2$CH$_3$, and C(O)NH$_2$.

Embodiment [75]

The compound of any one of embodiments [26]-[44], wherein R$^{a1}$, R$^{a2}$, R$^{a4}$, and R$^{a5}$ are each independently selected from hydrogen, halogen, O(C$_{1-3}$ aliphatic), C$_{1-3}$ aliphatic, (C$_{1-3}$ alkylene chain)-N(R$^{16}$)C(O)O(C$_{1-6}$ aliphatic), (C$_{1-3}$ alkylene chain)-N(R$^{21}$)$_2$, OCF$_3$, N(R$^{16}$)C(O) (C$_{1-6}$ aliphatic), N(R$^{16}$)S(O)$_2$(C$_{1-6}$aliphatic), CN, N(R$^{21}$)$_2$, S(O)$_2$N(R$^{21}$)$_2$, CF$_3$, S(C$_{1-3}$aliphatic), SCF$_3$, and C(O)N(R$^{21}$)$_2$ or two adjacent R$^{a1}$, R$^{a2}$, R$^{a3}$, R$^{a4}$, and R$^{a5}$ taken together with the atoms to which they are bound, form a ring selected from a 4-10-membered heterocycle having 1-5 heteroatoms independently selected from nitrogen, oxygen, and sulfur and R$^{16}$ and R$^{21}$ are as defined herein for formula I.

Embodiment [76]

The compound of any one of embodiments [26]-[44], wherein R$^{a1}$, R$^{a2}$, R$^{a4}$, and R$^{a5}$ are each independently selected from hydrogen, fluorine, chlorine, OCH$_3$, OCF$_3$, CH$_2$NHC(O)OtBu, CH$_2$NH$_2$, NHC(O)CH$_3$, CN, NH$_2$, OCH$_2$CH$_3$, SCF$_3$, CH$_3$, CH$_2$CH$_3$, and C(O)NH$_2$.

Embodiment [77]

The compound of any one of embodiments [25] or [27]-[44], wherein R$^{a6}$, R$^{a7}$, and R$^{a8}$ are all hydrogen.

Embodiment [78]

The compound of any one of embodiments [25] or [27]-[44], wherein one of R$^{a6}$, R$^{a7}$, and R$^{a8}$ is not hydrogen.

Embodiment [79]

The compound of embodiment [78], wherein the remaining R$^{a6}$, R$^{a7}$, and R$^{a8}$ are hydrogen.

Embodiment [80]

The compound of any one of embodiments [25] or [27]-[44], wherein R$^{a6}$, R$^{a7}$, and R$^{a8}$ are each independently selected from hydrogen, halogen, O(C$_{1-3}$ aliphatic), C$_{1-3}$ aliphatic, (C$_{1-3}$ alkylene chain)-N(R$^{16}$)C(O)O(C$_{1-6}$ aliphatic), (C$_{1-3}$ alkylene chain)-N(R$^{21}$)$_2$, OCF$_3$, N(R$^{16}$)C(O) (C$_{1-6}$ aliphatic), N(R$^{16}$)S(O)$_2$(C$_{1-6}$aliphatic), CN, and C(O)N(R$^{21}$)$_2$ or two adjacent R$^{a6}$, R$^{a7}$, and R$^{a8}$ taken together with the atoms to which they are bound, form a ring selected from a 5-10-membered heterocycle having 1-5 heteroatoms independently selected from nitrogen, oxygen, and sulfur and R$^{16}$ and R$^{21}$ are as defined herein for formula I.

Embodiment [81]

The compound of any one of embodiments [25] or [27]-[44], wherein R$^{a6}$, R$^{a7}$, and R$^{a8}$ are each independently selected from hydrogen, fluorine, chlorine, OCH$_3$, OCF$_3$, CH$_2$NHC(O)OtBu, CH$_2$NH$_2$, NHC(O)CH$_3$, CN, and C(O)NH$_2$ or two adjacent R$^{a1}$, R$^{a2}$, R$^{a3}$, R$^{a4}$, and R$^{a5}$ taken together with the atoms to which they are bound, form a ring selected from a 5-membered heterocycle having 1 oxygen atom.

Embodiment [82]

The compound of any one of embodiments [1]-[81], wherein T is a 5-10-membered heteroaryl having 1-5 heteroatoms independently selected from nitrogen, oxygen, and sulfur, wherein said heteroaryl is optionally substituted with one or more Rd, wherein Rd is as defined herein for formula I.

Embodiment [83]

The compound of any one of embodiments [1]-[82], wherein T is a 5-9-membered heteroaryl having 1-2 heteroatoms independently selected from nitrogen and sulfur, wherein said heteroaryl is optionally substituted with one or more R$^d$, wherein R$^d$ is as defined herein for formula I.

Embodiment [84]

The compound of any one of embodiments [1]-[83], wherein T is a 5-6 membered heteroaryl having 1-2 heteroatoms independently selected from nitrogen and sulfur and said heteroaryl is optionally substituted with one or more R$^d$, wherein R$^d$ is as defined herein for formula I.

Embodiment [85]

The compound of any one of embodiments [1]-[84], wherein T is a 5-membered heteroaryl having 1-2 heteroatoms independently selected from nitrogen and sulfur and said heteroaryl is optionally substituted with one or more R$^d$, wherein R$^d$ is as defined herein for formula I.

Embodiment [86]

The compound of any one of embodiments [1]-[85], wherein T is a 5-membered heteroaryl having two nitrogen heteroatoms and said heteroaryl is optionally substituted with one or more R$^d$, wherein R$^d$ is as defined herein for formula I.

Embodiment [87]

The compound of any one of embodiments [1]-[84], wherein T is a 6-membered heteroaryl having one nitrogen heteroatom and said heteroaryl is optionally substituted with one or more R$^d$, wherein R$^d$ is as defined herein for formula I.

Embodiment [88]

The compound of any one of embodiments [1]-[81], wherein T is selected from

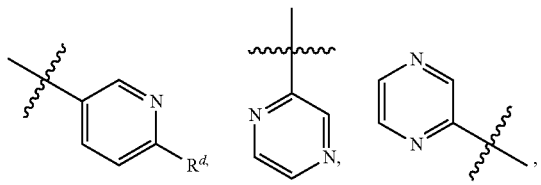

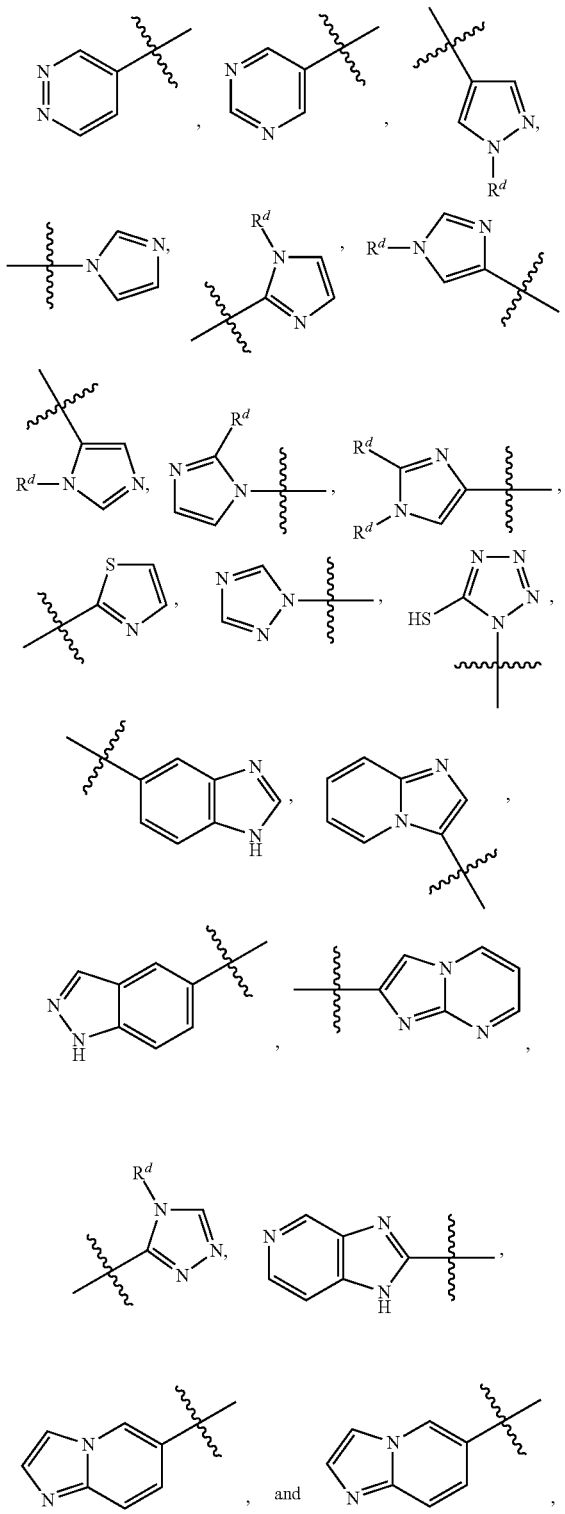
wherein $R^d$ is as defined herein for formula I.
Embodiment [89]
The compound of any one of embodiments [1]-[81], wherein T is selected from
wherein $R^d$ is as defined herein for formula I.

Embodiment [90]

The compound of any one of embodiments [1]-[89], wherein $R^d$ is hydrogen, $NH_2$, or $CH_3$.

Embodiment [91]

The compound of any one embodiments [1]-[89], wherein $R^d$ is hydrogen.

Embodiment [92]

The compound of any one of embodiments [1]-[89], wherein $R^d$ is $NH_2$.

Embodiment [93]

The compound of any one of embodiments [1]-[89], wherein $R^d$ is $CH_3$.

Embodiment [94]

The compound of any one of embodiments [1]-[5], [7]-[10], [15]-[26], or [35]-[93], wherein J is a direct bond.

Embodiment [95]

The compound of any one of embodiments [94], wherein T is a 8-10-membered bicyclic heteroaryl having 1-5 heteroatoms independently selected from nitrogen, oxygen, and sulfur, wherein said bicyclic heteroaryl is optionally substituted with one or more $R^d$ or a 5-6-membered monocyclic heteroaryl having 1-5 heteroatoms independently selected from nitrogen, oxygen, and sulfur, wherein said monocyclic heteroaryl is substituted with two $R^d$ taken together with the atom or atoms to which they are bound, form a 4-10-membered heterocycle having 1-5 heteroatoms independently selected from nitrogen, oxygen, and sulfur.

Embodiment [96]

The compound of embodiment [95], wherein T is a 8-10-membered bicyclic heteroaryl having 1-5 heteroatoms independently selected from nitrogen, oxygen, and sulfur, wherein said bicyclic heteroaryl is optionally substituted with one or more $R^d$, wherein $R^d$ is as defined herein for formula I.

Embodiment [97]

The compound of any one of embodiments [11]-[12], [17]-[34], or [45]-[96], wherein one of $R^{1A}$ and $R^{2A}$ is hydrogen.

Embodiment [98]

The compound of any one of embodiments [11]-[12], [17]-[34], or [45]-[96], wherein $R^{1A}$ is $C_{1-6}$ aliphatic, wherein said aliphatic is optionally substituted with one or more $R^k$.

Embodiment [99]

The compound of embodiment [98], wherein the $C_{1-6}$ aliphatic is selected from methyl, isopropyl, cyclopropyl, cyclobutyl, and cyclohexyl.

Embodiment [100]

The compound of any one of embodiments [11]-[12], [17]-[34], or [45]-[96], wherein $R^{1A}$ is selected from azaspiroheptane and tetrahydropyran.

Embodiment [101]

The compound of any one of embodiments [11]-[12], [17]-[34], or [45]-[96], wherein $R^{1A}$ and $R^{2A}$ taken together with the nitrogen atom to which they are bound, form a 4-7-membered heterocycle having 1-5 heteroatoms independently selected from nitrogen, oxygen and sulfur, wherein said heterocycle is optionally substituted with one or more $R^b$, wherein $R^b$ is as defined herein for formula I.

Embodiment [102]

The compound of any one of embodiments [11]-[12], [17]-[34], or [45]-[96], wherein $R^{1A}$ and $R^{2A}$ taken together with the nitrogen atom to which they are bound, form a heterocycle selected from piperidine, morpholine, azetidine, pyrrolidine, 3-azabicyclo[3.1.0]hexane, imidazolidinone, piperazine, piperazinone, azepane, oxa-azabicyclo[2.2.1]heptane, and thiomorpholinedioxide, wherein said heterocycle is optionally substituted with one or more $R^b$, wherein $R^b$ is as defined herein for formula I.

Embodiment [103]

The compound of any one of embodiments [11]-[12], [17]-[34], or [45]-[96], wherein $R^{1A}$ and $R^{2A}$ taken together with the nitrogen atom to which they are bound, form a heterocycle selected from

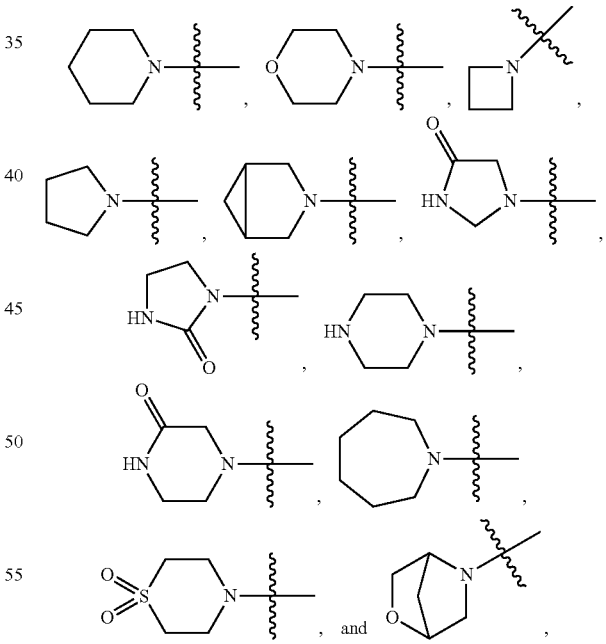

wherein said heterocycle is optionally substituted with one or more $R^b$, wherein $R^b$ is as described herein for formula I.

Embodiment [104]

The compound of any one of embodiments [11]-[12], [17]-[34], or [45]-[96], wherein $R^{1A}$ and $R^{2A}$ taken together with the nitrogen atom to which they are bound, form a heterocycle selected from

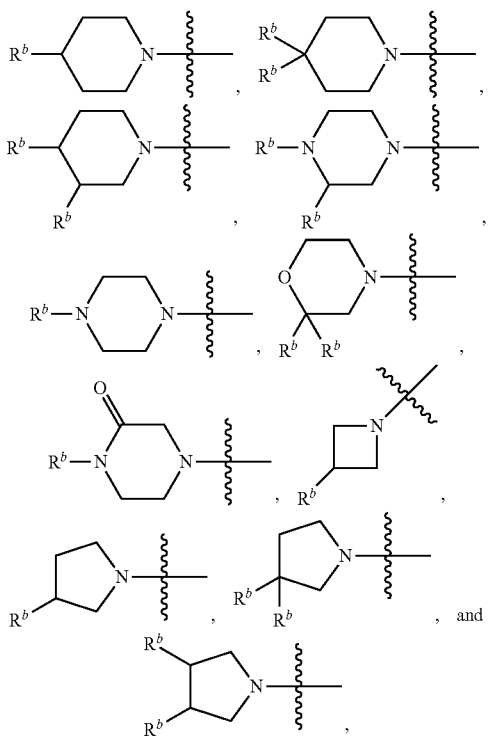

and $R^b$ is as defined herein for formula I.

Embodiment [105]

The compound of any one of embodiments [11]-[12], [17]-[34], or [45]-[96], wherein $R^{1A}$ and $R^{2A}$ taken together with the nitrogen atom to which they are bound, form a 6-membered heterocycle ring having 1-4 heteroatoms independently selected from nitrogen, oxygen and sulfur, wherein said heterocycle is optionally substituted with one or more $R^b$, wherein $R^b$ is as defined herein for formula I.

Embodiment [106]

The compound of any one of embodiments [11]-[12], [17]-[34], or [45]-[96], wherein $R^{1A}$ and $R^{2A}$ taken together with the nitrogen atom to which they are bound, form a 6-membered heterocycle having 1-2 heteroatoms independently selected from nitrogen, oxygen and sulfur, wherein said heterocycle is optionally substituted with one or more $R^b$, wherein $R^b$ is as defined herein for formula I.

Embodiment [107]

The compound of embodiment [105] or [106], wherein the heterocycle formed by $R^{1A}$ and $R^{2A}$ taken together with the nitrogen atom to which they are bound is unsubstituted (q=0).

Embodiment [108]

The compound of embodiment [105] or [106], wherein the heterocycle formed by $R^{1A}$ and $R^{2A}$ taken together with the nitrogen atom to which they are bound is substituted with one $R^b$ (q=1).

Embodiment [109]

The compound of any one of embodiments [11]-[12], [17]-[34], or [45]-[96], wherein $R^{1A}$ and $R^{2A}$ taken together with the nitrogen atom to which they are bound, form a 5-9 membered heteroaryl having 1-3 heteroatoms independently selected from nitrogen, oxygen and sulfur, wherein said heteroaryl is optionally substituted with one or more $R^b$, wherein $R^b$ is as defined herein for formula I.

Embodiment [110]

The compound of any one of embodiments [11]-[12], [17]-[34], or [45]-[96], wherein $R^{1A}$ and $R^{2A}$ taken together with the nitrogen atom to which they are bound, form a heteroaryl selected from triazole, imidazole, pyrazole, pyrrolopyridine, and indazole.

Embodiment [111]

The compound of any one of embodiments [1]-[12], [15]-[34], [45]-[96], or [101]-[106], wherein each occurrence of $R^b$ is independently selected from halogen, $S(O)_2R^6$, $N(R^{17})COR^6$, $N(R^{17})S(CO)_2R^6$, $CH_2N(R^{17})C(O)R^6$, $CH_2CH_2C(O)OR^6$, $C_{1-6}$ aliphatic, $C(O)R^6$, CN, $S(O)_2R^6$, $C(O)N(R^{17})$, $OR^7$, benzo[d]imidazol-2-(3H)-one, pyrrolidinone, piperidine, morpholine, imidazolidinone, piperazine, and pyrrolidine.

Embodiment [112]

The compound of embodiment [111], wherein $R^7$ is $C_{1-6}$ aliphatic or hydrogen.

Embodiment [113]

The compound of any one of embodiments [1]-[12], [15]-[34], [45]-[96], or [101]-[106], wherein each occurrence of $R^b$ is independently selected from

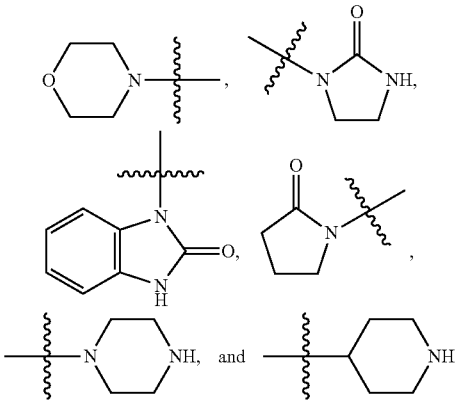

optionally substituted with one or more $R^c$, wherein $R^c$ is as defined herein for formula I.

Embodiment [114]

The compound of any one of embodiments [1]-[12], [15]-[34], [45]-[96], or [101]-[106], wherein each occurrence of $R^b$ is independently selected from $CH_2NHC(O)$ OtBu, NHC(O)OtBu, NHC(O)CH$_3$, NHSO$_2$CH$_3$, F, Cl, OH, OCH₃, OCH₂CH₃, OCF₃, S(O)₂CH₃, S(O)₂NH₂, CN, C(O)CH₃, C(O)OtBu, C(O)NH₂, CH₂CH₂C(O)OEt, and CH³.

Embodiment [115]

The compound of any one of embodiments [1]-[12], [15]-[34], [45]-[96], or [101]-[106], wherein $R^b$ is substituted with one $R^c$.

Embodiment [116]

The compound of embodiment [115], wherein each occurrence of $R^c$ is independently selected from $C_{1-6}$ aliphatic, $C(O)OR^9$, and $NR^{10}C(O)OR^{11}$.

Embodiment [117]

The compound of embodiment [116], wherein each occurrence of $R^c$ is independently selected from $CH_3$, C(O)Ot-butyl, and NHC(O)Ot-butyl.

Embodiment [118]

The compound of any one of embodiments [1]-[6], [17]-[34], or [45]-[96], wherein X is C and $R^1$, $R^2$, and $R^3$ are all hydrogen.

Embodiment [119]

The compound of any one of embodiments [1]-[6], [17]-[34], or [45]-[96], wherein X is C and any two of $R^1$, $R^2$, and $R^3$ taken together with the carbon atom to which they are bound, form a ring selected from 4-10-membered heterocycle and 3-10-membered cycloaliphatic, wherein said ring is optionally substituted with one or more $R^b$ and the remaining $R^1$, $R^2$, and $R^3$ is hydrogen or $CH_3$.

Embodiment [120]

The compound of any one of embodiments [1]-[6], [17]-[34], or [45]-[96], wherein X is C and any two of $R^1$, $R^2$, and $R^3$ taken together with the carbon atom to which they are bound, form a ring selected from 4-10-membered heterocycle having 1-5 heteroatoms independently selected from nitrogen, oxygen, and sulfur, and 3-10-membered cycloaliphatic, wherein said ring is optionally substituted with one or more $R^b$; $R^b$ is as defined herein for formula I and the remaining $R^1$, $R^2$, and $R^3$ is hydrogen.

Embodiment [121]

The compound of any one of embodiments [1]-[6], [17]-[34], or [45]-[96], wherein X is C and any two of $R^1$, $R^2$, and $R^3$ taken together with the carbon atom to which they are bound, form a 4-10-membered heterocycle having 1-5 heteroatoms independently selected from nitrogen, oxygen, and sulfur, and the remaining $R^1$, $R^2$, and $R^3$ is hydrogen Embodiment [122]

The compound of any one of embodiments [1]-[6], [17]-[34], or [45]-[96], wherein X is C and any two of $R^1$, $R^2$, and $R^3$ taken together with the carbon atom to which they are bound, form a 3-10-membered cycloaliphatic, and the remaining $R^1$, $R^2$, and $R^3$ is hydrogen.

Embodiment [123]

The compound of any one of embodiments [1]-[6], [17]-[34], or [45]-[96], wherein $XR^1R^2R^3$ is selected from:

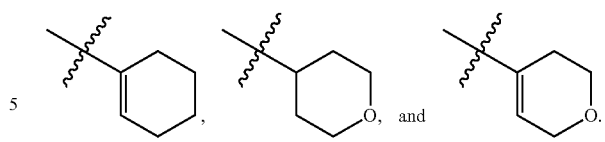

Embodiment [124]

The compound of any one of embodiments [1]-[6], [17]-[34], or [45]-[96], wherein X is C and taken together with the carbon atom to which they are bound, form a 5-10-membered heteroaryl having 1-4 heteroatoms independently selected from nitrogen, oxygen, and sulfur, wherein the heteroaryl optionally substituted with one or more $R^b$ and is selected from pyridine, thiazole, benzoimidazole, pyrazole, thiophene, furan, indole, pyrrole, pyrimidine, and imidazopyridine.

Embodiment [125]

The compound of any one of embodiments [1]-[6], [17]-[34], or [45]-[96], wherein X is C and one of $R^1$, $R^2$, and $R^3$ is a 4-10-membered heterocycle having 1-5 heteroatoms independently selected from nitrogen, oxygen, and sulfur, wherein said heterocycle is optionally substituted with one or more $R^k$.

Embodiment [126]

The compound of formula XXXVI:

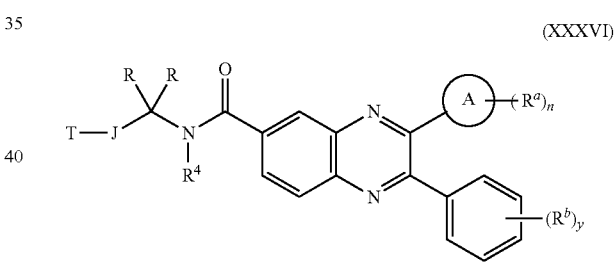

(XXXVI)

or a pharmaceutically acceptable salt thereof, wherein $R^b$, $R^4$, y, and R are as defined for formula I;

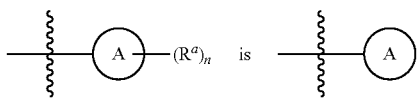

selected from 5-6-membered aromatic monocyclic ring having 0-1 heteroatom independently selected from nitrogen, oxygen, and sulfur, wherein said

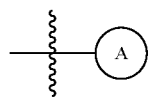

is optionally substituted with $R^a$, wherein $R^a$ is as defined herein for formula I and n=0, 1, 2, 3, 4, or 5;
J is selected from direct bond, $C_1$ aliphatic, and $C_2$ aliphatic;

T is selected from 5-6-membered monocyclic heteroaryl having 1-2 heteroatoms independently selected from nitrogen, oxygen, and sulfur and 9-membered bicyclic heteroaryl having 2-3 heteroatoms independently selected from nitrogen, oxygen, and sulfur, wherein the heteroaryl is optionally substituted with one or more $R^d$, wherein $R^d$ is as defined herein for formula I;

Embodiment [127]

The compound of any one of embodiments [1]-[16], [21]-[25], [27]-[44], or [82]-[126], wherein

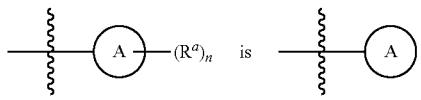

selected from phenyl, thiophene, pyrrole, and pyridine, wherein said

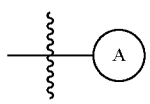

is optionally substituted with $R^a$, wherein $R^a$ is as defined herein for formula I and n=0, 1, 2, 3, 4, or 5.

Embodiment [128]

The compound of any one of embodiments [1]-[16], [21]-[25], [27]-[44], or [82]-[126], wherein

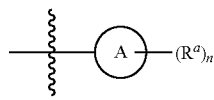

is selected from

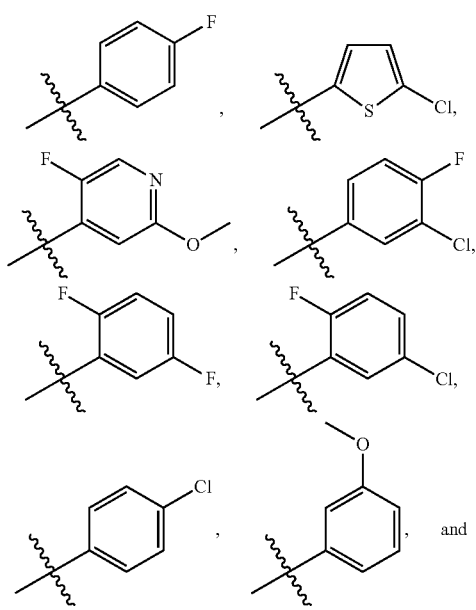

Embodiment [129]

The compound of any one of embodiments [1]-[12], [15]-[34], [45]-[96], [101]-[106], or [126]-[128], wherein $R^b$ is halogen and y is 1.

Embodiment [130]

The compound of any one of embodiments [1]-[81] or [90]-[130], wherein T is selected from imidazole, triazole, pyrazole, pyridine, benzoimidazole, and imidazopyridine, wherein T is optionally substituted with one or more $R^d$, wherein $R^d$ is as defined in formula I.

Embodiment [131]

The compound of any one of embodiments [1]-[81] or [90]-[130], wherein T is selected from

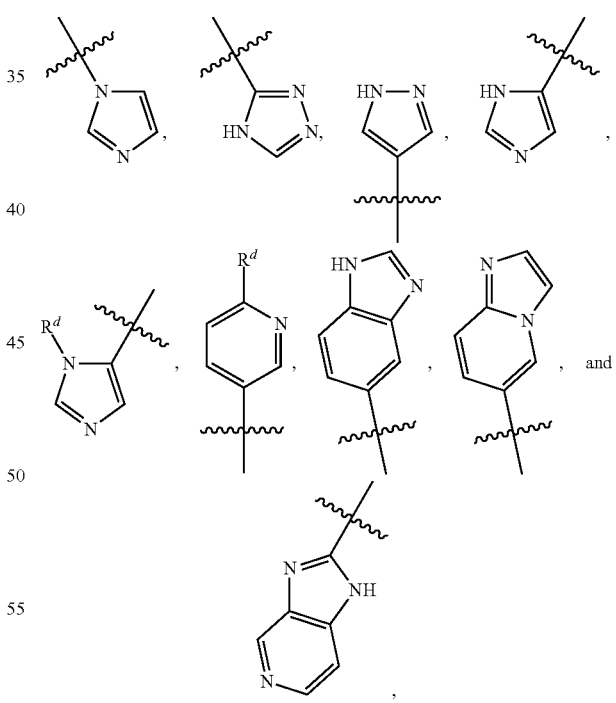

wherein $R^d$ is as defined for formula I.

Embodiment [132]

The compound of any one of embodiments [1]-[81] or [90]-[131], wherein T is selected from

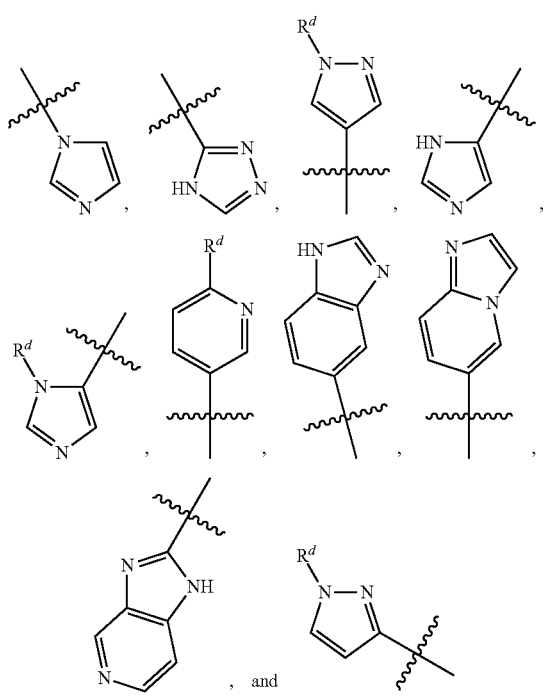

wherein $R^d$ is as defined for formula I.

Embodiment [133]

The compound of any one of embodiments [1]-[4], [7]-[10], [15]-[26], or [35]-[132], wherein

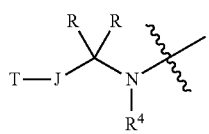

is selected from

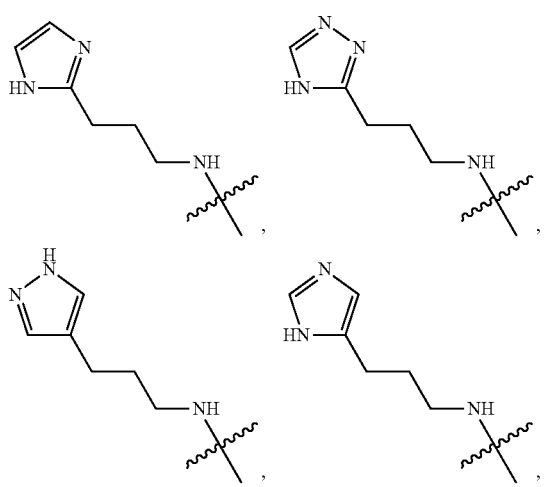

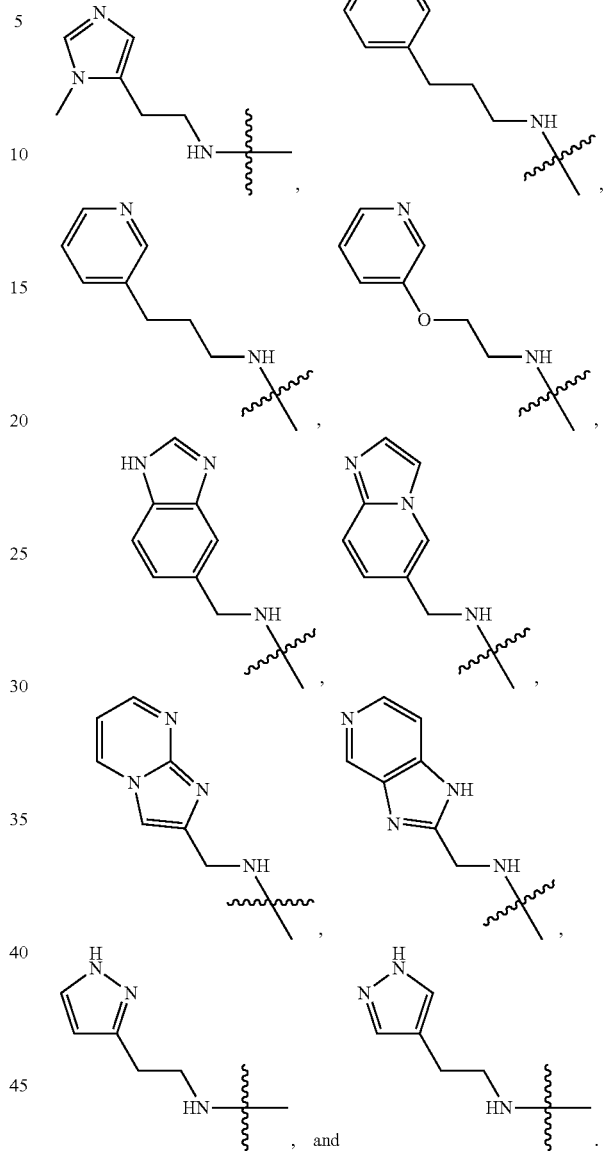

Embodiment [134]

The compound of any one of embodiments [1]-[6], [17]-[34], or [45]-[96], wherein X is halogen and $R^1$, $R^2$, and $R^3$ are absent.

Embodiment [135]

The compound of embodiment [134], wherein X is chlorine.

Embodiment [136]

The compound of any one of embodiments [1]-[6], [17]-[34], or [45]-[96], wherein X is O and one of $R^1$, $R^2$, and $R^3$ is $(CH_2)^s$-6-10-membered aryl, s is 0, 1, 2, or 3 and the remaining $R^1$, $R^2$, and $R^3$ are absent.

Embodiment [137]

The compound of any one of embodiments [1]-[6], [17]-[34], or [45]-[96], wherein X is O and one of $R^1$, $R^2$, and $R^3$ is 6-10-membered aryl and the remaining $R^1$, $R^2$, and $R^3$ are absent.

Embodiment [138]

The compound of any one of embodiments [1]-[6], [17]-[34], or [45]-[96], wherein X is O and one of $R^2$, and $R^3$ is $C_{1-6}$ aliphatic.

Embodiment [139]

The compound of any one of embodiments [1]-[6], [17]-[34], or [45]-[96], wherein X is O and one of $R^1$, $R^2$, and $R^3$ is 3-10-membered cycloaliphatic.

Embodiment [140]

The compound of any one of embodiments [1]-[6], [17]-[34], or [45]-[96], wherein X is O and one of $R^1$, $R^2$, and $R^3$ is 4-10-membered heterocycle having 1-5 heteroatoms selected from nitrogen, oxygen, and sulfur.

4. Uses, Formulation and Administration

As discussed above, the invention provides compounds that are useful as inhibitors of the enzyme NAMPT. The NAMPT inhibition of a compound of the invention can be measured using a variety of methods known in the art. For example, the ability of a compound of the invention to inhibit NAMPT enzyme activity can be measured using a homogeneous time resolved fluorescence (HTRF) assay using hNAMPT protein and anti 6His-Tb in buffer treated with a compound of the invention (or control e.g., DMSO) and BodiPY ligand. The TR-FRET signal can be measured using a high throughput microplate reader (e.g., Pherastar). Excitation can be carried out at 320 nm. The percent inhibition value at a single concentration of compound of the invention can be calculated relative to a control treated sample. A concentration response curve can be generated for each compound of the invention and the curve fitted to generate an $IC_{50}$ value. In one embodiment, a compound of the invention inhibits NAMPT with an $IC_{50}$ value of <100 nM. In one embodiment, a compound of the invention inhibits NAMPT with an $IC_{50}$ value of <500 nM. In one embodiment, a compound of the invention inhibits NAMPT with an $IC_{50}$ value of <1000 nM. In one embodiment, a compound of the invention inhibits NAMPT with an $IC_{50}$ value of <2000 nM. In one embodiment, a compound of the invention inhibits NAMPT with an $IC_{50}$ value of <10,000 nM.

The invention also provides compounds that inhibit cell growth. The ability of a compound of the invention to inhibit the growth of cells can be measured using a variety of methods known in the art. For example, the ability of a compound of the invention to inhibit the growth of PC3 cells can be measured. PC3 cells can be plated and incubated overnight under $CO_2$. For each measurement, a compound of the invention (or vehicle e.g., DMSO) can be diluted with AIM serum free medium and added to the cell plate. The cell plate can then be incubated for 72 h under $CO_2$. Cell-titer glo solution can be added and the plates can be incubated protected from light and the amount of luminescences can be measured. Concentration response curves can be generated by calculating the luminescence increase in test compound treated samples relative to DMSO-treated controls. Percentage remaining viability values at a single concentration can be measured. Growth inhibition ($GI_{50}$) or cell viability ($LD_{50}$) values can be determined from those curves. In one embodiment, a compound of the invention has a percent viability in a PC3 cell line of <1% when the concentration of the compound is about 1 μM, about 1.7 uM, or about 1.8 μM. In one embodiment, a compound of the invention has a percent viability in a PC3 cell line of <2% when the concentration of the compound is about 1 μM, about 1.7 uM, or about 1.8 μM. In one embodiment, a compound of the invention has a percent viability in a PC3 cell line of <3% when the concentration of the compound is about 1 μM, about 1.7 uM, or about 1.8 μM. In one embodiment, a compound of the invention has a percent viability in a PC3 cell line of <4% when the concentration of the compound is about 1 μM, 1.7 uM, or about 1.8 μM. In one embodiment, a compound of the invention has a percent viability in a PC3 cell line of <5% when the concentration of the compound is about 1 μM, about 1.7 uM, or about 1.8 μM. In one embodiment, a compound of the invention has a percent viability in a PC3 cell line of <10% when the concentration of the compound is about 1 μM, about 1.7 uM, or about 1.8 μM. In one embodiment, a compound of the invention has a percent viability in a PC3 cell line of <50% when the concentration of compound is about 1 μM, about 1.7 uM, or about 1.8 μM. In one embodiment, a compound of the invention does not include a compound having a percent viability in a PC3 cell line of >50% when the concentration of the compound is about 1 μM, about 1.7 uM, or about 1.8 μM.

As discussed above, the invention provides compounds that are useful as inhibitors of the enzyme NAMPT and thus, these compounds are useful for treating diseases, disorders, and symptoms that will respond to therapy with a NAMPT inhibitor. Consequently, the invention provides therapeutic methods for treating cancer, inflammatory conditions, and/or T-cell mediated autoimmune disease. These therapeutic methods involve treating a patient (either a human or another animal) in need of such treatment, with a therapeutically effective amount of one or more of the compounds of the invention or a pharmaceutical composition comprising a therapeutically effective amount of one or more of the compounds of the invention. Additionally, the invention provides the use of one or more of the compounds of the invention for the manufacture of a medicament useful for human therapy.

In some embodiments, the therapeutic method comprises a method of inhibiting abnormal cell growth or treating or preventing a hyperproliferative disorder in a subject comprising administering to the subject an effective amount of a compound of the invention or a pharmaceutically acceptable salt thereof. In some embodiments, the therapeutic method comprises therapy for the delaying the onset of, or reducing the symptoms of, cancer, an inflammatory disorder, or T-cell mediated autoimmune disease in a subject comprising administering to the subject an effective amount of a compound of the invention or a pharmaceutically acceptable salt thereof.

The invention also comprises treating isolated cells with a therapeutically effective amount of one or more of the compounds of the invention.

As used herein, the phrase "treating . . . with . . . a compound" means either administering one or more of the compounds of the invention directly to isolated cells or to a patient (animal or human).

In some embodiments, the invention provides a method of treating cancer, comprising administering a therapeutically effective amount of one or more compounds of the invention to a patient. In some embodiments, the patient is a human patient.

There are reports of NAMPT over-expression in colon cancers (Hufton et al., FEBS Lett. 463(1-2):77-82 (1999), Van Beijnum et al., Int. J. Cancer. 101(2):118-27 (2002)), ovarian cancers (Shackelford et al., Int J. Clin. Exp. Pathol. 3(5): 522-527 (2010)), prostate cancers (Wang et al., Oncogene 30: 907-921 (2011)) and glioblastoma multiforme (GBM) cancers (Reddy et al., Cancer Biol. Ther. 7(5):663-8 (2008)). Immunohistochemistry analyses suggest strong expression of NAMPT occurs in greater than 20% of biopsies of: breast, lung, malignant lymphoma, ovarian, pancreatic, prostate and testicular cancers (www.proteinatlas.org). Furthermore, the NAMPT transcript is known to be upregulated in colon cancers (van Beijnum J R, et al.; and Hufton S E, et al.) and glioblastoma cancers (Reddy P S, et al.).

In some embodiments, the invention provides a method of treating a cancer that overexpresses NAMPT, comprising administering a therapeutically effective amount of one or more compounds of the invention to a patient.

In view of the above, it is believed that inhibition of NAMPT activity would be effective in treating a wide range of cancers. The invention provides methods of treating a wide range of cancers by administering therapeutically effective amounts of one or more of the compounds of the invention. For example, cancer cell types corresponding to gastrointestinal, prostate, breast, testicular, sarcoma, renal, skin, myeloma, ovarian, leukemia, lymphoma, lung, cervical or brain cancers can be killed by one or more compounds of the invention.

In one aspect, the invention provides a method of treating cancer comprising administering a therapeutically effective amount of one or more compounds of the invention to a patient. In one aspect, the cancer is gastrointestinal cancer. In one aspect, the cancer is liver. In one aspect, the cancer is pancreatic. In one aspect, cancer is stomach (gastric). In one aspect, the cancer is esophageal. In one aspect, the cancer is colon. In one aspect, the cancer is large intestine cancer. In one aspect, the cancer is small intestine cancer. In one aspect, the cancer is prostate. In one aspect, the cancer is breast. In one aspect, the cancer is testicular. In one aspect, the cancer is lung. In one aspect, the cancer is non-small cell lung cancer (NSCLC). In one aspect, cancer is small cell lung cancer (SCLC). In one aspect, the cancer is sarcoma. In one aspect, the cancer is renal. In one aspect, the cancer is skin. In one aspect, the cancer is myeloma. In one aspect, the cancer is ovarian. In one aspect, the cancer is leukemia. In one aspect, the cancer is lymphoma. In one aspect, the cancer is cervical. In one aspect, the cancer is brain. In one aspect, the cancer is glioma.

In some embodiments, methods of the invention involve treating cancers that have been found to respond favorably to treatment with NAMPT inhibitors. Further, "treating cancer" should be understood as encompassing treating a patient who is at any one of the several stages of cancer, including diagnosed but as yet asymptomatic cancer.

Specific cancers that can be treated by the methods of the invention are those cancers that respond favorably to treatment with a NAMPT inhibitor. Such cancers include, but are not limited to, colon carcinoma, stomach carcinoma, malignant pancreatic insulinoma, pancreatic carcinoma, esophageal carcinoma, liver carcinoma, prostatic carcinoma, breast carcinoma, Wilms' tumor, renal cell carcinoma, melanoma, multiple myeloma, ovarian carcinoma, acute lymphocytic leukemia, chronic lymphocytic leukemia, acute myeloid leukemia, chronic granulocytic leukemia, acute granulocytic leukemia, hairy cell leukemia, Hodgkin's disease, non-Hodgkin's lymphoma, mantle-cell lymphoma, mycosis fungoides, essential primary macroglobulinemia, lung carcinoma, small-cell lung carcinoma, non-small cell carcinoma, cervical carcinoma, cervix adenocarcinoma, glioma, neuroblastoma, primary brain carcinoma, glioblastoma multiforme (GBM), testicular carcinoma, bladder carcinoma, malignant carcinoid carcinoma, choriocarcinoma, head or neck carcinoma, genitourinary carcinoma, thyroid carcinoma, endometrial carcinoma, thrombocytosis, adrenal cortex carcinoma, mammary carcinoma, soft-tissue sarcoma, osteogenic sarcoma, rhabdomyosarcoma, or Kaposi's sarcoma. Other disorders that can be treated by the methods of the invention are malignant hypercalcemia, cervical hyperplasia, or polycythemia vera.

Importantly, NAD+ can be generated by several NAMPT-independent pathways as well, including: (1) de novo synthesis from L-tryptophan via the kynurenine pathway; (2) from nicotinic acid (NA) via the Preiss-Handler pathway; and (3) from nicotinamide riboside or nicotinic acid riboside via nicotinamide/nicotinic acid riboside kinases (reviewed in Khan, J. A. et al. Expert Opin. Ther. Targets. 11(5):695-705 (2007)). However, these different routes of NAD+ synthesis are generally tissue specific: The de novo pathway is present in liver, brain, and immune cells, the Priess-Handler pathway is primarily active in the liver, kidney, and heart, and Nrk2, of the nicotinamide riboside kinase pathway, is expressed in brain, heart, and skeletal muscle (Bogan, K. L. and Brenner, C. Annu. Rev. Nutr. 28:115-30 (2008) and Tempel, W. et al., PLoS Biol. 5(10):e263 (2007)).

Of these alternative pathways of NAD+ synthesis, the Preiss-Handler pathway is perhaps the most important for cancer cells. The first and rate-limiting step of this pathway, the conversion of nicotinic acid (NA) to nicotinic acid mononucleotide (NAMN), is catalyzed by the enzyme NAPRT 1.

Some embodiments include a method of treating cancer, wherein cells of the cancer exhibit low levels of NAPRT1 expression. In one aspect, NAPRT1 expression is least in brain cancers, lung cancers, lymphoma, myeloma and osteosarcoma. For example, glioblastoma and sarcoma cell lines have been found to have reduced NAPRT1 expression (Watson, et al. Mol. Cell. Biol. 29(21):5872-88 (2009)). Thus, in some embodiments, the invention provides a method of treating a cancer that exhibits low levels of NAPRT1 expression, comprising administering a therapeutically effective amount of one or more compounds of the invention to a patient. In one aspect, the cancer is brain, such as glioblastoma. In one aspect, the cancer is lung. In one aspect, the cancer is osteosarcoma.

While those cancers with reduced or absent levels of NAPRT1 expression may be more susceptible to treatment with the NAMPT inhibitors of the invention, administration of NA to patients having such cancers could prevent toxicity in other tissues associated with NAMPT inhibition. To support this concept, experiments can be conducted to show that mice given NA survive doses of a NAMPT inhibitor above the maximum tolerated dose (see also Beauparlant P., et al. Anticancer Drugs. 20(5):346-54 (2009) and Watson, et al. Mol. Cell. Biol. 29(21):5872-88 (2009)). This phenomenon is referred to in the art as "NA rescue." Accordingly, in some embodiments, the methods of treating cancer disclosed herein further comprise administering nicotinic acid, or a compound that could form nicotinic acid or provide nicotinamide dinucleotide (NAD) from an alternate pathway, such as quinolinic acid (Sahm, F., et al. Cancer Res 73:3225 (2013); Henderson, T. D. et al. J. Biol. Chem. 170:261 (1947); Pittelli, M. et al. J. Biol. Chem. 285(44): 34106 (2010)) to the patient in addition to administering a compound of the invention. In some of such embodiments, the compound of the invention can be administered at dose that exceeds the maximum tolerated dose for that particular compound of the invention as determined for mono-therapy. In some embodiments, administering NA may include administering NA prior to administering one or more of the compounds of the invention, co-administering NA with one or more of the compounds of the invention, or first treating the patient with one or more of the compounds of the invention, followed by thereafter administering NA.

NAMPT expression in visceral adipose tissue has been found to correlate with the expression of proinflammatory genes, CD68 and TNF-alpha (Chang et al.; Metabolism. 59(1):93-9 (2010)). Several studies have noted an increase in reactive oxygen species and activation of NF-kappaB in response to NAMPT expression (Oita et al.; Pflugers Arch. (2009); Romacho et al.; Diabetologia. 52(11):2455-63 (2009)). NAMPT serum levels were found to have been increased in patients with inflammatory bowel diseases and correlated with disease activity (Moschen et al.; Mutat. Res. (2009)). One study has even suggested a specific mechanism for NAMPT in inflammation: High levels of NAMPT increase cellular NAD+ levels leading to a post-transcriptional upregulation of TNF via the NAD-dependent deacetylase, SirT6 (Van Gool et al. Nat. Med. 15(2):206-10 (2009)). Further, inhibition of NAMPT reduced levels of inflammatory cytokines IL-6 and TNF-alph. (Busso et al. PLoS One. 21; 3(5):e2267 (2008)). In another study, NAMPT inhibition was found to prevent TNF-alpha and IFN-gamma production in T-lymphocytes (Bruzzone et al.; PLoS One; 4(11): e7897 (2009)).

In view of the above, it is believed that inhibition of NAMPT activity would be effective in treating inflammatory conditions e.g., systemic or chronic inflammation resulting from a wide range of causes. Consequently, the invention provides methods of treating an inflammatory condition by administering therapeutically effective amounts of one or more of the compounds of the invention. NAMPT levels increased in a mouse model of arthritis and treatment of these mice with a NAMPT inhibitor reduced the arthritis symptoms (Busso et al. PLoS One. 21; 3(5):e2267 (2008)). In one aspect, the invention provides methods of treating rheumatoid arthritis by administering therapeutically effective amounts of one or more of the compounds of the invention to a patient.

In one aspect, the invention provides a method of treating an inflammatory condition comprising administering a therapeutically effective amount of one or more compounds of the invention to a patient. In one aspect, the inflammatory condition is rheumatoid arthritis. In one aspect, the inflammatory condition is inflammatory bowl disease. In one aspect, the inflammatory condition is asthma. In one aspect, the inflammatory condition is COPD (chronic obstructive pulmonary disease). In one aspect, the inflammatory condition is osteoarthritis. In one aspect, the inflammatory condition is osteoporosis. In one aspect, the inflammatory condition is sepsis. In one aspect, the inflammatory condition is related to a spinal cord injury. In one aspect, the inflammatory condition is related to an infection NAMPT expression has been shown to be upregulated in activated T-cells (Rongavaux et al.; J. Immunol. 181(7): 4685-95 2008)) and Phase I clinical trials report lymphopenia in patients treated with NAMPT inhibitors (reviewed in von Heideman et al.; Cancer Chemother. Pharmacol. (2009)). Additionally, in a mouse model of a T-cell autoimmune disease, experimental autoimmune encephalomyelitis (EAE), NAMPT inhibition reduced the clinical disease score and demyelination in the spinal cord (Bruzzone et al.; PLoS One. 4(11):e7897 (2009)). In view of the above, it is believed that inhibition of NAMPT activity would be effective in treating T-cell mediated autoimmune disease. Consequently, the invention provides methods of treating T-cell mediated autoimmune disease by administering therapeutically effective amounts of one or more of the compounds of the invention to a patient. In one aspect, the autoimmune disease is EAR In one aspect, the autoimmune disease is lupus.

While one or more of the compounds of the invention may be used in an application of monotherapy to treat a disorder, disease, or symptom, the compounds of the invention also may be used in combination therapy, in which the use of a compound of the invention is combined with the use of one or more other therapeutic agents for treating the same and/or other types of disorders, diseases, or symptoms. Combination therapy includes administration of the therapeutic agents concurrently or sequentially. Alternatively, the therapeutic agents can be combined into one composition which is administered to the patient. In some embodiments, the compounds of the invention are used in combination with other therapeutic agents, such as other inhibitors of NAMPT.

NAMPT inhibition has been shown to sensitize cells to the effects of various chemotherapeutic or cytotoxic agents. Specifically, NAMPT inhibition has been shown to sensitize cells to amiloride, mitomycin C, etoposide, mechlorethamine, streptozotocin, 5-fluorouracil, raltitrexed, methotrexate, bortezomib, dasatinib, olaparib, TRAIL, cyclosporine A, valproate, temozolomide (TMZ), methoxyamine hydrochloride (MX), cisplatin, FX11 (3-dihydroxy-6-methyl-7-(phenylmethyl)-4-propylnaphthalene-1-carboxylic acid), rituximab (RTX), Sirtinol, 1-methyl-D-tryptophan, and L-1-methyl tryptophan (Ekelund, S. et al. Chemotherapy 48:196-204 (2002)(lymphoma); Rongvaux, A. et al. The Journal of Immunology 181(7):4685-95 (2008); Martinsson, P. et al. British Journal of Pharmacology 137: 568-73 (2002)(lymphoma); Pogrebniak, A. et al. European Journal of Medical Research 11(8):313-21 (2006)(leukemia), Myrexis US 2013/0317027 (cancer); Bi, T., et al., Oncology Reports 26(5):1251-1257 (2011)(gastric); Bajrami, I., et al., EMBO Molecular Medicine 4(10):1087-1097 (2012)(TN breast cancer); Zoppoli, G., et al., Experimental Hematology, 38(11):979-988 (2010)(leukemia); Cea, M., et al., Haematologica 2009; 94[suppl.2]:495 abs. 1237 (leukemia); Goellner, E., et al. Cancer Research, 71:2308-2317 (2011); Travelli, C., et al., The Journal of Pharmacology, 338(3): 829-840 (2011)(neuroblastoma); Le, A., et al., PNAS 2009 107(5):2037-2042 (lymphoma and pancreatic); Nahimana, A., et al. Leuk & Lymphoma, early online: 1-10 (2014)(B-cell lymphoma) Bowlby, S. et al., PLOS, 7(6): e40195 (2012)(prostate); Watson, M. et al., Molecular and Cellular Biology, 29(21) 5872 (2009); and Goellner, E. et al, Cancer Research, 71: 2308 (2011). NAMPT inhibition has also been shown to increase the radiation sensitivity of certain tumors (Muruganandham, M., et al. Clin Cancer Res 11:3503-3513 (2005)(mammory carcinoma); Zerp, S. F. et al., Radiotherapy and Oncology ePub (prostate)).

In some embodiments, a compound of the invention is administered in combination with a second therapeutic agent. In one embodiment, the second therapeutic agent is amiloride, mitomycin C, etoposide, mechlorethamine, streptozotocin, 5-fluorouracil, raltitrexed, methotrexate, bortezomib, dasatinib, olaparib, TRAIL, cyclosporine A, valproate, temozolomide (TMZ), methoxyamine hydrochloride (MX), cisplatin, FX11 (3-dihydroxy-6-methyl-7-(phenylmethyl)-4-propylnaphthalene-1-carboxylic acid), rituximab (RTX), Sirtinol, 1-methyl-D-tryptophan, and L-1-methyl tryptophan. In some embodiments, the invention provides a method of treating cancer, comprising administering a therapeutically effective amount of one or more compounds of the present invention and one or more second agents selected from the second therapeutic agents described above. In one aspect, the cancer is any cancer described herein. In one aspect, the cancer is lymphoma, leukemia, gastric, breast, neuroblastoma, or pancreatic cancer.

Another aspect of the invention relates to inhibiting NAMPT activity in a biological sample or a patient, which method comprises administering to the patient, or contacting said biological sample with a compound of the invention or a composition comprising said compound. The term "biological sample", as used herein, generally includes in vivo, in vitro, and ex vivo materials, and also includes, without limitation, cell cultures or extracts thereof biopsied material obtained from a mammal or extracts thereof; and blood, saliva, urine, feces, semen, tears, or other body fluids or extracts thereof.

Still another aspect of this invention is to provide a kit comprising separate containers in a single package, wherein the compounds of the invention, compositions and/or salts thereof are used in combination with pharmaceutically acceptable carriers to treat disorders, symptoms and diseases where NAMPT plays a role.

Accordingly, in another aspect of the invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of the invention or an inhibitorily active metabolite or residue thereof. As used herein, the term "inhibitorily active metabolite or residue thereof" means that a metabolite or residue thereof is also an inhibitor of NAMPT.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of the invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound or a pharmaceutical composition to a subject in need thereof. In certain embodiments of the present invention an "effective amount" of the compound or pharmaceutical composition is that amount effective for treating cancer, an inflammatory condition or T-cell mediated autoimmune disease or is that amount effective for treating cancer. In other embodiments, an "effective amount" of a compound is an amount which inhibits NAMPT and thereby blocks the resulting production of NAD+.

The compounds and compositions, according to the method of the invention, may be administered using any amount and any route of administration effective for treating the disease. The exact amount required will vary from subject to subject, depending on the species, age, and general condition of the subject, the severity of the disease, the particular agent, its mode of administration, and the like. In one aspect, the compounds of the invention are formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, in one aspect, a mammal, and in another aspect, a human.

The pharmaceutically acceptable compositions of the invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease being treated. In certain embodiments, a compound of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In one aspect, compositions for rectal or vaginal administration are suppositories which can be prepared by mixing a compound of the invention with suitable non-irritating excipient or carrier such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the invention include ointments, pastes, creams, lotions, gels; powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the compounds of the invention may be used in an application of monotherapy to treat a disorder, disease or symptom, one or more of the compounds of the invention may also may be used in combination therapy, in which the use of a compound of the invention or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

EXPERIMENTAL PROCEDURES

I-a. Preparation of Certain Exemplary Compounds:

Compounds 1 through 514 (Shown in Table 1 below) were prepared using the general methods and specific examples described directly below.

1. General Synthetic Methods and Intermediates:

The compounds of the present invention can be prepared by methods known to one of ordinary skill in the art and/or by reference to the schemes shown below and the synthetic examples. Exemplary synthetic routes are set forth in Schemes below and in the Examples.

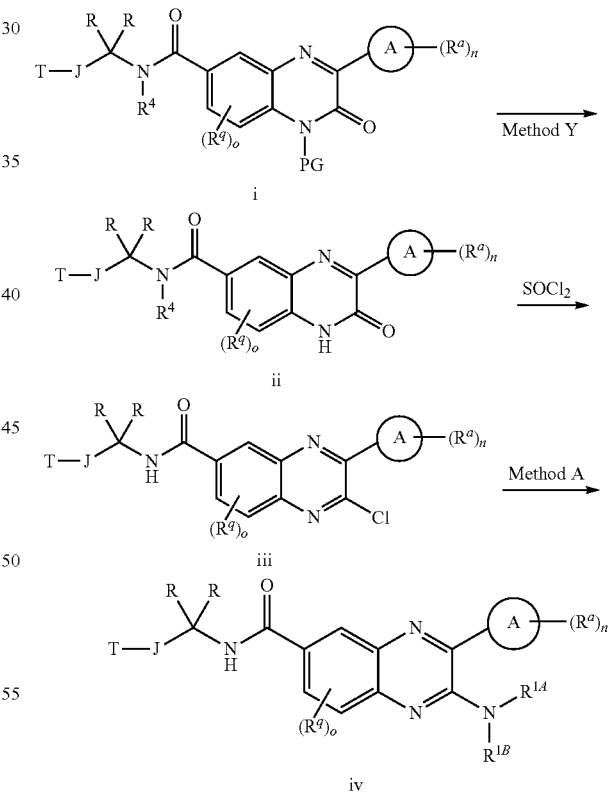

Scheme 1 shows a general route for the preparation of compounds of formula iv starting from intermediate i. The protecting group (PG) of i (such as PMB or tBu) can be removed by treatment with an acid, for example TFA, with optional presence of anisole (Method Y) to give a compound of formula ii. Upon treatment of ii with a halogenating agent, such as thionyl chloride, in an appropriate solvent, such as DMF, at elevated temperature, a compound of formula iii can be generated. Compound iii can then be treated with an amine, NHR$^{1A}$R$^{2A}$, under the conditions of Method A (in the presence of an appropriate base, such as DIPEA, KOAc, Et$_3$N or K$_2$CO$_3$ and in an appropriate solvent such as iPrOH, NMP, MeCN, DMF or DMSO) at elevated temperature to provide a compound of formula iv.

example, PMB or tBu gives compound viii. Compound viii can undergo reduction of the nitro group under the conditions of Method B (treatment with iron under acidic conditions in an appropriate solvent such as ethanol at elevated temperature) to give compound ix. Compound ix can undergo reaction with a compound of formula x under acidic conditions in an appropriate solvent, such as toluene, at

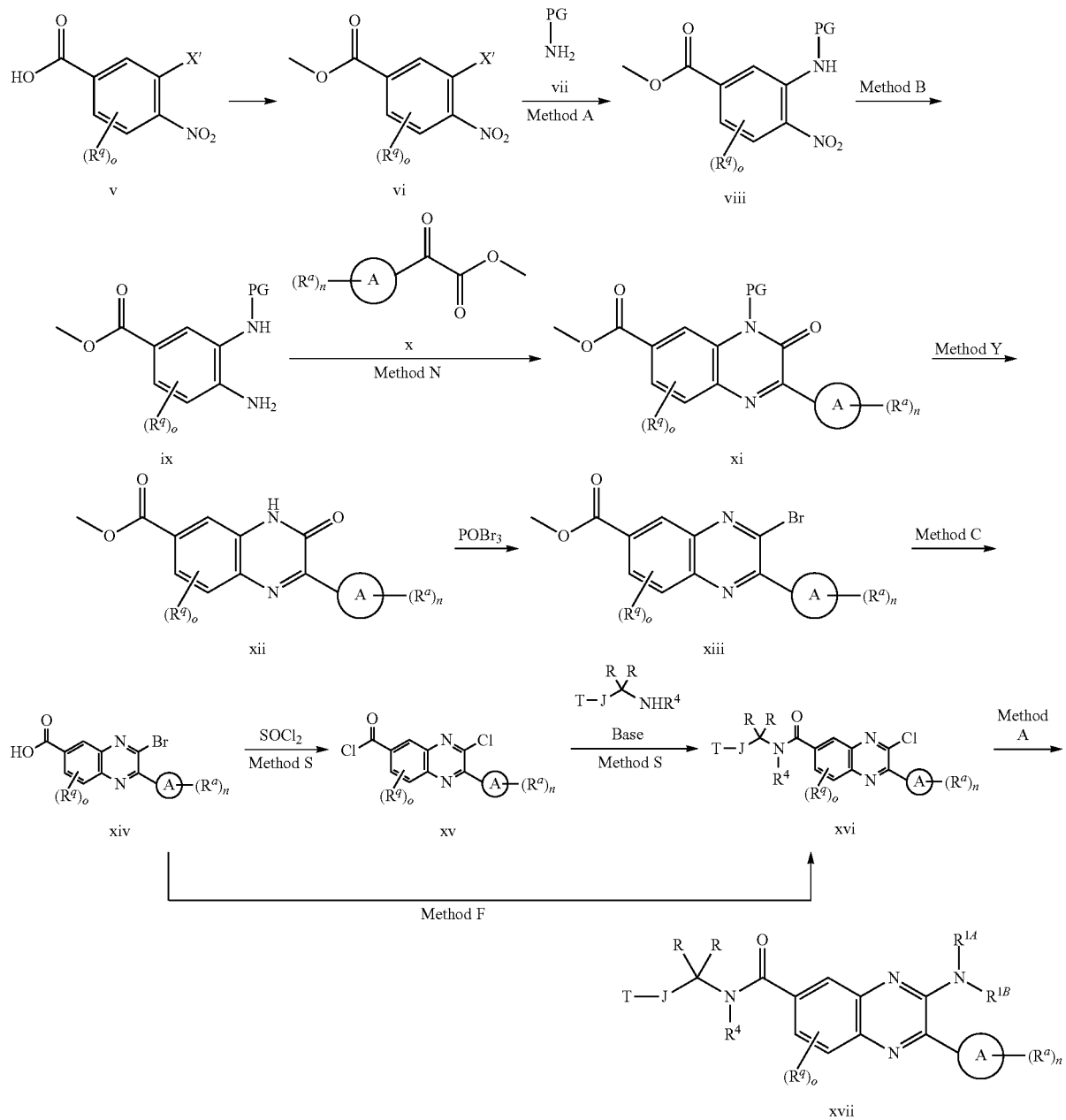

Scheme 2 shows a general route for the preparation of compounds of formula xvii starting from an optionally substituted 3-fluoro or 3-chloro-4-nitrobenzoic acid v (where X'=F or Cl). Treatment of v with an alcohol, such as methanol, under acidic conditions provides the ester vi. Reaction of vi with a protected amine using conditions of Method A, where the protecting group (PG) could be for elevated temperature (Method N) to give a compound of formula xi. Deprotection of xi can be realized by treatment with an acid, such as TFA with optional presence of anisole, (Method Y) to give a compound of formula xii. Treatment of xii with a brominating reagent, such as POBr$_3$, in an appropriate solvent, such as MeCN, at elevated temperature can give a compound of formula xiii. Treatment of xiii with the conditions of Method C (treatment with an aqueous base solution such as NaOH or LiOH in a solvent system such as THF with MeOH or i-PrOH at rt or elevated temperature) can provide a compound of the formula xiv, that can be isolated either as a carboxylic acid salt (such as Na, K, Li) or a free carboxylic acid when workup includes treatment with an acid such as aqueous HCl. Reaction of xiv with a halogenating reagent, such as thionyl chloride, in an appropriate solvent such as THF or DMF (Method S, Step 1) can give a compound of formula xv. Compound xv can be treated with an amine under basic conditions such as DIPEA or TEA in an appropriate solvent such as THF (Method S, Step 2) to give a compound of formula xvi. Alternatively, compound xiv can be treated with an amine under the conditions of Method F to give a compound of formula xvi. Compound xvi can then be treated with the conditions of Method A to provide a compound of formula xvii.

Scheme 3: General method for the preparation of compounds of formula xxvi

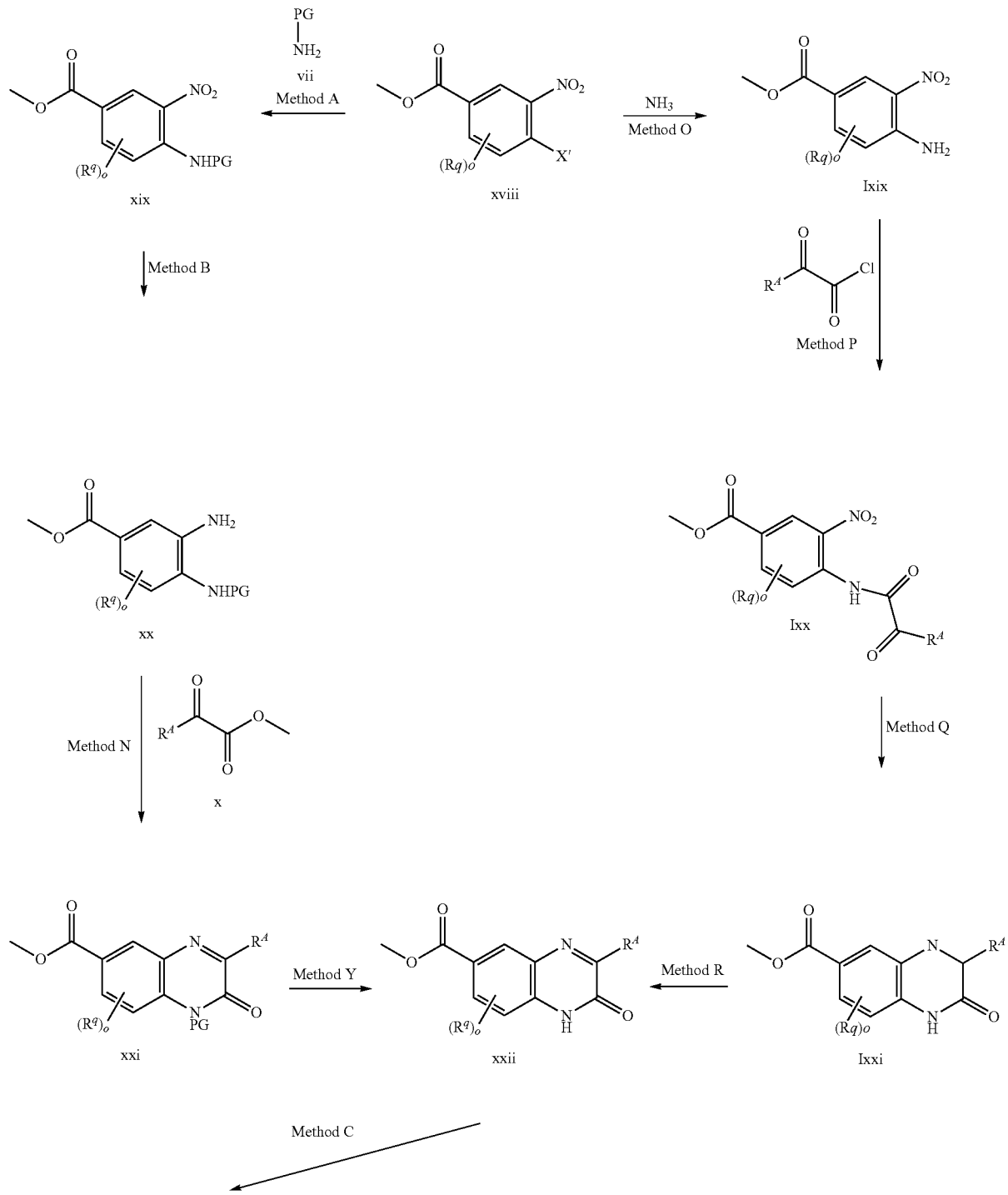

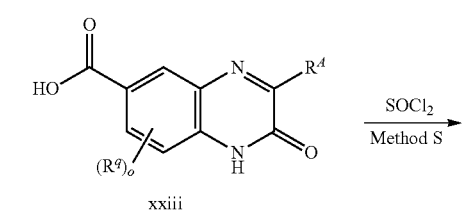
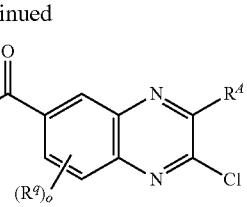
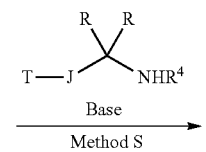
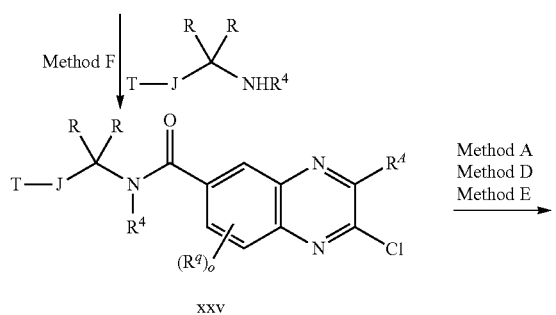
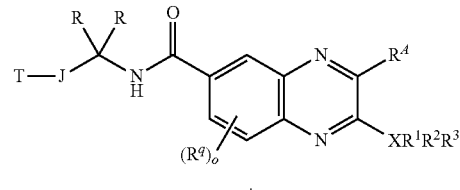

Scheme 3 shows a general route for the preparation of compounds of formula xxvi starting from an optionally substituted ester of 4-chloro-3-nitrobenzoic acid, or 4-fluoro-3-nitrobenzoic acid xviii (where X'=F or Cl). Reaction of xviii with a protected amine (where the protecting group could be for example, tBu or PMB) using the conditions of Method A gives compound xix. Compound xix can undergo reduction of the nitro group under the conditions of Method B to give xx. Treatment of xx with a compound of formula x under acidic conditions in an appropriate, such as, at elevated temperature (Method N) can give a compound of formula xxi. Deprotection of xxi can be realized by treatment with an acid, such as TFA with optional presence of anisole (Method Y), to give a compound of formula xxii. Alternatively, compound of formula xxii can be prepared using a sequence that starts by treatment of xviii with ammonia in a suitable solvent, such as dioxane with heating in a sealed container or under microwave irradiation (Method O). Treatment of the nitroaniline lxix with an acylhalide with a suitable base, such as TEA in an appropriate solvent, for example THF (Method P) gives compound of formula lxx. The amine of compound lxx can be then be reduced with hydrogen under Pd metal catalysis, for example 10% Pd on charcoal, in a suitable solvent, such as THF and methanol under pressure (Method Q) to provide tetrahydroquinoxaline lxxi. Transformation of lxxi to xxii can be accomplished by oxidation with a suitable reagent, for example DDQ in a suitable solvent, such as dioxane (Method R). Hydrolysis of the ester of compound xxii can be accomplished under the conditions of Method C to give a compound of formula xxiii. Reaction with a halogenating reagent such as, thionyl chloride, in an appropriate solvent, such as THF or DMF (Method S, Step 1), can give a compound of formula xxiv. Compound xxiv can be treated with an amine under basic conditions, such as DIPEA or TEA, in an appropriate solvent such as THF (Method S, Step 2) to give a compound of formula xxv. Alternatively, Method F can be used for the transformation of xxiii to xxv. Compound xxv can undergo reaction with an amine according to Method A, with a boronic acid or ester under the conditions of Method D (Suzuki coupling using a catalyst such as PdCl$_2$(dppf), Pd(amphos)Cl$_2$, or PdCl$_2$(PPh$_3$)$_2$, with a base such as Cs$_2$CO$_3$ or K$_2$CO$_3$, in a solvent such as DCM, DME, 1,4-dioxane, i-PrOH or DMF at elevated temperature) or with an alcohol or thiol, under the conditions of Method E (ether (oxo or thio) formation under basic conditions such as DIPEA, NaH, Cs$_2$CO$_3$, or potassium t-butoxide in a solvent such as DMF, NMP, or THF) to give a compound of formula xxvi where XR$^1$R$^2$R$^3$ is an amine (Method A) an aryl, heteroaryl or alkyl group (Method D) or an ether or thioether group (Method E). Note that for Method D, the starting halide can be a Cl or Br.

Scheme 4: General method for the preparation of compounds of formula xxxi

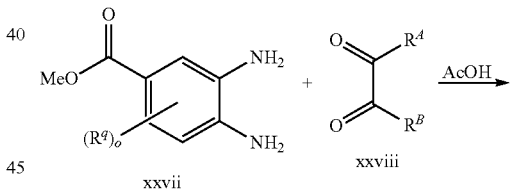
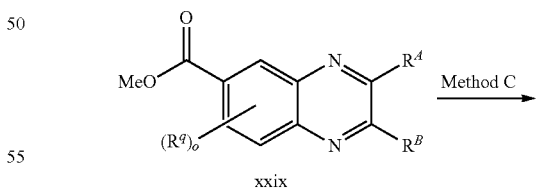
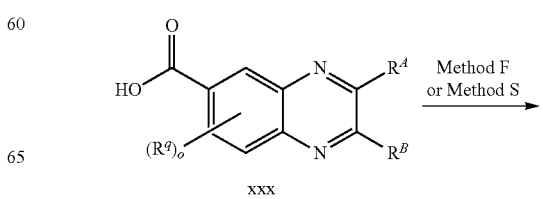

-continued

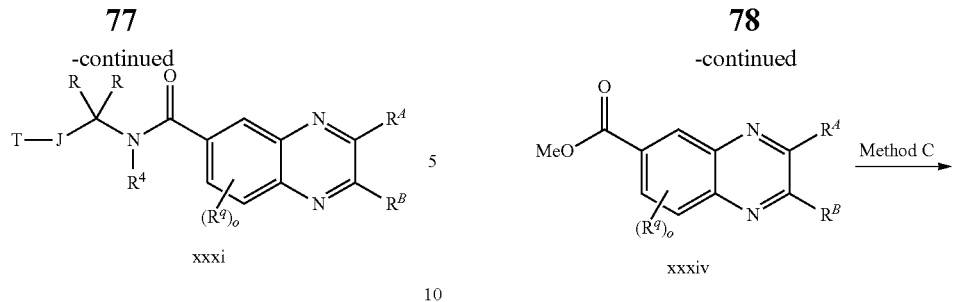
xxxi

Scheme 4 shows a general route for the preparation of compounds of formula xxxi ($R^A$ and $R^B$ are both rings) starting from xxvii. Starting material xxvii can be reacted with a diaryldiketone of formula xxviii under acidic conditions, such as acetic acid, in an appropriate solvent, such as toluene, at elevated temperature to give a compound of formula xxix. The ester of compound xxix can undergo hydrolysis with the reaction conditions of Method C to provide a compound of formula xxx. Compound xxx can be reacted with an amine, ($NHR^4C(R)_2JT$), under the conditions of Method F (reaction using a coupling reagent such as HATU, HOBt or EDCI in the presence of a base such as DIPEA or TEA in a suitable solvent such as DMSO, DMA or DMF) to give a compound of formula xxxi. Alternatively, Method S can be used for two step transformation of xxx to xxxi.

Scheme 5: General method for the preparation of compounds of formula xxxvi

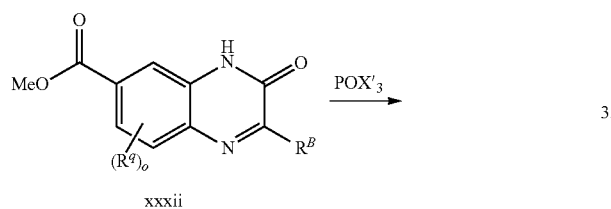
xxxii

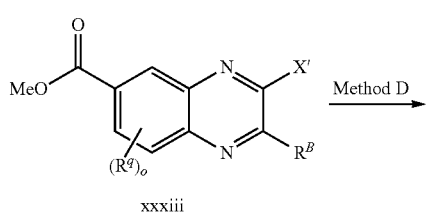
xxxiii

-continued

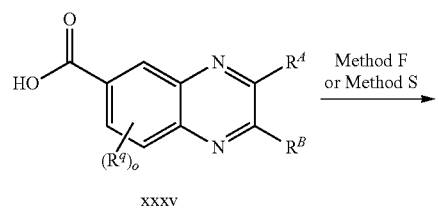
xxxiv

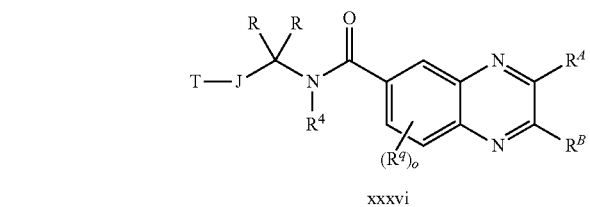
xxxv xxxvi

Scheme 5 shows a general route for the preparation of compounds of formula xxxvi starting from xxxii. Reaction of xxxii with a halogenating (brominating or chlorinating) reagent, such as $POBr_3$, $POCl_3$ in an appropriate solvent, such as acetonitrile, at elevated temperature gives a compound of formula xxxiii (where X'=Cl or Br). Compound xxxiii can be treated with the conditions of Method D with an aryl boronic ester or acid to give a compound of formula xxxiv. The ester of compound xxxiv can be hydrolyzed with the conditions of Method C to give a compound of the formula xxxv. Compound xxxv can undergo reaction with an amine ($NHR^4C(R)_2JT$), under the conditions of Method F to provide a compound of formula xxxvi. Alternatively, Method S can be used for two step transformation of xxxv to xxxvi.

Scheme 6: Alternate method for the preparation of compounds of formula xxxvi

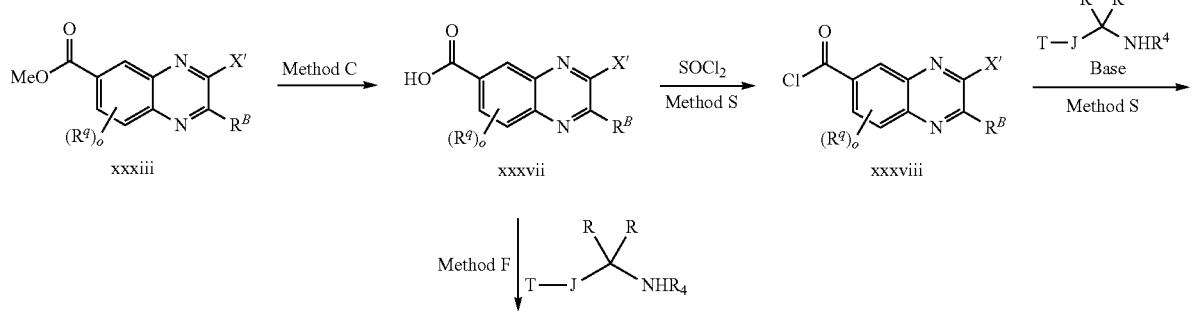

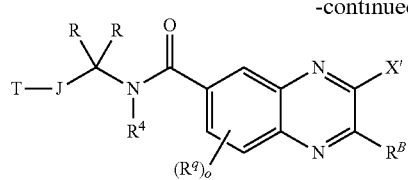

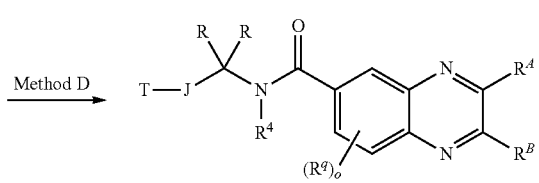

Scheme 6 shows an alternate method of preparation of compounds of formula xxxvi from starting material xxxiii. Treatment of compound xxxiii (where X'=Cl or Br) with the conditions of Method C gives compound xxxvii that can be isolated either as a salt (Na when sodium hydroxide is used) or a carboxylic acid when workup includes an acidic treatment, such as aqueous HCl. Compound xxxvii can be treated with a halogenating agent such, as thionyl chloride, in the presence of an appropriate base, such as TEA, in a suitable solvent such as DMF to give compound xxxviii. Compound xxxviii can be treated with an amine under basic conditions, such as TEA, to give a compound of formula xxxix. Alternatively, compound xxxvii can be transformed into xxxix using an amine and the conditions of Method F. Compound xxxix can be reacted with an aryl boronic ester or acid under the conditions of Method D to give a compound of formula xxxvi.

Scheme 7: General method for the preparation of compounds of formula xl

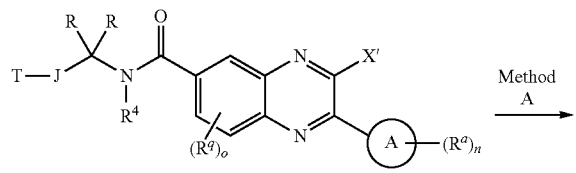

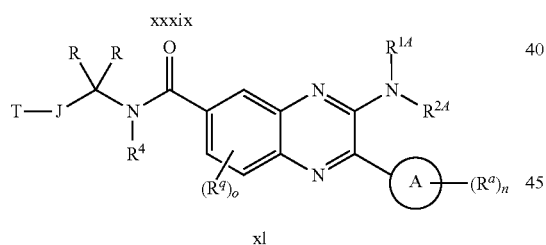

Scheme 7 shows a general method for preparation of compounds of the formula xl from starting from xxxix. Compound xxxix (where X'=Cl or Br) can be treated with amine (NHR$^{1A}$R$^{2A}$) under the conditions of Method A to provide a compound of formula xl.

Scheme 8: Alternate method for the preparation of compounds of formula xxxi

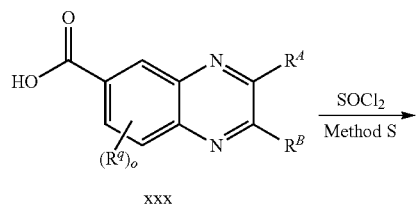

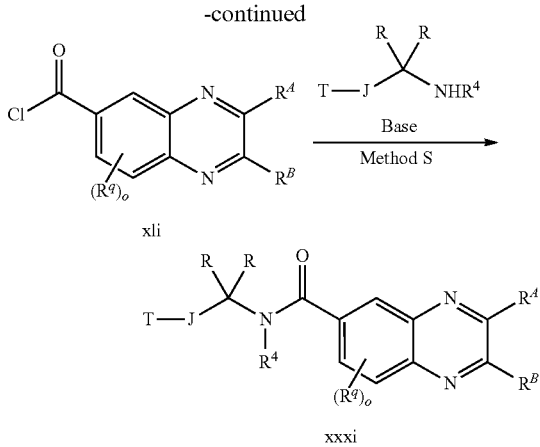

Scheme 8 shows an alternate method for the preparation of compounds of formula xxxi starting from xxx. Compound xxx can be treated with a chlorinating agent, such as thionyl chloride, in an appropriate solvent, such as THF (Method S, Step 1), to give a compound of formula xli. Compound xli can be treated with an amine under basic conditions, such as DIPEA, in an appropriate solvent such as THF (Method S, Step 2) to give a compound of formula xxxi.

Scheme 9: General method for the preparation of compounds of formula xliii

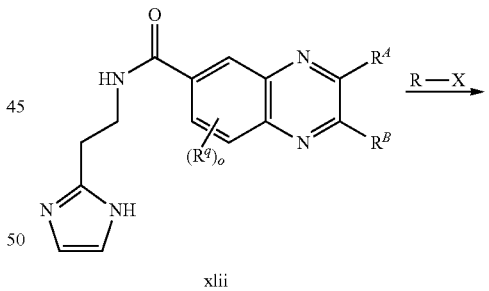

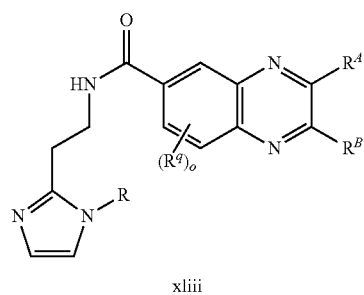

Scheme 9 shows a general method for the preparation of compounds of formula xliii starting from xlii. Compound xlii can be treated with an alkyl halide, such as methyl iodide under basic conditions, such as K₂CO₃, in an appropriate solvent such as DMF, to provide a compound of formula xliii.

Scheme 10: General method for the preparation of compounds of formula xlv

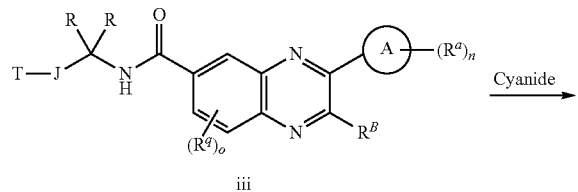

Scheme 10 shows a general method of preparation of compounds of formula xlv starting from iii. Compound iii can be treated with a cyanide, such as potassium cyanide, in the presence of sodium toluenesulfonate in an appropriate solvent, such as DMF, at elevated temperature to give a compound of formula xlv.

Scheme 11: General method for the preparation of compounds of formula I

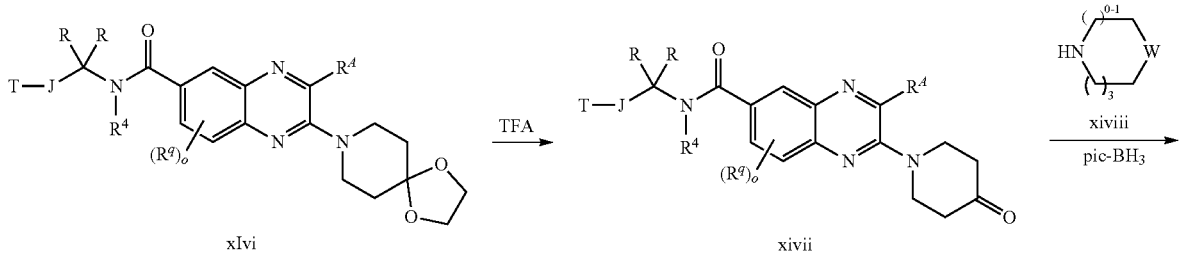

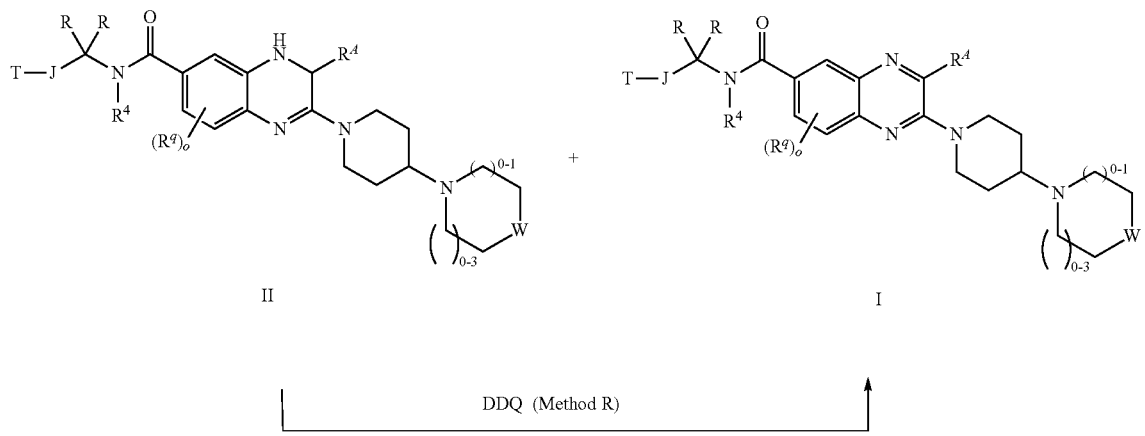

Scheme 11 shows a general method for the preparation of compounds of formula 1 starting from xlvi. Compound xlvi can be treated with an acid, such as TFA, to give a compound of formula xlvii. Compound xlvii can undergo reductive amination with an amine using a reagent such as picoline borane in a suitable solvent, such as MeOH, in the presence of an acid, such as AcOH, to give either a compound of formula il, a compound of formula 1 or a mixture of compounds of formula il and 1. Compound il can be treated with DDQ (Method R) to provide compound 1.

Scheme 12: General method for the preparation of compounds of formula lii

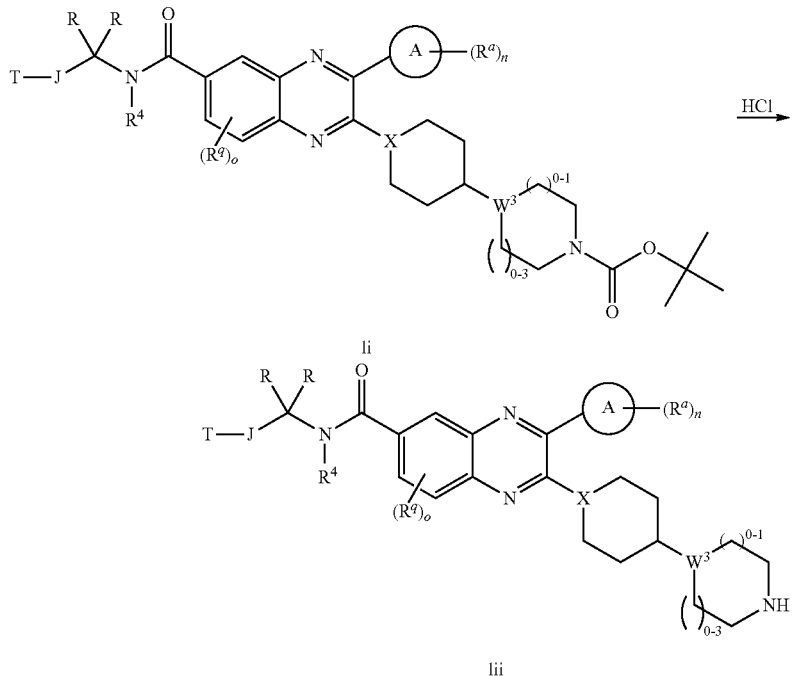

Scheme 12 shows a general method for the preparation of compounds of formula lii starting from li where X and W³ can be CH or nitrogen. Compound li can be treated with HCl in an appropriate solvent, such as EtOAc, to provide a compound of formula lii.

Scheme 13: Alternative method for the preparation of compounds of formula xxxvi

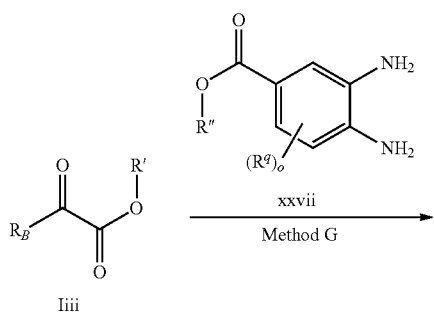

-continued

Scheme 13 shows alternative method for the preparation of compounds of formula xxxvi. The ketoester liii is treated under conditions of Method G (in an alcoholic solvent-such as ethanol under elevated temperature) with 3,4-diaminobenzoic ester xxvii, to provide a compound of formula liv, that can be further functionalized to a compound of formula xxxvi using other methods described herein (e.g., Scheme 5).

Scheme 14: General method for preparation of compounds of formula lxii

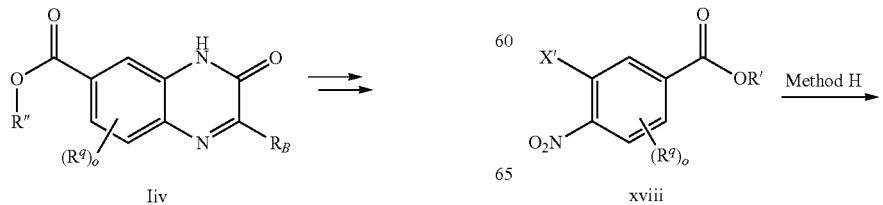

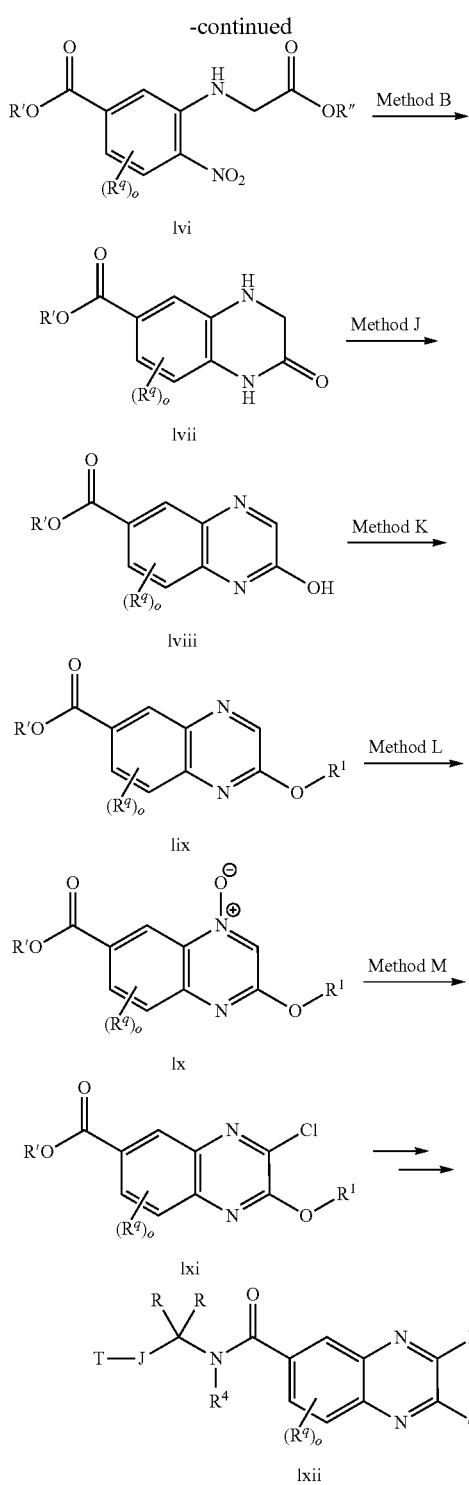

be carried out under the conditions of Method J (using a suitable oxidizing reagent, for example $MnO_2$). Ether formation can be effected under the conditions of Method K (using Mitsunobu conditions, such as alcohol (R'OH), $PPh_3$, DIAD in THF at elevated temperature) to produce a compound of formula lix. The resulting ether lix is then subsequently oxidized to produce an N-oxide lx under Method L (using an appropriate oxidant, for example mCPBA in DCM). Treatment of a compound of formula lx with oxalyl chloride in DMF provides a chloride lxi that can be subsequently transformed to compound lxii. Conversion of ester functionality is achieved using the following sequence of Method C, followed by Method F or Method S (Schemes 2-6). Conversion of chloride to C, O, N, S-substituted groups is achieved using Methods A (N-substitution), D, T, U (C-substitution using Suzuki, Grignard or Neishi coupling), E (O, S-substitution).

Scheme 15: General method for preparation of a compound of formula lxiii

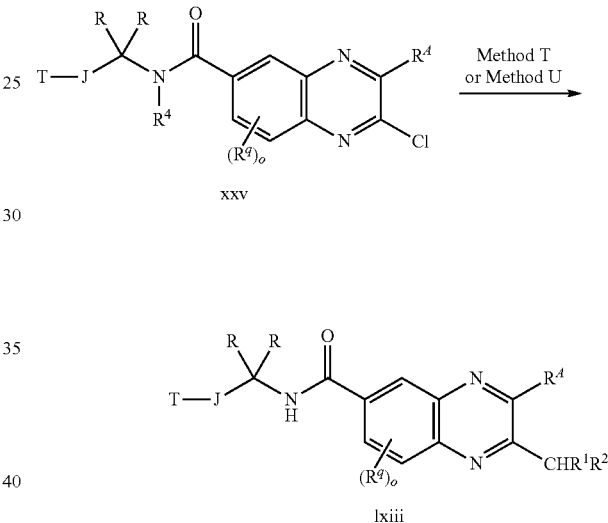

Scheme 15 shows a general method for the preparation of C-substituted quinoxalines of formula lxiii. Halide xxv can be treated with a Grignard reagent, for example a primary or secondary alkylmagnesium halide under Fe(III) catalysis, such as $Fe(acac)_3$ in a suitable solvent, e.g., THF (Method T) to afford a compound of formula lxiii. Alternatively, Negishi conditions can also be employed, for example Negishi conditions can be a substituted benzylzinc halide with Ni(II) catalysis, such as NiCl(dppp) in a suitable solvent, for example dioxane (Method U).

Scheme 14 shows a general method for the preparation of compounds of formula lxii. 3-Fluoro-4-nitrobenzoate or 3-chloro-4-nitrobenzoate xviii (where X'=F or Cl and R' is an alkyl group) can be treated using Method H (with a glycine ester under basic conditions, such as $K_2CO_3$ in acetonitrile at elevated temperature) to provide a compound of formula lvi, which can be subsequently reduced under the conditions of Method B (using a suitable reducing agent, such as Fe in AcOH with simultaneous cyclization) followed by oxidation to produce quinoxaline lviii. The oxidation can Scheme 16: General method for preparation of compounds of formula lxviii

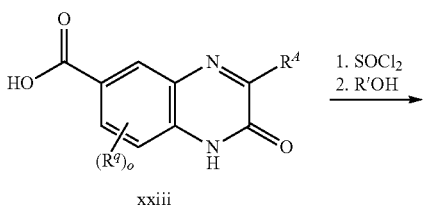

-continued

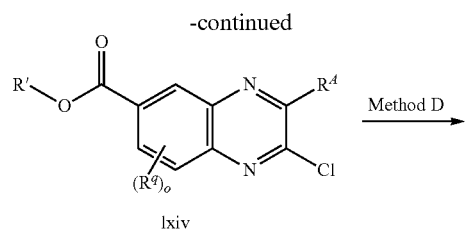
lxiv

Method D →

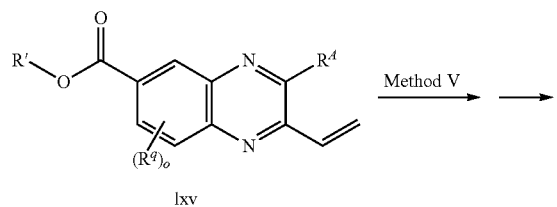
lxv

Method V →

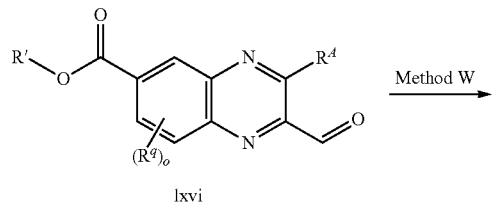
lxvi

Method W →

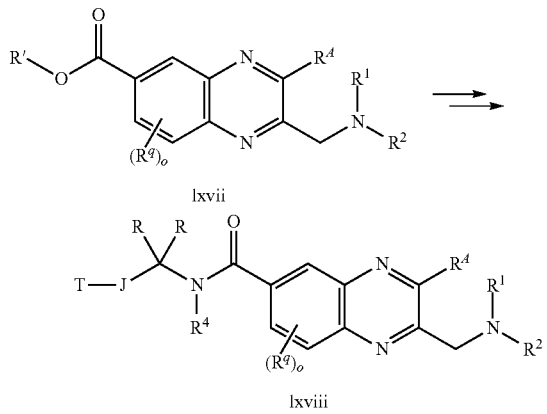
lxvii lxviii

Scheme 16 shows a general method for the preparation of compounds of formula lxviii. Carboxylic acid xxiii can be converted to compound lxiv using chlorination with a suitable reagent, such as $SOCl_2$ in the presence of catalytic amount of DMF, followed by treatment with an alcohol with a suitable base, such as TEA in a suitable solvent, for example THF. The halide lxiv can be treated with a vinyl-stannane or vinyl boronic acid under Pd catalysis, such as $Pd(PPh_3)_4$ in a suitable solvent, for example THF or toluene (Method D) to afford a compound of formula lxv, which can be subsequently oxidized to afford aldehyde lxvi. The oxidation can be performed using a suitable reagent, for example $OsO_4$, $NaIO_4$ in a suitable solvent, such as dioxane/water mixture (Method V). The aldehyde lxvi can then undergo reductive amination with a primary or secondary amine ($NHR^1R^2$) using appropriate conditions, such as sodium triacetoxyborohydride in a suitable solvent, for example DCM (Method W) to afford a compound of formula lxvii, which can be further transformed to a compound of formula lxviii using other methods described herein (e.g., Method C followed by Method F or Method S).

Scheme 17: General route for the synthesis of compounds lxxvi

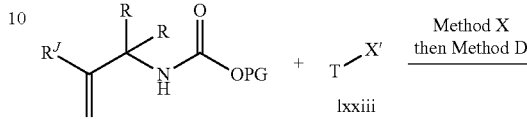
lxxii + lxxiii

Method X then Method D →

lxxiv

Method Y → lxxv

Method F or Method S →

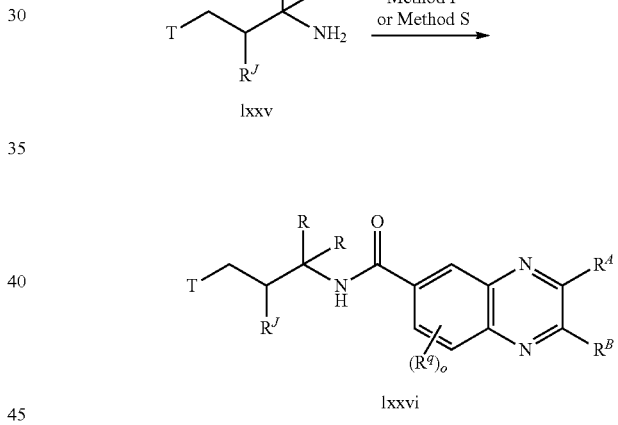
lxxvi

Scheme 17 shows general procedure for the synthesis of analogs lxxvi. Suitably protected (for example with a Boc protecting group (PG)) allylamine lxxii is converted to a boronic acid containing compound via hydroboration with a suitable reagent, such as 9-BBN in a suitable solvent, for example THF, followed by treatment with sodium hydroxide (Method X). The intermediate boronic acid can be coupled with aryl/heteroaryl halide lxxiii using Suzuki conditions, such as $Pd(PPh_3)_4$ in a suitable solvent, for example THF at elevated temperature (Method D) to provide compound lxxiv. Deprotection of lxxiv to lxxv can be carried out using suitable deprotection conditions, for example TFA in DCM for the Boc group (Method Y). The resulting amine lxxv can then be transformed to amide lxxvi using Methods F or S described above.

Examples

Table 1 below depicts certain compounds represented by compounds of formula I.

TABLE 1
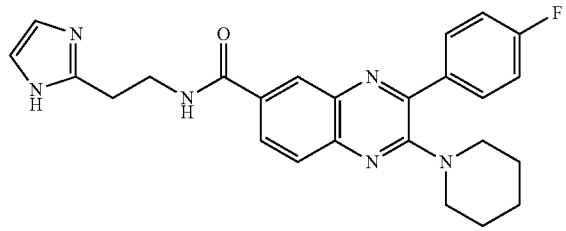 [SMILES: O=C(NCCc1ncc[nH]1)c1ccc2nc(N3CCCCC3)c(-c3ccc(F)cc3)nc2c1] I-1
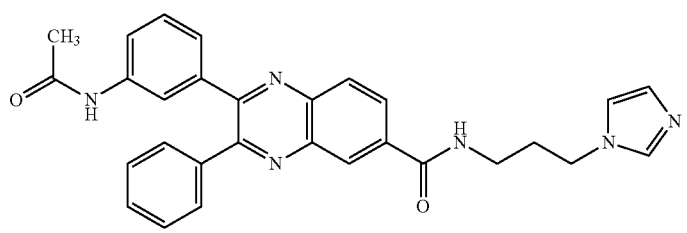 [SMILES: CC(=O)Nc1cccc(-c2nc3ccc(C(=O)NCCCn4ccnc4)cc3nc2-c2ccccc2)c1] I-2
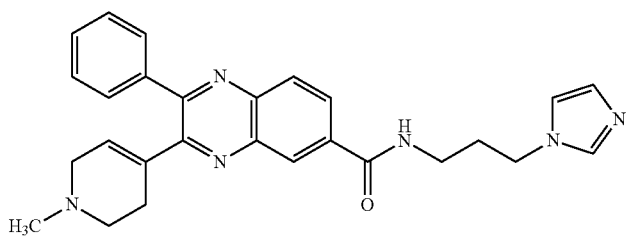 [SMILES: CN1CC=C(c2nc3cc(C(=O)NCCCn4ccnc4)ccc3nc2-c2ccccc2)CC1] I-3
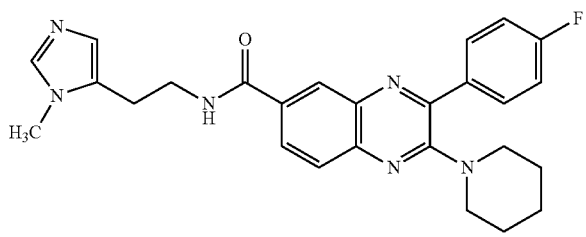 [SMILES: Cn1cncc1CCNC(=O)c1ccc2nc(N3CCCCC3)c(-c3ccc(F)cc3)nc2c1] I-4
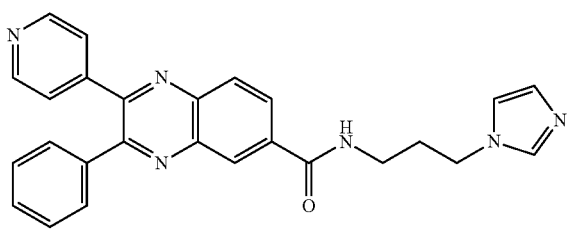 [SMILES: O=C(NCCCn1ccnc1)c1ccc2nc(-c3ccncc3)c(-c3ccccc3)nc2c1] I-5
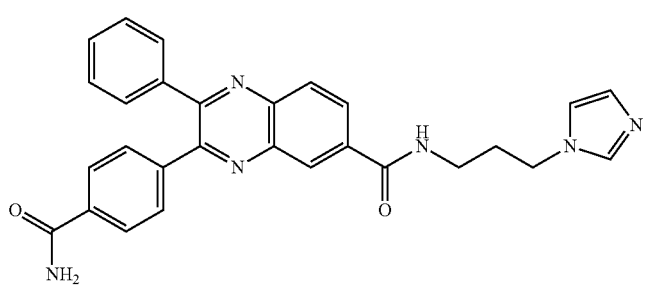 [SMILES: NC(=O)c1ccc(-c2nc3cc(C(=O)NCCCn4ccnc4)ccc3nc2-c2ccccc2)cc1] I-6

TABLE 1-continued
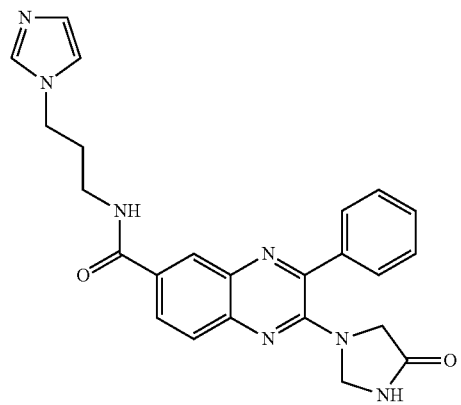 [SMILES: O=C1CN(c2nc3ccc(C(=O)NCCCn4ccnc4)cc3nc2-c2ccccc2)CN1]
I-7
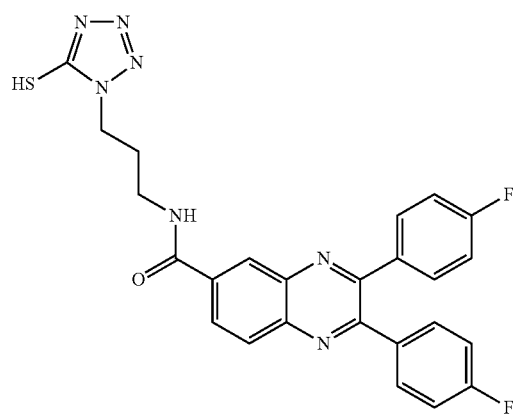 [SMILES: O=C(NCCCn1nnnc1S)c1ccc2nc(-c3ccc(F)cc3)c(-c3ccc(F)cc3)nc2c1]
I-8
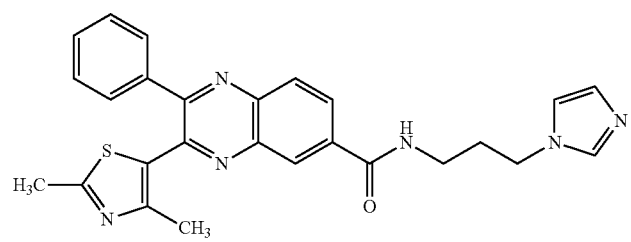 [SMILES: Cc1nc(C)c(-c2nc3cc(C(=O)NCCCn4ccnc4)ccc3nc2-c2ccccc2)s1]
I-9
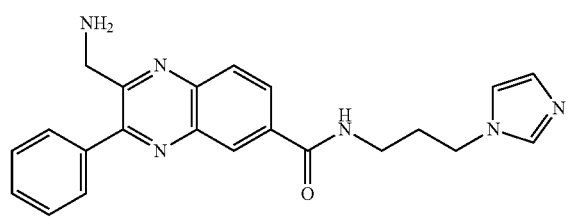 [SMILES: NCc1nc2ccc(C(=O)NCCCn3ccnc3)cc2nc1-c1ccccc1]
I-10

TABLE 1-continued
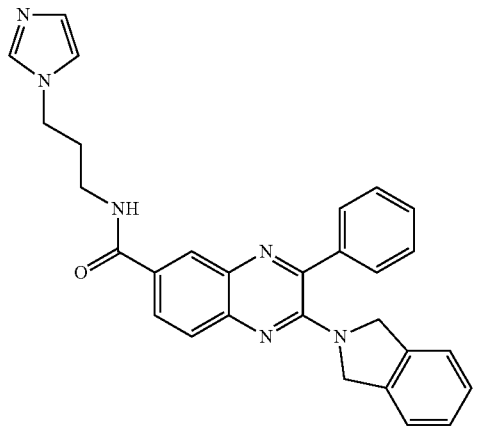 [SMILES: O=C(NCCCn1ccnc1)c1ccc2nc(N3Cc4ccccc4C3)c(-c3ccccc3)nc2c1]
I-11
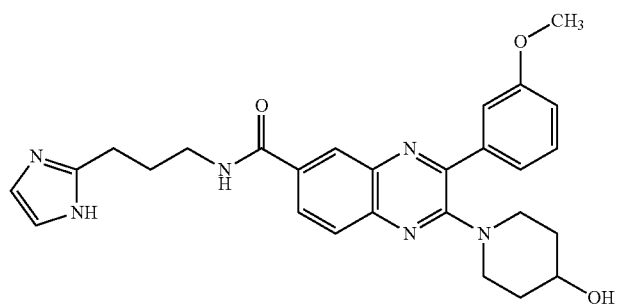 [SMILES: COc1cccc(-c2nc3cc(C(=O)NCCCc4ncc[nH]4)ccc3nc2N2CCC(O)CC2)c1]
I-12
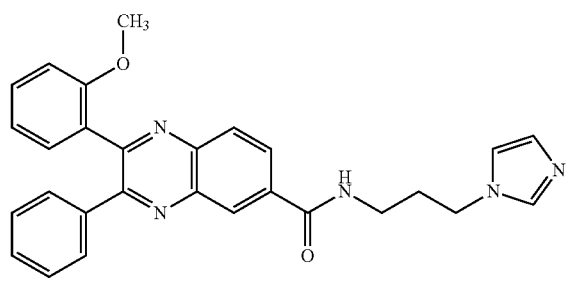 [SMILES: COc1ccccc1-c1nc2ccc(C(=O)NCCCn3ccnc3)cc2nc1-c1ccccc1]
I-13
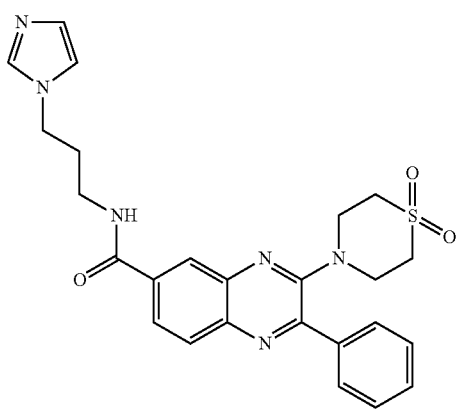 [SMILES: O=C(NCCCn1ccnc1)c1ccc2nc(-c3ccccc3)c(N3CCS(=O)(=O)CC3)nc2c1]
I-14

TABLE 1-continued
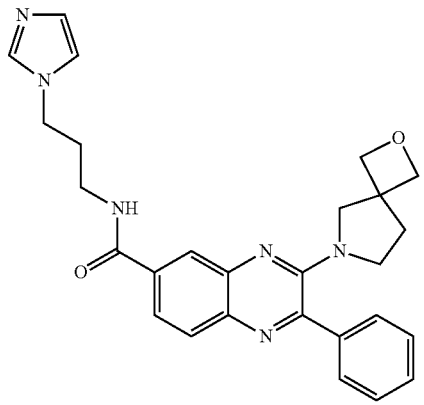 [SMILES: O=C(NCCCn1ccnc1)c1ccc2nc(-c3ccccc3)c(N3CCC4(COC4)C3)nc2c1]
I-15
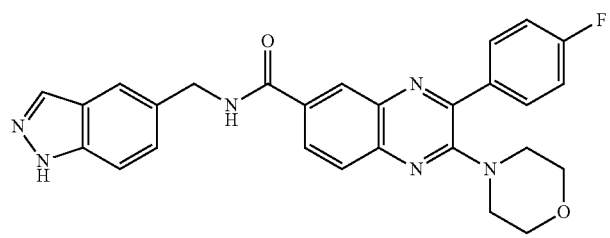
I-16
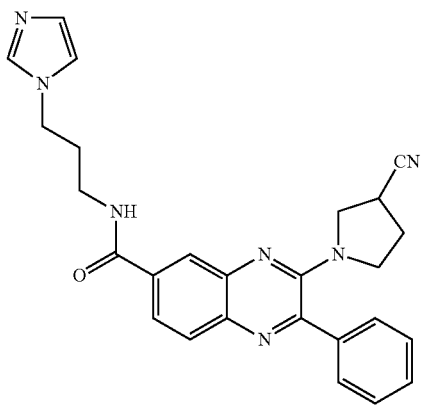 [SMILES: N#CC1CCN(c2nc3cc(C(=O)NCCCn4ccnc4)ccc3nc2-c2ccccc2)C1]
I-17
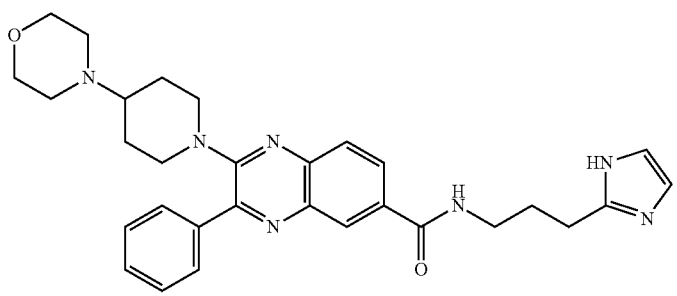 [SMILES: O=C(NCCCc1ncc[nH]1)c1ccc2nc(N3CCC(N4CCOCC4)CC3)c(-c3ccccc3)nc2c1]
I-18
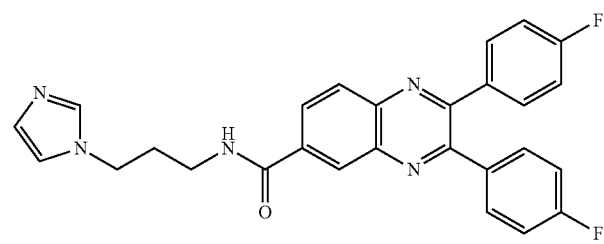 [SMILES: O=C(NCCCn1ccnc1)c1ccc2nc(-c3ccc(F)cc3)c(-c3ccc(F)cc3)nc2c1]
I-19

TABLE 1-continued
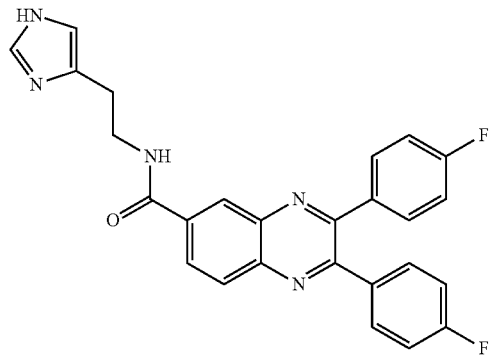 [SMILES: O=C(NCCc1c[nH]cn1)c1ccc2nc(-c3ccc(F)cc3)c(-c3ccc(F)cc3)nc2c1] I-20
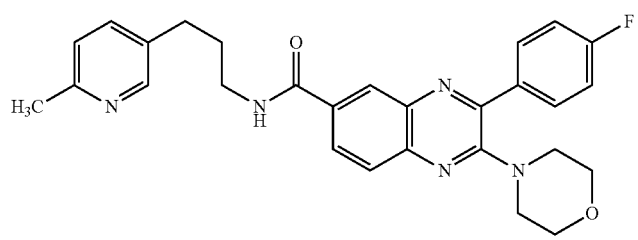 [SMILES: Cc1ccc(CCCNC(=O)c2ccc3nc(N4CCOCC4)c(-c4ccc(F)cc4)nc3c2)cn1] I-21
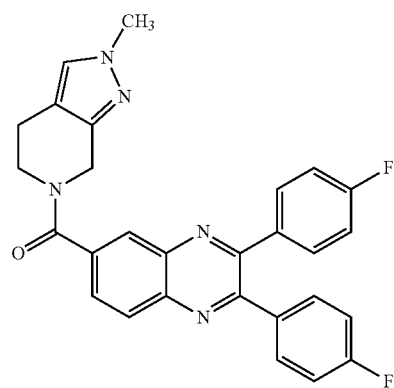 [SMILES: Cn1cc2c(n1)CN(C(=O)c1ccc3nc(-c4ccc(F)cc4)c(-c4ccc(F)cc4)nc3c1)CC2] I-22
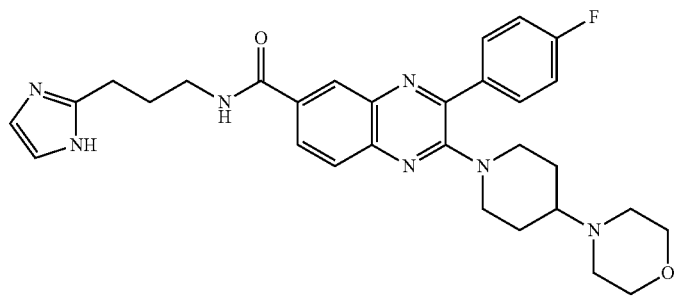 I-23
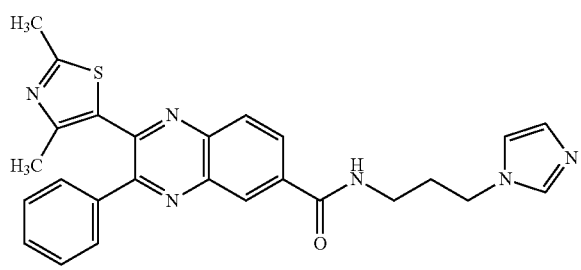 [SMILES: Cc1nc(C)c(-c2nc3ccc(C(=O)NCCCn4ccnc4)cc3nc2-c2ccccc2)s1] I-24

TABLE 1-continued
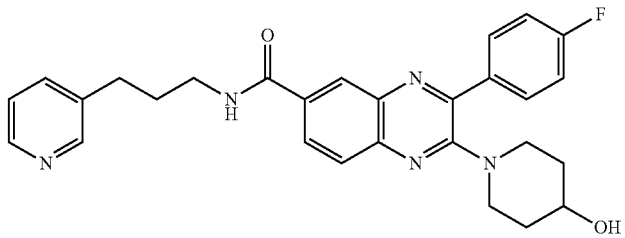 [SMILES: O=C(NCCCc1cccnc1)c1ccc2nc(N3CCC(O)CC3)c(-c3ccc(F)cc3)nc2c1]
I-25
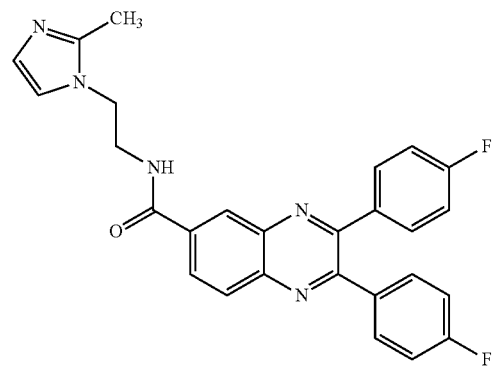 [SMILES: Cc1nccn1CCNC(=O)c1ccc2nc(-c3ccc(F)cc3)c(-c3ccc(F)cc3)nc2c1]
I-26
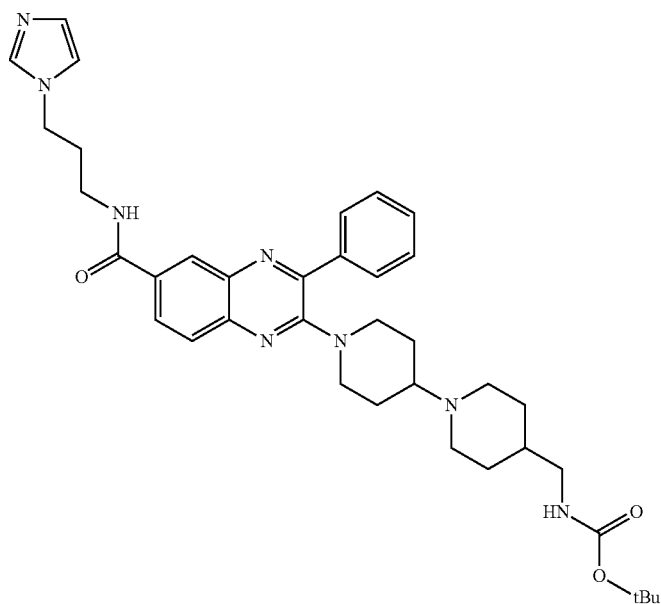 [SMILES: CC(C)(C)OC(=O)NCC1CCN(C2CCN(c3nc4ccc(C(=O)NCCCn5ccnc5)cc4nc3-c3ccccc3)CC2)CC1]
I-27
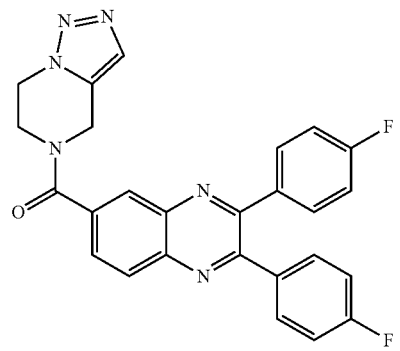 [SMILES: O=C(c1ccc2nc(-c3ccc(F)cc3)c(-c3ccc(F)cc3)nc2c1)N1CCn2nncc2C1]
I-28

TABLE 1-continued
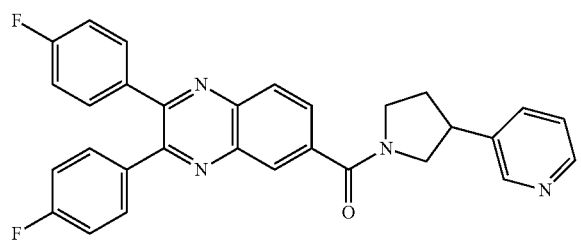 [SMILES: O=C(c1ccc2nc(-c3ccc(F)cc3)c(-c3ccc(F)cc3)nc2c1)N1CCC(c2cccnc2)C1]
I-29
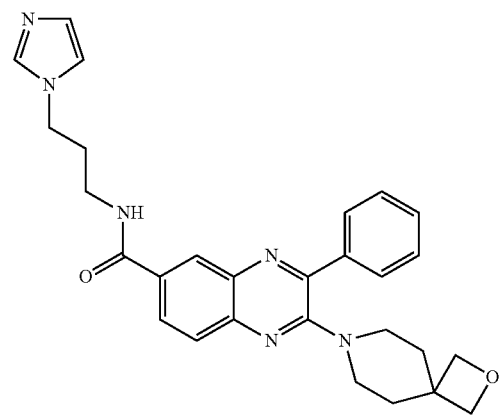 [SMILES: O=C(NCCCn1ccnc1)c1ccc2nc(N3CCC4(CC3)COC4)c(-c3ccccc3)nc2c1]
I-30
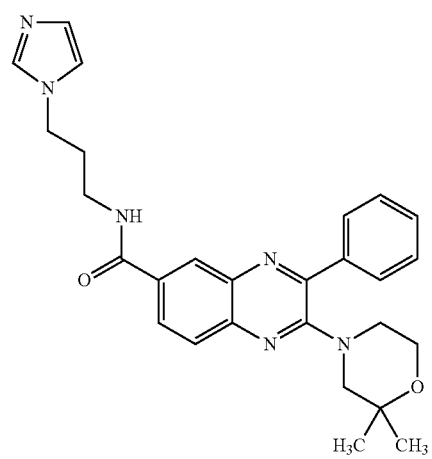 [SMILES: CC1(C)CN(c2nc3ccc(C(=O)NCCCn4ccnc4)cc3nc2-c2ccccc2)CCO1]
I-31
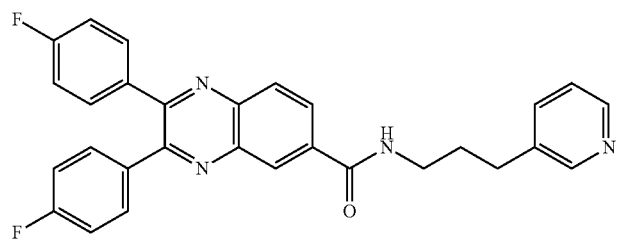 [SMILES: O=C(NCCCc1cccnc1)c1ccc2nc(-c3ccc(F)cc3)c(-c3ccc(F)cc3)nc2c1]
I-32

TABLE 1-continued
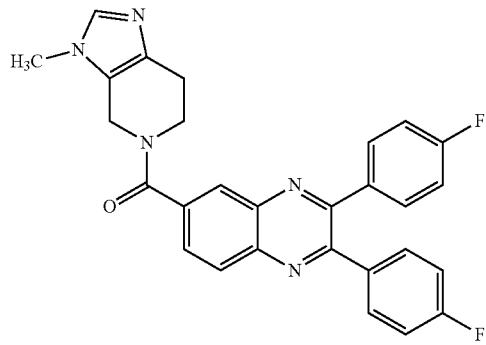 [SMILES: Cn1cnc2c1CN(C(=O)c1ccc3nc(-c4ccc(F)cc4)c(-c4ccc(F)cc4)nc3c1)CC2]
I-33
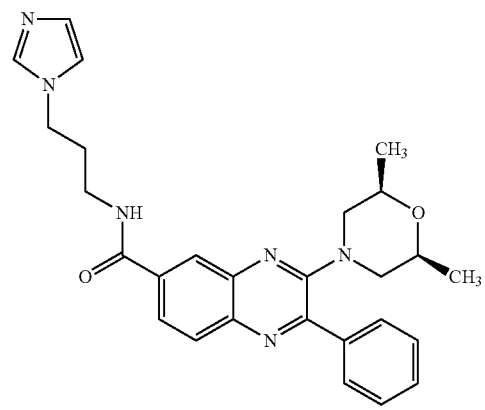 [SMILES: C[C@@H]1CN(c2nc3cc(C(=O)NCCCn4ccnc4)ccc3nc2-c2ccccc2)C[C@H](C)O1]
I-34
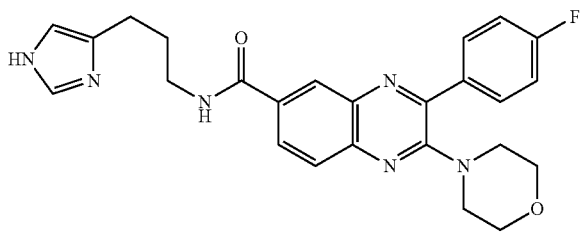 [SMILES: O=C(NCCCc1c[nH]cn1)c1ccc2nc(N3CCOCC3)c(-c3ccc(F)cc3)nc2c1]
I-35
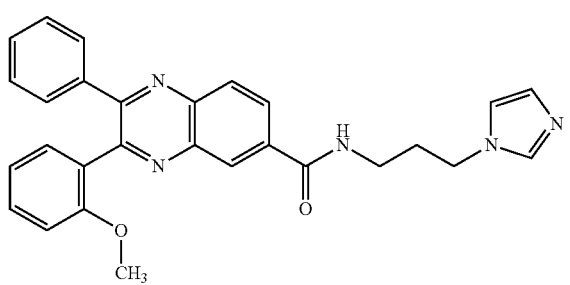 [SMILES: COc1ccccc1-c1nc2cc(C(=O)NCCCn3ccnc3)ccc2nc1-c1ccccc1]
I-36
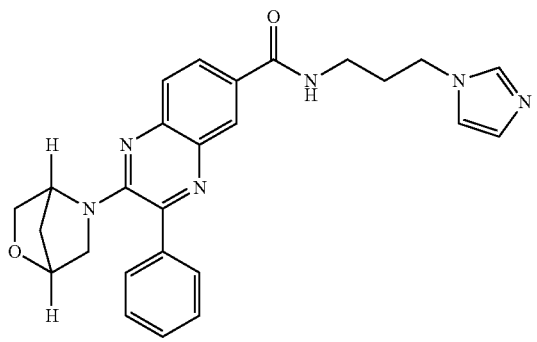 [SMILES: O=C(NCCCn1ccnc1)c1ccc2nc(N3CC4CC3CO4)c(-c3ccccc3)nc2c1]
I-37

TABLE 1-continued
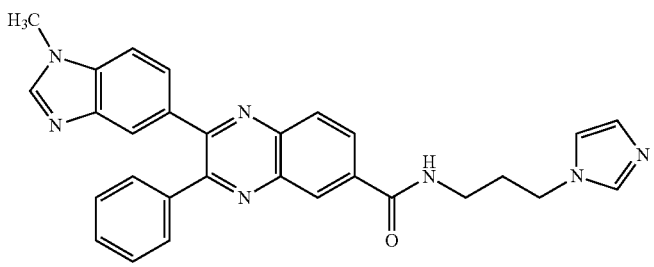 [SMILES: Cn1cnc2cc(-c3nc4ccc(C(=O)NCCCn5ccnc5)cc4nc3-c3ccccc3)ccc21] I-38
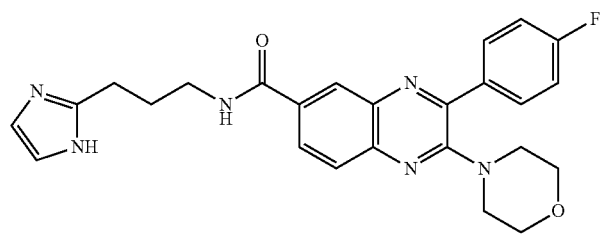 I-39
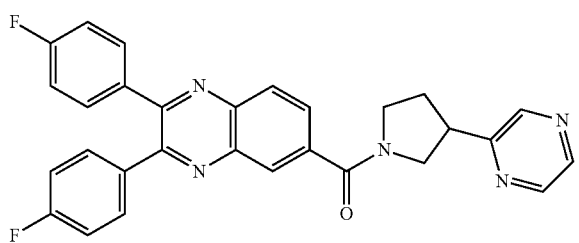 [SMILES: O=C(c1ccc2nc(-c3ccc(F)cc3)c(-c3ccc(F)cc3)nc2c1)N1CCC(c2cnccn2)C1] I-40
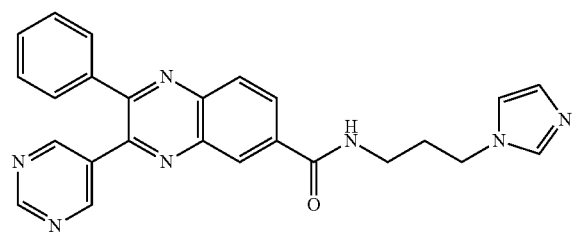 [SMILES: O=C(NCCCn1ccnc1)c1ccc2nc(-c3ccccc3)c(-c3cncnc3)nc2c1] I-41
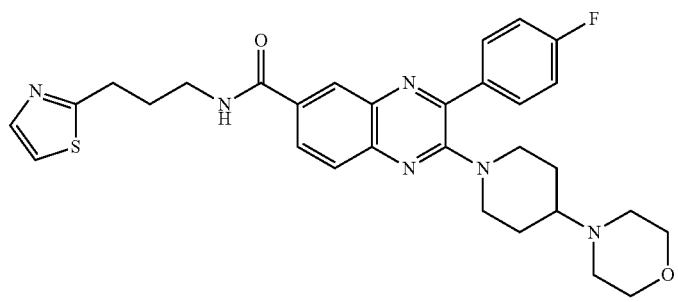 [SMILES: O=C(NCCCc1nccs1)c1ccc2nc(N3CCC(N4CCOCC4)CC3)c(-c3ccc(F)cc3)nc2c1] I-42

TABLE 1-continued
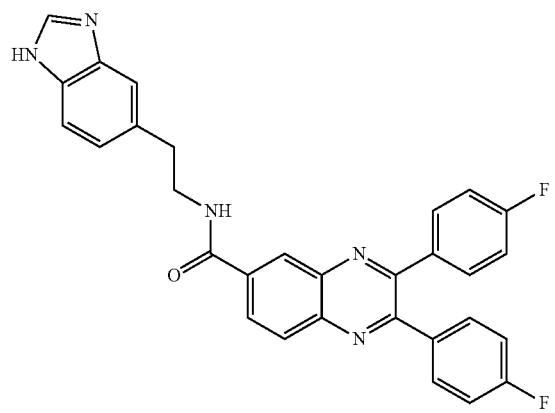 [SMILES: O=C(NCCc1ccc2[nH]cnc2c1)c1ccc2nc(-c3ccc(F)cc3)c(-c3ccc(F)cc3)nc2c1]
I-43
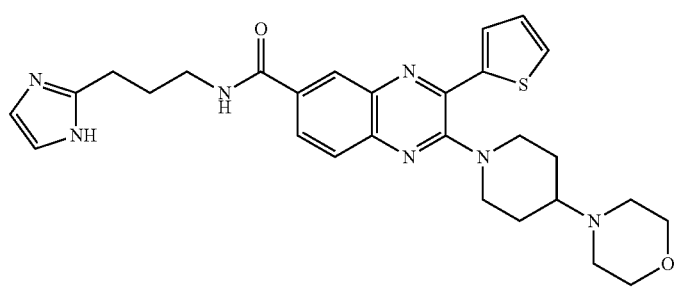 [SMILES: O=C(NCCCc1ncc[nH]1)c1ccc2nc(N3CCC(N4CCOCC4)CC3)c(-c3cccs3)nc2c1]
I-44
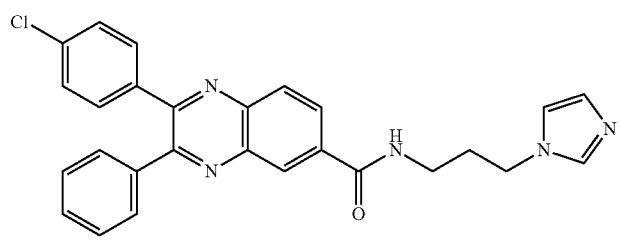 [SMILES: O=C(NCCCn1ccnc1)c1ccc2nc(-c3ccc(Cl)cc3)c(-c3ccccc3)nc2c1]
I-45
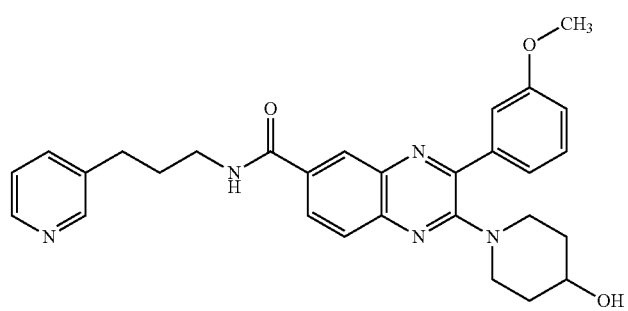 [SMILES: COc1cccc(-c2nc3cc(C(=O)NCCCc4cccnc4)ccc3nc2N2CCC(O)CC2)c1]
I-46
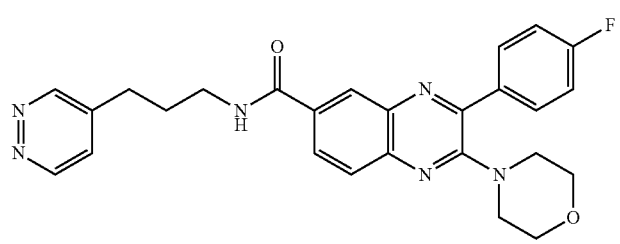 [SMILES: O=C(NCCCc1ccnnc1)c1ccc2nc(N3CCOCC3)c(-c3ccc(F)cc3)nc2c1]
I-47

TABLE 1-continued
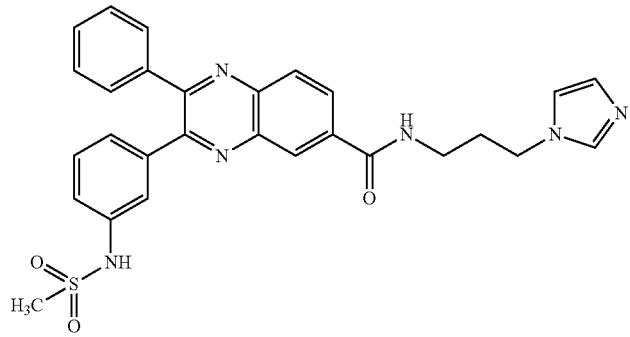 [SMILES: CS(=O)(=O)Nc1cccc(-c2nc3cc(C(=O)NCCCn4ccnc4)ccc3nc2-c2ccccc2)c1]
I-48
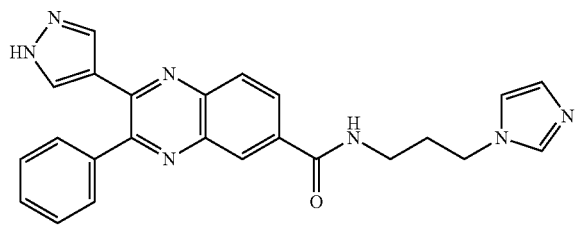 [SMILES: O=C(NCCCn1ccnc1)c1ccc2nc(-c3cn[nH]c3)c(-c3ccccc3)nc2c1]
I-49
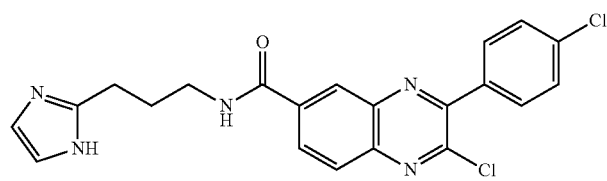 [SMILES: O=C(NCCCc1ncc[nH]1)c1ccc2nc(Cl)c(-c3ccc(Cl)cc3)nc2c1]
I-50
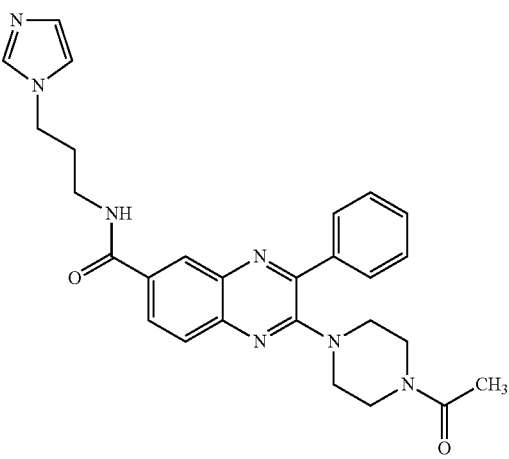 [SMILES: CC(=O)N1CCN(c2nc3ccc(C(=O)NCCCn4ccnc4)cc3nc2-c2ccccc2)CC1]
I-51
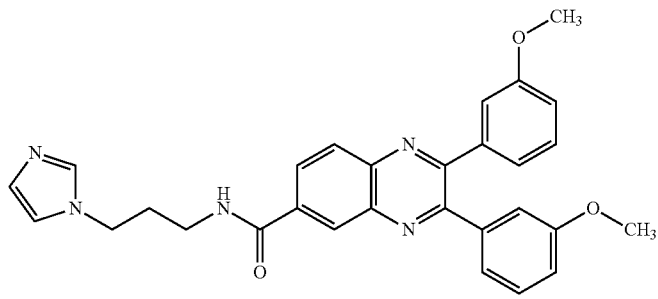 [SMILES: COc1cccc(-c2nc3ccc(C(=O)NCCCn4ccnc4)cc3nc2-c2cccc(OC)c2)c1]
I-52

TABLE 1-continued
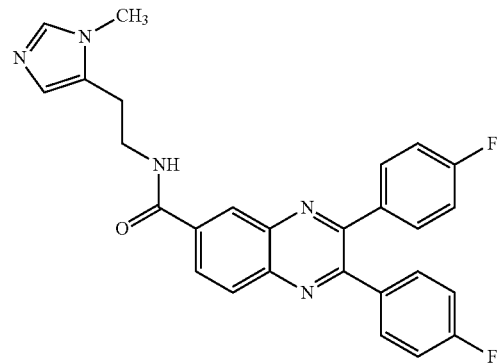 [SMILES: Cn1cncc1CCNC(=O)c1ccc2nc(-c3ccc(F)cc3)c(-c3ccc(F)cc3)nc2c1]
I-53
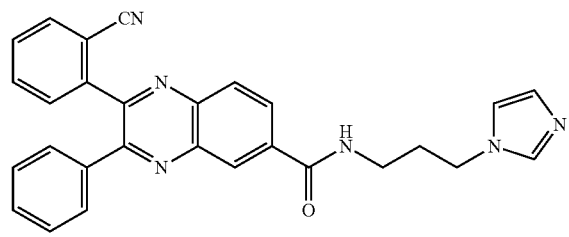 [SMILES: N#Cc1ccccc1-c1nc2ccc(C(=O)NCCCn3ccnc3)cc2nc1-c1ccccc1]
I-54
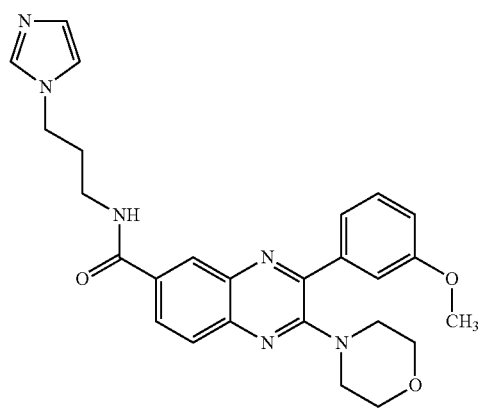 [SMILES: COc1cccc(-c2nc3cc(C(=O)NCCCn4ccnc4)ccc3nc2N2CCOCC2)c1]
I-55
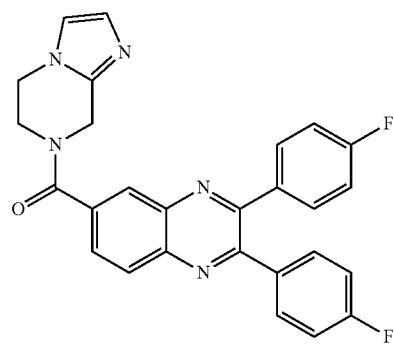 [SMILES: O=C(c1ccc2nc(-c3ccc(F)cc3)c(-c3ccc(F)cc3)nc2c1)N1CCn2ccnc2C1]
I-56

TABLE 1-continued
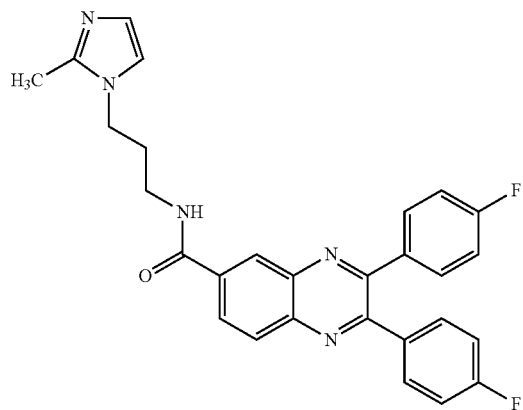 [SMILES: Cc1nccn1CCCNC(=O)c1ccc2nc(-c3ccc(F)cc3)c(-c3ccc(F)cc3)nc2c1]
I-57
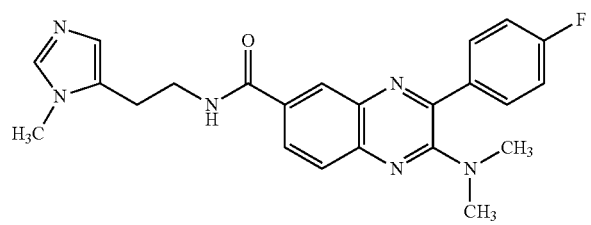 [SMILES: CN(C)c1nc2ccc(C(=O)NCCc3cncn3C)cc2nc1-c1ccc(F)cc1]
I-58
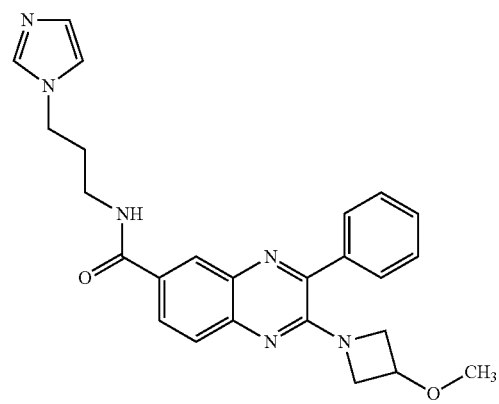 [SMILES: COC1CN(c2nc3ccc(C(=O)NCCCn4ccnc4)cc3nc2-c2ccccc2)C1]
I-59
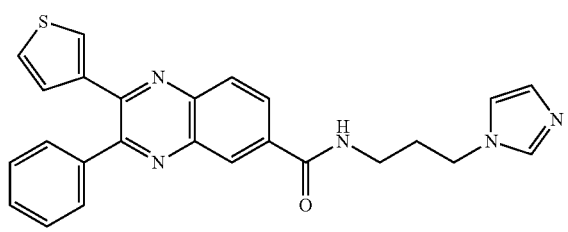 [SMILES: O=C(NCCCn1ccnc1)c1ccc2nc(-c3ccsc3)c(-c3ccccc3)nc2c1]
I-60
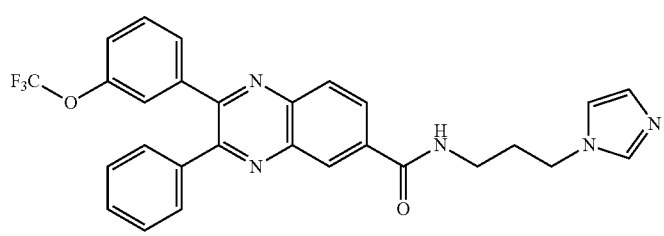 [SMILES: O=C(NCCCn1ccnc1)c1ccc2nc(-c3cccc(OC(F)(F)F)c3)c(-c3ccccc3)nc2c1]
I-61

TABLE 1-continued
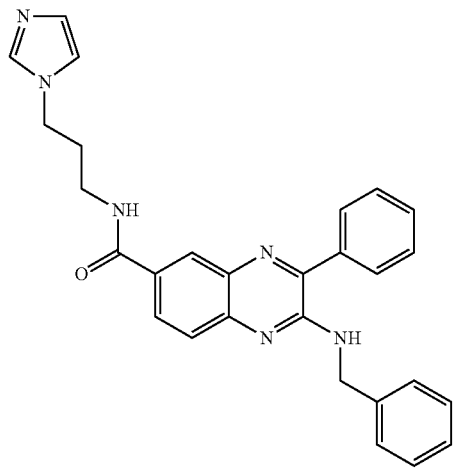 [SMILES: O=C(NCCCn1ccnc1)c1ccc2nc(NCc3ccccc3)c(-c3ccccc3)nc2c1]
I-62
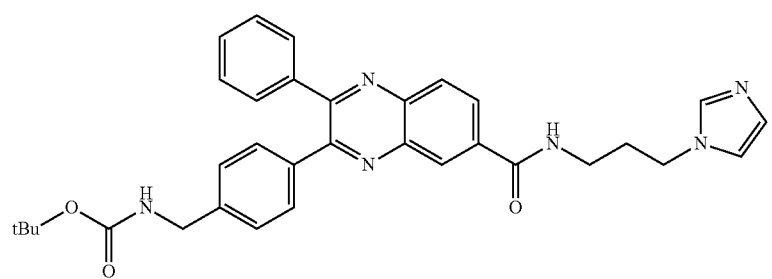 [SMILES: CC(C)(C)OC(=O)NCc1ccc(-c2nc3cc(C(=O)NCCCn4ccnc4)ccc3nc2-c2ccccc2)cc1]
I-63
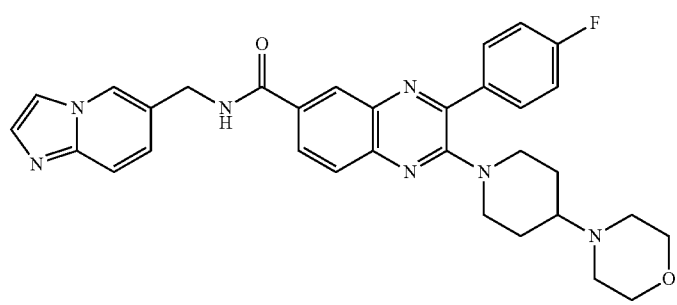 [SMILES: O=C(NCc1ccc2nccn2c1)c1ccc2nc(N3CCC(N4CCOCC4)CC3)c(-c3ccc(F)cc3)nc2c1]
I-64
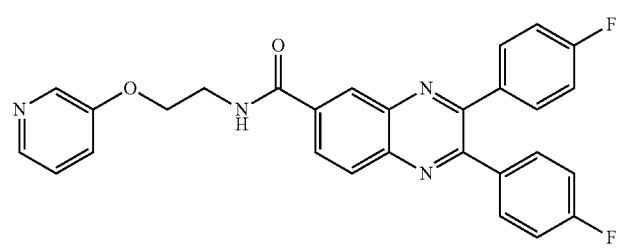 [SMILES: O=C(NCCOc1cccnc1)c1ccc2nc(-c3ccc(F)cc3)c(-c3ccc(F)cc3)nc2c1]
I-65

TABLE 1-continued
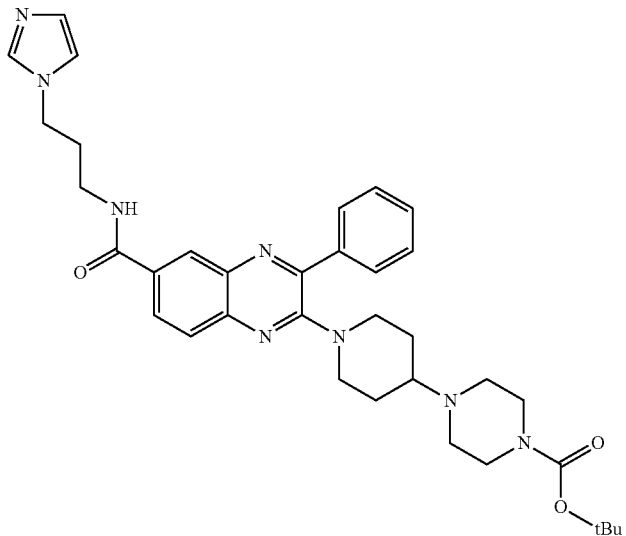 [SMILES: CC(C)(C)OC(=O)N1CCN(C2CCN(c3nc4ccc(C(=O)NCCCn5ccnc5)cc4nc3-c3ccccc3)CC2)CC1]
I-66
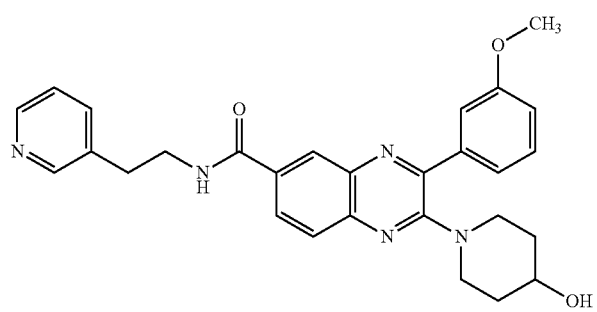 [SMILES: COc1cccc(-c2nc3cc(C(=O)NCCc4cccnc4)ccc3nc2N2CCC(O)CC2)c1]
I-67
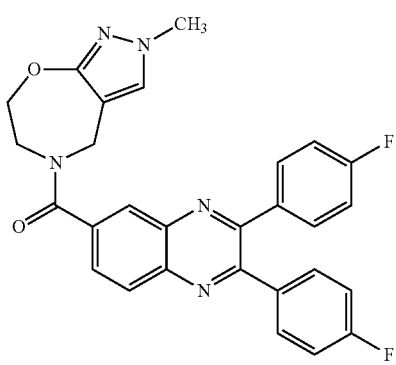 [SMILES: Cn1cc2c(n1)OCCN(C(=O)c1ccc3nc(-c4ccc(F)cc4)c(-c4ccc(F)cc4)nc3c1)C2]
I-68
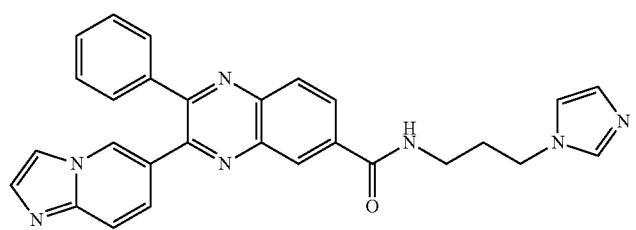 [SMILES: O=C(NCCCn1ccnc1)c1ccc2nc(-c3ccccc3)c(-c3ccc4nccn4c3)nc2c1]
I-69

TABLE 1-continued
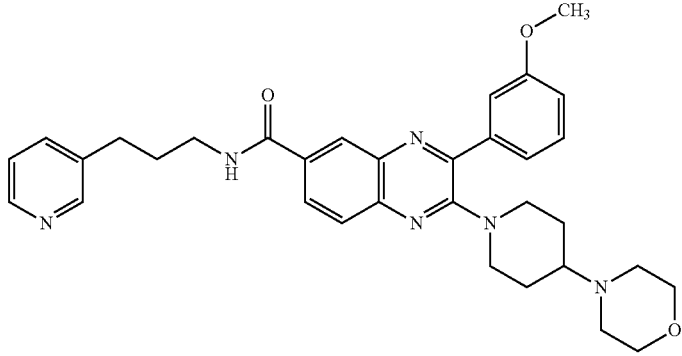 [SMILES: COc1cccc(-c2nc3cc(C(=O)NCCCc4cccnc4)ccc3nc2N2CCC(N3CCOCC3)CC2)c1]
I-70
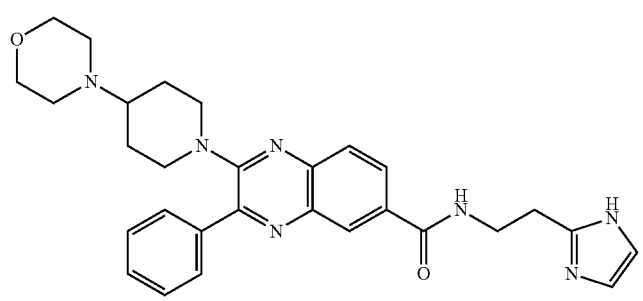 [SMILES: O=C(NCCc1ncc[nH]1)c1ccc2nc(N3CCC(N4CCOCC4)CC3)c(-c3ccccc3)nc2c1]
I-71
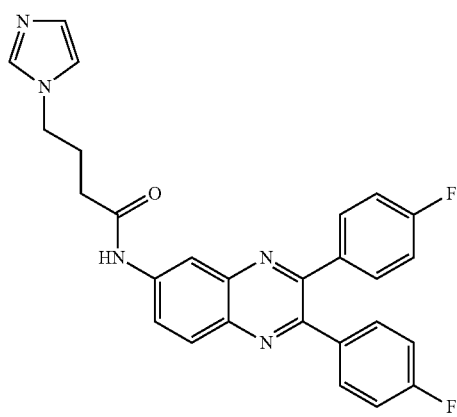 [SMILES: O=C(CCCn1ccnc1)Nc1ccc2nc(-c3ccc(F)cc3)c(-c3ccc(F)cc3)nc2c1]
I-72
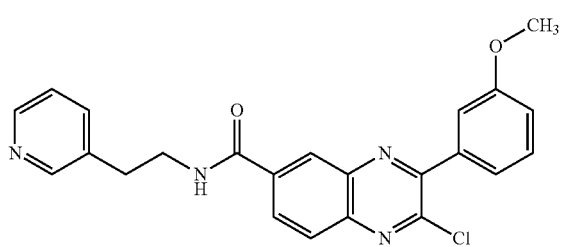 [SMILES: COc1cccc(-c2nc3cc(C(=O)NCCc4cccnc4)ccc3nc2Cl)c1]
I-73

TABLE 1-continued
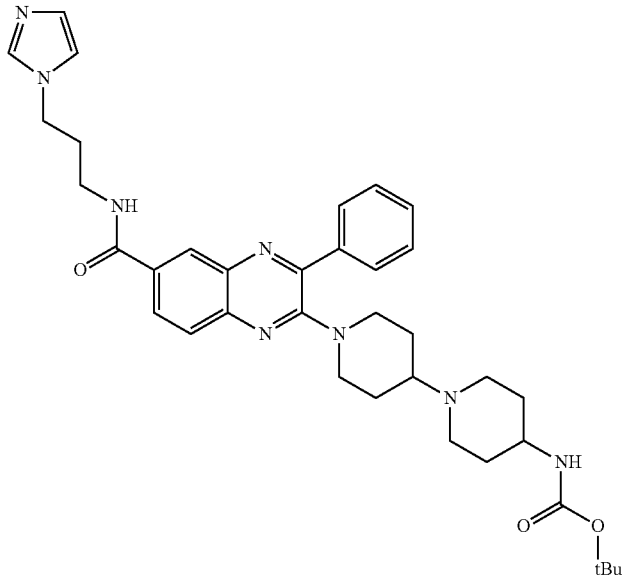 [SMILES: CC(C)(C)OC(=O)NC1CCN(C2CCN(c3nc4ccc(C(=O)NCCCn5ccnc5)cc4nc3-c3ccccc3)CC2)CC1]
I-74
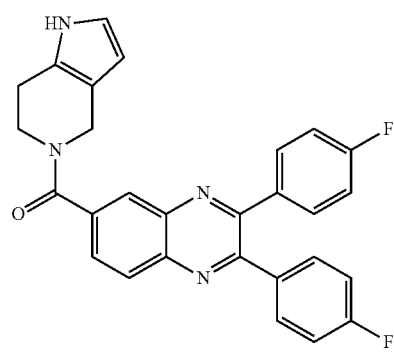 [SMILES: O=C(c1ccc2nc(-c3ccc(F)cc3)c(-c3ccc(F)cc3)nc2c1)N1CCc2[nH]ccc2C1]
I-75
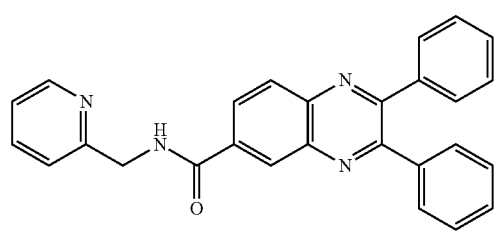 [SMILES: O=C(NCc1ccccn1)c1ccc2nc(-c3ccccc3)c(-c3ccccc3)nc2c1]
I-76
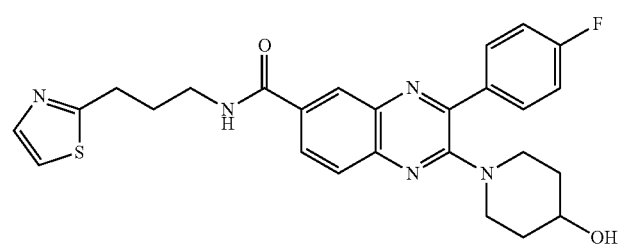 [SMILES: O=C(NCCCc1nccs1)c1ccc2nc(N3CCC(O)CC3)c(-c3ccc(F)cc3)nc2c1]
I-77
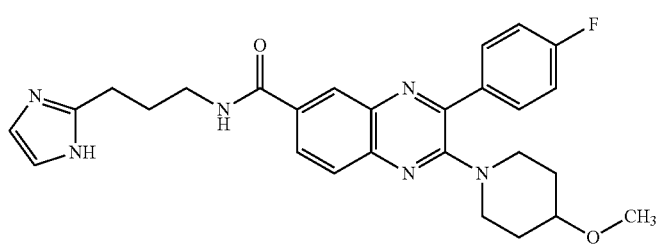 [SMILES: COC1CCN(c2nc3ccc(C(=O)NCCCc4ncc[nH]4)cc3nc2-c2ccc(F)cc2)CC1]
I-78

TABLE 1-continued
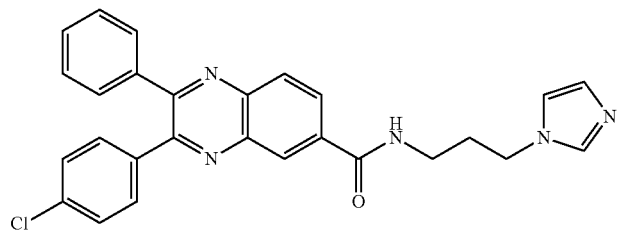 [SMILES: O=C(NCCCn1ccnc1)c1ccc2nc(-c3ccccc3)c(-c3ccc(Cl)cc3)nc2c1]
I-79
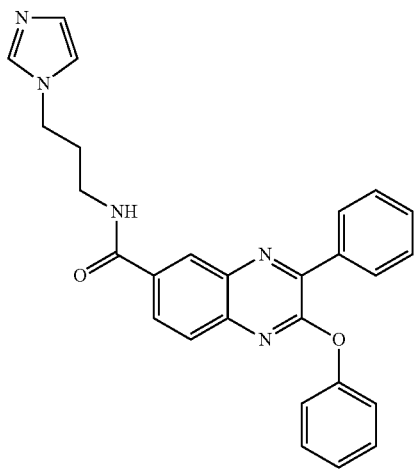 [SMILES: O=C(NCCCn1ccnc1)c1ccc2nc(Oc3ccccc3)c(-c3ccccc3)nc2c1]
I-80
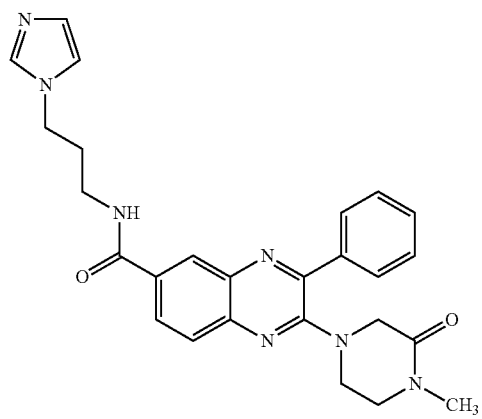 [SMILES: CN1CCN(c2nc3ccc(C(=O)NCCCn4ccnc4)cc3nc2-c2ccccc2)CC1=O]
I-81
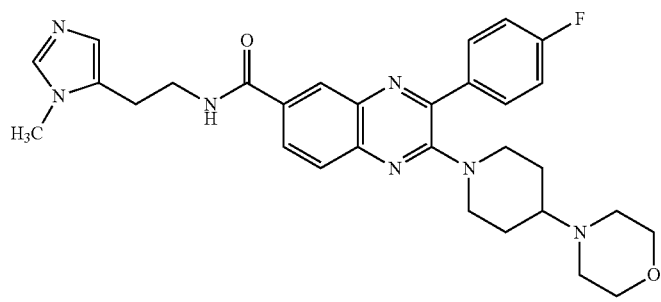 [SMILES: Cn1cncc1CCNC(=O)c1ccc2nc(N3CCC(N4CCOCC4)CC3)c(-c3ccc(F)cc3)nc2c1]
I-82

TABLE 1-continued
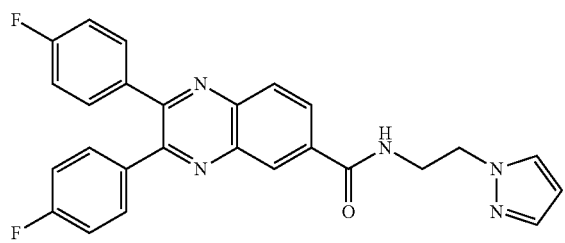 [SMILES: O=C(NCCn1cccn1)c1ccc2nc(-c3ccc(F)cc3)c(-c3ccc(F)cc3)nc2c1]
I-83
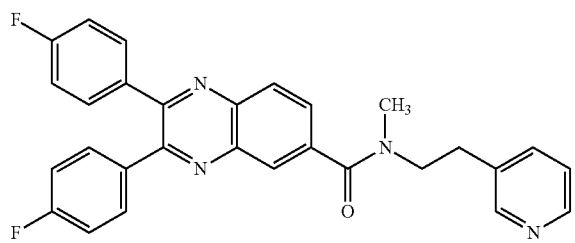 [SMILES: CN(CCc1cccnc1)C(=O)c1ccc2nc(-c3ccc(F)cc3)c(-c3ccc(F)cc3)nc2c1]
I-84
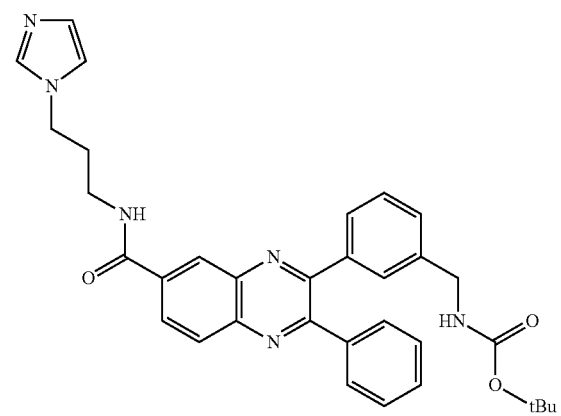 [SMILES: CC(C)(C)OC(=O)NCc1cccc(-c2nc3cc(C(=O)NCCCn4ccnc4)ccc3nc2-c2ccccc2)c1]
I-85
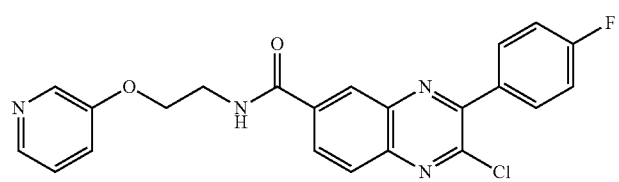 [SMILES: O=C(NCCOc1cccnc1)c1ccc2nc(Cl)c(-c3ccc(F)cc3)nc2c1]
I-86
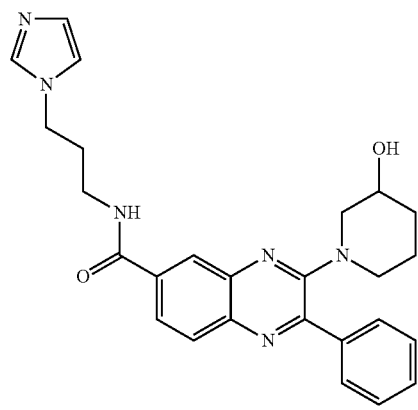 [SMILES: O=C(NCCCn1ccnc1)c1ccc2nc(-c3ccccc3)c(N3CCCC(O)C3)nc2c1]
I-87

TABLE 1-continued
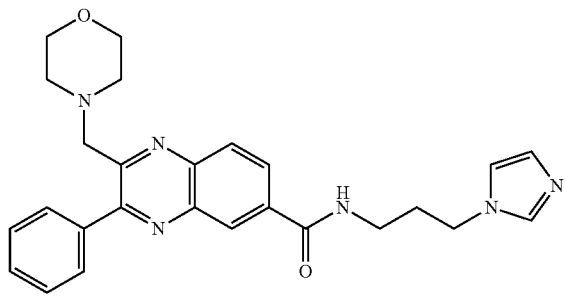 [SMILES: O=C(NCCCn1ccnc1)c1ccc2nc(CN3CCOCC3)c(-c3ccccc3)nc2c1]
I-88
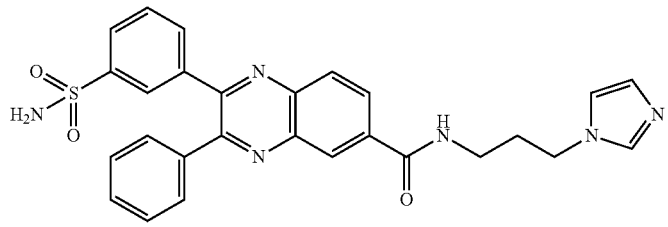 [SMILES: NS(=O)(=O)c1cccc(-c2nc3ccc(C(=O)NCCCn4ccnc4)cc3nc2-c2ccccc2)c1]
I-89
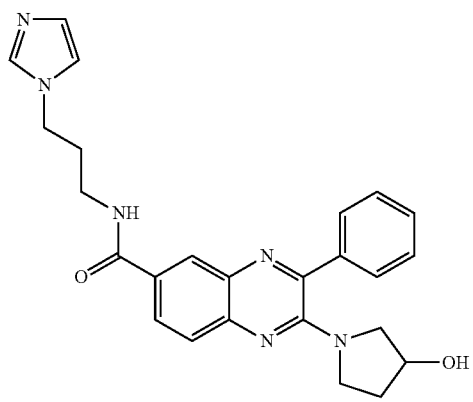
I-90
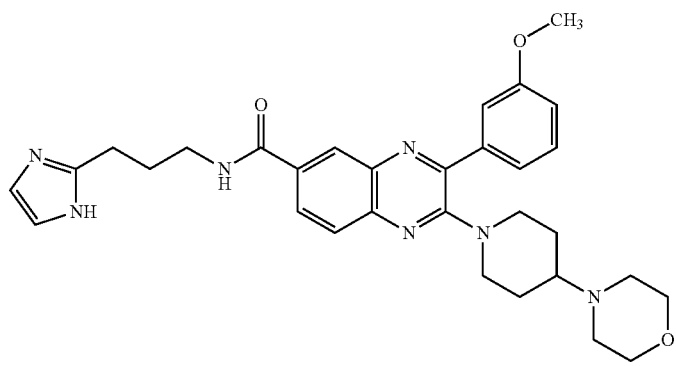 [SMILES: COc1cccc(-c2nc3cc(C(=O)NCCCc4ncc[nH]4)ccc3nc2N2CCC(N3CCOCC3)CC2)c1]
I-91
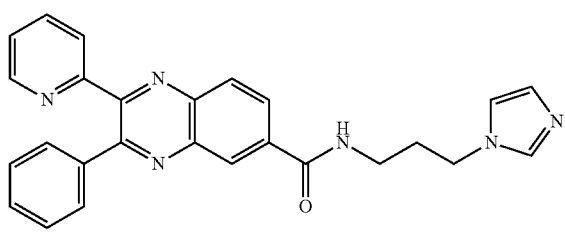 [SMILES: O=C(NCCCn1ccnc1)c1ccc2nc(-c3ccccn3)c(-c3ccccc3)nc2c1]
I-92

TABLE 1-continued
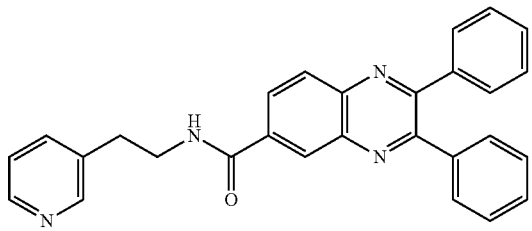 [SMILES: O=C(NCCc1cccnc1)c1ccc2nc(-c3ccccc3)c(-c3ccccc3)nc2c1]
I-93
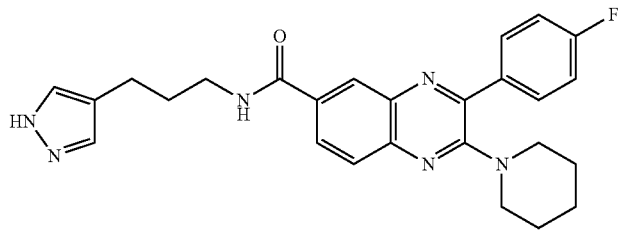 [SMILES: O=C(NCCCc1cn[nH]c1)c1ccc2nc(N3CCCCC3)c(-c3ccc(F)cc3)nc2c1]
I-94
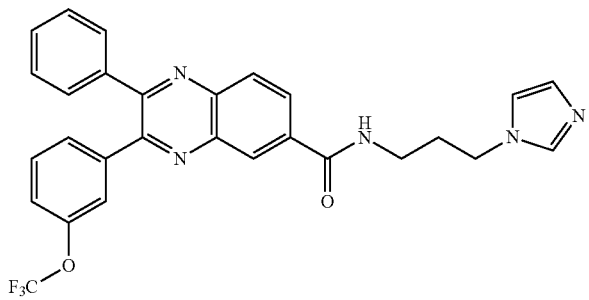 [SMILES: O=C(NCCCn1ccnc1)c1ccc2nc(-c3ccccc3)c(-c3cccc(OC(F)(F)F)c3)nc2c1]
I-95
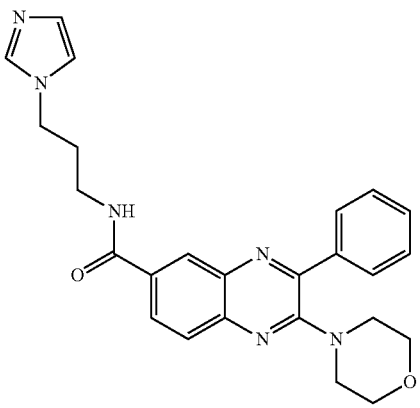 [SMILES: O=C(NCCCn1ccnc1)c1ccc2nc(N3CCOCC3)c(-c3ccccc3)nc2c1]
I-96
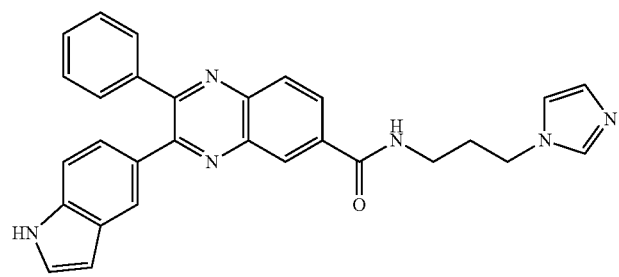 [SMILES: O=C(NCCCn1ccnc1)c1ccc2nc(-c3ccccc3)c(-c3ccc4[nH]ccc4c3)nc2c1]
I-97

TABLE 1-continued
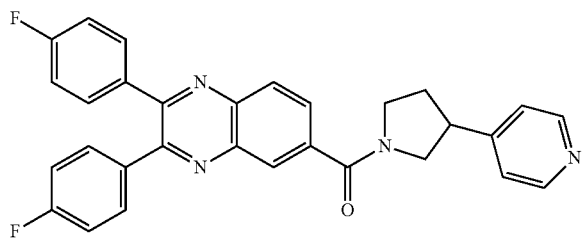 [SMILES: O=C(c1ccc2nc(-c3ccc(F)cc3)c(-c3ccc(F)cc3)nc2c1)N1CCC(c2ccncc2)C1]
I-98
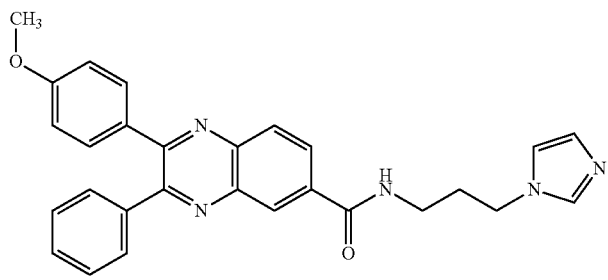 [SMILES: COc1ccc(-c2nc3ccc(C(=O)NCCCn4ccnc4)cc3nc2-c2ccccc2)cc1]
I-99
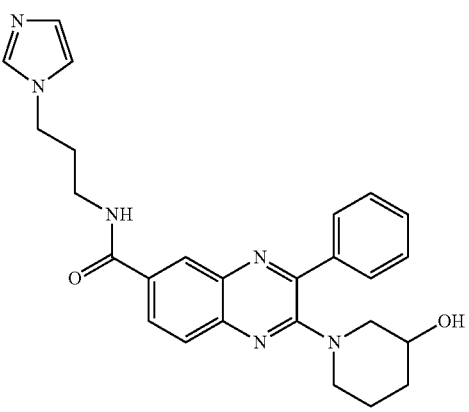 [SMILES: O=C(NCCCn1ccnc1)c1ccc2nc(N3CCCC(O)C3)c(-c3ccccc3)nc2c1]
I-100
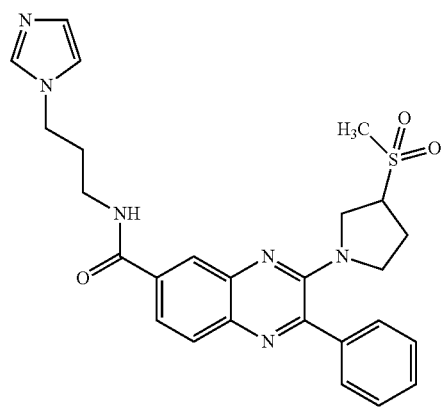 [SMILES: CS(=O)(=O)C1CCN(c2nc3cc(C(=O)NCCCn4ccnc4)ccc3nc2-c2ccccc2)C1]
I-101
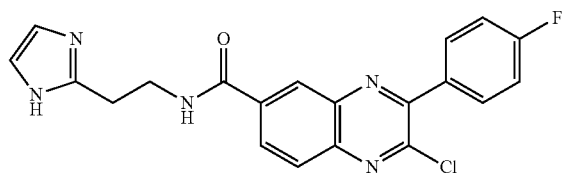 [SMILES: O=C(NCCc1ncc[nH]1)c1ccc2nc(Cl)c(-c3ccc(F)cc3)nc2c1]
I-102

TABLE 1-continued
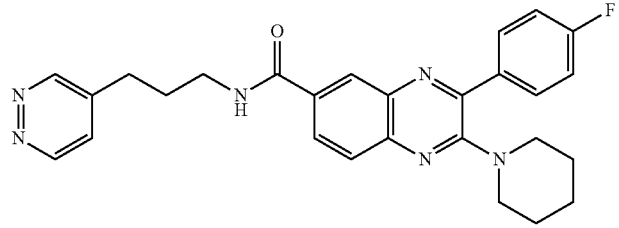 [SMILES: O=C(NCCCc1ccnnc1)c1ccc2nc(N3CCCCC3)c(-c3ccc(F)cc3)nc2c1] I-103
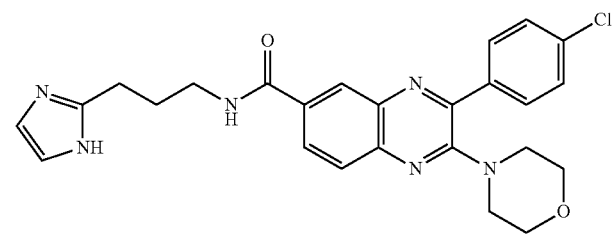 [SMILES: O=C(NCCCc1ncc[nH]1)c1ccc2nc(N3CCOCC3)c(-c3ccc(Cl)cc3)nc2c1] I-104
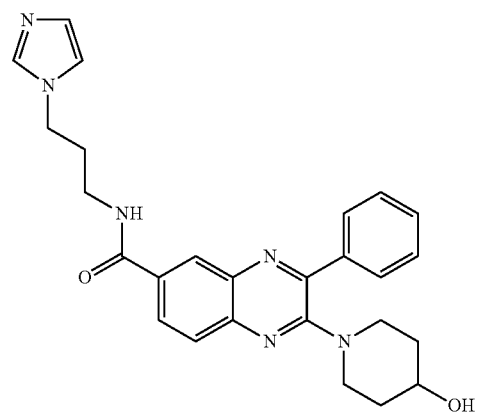 [SMILES: O=C(NCCCn1ccnc1)c1ccc2nc(N3CCC(O)CC3)c(-c3ccccc3)nc2c1] I-105
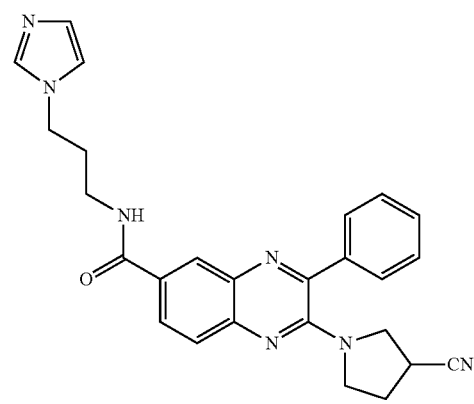 [SMILES: N#CC1CCN(c2nc3ccc(C(=O)NCCCn4ccnc4)cc3nc2-c2ccccc2)C1] I-106
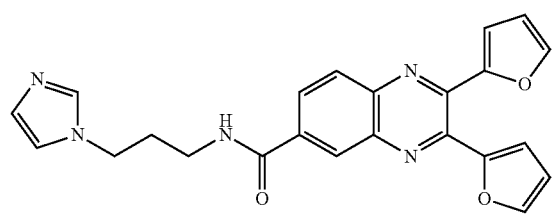 [SMILES: O=C(NCCCn1ccnc1)c1ccc2nc(-c3ccco3)c(-c3ccco3)nc2c1] I-107

TABLE 1-continued
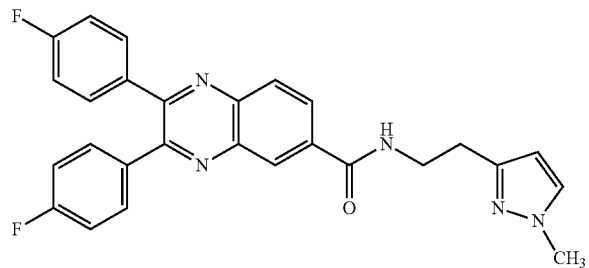 [SMILES: Cn1ccc(CCNC(=O)c2ccc3nc(-c4ccc(F)cc4)c(-c4ccc(F)cc4)nc3c2)n1] I-108
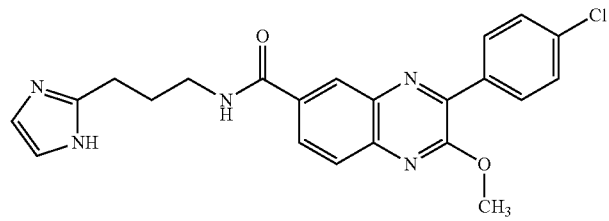 [SMILES: COc1nc2ccc(C(=O)NCCCc3ncc[nH]3)cc2nc1-c1ccc(Cl)cc1] I-109
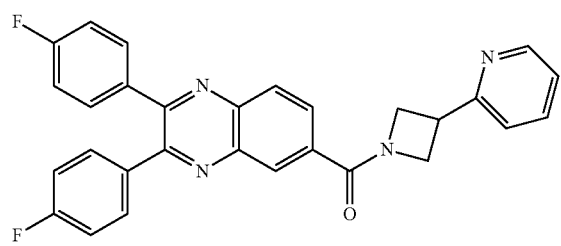 [SMILES: O=C(c1ccc2nc(-c3ccc(F)cc3)c(-c3ccc(F)cc3)nc2c1)N1CC(c2ccccn2)C1] I-110
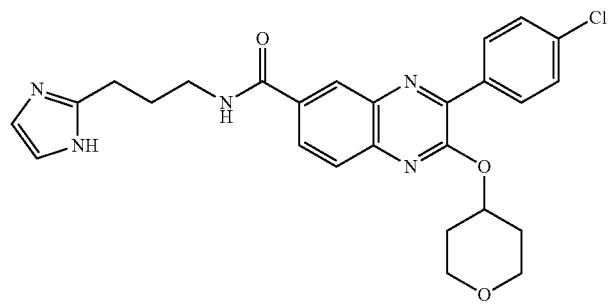 [SMILES: O=C(NCCCc1ncc[nH]1)c1ccc2nc(OC3CCOCC3)c(-c3ccc(Cl)cc3)nc2c1] I-111
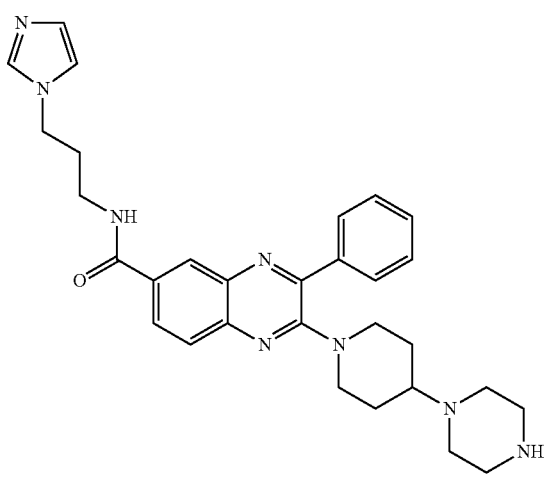 [SMILES: O=C(NCCCn1ccnc1)c1ccc2nc(N3CCC(N4CCNCC4)CC3)c(-c3ccccc3)nc2c1] I-112

TABLE 1-continued
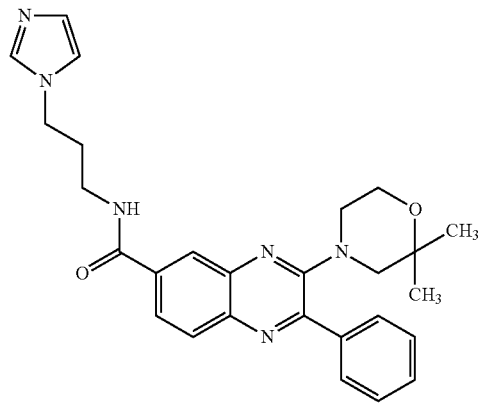 [SMILES: CC1(C)CN(c2nc3cc(C(=O)NCCCn4ccnc4)ccc3nc2-c2ccccc2)CCO1]
I-113
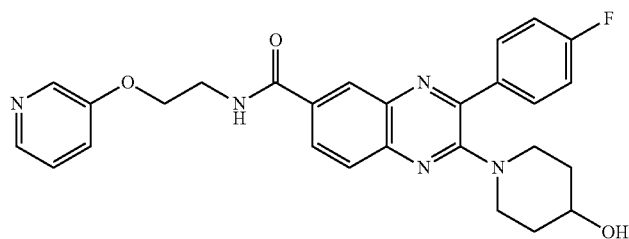 [SMILES: O=C(NCCOc1cccnc1)c1ccc2nc(N3CCC(O)CC3)c(-c3ccc(F)cc3)nc2c1]
I-114
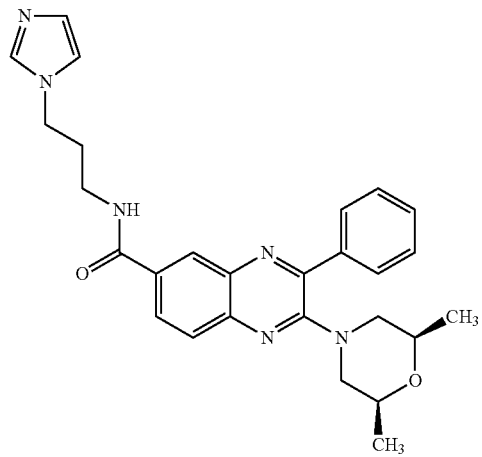 [SMILES: C[C@@H]1CN(c2nc3ccc(C(=O)NCCCn4ccnc4)cc3nc2-c2ccccc2)C[C@H](C)O1]
I-115
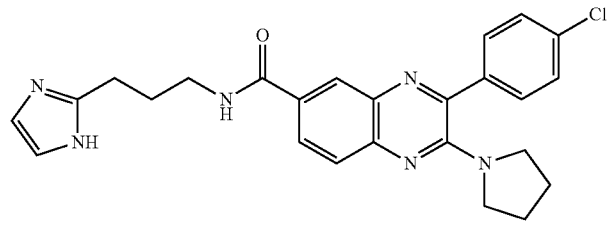 [SMILES: O=C(NCCCc1ncc[nH]1)c1ccc2nc(N3CCCC3)c(-c3ccc(Cl)cc3)nc2c1]
I-116
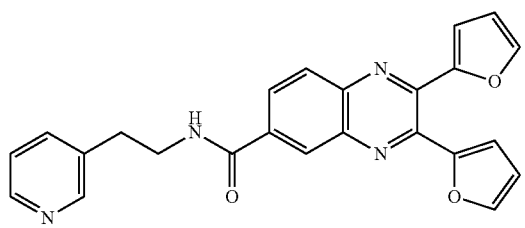 [SMILES: O=C(NCCc1cccnc1)c1ccc2nc(-c3ccco3)c(-c3ccco3)nc2c1]
I-117

TABLE 1-continued
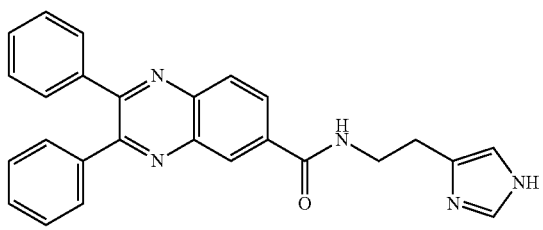 [SMILES: O=C(NCCc1c[nH]cn1)c1ccc2nc(-c3ccccc3)c(-c3ccccc3)nc2c1] I-118
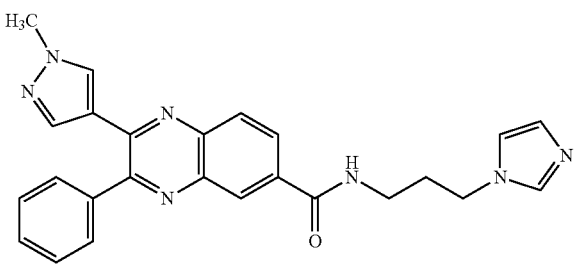 [SMILES: Cn1cc(-c2nc3ccc(C(=O)NCCCn4ccnc4)cc3nc2-c2ccccc2)cn1] I-119
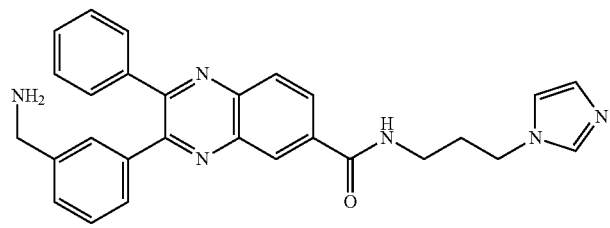 [SMILES: NCc1cccc(-c2nc3cc(C(=O)NCCCn4ccnc4)ccc3nc2-c2ccccc2)c1] I-120
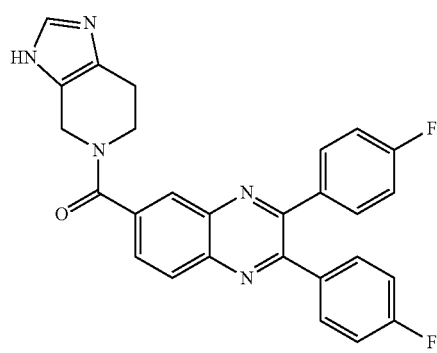 [SMILES: O=C(c1ccc2nc(-c3ccc(F)cc3)c(-c3ccc(F)cc3)nc2c1)N1CCc2nc[nH]c2C1] I-121
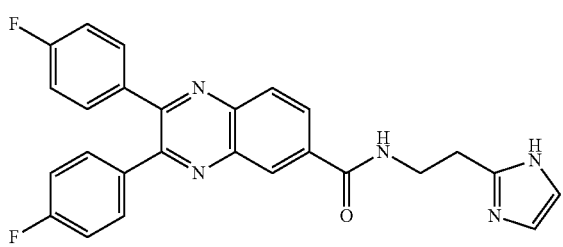 [SMILES: O=C(NCCc1ncc[nH]1)c1ccc2nc(-c3ccc(F)cc3)c(-c3ccc(F)cc3)nc2c1] I-122

TABLE 1-continued
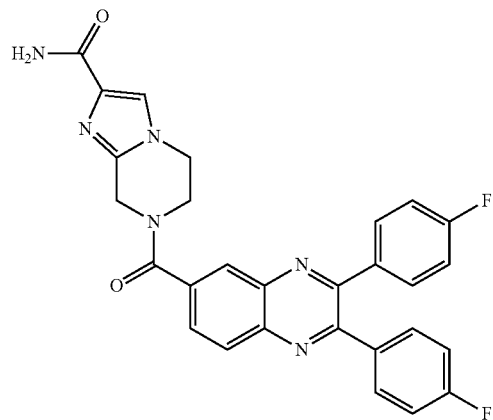 [SMILES: NC(=O)c1cn2c(n1)CN(C(=O)c1ccc3nc(-c4ccc(F)cc4)c(-c4ccc(F)cc4)nc3c1)CC2]
I-123
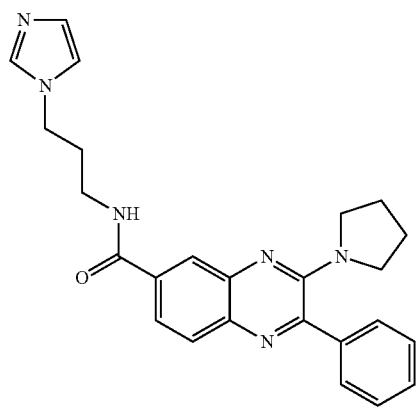 [SMILES: O=C(NCCCn1ccnc1)c1ccc2nc(-c3ccccc3)c(N3CCCC3)nc2c1]
I-124
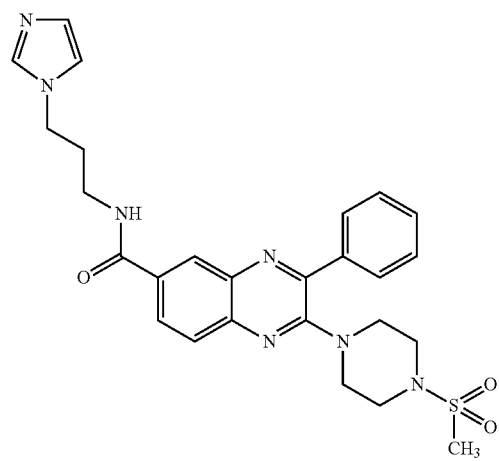 [SMILES: CS(=O)(=O)N1CCN(c2nc3ccc(C(=O)NCCCn4ccnc4)cc3nc2-c2ccccc2)CC1]
I-125

TABLE 1-continued
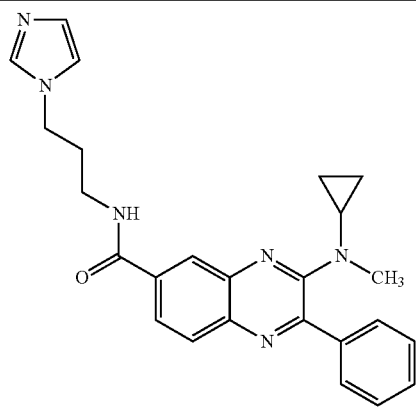
I-126
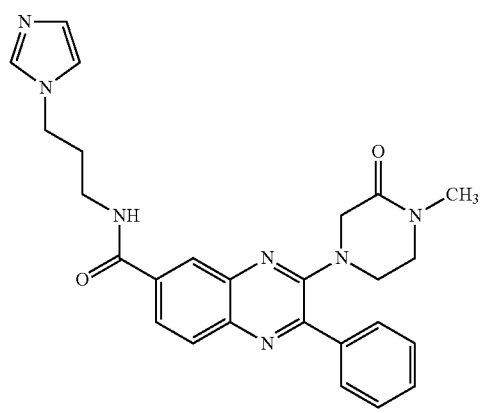 [SMILES: CN1CCN(c2nc3cc(C(=O)NCCCn4ccnc4)ccc3nc2-c2ccccc2)CC1=O]
I-127
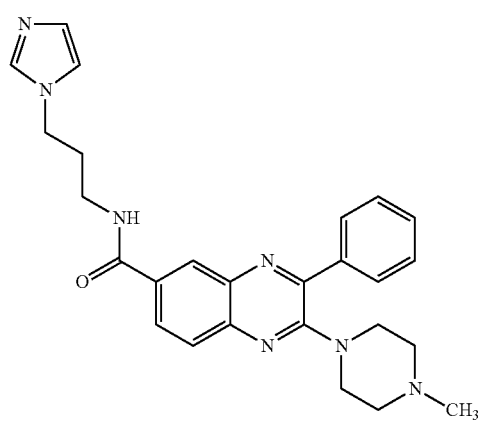 [SMILES: CN1CCN(c2nc3ccc(C(=O)NCCCn4ccnc4)cc3nc2-c2ccccc2)CC1]
I-128
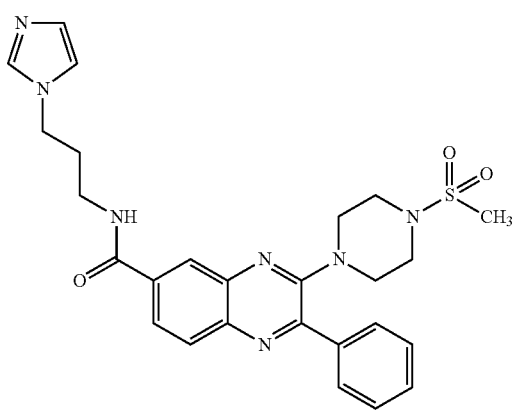 [SMILES: CS(=O)(=O)N1CCN(c2nc3cc(C(=O)NCCCn4ccnc4)ccc3nc2-c2ccccc2)CC1]
I-129

TABLE 1-continued
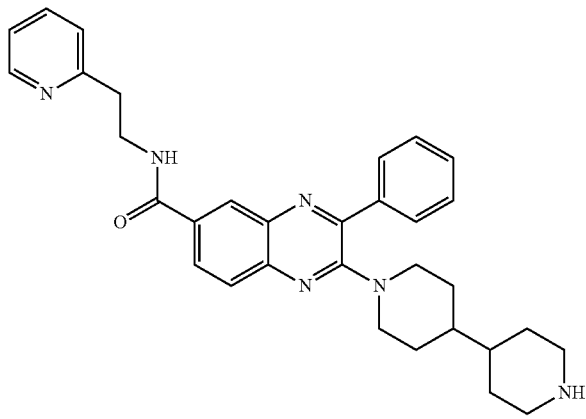 [SMILES: O=C(NCCc1ccccn1)c1ccc2nc(N3CCC(C4CCNCC4)CC3)c(-c3ccccc3)nc2c1]
I-130
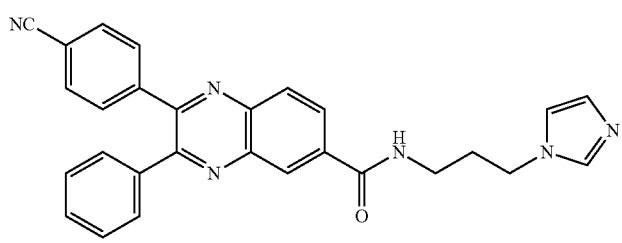 [SMILES: N#Cc1ccc(-c2nc3ccc(C(=O)NCCCn4ccnc4)cc3nc2-c2ccccc2)cc1]
I-131
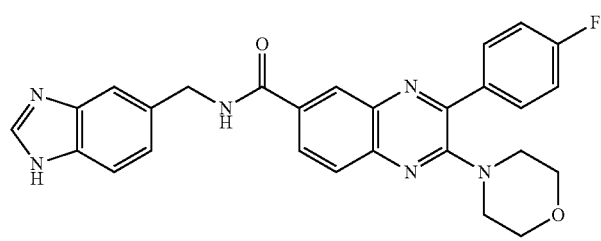 [SMILES: O=C(NCc1ccc2[nH]cnc2c1)c1ccc2nc(N3CCOCC3)c(-c3ccc(F)cc3)nc2c1]
I-132
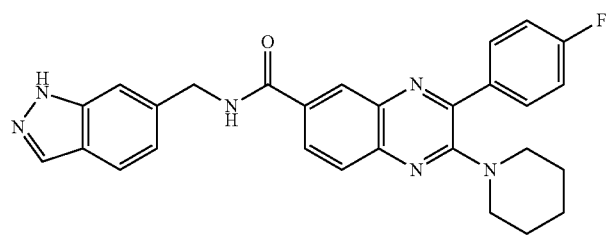 [SMILES: O=C(NCc1ccc2cn[nH]c2c1)c1ccc2nc(N3CCCCC3)c(-c3ccc(F)cc3)nc2c1]
I-133
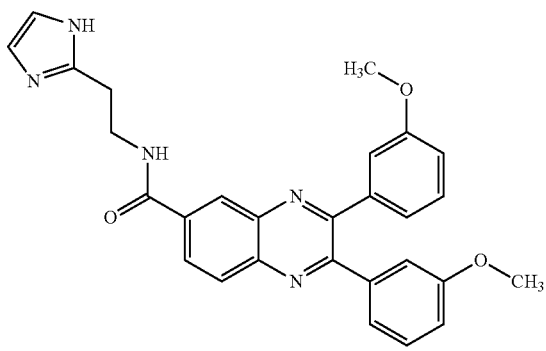 [SMILES: COc1cccc(-c2nc3ccc(C(=O)NCCc4ncc[nH]4)cc3nc2-c2cccc(OC)c2)c1]
I-134

TABLE 1-continued
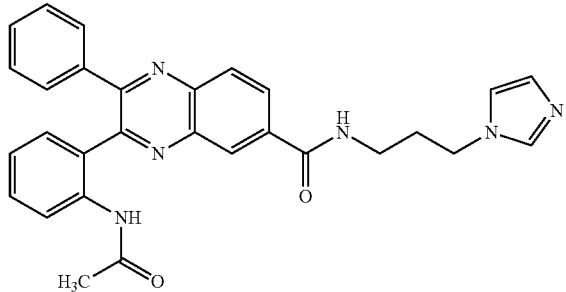 [SMILES: CC(=O)Nc1ccccc1-c1nc2cc(C(=O)NCCCn3ccnc3)ccc2nc1-c1ccccc1]
I-135
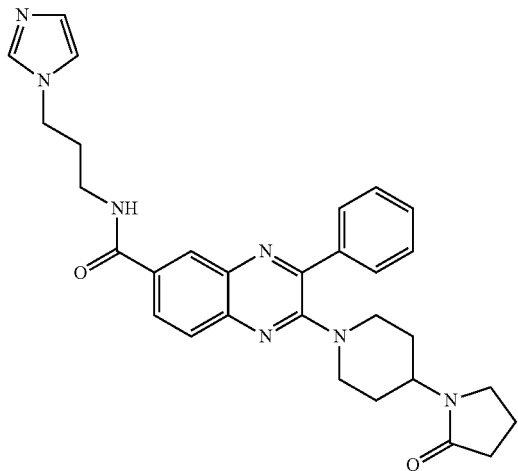 [SMILES: O=C(NCCCn1ccnc1)c1ccc2nc(N3CCC(N4CCCC4=O)CC3)c(-c3ccccc3)nc2c1]
I-136
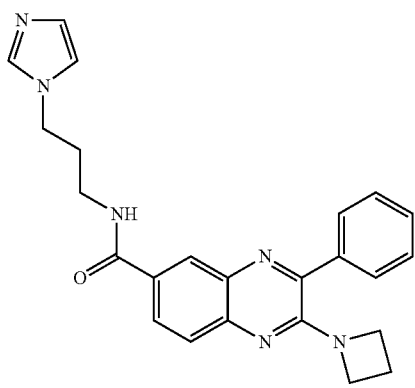 [SMILES: O=C(NCCCn1ccnc1)c1ccc2nc(N3CCC3)c(-c3ccccc3)nc2c1]
I-137
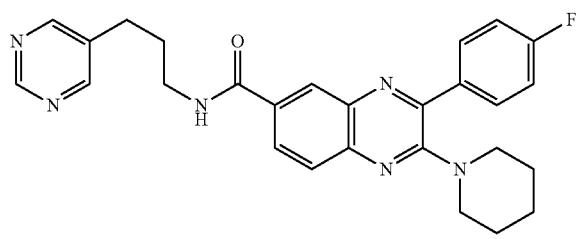
I-138

TABLE 1-continued
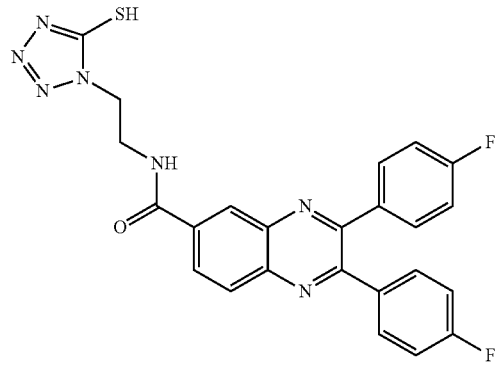 [SMILES: O=C(NCCn1nnnc1S)c1ccc2nc(-c3ccc(F)cc3)c(-c3ccc(F)cc3)nc2c1] I-139
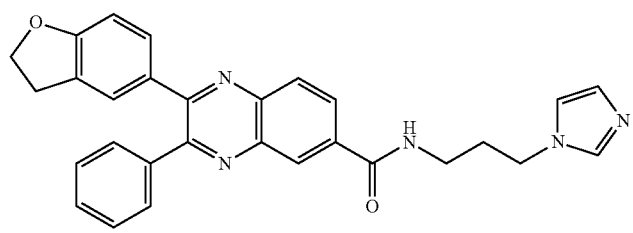 [SMILES: O=C(NCCCn1ccnc1)c1ccc2nc(-c3ccc4c(c3)CCO4)c(-c3ccccc3)nc2c1] I-140
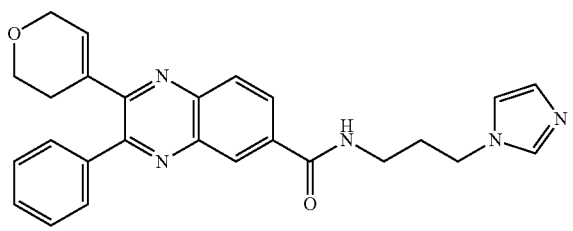 [SMILES: O=C(NCCCn1ccnc1)c1ccc2nc(C3=CCOCC3)c(-c3ccccc3)nc2c1] I-141
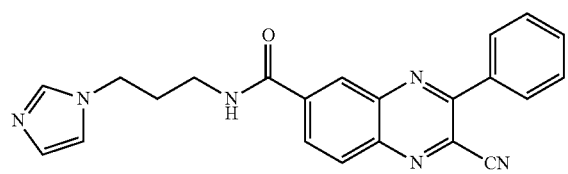 [SMILES: N#Cc1nc2ccc(C(=O)NCCCn3ccnc3)cc2nc1-c1ccccc1] I-142
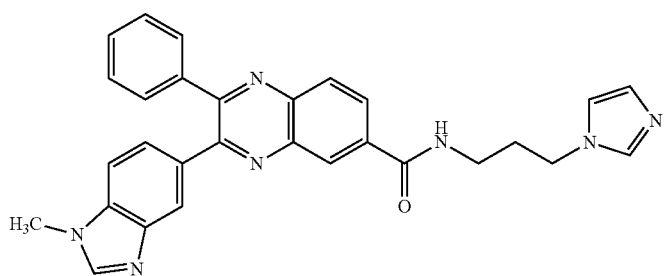 [SMILES: Cn1cnc2cc(-c3nc4cc(C(=O)NCCCn5ccnc5)ccc4nc3-c3ccccc3)ccc21] I-143

TABLE 1-continued
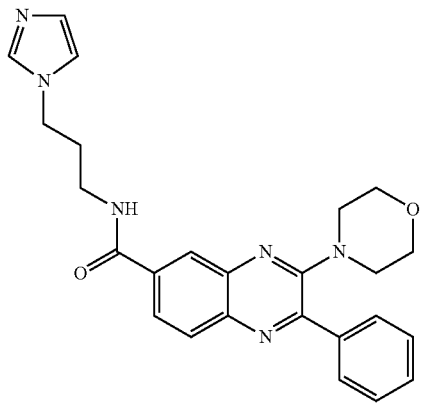 [SMILES: O=C(NCCCn1ccnc1)c1ccc2nc(-c3ccccc3)c(N3CCOCC3)nc2c1]
I-144
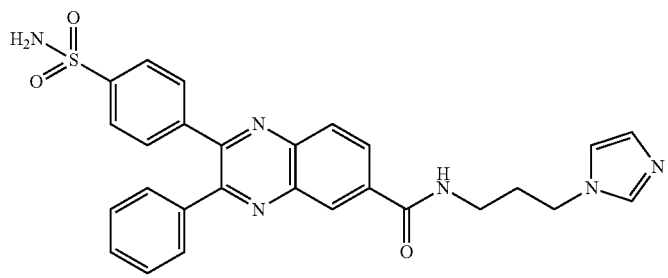 [SMILES: NS(=O)(=O)c1ccc(-c2nc3ccc(C(=O)NCCCn4ccnc4)cc3nc2-c2ccccc2)cc1]
I-145
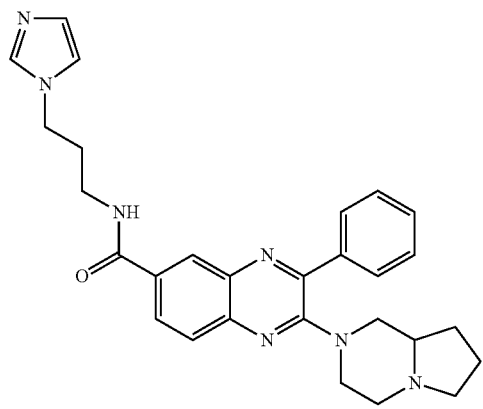 [SMILES: O=C(NCCCn1ccnc1)c1ccc2nc(N3CCN4CCCC4C3)c(-c3ccccc3)nc2c1]
I-146
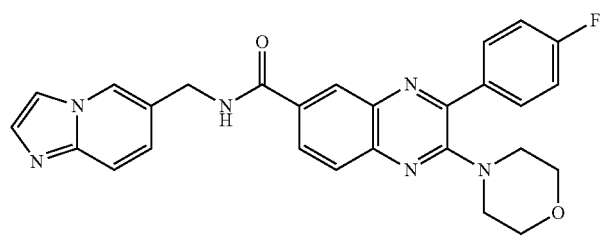 [SMILES: O=C(NCc1ccc2nccn2c1)c1ccc2nc(N3CCOCC3)c(-c3ccc(F)cc3)nc2c1]
I-147

TABLE 1-continued
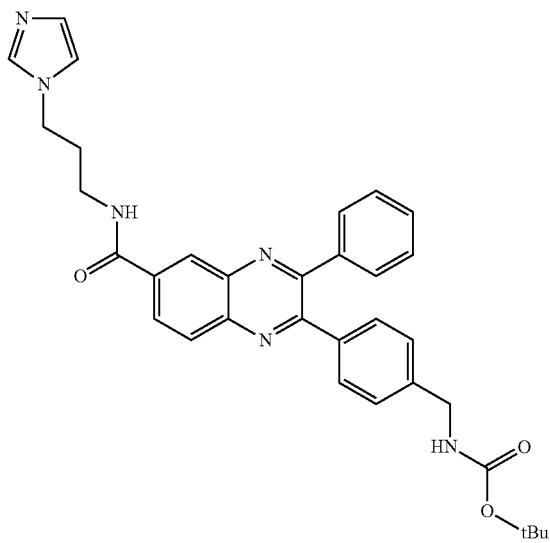 [SMILES: CC(C)(C)OC(=O)NCc1ccc(-c2nc3ccc(C(=O)NCCCn4ccnc4)cc3nc2-c2ccccc2)cc1]
I-148
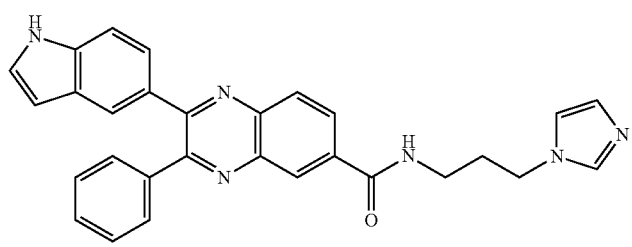 [SMILES: O=C(NCCCn1ccnc1)c1ccc2nc(-c3ccc4[nH]ccc4c3)c(-c3ccccc3)nc2c1]
I-149
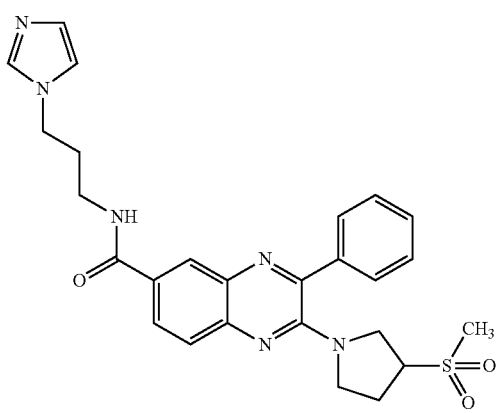 [SMILES: CS(=O)(=O)C1CCN(c2nc3ccc(C(=O)NCCCn4ccnc4)cc3nc2-c2ccccc2)C1]
I-150
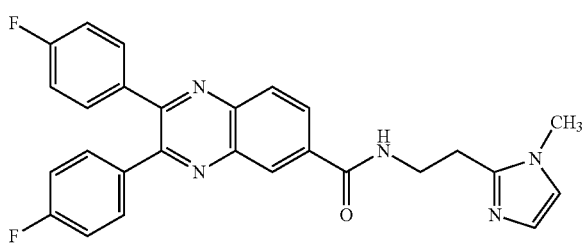 [SMILES: Cn1ccnc1CCNC(=O)c1ccc2nc(-c3ccc(F)cc3)c(-c3ccc(F)cc3)nc2c1]
I-151

TABLE 1-continued
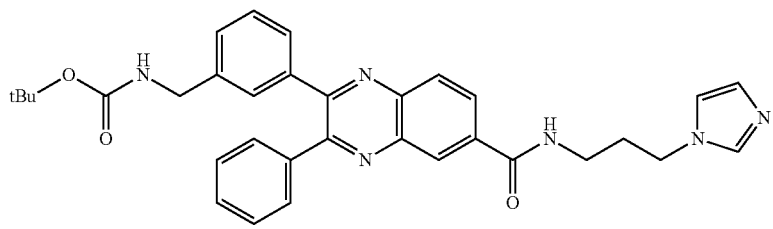 [SMILES: CC(C)(C)OC(=O)NCc1cccc(-c2nc3ccc(C(=O)NCCCn4ccnc4)cc3nc2-c2ccccc2)c1]
I-152
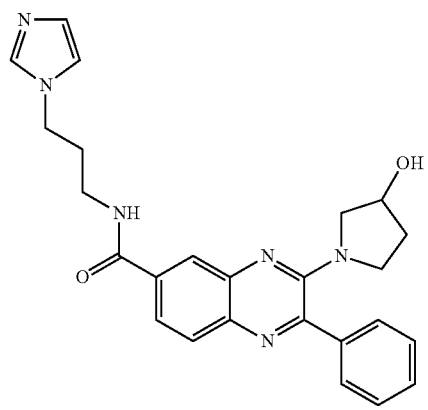
I-153
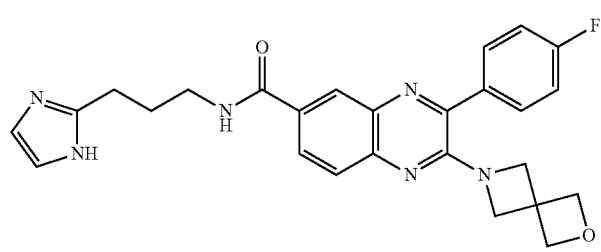 [SMILES: O=C(NCCCc1ncc[nH]1)c1ccc2nc(N3CC4(COC4)C3)c(-c3ccc(F)cc3)nc2c1]
I-154
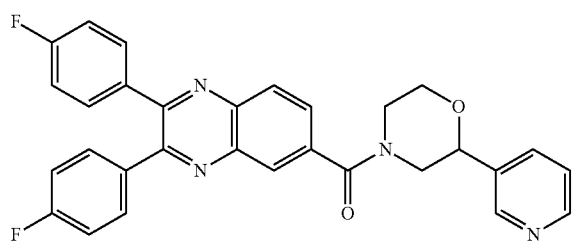 [SMILES: O=C(c1ccc2nc(-c3ccc(F)cc3)c(-c3ccc(F)cc3)nc2c1)N1CCOC(c2cccnc2)C1]
I-155
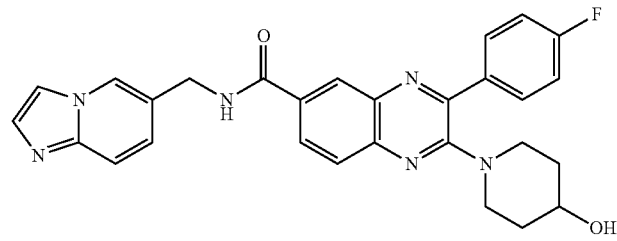 [SMILES: O=C(NCc1ccc2nccn2c1)c1ccc2nc(N3CCC(O)CC3)c(-c3ccc(F)cc3)nc2c1]
I-156
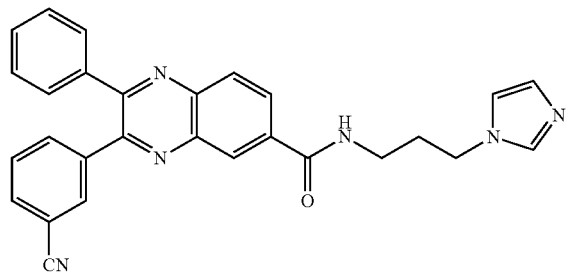 [SMILES: N#Cc1cccc(-c2nc3cc(C(=O)NCCCn4ccnc4)ccc3nc2-c2ccccc2)c1]
I-157

TABLE 1-continued
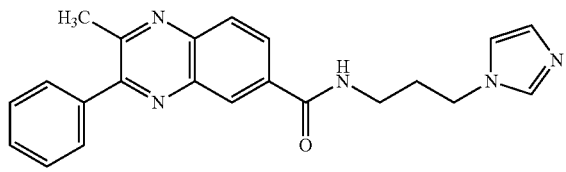 [SMILES: Cc1nc2ccc(C(=O)NCCCn3ccnc3)cc2nc1-c1ccccc1]  I-158
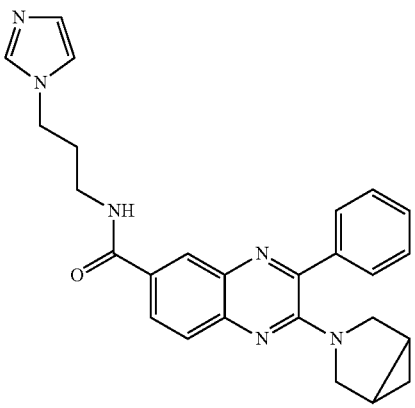 [SMILES: O=C(NCCCn1ccnc1)c1ccc2nc(N3CC4CC4C3)c(-c3ccccc3)nc2c1]  I-159
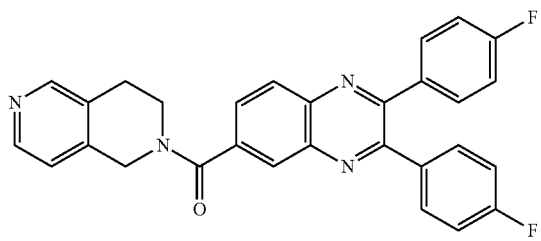 [SMILES: O=C(c1ccc2nc(-c3ccc(F)cc3)c(-c3ccc(F)cc3)nc2c1)N1CCc2cnccc2C1]  I-160
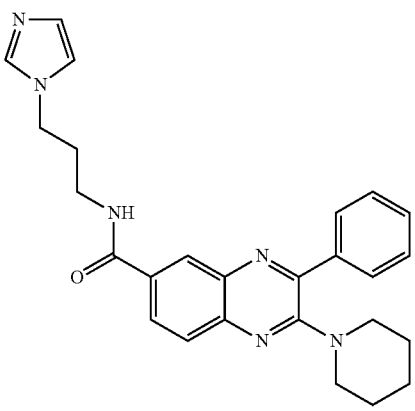 [SMILES: O=C(NCCCn1ccnc1)c1ccc2nc(N3CCCCC3)c(-c3ccccc3)nc2c1]  I-161
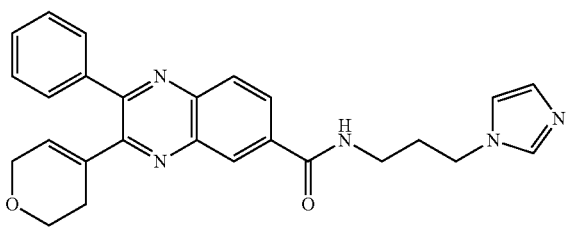 [SMILES: O=C(NCCCn1ccnc1)c1ccc2nc(-c3ccccc3)c(C3=CCOCC3)nc2c1]  I-162

TABLE 1-continued
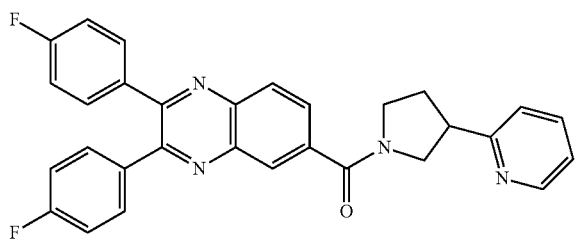 [SMILES: O=C(c1ccc2nc(-c3ccc(F)cc3)c(-c3ccc(F)cc3)nc2c1)N1CCC(c2ccccn2)C1] I-163
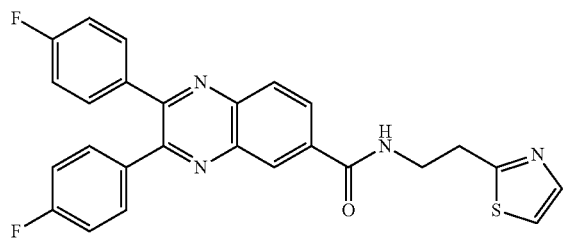 [SMILES: O=C(NCCc1nccs1)c1ccc2nc(-c3ccc(F)cc3)c(-c3ccc(F)cc3)nc2c1] I-164
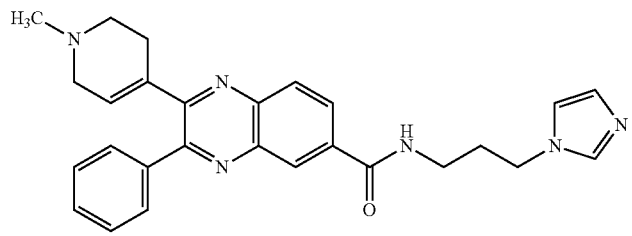 [SMILES: CN1CC=C(c2nc3ccc(C(=O)NCCCn4ccnc4)cc3nc2-c2ccccc2)CC1] I-165
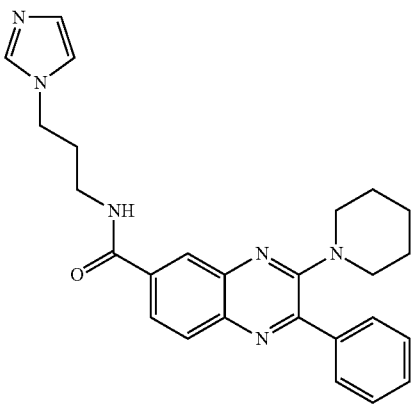 [SMILES: O=C(NCCCn1ccnc1)c1ccc2nc(-c3ccccc3)c(N3CCCCC3)nc2c1] I-166
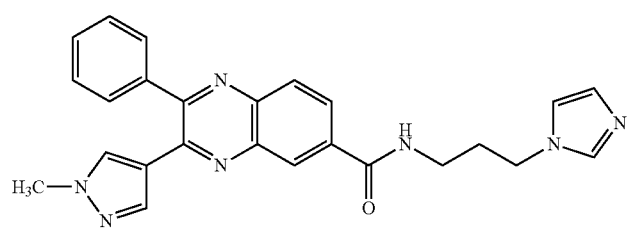 [SMILES: Cn1cc(-c2nc3cc(C(=O)NCCCn4ccnc4)ccc3nc2-c2ccccc2)cn1] I-167

TABLE 1-continued
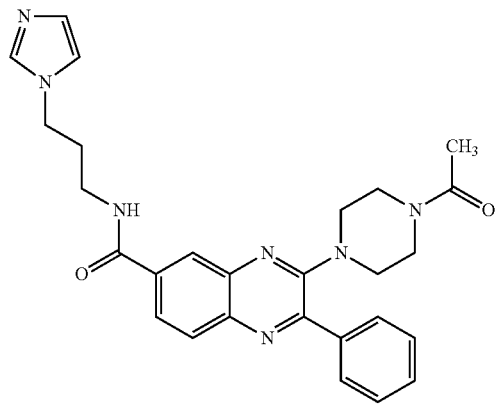 [SMILES: CC(=O)N1CCN(c2nc3cc(C(=O)NCCCn4ccnc4)ccc3nc2-c2ccccc2)CC1]
I-168
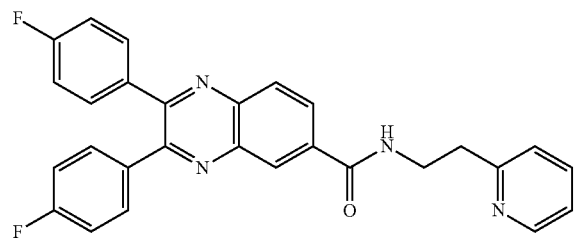 [SMILES: O=C(NCCc1ccccn1)c1ccc2nc(-c3ccc(F)cc3)c(-c3ccc(F)cc3)nc2c1]
I-169
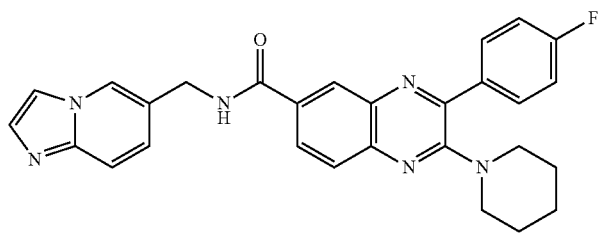 [SMILES: O=C(NCc1ccc2nccn2c1)c1ccc2nc(N3CCCCC3)c(-c3ccc(F)cc3)nc2c1]
I-170
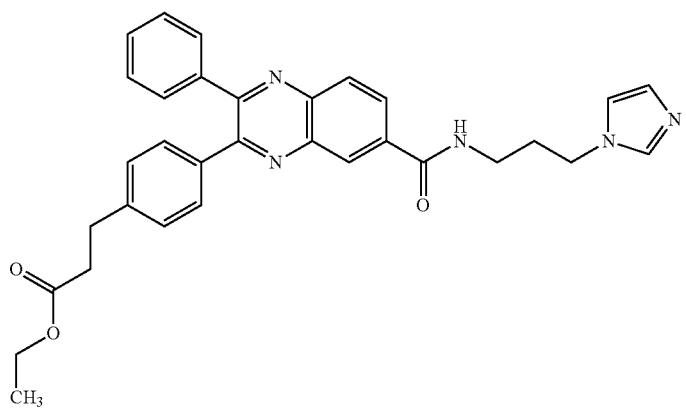 [SMILES: CCOC(=O)CCc1ccc(-c2nc3cc(C(=O)NCCCn4ccnc4)ccc3nc2-c2ccccc2)cc1]
I-171
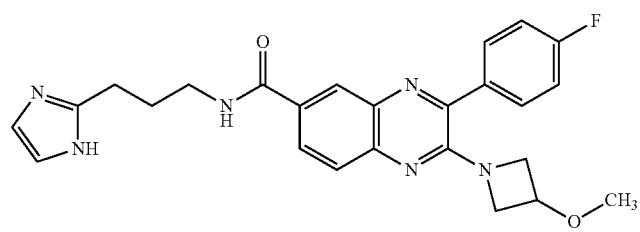 [SMILES: COC1CN(c2nc3ccc(C(=O)NCCCc4ncc[nH]4)cc3nc2-c2ccc(F)cc2)C1]
I-172

TABLE 1-continued
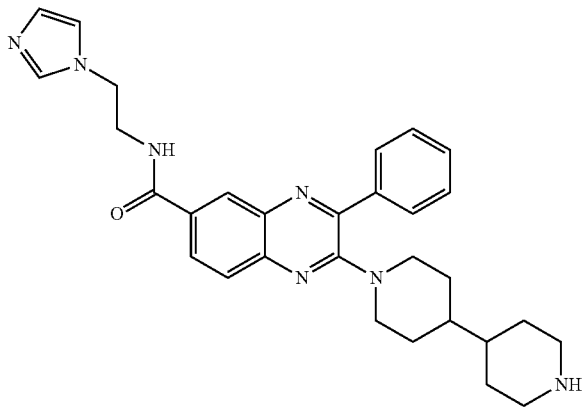 [SMILES: O=C(NCCn1ccnc1)c1ccc2nc(N3CCC(C4CCNCC4)CC3)c(-c3ccccc3)nc2c1]
I-173
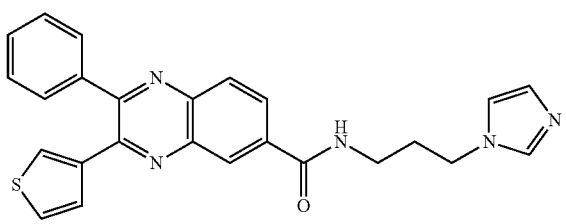 [SMILES: O=C(NCCCn1ccnc1)c1ccc2nc(-c3ccccc3)c(-c3ccsc3)nc2c1]
I-174
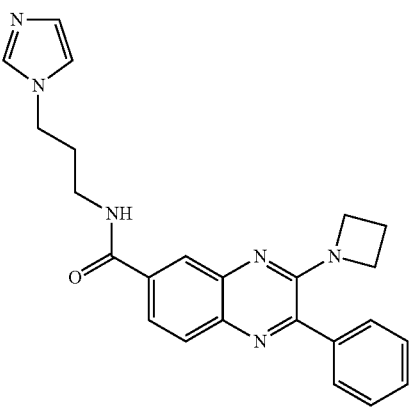 [SMILES: O=C(NCCCn1ccnc1)c1ccc2nc(-c3ccccc3)c(N3CCC3)nc2c1]
I-175
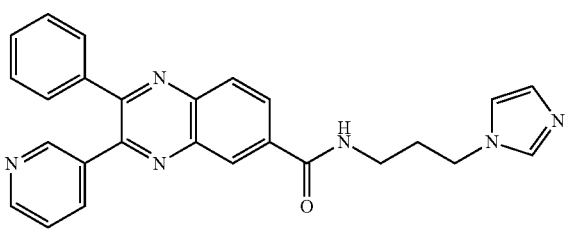 [SMILES: O=C(NCCCn1ccnc1)c1ccc2nc(-c3ccccc3)c(-c3cccnc3)nc2c1]
I-176
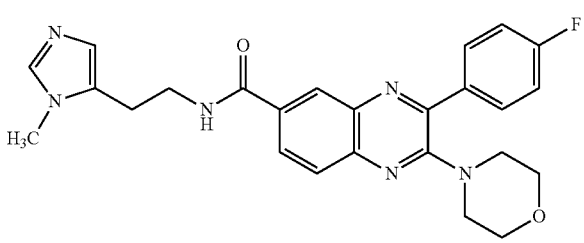 [SMILES: Cn1cncc1CCNC(=O)c1ccc2nc(N3CCOCC3)c(-c3ccc(F)cc3)nc2c1]
I-177

TABLE 1-continued
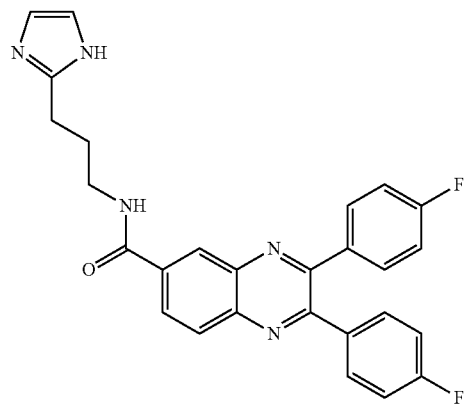 [SMILES: O=C(NCCCc1ncc[nH]1)c1ccc2nc(-c3ccc(F)cc3)c(-c3ccc(F)cc3)nc2c1]
I-178
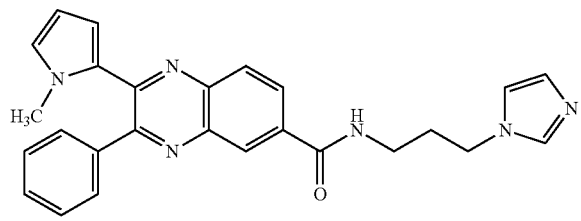 [SMILES: Cn1cccc1-c1nc2ccc(C(=O)NCCCn3ccnc3)cc2nc1-c1ccccc1]
I-179
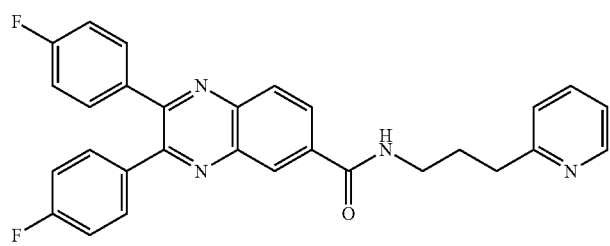 [SMILES: O=C(NCCCc1ccccn1)c1ccc2nc(-c3ccc(F)cc3)c(-c3ccc(F)cc3)nc2c1]
I-180
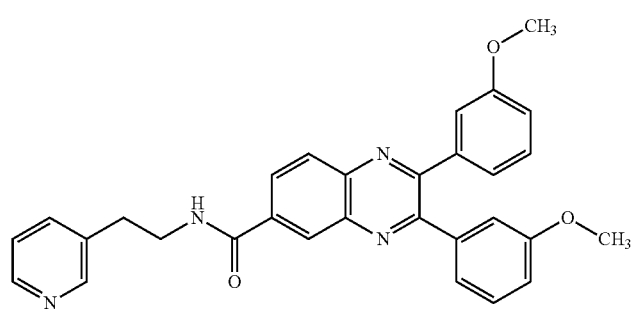 [SMILES: COc1cccc(-c2nc3ccc(C(=O)NCCc4cccnc4)cc3nc2-c2cccc(OC)c2)c1]
I-181
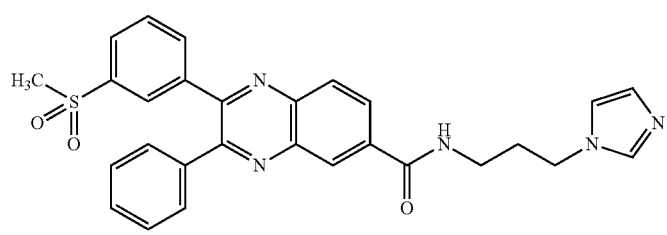 [SMILES: CS(=O)(=O)c1cccc(-c2nc3ccc(C(=O)NCCCn4ccnc4)cc3nc2-c2ccccc2)c1]
I-182

TABLE 1-continued
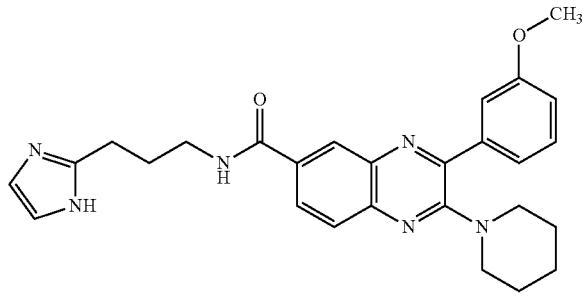 [SMILES: COc1cccc(-c2nc3cc(C(=O)NCCCc4ncc[nH]4)ccc3nc2N2CCCCC2)c1] I-183
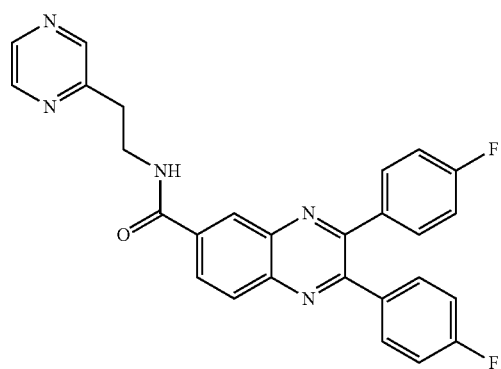 [SMILES: O=C(NCCc1cnccn1)c1ccc2nc(-c3ccc(F)cc3)c(-c3ccc(F)cc3)nc2c1] I-184
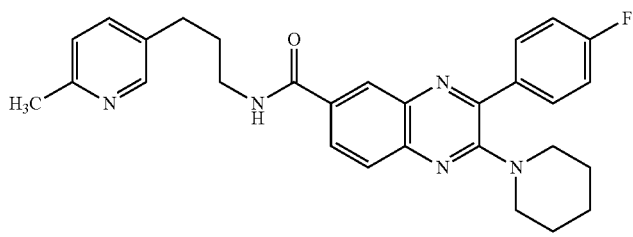 [SMILES: Cc1ccc(CCCNC(=O)c2ccc3nc(N4CCCCC4)c(-c4ccc(F)cc4)nc3c2)cn1] I-185
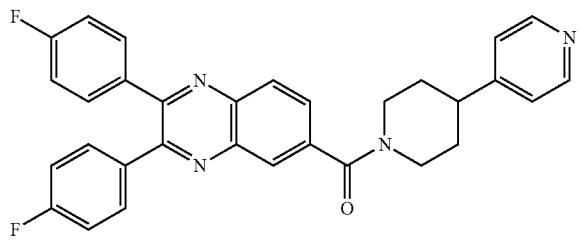 [SMILES: O=C(c1ccc2nc(-c3ccc(F)cc3)c(-c3ccc(F)cc3)nc2c1)N1CCC(c2ccncc2)CC1] I-186
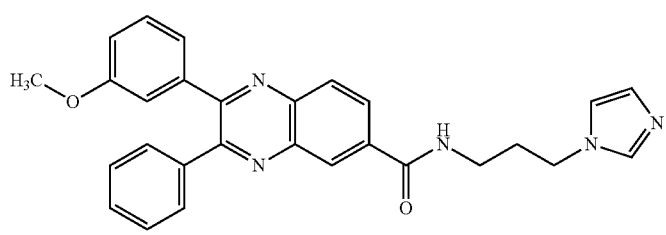 [SMILES: COc1cccc(-c2nc3ccc(C(=O)NCCCn4ccnc4)cc3nc2-c2ccccc2)c1] I-187

TABLE 1-continued
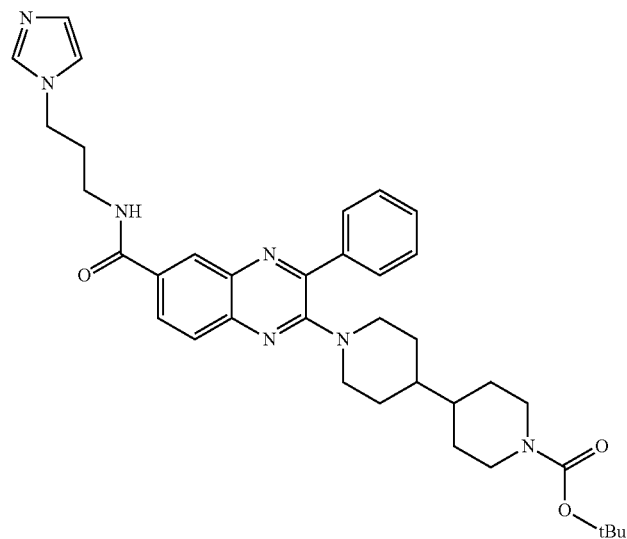 [SMILES: CC(C)(C)OC(=O)N1CCC(C2CCN(c3nc4ccc(C(=O)NCCCn5ccnc5)cc4nc3-c3ccccc3)CC2)CC1]
I-188
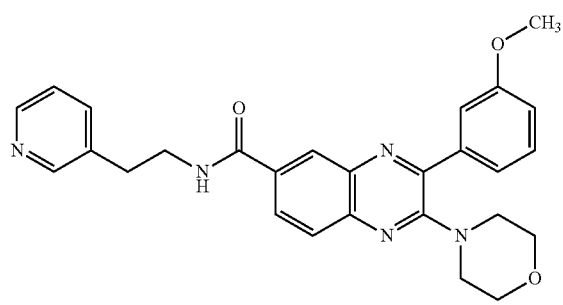 [SMILES: COc1cccc(-c2nc3cc(C(=O)NCCc4cccnc4)ccc3nc2N2CCOCC2)c1]
I-189
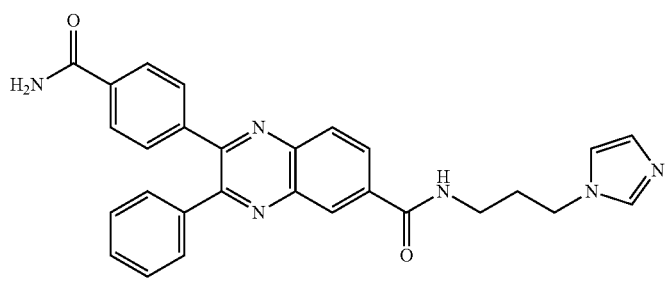 [SMILES: NC(=O)c1ccc(-c2nc3ccc(C(=O)NCCCn4ccnc4)cc3nc2-c2ccccc2)cc1]
I-190
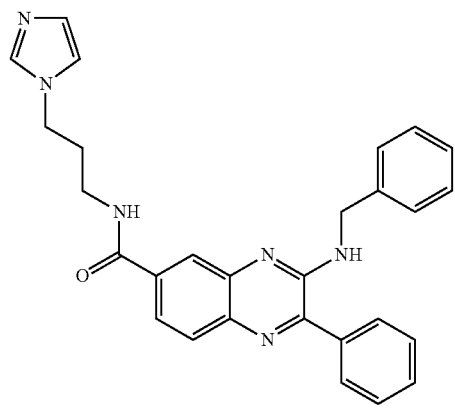 [SMILES: O=C(NCCCn1ccnc1)c1ccc2nc(-c3ccccc3)c(NCc3ccccc3)nc2c1]
I-191

TABLE 1-continued
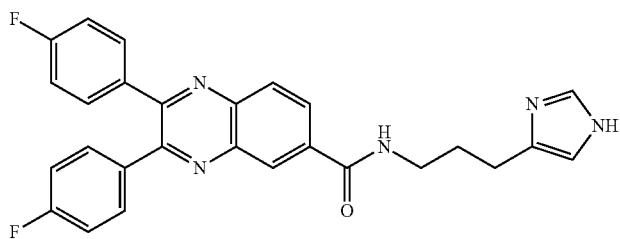 [SMILES: O=C(NCCCc1c[nH]cn1)c1ccc2nc(-c3ccc(F)cc3)c(-c3ccc(F)cc3)nc2c1]
I-192
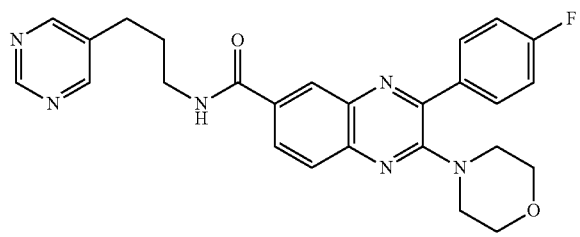 [SMILES: O=C(NCCCc1cncnc1)c1ccc2nc(N3CCOCC3)c(-c3ccc(F)cc3)nc2c1]
I-193
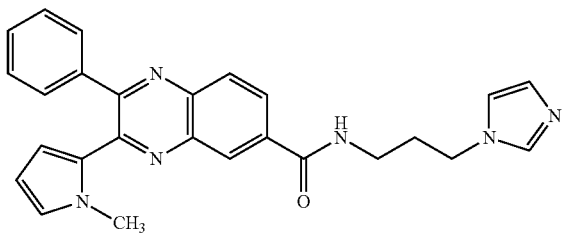 [SMILES: Cn1cccc1-c1nc2cc(C(=O)NCCCn3ccnc3)ccc2nc1-c1ccccc1]
I-194
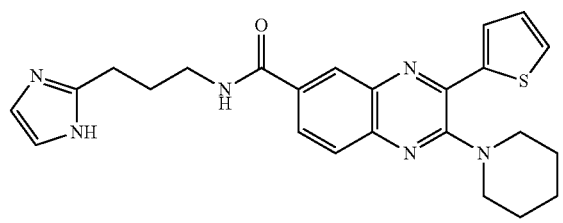 [SMILES: O=C(NCCCc1ncc[nH]1)c1ccc2nc(N3CCCCC3)c(-c3cccs3)nc2c1]
I-195
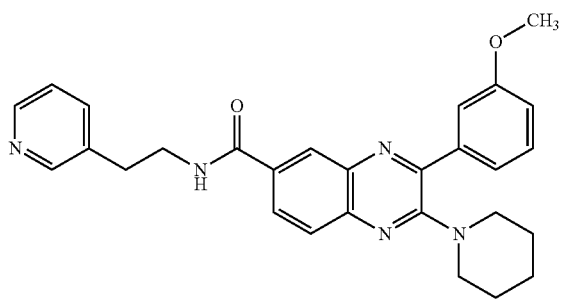 [SMILES: COc1cccc(-c2nc3cc(C(=O)NCCc4cccnc4)ccc3nc2N2CCCCC2)c1]
I-196
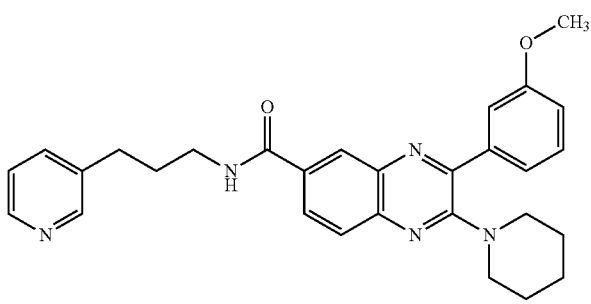 [SMILES: COc1cccc(-c2nc3cc(C(=O)NCCCc4cccnc4)ccc3nc2N2CCCCC2)c1]
I-197

TABLE 1-continued
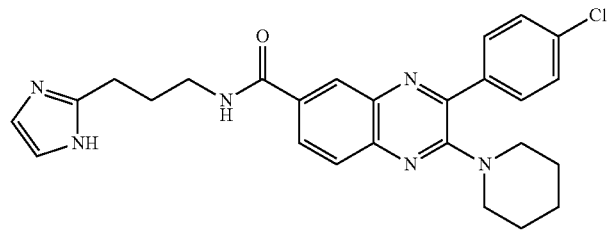 [SMILES: O=C(NCCCc1ncc[nH]1)c1ccc2nc(N3CCCCC3)c(-c3ccc(Cl)cc3)nc2c1]
I-198
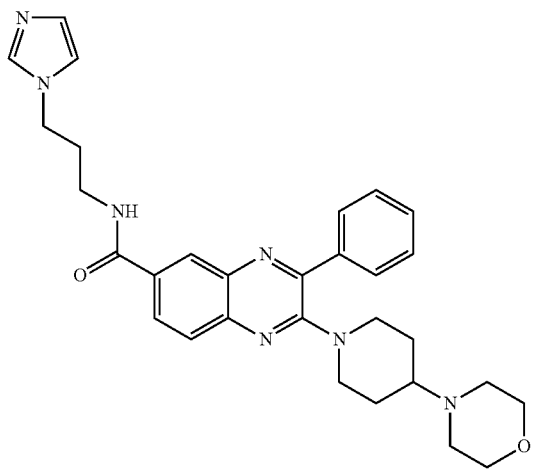 [SMILES: O=C(NCCCn1ccnc1)c1ccc2nc(N3CCC(N4CCOCC4)CC3)c(-c3ccccc3)nc2c1]
I-199
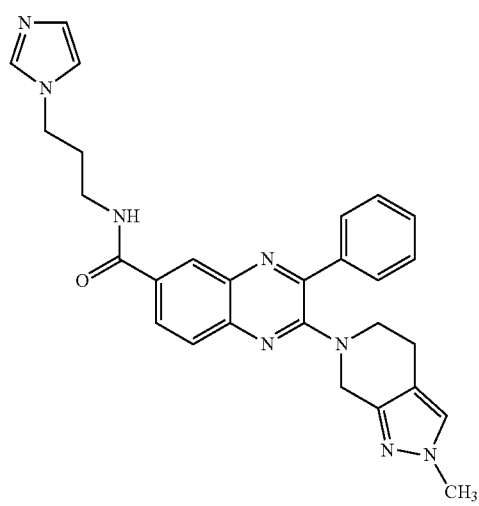 [SMILES: Cn1cc2c(n1)CN(c1nc3ccc(C(=O)NCCCn4ccnc4)cc3nc1-c1ccccc1)CC2]
I-200
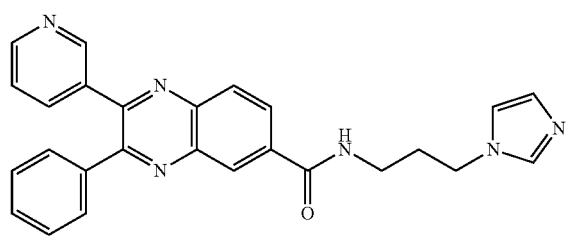 [SMILES: O=C(NCCCn1ccnc1)c1ccc2nc(-c3cccnc3)c(-c3ccccc3)nc2c1]
I-201

TABLE 1-continued
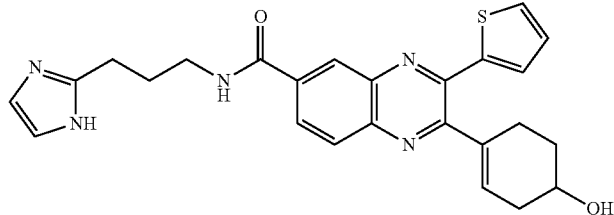 [SMILES: O=C(NCCCc1ncc[nH]1)c1ccc2nc(C3=CCC(O)CC3)c(-c3cccs3)nc2c1]
I-202
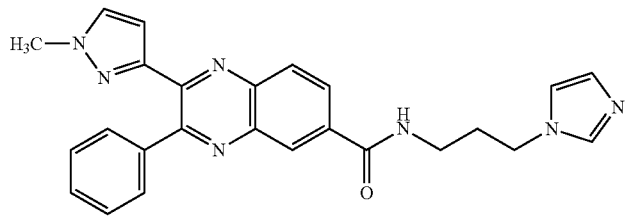 [SMILES: Cn1ccc(-c2nc3ccc(C(=O)NCCCn4ccnc4)cc3nc2-c2ccccc2)n1]
I-203
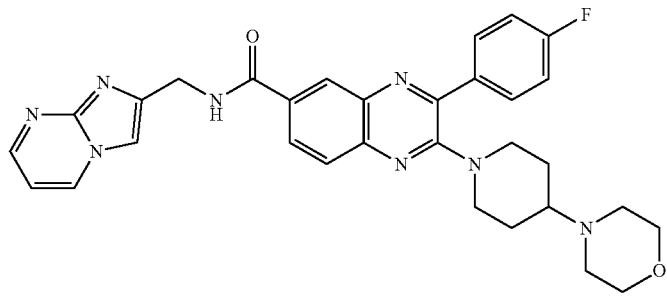 [SMILES: O=C(NCc1cn2cccnc2n1)c1ccc2nc(N3CCC(N4CCOCC4)CC3)c(-c3ccc(F)cc3)nc2c1]
I-204
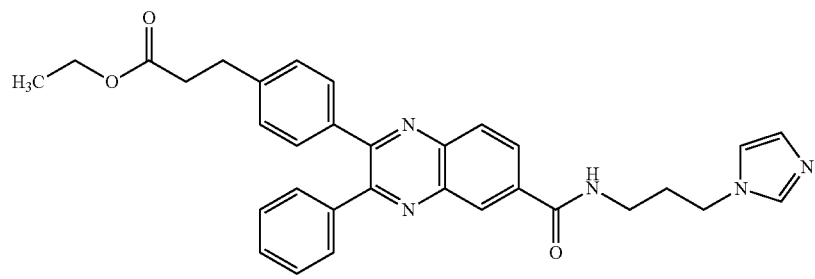 [SMILES: CCOC(=O)CCc1ccc(-c2nc3ccc(C(=O)NCCCn4ccnc4)cc3nc2-c2ccccc2)cc1]
I-205
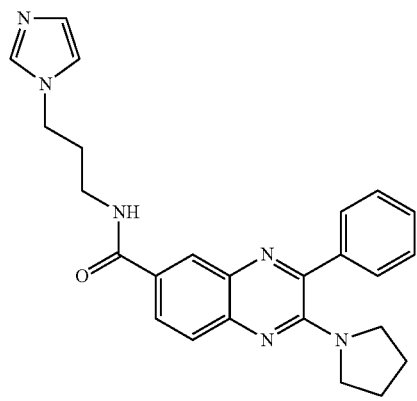 [SMILES: O=C(NCCCn1ccnc1)c1ccc2nc(N3CCCC3)c(-c3ccccc3)nc2c1]
I-206

TABLE 1-continued
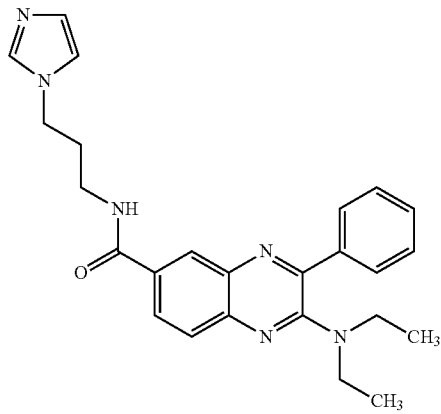 [SMILES: CCN(CC)c1nc2ccc(C(=O)NCCCn3ccnc3)cc2nc1-c1ccccc1]
I-207
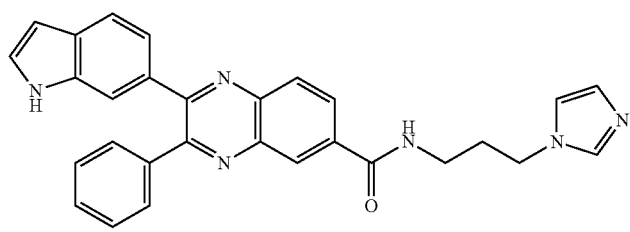 [SMILES: O=C(NCCCn1ccnc1)c1ccc2nc(-c3ccc4cc[nH]c4c3)c(-c3ccccc3)nc2c1]
I-208
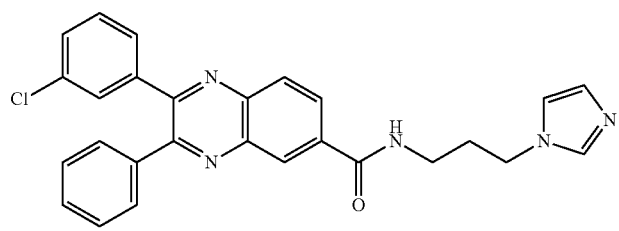 [SMILES: O=C(NCCCn1ccnc1)c1ccc2nc(-c3cccc(Cl)c3)c(-c3ccccc3)nc2c1]
I-209
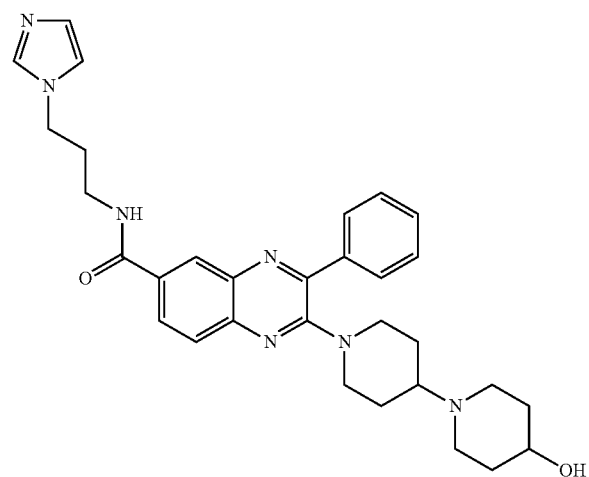 [SMILES: O=C(NCCCn1ccnc1)c1ccc2nc(N3CCC(N4CCC(O)CC4)CC3)c(-c3ccccc3)nc2c1]
I-210
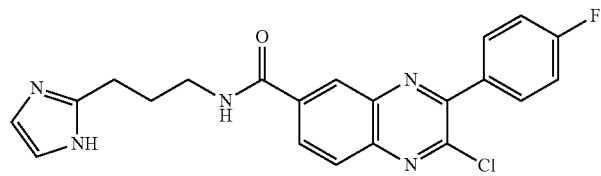 [SMILES: O=C(NCCCc1ncc[nH]1)c1ccc2nc(Cl)c(-c3ccc(F)cc3)nc2c1]
I-211

TABLE 1-continued
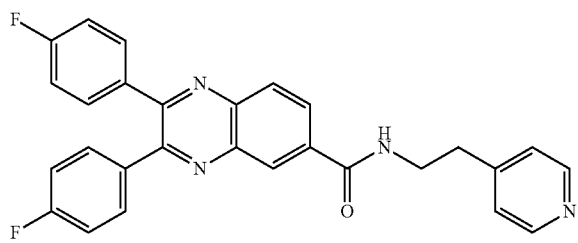 [SMILES: O=C(NCCc1ccncc1)c1ccc2nc(-c3ccc(F)cc3)c(-c3ccc(F)cc3)nc2c1] I-212
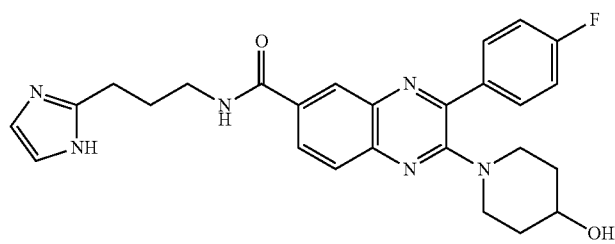 [SMILES: O=C(NCCCc1ncc[nH]1)c1ccc2nc(N3CCC(O)CC3)c(-c3ccc(F)cc3)nc2c1] I-213
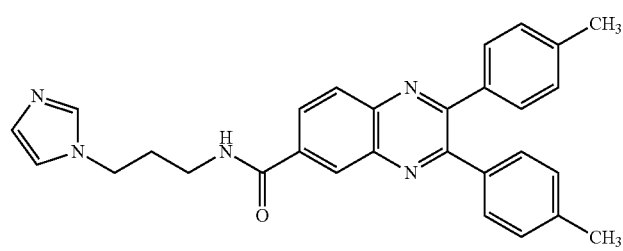 [SMILES: Cc1ccc(-c2nc3ccc(C(=O)NCCCn4ccnc4)cc3nc2-c2ccc(C)cc2)cc1] I-214
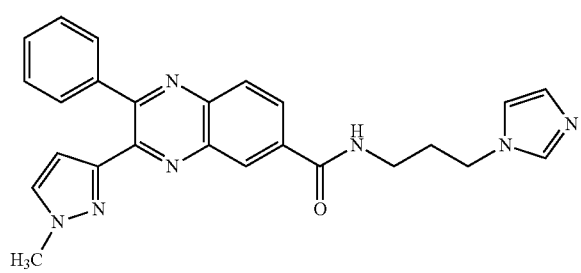 [SMILES: Cn1ccc(-c2nc3cc(C(=O)NCCCn4ccnc4)ccc3nc2-c2ccccc2)n1] I-215
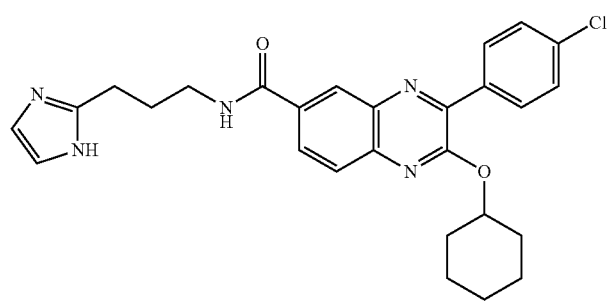 [SMILES: O=C(NCCCc1ncc[nH]1)c1ccc2nc(OC3CCCCC3)c(-c3ccc(Cl)cc3)nc2c1] I-216

TABLE 1-continued
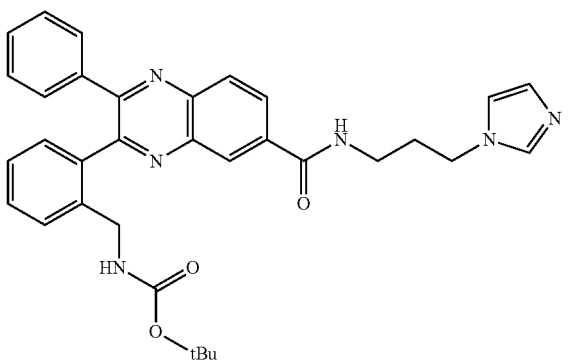 [SMILES: CC(C)(C)OC(=O)NCc1ccccc1-c1nc2cc(C(=O)NCCCn3ccnc3)ccc2nc1-c1ccccc1]
I-217
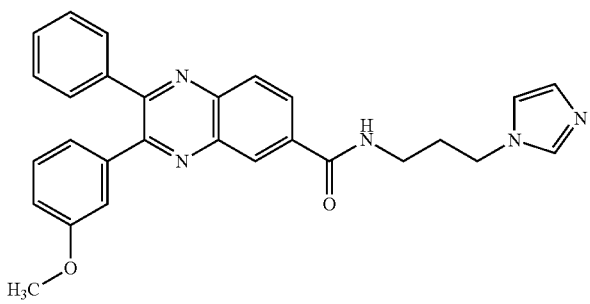 [SMILES: COc1cccc(-c2nc3cc(C(=O)NCCCn4ccnc4)ccc3nc2-c2ccccc2)c1]
I-218
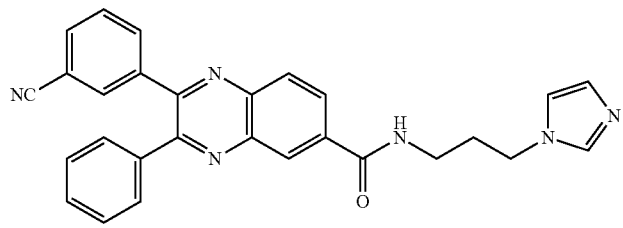 [SMILES: N#Cc1cccc(-c2nc3ccc(C(=O)NCCCn4ccnc4)cc3nc2-c2ccccc2)c1]
I-219
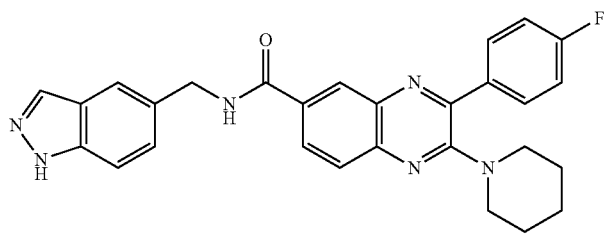
I-220
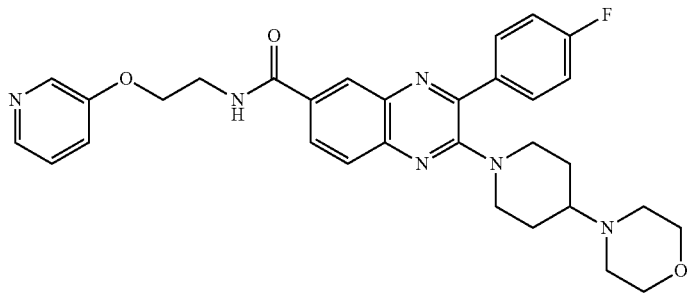 [SMILES: O=C(NCCOc1cccnc1)c1ccc2nc(N3CCC(N4CCOCC4)CC3)c(-c3ccc(F)cc3)nc2c1]
I-221

TABLE 1-continued
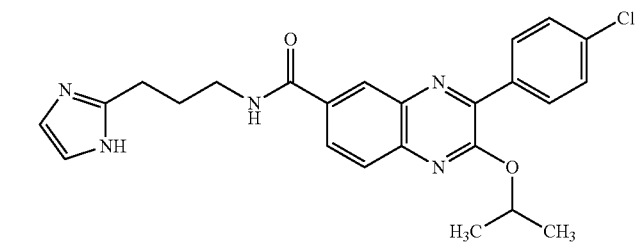 [SMILES: CC(C)Oc1nc2ccc(C(=O)NCCCc3ncc[nH]3)cc2nc1-c1ccc(Cl)cc1] I-222
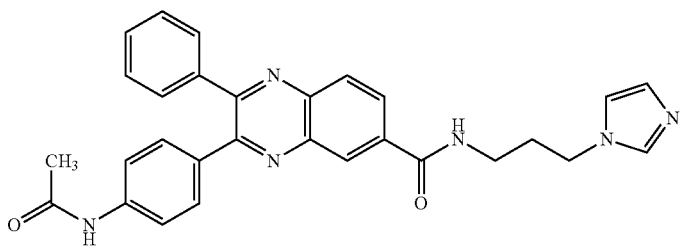 [SMILES: CC(=O)Nc1ccc(-c2nc3cc(C(=O)NCCCn4ccnc4)ccc3nc2-c2ccccc2)cc1] I-223
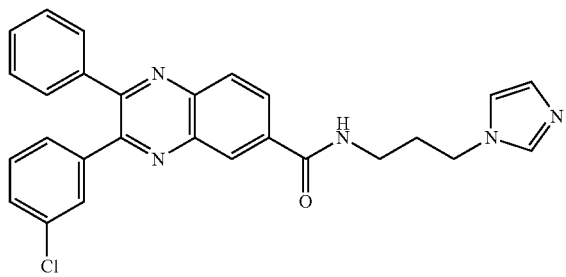 [SMILES: O=C(NCCCn1ccnc1)c1ccc2nc(-c3ccccc3)c(-c3cccc(Cl)c3)nc2c1] I-224
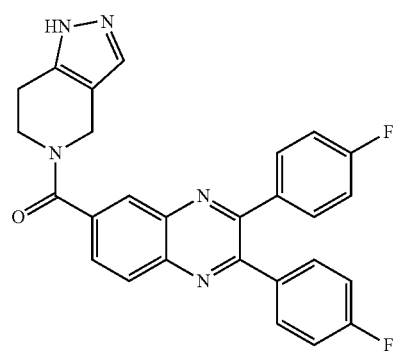 [SMILES: O=C(c1ccc2nc(-c3ccc(F)cc3)c(-c3ccc(F)cc3)nc2c1)N1CCc2[nH]ncc2C1] I-225
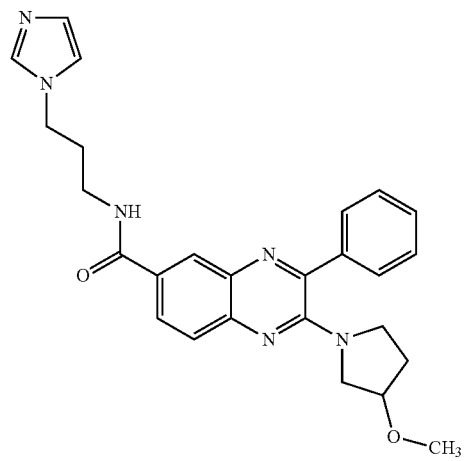 [SMILES: COC1CCN(c2nc3ccc(C(=O)NCCCn4ccnc4)cc3nc2-c2ccccc2)C1] I-226

TABLE 1-continued
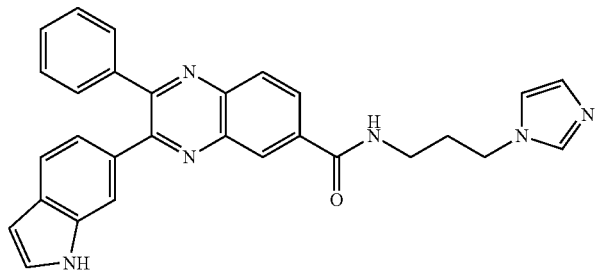 [SMILES: O=C(NCCCn1ccnc1)c1ccc2nc(-c3ccccc3)c(-c3ccc4cc[nH]c4c3)nc2c1]
I-227
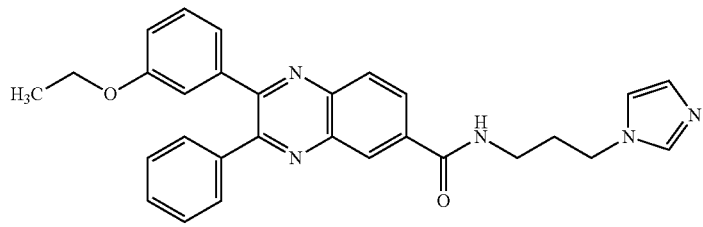 [SMILES: CCOc1cccc(-c2nc3ccc(C(=O)NCCCn4ccnc4)cc3nc2-c2ccccc2)c1]
I-228
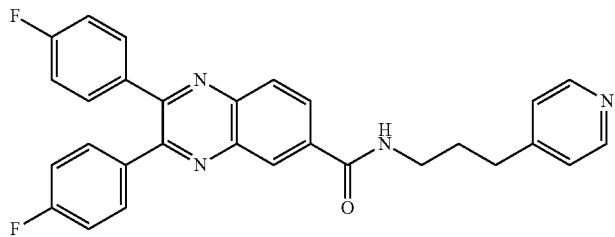 [SMILES: O=C(NCCCc1ccncc1)c1ccc2nc(-c3ccc(F)cc3)c(-c3ccc(F)cc3)nc2c1]
I-229
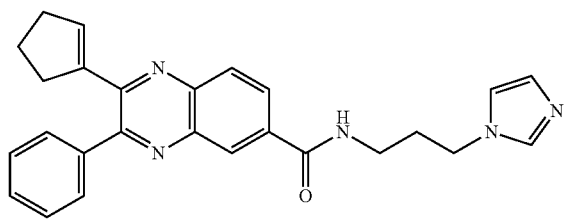 [SMILES: O=C(NCCCn1ccnc1)c1ccc2nc(C3=CCCC3)c(-c3ccccc3)nc2c1]
I-230
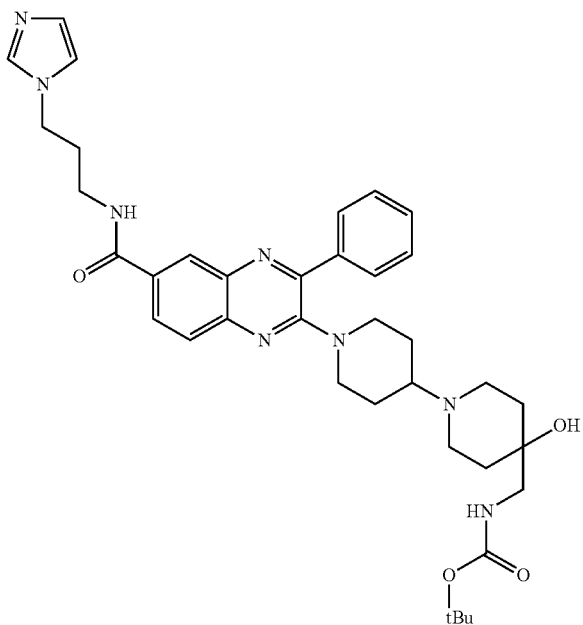 [SMILES: CC(C)(C)OC(=O)NCC1(O)CCN(C2CCN(c3nc4ccc(C(=O)NCCCn5ccnc5)cc4nc3-c3ccccc3)CC2)CC1]
I-231

TABLE 1-continued
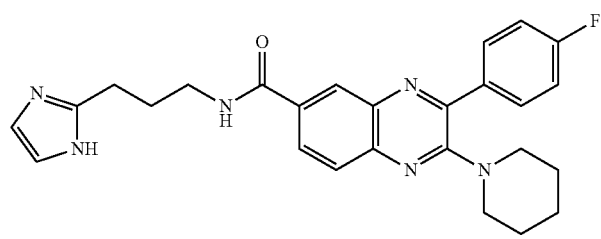 [SMILES: O=C(NCCCc1ncc[nH]1)c1ccc2nc(N3CCCCC3)c(-c3ccc(F)cc3)nc2c1]
I-232
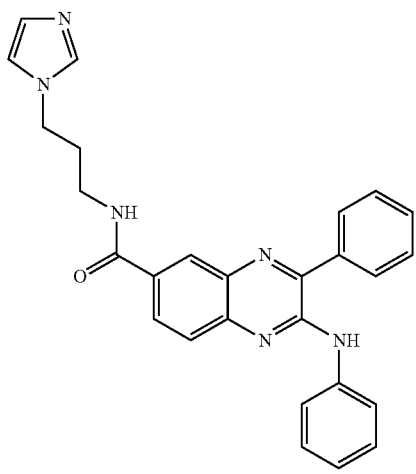 [SMILES: O=C(NCCCn1ccnc1)c1ccc2nc(Nc3ccccc3)c(-c3ccccc3)nc2c1]
I-233
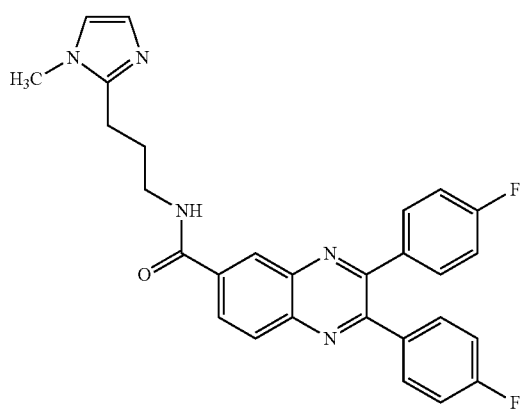 [SMILES: Cn1ccnc1CCCNC(=O)c1ccc2nc(-c3ccc(F)cc3)c(-c3ccc(F)cc3)nc2c1]
I-234
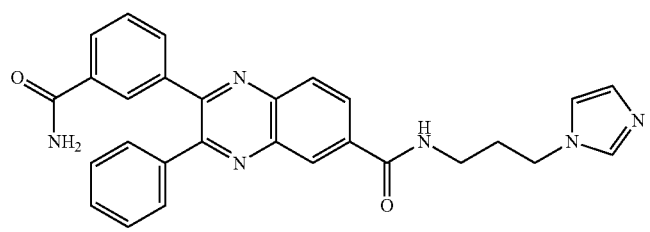 [SMILES: NC(=O)c1cccc(-c2nc3ccc(C(=O)NCCCn4ccnc4)cc3nc2-c2ccccc2)c1]
I-235
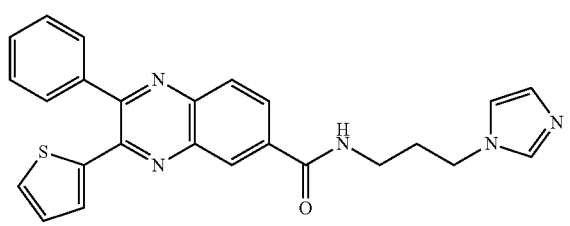 [SMILES: O=C(NCCCn1ccnc1)c1ccc2nc(-c3ccccc3)c(-c3cccs3)nc2c1]
I-236

TABLE 1-continued
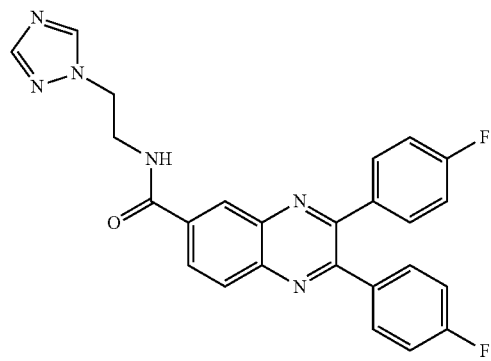 [SMILES: O=C(NCCn1cncn1)c1ccc2nc(-c3ccc(F)cc3)c(-c3ccc(F)cc3)nc2c1]
I-237
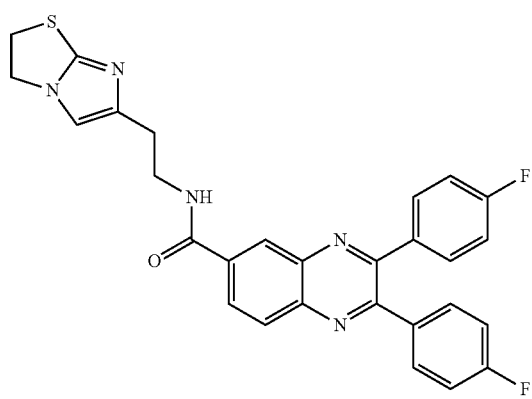 [SMILES: O=C(NCCc1cn2c(n1)SCC2)c1ccc2nc(-c3ccc(F)cc3)c(-c3ccc(F)cc3)nc2c1]
I-238
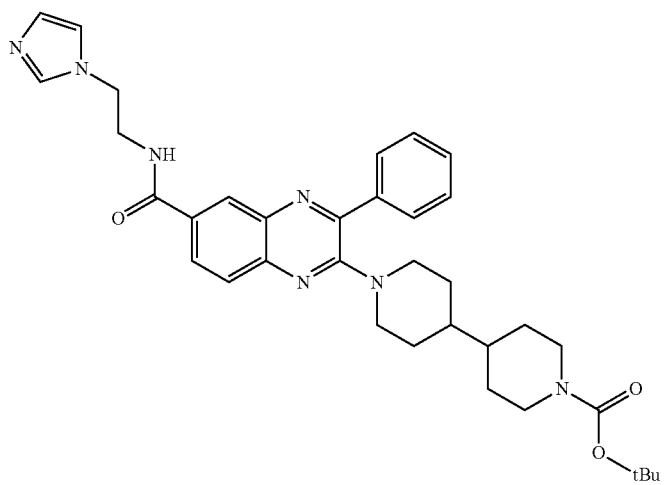 [SMILES: CC(C)(C)OC(=O)N1CCC(C2CCN(c3nc4ccc(C(=O)NCCn5ccnc5)cc4nc3-c3ccccc3)CC2)CC1]
I-239
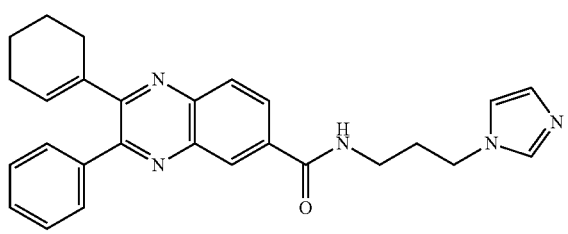 [SMILES: O=C(NCCCn1ccnc1)c1ccc2nc(C3=CCCCC3)c(-c3ccccc3)nc2c1]
I-240

TABLE 1-continued
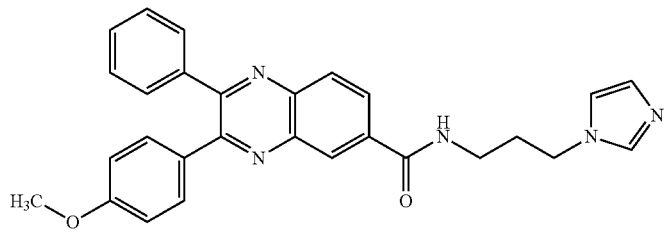 [SMILES: COc1ccc(-c2nc3cc(C(=O)NCCCn4ccnc4)ccc3nc2-c2ccccc2)cc1]
I-241
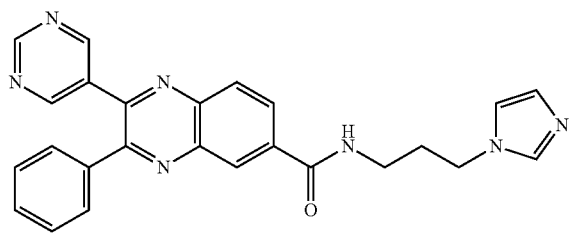 [SMILES: O=C(NCCCn1ccnc1)c1ccc2nc(-c3cncnc3)c(-c3ccccc3)nc2c1]
I-242
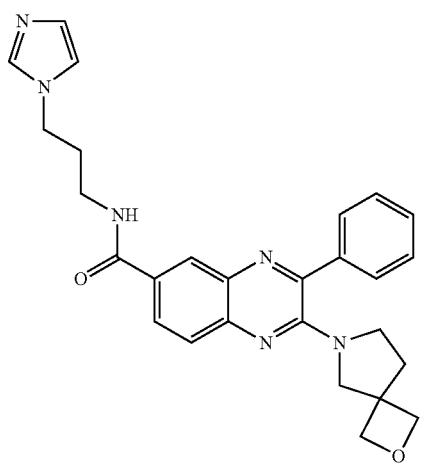 [SMILES: O=C(NCCCn1ccnc1)c1ccc2nc(N3CCC4(COC4)C3)c(-c3ccccc3)nc2c1]
I-243
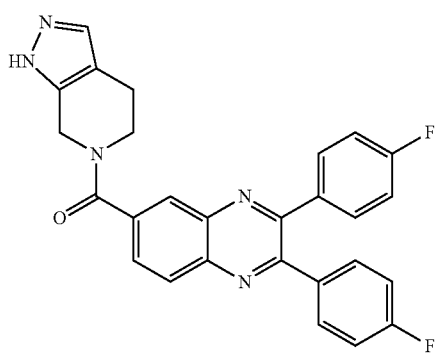 [SMILES: O=C(c1ccc2nc(-c3ccc(F)cc3)c(-c3ccc(F)cc3)nc2c1)N1CCc2cn[nH]c2C1]
I-244
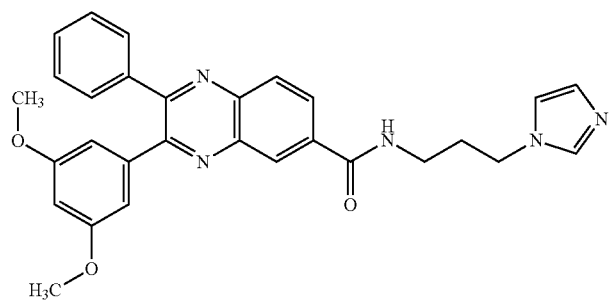 [SMILES: COc1cc(OC)cc(-c2nc3cc(C(=O)NCCCn4ccnc4)ccc3nc2-c2ccccc2)c1]
I-245

TABLE 1-continued
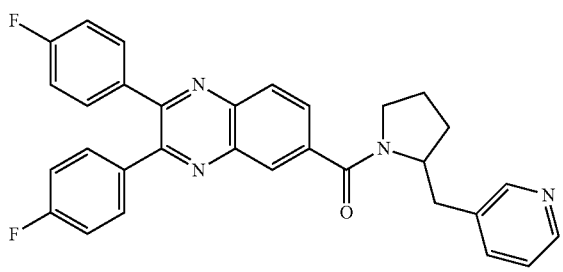 [SMILES: O=C(c1ccc2nc(-c3ccc(F)cc3)c(-c3ccc(F)cc3)nc2c1)N1CCCC1Cc1cccnc1] I-246
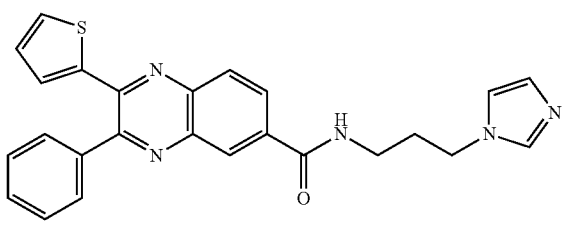 [SMILES: O=C(NCCCn1ccnc1)c1ccc2nc(-c3cccs3)c(-c3ccccc3)nc2c1] I-247
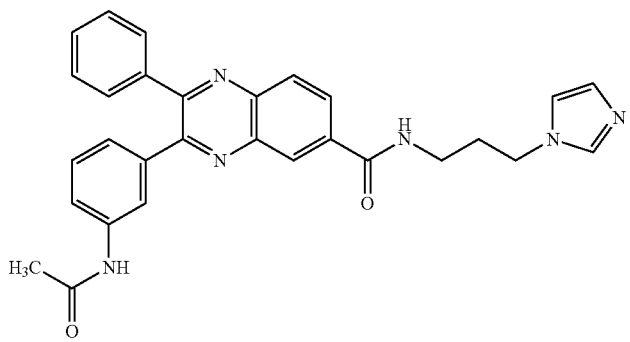 [SMILES: CC(=O)Nc1cccc(-c2nc3cc(C(=O)NCCCn4ccnc4)ccc3nc2-c2ccccc2)c1] I-248
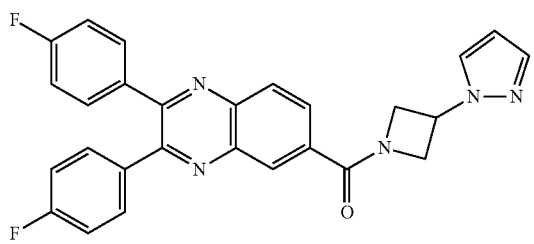 [SMILES: O=C(c1ccc2nc(-c3ccc(F)cc3)c(-c3ccc(F)cc3)nc2c1)N1CC(n2cccn2)C1] I-249
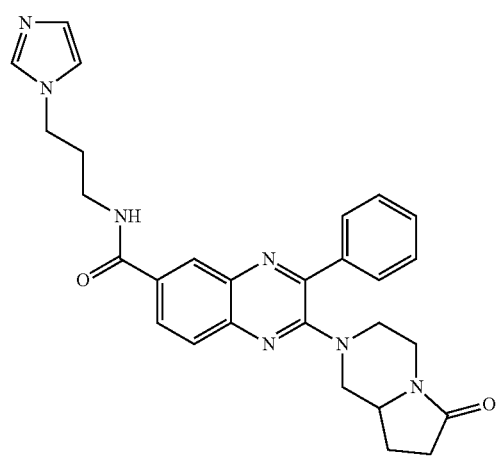 [SMILES: O=C(NCCCn1ccnc1)c1ccc2nc(N3CCN4C(=O)CCC4C3)c(-c3ccccc3)nc2c1] I-250

TABLE 1-continued
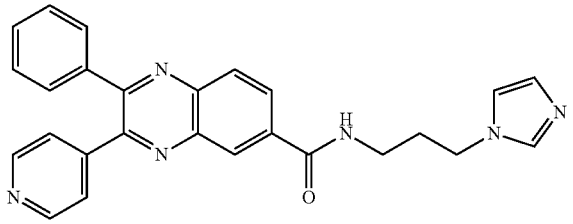 I-251
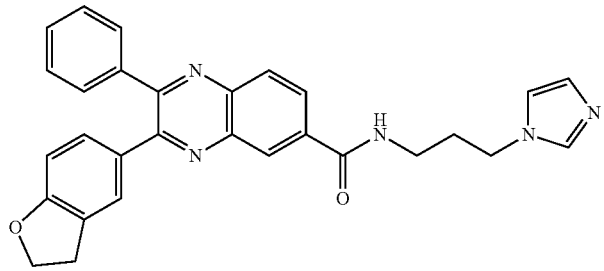 [SMILES: O=C(NCCCn1ccnc1)c1ccc2nc(-c3ccccc3)c(-c3ccc4c(c3)CCO4)nc2c1] I-252
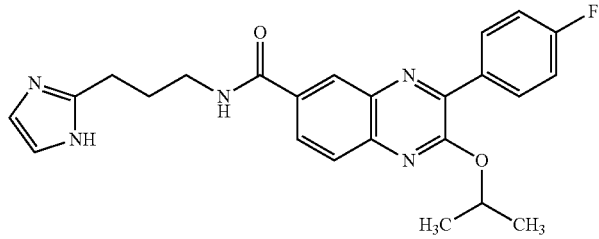 [SMILES: CC(C)Oc1nc2ccc(C(=O)NCCCc3ncc[nH]3)cc2nc1-c1ccc(F)cc1] I-253
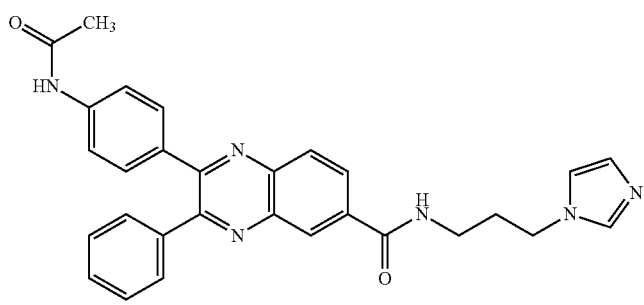 [SMILES: CC(=O)Nc1ccc(-c2nc3ccc(C(=O)NCCCn4ccnc4)cc3nc2-c2ccccc2)cc1] I-254
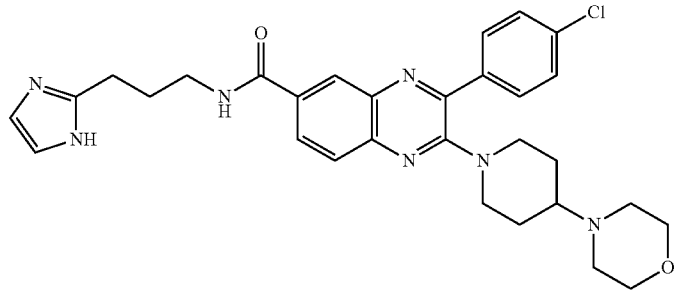 I-255
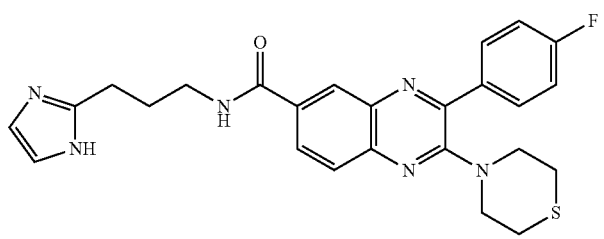 [SMILES: O=C(NCCCc1ncc[nH]1)c1ccc2nc(N3CCSCC3)c(-c3ccc(F)cc3)nc2c1] I-256

TABLE 1-continued
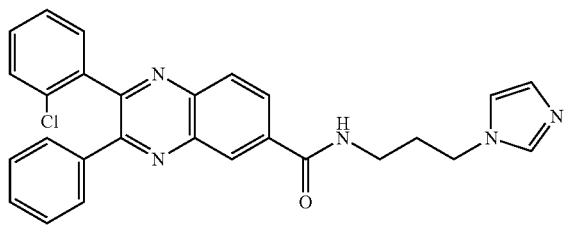 [SMILES: O=C(NCCCn1ccnc1)c1ccc2nc(-c3ccccc3Cl)c(-c3ccccc3)nc2c1]
I-257
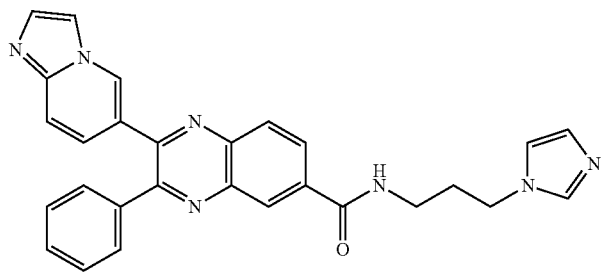 [SMILES: O=C(NCCCn1ccnc1)c1ccc2nc(-c3ccc4nccn4c3)c(-c3ccccc3)nc2c1]
I-258
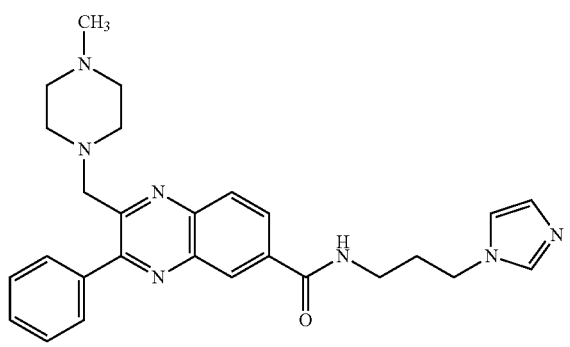 [SMILES: CN1CCN(Cc2nc3ccc(C(=O)NCCCn4ccnc4)cc3nc2-c2ccccc2)CC1]
I-259
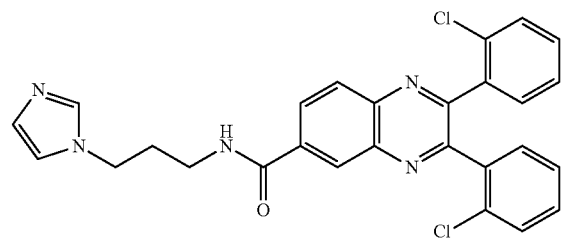 [SMILES: O=C(NCCCn1ccnc1)c1ccc2nc(-c3ccccc3Cl)c(-c3ccccc3Cl)nc2c1]
I-260
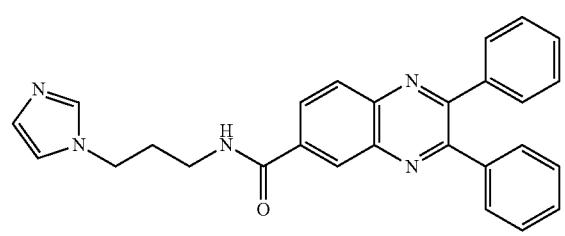 [SMILES: O=C(NCCCn1ccnc1)c1ccc2nc(-c3ccccc3)c(-c3ccccc3)nc2c1]
I-261

TABLE 1-continued
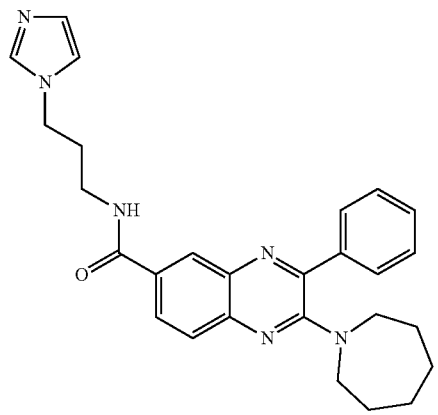 [SMILES: O=C(NCCCn1ccnc1)c1ccc2nc(N3CCCCCC3)c(-c3ccccc3)nc2c1]
I-262
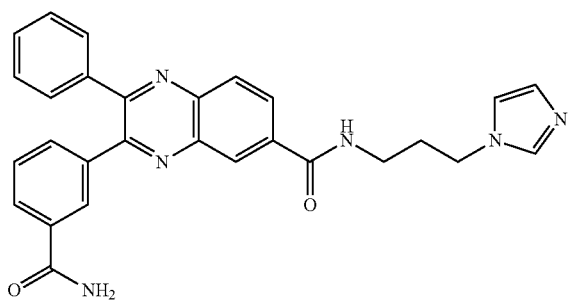 [SMILES: NC(=O)c1cccc(-c2nc3cc(C(=O)NCCCn4ccnc4)ccc3nc2-c2ccccc2)c1]
I-263
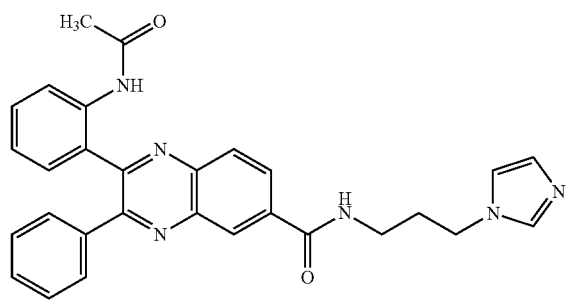 [SMILES: CC(=O)Nc1ccccc1-c1nc2ccc(C(=O)NCCCn3ccnc3)cc2nc1-c1ccccc1]
I-264
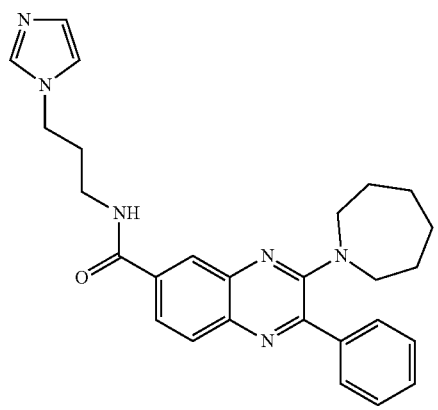 [SMILES: O=C(NCCCn1ccnc1)c1ccc2nc(-c3ccccc3)c(N3CCCCCC3)nc2c1]
I-265

TABLE 1-continued
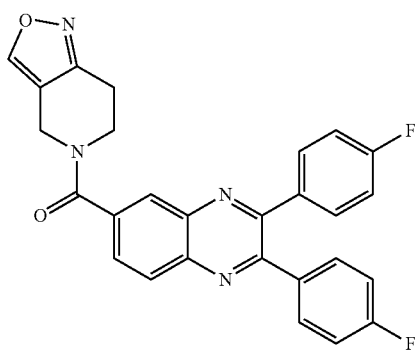 [SMILES: O=C(c1ccc2nc(-c3ccc(F)cc3)c(-c3ccc(F)cc3)nc2c1)N1CCc2nocc2C1]
I-266
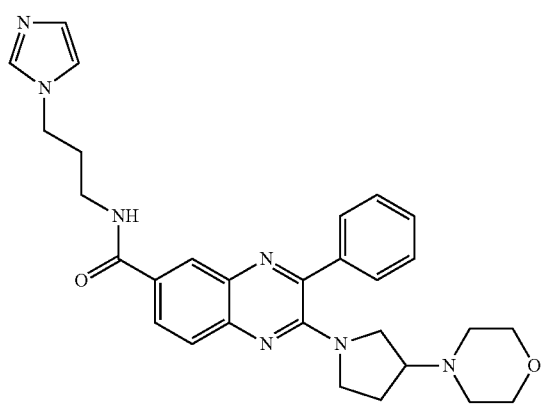 [SMILES: O=C(NCCCn1ccnc1)c1ccc2nc(N3CCC(N4CCOCC4)C3)c(-c3ccccc3)nc2c1]
I-267
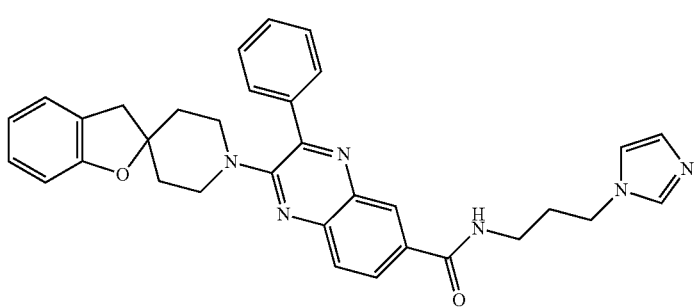 [SMILES: O=C(NCCCn1ccnc1)c1ccc2nc(N3CCC4(CC3)Cc3ccccc3O4)c(-c3ccccc3)nc2c1]
I-268
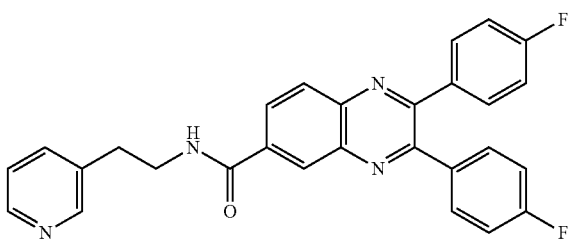 [SMILES: O=C(NCCc1cccnc1)c1ccc2nc(-c3ccc(F)cc3)c(-c3ccc(F)cc3)nc2c1]
I-269
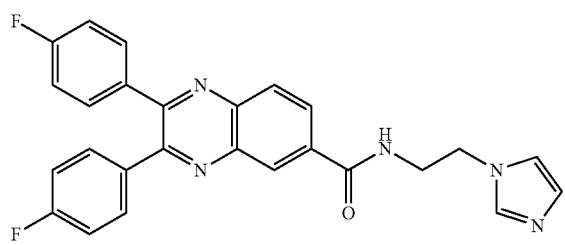 [SMILES: O=C(NCCn1ccnc1)c1ccc2nc(-c3ccc(F)cc3)c(-c3ccc(F)cc3)nc2c1]
I-270

TABLE 1-continued
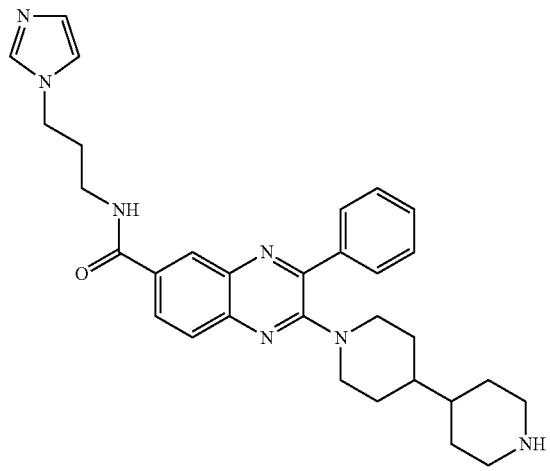 [SMILES: O=C(NCCCn1ccnc1)c1ccc2nc(N3CCC(C4CCNCC4)CC3)c(-c3ccccc3)nc2c1]
I-271
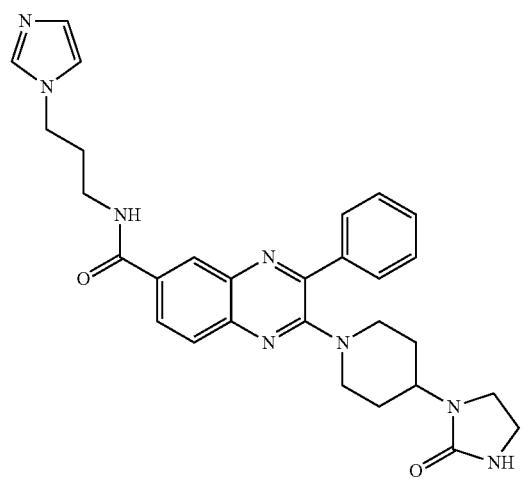 [SMILES: O=C(NCCCn1ccnc1)c1ccc2nc(N3CCC(N4CCNC4=O)CC3)c(-c3ccccc3)nc2c1]
I-272
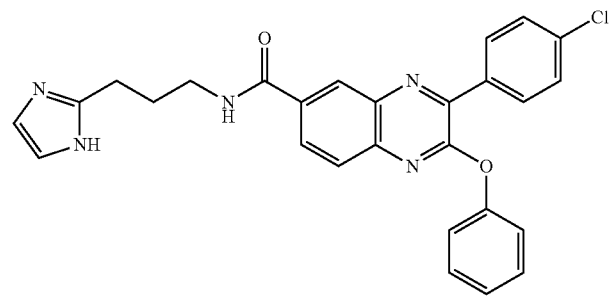 [SMILES: O=C(NCCCc1ncc[nH]1)c1ccc2nc(Oc3ccccc3)c(-c3ccc(Cl)cc3)nc2c1]
I-273

TABLE 1-continued
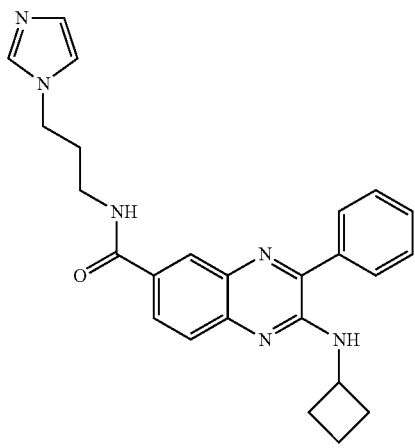 [SMILES: O=C(NCCCn1ccnc1)c1ccc2nc(NC3CCC3)c(-c3ccccc3)nc2c1]
I-274
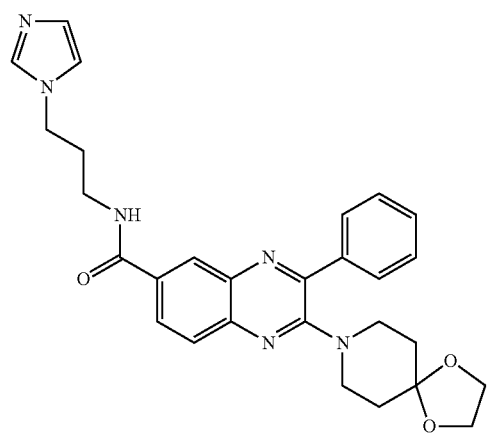 [SMILES: O=C(NCCCn1ccnc1)c1ccc2nc(N3CCC4(CC3)OCCO4)c(-c3ccccc3)nc2c1]
I-275
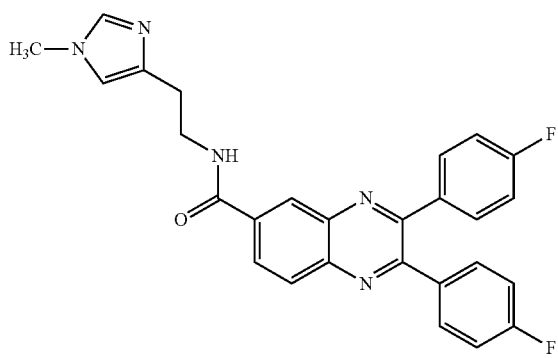 [SMILES: Cn1cnc(CCNC(=O)c2ccc3nc(-c4ccc(F)cc4)c(-c4ccc(F)cc4)nc3c2)c1]
I-276
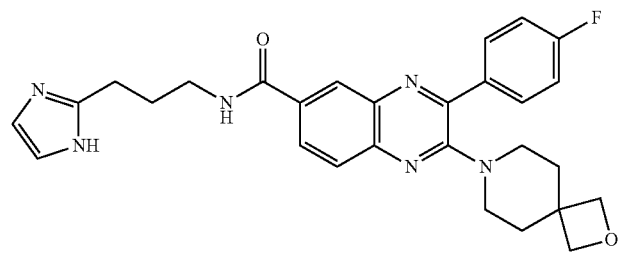 [SMILES: O=C(NCCCc1ncc[nH]1)c1ccc2nc(N3CCC4(CC3)COC4)c(-c3ccc(F)cc3)nc2c1]
I-277

TABLE 1-continued
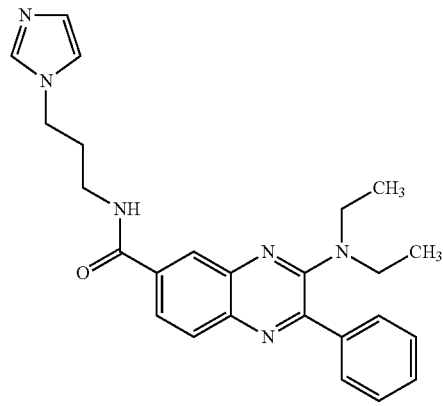 [SMILES: CCN(CC)c1nc2cc(C(=O)NCCCn3ccnc3)ccc2nc1-c1ccccc1]
I-278
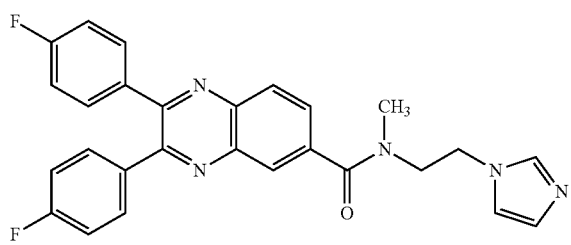 [SMILES: CN(CCn1ccnc1)C(=O)c1ccc2nc(-c3ccc(F)cc3)c(-c3ccc(F)cc3)nc2c1]
I-279
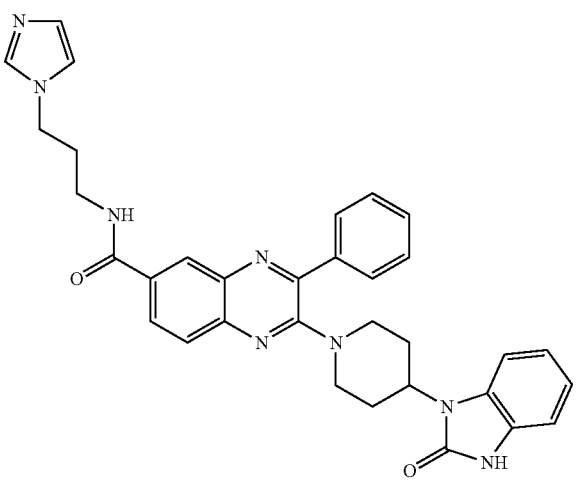 [SMILES: O=C(NCCCn1ccnc1)c1ccc2nc(N3CCC(n4c(=O)[nH]c5ccccc54)CC3)c(-c3ccccc3)nc2c1]
I-280
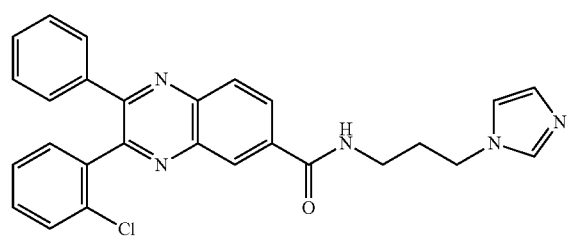 [SMILES: O=C(NCCCn1ccnc1)c1ccc2nc(-c3ccccc3)c(-c3ccccc3Cl)nc2c1]
I-281
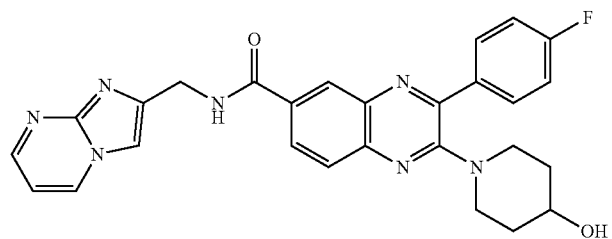 [SMILES: O=C(NCc1cn2cccnc2n1)c1ccc2nc(N3CCC(O)CC3)c(-c3ccc(F)cc3)nc2c1]
I-282

TABLE 1-continued
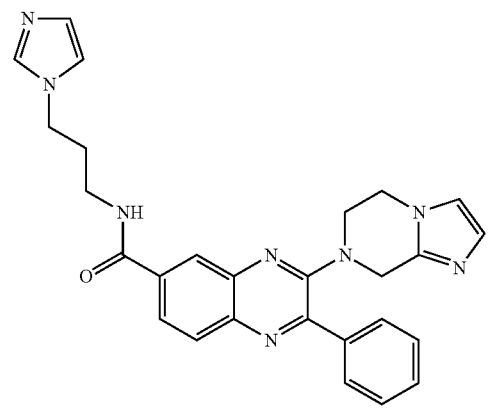 [SMILES: O=C(NCCCn1ccnc1)c1ccc2nc(-c3ccccc3)c(N3CCn4ccnc4C3)nc2c1]
I-283
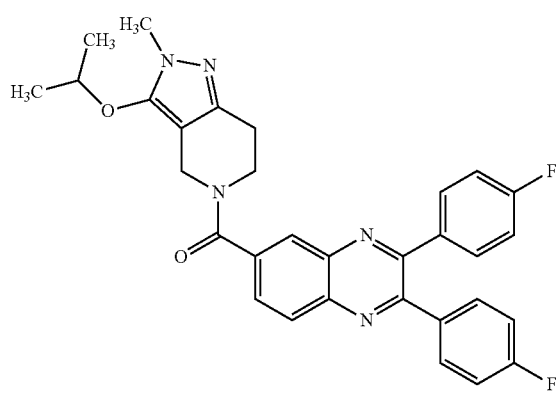 [SMILES: CC(C)Oc1c2c(nn1C)CCN(C(=O)c1ccc3nc(-c4ccc(F)cc4)c(-c4ccc(F)cc4)nc3c1)C2]
I-284
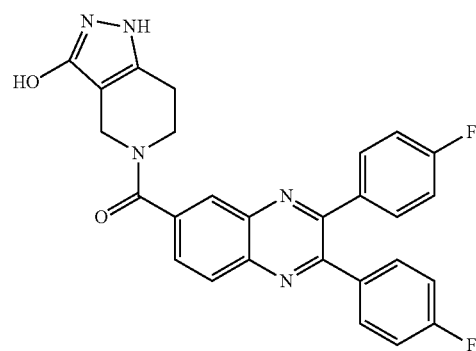 [SMILES: O=C(c1ccc2nc(-c3ccc(F)cc3)c(-c3ccc(F)cc3)nc2c1)N1CCc2[nH]nc(O)c2C1]
I-285
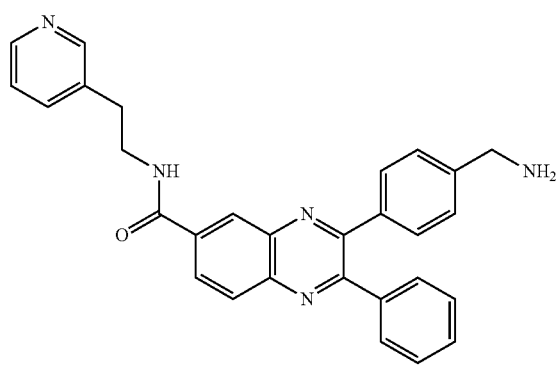 [SMILES: NCc1ccc(-c2nc3cc(C(=O)NCCc4cccnc4)ccc3nc2-c2ccccc2)cc1]
I-286

TABLE 1-continued
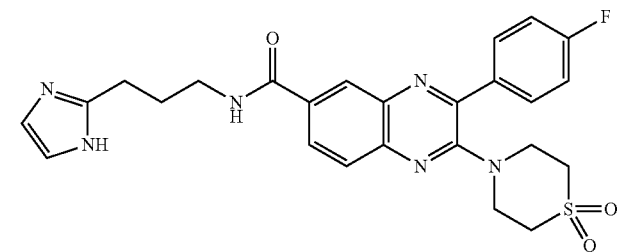 [SMILES: O=C(NCCCc1ncc[nH]1)c1ccc2nc(N3CCS(=O)(=O)CC3)c(-c3ccc(F)cc3)nc2c1]
I-287
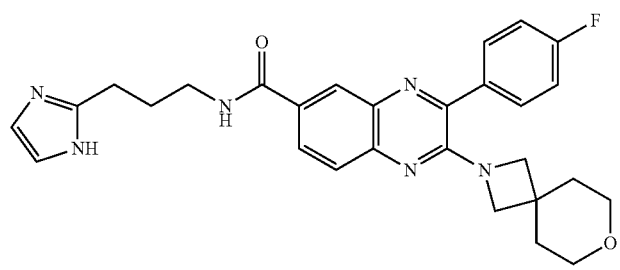 [SMILES: O=C(NCCCc1ncc[nH]1)c1ccc2nc(N3CC4(CCOCC4)C3)c(-c3ccc(F)cc3)nc2c1]
I-288
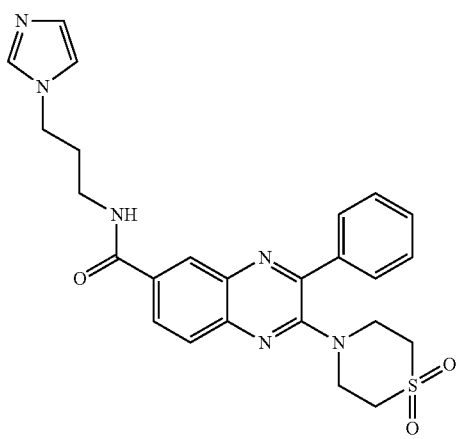 [SMILES: O=C(NCCCn1ccnc1)c1ccc2nc(N3CCS(=O)(=O)CC3)c(-c3ccccc3)nc2c1]
I-289
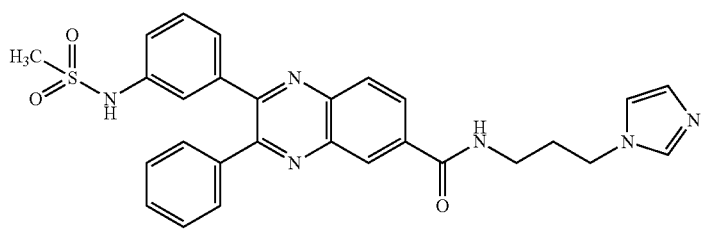 [SMILES: CS(=O)(=O)Nc1cccc(-c2nc3ccc(C(=O)NCCCn4ccnc4)cc3nc2-c2ccccc2)c1]
I-290
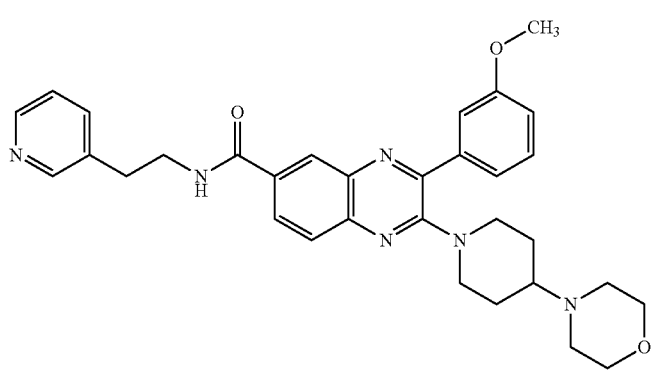 [SMILES: COc1cccc(-c2nc3cc(C(=O)NCCc4cccnc4)ccc3nc2N2CCC(N3CCOCC3)CC2)c1]
I-291

TABLE 1-continued
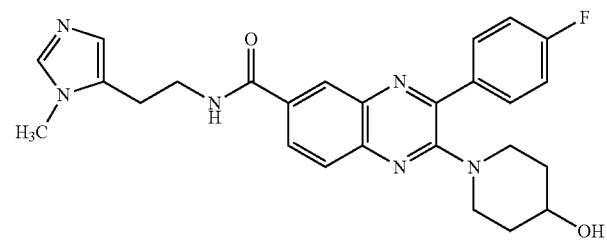 [SMILES: Cn1cncc1CCNC(=O)c1ccc2nc(N3CCC(O)CC3)c(-c3ccc(F)cc3)nc2c1] I-292
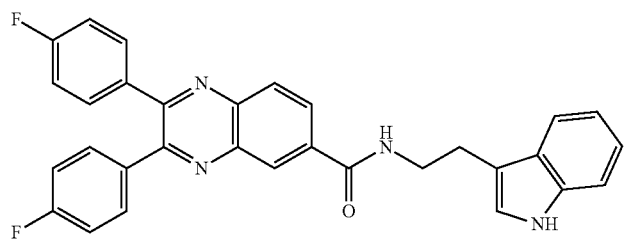 [SMILES: O=C(NCCc1c[nH]c2ccccc12)c1ccc2nc(-c3ccc(F)cc3)c(-c3ccc(F)cc3)nc2c1] I-293
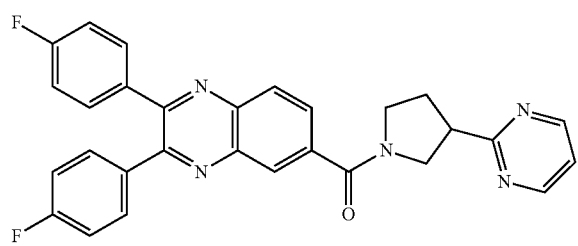 [SMILES: O=C(c1ccc2nc(-c3ccc(F)cc3)c(-c3ccc(F)cc3)nc2c1)N1CCC(c2ncccn2)C1] I-294
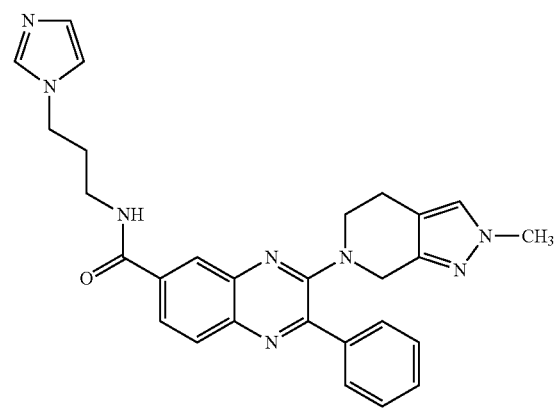 [SMILES: Cn1cc2c(n1)CN(c1nc3cc(C(=O)NCCCn4ccnc4)ccc3nc1-c1ccccc1)CC2] I-295
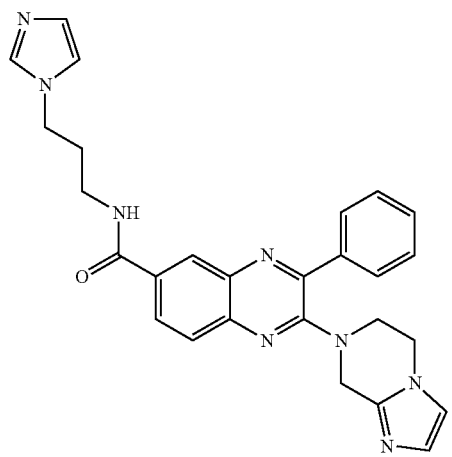 [SMILES: O=C(NCCCn1ccnc1)c1ccc2nc(N3CCn4ccnc4C3)c(-c3ccccc3)nc2c1] I-296

TABLE 1-continued
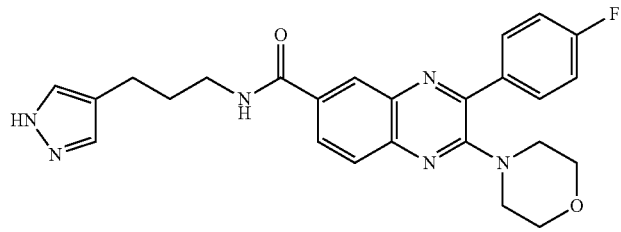 [SMILES: O=C(NCCCc1cn[nH]c1)c1ccc2nc(N3CCOCC3)c(-c3ccc(F)cc3)nc2c1] I-297
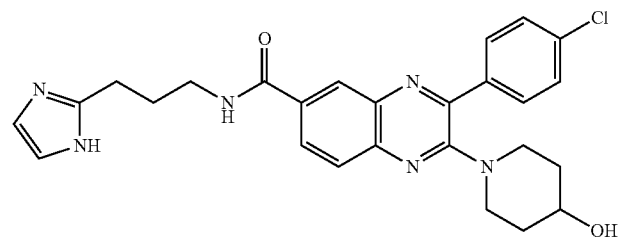 I-298
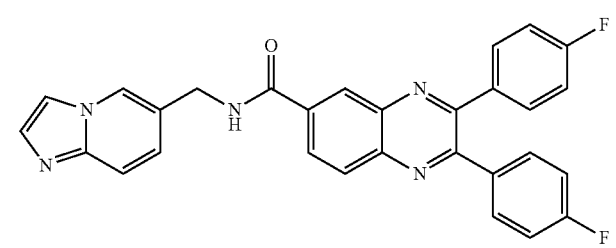 [SMILES: O=C(NCc1ccc2nccn2c1)c1ccc2nc(-c3ccc(F)cc3)c(-c3ccc(F)cc3)nc2c1] I-299
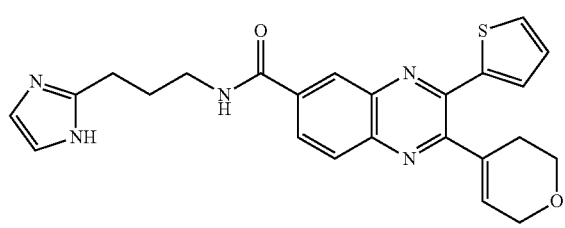 [SMILES: O=C(NCCCc1ncc[nH]1)c1ccc2nc(C3=CCOCC3)c(-c3cccs3)nc2c1] I-300
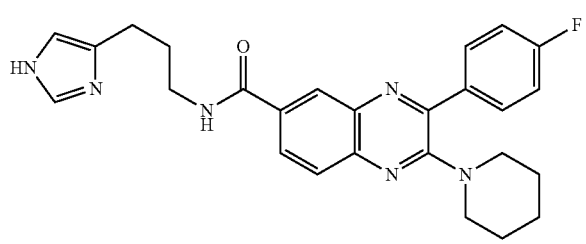 [SMILES: O=C(NCCCc1c[nH]cn1)c1ccc2nc(N3CCCCC3)c(-c3ccc(F)cc3)nc2c1] I-301
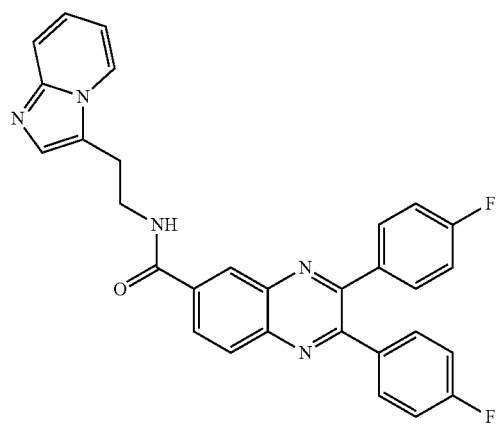 [SMILES: O=C(NCCc1cnc2ccccn12)c1ccc2nc(-c3ccc(F)cc3)c(-c3ccc(F)cc3)nc2c1] I-302

TABLE 1-continued
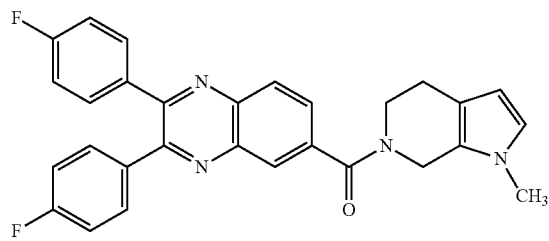 [SMILES: Cn1ccc2c1CN(C(=O)c1ccc3nc(-c4ccc(F)cc4)c(-c4ccc(F)cc4)nc3c1)CC2]
I-303
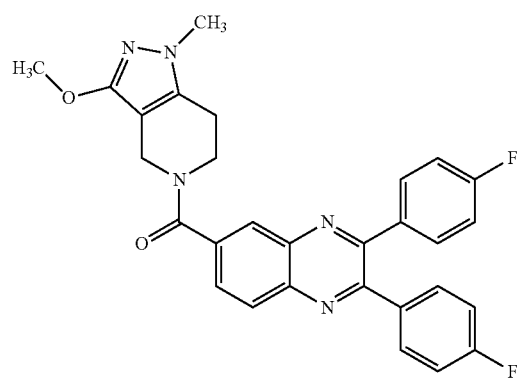 [SMILES: COc1nn(C)c2c1CN(C(=O)c1ccc3nc(-c4ccc(F)cc4)c(-c4ccc(F)cc4)nc3c1)CC2]
I-304
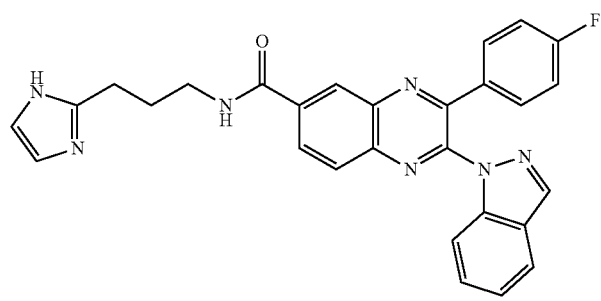 [SMILES: O=C(NCCCc1ncc[nH]1)c1ccc2nc(-n3ncc4ccccc43)c(-c3ccc(F)cc3)nc2c1]
I-305
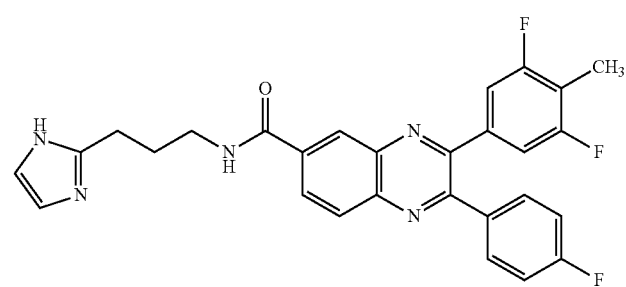 [SMILES: Cc1c(F)cc(-c2nc3cc(C(=O)NCCCc4ncc[nH]4)ccc3nc2-c2ccc(F)cc2)cc1F]
I-306
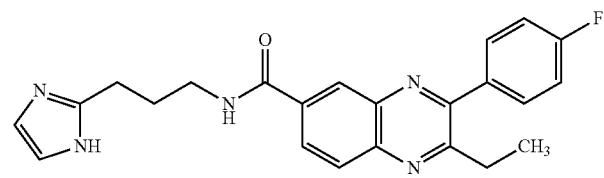 [SMILES: CCc1nc2ccc(C(=O)NCCCc3ncc[nH]3)cc2nc1-c1ccc(F)cc1]
I-307
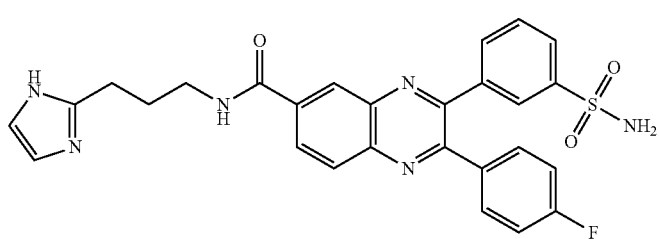 [SMILES: NS(=O)(=O)c1cccc(-c2nc3cc(C(=O)NCCCc4ncc[nH]4)ccc3nc2-c2ccc(F)cc2)c1]
I-308

TABLE 1-continued
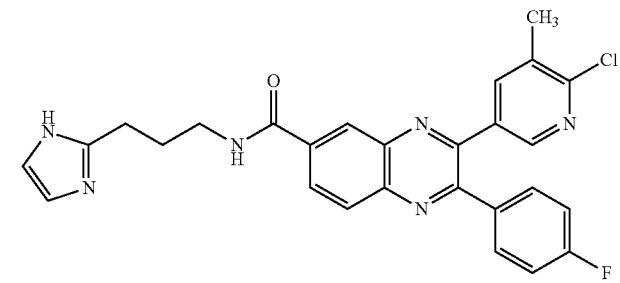 [SMILES: Cc1cc(-c2nc3cc(C(=O)NCCCc4ncc[nH]4)ccc3nc2-c2ccc(F)cc2)cnc1Cl] I-309
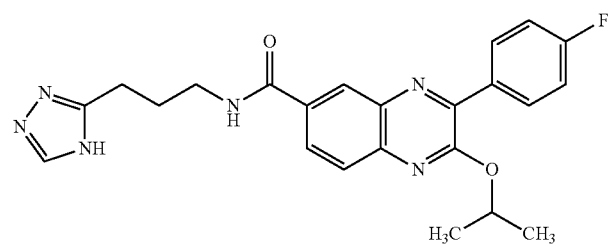 [SMILES: CC(C)Oc1nc2ccc(C(=O)NCCCc3nnc[nH]3)cc2nc1-c1ccc(F)cc1] I-310
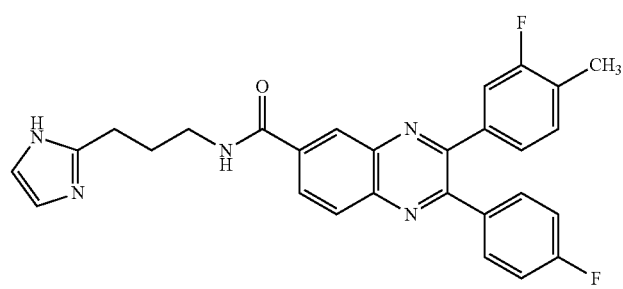 [SMILES: Cc1ccc(-c2nc3cc(C(=O)NCCCc4ncc[nH]4)ccc3nc2-c2ccc(F)cc2)cc1F] I-311
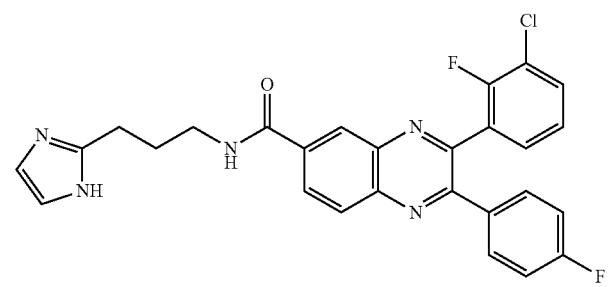 [SMILES: O=C(NCCCc1ncc[nH]1)c1ccc2nc(-c3ccc(F)cc3)c(-c3cccc(Cl)c3F)nc2c1] I-312
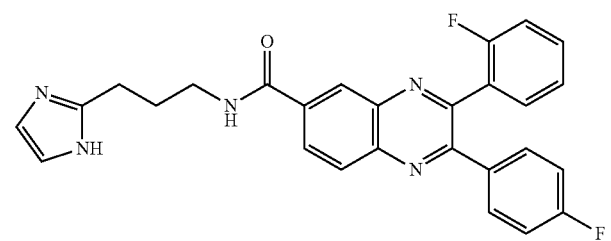 [SMILES: O=C(NCCCc1ncc[nH]1)c1ccc2nc(-c3ccc(F)cc3)c(-c3ccccc3F)nc2c1] I-313
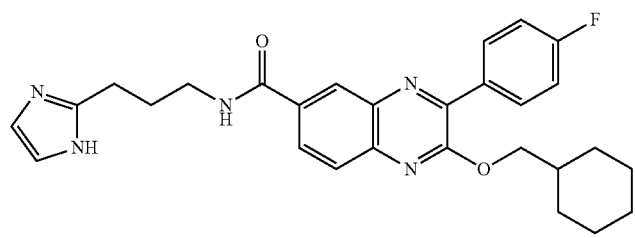 [SMILES: O=C(NCCCc1ncc[nH]1)c1ccc2nc(OCC3CCCCC3)c(-c3ccc(F)cc3)nc2c1] I-314

TABLE 1-continued
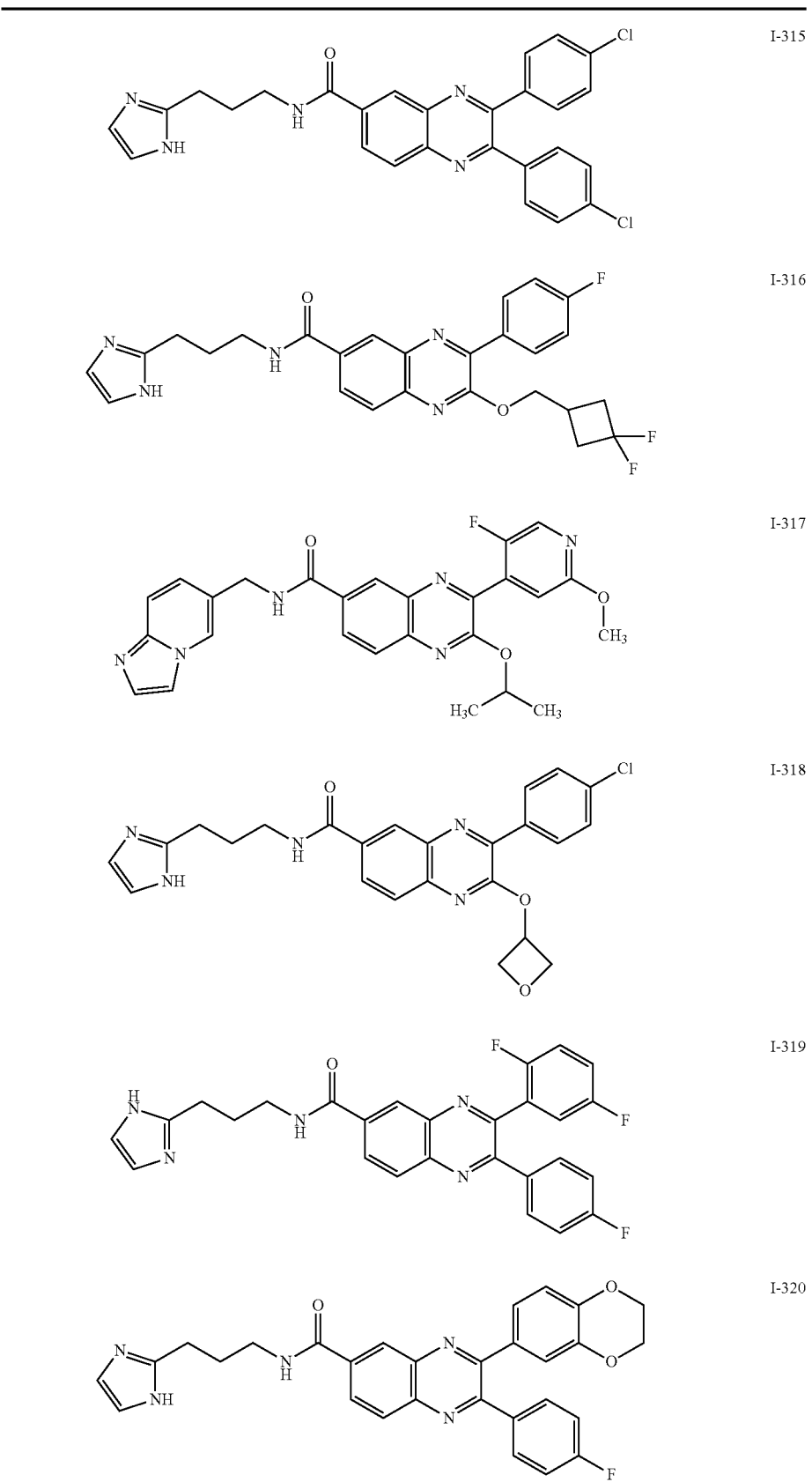
I-315
I-316
I-317
I-318
I-319
I-320

TABLE 1-continued
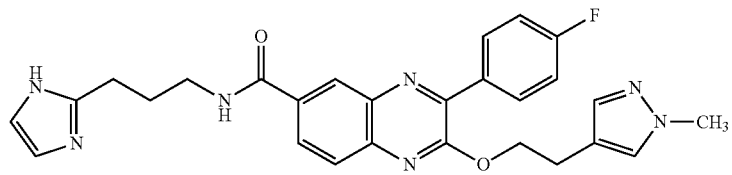 [SMILES: Cn1cc(CCOc2nc3ccc(C(=O)NCCCc4ncc[nH]4)cc3nc2-c2ccc(F)cc2)cn1] I-321
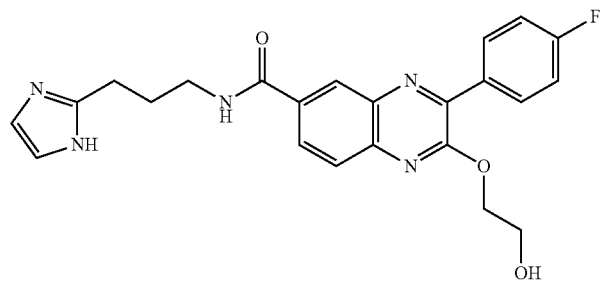 [SMILES: O=C(NCCCc1ncc[nH]1)c1ccc2nc(OCCO)c(-c3ccc(F)cc3)nc2c1] I-322
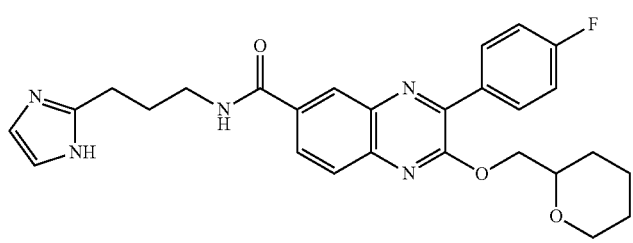 [SMILES: O=C(NCCCc1ncc[nH]1)c1ccc2nc(OCC3CCCCO3)c(-c3ccc(F)cc3)nc2c1] I-323
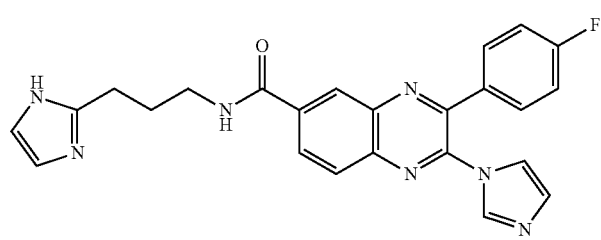 [SMILES: O=C(NCCCc1ncc[nH]1)c1ccc2nc(-n3ccnc3)c(-c3ccc(F)cc3)nc2c1] I-324
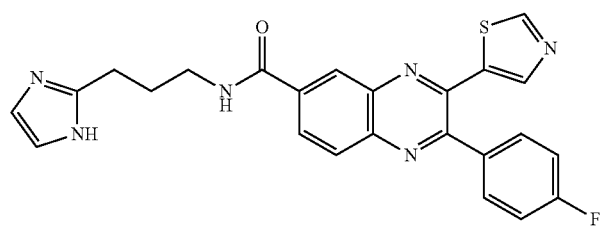 [SMILES: O=C(NCCCc1ncc[nH]1)c1ccc2nc(-c3ccc(F)cc3)c(-c3cncs3)nc2c1] I-325
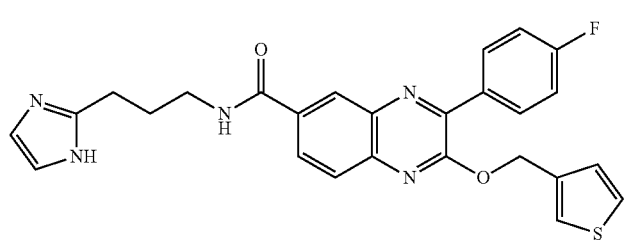 I-326
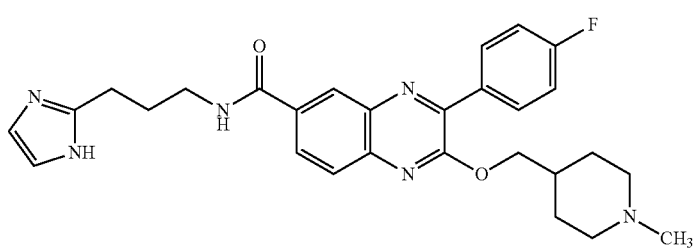 [SMILES: CN1CCC(COc2nc3ccc(C(=O)NCCCc4ncc[nH]4)cc3nc2-c2ccc(F)cc2)CC1] I-327

TABLE 1-continued
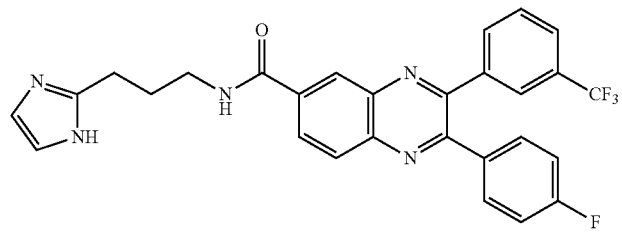 [SMILES: O=C(NCCCc1ncc[nH]1)c1ccc2nc(-c3ccc(F)cc3)c(-c3cccc(C(F)(F)F)c3)nc2c1] I-328
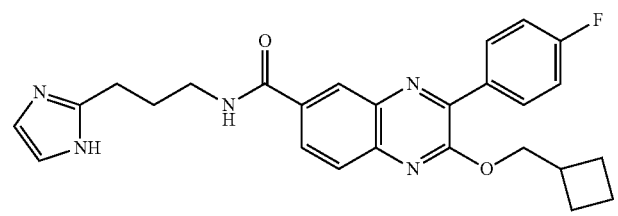 [SMILES: O=C(NCCCc1ncc[nH]1)c1ccc2nc(OCC3CCC3)c(-c3ccc(F)cc3)nc2c1] I-329
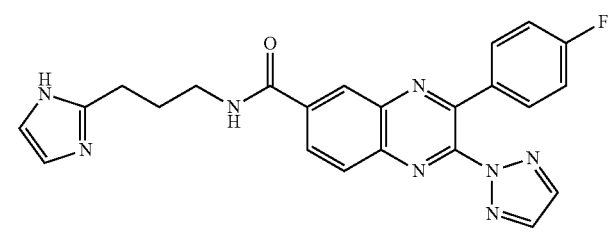 [SMILES: O=C(NCCCc1ncc[nH]1)c1ccc2nc(-n3nccn3)c(-c3ccc(F)cc3)nc2c1] I-330
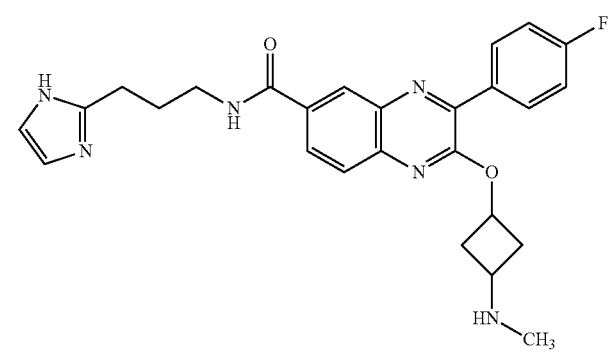 [SMILES: CNC1CC(Oc2nc3ccc(C(=O)NCCCc4ncc[nH]4)cc3nc2-c2ccc(F)cc2)C1] I-331
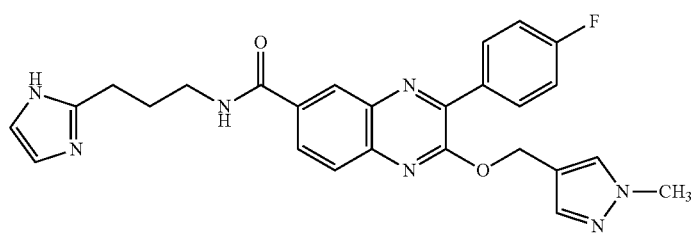 [SMILES: Cn1cc(COc2nc3ccc(C(=O)NCCCc4ncc[nH]4)cc3nc2-c2ccc(F)cc2)cn1] I-332
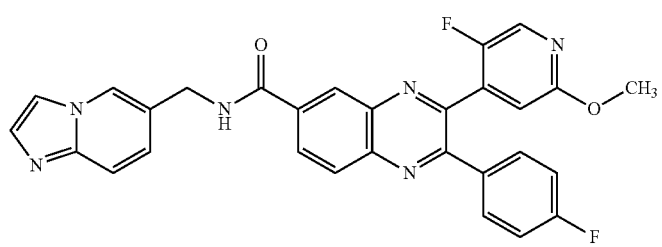 [SMILES: COc1cc(-c2nc3cc(C(=O)NCc4ccc5nccn5c4)ccc3nc2-c2ccc(F)cc2)c(F)cn1] I-333

TABLE 1-continued
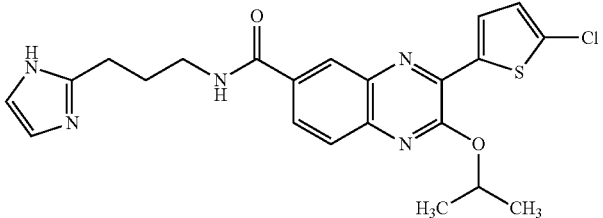 [SMILES: CC(C)Oc1nc2ccc(C(=O)NCCCc3ncc[nH]3)cc2nc1-c1ccc(Cl)s1] I-334
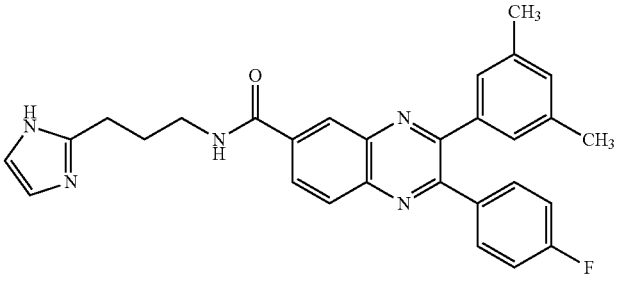 [SMILES: Cc1cc(C)cc(-c2nc3cc(C(=O)NCCCc4ncc[nH]4)ccc3nc2-c2ccc(F)cc2)c1] I-335
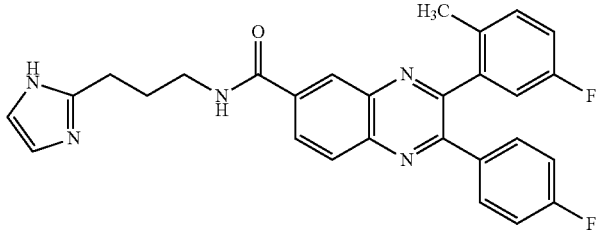 [SMILES: Cc1ccc(F)cc1-c1nc2cc(C(=O)NCCCc3ncc[nH]3)ccc2nc1-c1ccc(F)cc1] I-336
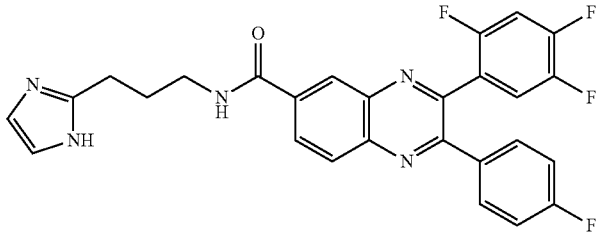 [SMILES: O=C(NCCCc1ncc[nH]1)c1ccc2nc(-c3ccc(F)cc3)c(-c3cc(F)c(F)cc3F)nc2c1] I-337
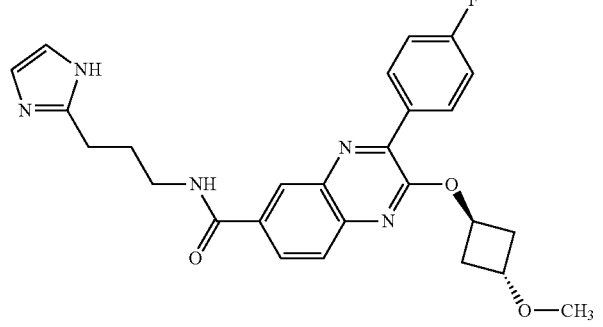 I-338
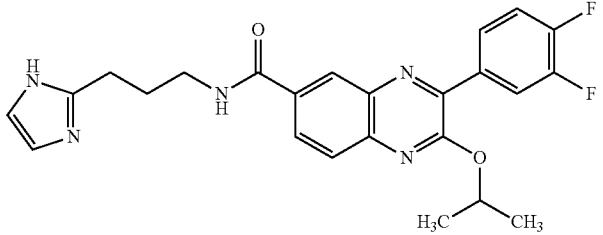 [SMILES: CC(C)Oc1nc2ccc(C(=O)NCCCc3ncc[nH]3)cc2nc1-c1ccc(F)c(F)c1] I-339

TABLE 1-continued
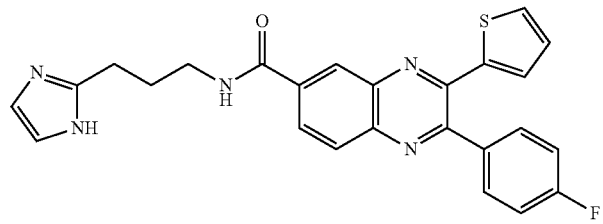 [SMILES: O=C(NCCCc1ncc[nH]1)c1ccc2nc(-c3ccc(F)cc3)c(-c3cccs3)nc2c1] I-340
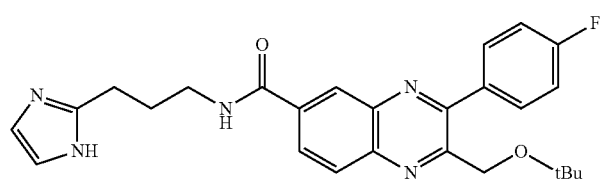 [SMILES: CC(C)(C)OCc1nc2ccc(C(=O)NCCCc3ncc[nH]3)cc2nc1-c1ccc(F)cc1] I-341
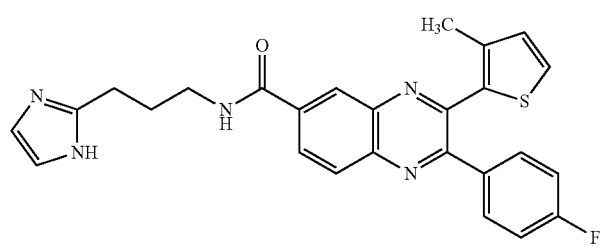 [SMILES: Cc1ccsc1-c1nc2cc(C(=O)NCCCc3ncc[nH]3)ccc2nc1-c1ccc(F)cc1] I-342
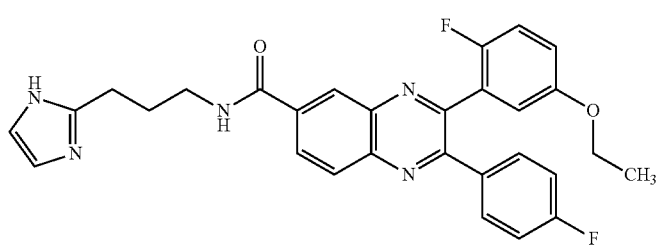 [SMILES: CCOc1ccc(F)c(-c2nc3cc(C(=O)NCCCc4ncc[nH]4)ccc3nc2-c2ccc(F)cc2)c1] I-343
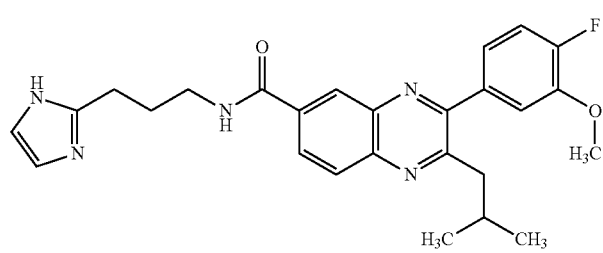 [SMILES: COc1cc(-c2nc3cc(C(=O)NCCCc4ncc[nH]4)ccc3nc2CC(C)C)ccc1F] I-344
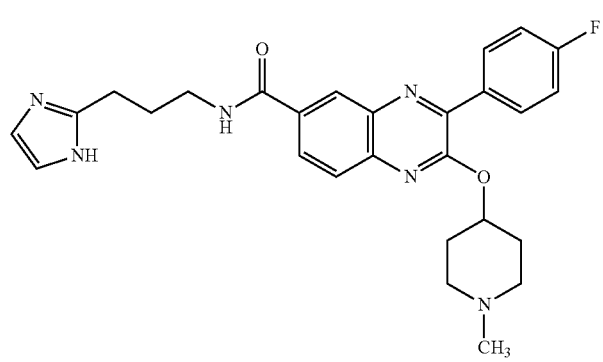 [SMILES: CN1CCC(Oc2nc3ccc(C(=O)NCCCc4ncc[nH]4)cc3nc2-c2ccc(F)cc2)CC1] I-345

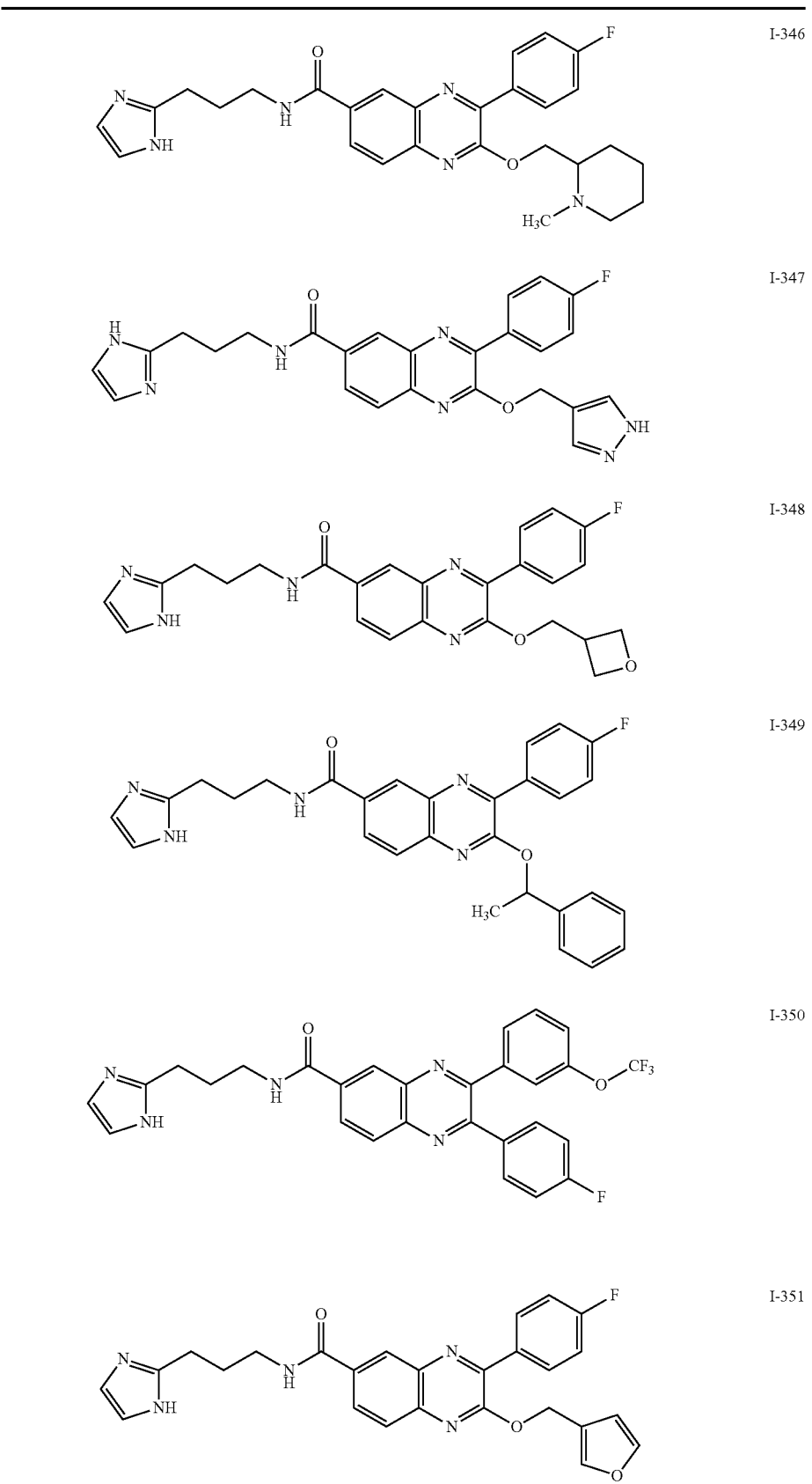
I-346
I-347
I-348
I-349
I-350
I-351

TABLE 1-continued
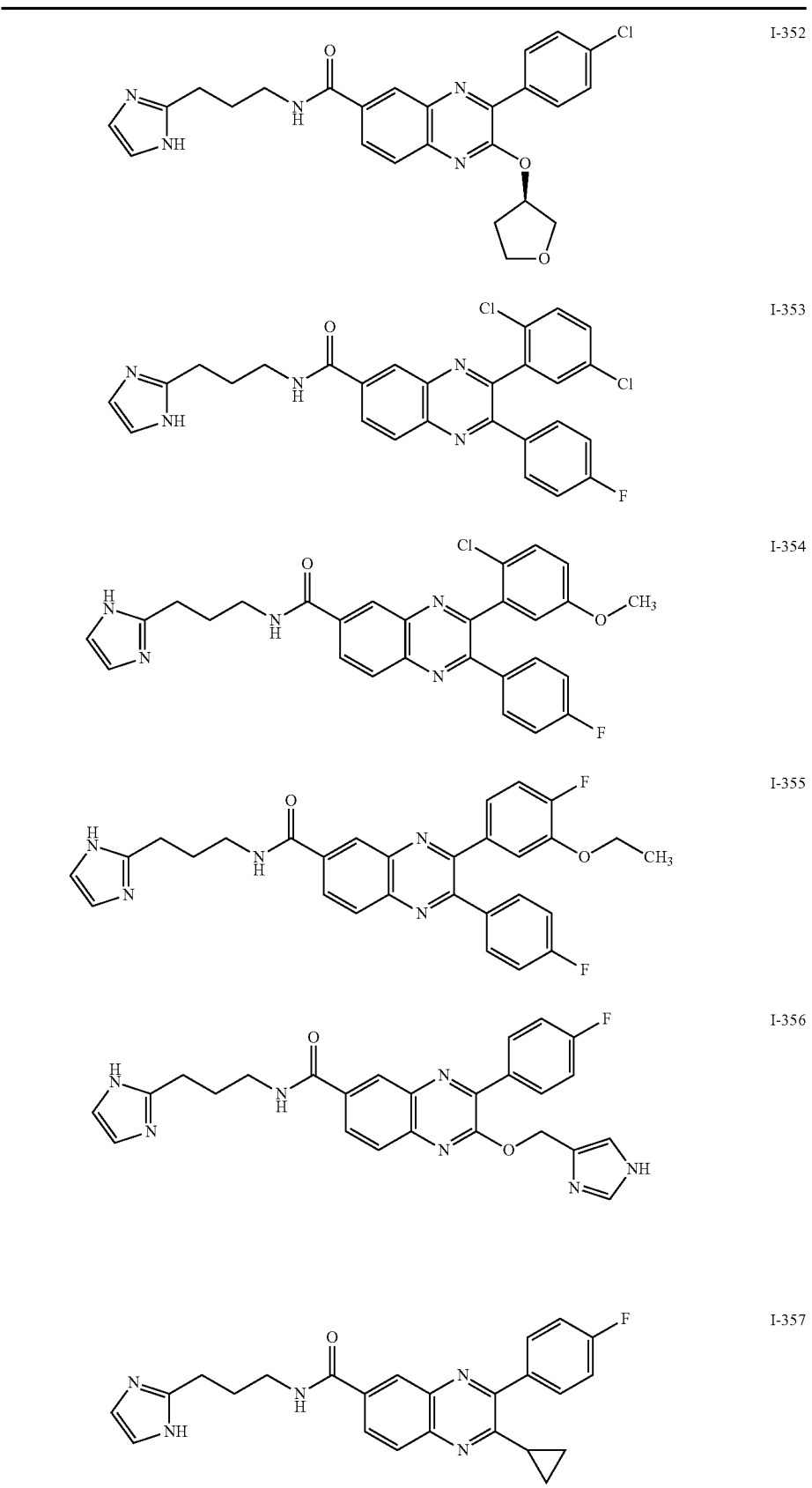
I-352
I-353
I-354
I-355
I-356
I-357

TABLE 1-continued
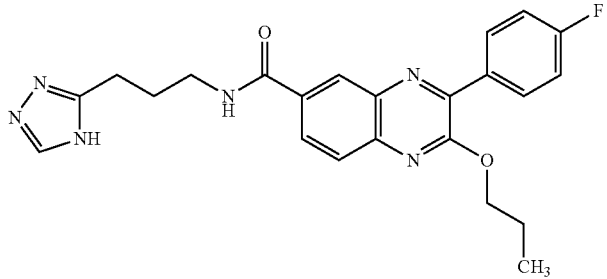 [SMILES: CCCOc1nc2ccc(C(=O)NCCCc3nnc[nH]3)cc2nc1-c1ccc(F)cc1] I-358
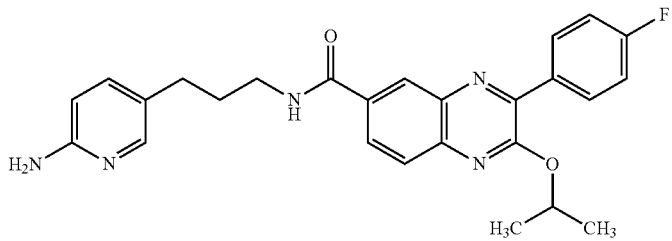 [SMILES: CC(C)Oc1nc2ccc(C(=O)NCCCc3ccc(N)nc3)cc2nc1-c1ccc(F)cc1] I-359
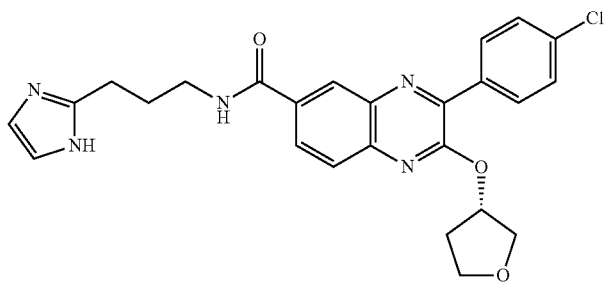 [SMILES: O=C(NCCCc1ncc[nH]1)c1ccc2nc(O[C@H]3CCOC3)c(-c3ccc(Cl)cc3)nc2c1] I-360
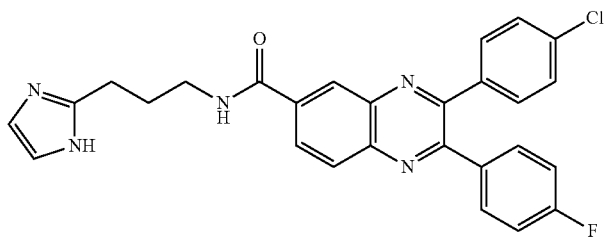 [SMILES: O=C(NCCCc1ncc[nH]1)c1ccc2nc(-c3ccc(F)cc3)c(-c3ccc(Cl)cc3)nc2c1] I-361
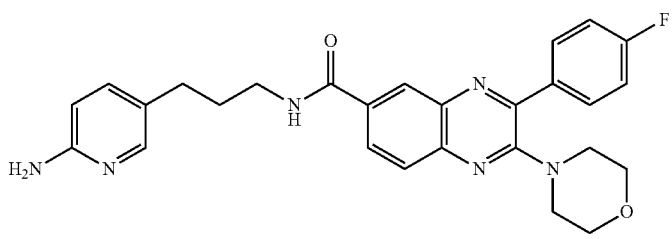 [SMILES: Nc1ccc(CCCNC(=O)c2ccc3nc(N4CCOCC4)c(-c4ccc(F)cc4)nc3c2)cn1] I-362
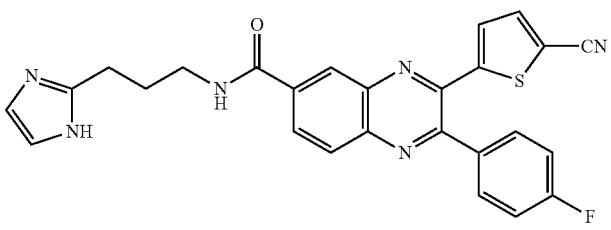 [SMILES: N#Cc1ccc(-c2nc3cc(C(=O)NCCCc4ncc[nH]4)ccc3nc2-c2ccc(F)cc2)s1] I-363

TABLE 1-continued
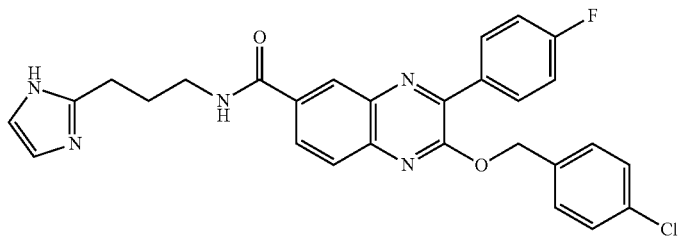 [SMILES: O=C(NCCCc1ncc[nH]1)c1ccc2nc(OCc3ccc(Cl)cc3)c(-c3ccc(F)cc3)nc2c1] I-364
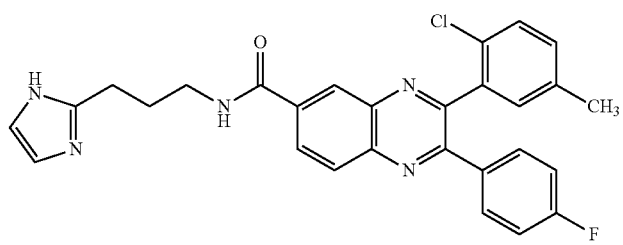 [SMILES: Cc1ccc(Cl)c(-c2nc3cc(C(=O)NCCCc4ncc[nH]4)ccc3nc2-c2ccc(F)cc2)c1] I-365
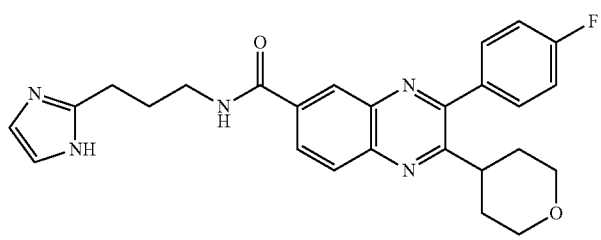 [SMILES: O=C(NCCCc1ncc[nH]1)c1ccc2nc(C3CCOCC3)c(-c3ccc(F)cc3)nc2c1] I-366
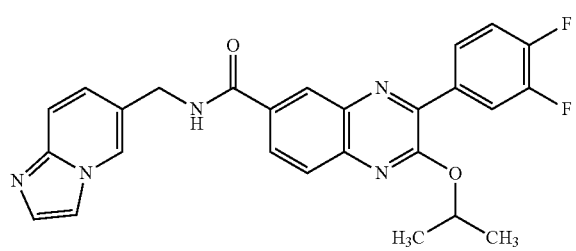 [SMILES: CC(C)Oc1nc2ccc(C(=O)NCc3ccc4nccn4c3)cc2nc1-c1ccc(F)c(F)c1] I-367
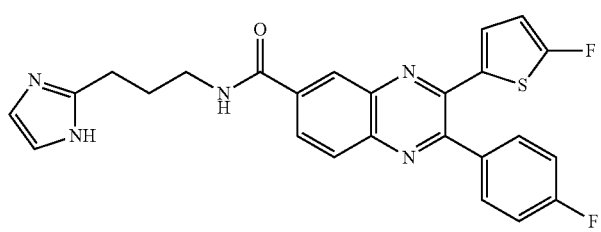 [SMILES: O=C(NCCCc1ncc[nH]1)c1ccc2nc(-c3ccc(F)cc3)c(-c3ccc(F)s3)nc2c1] I-368
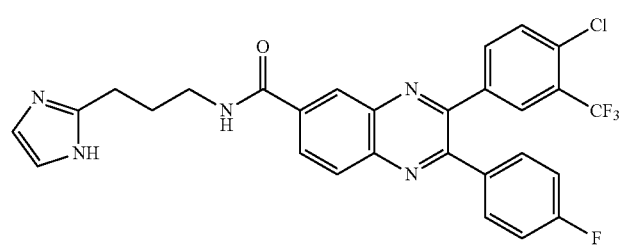 [SMILES: O=C(NCCCc1ncc[nH]1)c1ccc2nc(-c3ccc(F)cc3)c(-c3ccc(Cl)c(C(F)(F)F)c3)nc2c1] I-369

TABLE 1-continued

| | |
|---|---|
| (structure) | I-370 |
| (structure) | I-371 |
| (structure) | I-372 |
| (structure) | I-373 |
| (structure) | I-374 |
| (structure) | I-375 |

TABLE 1-continued
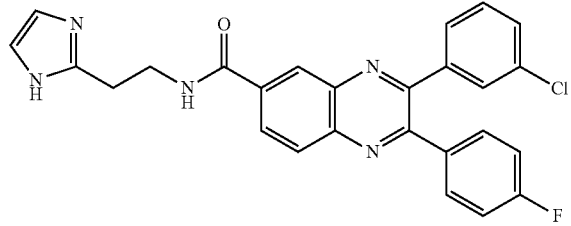 [SMILES: O=C(NCCc1ncc[nH]1)c1ccc2nc(-c3ccc(F)cc3)c(-c3cccc(Cl)c3)nc2c1] I-376
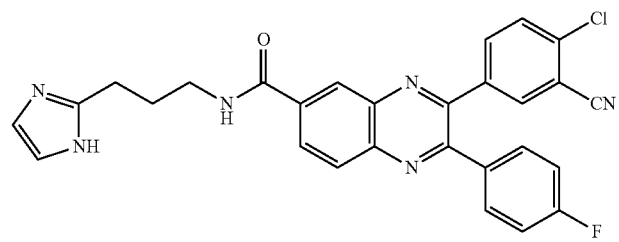 I-377
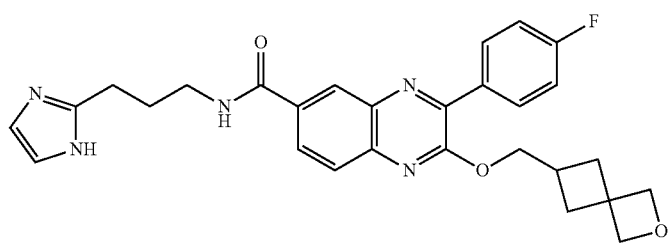 [SMILES: O=C(NCCCc1ncc[nH]1)c1ccc2nc(OCC3CC4(COC4)C3)c(-c3ccc(F)cc3)nc2c1] I-378
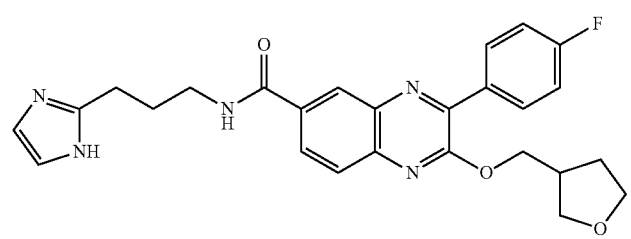 [SMILES: O=C(NCCCc1ncc[nH]1)c1ccc2nc(OCC3CCOC3)c(-c3ccc(F)cc3)nc2c1] I-379
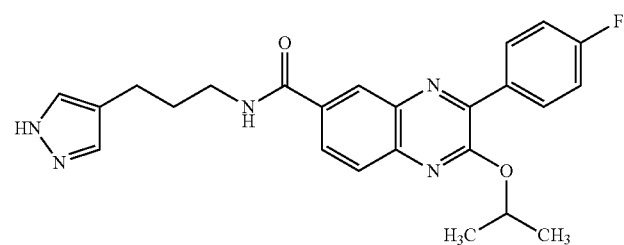 [SMILES: CC(C)Oc1nc2ccc(C(=O)NCCCc3cn[nH]c3)cc2nc1-c1ccc(F)cc1] I-380
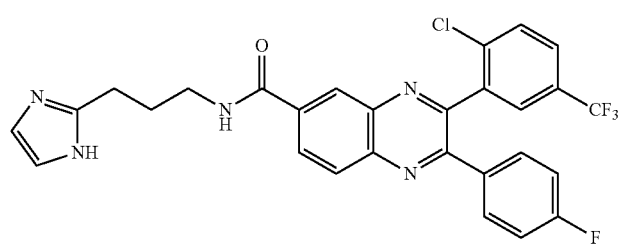 [SMILES: O=C(NCCCc1ncc[nH]1)c1ccc2nc(-c3ccc(F)cc3)c(-c3cc(C(F)(F)F)ccc3Cl)nc2c1] I-381

TABLE 1-continued
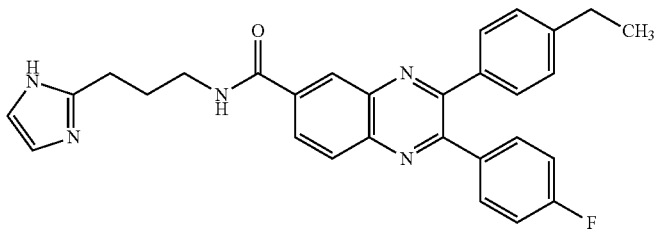 [SMILES: CCc1ccc(-c2nc3cc(C(=O)NCCCc4ncc[nH]4)ccc3nc2-c2ccc(F)cc2)cc1] I-382
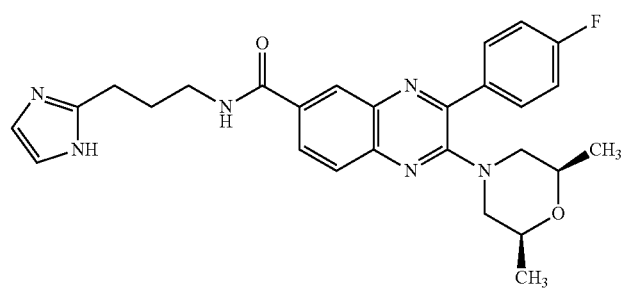 [SMILES: C[C@@H]1CN(c2nc3ccc(C(=O)NCCCc4ncc[nH]4)cc3nc2-c2ccc(F)cc2)C[C@H](C)O1] I-383
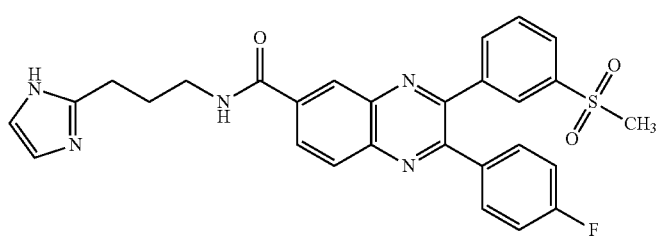 [SMILES: CS(=O)(=O)c1cccc(-c2nc3cc(C(=O)NCCCc4ncc[nH]4)ccc3nc2-c2ccc(F)cc2)c1] I-384
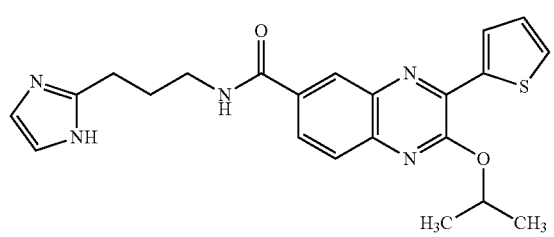 [SMILES: CC(C)Oc1nc2ccc(C(=O)NCCCc3ncc[nH]3)cc2nc1-c1cccs1] I-385
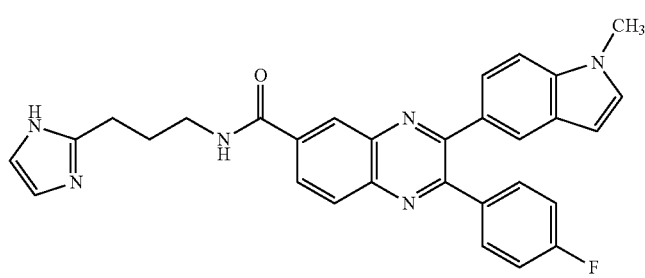 [SMILES: Cn1ccc2cc(-c3nc4cc(C(=O)NCCCc5ncc[nH]5)ccc4nc3-c3ccc(F)cc3)ccc21] I-386
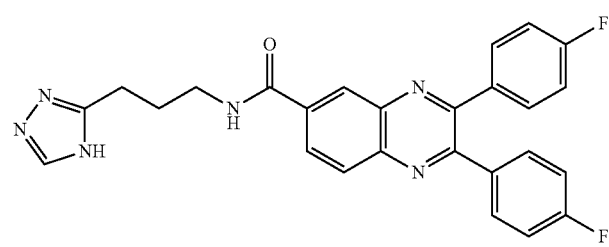 [SMILES: O=C(NCCCc1nnc[nH]1)c1ccc2nc(-c3ccc(F)cc3)c(-c3ccc(F)cc3)nc2c1] I-387

TABLE 1-continued
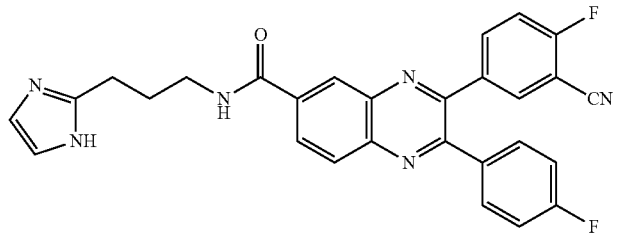 I-388
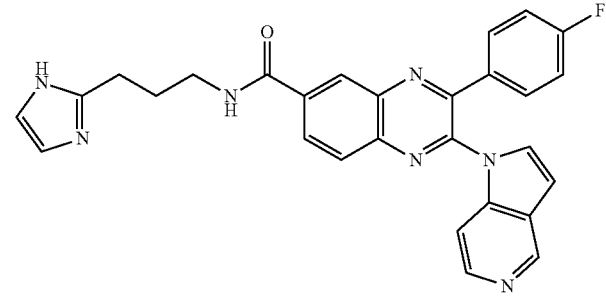 [SMILES: O=C(NCCCc1ncc[nH]1)c1ccc2nc(-n3ccc4cnccc43)c(-c3ccc(F)cc3)nc2c1] I-389
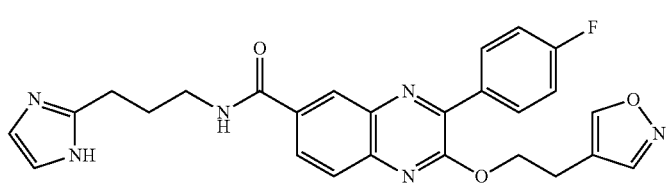 [SMILES: O=C(NCCCc1ncc[nH]1)c1ccc2nc(OCCc3cnoc3)c(-c3ccc(F)cc3)nc2c1] I-390
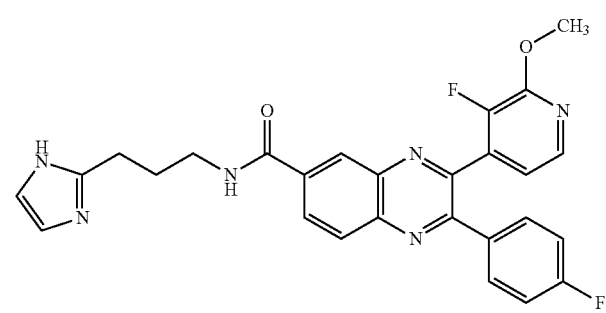 [SMILES: COc1nccc(-c2nc3cc(C(=O)NCCCc4ncc[nH]4)ccc3nc2-c2ccc(F)cc2)c1F] I-391
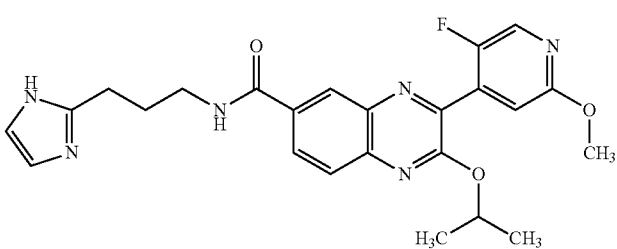 [SMILES: COc1cc(-c2nc3cc(C(=O)NCCCc4ncc[nH]4)ccc3nc2OC(C)C)c(F)cn1] I-392
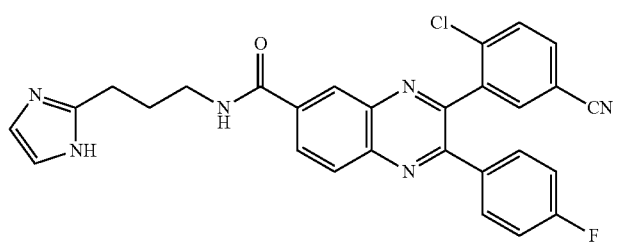 [SMILES: N#Cc1ccc(Cl)c(-c2nc3cc(C(=O)NCCCc4ncc[nH]4)ccc3nc2-c2ccc(F)cc2)c1] I-393

TABLE 1-continued
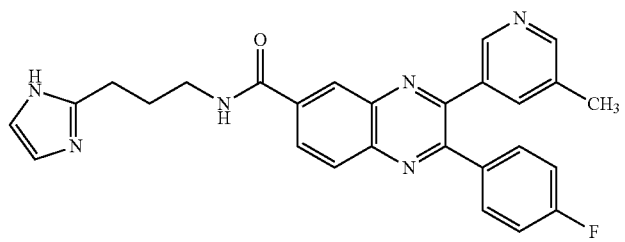 [SMILES: Cc1cncc(-c2nc3cc(C(=O)NCCCc4ncc[nH]4)ccc3nc2-c2ccc(F)cc2)c1] I-394
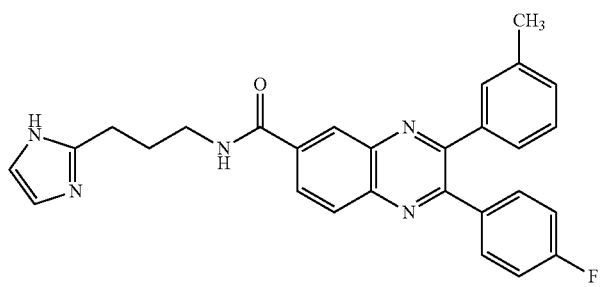 [SMILES: Cc1cccc(-c2nc3cc(C(=O)NCCCc4ncc[nH]4)ccc3nc2-c2ccc(F)cc2)c1] I-395
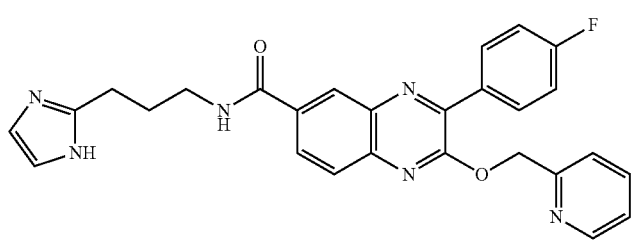 [SMILES: O=C(NCCCc1ncc[nH]1)c1ccc2nc(OCc3ccccn3)c(-c3ccc(F)cc3)nc2c1] I-396
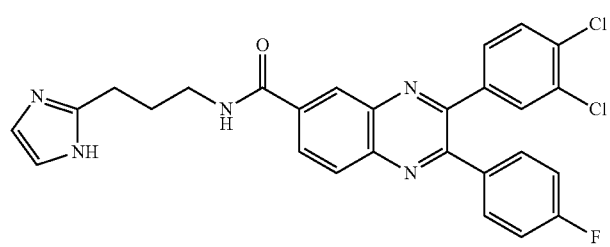 [SMILES: O=C(NCCCc1ncc[nH]1)c1ccc2nc(-c3ccc(F)cc3)c(-c3ccc(Cl)c(Cl)c3)nc2c1] I-397
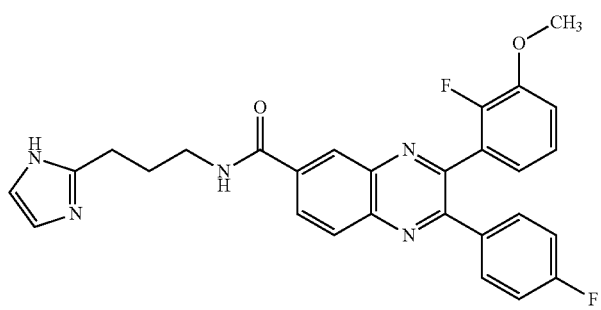 [SMILES: COc1cccc(-c2nc3cc(C(=O)NCCCc4ncc[nH]4)ccc3nc2-c2ccc(F)cc2)c1F] I-398
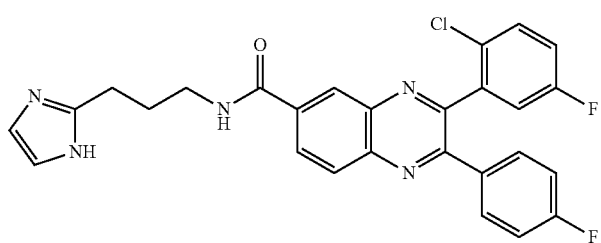 [SMILES: O=C(NCCCc1ncc[nH]1)c1ccc2nc(-c3ccc(F)cc3)c(-c3cc(F)ccc3Cl)nc2c1] I-399

TABLE 1-continued
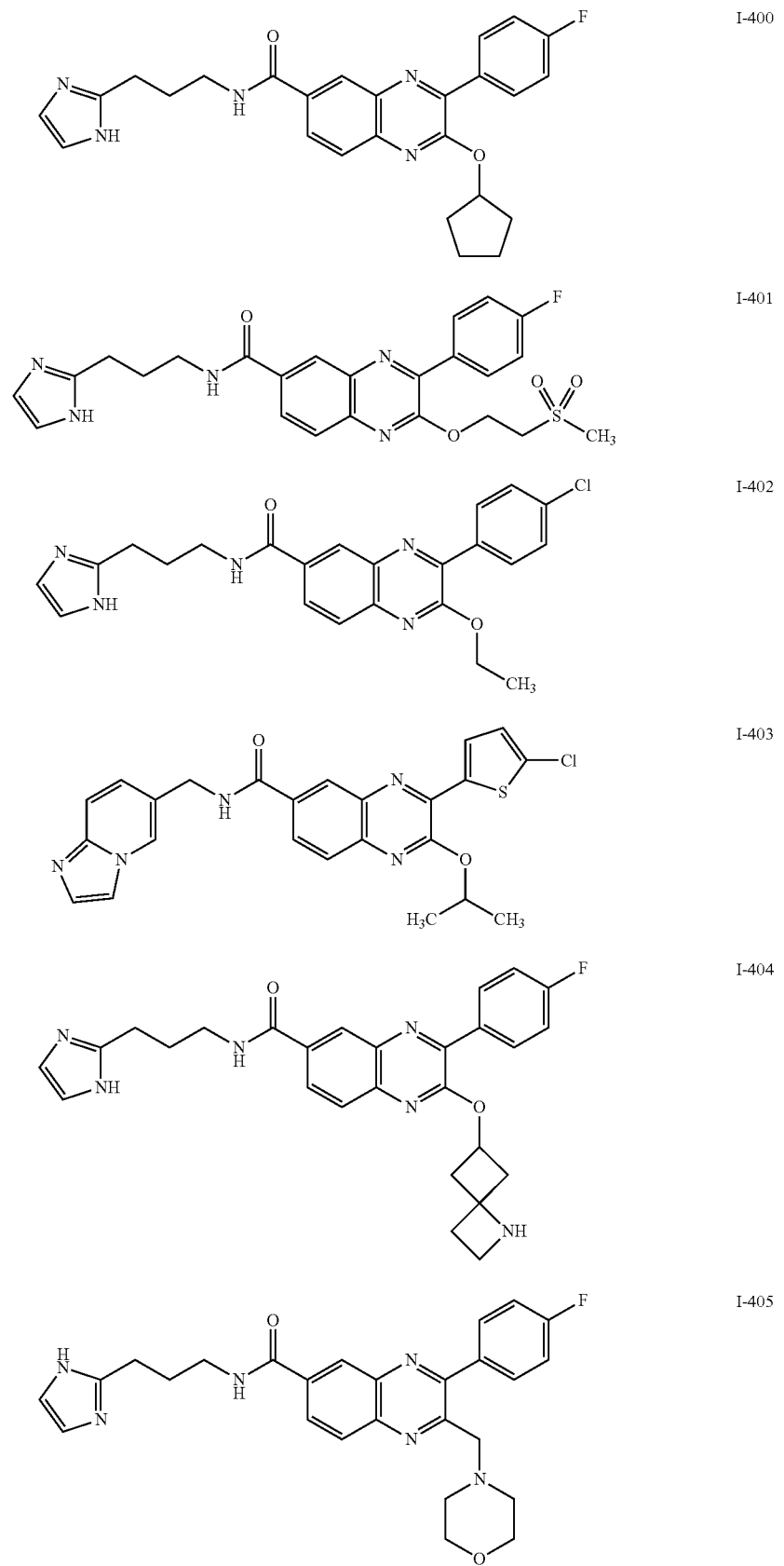
I-400
I-401
I-402
I-403
I-404
I-405

TABLE 1-continued
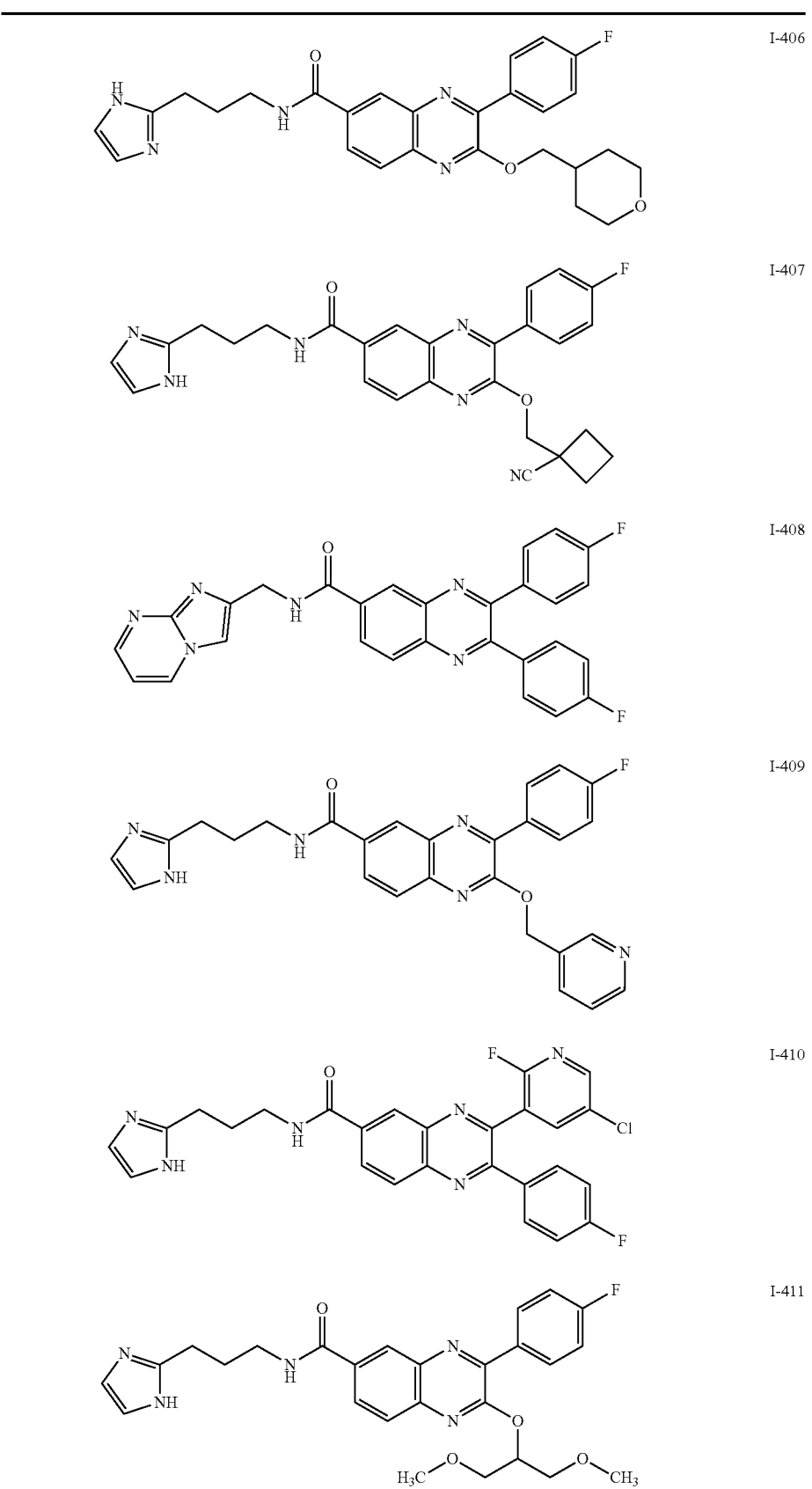
I-406
I-407
I-408
I-409
I-410
I-411

TABLE 1-continued
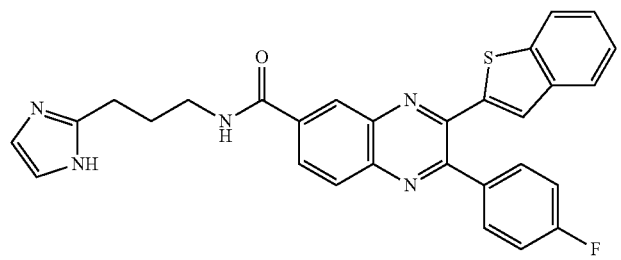 [SMILES: O=C(NCCCc1ncc[nH]1)c1ccc2nc(-c3ccc(F)cc3)c(-c3cc4ccccc4s3)nc2c1] I-412
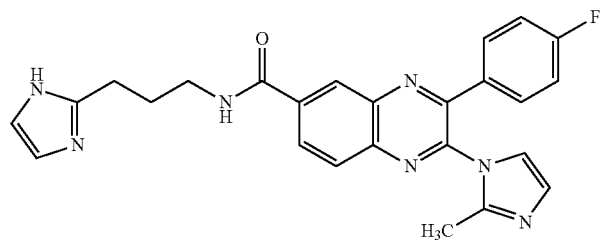 [SMILES: Cc1nccn1-c1nc2ccc(C(=O)NCCCc3ncc[nH]3)cc2nc1-c1ccc(F)cc1] I-413
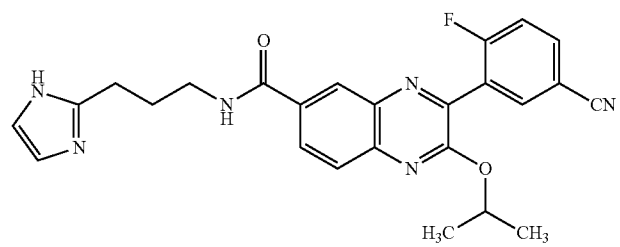 [SMILES: CC(C)Oc1nc2ccc(C(=O)NCCCc3ncc[nH]3)cc2nc1-c1cc(C#N)ccc1F] I-414
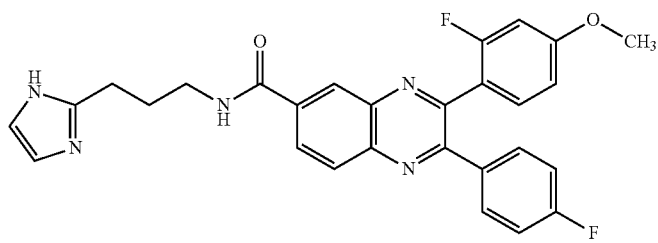 [SMILES: COc1ccc(-c2nc3cc(C(=O)NCCCc4ncc[nH]4)ccc3nc2-c2ccc(F)cc2)c(F)c1] I-415
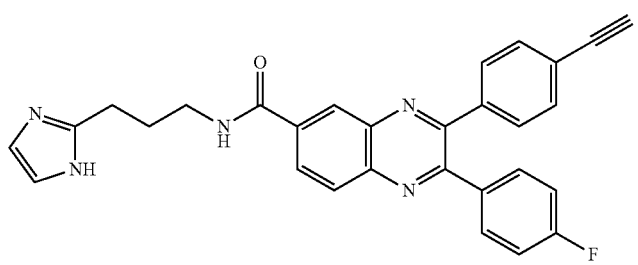 [SMILES: C#Cc1ccc(-c2nc3cc(C(=O)NCCCc4ncc[nH]4)ccc3nc2-c2ccc(F)cc2)cc1] I-416
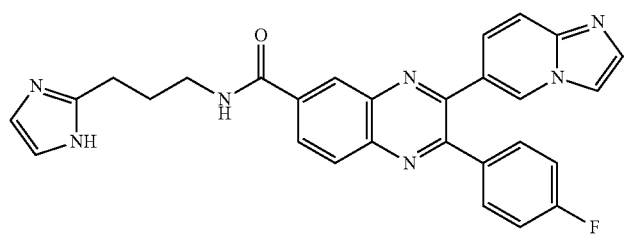 [SMILES: O=C(NCCCc1ncc[nH]1)c1ccc2nc(-c3ccc(F)cc3)c(-c3ccc4nccn4c3)nc2c1] I-417

TABLE 1-continued
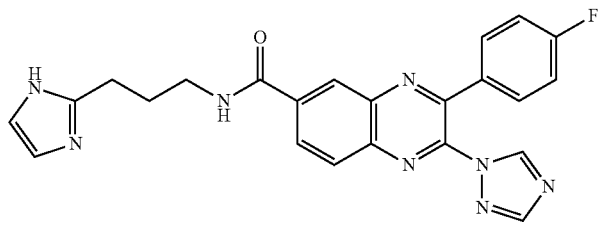 [SMILES: O=C(NCCCc1ncc[nH]1)c1ccc2nc(-n3cncn3)c(-c3ccc(F)cc3)nc2c1] I-418
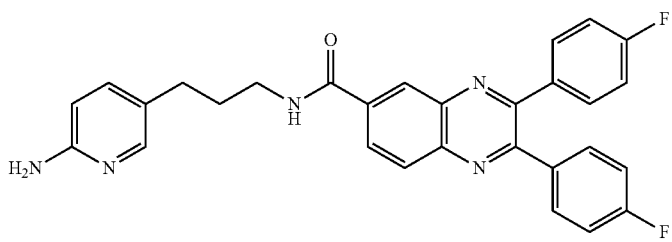 [SMILES: Nc1ccc(CCCNC(=O)c2ccc3nc(-c4ccc(F)cc4)c(-c4ccc(F)cc4)nc3c2)cn1] I-419
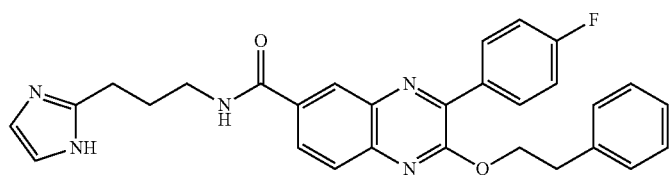 [SMILES: O=C(NCCCc1ncc[nH]1)c1ccc2nc(OCCc3ccccc3)c(-c3ccc(F)cc3)nc2c1] I-420
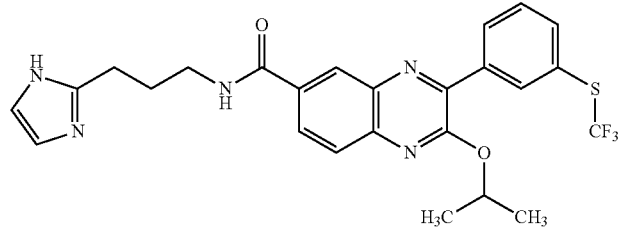 [SMILES: CC(C)Oc1nc2ccc(C(=O)NCCCc3ncc[nH]3)cc2nc1-c1cccc(SC(F)(F)F)c1] I-421
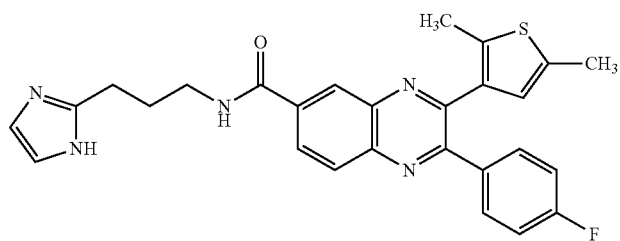 [SMILES: Cc1cc(-c2nc3cc(C(=O)NCCCc4ncc[nH]4)ccc3nc2-c2ccc(F)cc2)c(C)s1] I-422
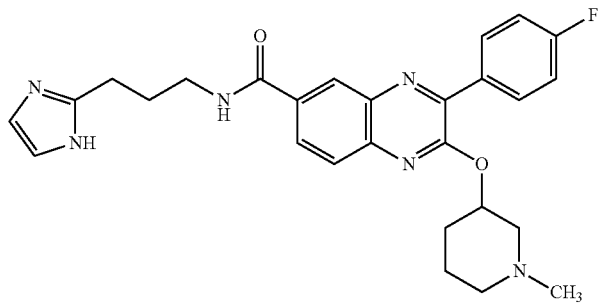 [SMILES: CN1CCCC(Oc2nc3ccc(C(=O)NCCCc4ncc[nH]4)cc3nc2-c2ccc(F)cc2)C1] I-423

TABLE 1-continued
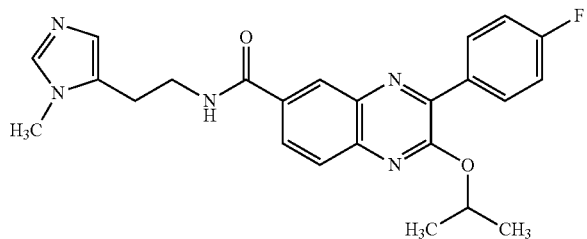 [SMILES: CC(C)Oc1nc2ccc(C(=O)NCCc3cncn3C)cc2nc1-c1ccc(F)cc1] I-424
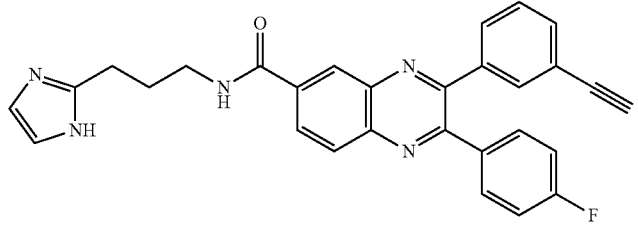 [SMILES: C#Cc1cccc(-c2nc3cc(C(=O)NCCCc4ncc[nH]4)ccc3nc2-c2ccc(F)cc2)c1] I-425
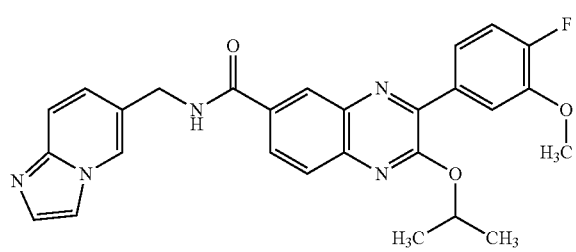 [SMILES: COc1cc(-c2nc3cc(C(=O)NCc4ccc5nccn5c4)ccc3nc2OC(C)C)ccc1F] I-426
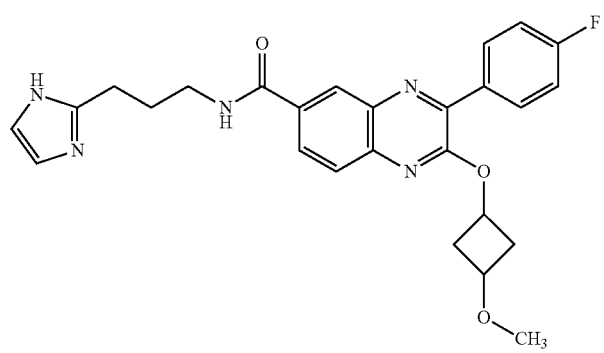 [SMILES: COC1CC(Oc2nc3ccc(C(=O)NCCCc4ncc[nH]4)cc3nc2-c2ccc(F)cc2)C1] I-427
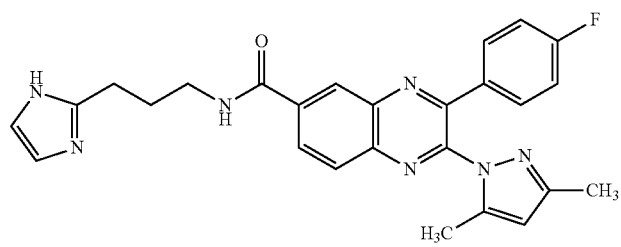 [SMILES: Cc1cc(C)n(-c2nc3ccc(C(=O)NCCCc4ncc[nH]4)cc3nc2-c2ccc(F)cc2)n1] I-428
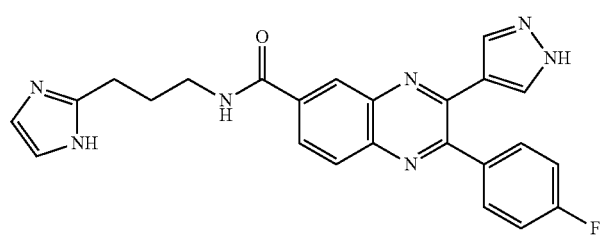 [SMILES: O=C(NCCCc1ncc[nH]1)c1ccc2nc(-c3ccc(F)cc3)c(-c3cn[nH]c3)nc2c1] I-429

TABLE 1-continued
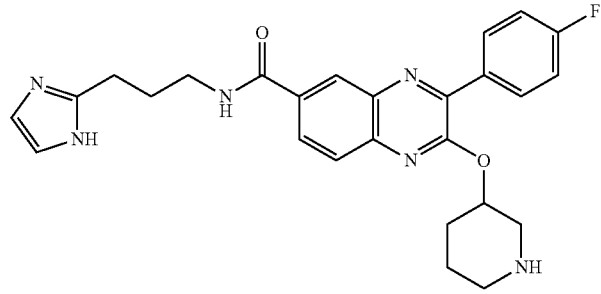 [SMILES: O=C(NCCCc1ncc[nH]1)c1ccc2nc(OC3CCCNC3)c(-c3ccc(F)cc3)nc2c1] I-430
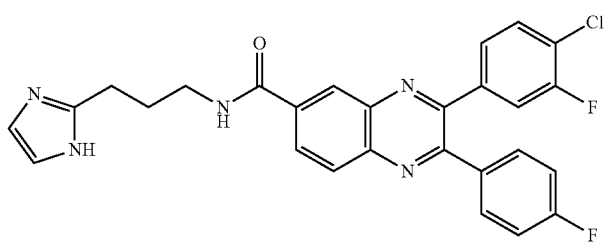 [SMILES: O=C(NCCCc1ncc[nH]1)c1ccc2nc(-c3ccc(F)cc3)c(-c3ccc(Cl)c(F)c3)nc2c1] I-431
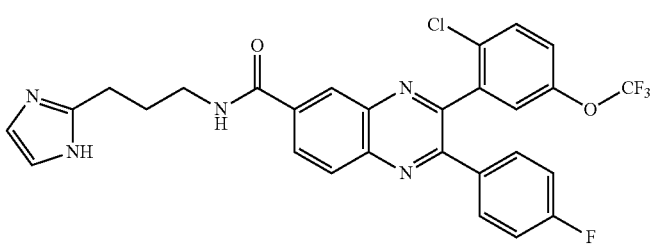 [SMILES: O=C(NCCCc1ncc[nH]1)c1ccc2nc(-c3ccc(F)cc3)c(-c3cc(OC(F)(F)F)ccc3Cl)nc2c1] I-432
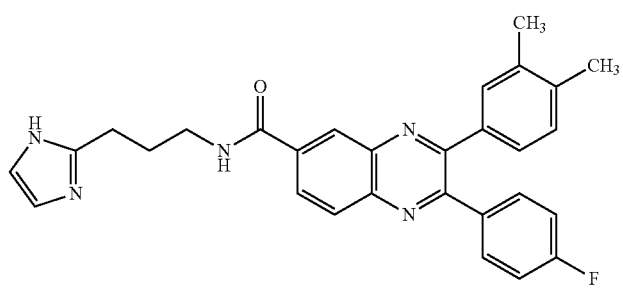 [SMILES: Cc1ccc(-c2nc3cc(C(=O)NCCCc4ncc[nH]4)ccc3nc2-c2ccc(F)cc2)cc1C] I-433
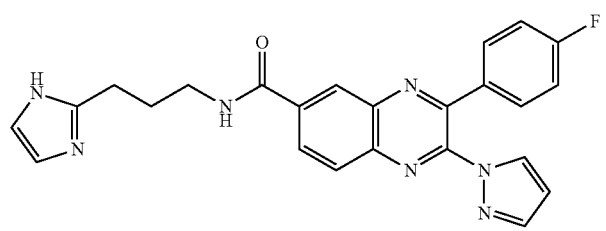 [SMILES: O=C(NCCCc1ncc[nH]1)c1ccc2nc(-n3cccn3)c(-c3ccc(F)cc3)nc2c1] I-434
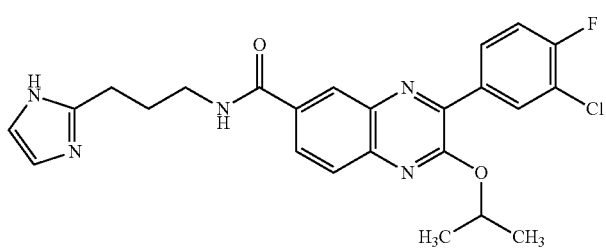 [SMILES: CC(C)Oc1nc2ccc(C(=O)NCCCc3ncc[nH]3)cc2nc1-c1ccc(F)c(Cl)c1] I-435

TABLE 1-continued
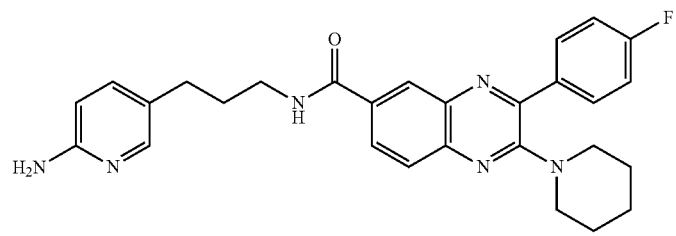 [SMILES: Nc1ccc(CCCNC(=O)c2ccc3nc(N4CCCCC4)c(-c4ccc(F)cc4)nc3c2)cn1] I-436
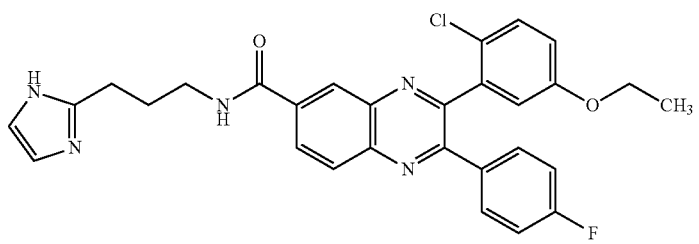 [SMILES: CCOc1ccc(Cl)c(-c2nc3cc(C(=O)NCCCc4ncc[nH]4)ccc3nc2-c2ccc(F)cc2)c1] I-437
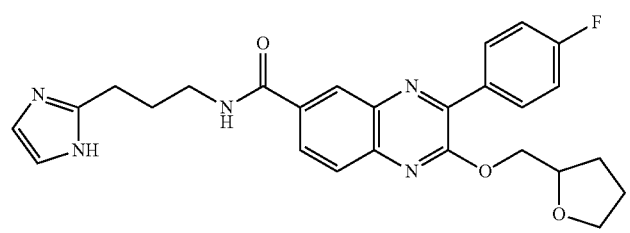 [SMILES: O=C(NCCCc1ncc[nH]1)c1ccc2nc(OCC3CCCO3)c(-c3ccc(F)cc3)nc2c1] I-438
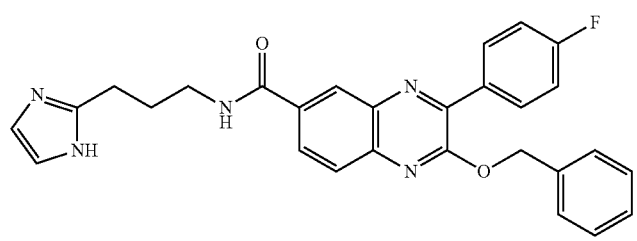 [SMILES: O=C(NCCCc1ncc[nH]1)c1ccc2nc(OCc3ccccc3)c(-c3ccc(F)cc3)nc2c1] I-439
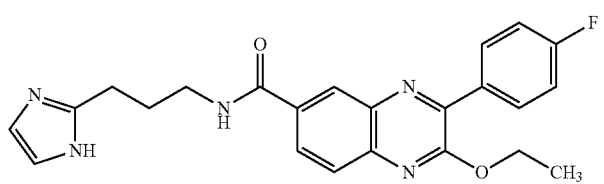 [SMILES: CCOc1nc2ccc(C(=O)NCCCc3ncc[nH]3)cc2nc1-c1ccc(F)cc1] I-440
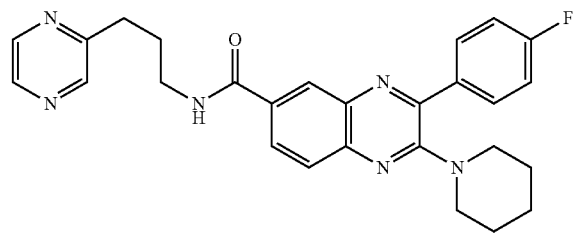 [SMILES: O=C(NCCCc1cnccn1)c1ccc2nc(N3CCCCC3)c(-c3ccc(F)cc3)nc2c1] I-441
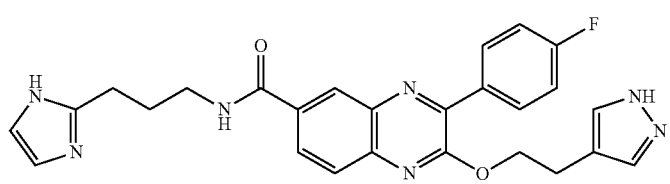 [SMILES: O=C(NCCCc1ncc[nH]1)c1ccc2nc(OCCc3cn[nH]c3)c(-c3ccc(F)cc3)nc2c1] I-442

TABLE 1-continued
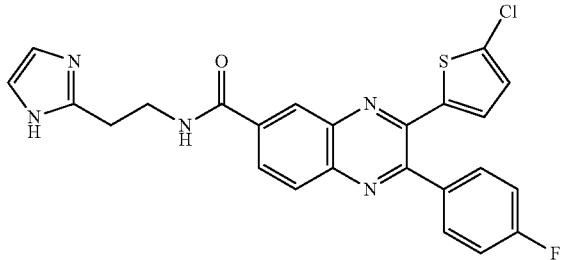 [SMILES: O=C(NCCc1ncc[nH]1)c1ccc2nc(-c3ccc(F)cc3)c(-c3ccc(Cl)s3)nc2c1]
I-443
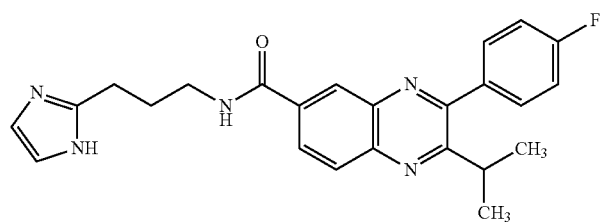 [SMILES: CC(C)c1nc2ccc(C(=O)NCCCc3ncc[nH]3)cc2nc1-c1ccc(F)cc1]
I-444
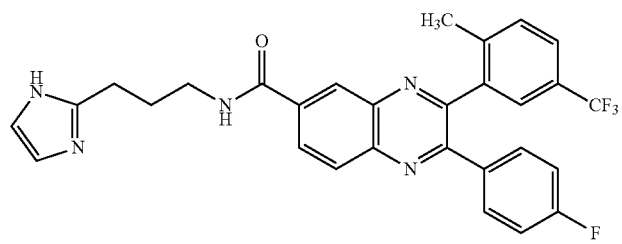 [SMILES: Cc1ccc(C(F)(F)F)cc1-c1nc2cc(C(=O)NCCCc3ncc[nH]3)ccc2nc1-c1ccc(F)cc1]
I-445
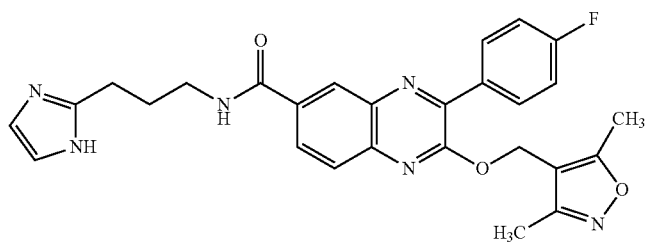 [SMILES: Cc1noc(C)c1COc1nc2ccc(C(=O)NCCCc3ncc[nH]3)cc2nc1-c1ccc(F)cc1]
I-446
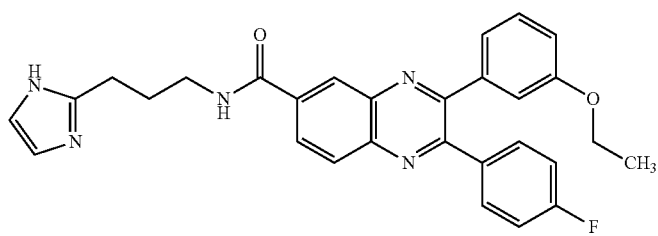 [SMILES: CCOc1cccc(-c2nc3cc(C(=O)NCCCc4ncc[nH]4)ccc3nc2-c2ccc(F)cc2)c1]
I-447
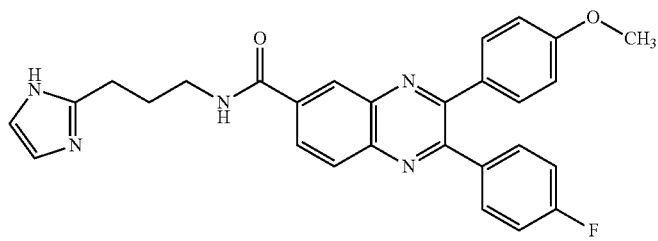 [SMILES: COc1ccc(-c2nc3cc(C(=O)NCCCc4ncc[nH]4)ccc3nc2-c2ccc(F)cc2)cc1]
I-448

TABLE 1-continued
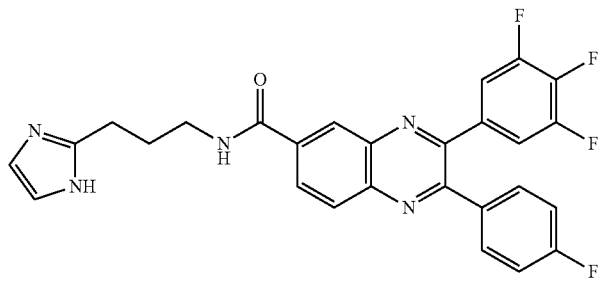 [SMILES: O=C(NCCCc1ncc[nH]1)c1ccc2nc(-c3ccc(F)cc3)c(-c3cc(F)c(F)c(F)c3)nc2c1]
I-449
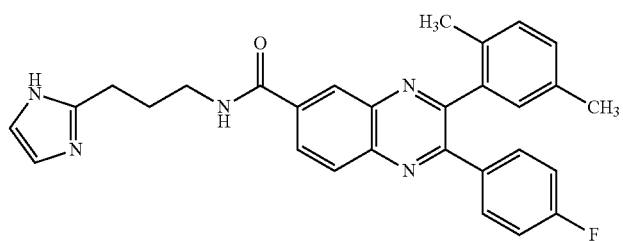 [SMILES: Cc1ccc(C)c(-c2nc3cc(C(=O)NCCCc4ncc[nH]4)ccc3nc2-c2ccc(F)cc2)c1]
I-450
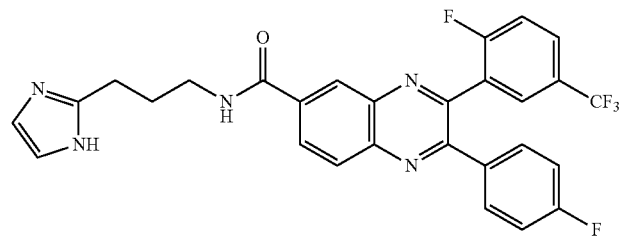 [SMILES: O=C(NCCCc1ncc[nH]1)c1ccc2nc(-c3ccc(F)cc3)c(-c3cc(C(F)(F)F)ccc3F)nc2c1]
I-451
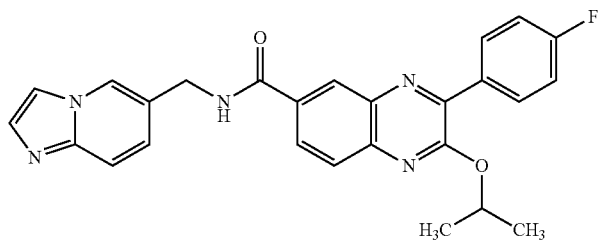 [SMILES: CC(C)Oc1nc2ccc(C(=O)NCc3ccc4nccn4c3)cc2nc1-c1ccc(F)cc1]
I-452
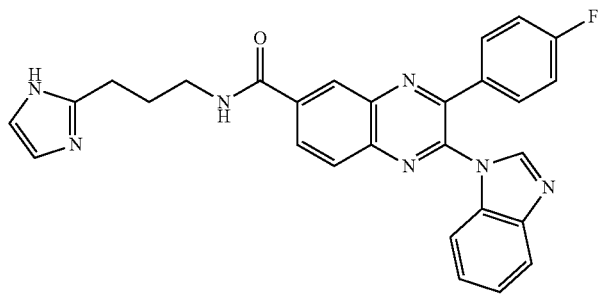 [SMILES: O=C(NCCCc1ncc[nH]1)c1ccc2nc(-n3cnc4ccccc43)c(-c3ccc(F)cc3)nc2c1]
I-453
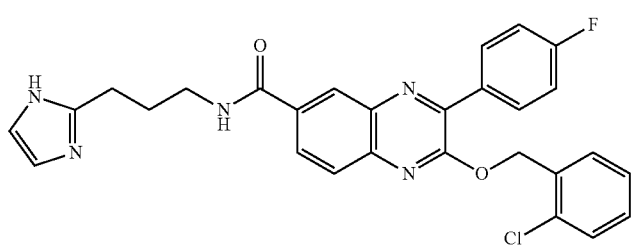 [SMILES: O=C(NCCCc1ncc[nH]1)c1ccc2nc(OCc3ccccc3Cl)c(-c3ccc(F)cc3)nc2c1]
I-454

TABLE 1-continued
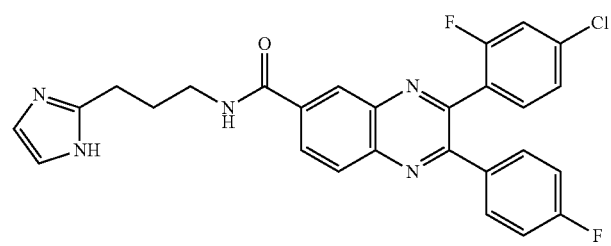 [SMILES: O=C(NCCCc1ncc[nH]1)c1ccc2nc(-c3ccc(F)cc3)c(-c3ccc(Cl)cc3F)nc2c1] I-455
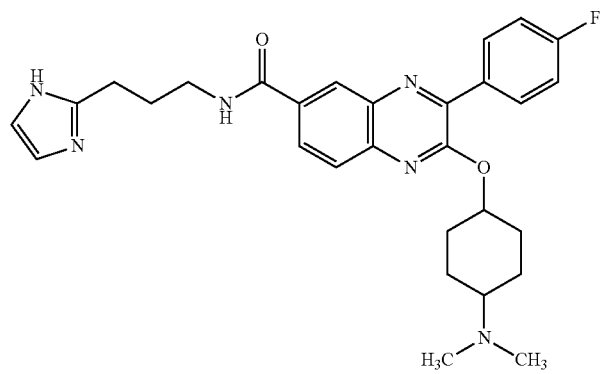 [SMILES: CN(C)C1CCC(Oc2nc3ccc(C(=O)NCCCc4ncc[nH]4)cc3nc2-c2ccc(F)cc2)CC1] I-456
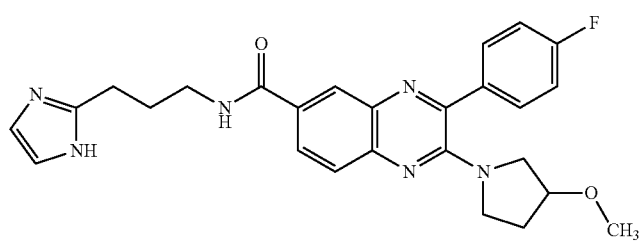 [SMILES: COC1CCN(c2nc3ccc(C(=O)NCCCc4ncc[nH]4)cc3nc2-c2ccc(F)cc2)C1] I-457
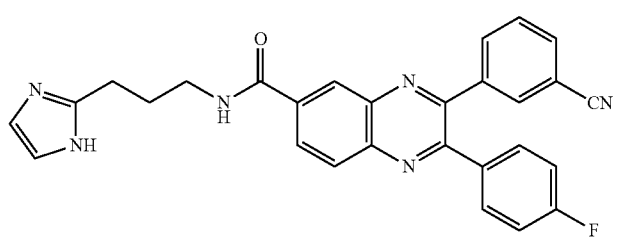 [SMILES: N#Cc1cccc(-c2nc3cc(C(=O)NCCCc4ncc[nH]4)ccc3nc2-c2ccc(F)cc2)c1] I-458
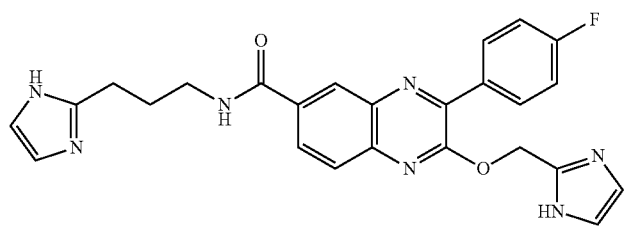 [SMILES: O=C(NCCCc1ncc[nH]1)c1ccc2nc(OCc3ncc[nH]3)c(-c3ccc(F)cc3)nc2c1] I-459
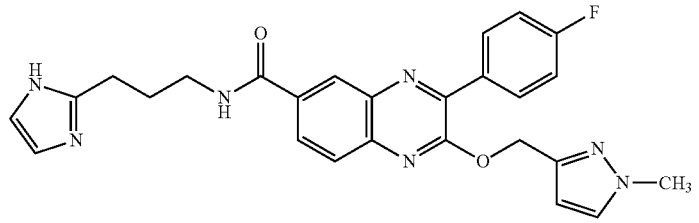 [SMILES: Cn1ccc(COc2nc3ccc(C(=O)NCCCc4ncc[nH]4)cc3nc2-c2ccc(F)cc2)n1] I-460

TABLE 1-continued
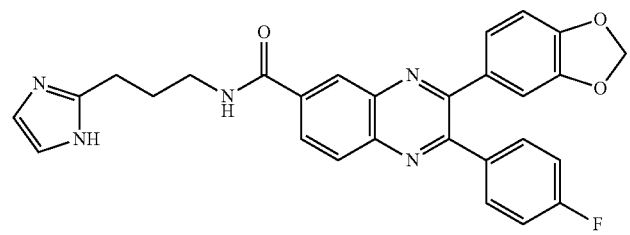 [SMILES: O=C(NCCCc1ncc[nH]1)c1ccc2nc(-c3ccc(F)cc3)c(-c3ccc4c(c3)OCO4)nc2c1] I-461
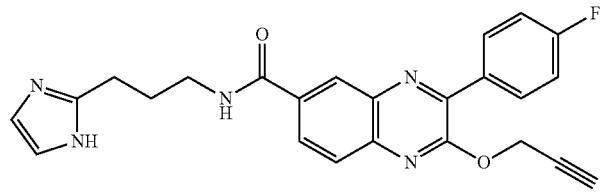 [SMILES: C#CCOc1nc2ccc(C(=O)NCCCc3ncc[nH]3)cc2nc1-c1ccc(F)cc1] I-462
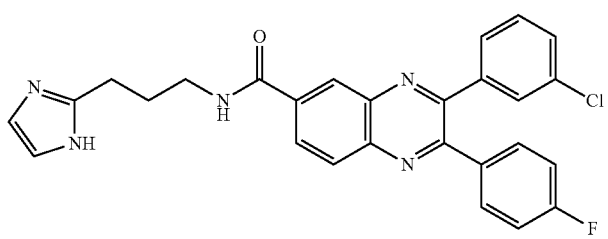 [SMILES: O=C(NCCCc1ncc[nH]1)c1ccc2nc(-c3ccc(F)cc3)c(-c3cccc(Cl)c3)nc2c1] I-463
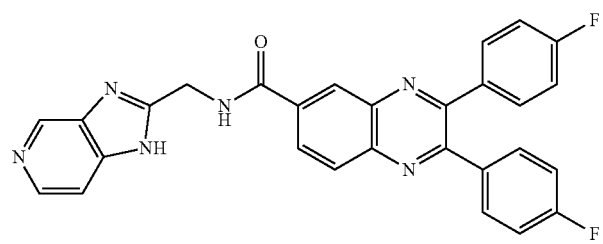 [SMILES: O=C(NCc1nc2cnccc2[nH]1)c1ccc2nc(-c3ccc(F)cc3)c(-c3ccc(F)cc3)nc2c1] I-464
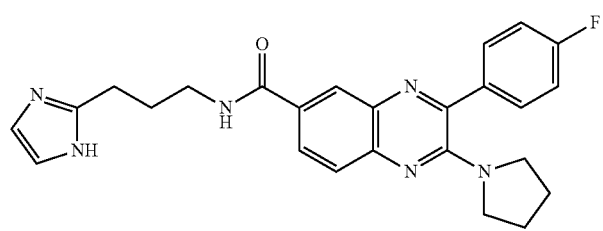 [SMILES: O=C(NCCCc1ncc[nH]1)c1ccc2nc(N3CCCC3)c(-c3ccc(F)cc3)nc2c1] I-465
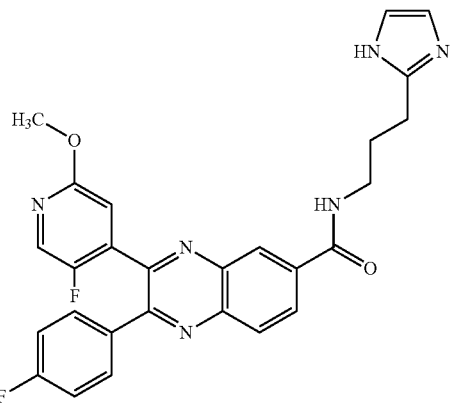 [SMILES: COc1cc(-c2nc3cc(C(=O)NCCCc4ncc[nH]4)ccc3nc2-c2ccc(F)cc2)c(F)cn1] I-466

TABLE 1-continued
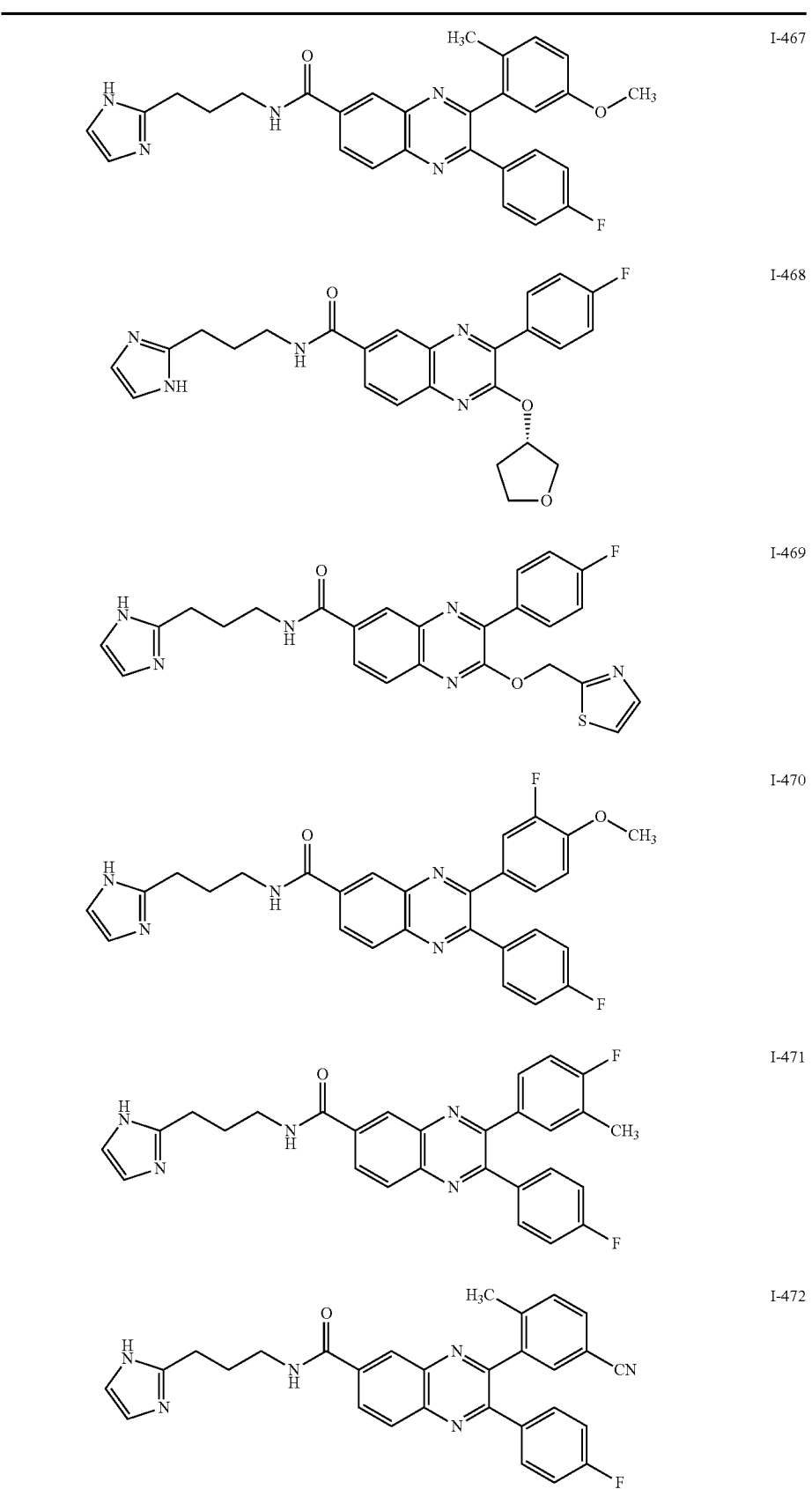
I-467
I-468
I-469
I-470
I-471
I-472

TABLE 1-continued
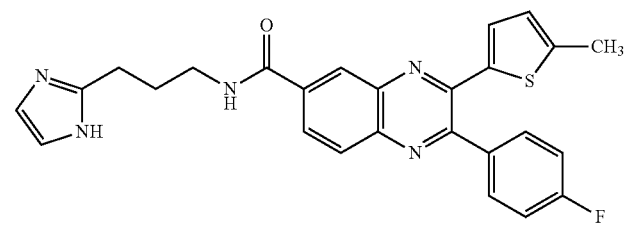 [SMILES: Cc1ccc(-c2nc3cc(C(=O)NCCCc4ncc[nH]4)ccc3nc2-c2ccc(F)cc2)s1] I-473
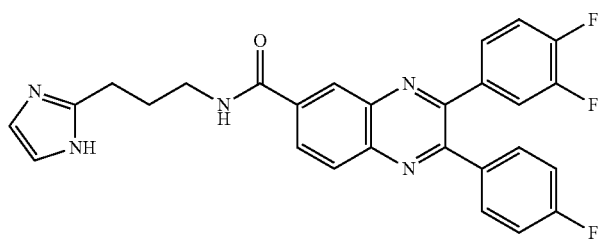 [SMILES: O=C(NCCCc1ncc[nH]1)c1ccc2nc(-c3ccc(F)cc3)c(-c3ccc(F)c(F)c3)nc2c1] I-474
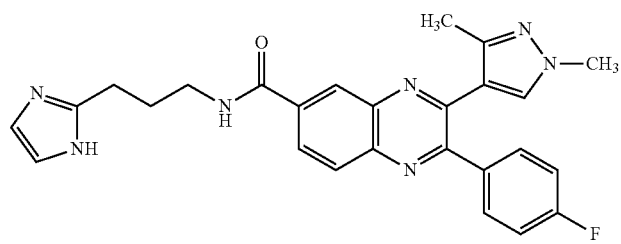 [SMILES: Cc1nn(C)cc1-c1nc2cc(C(=O)NCCCc3ncc[nH]3)ccc2nc1-c1ccc(F)cc1] I-475
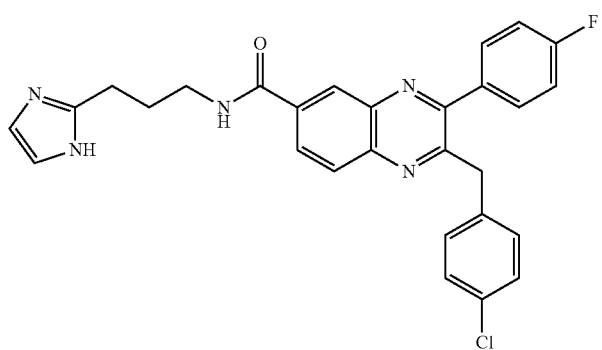 [SMILES: O=C(NCCCc1ncc[nH]1)c1ccc2nc(Cc3ccc(Cl)cc3)c(-c3ccc(F)cc3)nc2c1] I-476
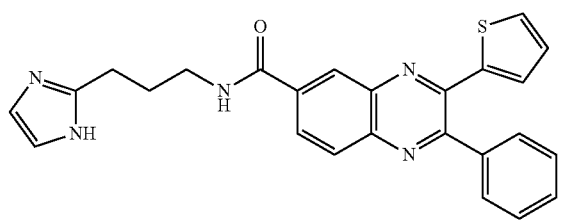 [SMILES: O=C(NCCCc1ncc[nH]1)c1ccc2nc(-c3ccccc3)c(-c3cccs3)nc2c1] I-477
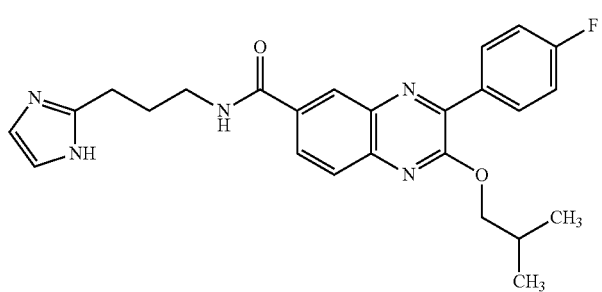 [SMILES: CC(C)COc1nc2ccc(C(=O)NCCCc3ncc[nH]3)cc2nc1-c1ccc(F)cc1] I-478

TABLE 1-continued
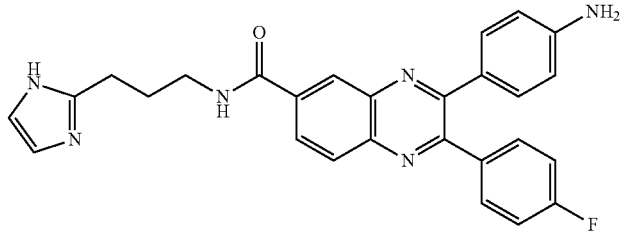 [SMILES: Nc1ccc(-c2nc3cc(C(=O)NCCCc4ncc[nH]4)ccc3nc2-c2ccc(F)cc2)cc1] I-479
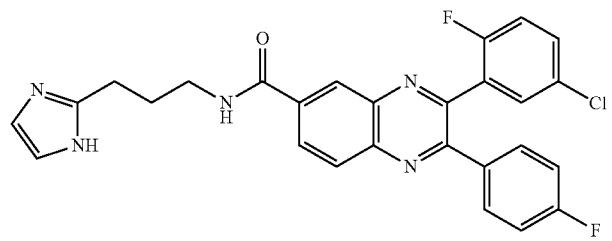 [SMILES: O=C(NCCCc1ncc[nH]1)c1ccc2nc(-c3ccc(F)cc3)c(-c3cc(Cl)ccc3F)nc2c1] I-480
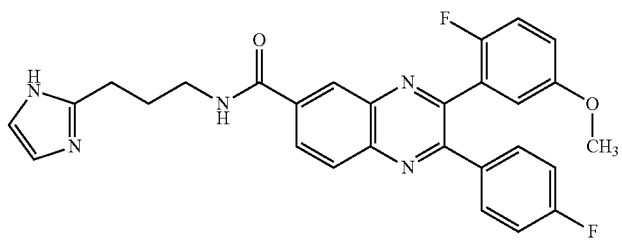 [SMILES: COc1ccc(F)c(-c2nc3cc(C(=O)NCCCc4ncc[nH]4)ccc3nc2-c2ccc(F)cc2)c1] I-481
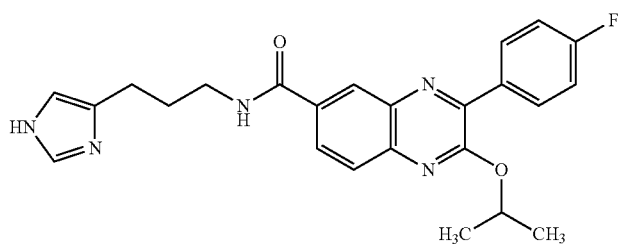 [SMILES: CC(C)Oc1nc2ccc(C(=O)NCCCc3c[nH]cn3)cc2nc1-c1ccc(F)cc1] I-482
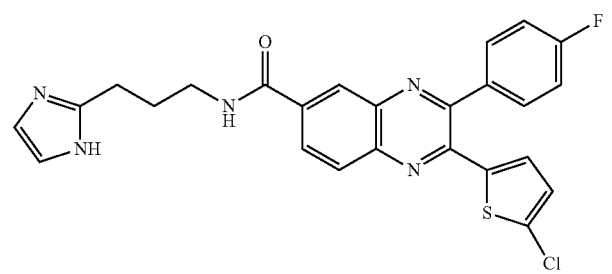 [SMILES: O=C(NCCCc1ncc[nH]1)c1ccc2nc(-c3ccc(Cl)s3)c(-c3ccc(F)cc3)nc2c1] I-483
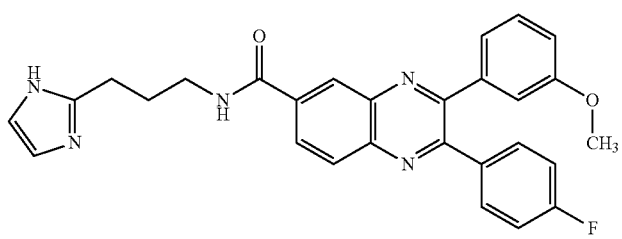 [SMILES: COc1cccc(-c2nc3cc(C(=O)NCCCc4ncc[nH]4)ccc3nc2-c2ccc(F)cc2)c1] I-484

TABLE 1-continued
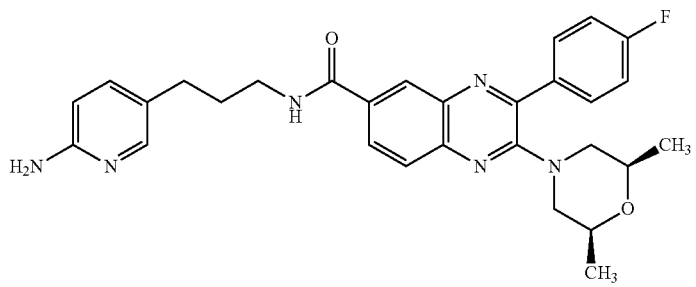 [SMILES: C[C@@H]1CN(c2nc3ccc(C(=O)NCCCc4ccc(N)nc4)cc3nc2-c2ccc(F)cc2)C[C@H](C)O1] I-485
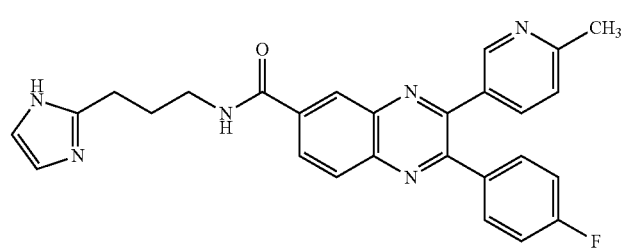 [SMILES: Cc1ccc(-c2nc3cc(C(=O)NCCCc4ncc[nH]4)ccc3nc2-c2ccc(F)cc2)cn1] I-486
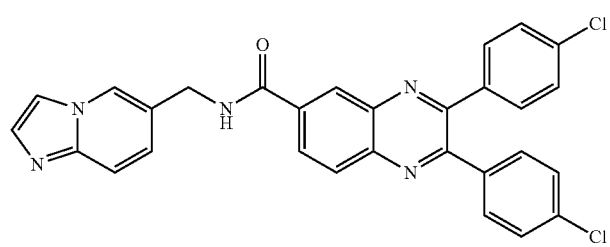 [SMILES: O=C(NCc1ccc2nccn2c1)c1ccc2nc(-c3ccc(Cl)cc3)c(-c3ccc(Cl)cc3)nc2c1] I-487
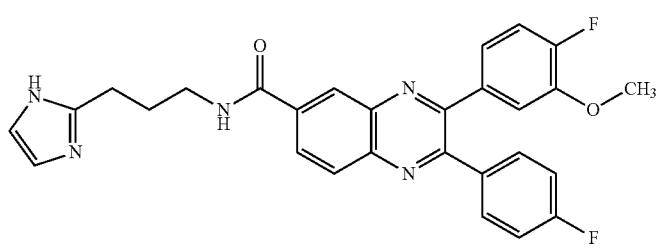 [SMILES: COc1cc(-c2nc3cc(C(=O)NCCCc4ncc[nH]4)ccc3nc2-c2ccc(F)cc2)ccc1F] I-488
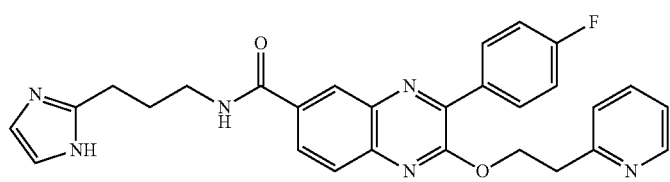 [SMILES: O=C(NCCCc1ncc[nH]1)c1ccc2nc(OCCc3ccccn3)c(-c3ccc(F)cc3)nc2c1] I-489
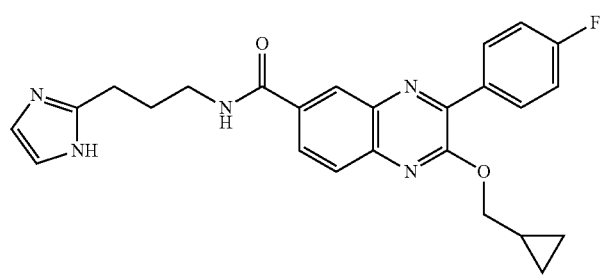 [SMILES: O=C(NCCCc1ncc[nH]1)c1ccc2nc(OCC3CC3)c(-c3ccc(F)cc3)nc2c1] I-490

TABLE 1-continued
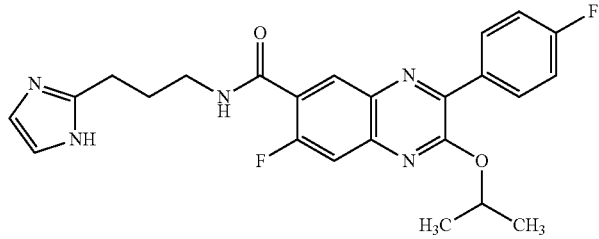 I-491
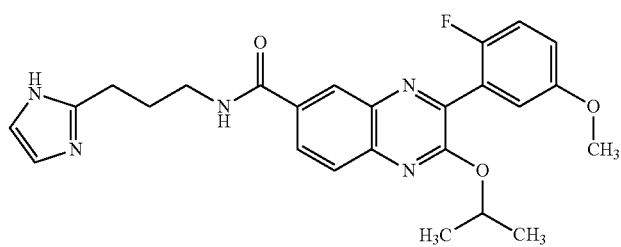 [SMILES: COc1ccc(F)c(-c2nc3cc(C(=O)NCCCc4ncc[nH]4)ccc3nc2OC(C)C)c1] I-492
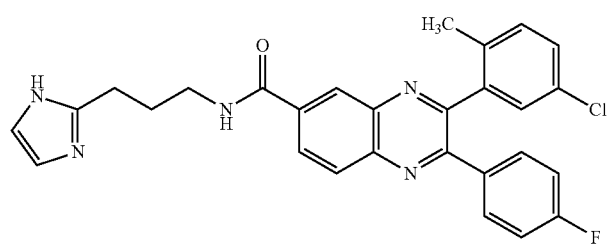 [SMILES: Cc1ccc(Cl)cc1-c1nc2cc(C(=O)NCCCc3ncc[nH]3)ccc2nc1-c1ccc(F)cc1] I-493
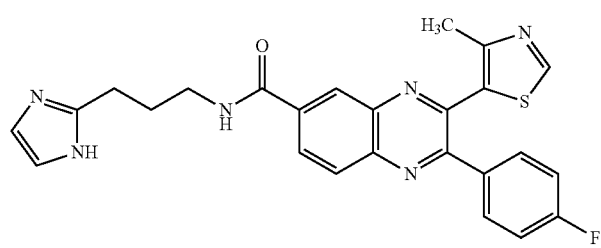 [SMILES: Cc1ncsc1-c1nc2cc(C(=O)NCCCc3ncc[nH]3)ccc2nc1-c1ccc(F)cc1] I-494
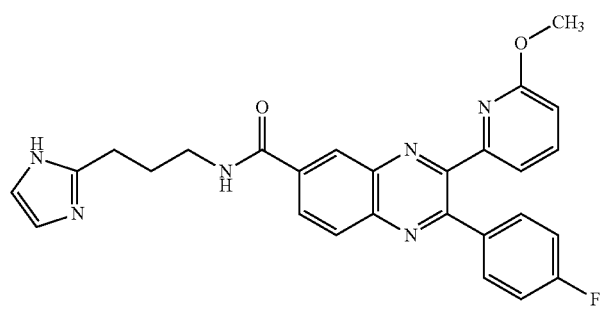 [SMILES: COc1cccc(-c2nc3cc(C(=O)NCCCc4ncc[nH]4)ccc3nc2-c2ccc(F)cc2)n1] I-495
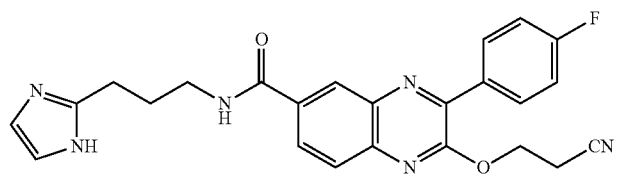 [SMILES: N#CCCOc1nc2ccc(C(=O)NCCCc3ncc[nH]3)cc2nc1-c1ccc(F)cc1] I-496

TABLE 1-continued
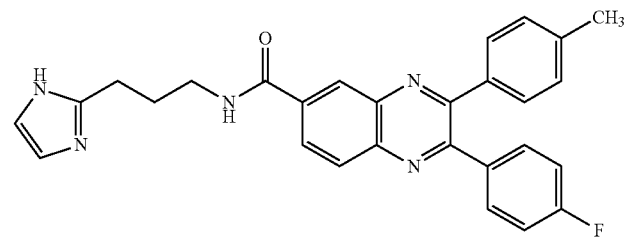 [SMILES: Cc1ccc(-c2nc3cc(C(=O)NCCCc4ncc[nH]4)ccc3nc2-c2ccc(F)cc2)cc1] I-497
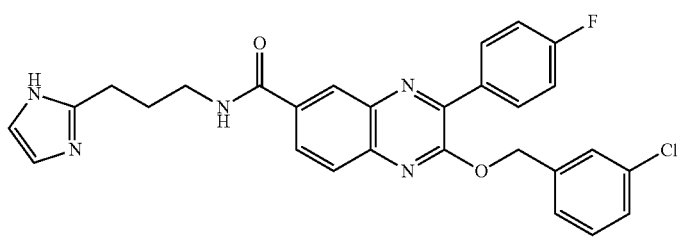 [SMILES: O=C(NCCCc1ncc[nH]1)c1ccc2nc(OCc3cccc(Cl)c3)c(-c3ccc(F)cc3)nc2c1] I-498
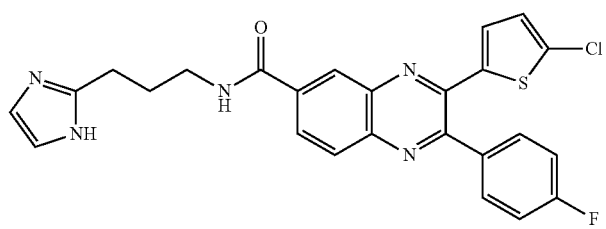 [SMILES: O=C(NCCCc1ncc[nH]1)c1ccc2nc(-c3ccc(F)cc3)c(-c3ccc(Cl)s3)nc2c1] I-499
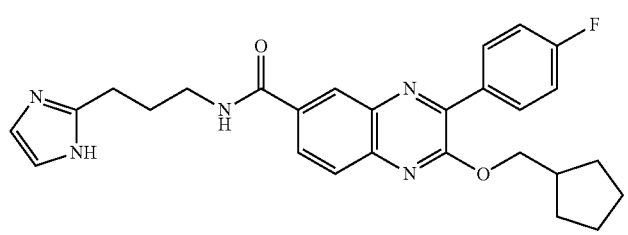 [SMILES: O=C(NCCCc1ncc[nH]1)c1ccc2nc(OCC3CCCC3)c(-c3ccc(F)cc3)nc2c1] I-500
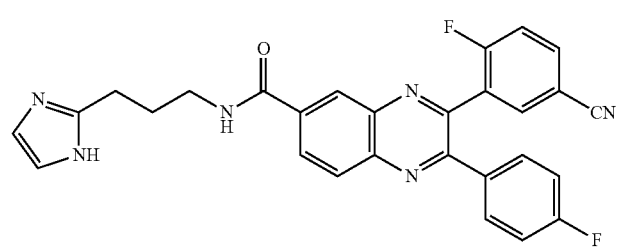 [SMILES: N#Cc1ccc(F)c(-c2nc3cc(C(=O)NCCCc4ncc[nH]4)ccc3nc2-c2ccc(F)cc2)c1] I-501
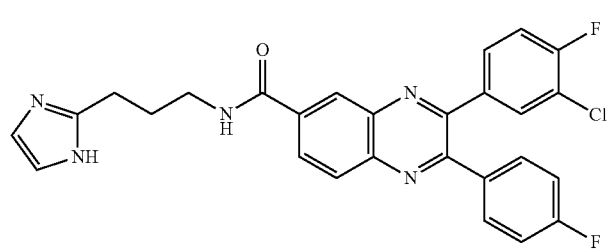 I-502

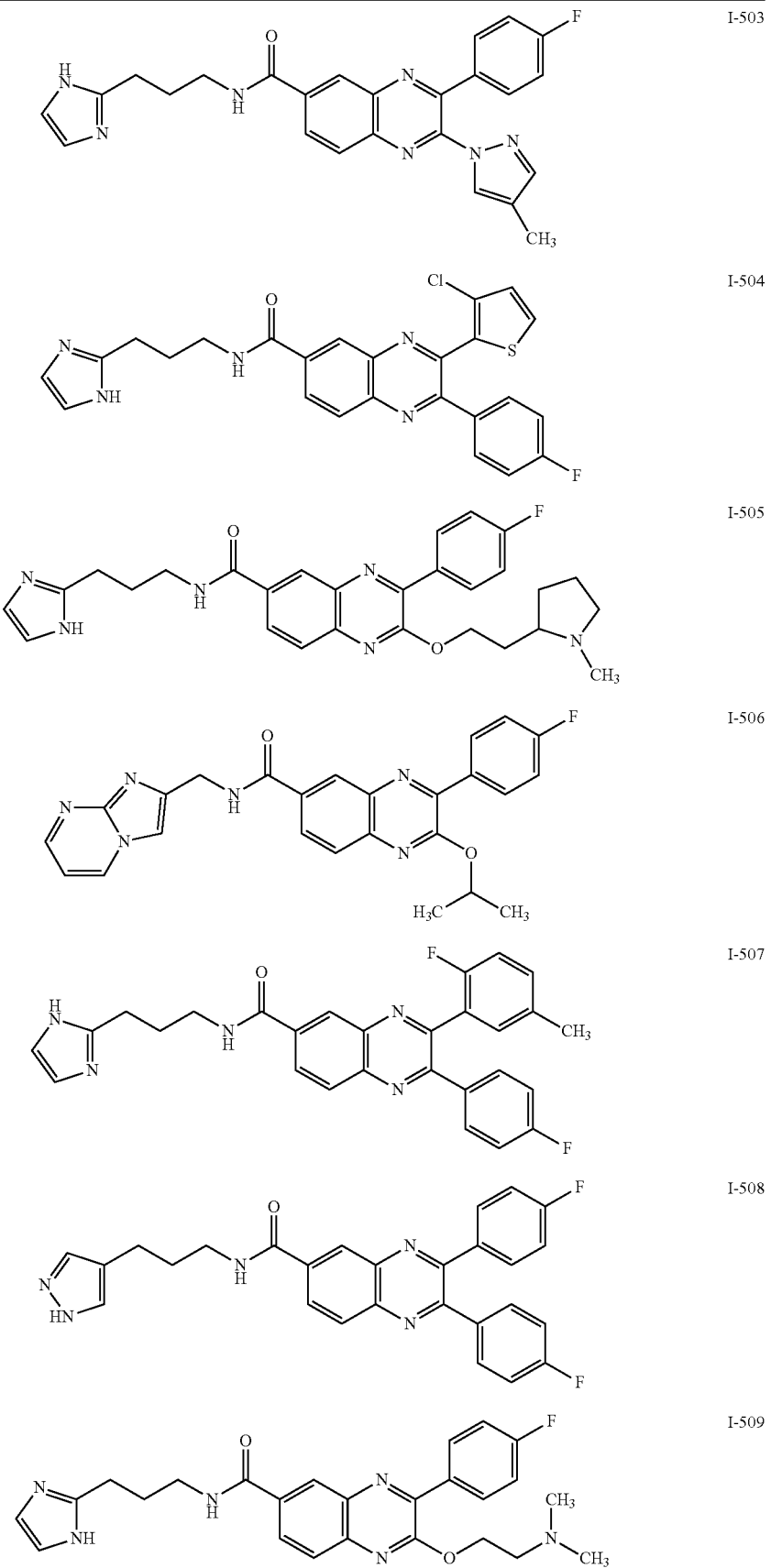

TABLE 1-continued
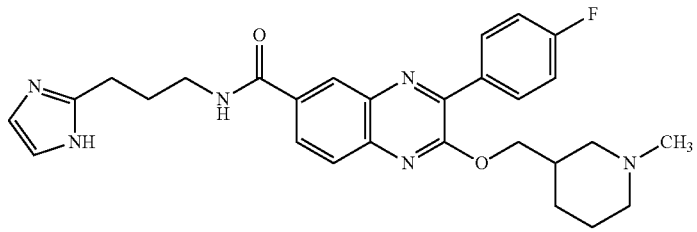 [SMILES: CN1CCCC(COc2nc3ccc(C(=O)NCCCc4ncc[nH]4)cc3nc2-c2ccc(F)cc2)C1]
I-510
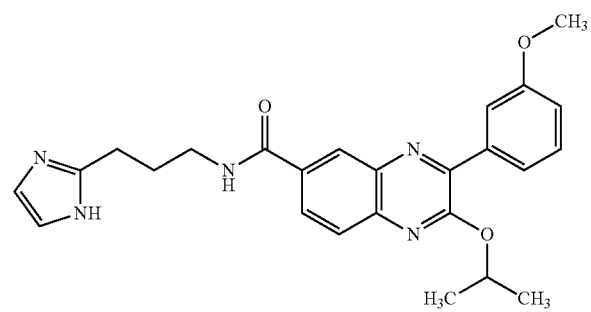 [SMILES: COc1cccc(-c2nc3cc(C(=O)NCCCc4ncc[nH]4)ccc3nc2OC(C)C)c1]
I-511
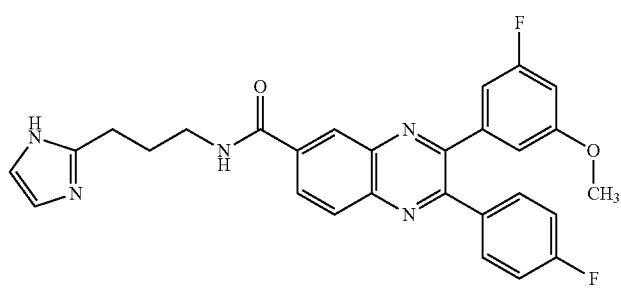 [SMILES: COc1cc(F)cc(-c2nc3cc(C(=O)NCCCc4ncc[nH]4)ccc3nc2-c2ccc(F)cc2)c1]
I-512
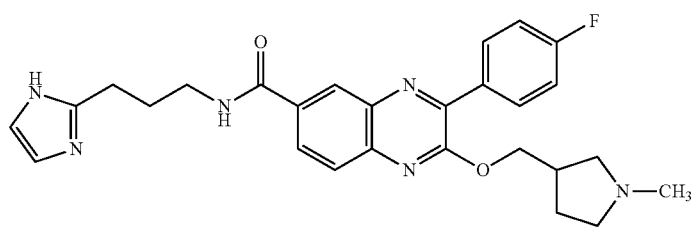 [SMILES: CN1CCC(COc2nc3ccc(C(=O)NCCCc4ncc[nH]4)cc3nc2-c2ccc(F)cc2)C1]
I-513
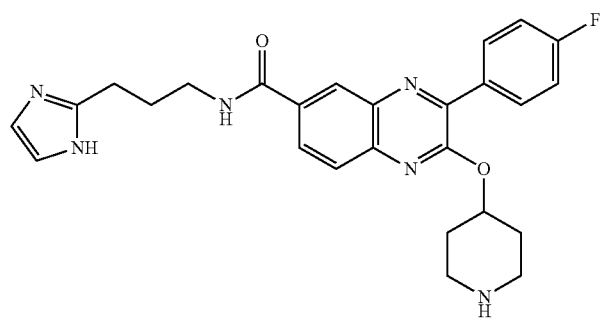 [SMILES: O=C(NCCCc1ncc[nH]1)c1ccc2nc(OC3CCNCC3)c(-c3ccc(F)cc3)nc2c1]
I-514
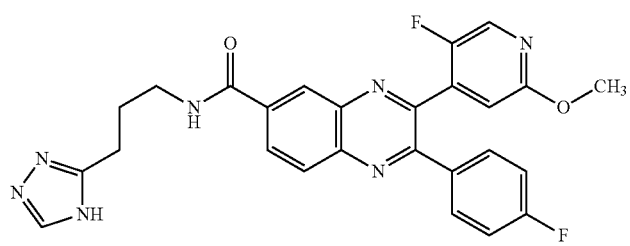 [SMILES: COc1cc(-c2nc3cc(C(=O)NCCCc4nnc[nH]4)ccc3nc2-c2ccc(F)cc2)c(F)cn1]
I-515

TABLE 1-continued

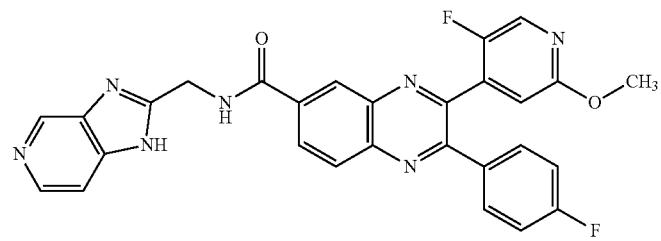 [SMILES: COc1cc(-c2nc3cc(C(=O)NCc4nc5cnccc5[nH]4)ccc3nc2-c2ccc(F)cc2)c(F)cn1]

I-516

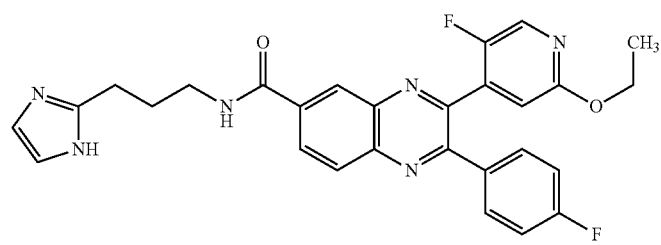 [SMILES: CCOc1cc(-c2nc3cc(C(=O)NCCCc4ncc[nH]4)ccc3nc2-c2ccc(F)cc2)c(F)cn1]

I-517

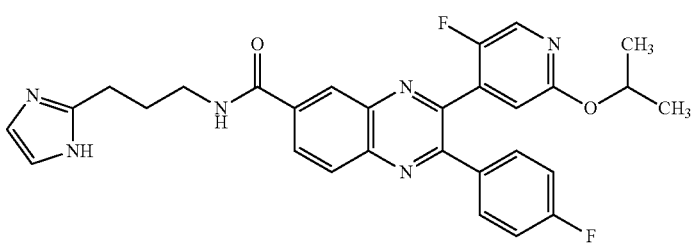 [SMILES: CC(C)Oc1cc(-c2nc3cc(C(=O)NCCCc4ncc[nH]4)ccc3nc2-c2ccc(F)cc2)c(F)cn1]

I-518

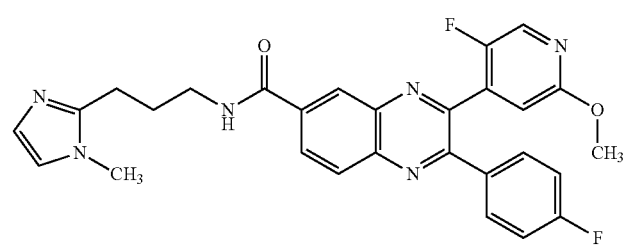 [SMILES: COc1cc(-c2nc3cc(C(=O)NCCCc4nccn4C)ccc3nc2-c2ccc(F)cc2)c(F)cn1]

I-519

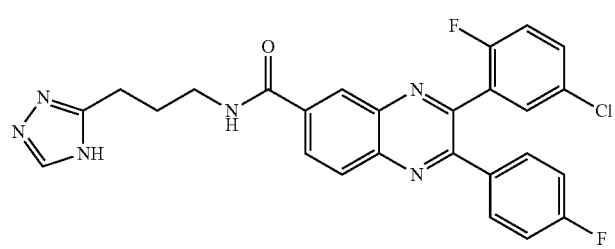 [SMILES: O=C(NCCCc1nnc[nH]1)c1ccc2nc(-c3ccc(F)cc3)c(-c3cc(Cl)ccc3F)nc2c1]

I-520

| Compound No. | IUPAC Name |
|---|---|
| I-1 | 3-(4-fluorophenyl)-N-[2-(1H-imidazol-2-yl)ethyl]-2-(piperidin-1-yl)quinoxaline-6-carboxamide |
| I-2 | 2-(3-acetamidophenyl)-N-[3-(1H-imidazol-1-yl)propyl]-3-phenylquinoxaline-6-carboxamide |
| I-3 | N-[3-(1H-imidazol-1-yl)propyl]-3-(1-methyl-1,2,3,6-tetrahydropyridin-4-yl)-2-phenylquinoxaline-6-carboxamide |
| I-4 | 3-(4-fluorophenyl)-N-[2-(1-methyl-1H-imidazol-5-yl)ethyl]-2-(piperidin-1-yl)quinoxaline-6-carboxamide |
| I-5 | N-[3-(1H-imidazol-1-yl)propyl]-3-phenyl-2-(pyridin-4-yl)quinoxaline-6-carboxamide |
| I-6 | 3-(4-carbamoylphenyl)-N-[3-(1H-imidazol-1-yl)propyl]-2-phenylquinoxaline-6-carboxamide |
| I-7 | N-[3-(1H-imidazol-1-yl)propyl]-2-(4-oxoimidazolidin-1-yl)-3-phenylquinoxaline-6-carboxamide |
| I-8 | 2,3-bis(4-fluorophenyl)-N-[3-(5-sulfanyl-1H-tetrazol-1-yl)propyl]quinoxaline-6-carboxamide |
| I-9 | 3-(2,4-dimethyl-1,3-thiazol-5-yl)-N-[3-(1H-imidazol-1-yl)propyl]-2-phenylquinoxaline-6-carboxamide |

TABLE 1-continued

| | |
|---|---|
| I-10 | 2-(aminomethyl)-N-[3-(1H-imidazol-1-yl)propyl]-3-phenylquinoxaline-6-carboxamide |
| I-11 | 2-(1,3-dihydro-2H-isoindol-2-yl)-N-[3-(1H-imidazol-1-yl)propyl]-3-phenylquinoxaline-6-carboxamide |
| I-12 | 2-(4-hydroxypiperidin-1-yl)-N-[3-(1H-imidazol-2-yl)propyl]-3-(3-methoxyphenyl)quinoxaline-6-carboxamide |
| I-13 | N-[3-(1H-imidazol-1-yl)propyl]-2-(2-methoxyphenyl)-3-phenylquinoxaline-6-carboxamide |
| I-14 | 3-(1,1-dioxidothiomorpholin-4-yl)-N-[3-(1H-imidazol-1-yl)propyl]-2-phenylquinoxaline-6-carboxamide |
| I-15 | N-[3-(1H-imidazol-1-yl)propyl]-3-(2-oxa-6-azaspiro[3.4]oct-6-yl)-2-phenylquinoxaline-6-carboxamide |
| I-16 | 3-(4-fluorophenyl)-N-(1H-indazol-5-ylmethyl)-2-(morpholin-4-yl)quinoxaline-6-carboxamide |
| I-17 | 3-(3-cyanopyrrolidin-1-yl)-N-[3-(1H-imidazol-1-yl)propyl]-2-phenylquinoxaline-6-carboxamide |
| I-18 | N-[3-(1H-imidazol-2-yl)propyl]-2-[4-(morpholin-4-yl)piperidin-1-yl]-3-phenylquinoxaline-6-carboxamide |
| I-19 | 2,3-bis(4-fluorophenyl)-N-[3-(1H-imidazol-1-yl)propyl]quinoxaline-6-carboxamide |
| I-20 | 2,3-bis(4-fluorophenyl)-N-[2-(1H-imidazol-4-yl)ethyl]quinoxaline-6-carboxamide |
| I-21 | 3-(4-fluorophenyl)-N-[3-(6-methylpyridin-3-yl)propyl]-2-(morpholin-4-yl)quinoxaline-6-carboxamide |
| I-22 | [2,3-bis(4-fluorophenyl)quinoxalin-6-yl](2-methyl-2,4,5,7-tetrahydro-6H-pyrazolo[3,4-c]pyridin-6-yl)methanone |
| I-23 | 3-(4-fluorophenyl)-N-[3-(1H-imidazol-2-yl)propyl]-2-[4-(morpholin-4-yl)piperidin-1-yl]quinoxaline-6-carboxamide |
| I-24 | 2-(2,4-dimethyl-1,3-thiazol-5-yl)-N-[3-(1H-imidazol-1-yl)propyl]-3-phenylquinoxaline-6-carboxamide |
| I-25 | 3-(4-fluorophenyl)-2-(4-hydroxypiperidin-1-yl)-N-[3-(pyridin-3-yl)propyl]quinoxaline-6-carboxamide |
| I-26 | 2,3-bis(4-fluorophenyl)-N-[2-(2-methyl-1H-imidazol-1-yl)ethyl]quinoxaline-6-carboxamide |
| I-27 | tert-butyl{[1'-(6-{[3-(1H-imidazol-1-yl)propyl]carbamoyl}-3-phenylquinoxalin-2-yl)-1,4'-bipiperidin-4-yl]methyl}carbamate |
| I-28 | [2,3-bis(4-fluorophenyl)quinoxalin-6-yl](6,7-dihydro[1,2,3]triazolo[1,5-a]pyrazin-5(4H)-yl)methanone |
| I-29 | [2,3-bis(4-fluorophenyl)quinoxalin-6-yl][3-(pyridin-3-yl)pyrrolidin-1-yl]methanone |
| I-30 | N-[3-(1H-imidazol-1-yl)propyl]-2-(2-oxa-7-azaspiro[3.5]non-7-yl)-3-phenylquinoxaline-6-carboxamide |
| I-31 | 2-(2,2-dimethylmorpholin-4-yl)-N-[3-(1H-imidazol-1-yl)propyl]-3-phenylquinoxaline-6-carboxamide |
| I-32 | 2,3-bis(4-fluorophenyl)-N-[3-(pyridin-3-yl)propyl]quinoxaline-6-carboxamide |
| I-33 | [2,3-bis(4-fluorophenyl)quinoxalin-6-yl](3-methyl-3,4,6,7-tetrahydro-5H-imidazo[4,5-c]pyridin-5-yl)methanone |
| I-34 | cis-3-[(2R,6S)-2,6-dimethylmorpholin-4-yl]-N-[3-(1H-imidazol-1-yl)propyl]-2-phenylquinoxaline-6-carboxamide |
| I-35 | 3-(4-fluorophenyl)-N-[3-(1H-imidazol-4-yl)propyl]-2-(morpholin-4-yl)quinoxaline-6-carboxamide |
| I-36 | N-[3-(1H-imidazol-1-yl)propyl]-3-(2-methoxyphenyl)-2-phenylquinoxaline-6-carboxamide |
| I-37 | N-[3-(1H-imidazol-1-yl)propyl]-2-(2-oxa-5-azabicyclo[2.2.1]hept-5-yl)-3-phenylquinoxaline-6-carboxamide |
| I-38 | N-[3-(1H-imidazol-1-yl)propyl]-2-(1-methyl-1H-benzimidazol-5-yl)-3-phenylquinoxaline-6-carboxamide |
| I-39 | 3-(4-fluorophenyl)-N-[3-(1H-imidazol-2-yl)propyl]-2-(morpholin-4-yl)quinoxaline-6-carboxamide |
| I-40 | [2,3-bis(4-fluorophenyl)quinoxalin-6-yl][3-(pyrazin-2-yl)pyrrolidin-1-yl]methanone |
| I-41 | N-[3-(1H-imidazol-1-yl)propyl]-2-phenyl-3-(pyrimidin-5-yl)quinoxaline-6-carboxamide |
| I-42 | 3-(4-fluorophenyl)-2-[4-(morpholin-4-yl)piperidin-1-yl]-N-[3-(1,3-thiazol-2-yl)propyl]quinoxaline-6-carboxamide |
| I-43 | N-[2-(1H-benzimidazol-5-yl)ethyl]-2,3-bis(4-fluorophenyl)quinoxaline-6-carboxamide |
| I-44 | N-[3-(1H-imidazol-2-yl)propyl]-2-[4-(morpholin-4-yl)piperidin-1-yl]-3-(2-thienyl)quinoxaline-6-carboxamide |
| I-45 | 2-(4-chlorophenyl)-N-[3-(1H-imidazol-1-yl)propyl]-3-phenylquinoxaline-6-carboxamide |
| I-46 | 2-(4-hydroxypiperidin-1-yl)-3-(3-methoxyphenyl)-N-[3-(pyridin-3-yl)propyl]quinoxaline-6-carboxamide |
| I-47 | 3-(4-fluorophenyl)-2-(morpholin-4-yl)-N-[3-(pyridazin-4-yl)propyl]quinoxaline-6-carboxamide |
| I-48 | N-[3-(1H-imidazol-1-yl)propyl]-3-{3-[(methylsulfonyl)amino]phenyl}-2-phenylquinoxaline-6-carboxamide |
| I-49 | N-[3-(1H-imidazol-1-yl)propyl]-3-phenyl-2-(1H-pyrazol-4-yl)quinoxaline-6-carboxamide |
| I-50 | 2-chloro-3-(4-chlorophenyl)-N-[3-(1H-imidazol-2-yl)propyl]quinoxaline-6-carboxamide |
| I-51 | 2-(4-acetylpiperazin-1-yl)-N-[3-(1H-imidazol-1-yl)propyl]-3-phenylquinoxaline-6-carboxamide |
| I-52 | N-[3-(1H-imidazol-1-yl)propyl]-2,3-bis(3-methoxyphenyl)quinoxaline-6-carboxamide |

TABLE 1-continued

| | |
|---|---|
| I-53 | 2,3-bis(4-fluorophenyl)-N-[2-(1-methyl-1H-imidazol-5-yl)ethyl]quinoxaline-6-carboxamide |
| I-54 | 2-(2-cyanophenyl)-N-[3-(1H-imidazol-1-yl)propyl]-3-phenylquinoxaline-6-carboxamide |
| I-55 | N-[3-(1H-imidazol-1-yl)propyl]-3-(3-methoxyphenyl)-2-(morpholin-4-yl)quinoxaline-6-carboxamide |
| I-56 | [2,3-bis(4-fluorophenyl)quinoxalin-6-yl](5,6-dihydroimidazo[1,2-a]pyrazin-7(8H)-yl)methanone |
| I-57 | 2,3-bis(4-fluorophenyl)-N-[3-(2-methyl-1H-imidazol-1-yl)propyl]quinoxaline-6-carboxamide |
| I-58 | 2-(dimethylamino)-3-(4-fluorophenyl)-N-[2-(1-methyl-1H-imidazol-5-yl)ethyl]quinoxaline-6-carboxamide |
| I-59 | N-[3-(1H-imidazol-1-yl)propyl]-2-(3-methoxyazetidin-1-yl)-3-phenylquinoxaline-6-carboxamide |
| I-60 | N-[3-(1H-imidazol-1-yl)propyl]-3-phenyl-2-(3-thienyl)quinoxaline-6-carboxamide |
| I-61 | N-[3-(1H-imidazol-1-yl)propyl]-3-phenyl-2-[3-(trifluoromethoxy)phenyl]quinoxaline-6-carboxamide |
| I-62 | 2-(benzylamino)-N-[3-(1H-imidazol-1-yl)propyl]-3-phenylquinoxaline-6-carboxamide |
| I-63 | tert-butyl[4-(7-{[3-(1H-imidazol-1-yl)propyl]carbamoyl}-3-phenylquinoxalin-2-yl)benzyl]carbamate |
| I-64 | 3-(4-fluorophenyl)-N-(imidazo[1,2-a]pyridin-6-ylmethyl)-2-[4-(morpholin-4-yl)piperidin-1-yl]quinoxaline-6-carboxamide |
| I-65 | 2,3-bis(4-fluorophenyl)-N-[2-(pyridin-3-yloxy)ethyl]quinoxaline-6-carboxamide |
| I-66 | tert-butyl 4-[1-(6-{[3-(1H-imidazol-1-yl)propyl]carbamoyl}-3-phenylquinoxalin-2-yl)piperidin-4-yl]piperazine-1-carboxylate |
| I-67 | 2-(4-hydroxypiperidin-1-yl)-3-(3-methoxyphenyl)-N-[2-(pyridin-3-yl)ethyl]quinoxaline-6-carboxamide |
| I-68 | [2,3-bis(4-fluorophenyl)quinoxalin-6-yl](2-methyl-2,4,6,7-tetrahydro-5H-pyrazolo[4,3-f][1,4]oxazepin-5-yl)methanone |
| I-69 | N-[3-(1H-imidazol-1-yl)propyl]-3-(imidazo[1,2-a]pyridin-6-yl)-2-phenylquinoxaline-6-carboxamide |
| I-70 | 3-(3-methoxyphenyl)-2-[4-(morpholin-4-yl)piperidin-1-yl]-N-[3-(pyridin-3-yl)propyl]quinoxaline-6-carboxamide |
| I-71 | N-[2-(1H-imidazol-2-yl)ethyl]-2-[4-(morpholin-4-yl)piperidin-1-yl]-3-phenylquinoxaline-6-carboxamide |
| I-72 | N-[2,3-bis(4-fluorophenyl)quinoxalin-6-yl]-4-(1H-imidazol-1-yl)butanamide |
| I-73 | 2-chloro-3-(3-methoxyphenyl)-N-[2-(pyridin-3-yl)ethyl]quinoxaline-6-carboxamide |
| I-74 | tert-butyl[1'-(6-{[3-(1H-imidazol-1-yl)propyl]carbamoyl}-3-phenylquinoxalin-2-yl)-1,4'-bipiperidin-4-yl]carbamate |
| I-75 | [2,3-bis(4-fluorophenyl)quinoxalin-6-yl](1,4,6,7-tetrahydro-5H-pyrrolo[3,2-c]pyridin-5-yl)methanone |
| I-76 | 2,3-diphenyl-N-(pyridin-2-ylmethyl)quinoxaline-6-carboxamide |
| I-77 | 3-(4-fluorophenyl)-2-(4-hydroxypiperidin-1-yl)-N-[3-(1,3-thiazol-2-yl)propyl]quinoxaline-6-carboxamide |
| I-78 | 3-(4-fluorophenyl)-N-[3-(1H-imidazol-2-yl)propyl]-2-(4-methoxypiperidin-1-yl)quinoxaline-6-carboxamide |
| I-79 | 3-(4-chlorophenyl)-N-[3-(1H-imidazol-1-yl)propyl]-2-phenylquinoxaline-6-carboxamide |
| I-80 | N-[3-(1H-imidazol-1-yl)propyl]-2-phenoxy-3-phenylquinoxaline-6-carboxamide |
| I-81 | N-[3-(1H-imidazol-1-yl)propyl]-2-(4-methyl-3-oxopiperazin-1-yl)-3-phenylquinoxaline-6-carboxamide |
| I-82 | 3-(4-fluorophenyl)-N-[2-(1-methyl-1H-imidazol-5-yl)ethyl]-2-[4-(morpholin-4-yl)piperidin-1-yl]quinoxaline-6-carboxamide |
| I-83 | 2,3-bis(4-fluorophenyl)-N-[2-(1H-pyrazol-1-yl)ethyl]quinoxaline-6-carboxamide |
| I-84 | 2,3-bis(4-fluorophenyl)-N-methyl-N-[2-(pyridin-3-yl)ethyl]quinoxaline-6-carboxamide |
| I-85 | tert-butyl[3-(7-{[3-(1H-imidazol-1-yl)propyl]carbamoyl}-3-phenylquinoxalin-2-yl)benzyl]carbamate |
| I-86 | 2-chloro-3-(4-fluorophenyl)-N-[2-(pyridin-3-yloxy)ethyl]quinoxaline-6-carboxamide |
| I-87 | 3-(3-hydroxypiperidin-1-yl)-N-[3-(1H-imidazol-1-yl)propyl]-2-phenylquinoxaline-6-carboxamide |
| I-88 | N-[3-(1H-imidazol-1-yl)propyl]-2-(morpholin-4-ylmethyl)-3-phenylquinoxaline-6-carboxamide |
| I-89 | N-[3-(1H-imidazol-1-yl)propyl]-3-phenyl-2-(3-sulfamoylphenyl)quinoxaline-6-carboxamide |
| I-90 | 2-(3-hydroxypyrrolidin-1-yl)-N-[3-(1H-imidazol-1-yl)propyl]-3-phenylquinoxaline-6-carboxamide |
| I-91 | N-[3-(1H-imidazol-2-yl)propyl]-3-(3-methoxyphenyl)-2-[4-(morpholin-4-yl)piperidin-1-yl]quinoxaline-6-carboxamide |
| I-92 | N-[3-(1H-imidazol-1-yl)propyl]-3-phenyl-2-(pyridin-2-yl)quinoxaline-6-carboxamide |
| I-93 | 2,3-diphenyl-N-[2-(pyridin-3-yl)ethyl]quinoxaline-6-carboxamide |
| I-94 | 3-(4-fluorophenyl)-2-(piperidin-1-yl)-N-[3-(1H-pyrazol-4-yl)propyl]quinoxaline-6-carboxamide |
| I-95 | N-[3-(1H-imidazol-1-yl)propyl]-2-phenyl-3-[3-(trifluoromethoxy)phenyl]quinoxaline-6-carboxamide |
| I-96 | N-[3-(1H-imidazol-1-yl)propyl]-2-(morpholin-4-yl)-3-phenylquinoxaline-6-carboxamide |

TABLE 1-continued

| | |
|---|---|
| I-97 | N-[3-(1H-imidazol-1-yl)propyl]-3-(1H-indol-5-yl)-2-phenylquinoxaline-6-carboxamide |
| I-98 | [2,3-bis(4-fluorophenyl)quinoxalin-6-yl][3-(pyridin-4-yl)pyrrolidin-1-yl]methanone |
| I-99 | N-[3-(1H-imidazol-1-yl)propyl]-2-(4-methoxyphenyl)-3-phenylquinoxaline-6-carboxamide |
| I-100 | 2-(3-hydroxypiperidin-1-yl)-N-[3-(1H-imidazol-1-yl)propyl]-3-phenylquinoxaline-6-carboxamide |
| I-101 | N-[3-(1H-imidazol-1-yl)propyl]-3-[3-(methylsulfonyl)pyrrolidin-1-yl]-2-phenylquinoxaline-6-carboxamide |
| I-102 | 2-chloro-3-(4-fluorophenyl)-N-[2-(1H-imidazol-2-yl)ethyl]quinoxaline-6-carboxamide |
| I-103 | 3-(4-fluorophenyl)-2-(piperidin-1-yl)-N-[3-(pyridazin-4-yl)propyl]quinoxaline-6-carboxamide |
| I-104 | 3-(4-chlorophenyl)-N-[3-(1H-imidazol-2-yl)propyl]-2-(morpholin-4-yl)quinoxaline-6-carboxamide |
| I-105 | 2-(4-hydroxypiperidin-1-yl)-N-[3-(1H-imidazol-1-yl)propyl]-3-phenylquinoxaline-6-carboxamide |
| I-106 | 2-(3-cyanopyrrolidin-1-yl)-N-[3-(1H-imidazol-1-yl)propyl]-3-phenylquinoxaline-6-carboxamide |
| I-107 | 2,3-di(2-furyl)-N-[3-(1H-imidazol-1-yl)propyl]quinoxaline-6-carboxamide |
| I-108 | 2,3-bis(4-fluorophenyl)-N-[2-(1-methyl-1H-pyrazol-3-yl)ethyl]quinoxaline-6-carboxamide |
| I-109 | 3-(4-chlorophenyl)-N-[3-(1H-imidazol-2-yl)propyl]-2-methoxyquinoxaline-6-carboxamide |
| I-110 | [2,3-bis(4-fluorophenyl)quinoxalin-6-yl][3-(pyridin-2-yl)azetidin-1-yl]methanone |
| I-111 | 3-(4-chlorophenyl)-N-[3-(1H-imidazol-2-yl)propyl]-2-(tetrahydro-2H-pyran-4-yloxy)quinoxaline-6-carboxamide |
| I-112 | N-[3-(1H-imidazol-1-yl)propyl]-3-phenyl-2-[4-(piperazin-1-yl)piperidin-1-yl]quinoxaline-6-carboxamide |
| I-113 | 3-(2,2-dimethylmorpholin-4-yl)-N-[3-(1H-imidazol-1-yl)propyl]-2-phenylquinoxaline-6-carboxamide |
| I-114 | 3-(4-fluorophenyl)-2-(4-hydroxypiperidin-1-yl)-N-[2-(pyridin-3-yloxy)ethyl]quinoxaline-6-carboxamide |
| I-115 | cis-2-[(2R,6S)-2,6-dimethylmorpholin-4-yl]-N-[3-(1H-imidazol-1-yl)propyl]-3-phenylquinoxaline-6-carboxamide |
| I-116 | 3-(4-chlorophenyl)-N-[3-(1H-imidazol-2-yl)propyl]-2-(pyrrolidin-1-yl)quinoxaline-6-carboxamide |
| I-117 | 2,3-di(2-furyl)-N-[2-(pyridin-3-yl)ethyl]quinoxaline-6-carboxamide |
| I-118 | N-[2-(1H-imidazol-4-yl)ethyl]-2,3-diphenylquinoxaline-6-carboxamide |
| I-119 | N-[3-(1H-imidazol-1-yl)propyl]-2-(1-methyl-1H-pyrazol-4-yl)-3-phenylquinoxaline-6-carboxamide |
| I-120 | 3-[3-(aminomethyl)phenyl]-N-[3-(1H-imidazol-1-yl)propyl]-2-phenylquinoxaline-6-carboxamide |
| I-121 | [2,3-bis(4-fluorophenyl)quinoxalin-6-yl](3,4,6,7-tetrahydro-5H-imidazo[4,5-c]pyridin-5-yl)methanone |
| I-122 | 2,3-bis(4-fluorophenyl)-N-[2-(1H-imidazol-2-yl)ethyl]quinoxaline-6-carboxamide |
| I-123 | 7-{[2,3-bis(4-fluorophenyl)quinoxalin-6-yl]carbonyl}-5,6,7,8-tetrahydroimidazo[1,2-a]pyrazine-2-carboxamide |
| I-124 | N-[3-(1H-imidazol-1-yl)propyl]-2-phenyl-3-(pyrrolidin-1-yl)quinoxaline-6-carboxamide |
| I-125 | N-[3-(1H-imidazol-1-yl)propyl]-2-[4-(methylsulfonyl)piperazin-1-yl]-3-phenylquinoxaline-6-carboxamide |
| I-126 | 3-[cyclopropyl(methyl)amino]-N-[3-(1H-imidazol-1-yl)propyl]-2-phenylquinoxaline-6-carboxamide |
| I-127 | N-[3-(1H-imidazol-1-yl)propyl]-3-(4-methyl-3-oxopiperazin-1-yl)-2-phenylquinoxaline-6-carboxamide |
| I-128 | N-[3-(1H-imidazol-1-yl)propyl]-2-(4-methylpiperazin-1-yl)-3-phenylquinoxaline-6-carboxamide |
| I-129 | N-[3-(1H-imidazol-1-yl)propyl]-3-[4-(methylsulfonyl)piperazin-1-yl]-2-phenylquinoxaline-6-carboxamide |
| I-130 | 2-(4,4'-bipiperidin-1-yl)-3-phenyl-N-[2-(pyridin-2-yl)ethyl]quinoxaline-6-carboxamide |
| I-131 | 2-(4-cyanophenyl)-N-[3-(1H-imidazol-1-yl)propyl]-3-phenylquinoxaline-6-carboxamide |
| I-132 | N-(1H-benzimidazol-5-ylmethyl)-3-(4-fluorophenyl)-2-(morpholin-4-yl)quinoxaline-6-carboxamide |
| I-133 | 3-(4-fluorophenyl)-N-(1H-indazol-6-ylmethyl)-2-(piperidin-1-yl)quinoxaline-6-carboxamide |
| I-134 | N-[2-(1H-imidazol-2-yl)ethyl]-2,3-bis(3-methoxyphenyl)quinoxaline-6-carboxamide |
| I-135 | 3-(2-acetamidophenyl)-N-[3-(1H-imidazol-1-yl)propyl]-2-phenylquinoxaline-6-carboxamide |
| I-136 | N-[3-(1H-imidazol-1-yl)propyl]-2-[4-(2-oxopyrrolidin-1-yl)piperidin-1-yl]-3-phenylquinoxaline-6-carboxamide |
| I-137 | 2-(azetidin-1-yl)-N-[3-(1H-imidazol-1-yl)propyl]-3-phenylquinoxaline-6-carboxamide |
| I-138 | 3-(4-fluorophenyl)-2-(piperidin-1-yl)-N-[3-(pyrimidin-5-yl)propyl]quinoxaline-6-carboxamide |
| I-139 | 2,3-bis(4-fluorophenyl)-N-[2-(5-sulfanyl-1H-tetrazol-1-yl)ethyl]quinoxaline-6-carboxamide |
| I-140 | 2-(2,3-dihydro-1-benzofuran-5-yl)-N-[3-(1H-imidazol-1-yl)propyl]-3-phenylquinoxaline-6-carboxamide |

TABLE 1-continued

| | |
|---|---|
| I-141 | 2-(3,6-dihydro-2H-pyran-4-yl)-N-[3-(1H-imidazol-1-yl)propyl]-3-phenylquinoxaline-6-carboxamide |
| I-142 | 2-cyano-N-[3-(1H-imidazol-1-yl)propyl]-3-phenylquinoxaline-6-carboxamide |
| I-143 | N-[3-(1H-imidazol-1-yl)propyl]-3-(1-methyl-1H-benzimidazol-5-yl)-2-phenylquinoxaline-6-carboxamide |
| I-144 | N-[3-(1H-imidazol-1-yl)propyl]-3-(morpholin-4-yl)-2-phenylquinoxaline-6-carboxamide |
| I-145 | N-[3-(1H-imidazol-1-yl)propyl]-3-phenyl-2-(4-sulfamoylphenyl)quinoxaline-6-carboxamide |
| I-146 | 2-(hexahydropyrrolo[1,2-a]pyrazin-2(1H)-yl)-N-[3-(1H-imidazol-1-yl)propyl]-3-phenylquinoxaline-6-carboxamide |
| I-147 | 3-(4-fluorophenyl)-N-(imidazo[1,2-a]pyridin-6-ylmethyl)-2-(morpholin-4-yl)quinoxaline-6-carboxamide |
| I-148 | tert-butyl[4-(6-{[3-(1H-imidazol-1-yl)propyl]carbamoyl}-3-phenylquinoxalin-2-yl)benzyl]carbamate |
| I-149 | N-[3-(1H-imidazol-1-yl)propyl]-2-(1H-indol-5-yl)-3-phenylquinoxaline-6-carboxamide |
| I-150 | N-[3-(1H-imidazo-1-yl)propyl]-2-[3-(methylsulfonyl)pyrrolidin-1-yl]-3-phenylquinoxaline-6-carboxamide |
| I-151 | 2,3-bis(4-fluorophenyl)-N-[2-(1-methyl-1H-imidazol-2-yl)ethyl]quinoxaline-6-carboxamide |
| I-152 | tert-butyl[3-(6-{[3-(1H-imidazol-1-yl)propyl]carbamoyl}-3-phenylquinoxalin-2-yl)benzyl]carbamate |
| I-153 | 3-(3-hydroxypyrrolidin-1-yl)-N-[3-(1H-imidazol-1-yl)propyl]-2-phenylquinoxaline-6-carboxamide |
| I-154 | 3-(4-fluorophenyl)-N-[3-(1H-imidazol-2-yl)propyl]-2-(2-oxa-6-azaspiro[3.3]hept-6-yl)quinoxaline-6-carboxamide |
| I-155 | [2,3-bis(4-fluorophenyl)quinoxalin-6-yl][2-(pyridin-3-yl)morpholin-4-yl]methanone |
| I-156 | 3-(4-fluorophenyl)-2-(4-hydroxypiperidin-1-yl)-N-(imidazo[1,2-a]pyridin-6-ylmethyl)quinoxaline-6-carboxamide |
| I-157 | 3-(3-cyanophenyl)-N-[3-(1H-imidazol-1-yl)propyl]-2-phenylquinoxaline-6-carboxamide |
| I-158 | N-[3-(1H-imidazol-1-yl)propyl]-2-methyl-3-phenylquinoxaline-6-carboxamide |
| I-159 | 2-(3-azabicyclo[3.1.0]hex-3-yl)-N-[3-(1H-imidazol-1-yl)propyl]-3-phenylquinoxaline-6-carboxamide |
| I-160 | [2,3-bis(4-fluorophenyl)quinoxalin-6-yl](3,4-dihydro-2,6-naphthyridin-2(1H)-yl)methanone |
| I-161 | N-[3-(1H-imidazol-1-yl)propyl]-3-phenyl-2-(piperidin-1-yl)quinoxaline-6-carboxamide |
| I-162 | 3-(3,6-dihydro-2H-pyran-4-yl)-N-[3-(1H-imidazol-1-yl)propyl]-2-phenylquinoxaline-6-carboxamide |
| I-163 | [2,3-bis(4-fluorophenyl)quinoxalin-6-yl][3-(pyridin-2-yl)pyrrolidin-1-yl]methanone |
| I-164 | 2,3-bis(4-fluorophenyl)-N-[2-(1,3-thiazol-2-yl)ethyl]quinoxaline-6-carboxamide |
| I-165 | N-[3-(1H-imidazol-1-yl)propyl]-2-(1-methyl-1,2,3,6-tetrahydropyridin-4-yl)-3-phenylquinoxaline-6-carboxamide |
| I-166 | N-[3-(1H-imidazol-1-yl)propyl]-2-phenyl-3-(piperidin-1-yl)quinoxaline-6-carboxamide |
| I-167 | N-[3-(1H-imidazol-1-yl)propyl]-3-(1-methyl-1H-pyrazol-4-yl)-2-phenylquinoxaline-6-carboxamide |
| I-168 | 3-(4-acetylpiperazin-1-yl)-N-[3-(1H-imidazol-1-yl)propyl]-2-phenylquinoxaline-6-carboxamide |
| I-169 | 2,3-bis(4-fluorophenyl)-N-[2-(pyridin-2-yl)ethyl]quinoxaline-6-carboxamide |
| I-170 | 3-(4-fluorophenyl)-N-imidazo[1,2-a]pyridin-6-ylmethyl-2-(piperidin-1-yl)quinoxaline-6-carboxamide |
| I-171 | ethyl 3-[4-(7-{[3-(1H-imidazol-1-yl)propyl]carbamoyl}-3-phenylquinoxalin-2-yl)phenyl]propanoate |
| I-172 | 3-(4-fluorophenyl)-N-[3-(1H-imidazol-2-yl)propyl]-2-(3-methoxyazetidin-1-yl)quinoxaline-6-carboxamide |
| I-173 | 2-(4,4'-bipiperidin-1-yl)-N-[2-(1H-imidazol-1-yl)ethyl]-3-phenylquinoxaline-6-carboxamide |
| I-174 | N-[3-(1H-imidazol-1-yl)propyl]-2-phenyl-3-(3-thienyl)quinoxaline-6-carboxamide |
| I-175 | 3-(azetidin-1-yl)-N-[3-(1H-imidazol-1-yl)propyl]-2-phenylquinoxaline-6-carboxamide |
| I-176 | N-[3-(1H-imidazol-1-yl)propyl]-2-phenyl-3-(pyridin-3-yl)quinoxaline-6-carboxamide |
| I-177 | 3-(4-fluorophenyl)-N-[2-(1-methyl-1H-imidazol-5-yl)ethyl]-2-(morpholin-4-yl)quinoxaline-6-carboxamide |
| I-178 | 2,3-bis(4-fluorophenyl)-N-[3-(1H-imidazol-2-yl)propyl]quinoxaline-6-carboxamide |
| I-179 | N-[3-(1H-imidazol-1-yl)propyl]-2-(1-methyl-1H-pyrrol-2-yl)-3-phenylquinoxaline-6-carboxamide |
| I-180 | 2,3-bis(4-fluorophenyl)-N-[3-(pyridin-2-yl)propyl]quinoxaline-6-carboxamide |
| I-181 | 2,3-bis(3-methoxyphenyl)-N-[2-(pyridin-3-yl)ethyl]quinoxaline-6-carboxamide |
| I-182 | N-[3-(1H-imidazol-1-yl)propyl]-2-[3-(methylsulfonyl)phenyl]-3-phenylquinoxaline-6-carboxamide |
| I-183 | N-[3-(1H-imidazol-2-yl)propyl]-3-(3-methoxyphenyl)-2-(piperidin-1-yl)quinoxaline-6-carboxamide |

TABLE 1-continued

| | |
|---|---|
| I-184 | 2,3-bis(4-fluorophenyl)-N-[2-(pyrazin-2-yl)ethyl]quinoxaline-6-carboxamide |
| I-185 | 3-(4-fluorophenyl)-N-[3-(6-methylpyridin-3-yl)propyl]-2-(piperidin-1-yl)quinoxaline-6-carboxamide |
| I-186 | [2,3-bis(4-fluorophenyl)quinoxalin-6-yl][4-(pyridin-4-yl)piperidin-1-yl]methanone |
| I-187 | N-[3-(1H-imidazol-1-yl)propyl]-2-(3-methoxyphenyl)-3-phenylquinoxaline-6-carboxamide |
| I-188 | tert-butyl 1'-(6-{[3-(1H-imidazol-1-yl)propyl]carbamoyl}-3-phenylquinoxalin-2-yl)-4,4'-bipiperidine-1-carboxylate |
| I-189 | 3-(3-methoxyphenyl)-2-(morpholin-4-yl)-N-[2-(pyridin-3-yl)ethyl]quinoxaline-6-carboxamide |
| I-190 | 2-(4-carbamoylphenyl)-N-[3-(1H-imidazol-1-yl)propyl]-3-phenylquinoxaline-6-carboxamide |
| I-191 | 3-(benzylamino)-N-[3-(1H-imidazol-1-yl)propyl]-2-phenylquinoxaline-6-carboxamide |
| I-192 | 2,3-bis(4-fluorophenyl)-N-[3-(1H-imidazol-4-yl)propyl]quinoxaline-6-carboxamide |
| I-193 | 3-(4-fluorophenyl)-2-(morpholin-4-yl)-N-[3-(pyrimidin-5-yl)propyl]quinoxaline-6-carboxamide |
| I-194 | N-[3-(1H-imidazol-1-yl)propyl]-3-(1-methyl-1H-pyrrol-2-yl)-2-phenylquinoxaline-6-carboxamide |
| I-195 | N-[3-(1H-imidazol-2-yl)propyl]-2-(piperidin-1-yl)-3-(2-thienyl)quinoxaline-6-carboxamide |
| I-196 | 3-(3-methoxyphenyl)-2-(piperidin-1-yl)-N-[2-(pyridin-3-yl)ethyl]quinoxaline-6-carboxamide |
| I-197 | 3-(3-methoxyphenyl)-2-(piperidin-1-yl)-N-[3-(pyridin-3-yl)propyl]quinoxaline-6-carboxamide |
| I-198 | 3-(4-chlorophenyl)-N-[3-(1H-imidazol-2-yl)propyl]-2-(piperidin-1-yl)quinoxaline-6-carboxamide |
| I-199 | N-[3-(1H-imidazol-1-yl)propyl]-2-[4-(morpholin-4-yl)piperidin-1-yl]-3-phenylquinoxaline-6-carboxamide |
| I-200 | N-[3-(1H-imidazol-1-yl)propyl]-2-(2-methyl-2,4,5,7-tetrahydro-6H-pyrazolo[3,4-c]pyridin-6-yl)-3-phenylquinoxaline-6-carboxamide |
| I-201 | N-[3-(1H-imidazol-1-yl)propyl]-3-phenyl-2-(pyridin-3-yl)quinoxaline-6-carboxamide |
| I-202 | 2-(4-hydroxycyclohex-1-en-1-yl)-N-[3-(1H-imidazol-2-yl)propyl]-3-(2-thienyl)quinoxaline-6-carboxamide |
| I-203 | N-[3-(1H-imidazol-1-yl)propyl]-2-(1-methyl-1H-pyrazol-3-yl)-3-phenylquinoxaline-6-carboxamide |
| I-204 | 3-(4-fluorophenyl)-N-(imidazo[1,2-a]pyrimidin-2-ylmethyl)-2-[4-(morpholin-4-yl)piperidin-1-yl]quinoxaline-6-carboxamide |
| I-205 | ethyl 3-[4-(6-{[3-(1H-imidazol-1-yl)propyl]carbamoyl}-3-phenylquinoxalin-2-yl)phenyl]propanoate |
| I-206 | N-[3-(1H-imidazol-1-yl)propyl]-3-phenyl-2-(pyrrolidin-1-yl)quinoxaline-6-carboxamide |
| I-207 | 2-(diethylamino)-N-[3-(1H-imidazol-1-yl)propyl]-3-phenylquinoxaline-6-carboxamide |
| I-208 | N-[3-(1H-imidazol-1-yl)propyl]-2-(1H-indol-6-yl)-3-phenylquinoxaline-6-carboxamide |
| I-209 | 2-(3-chlorophenyl)-N-[3-(1H-imidazol-1-yl)propyl]-3-phenylquinoxaline-6-carboxamide |
| I-210 | 2-(4-hydroxy-1,4'-bipiperidin-1'-yl)-N-[3-(1H-imidazol-1-yl)propyl]-3-phenylquinoxaline-6-carboxamide |
| I-211 | 2-chloro-3-(4-fluorophenyl)-N-[3-(1H-imidazol-2-yl)propyl]quinoxaline-6-carboxamide |
| I-212 | 2,3-bis(4-fluorophenyl)-N-[2-(pyridin-4-yl)ethyl]quinoxaline-6-carboxamide |
| I-213 | 3-(4-fluorophenyl)-2-(4-hydroxypiperidin-1-yl)-N-[3-(1H-imidazol-2-yl)propyl]quinoxaline-6-carboxamide |
| I-214 | N-[3-(1H-imidazol-1-yl)propyl]-2,3-bis(4-methylphenyl)quinoxaline-6-carboxamide |
| I-215 | N-[3-(1H-imidazol-1-yl)propyl]-3-(1-methyl-1H-pyrazol-3-yl)-2-phenylquinoxaline-6-carboxamide |
| I-216 | 3-(4-chlorophenyl)-2-(cyclohexyloxy)-N-[3-(1H-imidazol-2-yl)propyl]quinoxaline-6-carboxamide |
| I-217 | tert-butyl[2-(7-{[3-(1H-imidazol-1-yl)propyl]carbamoyl}-3-phenylquinoxalin-2-yl)benzyl]carbamate |
| I-218 | N-[3-(1H-imidazol-1-yl)propyl]-3-(3-methoxyphenyl)-2-phenylquinoxaline-6-carboxamide |
| I-219 | 2-(3-cyanophenyl)-N-[3-(1H-imidazol-1-yl)propyl]-3-phenylquinoxaline-6-carboxamide |
| I-220 | 3-(4-fluorophenyl)-N-(1H-indazol-5-ylmethyl)-2-(piperidin-1-yl)quinoxaline-6-carboxamide |
| I-221 | 3-(4-fluorophenyl)-2-[4-(morpholin-4-yl)piperidin-1-yl]-N-[2-(pyridin-3-yloxy)ethyl]quinoxaline-6-carboxamide |
| I-222 | 3-(4-chlorophenyl)-N-[3-(1H-imidazol-2-yl)propyl]-2-isopropoxyquinoxaline-6-carboxamide |
| I-223 | 3-(4-acetamidophenyl)-N-[3-(1H-imidazol-1-yl)propyl]-2-phenylquinoxaline-6-carboxamide |
| I-224 | 3-(3-chlorophenyl)-N-[3-(1H-imidazol-1-yl)propyl]-2-phenylquinoxaline-6-carboxamide |
| I-225 | [2,3-bis(4-fluorophenyl)quinoxalin-6-yl](1,4,6,7-tetrahydro-5H-pyrazolo[4,3-c]pyridin-5-yl)methanone |
| I-226 | N-[3-(1H-imidazol-1-yl)propyl]-2-(3-methoxypyrrolidin-1-yl)-3-phenylquinoxaline-6-carboxamide |

TABLE 1-continued

| | |
|---|---|
| I-227 | N-[3-(1H-imidazol-1-yl)propyl]-3-(1H-indol-6-yl)-2-phenylquinoxaline-6-carboxamide |
| I-228 | 2-(3-ethoxyphenyl)-N-[3-(1H-imidazol-1-yl)propyl]-3-phenylquinoxaline-6-carboxamide |
| I-229 | 2,3-bis(4-fluorophenyl)-N-[3-(pyridin-4-yl)propyl]quinoxaline-6-carboxamide |
| I-230 | 2-(cyclopent-1-en-1-yl)-N-[3-(1H-imidazol-1-yl)propyl]-3-phenylquinoxaline-6-carboxamide |
| I-231 | tert-butyl{[4-hydroxy-1'-(6-{[3-(1H-imidazol-1-yl)propyl]carbamoyl}-3-phenylquinoxalin-2-yl)-1,4'-bipiperidin-4-yl]methyl}carbamate |
| I-232 | 3-(4-fluorophenyl)-N-[3-(1H-imidazol-2-yl)propyl]-2-(piperidin-1-yl)quinoxaline-6-carboxamide |
| I-233 | 2-anilino-N-[3-(1H-imidazol-1-yl)propyl]-3-phenylquinoxaline-6-carboxamide |
| I-234 | 2,3-bis(4-fluorophenyl)-N-[3-(1-methyl-1H-imidazol-2-yl)propyl]quinoxaline-6-carboxamide |
| I-235 | 2-(3-carbamoylphenyl)-N-[3-(1H-imidazol-1-yl)propyl]-3-phenylquinoxaline-6-carboxamide |
| I-236 | N-[3-(1H-imidazol-1-yl)propyl]-2-phenyl-3-(2-thienyl)quinoxaline-6-carboxamide |
| I-237 | 2,3-bis(4-fluorophenyl)-N-[2-(1H-1,2,4-triazol-1-yl)ethyl]quinoxaline-6-carboxamide |
| I-238 | N-[2-(2,3-dihydroimidazo[2,1-b][1,3]thiazol-6-yl)ethyl]-2,3-bis(4-fluorophenyl)quinoxaline-6-carboxamide |
| I-239 | tert-butyl 1'-(6-{[2-(1H-imidazol-1-yl)ethyl]carbamoyl}-3-phenylquinoxalin-2-yl)-4,4'-bipiperidine-1-carboxylate |
| I-240 | 2-(cyclohex-1-en-1-yl)-N-[3-(1H-imidazol-1-yl)propyl]-3-phenylquinoxaline-6-carboxamide |
| I-241 | N-[3-(1H-imidazol-1-yl)propyl]-3-(4-methoxyphenyl)-2-phenylquinoxaline-6-carboxamide |
| I-242 | N-[3-(1H-imidazol-1-yl)propyl]-3-phenyl-2-(pyrimidin-5-yl)quinoxaline-6-carboxamide |
| I-243 | N-[3-(1H-imidazol-1-yl)propyl]-2-(2-oxa-6-azaspiro[3.4]oct-6-yl)-3-phenylquinoxaline-6-carboxamide |
| I-244 | [2,3-bis(4-fluorophenyl)quinoxalin-6-yl](1,4,5,7-tetrahydro-6H-pyrazolo[3,4-c]pyridin-6-yl)methanone |
| I-245 | 3-(3,5-dimethoxyphenyl)-N-[3-(1H-imidazol-1-yl)propyl]-2-phenylquinoxaline-6-carboxamide |
| I-246 | [2,3-bis(4-fluorophenyl)quinoxalin-6-yl][2-(pyridin-3-ylmethyl)pyrrolidin-1-yl]methanone |
| I-247 | N-[3-(1H-imidazol-1-yl)propyl]-3-phenyl-2-(2-thienyl)quinoxaline-6-carboxamide |
| I-248 | 3-(3-acetamidophenyl)-N-[3-(1H-imidazol-1-yl)propyl]-2-phenylquinoxaline-6-carboxamide |
| I-249 | [2,3-bis(4-fluorophenyl)quinoxalin-6-yl][3-(1H-pyrazol-1-yl)azetidin-1-yl]methanone |
| I-250 | N-[3-(1H-imidazol-1-yl)propyl]-2-(6-oxohexahydropyrrolo[1,2-a]pyrazin-2(1H)-yl)-3-phenylquinoxaline-6-carboxamide |
| I-251 | N-[3-(1H-imidazol-1-yl)propyl]-2-phenyl-3-(pyridin-4-yl)quinoxaline-6-carboxamide |
| I-252 | 3-(2,3-dihydro-1-benzofuran-5-yl)-N-[3-(1H-imidazol-1-yl)propyl]-2-phenylquinoxaline-6-carboxamide |
| I-253 | 3-(4-fluorophenyl)-N-[3-(1H-imidazol-2-yl)propyl]-2-isopropoxyquinoxaline-6-carboxamide |
| I-254 | 2-(4-acetamidophenyl)-N-[3-(1H-iniidazol-1-yl)propyl]-3-phenylquinoxaline-6-carboxamide |
| I-255 | 3-(4-chlorophenyl)-N-[3-(1H-imidazol-2-yl)propyl]-2-[4-(morpholin-4-yl)piperidin-1-yl]quinoxaline-6-carboxamide |
| I-256 | 3-(4-fluorophenyl)-N-[3-(1H-imidazol-2-yl)propyl]-2-(thiomorpholin-4-yl)quinoxaline-6-carboxamide |
| I-257 | 2-(2-chlorophenyl)-N-[3-(1H-imidazol-1-yl)propyl]-3-phenylquinoxaline-6-carboxamide |
| I-258 | N-[3-(1H-imidazol-1-yl)propyl]-2-(imidazo[1,2-a]pyridin-6-yl)-3-phenylquinoxaline-6-carboxamide |
| I-259 | N-[3-(1H-imidazol-1-yl)propyl]-2-[(4-methylpiperazin-1-yl)methyl]-3-phenylquinoxaline-6-carboxamide |
| I-260 | 2,3-bis(2-chlorophenyl)-N-[3-(1H-imidazol-1-yl)propyl]quinoxaline-6-carboxamide |
| I-261 | N-[3-(1H-imidazol-1-yl)propyl]-2,3-diphenylquinoxaline-6-carboxamide |
| I-262 | 2-(azepan-1-yl)-N-[3-(1H-imidazol-1-yl)propyl]-3-phenylquinoxaline-6-carboxamide |
| I-263 | 3-(3-carbamoylphenyl)-N-[3-(1H-imidazol-1-yl)propyl]-2-phenylquinoxaline-6-carboxamide |
| I-264 | 2-(2-acetamidophenyl)-N-[3-(1H-imidazol-1-yl)propyl]-3-phenylquinoxaline-6-carboxamide |
| I-265 | 3-(azepan-1-yl)-N-[3-(1H-imidazol-1-yl)propyl]-2-phenylquinoxaline-6-carboxamide |
| I-266 | [2,3-bis(4-fluorophenyl)quinoxalin-6-yl](6,7-dihydroisoxazolo[4,3-c]pyridin-5(4H)-yl)methanone |
| I-267 | N-[3-(1H-imidazol-1-yl)propyl]-2-[3-(morpholin-4-yl)pyrrolidin-1-yl]-3-phenylquinoxaline-6-carboxamide |
| I-268 | N-[3-(1H-imidazol-1-yl)propyl]-3-phenyl-2-(1'H,3H-spiro[1-benzofuran-2,4'-piperidin]-1'-yl)quinoxaline-6-carboxamide |
| I-269 | 2,3-bis(4-fluorophenyl)-N-[2-(pyridin-3-yl)ethyl]quinoxaline-6-carboxamide |

TABLE 1-continued

| | |
|---|---|
| I-270 | 2,3-bis(4-fluorophenyl)-N-[2-(1H-imidazol-1-yl)ethyl]quinoxaline-6-carboxamide |
| I-271 | 2-(4,4'-bipiperidin-1-yl)-N-[3-(1H-imidazol-1-yl)propyl]-3-phenylquinoxaline-6-carboxamide |
| I-272 | N-[3-(1H-imidazol-1-yl)propyl]-2-[4-(2-oxoimidazolidin-1-yl)piperidin-1-yl]-3-phenylquinoxaline-6-carboxamide |
| I-273 | 3-(4-chlorophenyl)-N-[3-(1H-imidazol-2-yl)propyl]-2-phenoxyquinoxaline-6-carboxamide |
| I-274 | 2-(cyclobutylamino)-N-[3-(1H-imidazol-1-yl)propyl]-3-phenylquinoxaline-6-carboxamide |
| I-275 | 2-(1,4-dioxa-8-azaspiro[4.5]dec-8-yl)-N-[3-(1H-imidazol-1-yl)propyl]-3-phenylquinoxaline-6-carboxamide |
| I-276 | 2,3-bis(4-fluorophenyl)-N-[2-(1-methyl-1H-imidazol-4-yl)ethyl]quinoxaline-6-carboxamide |
| I-277 | 3-(4-fluorophenyl)-N-[3-(1H-imidazol-2-yl)propyl]-2-(2-oxa-7-azaspiro[3.5]non-7-yl)quinoxaline-6-carboxamide |
| I-278 | 3-(diethylamino)-N-[3-(1H-imidazol-1-yl)propyl]-2-phenylquinoxaline-6-carboxamide |
| I-279 | 2,3-bis(4-fluorophenyl)-N-[2-(1H-imidazol-1-yl)ethyl]-N-methylquinoxaline-6-carboxamide |
| I-280 | N-[3-(1H-imidazol-1-yl)propyl]-2-[4-(2-oxo-2,3-dihydro-1H-benzimidazol-1-yl)piperidin-1-yl]-3-phenylquinoxaline-6-carboxamide |
| I-281 | 3-(2-chlorophenyl)-N-[3-(1H-imidazol-1-yl)propyl]-2-phenylquinoxaline-6-carboxamide |
| I-282 | 3-(4-fluorophenyl)-2-(4-hydroxypiperidin-1-yl)-N-(imidazo[1,2-a]pyrimidin-2-ylmethyl)quinoxaline-6-carboxamide |
| I-283 | 3-(5,6-dihydroimidazo[1,2-a]pyrazin-7(8H)-yl)-N-[3-(1H-imidazol-1-yl)propyl]-2-phenylquinoxaline-6-carboxamide |
| I-284 | [2,3-bis(4-fluorophenyl)quinoxalin-6-yl](3-isopropoxy-2-methyl-2,4,6,7-tetrahydro-5H-pyrazolo[4,3-c]pyridin-5-yl)methanone |
| I-285 | [2,3-bis(4-fluorophenyl)quinoxalin-6-yl](3-hydroxy-1,4,6,7-tetrahydro-5H-pyrazolo[4,3-c]pyridin-5-yl)methanone |
| I-286 | 3-[4-(aminomethyl)phenyl]-2-phenyl-N-[2-(pyridin-3-yl)ethyl]quinoxaline-6-carboxamide |
| I-287 | 2-(1,1-dioxidothiomorpholin-4-yl)-3-(4-fluorophenyl)-N-[3-(1H-imidazol-2-yl)propyl]quinoxaline-6-carboxamide |
| I-288 | 3-(4-fluorophenyl)-N-[3-(1H-imidazol-2-yl)propyl]-2-(7-oxa-2-azaspiro[3.5]non-2-yl)quinoxaline-6-carboxamide |
| I-289 | 2-(1,1-dioxidothiomorpholin-4-yl)-N-[3-(1H-imidazol-1-yl)propyl]-3-phenylquinoxaline-6-carboxamide |
| I-290 | N-[3-(1H-imidazol-1-yl)propyl]-2-{3-[(methylsulfonyl)amino]phenyl}-3-phenylquinoxaline-6-carboxamide |
| I-291 | 3-(3-methoxyphenyl)-2-[4-(morpholin-4-yl)piperidin-1-yl]-N-[2-(pyridin-3-yl)ethyl]quinoxaline-6-carboxamide |
| I-292 | 3-(4-fluorophenyl)-2-(4-hydroxypiperidin-1-yl)-N-[2-(1-methyl-1H-imidazol-5-yl)ethyl]quinoxaline-6-carboxamide |
| I-293 | 2,3-bis(4-fluorophenyl)-N-[2-(1H-indol-3-yl)ethyl]quinoxaline-6-carboxamide |
| I-294 | [2,3-bis(4-fluorophenyl)quinoxalin-6-yl][3-(pyrimidin-2-yl)pyrrolidin-1-yl]methanone |
| I-295 | N-[3-(1H-imidazol-1-yl)propyl]-3-(2-methyl-2,4,5,7-tetrahydro-6H-pyrazolo[3,4-c]pyridin-6-yl)-2-phenylquinoxaline-6-carboxamide |
| I-296 | 2-(5,6-dihydroimidazo[1,2-a]pyrazin-7(8H)-yl)-N-[3-(1H-imidazol-1-yl)propyl]-3-phenylquinoxaline-6-carboxamide |
| I-297 | 3-(4-fluorophenyl)-2-(morpholin-4-yl)-N-[3-(1H-pyrazol-4-yl)propyl]quinoxaline-6-carboxamide |
| I-298 | 3-(4-chlorophenyl)-2-(4-hydroxypiperidin-1-yl)-N-[3-(1H-imidazol-2-yl)propyl]quinoxaline-6-carboxamide |
| I-299 | 2,3-bis(4-fluorophenyl)-N-(imidazo[1,2-a]pyridin-6-ylmethyl)quinoxaline-6-carboxamide |
| I-300 | 2-(3,6-dihydro-2H-pyran-4-yl)-N-[3-(1H-imidazol-2-yl)propyl]-3-(2-thienyl)quinoxaline-6-carboxamide |
| I-301 | 3-(4-fluorophenyl)-N-[3-(1H-imidazol-4-yl)propyl]-2-(piperidin-1-yl)quinoxaline-6-carboxamide |
| I-302 | 2,3-bis(4-fluorophenyl)-N-[2-(imidazo[1,2-a]pyridin-3-yl)ethyl]quinoxaline-6-carboxamide |
| I-303 | [2,3-bis(4-fluorophenyl)quinoxalin-6-yl](1-methyl-1,4,5,7-tetrahydro-6H-pyrrolo[2,3-c]pyridin-6-yl)methanone |
| I-304 | [2,3-bis(4-fluorophenyl)quinoxalin-6-yl](3-methoxy-1-methyl-1,4,6,7-tetrahydro-5H-pyrazolo[4,3-c]pyridin-5-yl)methanone |
| I-305 | 3-(4-fluorophenyl)-N-[3-(1H-imidazol-2-yl)propyl]-2-(1H-indazol-1-yl)quinoxaline-6-carboxamide |
| I-306 | 3-(3,5-difluoro-4-methylphenyl)-2-(4-fluorophenyl)-N-[3-(1H-imidazol-2-yl)propyl]quinoxaline-6-carboxamide |
| I-307 | 2-ethyl-3-(4-fluorophenyl)-N-[3-(1H-imidazol-2-yl)propyl]quinoxaline-6-carboxamide |
| I-308 | 2-(4-fluorophenyl)-N-[3-(1H-imidazol-2-yl)propyl]-3-(3-sulfamoylphenyl)quinoxaline-6-carboxamide |
| I-309 | 3-(6-chloro-5-methylpyridin-3-yl)-2-(4-fluorophenyl)-N-[3-(1H-imidazol-2-yl)propyl]quinoxaline-6-carboxamide |
| I-310 | 3-(4-fluorophenyl)-2-isopropoxy-N-[3-(4H-1,2,4-triazol-3-yl)propyl]quinoxaline-6-carboxamide |
| I-311 | 3-(3-fluoro-4-methylphenyl)-2-(4-fluorophenyl)-N-[3-(1H-imidazol-2-yl)propyl]quinoxaline-6-carboxamide |
| I-312 | 3-(3-chloro-2-fluorophenyl)-2-(4-fluorophenyl)-N-[3-(1H-imidazol-2-yl)propyl]quinoxaline-6-carboxamide |

TABLE 1-continued

| | |
|---|---|
| I-313 | 3-(2-fluorophenyl)-2-(4-fluorophenyl)-N-[3-(1H-imidazol-2-yl)propyl]quinoxaline-6-carboxamide |
| I-314 | 2-(cyclohexylmethoxy)-3-(4-fluorophenyl)-N-[3-(1H-imidazol-2-yl)propyl]quinoxaline-6-carboxamide |
| I-315 | 2,3-bis(4-chlorophenyl)-N-[3-(1H-imidazol-2-yl)propyl]quinoxaline-6-carboxamide |
| I-316 | 2-[(3,3-difluorocyclobutyl)methoxy]-3-(4-fluorophenyl)-N-[3-(1H-imidazol-2-yl)propyl]quinoxaline-6-carboxamide |
| I-317 | 3-(5-fluoro-2-methoxypyridin-4-yl)-N-(imidazo[1,2-a]pyridin-6-ylmethyl)-2-isopropoxyquinoxaline-6-carboxamide |
| I-318 | 3-(4-chlorophenyl)-N-[3-(1H-imidazol-2-yl)propyl]-2-(oxetan-3-yloxy)quinoxaline-6-carboxamide |
| I-319 | 3-(2,5-difluorophenyl)-2-(4-fluorophenyl)-N-[3-(1H-imidazol-2-yl)propyl]quinoxaline-6-carboxamide |
| I-320 | 3-(2,3-dihydro-1,4-benzodioxin-6-yl)-2-(4-fluorophenyl)-N-[3-(1H-imidazol-2-yl)propyl]quinoxaline-6-carboxamide |
| I-321 | 3-(4-fluorophenyl)-N-[3-(1H-imidazol-2-yl)propyl]-2-[2-(1-methyl-1H-pyrazol-4-yl)ethoxy]quinoxaline-6-carboxamide |
| I-322 | 3-(4-fluorophenyl)-2-(2-hydroxyethoxy)-N-[3-(1H-imidazol-2-yl)propyl]quinoxaline-6-carboxamide |
| I-323 | 3-(4-fluorophenyl)-N-[3-(1H-imidazol-2-yl)propyl]-2-(tetrahydro-2H-pyran-2-ylmethoxy)quinoxaline-6-carboxamide |
| I-324 | 3-(4-fluorophenyl)-2-(1H-imidazol-1-yl)-N-[3-(1H-imidazol-2-yl)propyl]quinoxaline-6-carboxamide |
| I-325 | 2-(4-fluorophenyl)-N-[3-(1H-imidazol-2-yl)propyl]-3-(1,3-thiazol-5-yl)quinoxaline-6-carboxamide |
| I-326 | 3-(4-fluorophenyl)-N-[3-(1H-imidazol-2-yl)propyl]-2-(3-thienylmethoxy)quinoxaline-6-carboxamide |
| I-327 | 3-(4-fluorophenyl)-N-[3-(1H-imidazol-2-yl)propyl]-2-[(1-methylpiperidin-4-yl)methoxy]quinoxaline-6-carboxamide |
| I-328 | 2-(4-fluorophenyl)-N-[3-(1H-imidazol-2-yl)propyl]-3-[3-(trifluoromethyl)phenyl]quinoxaline-6-carboxamide |
| I-329 | 2-(cyclobutylmethoxy)-3-(4-fluorophenyl)-N-[3-(1H-imidazol-2-yl)propyl]quinoxaline-6-carboxamide |
| I-330 | 3-(4-fluorophenyl)-N-[3-(1H-imidazol-2-yl)propyl]-2-(2H-1,2,3-triazol-2-yl)quinoxaline-6-carboxamide |
| I-331 | 3-(4-fluorophenyl)-N-[3-(1H-imidazol-2-yl)propyl]-2-{[3-(methylamino)cyclobutyl]oxy}quinoxaline-6-carboxamide |
| I-332 | 3-(4-fluorophenyl)-N-[3-(1H-imidazol-2-yl)propyl]-2-[(1-methyl-1H-pyrazol-4-yl)methoxy]quinoxaline-6-carboxamide |
| I-333 | 3-(5-fluoro-2-methoxypyridin-4-yl)-2-(4-fluorophenyl)-N-(imidazo[1,2-a]pyridin-6-ylmethyl)quinoxaline-6-carboxamide |
| I-334 | 3-(5-chloro-2-thienyl)-N-[3-(1H-imidazol-2-yl)propyl]-2-isopropoxyquinoxaline-6-carboxamide |
| I-335 | 3-(3,5-dimethylphenyl)-2-(4-fluorophenyl)-N-[3-(1H-imidazol-2-yl)propyl]quinoxaline-6-carboxamide |
| I-336 | 3-(5-fluoro-2-methylphenyl)-2-(4-fluorophenyl)-N-[3-(1H-imidazol-2-yl)propyl]quinoxaline-6-carboxamide |
| I-337 | 2-(4-fluorophenyl)-N-[3-(1H-imidazol-2-yl)propyl]-3-(2,4,5-trifluorophenyl)quinoxaline-6-carboxamide |
| I-338 | 3-(4-fluorophenyl)-N-[3-(1H-imidazol-2-yl)propyl]-2-[(trans-3-methoxycyclobutyl)oxy]quinoxaline-6-carboxamide |
| I-339 | 3-(3,4-difluorophenyl)-N-[3-(1H-imidazol-2-yl)propyl]-2-isopropoxyquinoxaline-6-carboxamide |
| I-340 | 2-(4-fluorophenyl)-N-[3-(1H-imidazol-2-yl)propyl]-3-(2-thienyl)quinoxaline-6-carboxamide |
| I-341 | 2-(tert-butoxymethyl)-3-(4-fluorophenyl)-N-[3-(1H-imidazol-2-yl)propyl]quinoxaline-6-carboxamide |
| I-342 | 2-(4-fluorophenyl)-N-[3-(1H-imidazol-2-yl)propyl]-3-(3-methyl-2-thienyl)quinoxaline-6-carboxamide |
| I-343 | 3-(5-ethoxy-2-fluorophenyl)-2-(4-fluorophenyl)-N-[3-(1H-imidazol-2-yl)propyl]quinoxaline-6-carboxamide |
| I-344 | 3-(4-fluoro-3-methoxyphenyl)-N-[3-(1H-imidazol-2-yl)propyl]-2-isopropoxyquinoxaline-6-carboxamide |
| I-345 | 3-(4-fluorophenyl)-N-[3-(1H-imidazol-2-yl)propyl]-2-[(1-methylpiperidin-4-yl)oxy]quinoxaline-6-carboxamide |
| I-346 | 3-(4-fluorophenyl)-N-[3-(1H-imidazol-2-yl)propyl]-2-[(1-methylpiperidin-2-yl)methoxy]quinoxaline-6-carboxamide |
| I-347 | 3-(4-fluorophenyl)-N-[3-(1H-imidazol-2-yl)propyl]-2-(1H-pyrazol-4-ylmethoxy)quinoxaline-6-carboxamide |
| I-348 | 3-(4-fluorophenyl)-N-[3-(1H-imidazol-2-yl)propyl]-2-(oxetan-3-ylmethoxy)quinoxaline-6-carboxamide |
| I-349 | 3-(4-fluorophenyl)-N-[3-(1H-imidazol-2-yl)propyl]-2-(1-phenylethoxy)quinoxaline-6-carboxamide |
| I-350 | 2-(4-fluorophenyl)-N-[3-(1H-imidazol-2-yl)propyl]-3-[3-(trifluoromethoxy)phenyl]quinoxaline-6-carboxamide |
| I-351 | 3-(4-fluorophenyl)-2-(3-furylmethoxy)-N-[3-(1H-imidazol-2-yl)propyl]quinoxaline-6-carboxamide |
| I-352 | 3-(4-chlorophenyl)-N-[3-(1H-imidazol-2-yl)propyl]-2-[(3R)-tetrahydrofuran-3-yloxy]quinoxaline-6-carboxamide |
| I-353 | 3-(2,5-dichlorophenyl)-2-(4-fluorophenyl)-N-[3-(1H-imidazol-2-yl)propyl]quinoxaline-6-carboxamide |
| I-354 | 3-(2-chloro-5-methoxyphenyl)-2-(4-fluorophenyl)-N-[3-(1H-imidazol-2-yl)propyl]quinoxaline-6-carboxamide |
| I-355 | 3-(3-ethoxy-4-fluorophenyl)-2-(4-fluorophenyl)-N-[3-(1H-imidazol-2-yl)propyl]quinoxaline-6-carboxamide |

TABLE 1-continued

| | |
|---|---|
| I-356 | 3-(4-fluorophenyl)-2-(1H-imidazol-4-ylmethoxy)-N-[3-(1H-imidazol-2-yl)propyl]quinoxaline-6-carboxamide |
| I-357 | 2-cyclopropyl-3-(4-fluorophenyl)-N-[3-(1H-imidazol-2-yl)propyl]quinoxaline-6-carboxamide |
| I-358 | 3-(4-fluorophenyl)-2-propoxy-N-[3-(4H-1,2,4-triazol-3-yl)propyl]quinoxaline-6-carboxamide |
| I-359 | N-[3-(6-aminopyridin-3-yl)propyl]-3-(4-fluorophenyl)-2-isopropoxyquinoxaline-6-carboxamide |
| I-360 | 3-(4-chlorophenyl)-N-[3-(1H-imidazol-2-yl)propyl]-2-[(3S)-tetrahydrofuran-3-yloxy]quinoxaline-6-carboxamide |
| I-361 | 3-(4-chlorophenyl)-2-(4-fluorophenyl)-N-[3-(1H-imidazol-2-yl)propyl]quinoxaline-6-carboxamide |
| I-362 | N-[3-(6-aminopyridin-3-yl)propyl]-3-(4-fluorophenyl)-2-(morpholin-4-yl)quinoxaline-6-carboxamide |
| I-363 | 3-(5-cyano-2-thienyl)-2-(4-fluorophenyl)-N-[3-(1H-imidazol-2-yl)propyl]quinoxaline-6-carboxamide |
| I-364 | 2-[(4-chlorobenzyl)oxy]-3-(4-fluorophenyl)-N-[3-(1H-imidazol-2-yl)propyl]quinoxaline-6-carboxamide |
| I-365 | 3-(2-chloro-5-methylphenyl)-2-(4-fluorophenyl)-N-[3-(1H-imidazol-2-yl)propyl]quinoxaline-6-carboxamide |
| I-366 | 3-(4-fluorophenyl)-N-[3-(1H-imidazol-2-yl)propyl]-2-(tetrahydro-2H-pyran-4-yl)quinoxaline-6-carboxamide |
| I-367 | 3-(3,4-difluorophenyl)-N-(imidazo[1,2-a]pyridin-6-ylmethyl)-2-isopropoxyquinoxaline-6-carboxamide |
| I-368 | 2-(4-fluorophenyl)-3-(5-fluoro-2-thienyl)-N-[3-(1H-imidazol-2-yl)propyl]quinoxaline-6-carboxamide |
| I-369 | 3-[4-chloro-3-(trifluoromethyl)phenyl]-2-(4-fluorophenyl)-N-[3-(1H-imidazol-2-yl)propyl]quinoxaline-6-carboxamide |
| I-370 | 3-(5-acetyl-2-thienyl)-2-(4-fluorophenyl)-N-[3-(1H-imidazol-2-yl)propyl]quinoxaline-6-carboxamide |
| I-371 | 3-(4-fluorophenyl)-N-[3-(1H-imidazol-2-yl)propyl]-2-propoxyquinoxaline-6-carboxamide |
| I-372 | 3-(4-fluorophenyl)-N-[3-(1H-imidazol-2-yl)propyl]-2-[(3R)-tetrahydrofuran-3-yloxy]quinoxaline-6-carboxamide |
| I-373 | 3-(2,4-difluorophenyl)-2-(4-fluorophenyl)-N-[3-(1H-imidazol-2-yl)propyl]quinoxaline-6-carboxamide |
| I-374 | 3-(4-fluorophenyl)-N-[3-(1H-imidazol-2-yl)propyl]-2-(1H-1,2,3-triazol-1-yl)quinoxaline-6-carboxamide |
| I-375 | 3-(4-fluorophenyl)-N-[3-(1H-imidazol-2-yl)propyl]-2-(isopropylsulfanyl)quinoxaline-6-carboxamide |
| I-376 | 3-(3-chlorophenyl)-2-(4-fluorophenyl)-N-[2-(1H-imidazol-2-yl)ethyl]quinoxaline-6-carboxamide |
| I-377 | 3-(4-chloro-3-cyanophenyl)-2-(4-fluorophenyl)-N-[3-(1H-imidazol-2-yl)propyl]quinoxaline-6-carboxamide |
| I-378 | 3-(4-fluorophenyl)-N-[3-(1H-imidazol-2-yl)propyl]-2-(2-oxaspiro[3.3]hept-6-ylmethoxy)quinoxaline-6-carboxamide |
| I-379 | 3-(4-fluorophenyl)-N-[3-(1H-imidazol-2-yl)propyl]-2-(tetrahydrofuran-3-ylmethoxy)quinoxaline-6-carboxamide |
| I-380 | 3-(4-fluorophenyl)-2-isopropoxy-N-[3-(1H-pyrazol-4-yl)propyl]quinoxaline-6-carboxamide |
| I-381 | 3-[2-chloro-5-(trifluoromethyl)phenyl]-2-(4-fluorophenyl)-N-[3-(1H-imidazol-2-yl)propyl]quinoxaline-6-carboxamide |
| I-382 | 3-(4-ethylphenyl)-2-(4-fluorophenyl)-N-[3-(1H-imidazol-2-yl)propyl]quinoxaline-6-carboxamide |
| I-383 | 2-[cis-2,6-dimethylmorpholin-4-yl]-3-(4-fluorophenyl)-N-[3-(1H-imidazol-2-yl)propyl]quinoxaline-6-carboxamide |
| I-384 | 2-(4-fluorophenyl)-N-[3-(1H-imidazol-2-yl)propyl]-3-[3-(methylsulfonyl)phenyl]quinoxaline-6-carboxamide |
| I-385 | N-[3-(1H-imidazol-2-yl)propyl]-2-isopropoxy-3-(2-thienyl)quinoxaline-6-carboxamide |
| I-386 | 2-(4-fluorophenyl)-N-[3-(1H-imidazol-2-yl)propyl]-3-(1-methyl-1H-indol-5-yl)quinoxaline-6-carboxamide |
| I-387 | 2,3-bis(4-fluorophenyl)-N-[3-(4H-1,2,4-triazol-3-yl)propyl]quinoxaline-6-carboxamide |
| I-388 | 3-(3-cyano-4-fluorophenyl)-2-(4-fluorophenyl)-N-[3-(1H-imidazol-2-yl)propyl]quinoxaline-6-carboxamide |
| I-389 | 3-(4-fluorophenyl)-N-[3-(1H-imidazol-2-yl)propyl]-2-(1H-pyrrolo[3,2-c]pyridin-1-yl)quinoxaline-6-carboxamide |
| I-390 | 3-(4-fluorophenyl)-N-[3-(1H-imidazol-2-yl)propyl]-2-[2-(isoxazol-4-yl)ethoxy]quinoxaline-6-carboxamide |
| I-391 | 3-(3-fluoro-2-methoxypyridin-4-yl)-2-(4-fluorophenyl)-N-[3-(1H-imidazol-2-yl)propyl]quinoxaline-6-carboxamide |
| I-392 | 3-(5-fluoro-2-methoxypyridin-4-yl)-N-[3-(1H-imidazol-2-yl)propyl]-2-isopropoxyquinoxaline-6-carboxamide |
| I-393 | 3-(2-chloro-5-cyanophenyl)-2-(4-fluorophenyl)-N-[3-(1H-imidazol-2-yl)propyl]quinoxaline-6-carboxamide |
| I-394 | 2-(4-fluorophenyl)-N-[3-(1H-imidazol-2-yl)propyl]-3-(5-methylpyridin-3-yl)quinoxaline-6-carboxamide |
| I-395 | 2-(4-fluorophenyl)-N-[3-(1H-imidazol-2-yl)propyl]-3-(3-methylphenyl)quinoxaline-6-carboxamide |
| I-396 | 3-(4-fluorophenyl)-N-[3-(1H-imidazol-2-yl)propyl]-2-(pyridin-2-ylmethoxy)quinoxaline-6-carboxamide |
| I-397 | 3-(3,4-dichlorophenyl)-2-(4-fluorophenyl)-N-[3-(1H-imidazol-2-yl)propyl]quinoxaline-6-carboxamide |
| I-398 | 3-(2-fluoro-3-methoxyphenyl)-2-(4-fluorophenyl)-N-[3-(1H-imidazol-2-yl)propyl]quinoxaline-6-carboxamide |

TABLE 1-continued

| | |
|---|---|
| I-399 | 3-(2-chloro-5-fluorophenyl)-2-(4-fluorophenyl)-N-[3-(1H-imidazol-2-yl)propyl]quinoxaline-6-carboxamide |
| I-400 | 2-(cyclopentyloxy)-3-(4-fluorophenyl)-N-[3-(1H-imidazol-2-yl)propyl]quinoxaline-6-carboxamide |
| I-401 | 3-(4-fluorophenyl)-N-[3-(1H-imidazol-2-yl)propyl]-2-[2-(methylsulfonyl)ethoxy]quinoxaline-6-carboxamide |
| I-402 | 3-(4-chlorophenyl)-2-ethoxy-N-[3-(1H-imidazol-2-yl)propyl]quinoxaline-6-carboxamide |
| I-403 | 3-(5-chloro-2-thienyl)-N-(imidazo[1,2-a]pyridin-6-ylmethyl)-2-isopropoxyquinoxaline-6-carboxamide |
| I-404 | 2-(1-azaspiro[3.3]hept-6-yloxy)-3-(4-fluorophenyl)-N-[3-(1H-imidazol-2-yl)propyl]quinoxaline-6-carboxamide |
| I-405 | 3-(4-fluorophenyl)-N-[3-(1H-imidazol-2-yl)propyl]-2-(morpholin-4-ylmethyl)quinoxaline-6-carboxamide |
| I-406 | 3-(4-fluorophenyl)-N-[3-(1H-imidazol-2-yl)propyl]-2-(tetrahydro-2H-pyran-4-ylmethoxy)quinoxaline-6-carboxamide |
| I-407 | 2-[(1-cyanocyclobutyl)methoxy]-3-(4-fluorophenyl)-N-[3-(1H-imidazol-2-yl)propyl]quinoxaline-6-carboxamide |
| I-408 | 2,3-bis(4-fluorophenyl)-N-(imidazo[1,2-a]pyrimidin-2-ylmethyl)quinoxaline-6-carboxamide |
| I-409 | 3-(4-fluorophenyl)-N-[3-(1H-imidazol-2-yl)propyl]-2-(pyridin-3-ylmethoxy)quinoxaline-6-carboxamide |
| I-410 | 3-(5-chloro-2-fluoropyridin-3-yl)-2-(4-fluorophenyl)-N-[3-(1H-imidazol-2-yl)propyl]quinoxaline-6-carboxamide |
| I-411 | 2-[(1,3-dimethoxypropan-2-yl)oxy]-3-(4-fluorophenyl)-N-[3-(1H-imidazol-2-yl)propyl]quinoxaline-6-carboxamide |
| I-412 | 3-(1-benzothiophen-2-yl)-2-(4-fluorophenyl)-N-[3-(1H-imidazol-2-yl)propyl]quinoxaline-6-carboxamide |
| I-413 | 3-(4-fluorophenyl)-N-[3-(1H-imidazol-2-yl)propyl]-2-(2-methyl-1H-imidazol-1-yl)quinoxaline-6-carboxamide |
| I-414 | 3-(5-cyano-2-fluorophenyl)-N-[3-(1H-imidazol-2-yl)propyl]-2-isopropoxyquinoxaline-6-carboxamide |
| I-415 | 3-(2-fluoro-4-methoxyphenyl)-2-(4-fluorophenyl)-N-[3-(1H-imidazol-2-yl)propyl]quinoxaline-6-carboxamide |
| I-416 | 3-(4-ethynylphenyl)-2-(4-fluorophenyl)-N-[3-(1H-imidazol-2-yl)propyl]quinoxaline-6-carboxamide |
| I-417 | 2-(4-fluorophenyl)-N-[3-(1H-imidazol-2-yl)propyl]-3-(imidazo[1,2-a]pyridin-6-yl)quinoxaline-6-carboxamide |
| I-418 | 3-(4-fluorophenyl)-N-[3-1H-imidazol-2-yl)propyl]-2-(1H-1,2,4-triazol-1-yl)quinoxaline-6-carboxamide |
| I-419 | N-[3-(6-aminopyridin-3-yl)propyl]-2,3-bis(4-fluorophenyl)quinoxaline-6-carboxamide |
| I-420 | 3-(4-fluorophenyl)-N-[3-(1H-imidazol-2-yl)propyl]-2-(2-phenylethoxy)quinoxaline-6-carboxamide |
| I-421 | N-[3-(1H-imidazol-2-yl)propyl]-2-isopropoxy-3-{3-[(trifluoromethyl)sulfanyl]phenyl}quinoxaline-6-carboxamide |
| I-422 | 3-(2,5-dimethyl-3-thienyl)-2-(4-fluorophenyl)-N-[3-(1H-imidazol-2-yl)propyl]quinoxaline-6-carboxamide |
| I-423 | 3-(4-fluorophenyl)-N-[3-(1H-imidazol-2-yl)propyl]-2-[(1-methylpiperidin-3-yl)oxy]quinoxaline-6-carboxamide |
| I-424 | 3-(4-fluorophenyl)-2-isopropoxy-N-[2-(1-methyl-1H-imidazol-5-yl)ethyl]quinoxaline-6-carboxamide |
| I-425 | 3-(3-ethynylphenyl)-2-(4-fluorophenyl)-N-[3-(1H-imidazol-2-yl)propyl]quinoxaline-6-carboxamide |
| I-426 | 3-(4-fluoro-3-methoxyphenyl)-N-(imidazo[1,2-a]pyridin-6-ylmethyl)-2-isopropoxyquinoxaline-6-carboxamide |
| I-427 | 3-(4-fluorophenyl)-N-[3-(1H-imidazol-2-yl)propyl]-2-[(3-methoxycyclobutyl)oxy]quinoxaline-6-carboxamide |
| I-428 | 2-(3,5-dimethyl-1H-pyrazol-1-yl)-3-(4-fluorophenyl)-N-[3-(1H-imidazol-2-yl)propyl]quinoxaline-6-carboxamide |
| I-429 | 2-(4-fluorophenyl)-N-[3-(1H-imidazol-2-yl)propyl]-3-(1H-pyrazol-4-yl)quinoxaline-6-carboxamide |
| I-430 | 3-(4-fluorophenyl)-N-[3-(1H-imidazol-2-yl)propyl]-2-(piperidin-3-yloxy)quinoxaline-6-carboxamide |
| I-431 | 3-(4-chloro-3-fluorophenyl)-2-(4-fluorophenyl)-N-[3-(1H-imidazol-2-yl)propyl]quinoxaline-6-carboxamide |
| I-432 | 3-[2-chloro-5-(trifluoromethoxy)phenyl]-2-(4-fluorophenyl)-N-[3-(1H-imidazol-2-yl)propyl]quinoxaline-6-carboxamide |
| I-433 | 3-(3,4-dimethylphenyl)-2-(4-fluorophenyl)-N-[3-(1H-imidazol-2-yl)propyl]quinoxaline-6-carboxamide |
| I-434 | 3-(4-fluorophenyl)-N-[3-(1H-imidazol-2-yl)propyl]-2-(1H-pyrazol-1-yl)quinoxaline-6-carboxamide |
| I-435 | 3-(3-chloro-4-fluorophenyl)-N-[3-(1H-imidazol-2-yl)propyl]-2-isopropoxyquinoxaline-6-carboxamide |
| I-436 | N-[3-(6-aminopyridin-3-yl)propyl]-3-(4-fluorophenyl)-2-(piperidin-1-yl)quinoxaline-6-carboxamide |
| I-437 | 3-(2-chloro-5-ethoxyphenyl)-2-(4-fluorophenyl)-N-[3-(1H-imidazol-2-yl)propyl]quinoxaline-6-carboxamide |
| I-438 | 3-(4-fluorophenyl)-N-[3-(1H-imidazol-2-yl)propyl]-2-(tetrahydrofuran-2-ylmethoxy)quinoxaline-6-carboxamide |
| I-439 | 2-(benzyloxy)-3-(4-fluorophenyl)-N-[3-(1H-imidazol-2-yl)propyl]quinoxaline-6-carboxamide |
| I-440 | 2-ethoxy-3-(4-fluorophenyl)-N-[3-(1H-imidazol-2-yl)propyl]quinoxaline-6-carboxamide |
| I-441 | 3-(4-fluorophenyl)-2-(piperidin-1-yl)-N-[3-(pyrazin-2-yl)propyl]quinoxaline-6-carboxamide |

TABLE 1-continued

| | |
|---|---|
| I-442 | 3-(4-fluorophenyl)-N-[3-(1H-imidazol-2-yl)propyl]-2-[2-(1H-pyrazol-4-yl)ethoxy]quinoxaline-6-carboxamide |
| I-443 | 3-(5-chloro-2-thienyl)-2-(4-fluorophenyl)-N-[2-(1H-imidazol-2-yl)ethyl]quinoxaline-6-carboxamide |
| I-444 | 3-(4-fluorophenyl)-N-[3-(1H-imidazol-2-yl)propyl]-2-isopropylquinoxaline-6-carboxamide |
| I-445 | 2-(4-fluorophenyl)-N-[3-(1H-imidazol-2-yl)propyl]-3-[2-methyl-5-(trifluoromethyl)phenyl]quinoxaline-6-carboxamide |
| I-446 | 2-[(3,5-dimethylisoxazol-4-yl)methoxy]-3-(4-fluorophenyl)-N-[3-(1H-imidazol-2-yl)propyl]quinoxaline-6-carboxamide |
| I-447 | 3-(3-ethoxyphenyl)-2-(4-fluorophenyl)-N-[3-(1H-imidazol-2-yl)propyl]quinoxaline-6-carboxamide |
| I-448 | 2-(4-fluorophenyl)-N-[3-(1H-imidazol-2-yl)propyl]-3-(4-methoxyphenyl)quinoxaline-6-carboxamide |
| I-449 | 2-(4-fluorophenyl)-N-[3-(1H-imidazol-2-yl)propyl]-3-(3,4,5-trifluorophenyl)quinoxaline-6-carboxamide |
| I-450 | 3-(2,5-dimethylphenyl)-2-(4-fluorophenyl)-N-[3-(1H-imidazol-2-yl)propyl]quinoxaline-6-carboxamide |
| I-451 | 2-(4-fluorophenyl)-3-[2-fluoro-5-(trifluoromethyl)phenyl]-N-[3-(1H-imidazol-2-yl)propyl]quinoxaline-6-carboxamide |
| I-452 | 3-(4-fluorophenyl)-N-(imidazo[1,2-a]pyridin-6-ylmethyl)-2-isopropoxyquinoxaline-6-carboxamide |
| I-453 | 2-(1H-benzimidazol-1-yl)-3-(4-fluorophenyl)-N-[3-(1H-imidazol-2-yl)propyl]quinoxaline-6-carboxamide |
| I-454 | 2-[(2-chlorobenzyl)oxy]-3-(4-fluorophenyl)-N-[3-(1H-imidazol-2-yl)propyl]quinoxaline-6-carboxamide |
| I-455 | 3-(4-chloro-2-fluorophenyl)-2-(4-fluorophenyl)-N-[3-(1H-imidazol-2-yl)propyl]quinoxaline-6-carboxamide |
| I-456 | 2-{[4-(dimethylamino)cyclohexyl]oxy}-3-(4-fluorophenyl)-N-[3-(1H-imidazol-2-yl)propyl]quinoxaline-6-carboxamide |
| I-457 | 3-(4-fluorophenyl)-N-[3-(1H-imidazol-2-yl)propyl]-2-(3-methoxypyrrolidin-1-yl)quinoxaline-6-carboxamide |
| I-458 | 3-(3-cyanophenyl)-2-(4-fluorophenyl)-N-[3-(1H-imidazol-2-yl)propyl]quinoxaline-6-carboxamide |
| I-459 | 3-(4-fluorophenyl)-2-(1H-imidazol-2-ylmethoxy)-N-[3-(1H-imidazol-2-yl)propyl]quinoxaline-6-carboxamide |
| I-460 | 3-(4-fluorophenyl)-N-[3-(1H-imidazol-2-yl)propyl]-2-[(1-methyl-1H-pyrazol-3-yl)methoxy]quinoxaline-6-carboxamide |
| I-461 | 3-(1,3-benzodioxol-5-yl)-2-(4-fluorophenyl)-N-[3-(1H-imidazol-2-yl)propyl]quinoxaline-6-carboxamide |
| I-462 | 3-(4-fluorophenyl)-N-[3-(1H-imidazol-2-yl)propyl]-2-(prop-2-yn-1-yloxy)quinoxaline-6-carboxamide |
| I-463 | 3-(3-chlorophenyl)-2-(4-fluorophenyl)-N-[3-(1H-imidazol-2-yl)propyl]quinoxaline-6-carboxamide |
| I-464 | 2,3-bis(4-fluorophenyl)-N-(1H-imidazo[4,5-c]pyridin-2-ylmethyl)quinoxaline-6-carboxamide |
| I-465 | 3-(4-fluorophenyl)-N-[3-(1H-imidazol-2-yl)propyl]-2-(pyrrolidin-1-yl)quinoxaline-6-carboxamide |
| I-466 | 3-(5-fluoro-2-methoxypyridin-4-yl)-2-(4-fluorophenyl)-N-[3-(1H-imidazol-2-yl)propyl]quinoxaline-6-carboxamide |
| I-467 | 2-(4-fluorophenyl)-N-[3-(1H-imidazol-2-yl)propyl]-3-(5-methoxy-2-methylphenyl)quinoxaline-6-carboxamide |
| I-468 | 3-(4-fluorophenyl)-N-[3-(1H-imidazol-2-yl)propyl]-2-[(3S)-tetrahydrofuran-3-yloxy]quinoxaline-6-carboxamide |
| I-469 | 3-(4-fluorophenyl)-N-[3-(1H-imidazol-2-yl)propyl]-2-(1,3-thiazol-2-ylmethoxy)quinoxaline-6-carboxamide |
| I-470 | 3-(3-fluoro-4-methoxyphenyl)-2-(4-fluorophenyl)-N-[3-(1H-imidazol-2-yl)propyl]quinoxaline-6-carboxamide |
| I-471 | 3-(4-fluoro-3-methylphenyl)-2-(4-fluorophenyl)-N-[3-(1H-imidazol-2-yl)propyl]quinoxaline-6-carboxamide |
| I-472 | 3-(5-cyano-2-methylphenyl)-2-(4-fluorophenyl)-N-[3-(1H-imidazol-2-yl)propyl]quinoxaline-6-carboxamide |
| I-473 | 2-(4-fluorophenyl)-N-[3-(1H-imidazol-2-yl)propyl]-3-(5-methyl-2-thienyl)quinoxaline-6-carboxamide |
| I-474 | 3-(3,4-difluorophenyl)-2-(4-fluorophenyl)-N-[3-(1H-imidazol-2-yl)propyl]quinoxaline-6-carboxamide |
| I-475 | 3-(1,3-dimethyl-1H-pyrazol-4-yl)-2-(4-fluorophenyl)-N-[3-(1H-imidazol-2-yl)propyl]quinoxaline-6-carboxamide |
| I-476 | 2-(4-chlorobenzyl)-3-(4-fluorophenyl)-N-[3-(1H-imidazol-2-yl)propyl]quinoxaline-6-carboxamide |
| I-477 | N-[3-(1H-imidazol-2-yl)propyl]-2-phenyl-3-(2-thienyl)quinoxaline-6-carboxamide |
| I-478 | 3-(4-fluorophenyl)-N-[3-(1H-imidazol-2-yl)propyl]-2-isobutoxyquinoxaline-6-carboxamide |
| I-479 | 3-(4-aminophenyl)-2-(4-fluorophenyl)-N-[3-(1H-imidazol-2-yl)propyl]quinoxaline-6-carboxamide |
| I-480 | 3-(5-chloro-2-fluorophenyl)-2-(4-fluorophenyl)-N-[3-(1H-imidazol-2-yl)propyl]quinoxaline-6-carboxainide |
| I-481 | 3-(2-fluoro-5-methoxyphenyl)-2-(4-fluorophenyl)-N-[3-(1H-imidazol-2-yl)propyl]quinoxaline-6-carboxamide |
| I-482 | 3-(4-fluorophenyl)-N-[3-(1H-imidazol-4-yl)propyl]-2-isopropoxyquinoxaline-6-carboxamide |
| I-483 | 2-(5-chloro-2-thienyl)-3-(4-fluorophenyl)-N-[3-(1H-imidazol-2-yl)propyl]quinoxaline-6-carboxamide |
| I-484 | 2-(4-fluorophenyl)-N-[3-(1H-imidazol-2-yl)propyl]-3-(3-methoxyphenyl)quinoxaline-6-carboxamide |

TABLE 1-continued

| | |
|---|---|
| I-485 | N-[3-(6-aminopyridin-3-yl)propyl]-2-[cis-2,6-dimethylmorpholin-4-yl]-3-(4-fluorophenyl)quinoxaline-6-carboxamide |
| I-486 | 2-(4-fluorophenyl)-N-[3-(1H-imidazol-2-yl)propyl]-3-(6-methylpyridin-3-yl)quinoxaline-6-carboxamide |
| I-487 | 2,3-bis(4-chlorophenyl)-N-(imidazo[1,2-a]pyridin-6-ylmethyl)quinoxaline-6-carboxamide |
| I-488 | 3-(4-fluoro-3-methoxyphenyl)-2-(4-fluorophenyl)-N-[3-(1H-imidazol-2-yl)propyl]quinoxaline-6-carboxamide |
| I-489 | 3-(4-fluorophenyl)-N-[3-(1H-imidazol-2-yl)propyl]-2-[2-(pyridin-2-yl)ethoxy]quinoxaline-6-carboxamide |
| I-490 | 2-(cyclopropylmethoxy)-3-(4-fluorophenyl)-N-[3-(1H-imidazol-2-yl)propyl]quinoxaline-6-carboxamide |
| I-491 | 7-fluoro-3-(4-fluorophenyl)-N-[3-(1H-imidazol-2-yl)propyl]-2-isopropoxyquinoxaline-6-carboxamide |
| I-492 | 3-(2-fluoro-5-methoxyphenyl)-N-[3-(1H-imidazol-2-yl)propyl]-2-isopropoxyquinoxaline-6-carboxamide |
| I-493 | 3-(5-chloro-2-methylphenyl)-2-(4-fluorophenyl)-N-[3-(1H-imidazol-2-yl)propyl]quinoxaline-6-carboxamide |
| I-494 | 2-(4-fluorophenyl)-N-[3-(1H-imidazol-2-yl)propyl]-3-(4-methyl-1,3-thiazol-5-yl)quinoxaline-6-carboxamide |
| I-495 | 2-(4-fluorophenyl)-N-[3-(1H-imidazol-2-yl)propyl]-3-(6-methoxypyridin-2-yl)quinoxaline-6-carboxamide |
| I-496 | 2-(2-cyanoethoxy)-3-(4-fluorophenyl)-N-[3-(1H-imidazol-2-yl)propyl]quinoxaline-6-carboxamide |
| I-497 | 2-(4-fluorophenyl)-N-[3-(1H-imidazol-2-yl)propyl]-3-(4-methylphenyl)quinoxaline-6-carboxamide |
| I-498 | 2-[(3-chlorobenzyl)oxy]-3-(4-fluorophenyl)-N-[3-(1H-imidazol-2-yl)propyl]quinoxaline-6-carboxamide |
| I-499 | 3-(5-chloro-2-thienyl)-2-(4-fluorophenyl)-N-[3-(1H-imidazol-2-yl)propyl]quinoxaline-6-carboxamide |
| I-500 | 2-(cyclopentylmethoxy)-3-(4-fluorophenyl)-N-[3-(1H-imidazol-2-yl)propyl]quinoxaline-6-carboxamide |
| I-501 | 3-(5-cyano-2-fluorophenyl)-2-(4-fluorophenyl)-N-[3-(1H-imidazol-2-yl)propyl]quinoxaline-6-carboxamide |
| I-502 | 3-(3-chloro-4-fluorophenyl)-2-(4-fluorophenyl)-N-[3-(1H-imidazol-2-yl)propyl]quinoxaline-6-carboxamide |
| I-503 | 3-(4-fluorophenyl)-N-[3-(1H-imidazol-2-yl)propyl]-2-(4-methyl-1H-pyrazol-1-yl)quinoxaline-6-carboxamide |
| I-504 | 3-(3-chloro-2-thienyl)-2-(4-fluorophenyl)-N-[3-(1H-imidazol-2-yl)propyl]quinoxaline-6-carboxamide |
| I-505 | 3-(4-fluorophenyl)-N-[3-(1H-imidazol-2-yl)propyl]-2-[2-(1-methylpyrrolidin-2-yl)ethoxy]quinoxaline-6-carboxamide |
| I-506 | 3-(4-fluorophenyl)-N-(imidazo[1,2-a]pyrimidin-2-ylmethyl)-2-isopropoxyquinoxaline-6-carboxamide |
| I-507 | 3-(2-fluoro-5-methylphenyl)-2-(4-fluorophenyl)-N-[3-(1H-imidazol-2-yl)propyl]quinoxaline-6-carboxamide |
| I-508 | 2,3-bis(4-fluorophenyl)-N-[3-(1H-pyrazol-4-yl)propyl]quinoxaline-6-carboxamide |
| I-509 | 2-[2-(dimethylamino)ethoxy]-3-(4-fluorophenyl)-N-[3-(1H-imidazol-2-yl)propyl]quinoxaline-6-carboxamide |
| I-510 | 3-(4-fluorophenyl)-N-[3-(1H-imidazol-2-yl)propyl]-2-[(1-methylpiperidin-3-yl)methoxy]quinoxaline-6-carboxamide |
| I-511 | N-[3-(1H-imidazol-2-yl)propyl]-2-isopropoxy-3-(3-methoxyphenyl)quinoxaline-6-carboxamide |
| I-512 | 3-(3-fluoro-5-methoxyphenyl)-2-(4-fluorophenyl)-N-[3-(1H-imidazol-2-yl)propyl]quinoxaline-6-carboxamide |
| I-513 | 3-(4-fluorophenyl)-N-[3-(1H-imidazol-2-yl)propyl]-2-[(1-methylpyrrolidin-3-yl)methoxy]quinoxaline-6-carboxamide |
| I-514 | 3-(4-fluorophenyl)-N-[3-(1H-imidazol-2-yl)propyl]-2-(piperidin-4-yloxy)quinoxaline-6-carboxamide |
| I-515 | 3-(5-fluoro-2-methoxypyridin-4-yl)-2-(4-fluorophenyl)-N-[3-(4H-1,2,4-triazol-3-yl)propyl]quinoxaline-6-carboxamide |
| I-516 | 3-(5-fluoro-2-methoxypyridin-4-yl)-2-(4-fluorophenyl)-N-(1H-imidazo[4,5-c]pyridin-2-ylmethyl)quinoxaline-6-carboxamide |
| I-517 | 3-(2-ethoxy-5-fluoropyridin-4-yl)-2-(4-fluorophenyl)-N-[3-(1H-imidazol-2-yl)propyl]quinoxaline-6-carboxamide |
| I-518 | 3-(5-fluoro-2-isopropoxypyridin-4-yl)-2-(4-fluorophenyl)-N-[3-(1H-imidazol-2-yl)propyl]quinoxaline-6-carboxamide |
| I-519 | 3-(5-fluoro-2-methoxypyridin-4-yl)-2-(4-fluorophenyl)-N-[3-(1-methyl-1H-imidazol-2-yl)propyl]quinoxaline-6-carboxamide |
| I-520 | 3-(5-chloro-2-fluorophenyl)-2-(4-fluorophenyl)-N-[3-(4H-1,2,4-triazol-3-yl)propyl]quinoxaline-6-carboxamide |

1. Preparation of Exemplary Compounds

Definitions

AA LCMS method using ammonium acetate
Ac acetate
ADDP 1,1'-(Azodicarbonyl)dipiperidine
tAmPH 2-methyl-2-butanol
Amphos bis(di-tert-butyl(4-dimethylamino)phosphine)
C Celsius
CDCl$_3$ deuterated chloroform
DABCO 1,4-diazabicyclo[5.4.0]octane
DCM dichloromethane
dba dibenzylidineacetone
DDQ 2,3-dichloro-5,6-dicyano-1,4-benzoquinone
DIPEA diisopropylethylamine
DMA dimethylacetamide
DME dimethoxyethane
DMF N,N-dimethylformamide
DMSO dimethylsulfoxide DPPA diphenylphosphoryl azide
dppf 1,1'-bis(diphenylphosphino) ferrocene
EDCI 1-(3-dimethylaminopropyl)-3-ethylcarbodiimide hydrochloride
EtOAc ethyl acetate
FA LCMS method using formic acid
h hours
HATU (1-[bis(dimethylamino)methylene]-1H-1,2,3-triazolo[4,5-b]pyridinium 3-oxide hexafluorophosphate)
HOBt 1-hydroxybenotriazole
HPLC high pressure liquid chromatography
$IC_{50}$ inhibitory concentration 50%
LCMS liquid chromatography mass spectrometry
MeCN acetonitrile
m/z mass to charge
min minutes
NBS N-bromosuccinimide
NMP N-methyl-2-pyrrolidone
PE petroleum ether
pic picoline
Ph phenyl
PHPB pyridinium hydrobromideperbromide
PMB para-methoxybenzyl
psi pounds per square inch
rt room temperature
TEA triethylamine
TFA trifluoroacetic acid
THF tetrahydrofuran
Xantphos 4,5-bis(diphenylphosphino)-9,9-dimethylxanthene
Analytical Methods
NMR Conditions:

$^1$H NMR spectra were collected by the following methods: A) On a Bruker AVANCE II (300 MHz) or AVANCE 111-400 (400 MHz) spectrometer B) On a 400 MHz Bruker Avance III spectrometer equipped with a 5 mm BBFO probe or 400 MHz Bruker Avance II spectrometer equipped with a 5 mm QNP probe for the measurement. Chemical shifts for $^1$H NMR were reported in parts per million (ppm) downfield from tetramethylsilane (δ) as the internal standard in deuterated solvent and coupling constants (J) are in Hertz (Hz). The following abbreviations are used for spin multiplicity: s=singlet, d=doublet, t=triplet, q=quartet, m=multiplet and br=broad.

LCMS Conditions:

LCMS spectra were recorded by one of the following methods. A) On a Hewlett-Packard HP1100 or Agilent 1100 Series LC system connected to a Micromass mass spectrometer using reverse phase C18 columns. Various gradients and run times were selected in order to best characterize the compounds. Mobile phases were based on ACN/water gradients and contained either 0.1% formic acid (methods indicated FA) or 10 mM ammonium acetate (methods indicated AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run. B) By flow injection mass spectrometry analysis performed on a Shimadzu 20A system without column, eluting with 5 mmol/L $AcONH_4$ in water/acetonitrile=34/66, using the isocratic mode over 1 minute at a flow rate of 0.1 mL/min. MS spectra were recorded using an ABSciex API3200 with electrospray ionization. This method was used for final compounds. C) By liquid chromatography-mass spectrometry (LC/MS) analysis was performed on a an Agilent 1200, equipped with a L-column2 ODS (3.0×50 mm I.D., 3 μm-particle size, CERI, Japan), eluting with 5 mM $AcONH_4$ in ultrapure water/acetonitrile=90/10 (Mobile phase A), and 5 mM $AcONH_4$ in ultrapure water/acetonitrile=10/90 (Mobile phase B), using the following elution gradient of 5% B to 90% B over 0.9 min followed by 90% B isocratic over 1.1 min at a flow rate of 1.5 mL/min (detection at 220 nm or 254 nm). MS spectra were recorded using an Agilent 6130 with electrospray ionization. This method was used for intermediates. D) By liquid chromatography-mass spectrometry (LC/MS) analysis was performed on a Shimadzu LC-20AD, equipped with a L-column2 ODS (3.0×50 mm I.D., 3 μm-particle size, CERT, Japan), eluting with 0.05% TFA in ultrapure water (Mobile phase A), and 0.05% TFA in acetonitrile (Mobile phase B), using the following elution gradient of 5% B to 90% B over 0.9 min followed by 90% B isocratic over 1.1 min at a flow rate of 1.5 mL/min (detection at 220 nm). MS spectra were recorded using a Shimadzu LCMS-2020 with electrospray ionization. This method was used for intermediates. E) LCMS spectra were recorded on an Agilent 1290 Infinity UPLC system connected to an Agilent 6130 mass spectrometer, a Waters Acquity UPLC system connected to a Waters Acquity SQ mass spectrometer, or an Agilent 1100 Series HPLC system connected to a Waters Micromass ZQ mass spectrometer using reverse phase C18 columns.

One of ordinary skill in the art will recognize that modifications of the gradient, column length, and flow rate are possible and that some conditions may be suitable for compound characterization than others, depending on the chemical species being analyzed.

Preparative HPLC:

Preparative HPLC are conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

One of ordinary skill in the art will recognize that modifications of the gradient, column length, and flow rate are possible and that some conditions may be suitable for compound characterization than others, depending on the chemical species being analyzed.

Example 1: N-[3-(1H-Imidazol-1-yl)propyl]-3-(3-methoxyphenyl)-2-(morpholin-4-yl)quinoxaline-6-carboxamide (I-55)

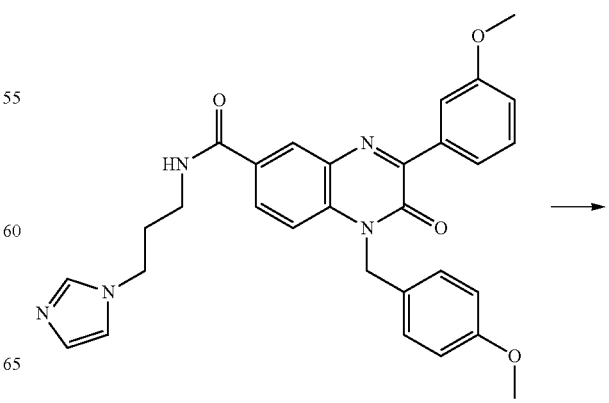

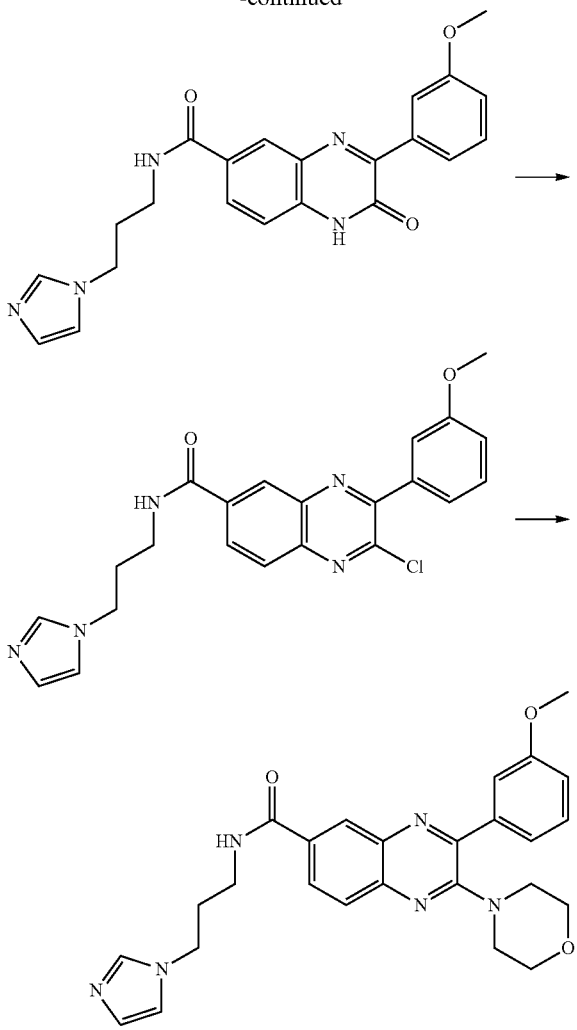

hydroquinoxaline-6-carboxamide (300 mg, 0.74 mmol) in SOCl$_2$ (0.271 mL, 3.72 mmol) at rt. The mixture was stirred at 60° C. for 2 h. The mixture was concentrated in vacuo. The residue was diluted with EtOAc and sat. NaHCO$_3$ aq., and extracted with ethyl acetate. The organic layer was separated, washed with water and brine, dried over MgSO$_4$ and concentrated in vacuo. The residue was purified by NH silica gel chromatography to give an impure white solid (110.5 mg) that was taken on without further purification.

Step 3: N-[3-(1H-Imidazol-1-yl)propyl]-3-(3-methoxyphenyl)-2-(morpholin-4-yl)quinoxaline-6-carboxamide A mixture of 80 mg of white solid obtained in the previous step, DIPEA (0.099 mL, 0.57 mmol), morpholine (0.050 mL, 0.57 mmol), and 2-propanol (3 mL) was heated at 170° C. for 1 h under microwave irradiation. The mixture was poured into water and extracted with EtOAc. The organic layer was separated, washed with water and brine, dried over MgSO$_4$ and concentrated in vacuo. The residue was purified by NH silica gel chromatography to give N-(3-(1H-imidazol-1-yl)propyl)-3-(3-methoxyphenyl)-2-morpholinoquinoxaline-6-carboxamide (15.3 mg, 67%). $^1$H NMR (300 MHz, CDCl$_3$) 1.97-2.21 (m, 2H), 3.18-3.39 (m, 4H), 3.41-3.56 (m, 2H), 3.57-3.77 (m, 4H), 3.89 (s, 3H), 4.06 (t, J=6.8 Hz, 2H), 6.80-7.15 (m, 4H), 7.35-7.61 (m, 4H), 7.82 (d, J=8.7 Hz, 1H), 8.06 (dd, J=8.7, 1.7 Hz, 1H), 8.32 (d, J=1.7 Hz, 1H).

Example 2: 3-(Azetidin-1-yl)-N-[3-(1H-imidazol-1-yl)propyl]-2-phenylquinoxaline-6-carboxamide
(I-175)

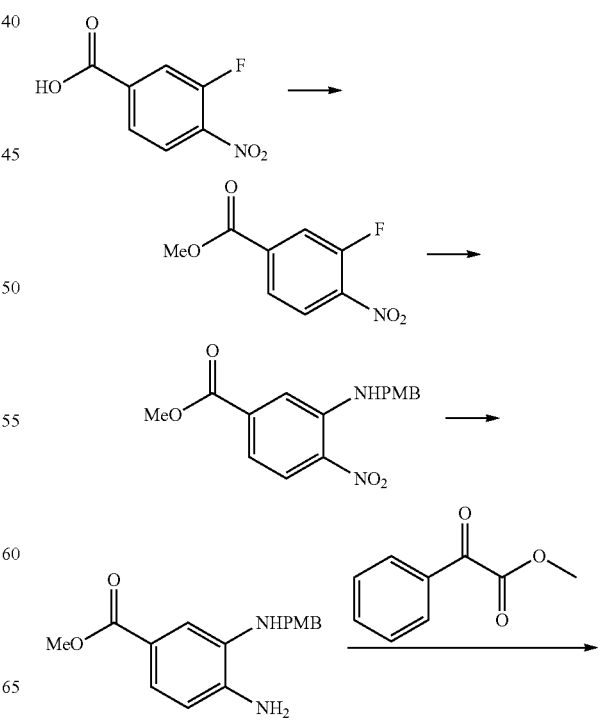

Step 1: N-[3-(1H-Imidazol-1-yl)propyl]-3-(3-methoxyphenyl)-2-oxo-1,2-dihydroquinoxaline-6-carboxamide A mixture of N-(3-(1H-imidazol-1-yl)propyl)-1-(4-methoxybenzyl)-3-(3-methoxyphenyl)-2-oxo-1,2-dihydroquinoxaline-6-carboxamide (800 mg, 1.53 mmol) (prepared similarly to Example 2, step 4) and anisole (0.332 mL, 3.06 mmol) in TFA (5 mL, 64.9 mmol) was stirred at 70° C. overnight. The mixture was concentrated in vacuo. The mixture was diluted with sat. NaHCO$_3$ and extracted with EtOAc/THF. The organic layer was separated, washed with water and brine, dried over MgSO$_4$ and concentrated in vacuo. The residue was triturated with hexane/iPr$_2$O to give as N-(3-(1H-imidazol-1-yl)propyl)-3-(3-methoxyphenyl)-2-oxo-1,2-dihydroquinoxaline-6-carboxamide (550 mg, 89%). $^1$H NMR (300 MHz, DMSO-d$_6$) δ 1.99 (t, J=6.6 Hz, 2H), 3.28 (d, J=6.2 Hz, 2H), 3.83 (s, 3H), 4.05 (t, J=6.8 Hz, 2H), 6.91 (br s, 1H), 7.04-7.17 (m, 1H), 7.23 (s, 1H), 7.31-7.51 (m, 2H), 7.69 (s, 1H), 7.81-8.16 (m, 3H), 8.40 (s, 1H), 8.55-8.87 (m, 1H), 12.75 (br s, 1H).

Step 2: 2-Chloro-N-[3-(1H-imidazol-1-yl)propyl]-3-(3-methoxyphenyl) quinoxaline-6-carboxamide 3 drops of DMF were added to a solution of N-(3-(1H-imidazol-1-yl)propyl)-3-(3-methoxyphenyl)-2-oxo-1,2-di-

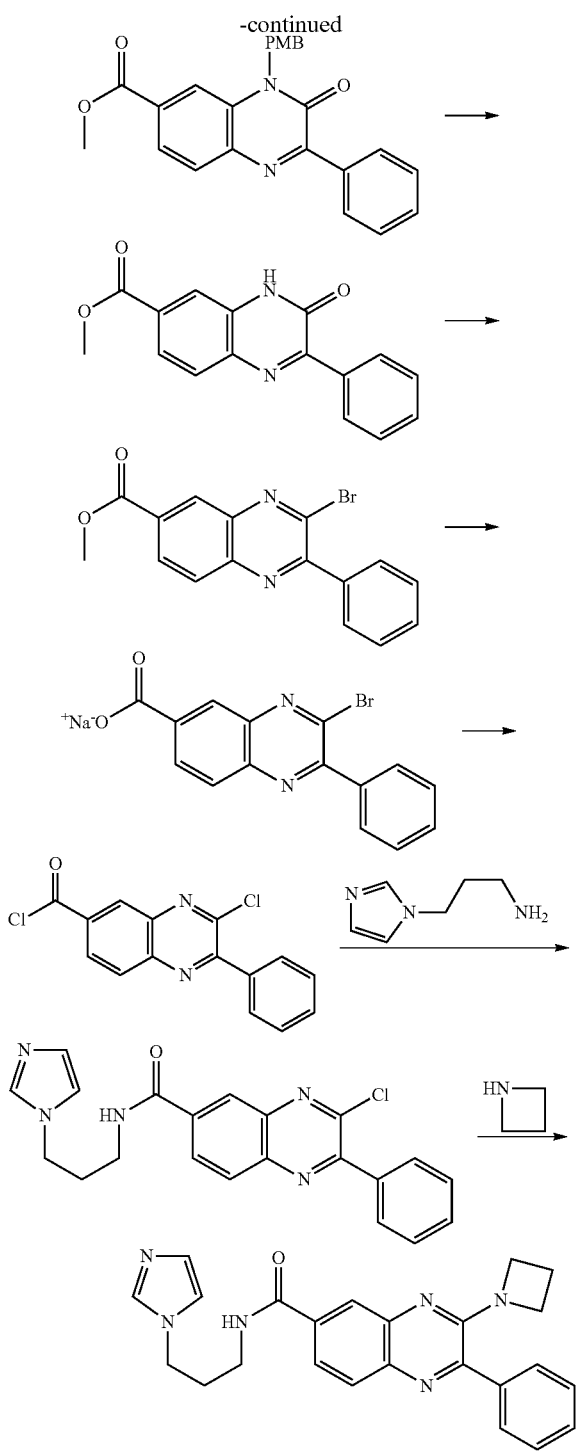

vacuo to give methyl 3-fluoro-4-nitrobenzoicacidmethyl-ester (25.5 g, 93%) as a colorless solid. $^1$H NMR (300 MHz, CDCl$_3$) δ 3.98 (s, 3H), 7.94 (d, J=2.8 Hz, 1H), 7.96 (s, 1H), 8.08-8.12 (m, 1H).

Step 2: Methyl 3-[(4-methoxybenzyl)amino]-4-nitrobenzoate (4-Methoxyphenyl) methanamine (23.0 g, 168 mmol) was added to a solution of methyl 3-fluoro-4-nitrobenzoicacid-methyl ester (25.0 g, 126 mmol) and TEA (37.0 g, 366 mmol) in DMF (200 mL). The mixture was stirred at 85° C. for 2 h. After cooling, the mixture was poured into crushed ice (300 g). The resulting mixture was extracted with EtOAc. The combined organic layers were washed with brine, and concentrated in vacuo to give methyl 3-[(4-methoxybenzyl)amino]-4-nitrobenzoate (39.0 g, 98%) as an orange solid. $^1$H NMR (400 MHz, CDCl$_3$) δ 3.81 (s, 3H), 3.92 (s, 3H), 4.51 (d, J=5.2 Hz, 2H), 6.92 (d, J=8.8 Hz, 2H), 7.23 (d, J=1.6 Hz, 1H), 7.30 (d, J=8.8 Hz, 2H), 7.60 (d, J=1.2 Hz, 1H), 8.23 (d, J=8.8 Hz, 2H).

Step 3: Methyl 4-amino-3-[(4-methoxybenzyl)amino]benzoate

To a solution of methyl 3-[(4-methoxybenzyl)amino]-4-nitrobenzoate (30.0 g, 94.9 mmol) in EtOH (500 mL) at −78° C. was added iron powder (22.5 g, 402 mmol), followed by a solution of NH$_4$Cl (50.0 g, 935 mmol) in water (280 mL). The mixture was refluxed for 2 h. After cooling, insoluble materials were removed by filtration through a celite pad. The filtrate was concentrated in vacuo to remove the EtOH. The residue was suspended in saturated aqueous solution of NaHCO$_3$ and then extracted with EtOAc. The organic layer was separated, washed with water and brine, dried over MgSO$_4$ and concentrated in vacuo to give crude methyl 4-amino-3-[(4-methoxybenzyl)amino] benzoate (26.7 g) as a sticky orange oil, which was used in the next step without further purification.

Step 4: Methyl 4-(4-methoxybenzyl)-3-oxo-2-phenyl-3,4-dihydroquinoxaline-6-carboxylate AcOH (4.70 g, 78.3 mmol) was added to a solution of crude methyl 4-amino-3-[(4-methoxybenzyl)amino]benzoate (38.0 g, 94.9 mmol) and methyl 2-oxo-2-phenylacetate (18.4 g, 112 mmol) in toluene (400 mL). The mixture was stirred for 40 h at 90° C. After cooling, the precipitated solid was collected by filtration and washed with petroleum ether to give methyl 4-(4-methoxybenzyl)-3-oxo-2-phenyl-3,4-dihydroquinoxaline-6-carboxylate (33.0 g, 87%) as a yellow solid. $^1$H NMR (400 MHz, CDCl$_3$) δ 3.76 (s, 3H), 3.96 (s, 3H), 5.54 (s, 2H), 6.86 (d, J=8.4 Hz, 2H), 7.35 (d, J=8.4 Hz, 2H), 7.50-7.52 (m, 3H), 7.96-7.99 (m, 2H), 8.13 (s, 1H), 8.37-8.39 (in, 2H).

Step 5: Methyl 3-oxo-2-phenyl-3,4-dihydroquinoxaline-6-carboxylate

A solution of methyl 4-(4-methoxybenzyl)-3-oxo-2-phenyl-3,4-dihydroquinoxaline-6-carboxylate (16.1 g, 40.2 mmol) in anisole (47 mL) and TFA (200 mL) was refluxed for 24 h. After cooling, the mixture was diluted with MeOH (200 mL) and the precipitate was collected by filtration and washed with MeOH to give methyl 3-oxo-2-phenyl-3,4-dihydroquinoxaline-6-carboxylate (8.30 g, 74%).

Step 1:
Methyl-3-fluoro-4-nitrobenzoicacidmethylester

12 M HCl (5.00 mL) was added to a solution of 3-fluoro-4-nitro-benzoic acid (25.0 g, 135 mmol) in MeOH (400 mL). The reaction mixture was refluxed for 18 h. After cooling, the mixture was concentrated in vacuo. The residue was diluted with EtOAc and water. The organic layer was separated, washed with saturated aqueous solution of NaHCO$_3$ and brine, dried over MgSO$_4$ and concentrated in ¹H NMR (400 MHz, CDCl₃) δ 3.90 (s, 3H), 7.49-7.55 (m, 3H), 7.84 (dd, J=1.6, 8.4 Hz, 1H), 7.94 (dd, J=3.6, 5.6 Hz, 2H), 8.33 (t, J=6.4 Hz, 2H), 12.72 (s, 1H).

Step 6: Methyl 3-bromo-2-phenylquinoxaline-6-carboxylate

A solution of methyl 3-oxo-2-phenyl-3,4-dihydroquinoxaline-6-carboxylate (18.5 g, 66.1 mmol) and phosphoryl bromide (185 g, 645 mmol) in MeCN (400 mL) was refluxed for 18 h. After cooling, the mixture was concentrated in vacuo. The residue was diluted with CH₂Cl₂ and poured into ice water. The resulting mixture was neutralized to a pH of 7-8 with saturated aqueous solution of NaHCO₃ and then extracted with CH₂Cl₂. The combined organic layers were washed with brine, dried over MgSO₄ and concentrated in vacuo. The resulting solid was washed with petroleum ether to give methyl 3-bromo-2-phenylquinoxaline-6-carboxylate (21.0 g, 92%). ¹H NMR (400 MHz, CDCl₃) δ 4.03 (s, 3H), 7.54-7.56 (m, 3H), 7.83-7.85 (m, 2H), 8.19 (d, J=8.8 Hz, 1H), 8.41 (dd, J=2.0, 8.8 Hz, 1H), 8.79 (d, J=1.6 Hz, 1H).

Step 7: Sodium 3-bromo-2-phenylquinoxaline-6-carboxylate

NaOH (2.0 M in water, 17.5 mL, 35.0 mmol) was added to a solution of methyl 3-bromo-2-phenylquinoxaline-6-carboxylate (6.00 g, 17.48 mmol) in 2-propanol (70 mL) and THF (70 mL) at rt. The mixture was stirred at 60° C. for 2 h. After cooling, the precipitate was collected by filtration, and washed with isopropyl ether to give sodium 3-bromo-2-phenylquinoxaline-6-carboxylate (6.01 g, 98%) as an off-white solid. ¹H NMR (300 MHz, DMSO-d₆) δ 7.46-7.63 (m, 3H), 7.71-7.88 (m, 2H), 7.96-8.04 (m, 1H), 8.33-8.43 (m, 2H).

Step 8: 3-Chloro-2-phenylquinoxaline-6-carbonyl chloride 5 drops of DMF were added to a solution of thionyl chloride (6.24 mL, 85.4 mmol) and sodium 3-bromo-2-phenylquinoxaline-6-carboxylate (6.00 g, 17.1 mmol) in THF (200 mL) at rt. The mixture was stirred at 50° C. for 4 h. After cooling, the mixture was concentrated in vacuo to give crude 3-chloro-2-phenylquinoxaline-6-carbonyl chloride. The resulting off-white solid was taken on without further purification.

Step 9: 3-Chloro-N-[3-(1H-imidazol-1-yl)propyl]-2-phenylquinoxaline-6-carboxamide Crude 3-chloro-2-phenylquinoxaline-6-carbonyl chloride (5.18 g, 85.4 mmol) was dissolved in THF (200 mL), then TEA (7.15 mL, 51.3 mmol) and 3-(1H-imidazol-1-yl)propan-1-amine (2.45 mL, 20.5 mmol) were added. The mixture was stirred at rt for 1 h. The reaction was quenched by the addition of saturated aqueous solution of NaHCO₃ and extracted with EtOAc. The organic layer was separated, washed with water and brine, dried over MgSO₄ and concentrated in vacuo. The resulting solid was washed with isopropyl ether/hexane (1:1, 100 mL) to give 3-chloro-N-(3-(1H-imidazol-1-yl)propyl)-2-phenylquinoxaline-6-carboxamide (5.17 g, 77%) as a light brown solid. ¹H NMR (300 MHz, DMSO-d₆) δ 1.92-2.12 (m, 2H), 3.19-3.47 (m, 2H), 4.08 (t, J=6.9 Hz, 2H), 6.91 (s, 1H), 7.13-7.31 (m, 1H), 7.47-7.63 (m, 3H), 7.70 (s, 1H), 7.77-7.99 (m, 2H), 8.16-8.42 (m, 2H), 8.48-8.67 (m, 1H), 8.93 (t, J=5.4 Hz, 1H).

Step 10: 3-(Azetidin-1-yl)-N-[3-(1H-imidazol-1-yl) propyl]-2-phenylquinoxaline-6-carboxamide A mixture of 3-chloro-N-(3-(1H-imidazol-1-yl)propyl)-2-phenylquinoxaline-6-carboxamide (31.0 mg, 80 μmol), azetidine (27 μL, 400 μmol), DIPEA (420 μL, 240 μmol) and NMP (1 mL) was heated at 170° C. for 30 min under microwave irradiation. After cooling, the reaction mixture was poured into EtOAc and water, and stirred for 5 min. The organic layer was concentrated by blowing away solvent with air at 60° C. The residue was purified by preparative HPLC to give 3-(azetidin-1-yl)-N-[3-(1H-imidazol-1-yl) propyl]-2-phenylquinoxaline-6-carboxamide (17.6 mg, 53%). LCMS (ESI+): m/z=413.2 (M+H)

The compounds listed in the table below were prepared in an analogous fashion to that described above starting from the appropriate starting materials:

| Starting Material Step 10 | Compound No. or Name | LCMS Data |
|---|---|---|
| morpholine | I-144 | LCMS (ESI+): m/z = 443.2 (M + H) |
| benzylamine | I-191 | LCMS (ESI+): m/z = 463.1 (M + H) |
| pyrrolidine | I-124 | LCMS (ESI+): m/z = 427.2 (M + H) |
| 3-hydroxypyrrolidine | I-153 | LCMS (ESI+): m/z = 443.2 (M + H) |
| 3-(methylsulfonyl)pyrrolidine | I-101 | LCMS (ESI+): m/z = 505.2 (M + H) |
| 2-oxa-6-azaspiro[3.4]octane | I-15 | LCMS (ESI+): m/z = 469.2 (M + H) |
| 3-cyanopyrrolidine | I-17 | LCMS (ESI+): m/z = 452.2 (M + H) |
| piperidine | I-166 | LCMS (ESI+): m/z = 441.2 (M + H) |
| 4-(methylsulfonyl)piperazine | I-129 | LCMS (ESI+): m/z = 520.2 (M + H) |

| Starting Material Step 10 | Compound No. or Name | LCMS Data |
|---|---|---|
| | I-87 | LCMS (ESI+): m/z = 457.2 (M + H) |
| | I-34 | LCMS (ESI+): m/z = 471.3 (M + H) |
| | I-127 | LCMS (ESI+): m/z = 470.2 (M + H) |
| | I-113 | LCMS (ESI+): m/z = 471.3 (M + H) |
| | I-14 | LCMS (ESI+): m/z = 491.2 (M + H) |
| | I-295 | LCMS (ESI+): m/z = 493.3 (M + H) |
| | I-283 | LCMS (ESI+): m/z = 479.2 (M + H) |
| | I-265 | LCMS (ESI+): m/z = 455.2 (M + H) |
| | I-278 | LCMS (ESI+): m/z = 429.2 (M + H) |
| | I-126 | LCMS (ESI+): m/z = 427.2 (M + H) |

Example 3: N-[3-(1H-Imidazol-1-yl)propyl]-2-methyl-3-phenylquinoxaline-6-carboxamide (I-158)

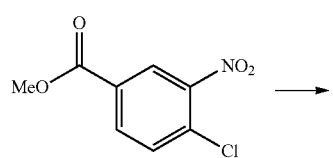

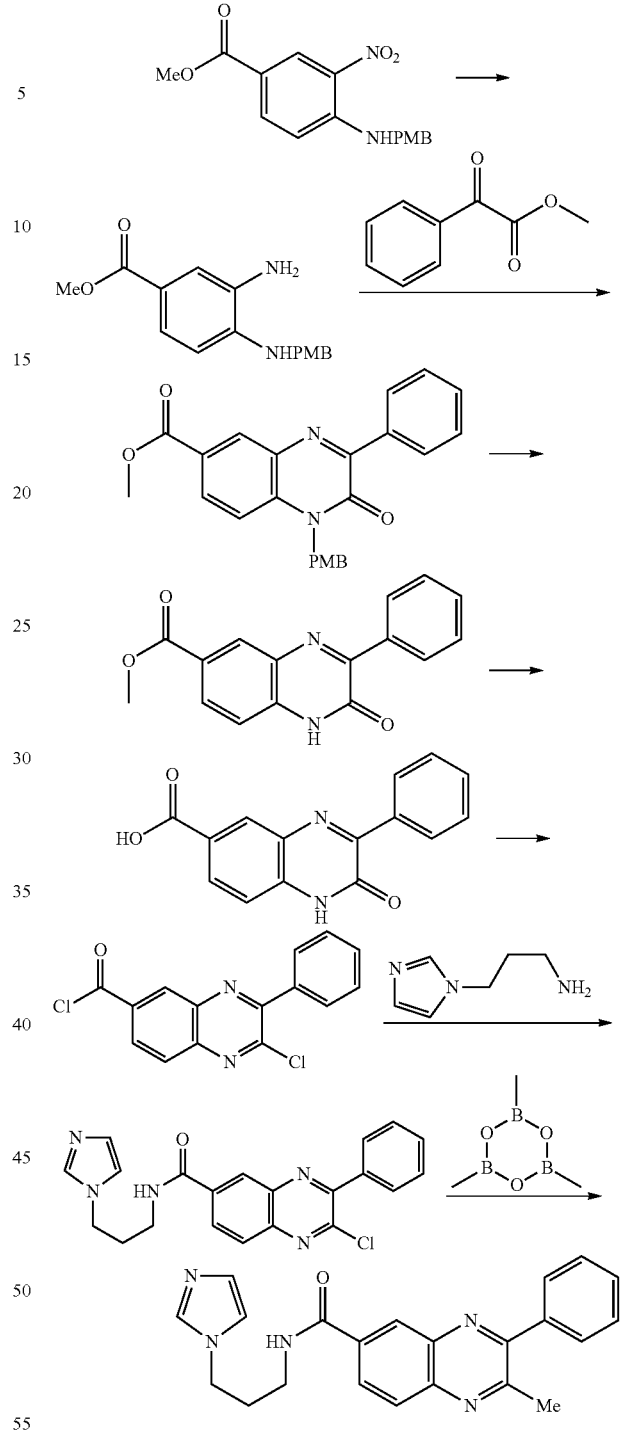

Step 1: Methyl 4-[(4-methoxybenzyl)amino]-3-nitrobenzoate

To a solution of methyl 4-chloro-3-nitrobenzoate (12.0 g, 55.6 mmol) in MeCN (100 mL) was added p-methoxybenxylamine (11.4 g, 83.5 mmol) and KOAc (10.9 g, 111 mmol). The reaction mixture was stirred for 5 h at 80° C. After cooling, the mixture was poured into water (500 mL) and stirred for 1 h. The precipitate was collected by filtration, and washed with water, followed by cold ether to give methyl 4-[(4-methoxybenzyl)amino]-3-nitrobenzoate (16.6 g, 94%). $^1$H NMR (300 MHz, DMSO-$d_6$) δ 3.72 (s, 3H), 3.81 (s, 3H), 4.61 (d, J=6.0 Hz, 2H), 6.84-6.97 (m, 2H), 7.04 (d, J=9.1 Hz, 1H), 7.31 (d, J=8.6 Hz, 2H), 7.90 (dd, J=9.1, 2.1 Hz, 1H), 8.63 (d, J=2.1 Hz, 1H), 9.01 (t, J=6.0 Hz, 1H).

Step 2: Methyl 3-amino-4-[(4-methoxybenzyl) amino]benzoate

A suspension of methyl 4-[(4-methoxybenzyl)amino]-3-nitrobenzoate (16.6 g, 52.5 mmol) in 100 mL of EtOH was heated to reflux for 20 min and then iron powder (11.7 g, 209.7 mmol) was added, followed by 100 mL of 1 N aqueous NH$_4$Cl. The reaction mixture was refluxed for 2 h and then cooled to rt. The mixture was filtered through a celite pad to remove the insoluble materials and the filtrate was concentrated under reduced pressure. The residue was partitioned between water and EtOAc. The organic layer was separated and the aqueous layer was extracted with EtOAc. The combined organic phase was dried over anhydrous MgSO$_4$, filtered and concentrated under reduced pressure to give methyl 3-amino-4-[(4-methoxybenzyl)amino] benzoate, which was used for the next step without further purification.

Step 3: Methyl 1-(4-methoxybenzyl)-2-oxo-3-phenyl-1,2-dihydroquinoxaline-6-carboxylate To a solution of methyl benzoylformate (10.3 g, 62.7 mmol) and methyl 3-amino-4-[(4-methoxybenzyl)amino] benzoate (16.3 g, 52.5 mmol) in toluene (100 mL) was added acetic acid (2.4 g, 36.7 mmol). The reaction mixture was heated under reflux for 2 h and then additional acetic acid (1.2 g, 18.4 mmol) was added. The resulting mixture was stirred at 90° C. for 16 h and then cooled to rt. The precipitate was collected by filtration, washed with petroleum and dried in vacuum to give methyl 1-(4-methoxybenzyl)-2-oxo-3-phenyl-1,2-dihydroquinoxaline-6-carboxylate (12.2 g, 58%). $^1$H NMR (400 MHz, CDCl$_3$) δ 3.76 (s, 3H), 3.95 (s, 3H), 5.51 (s, 2H), 6.84 (d, J=6.6 Hz, 2H), 7.24-7.26 (m, 2H), 7.38 (d, J=6.6 Hz, 1H), 7.50-7.51 (m, 3H), 8.09-8.12 (m, 1H), 8.36-8.38 (m, 2H), 8.62-8.63 (m, 1H).

Step 4: Methyl 2-oxo-3-phenyl-1,2-dihydroquinoxaline-6-carboxylate

A solution of methyl 1-(4-methoxybenzyl)-2-oxo-3-phenyl-1,2-dihydroquinoxaline-6-carboxylate (56.0 g, 140 mmol) in TFA (500 mL) and anisole (100 mL) was heated under reflux for 48 h. After being cooled to rt, the solvent was removed under reduced pressure and the residue was diluted with MeOH (500 mL), vigorously stirred for 1 h. The resulting solid was filtered out and dried in vacuum to give methyl 2-oxo-3-phenyl-1,2-dihydroquinoxaline-6-carboxylate (26.0 g, 66%). $^1$H NMR (400 MHz, CDCl$_3$) δ 3.97 (s, 3H), 7.36 (d, J=8.4 Hz, 1H), 7.51-7.55 (m, 3H), 8.19 (dd, J=2.0, 8.8 Hz, 1H), 8.41-8.44 (m, 2H), 8.65 (d, J=1.6 Hz, 1H), 11.79 (br s, 1H).

Step 5: 2-Oxo-3-phenyl-1,2-dihydroquinoxaline-6-carboxylic acid

NaOH (2.0 M in water, 21.4 mL, 42.8 mmol) was added to a solution of methyl 2-oxo-3-phenyl-1,2-dihydroquinoxaline-6-carboxylate (3.0 g, 10.7 mmol) in MeOH (100 mL) and THF (100 mL) at rt. The mixture was stirred at 60° C. for 3 h. After cooling, the mixture was quenched with 1N HCl aq. to bring the pH of the solution to 2-3. The precipitate was collected by filtration and washed with water to give 2-oxo-3-phenyl-1,2-dihydroquinoxaline-6-carboxylic acid (2.78 g, 98%). $^1$H NMR (300 MHz, DMSO-$d_6$) δ 7.42 (d, J=8.5 Hz, 1H), 7.47-7.59 (m, 3H), 8.07 (dd, J=8.5, 1.8 Hz, 1H), 8.19-8.43 (m, 3H), 12.85 (br s, 1H), 13.08 (br s, 1H).

Step 6: 2-Chloro-3-phenylquinoxaline-6-carbonyl chloride 5 drops of DMF were added to a suspension of 2-oxo-3-phenyl-1,2-dihydroquinoxaline-6-carboxylic acid (1.80 g, 6.76 mmol) and thionyl chloride (60.0 mL, 822 mmol) at rt. The mixture was refluxed for 1 h. After cooling, the mixture was concentrated in vacuo to give crude 2-chloro-3-phenylquinoxaline-6-carbonyl chloride. The resulting off-white solid was used without further purification.

Step 7: 2-Chloro-N-[3-(1H-imidazol-1-yl)propyl]-3-phenylquinoxaline-6-carboxamide Crude 2-chloro-3-phenylquinoxaline-6-carbonyl chloride from the previous step was dissolved in THF (100 mL) then TEA (2.83 mL, 20.3 mmol) and 3-(1H-imidazol-1-yl)propan-1-amine (1.13 mL, 8.11 mmol) were added. After being stirred at rt for 1 h, the reaction was quenched by the addition of saturated aqueous solution of NaHCO$_3$ and extracted with EtOAc. The organic layer was separated, washed with water and brine, passed through an NH silica gel pad. The filtrate was concentrated and the residue was triturated with diisopropyl ether/hexane (1:1, 30 mL) to give 2-chloro-N-(3-(1H-imidazol-1-yl)propyl)-3-phenylquinoxaline-6-carboxamide (2.10 g, 79%). $^1$H NMR (300 MHz, DMSO-$d_6$) δ 1.84-2.18 (m, 2H), 3.15-3.45 (m, 2H), 4.07 (t, J=6.9 Hz, 2H), 6.90 (s, 1H), 7.23 (s, 1H), 7.52-7.63 (m, 3H), 7.67 (s, 1H), 7.78-7.96 (m, 2H), 8.07-8.43 (m, 2H), 8.67 (d, J=1.7 Hz, 1H), 8.93 (t, J=5.5 Hz, 1H).

Step 8: N-[3-(1H-Imidazol-1-yl)propyl]-2-methyl-3-phenylquinoxaline-6-carboxamide Pd(amphos)Cl$_2$ (0.6 mg, 8.0 μmol) was added to a solution of 2-chloro-N-(3-(1H-imidazol-1-yl)propyl)-3-phenylquinoxaline-6-carboxamide (31 mg, 80 mop, 2,4,6-trimethylboroxin (210 mg, 320 μmol) and Cs$_2$CO$_3$ (2.0 M in water, 0.1 mL) in DME (1 mL). The mixture was stirred at 100° C. overnight. After cooling, to the mixture was added additional 2,4,6-trimethylboroxin (40 mg, 160 μmol) and Pd(amphos)Cl$_2$ (0.6 mg, 8.0 μmol). The mixture was stirred at 100° C. overnight. After cooling, the reaction mixture was poured into EtOAc and water, and stirred for 5 min. The organic layer was concentrated by blowing away solvent with air at 60° C. The residue was purified by preparative HPLC to give 3-(1H-Imidazol-1-yl)propyl)-2-methyl-3-phenylquinoxaline-6-carboxamide (0.8 mg, 3%). LCMS (ESI+) m/z=372.2 (M+H).

Example 4: tert-Butyl [4-(6-{[3-(1H-imidazol-1-yl)propyl]carbamoyl}-3-phenylquinoxalin-2-yl)benzyl]carbamate (I-148)

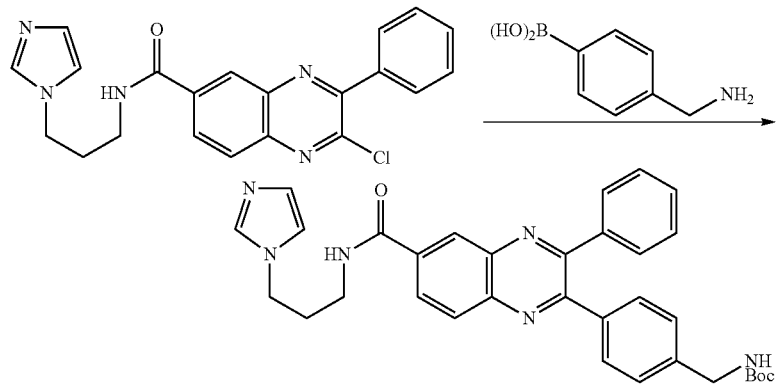

Boc₂O (178 µL, 0.77 mmol) was added to a solution of (4-(aminomethyl)phenyl)boronic acid hydrochloride (143 mg, 0.77 mmol) and $Cs_2CO_3$ (665 mg, 2.04 mmol) in DME (10 mL) and water (1.0 mL) at rt. After being stirred at rt for 30 min, Suzuki coupling was carried out as follow: 2-chloro-N-(3-(1H-imidazol-1-yl)propyl)-3-phenylquinoxaline-6-carboxamide (201 mg, 0.54 mmol) (prepared according to Example 3, step 7) and Pd(dppf)Cl₂.CH₂Cl₂ (42.0 mg, 51.4 µmol) were added to the reaction mixture. The mixture was heated at 100° C. for 10 h under microwave irradiation. After cooling, the mixture was poured into saturated aqueous solution of NaHCO₃ and extracted with EtOAc. The organic layer was separated, washed with water and brine, dried over MgSO₄ and concentrated in vacuo. The residue was purified by NH silica gel chromatography to give tert-butyl [4-(6-{[3-(1H-imidazol-1-yl)propyl]carbamoyl}-3-phenylquinoxalin-2-yl)benzyl]carbamate (187 mg, 65%. ¹H NMR (300 MHz, DMSO-d₆) δ 1.23-1.52 (m, 9H), 2.00-2.12 (m, 2H), 3.32-3.39 (m, 2H), 4.05-4.19 (m, 4H), 6.91 (s, 1H), 7.10-7.30 (m, 3H), 7.32-7.77 (m, 9H), 8.12-8.38 (m, 2H), 8.69 (d, J=1.3 Hz, 1H), 8.91 (t, J=5.2 Hz, 1H).

The compounds listed in the table below were prepared in an analogous fashion to that described above starting from the appropriate starting materials:

| Starting Material | Compound No. or Name | LCMS Data |
|---|---|---|
| H₂N-CH₂-C₆H₄-B(OH)₂ (meta) | I-152 | LCMS (ESI+): m/z = 536.2 (M + H) |
| 2-methoxyphenylboronic acid | I-13* | LCMS (ESI+): m/z = 464.2 (M + H) |
| 3-methoxyphenylboronic acid | I-187* | LCMS (ESI+): m/z = 464.2 (M + H) |
| 4-methoxyphenylboronic acid | I-99* | LCMS (ESI+): m/z = 464.2 (M + H) |
| 2,3-dihydrobenzofuran-5-boronic acid | I-140* | LCMS (ESI+): m/z = 476.3 (M + H) |
| 3-(trifluoromethoxy)phenylboronic acid | I-61* | LCMS (ESI+): m/z = 518.1 (M + H) |
| 2-chlorophenylboronic acid | I-257* | LCMS (ESI+): m/z = 468.2 (M + H) |
| 3-chlorophenylboronic acid | I-209* | LCMS (ESI+): m/z = 468.2 (M + H) |

| Starting Material | Compound No. or Name | LCMS Data |
|---|---|---|
| 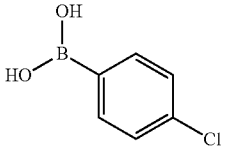 | I-45* | LCMS (ESI+): m/z = 468.2 (M + H) |
| 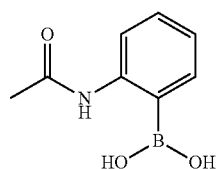 | I-264* | LCMS (ESI+): m/z = 491.3 (M + H) |
| 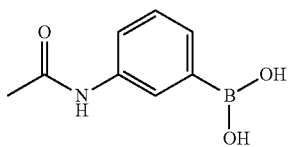 | I-2* | LCMS (ESI+): m/z = 491.3 (M + H) |
| 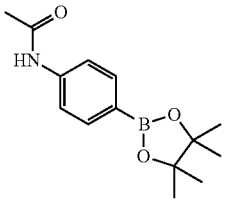 | I-254* | LCMS (ESI+): m/z = 491.3 (M + H) |
| 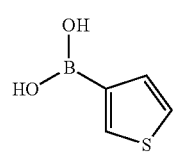 | I-60* | LCMS (ESI+): m/z = 440.1 (M + H) |
| 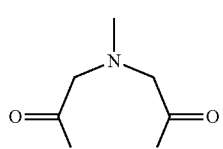 | I-247* | LCMS (ESI+): m/z = 440.1 (M + H) |
| 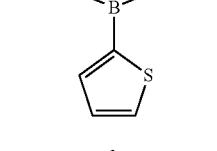 | I-179* | LCMS (ESI+): m/z = 437.2 (M + H) |
| 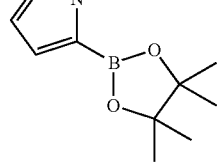 | I-92* | LCMS (ESI+): m/z = 435.1 (M + H) |

| Starting Material | Compound No. or Name | LCMS Data |
|---|---|---|
| 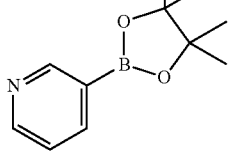 | I-201* | LCMS (ESI+): m/z = 435.1 (M + H) |
| 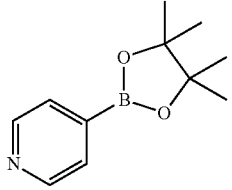 | I-5* | LCMS (ESI+): m/z = 435.2 (M + H) |
| 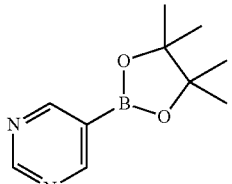 | I-242* | LCMS (ESI+): m/z = 436.2 (M + H) |
| 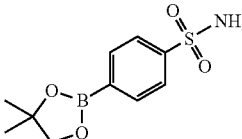 | I-145* | LCMS (ESI+): m/z = 513.1 (M + H) |
| 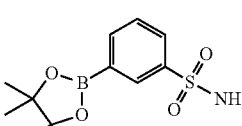 | I-89* | LCMS (ESI+): m/z = 513.1 (M + H) |
| 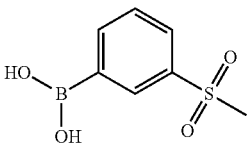 | I-182* | LCMS (ESI+): m/z = 512.1 (M + H) |
| 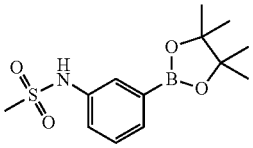 | I-290* | LCMS (ESI+): m/z = 527.2 (M + H) |
| 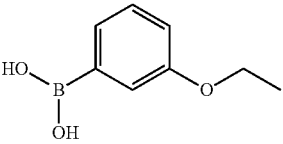 | I-228* | LCMS (ESI+): m/z = 478.2 (M + H) |

329
-continued

| Starting Material | Compound No. or Name | LCMS Data |
|---|---|---|
| 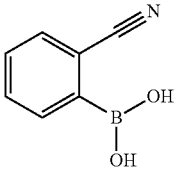 [SMILES: N#Cc1ccccc1B(O)O] | I-54* | LCMS (ESI+): m/z = 459.2 (M + H) |
| 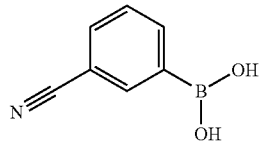 | I-219* | LCMS (ESI+): m/z = 459.2 (M + H) |
| 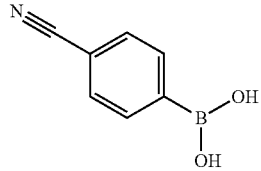 [SMILES: N#Cc1ccc(B(O)O)cc1] | I-131* | LCMS (ESI+): m/z = 459.2 (M + H) |
| 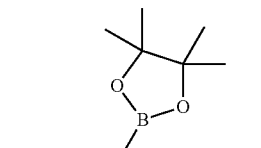 | I-203* | LCMS (ESI+): m/z = 438.2 (M + H) |
| 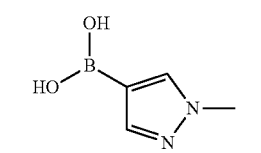 | I-119* | LCMS (ESI+): m/z = 438.2 (M + H) |
| 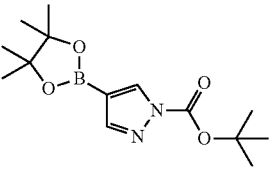 | I-49*, ** | LCMS (ESI+): m/z = 424.1 (M + H) |
| 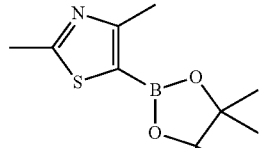 | I-24* | LCMS (ESI+): m/z = 469.2 (M + H) |
| 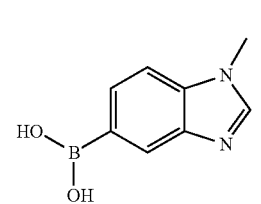 | I-38* | LCMS (ESI+): m/z = 488.2 (M + H) |

330
-continued

| Starting Material | Compound No. or Name | LCMS Data |
|---|---|---|
| 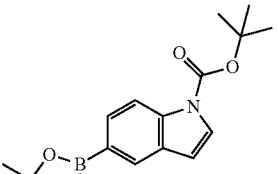 | I-149*, ** | LCMS (ESI+): m/z = 473.2 (M + H) |
| 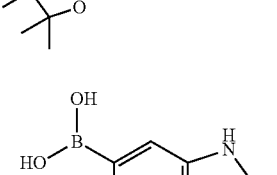 | I-208* | LCMS (ESI+): m/z = 473.3 (M + H) |
| 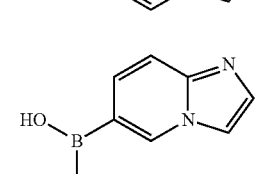 | I-258* | LCMS (ESI+): m/z = 474.2 (M + H) |
| 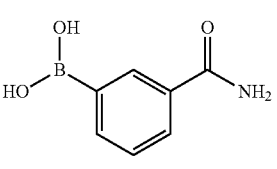 [SMILES: NC(=O)c1cccc(B(O)O)c1] | I-235* | LCMS (ESI+): m/z = 477.2 (M + H) |
| 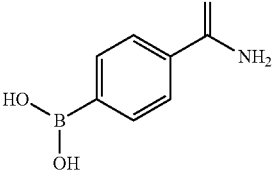 | I-190* | LCMS (ESI+): m/z = 477.2 (M + H) |
| 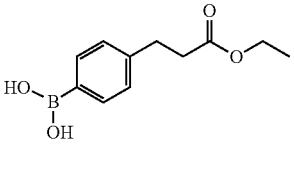 | I-205* | LCMS (ESI+): m/z = 534.2 (M + H) |
| 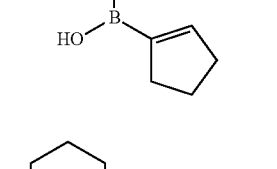 | I-230* | LCMS (ESI+): m/z = 424.2 (M + H) |
| 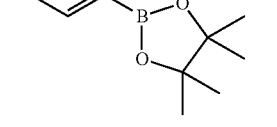 | I-240* | LCMS (ESI+): m/z = 438.2 (M + H) |

331
-continued

| Starting Material | Compound No. or Name | LCMS Data |
|---|---|---|
| (4,5-dihydro-2H-pyran-4-yl boronic acid pinacol ester) | I-141* | LCMS (ESI+): m/z = 440.2 (M + H) |
| (1-methyl-1,2,3,6-tetrahydropyridin-4-yl boronic acid pinacol ester) | I-165* | LCMS (ESI+): m/z = 453.3 (M + H) |
| (potassium (Boc-aminomethyl)trifluoroborate) | I-10*, ** | LCMS (ESI+): m/z = 387.2 (M + H) |
| (potassium (morpholinomethyl)trifluoroborate) | I-88* | LCMS (ESI+): m/z = 457.2 (M + H) |
| (potassium ((4-methylpiperazin-1-yl)methyl)trifluoroborate) | I-259* | LCMS (ESI+): m/z = 470.2 (M + H) |

*No Boc₂O or Cs₂CO₃ were added; the reaction began directly with Suzuki coupling.
**The Boc group was deprotected during the course of the reaction.

Example 5: N-[3-(1H-Imidazol-1-yl)propyl]-2-phenoxy-3-phenylquinoxaline-6-carboxamide (I-80)

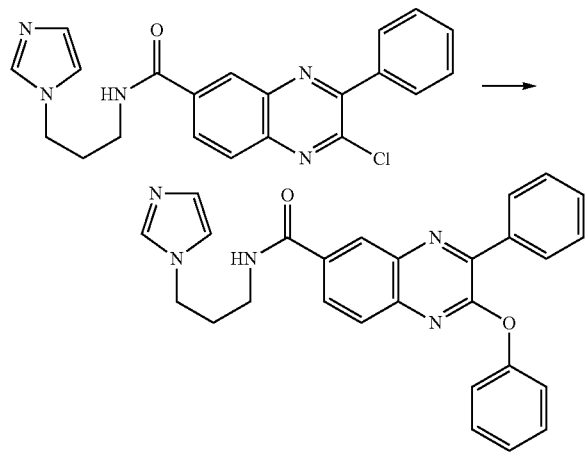

A mixture of DIPEA (67 µL, 0.38 mmol), phenol (60 mg, 0.64 mmol), 2-chloro-N-(3-(1H-imidazol-1-yl)propyl)-3-phenylquinoxaline-6-carboxamide (50 mg, 0.13 mmol) (prepared according to Example 3, step 7) and DMF (3.0 mL) was heated at 170° C. for 4 h under microwave irradiation. The reaction was quenched by the addition of water and extracted with EtOAc. The organic layer was separated, washed with water and brine, dried over MgSO₄ and concentrated in vacuo. The residue was purified by NH silica gel chromatography and then by preparative HPLC to give N-[3-(1H-Imidazol-1-yl)propyl]-2-phenoxy-3-phenylquinoxaline-6-carboxamide (19 mg, 32%). ¹H NMR (300 MHz, DMSO-d₆) δ 1.90-2.10 (m, 2H), 3.19-3.38 (m, 2H), 4.06 (t, J=6.9 Hz, 2H), 6.90 (t, J=1.1 Hz, 1H), 7.23 (t, J=1.1 Hz, 1H), 7.29-7.44 (m, 3H), 7.45-7.55 (m, 2H), 7.56-7.64 (m, 3H), 7.68 (s, 1H), 7.75 (d, J=8.7 Hz, 1H), 8.06-8.30 (m, 3H), 8.64 (d, J=1.8 Hz, 1H), 8.83 (t, J=5.4 Hz, 1H).

Example 6: 2-(Azetidin-1-yl)-N-[3-(1H-imidazol-1-yl)propyl]-3-phenylquinoxaline-6-carboxamide (I-137)

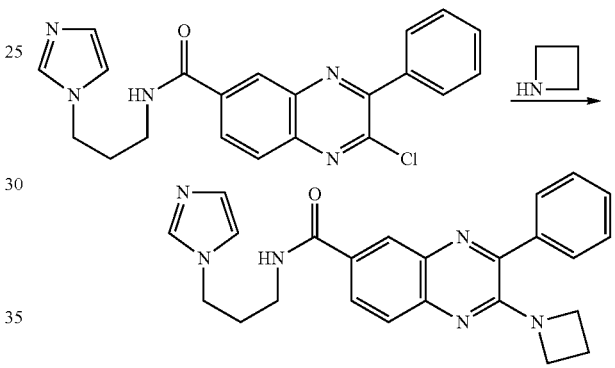

A mixture of 3-chloro-N-(3-(1H-imidazol-1-yl)propyl)-2-phenylquinoxaline-6-carboxamide (31 mg, 80 µmol) (prepared according to Example 3, step 7), azetidine ((27 µL, 400 µmol), DIPEA (42 µL, 240 µmol) and NMP (1 mL) was heated at 170° C. for 30 min under microwave irradiation. After cooling, the reaction mixture was poured into EtOAc and water, and stirred for 5 min. The organic layer was evaporated by blowing away solvent with air at 60° C. The residue was purified by preparative HPLC to give 2-(azetidin-1-yl)-N-[3-(1H-imidazol-1-yl)propyl]-3-phenylquinoxaline-6-carboxamide (19 mg, 59%). LCMS (ESI+) m/z=413.2 (M+H).

The compounds listed in the table below were prepared in an analogous fashion to that described above starting from the appropriate starting materials:

| Starting Material | Compound No. or Name | LCMS Data |
|---|---|---|
| (morpholine) | I-96* | LCMS (ESI+): m/z = 443.2 (M + H) |
| (3-methoxyazetidine) | I-59 | LCMS (ESI+): m/z = 443.2 (M + H) |

| Starting Material | Compound No. or Name | LCMS Data |
|---|---|---|
| pyrrolidine | I-206 | LCMS (ESI+): m/z = 427.2 (M + H) |
| 3-azabicyclo[3.1.0]hexane | I-159 | LCMS (ESI+): m/z = 439.2 (M + H) |
| 3-hydroxypyrrolidine | I-90 | LCMS (ESI+): m/z = 443.2 (M + H) |
| 3-(methylsulfonyl)pyrrolidine | I-150 | LCMS (ESI+): m/z = 505.2 (M + H) |
| 3-methoxypyrrolidine | I-226 | LCMS (ESI+): m/z = 457.2 (M + H) |
| 2-oxa-6-azaspiro[3.4]octane | I-243** | LCMS (ESI+): m/z = 469.2 (M + H) |
| 3-cyanopyrrolidine | I-106 | LCMS (ESI+): m/z = 452.2 (M + H) |
| imidazolidin-2-one | I-7*** | LCMS (ESI+): m/z = 442.2 (M + H) |
| 1-(piperidin-4-yl)imidazolidin-2-one | I-272 | LCMS (ESI+): m/z = 525.3 (M + H) |
| 3-morpholinopyrrolidine | I-267 | LCMS (ESI+): m/z = 512.2 (M + H) |
| 4-morpholinopiperidine | I-199 | LCMS (ESI+): m/z = 526.3 (M + H) |
| isoindoline | I-11 | LCMS (ESI+): m/z = 475.2 (M + H) |
| 1-acetylpiperazine | I-51 | LCMS (ESI+): m/z = 484.2 (M + H) |
| 1-(piperidin-4-yl)-1H-benzo[d]imidazol-2(3H)-one | I-280*** | LCMS (ESI+): m/z = 573.3 (M + H) |
| 1-(piperidin-4-yl)pyrrolidin-2-one | I-136*** | LCMS (ESI+): m/z = 524.3 (M + H) |
| spiro[benzofuran-3,4'-piperidine] | I-268 | LCMS (ESI+): m/z = 545.2 (M + H) |
| piperidine | I-161 | LCMS (ESI+): m/z = 441.2 (M + H) |
| hexahydropyrrolo[1,2-a]pyrazin-6(2H)-one | I-250 | LCMS (ESI+): m/z = 496.1 (M + H) |
| 1-(methylsulfonyl)piperazine | I-125 | LCMS (ESI+): m/z = 520.2 (M + H) |
| 1-methylpiperazine | I-128 | LCMS (ESI+): m/z = 456.2 (M + H) |
| 4-hydroxypiperidine | I-105 | LCMS (ESI+): m/z = 457.2 (M + H) |
| 3-hydroxypiperidine | I-100 | LCMS (ESI+): m/z = 457.2 (M + H) |
| (2R,6S)-2,6-dimethylmorpholine | I-115 | LCMS (ESI+): m/z = 471.3 (M + H) |

335
-continued

| Starting Material | Compound No. or Name | LCMS Data |
|---|---|---|
| [structure: N-methyl piperazinone] | I-81 | LCMS (ESI+): m/z = 470.2 (M + H) |
| [structure: 2,2-dimethyl morpholine] | I-31 | LCMS (ESI+): m/z = 471.3 (M + H) |
| [structure: thiomorpholine 1,1-dioxide] | I-289 | LCMS (ESI+): m/z = 491.2 (M + H) |
| [structure: octahydropyrrolo[1,2-a]pyrazine] | I-146 | LCMS (ESI+): m/z = 482.2 (M + H) |
| [structure: 2-oxa-6-azaspiro[3.5]nonane] | I-30** | LCMS (ESI+): m/z = 483.2 (M + H) |
| [structure: 2-methyl-4,5,6,7-tetrahydro-2H-pyrazolo[3,4-c]pyridine] | I-200 | LCMS (ESI+): m/z = 493.3 (M + H) |
| [structure: 4,5,6,7-tetrahydroimidazo[1,2-a]pyrazine] | I-296 | LCMS (ESI+): m/z = 479.2 (M + H) |
| [structure: azepane] | I-262 | LCMS (ESI+): m/z = 455.2 (M + H) |
| [structure: diethylamine] | I-207 | LCMS (ESI+): m/z = 429.2 (M + H) |
| [structure: cyclobutylamine] | I-274 | LCMS (ESI+): m/z = 427.2 (M + H) |
| [structure: benzylamine] | I-62 | LCMS (ESI+): m/z = 463.1 (M + H) |
| [structure: 2-oxa-5-azabicyclo[2.2.1]heptane] | I-37 | LCMS (ESI+): m/z = 455.2 (M + H) |
| [structure: tert-butyl 4-(piperidin-4-yl)piperidine-1-carboxylate] | I-188* | LCMS (ESI+): m/z = 624.3 (M + H) |

336
-continued

| Starting Material | Compound No. or Name | LCMS Data |
|---|---|---|
| [structure: 1,4-dioxa-8-azaspiro[4.5]decane] | I-275 | LCMS (ESI+): m/z = 499.2 (M + H) |
| [structure: tert-butyl 4-(piperidin-4-yl)piperazine-1-carboxylate] | I-66* | LCMS (ESI+): m/z = 625.3 (M + H) |

*iPrOH was used as solvent.

**The reaction was carried out at 140° C.

***The reaction was carried out at 120° C.

Example 7: N-[3-(1H-imidazol-2-yl)propyl]-2-[4-(morpholin-4-yl)piperidin-1-yl]-3-phenylquinoxaline-6-carboxamide (I-18) dihydrochloride

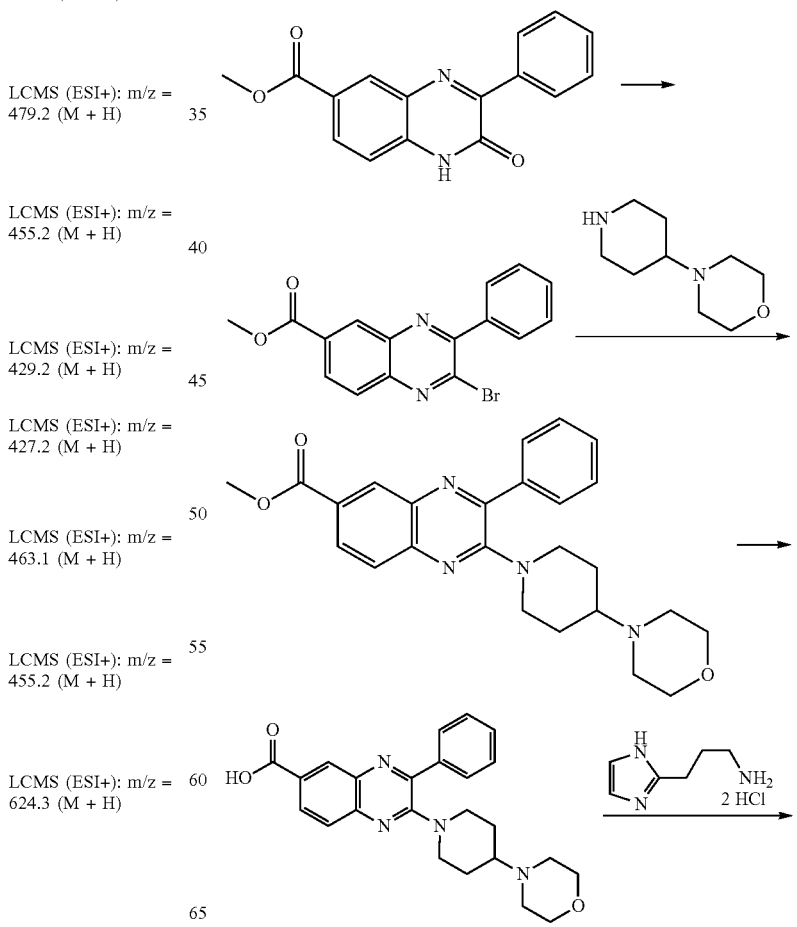

-continued

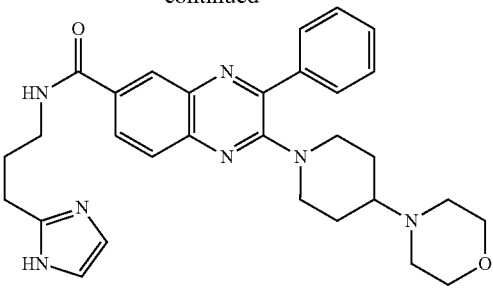

Step 1: Methyl 2-bromo-3-phenylquinoxaline-6-carboxylate

A solution of methyl 2-oxo-3-phenyl-1,2-dihydroquinoxaline-6-carboxylate (15.0 g, 53.5 mmol) (prepared in Example 3, step 4) in MeCN (400 mL) and POBr$_3$ (100 g, 349 mmol) was heated under reflux for 16 h. After being cooled to rt, the mixture was concentrated under reduced pressure to remove the solvent. The residue was carefully diluted with ice-water and neutralized to a pH of 7 with saturated aqueous K$_2$CO$_3$. The resulting mixture was extracted with DCM and the combined organic solution was dried over anhydrous Na$_2$SO$_4$, filtered and concentrated under reduced pressure. The resulting solid was washed with petroleum ether and dried in vacuum to give methyl 2-bromo-3-phenylquinoxaline-6-carboxylate (16.2 g, 73%). $^1$H NMR (400 MHz, CDCl$_3$): δ 4.01 (s, 3H), 7.51-7.55 (m, 3H), 7.82-7.84 (m, 2H), 8.13 (d, J=8.8 Hz, 1H), 8.39 (d, J=8.8 Hz, 1H), 8.85 (s, 1H).

Step 2: Methyl 2-[4-(morpholin-4-yl)piperidin-1-yl]-3-phenylquinoxaline-6-carboxylate Methyl 2-bromo-3-phenylquinoxaline-6-carboxylate (1.09 g, 3.18 mmol) and 4-(piperidin-4-yl)morpholine (1.09 g, 6.40 mmol) were suspended in DMSO (30 ml). To the mixture K$_2$CO$_3$ (2.36 g, 17.08 mmol) was added and the mixture was stirred for 1.5 h at 100° C. The mixture was allowed to cool to rt and then insoluble materials were removed by filtration. To the filtrate, EtOAc and water were added and the resulting biphasic mixture was vigorously stirred for 30 min at rt. The aqueous phase was separated and then extracted with EtOAc. The combined organic phase was washed with brine, dried over anhydrous MgSO$_4$, filtered and concentrated in vacuo. The residue was suspended in EtOAc (30 mL) and the suspension was sonicated. The insoluble yellow crystalline solid was collected by filtration to obtain a first crop of crystals (970 mg). The mother liquid was purified by NH silica gel chromatography to obtain second crop of crystals (210 mg). Combined the purified lots of crystals gave methyl 2-(4-morpholinopiperidin-1-yl)-3-phenylquinoxaline-6-carboxylate (1.180 g, 86%). $^1$H NMR (300 MHz, DMSO-d$_6$) δ 1.40 (q, J=12.2 Hz, 2H), 1.75 (d, J=12.1 Hz, 2H), 2.19-2.35 (m, 1H), 2.42 (s, 4H), 2.79 (t, J=12.4 Hz, 2H), 3.55 (s, 4H), 3.83 (d, J=13.5 Hz, 2H), 3.91 (s, 3H), 7.47-7.63 (m, 3H), 7.80 (d, J=8.7 Hz, 1H), 7.93 (s, 2H), 8.12 (dd, J=8.7, 2.0 Hz, 1H), 8.43 (d, J=1.8 Hz, 1H).

Step 3: 2-[4-(Morpholin-4-yl)piperidin-1-yl]-3-phenylquinoxaline-6-carboxylic acid Methyl 2-(4-morpholinopiperidin-1-yl)-3-phenylquinoxaline-6-carboxylate (1.18 g, 2.73 mmol) was suspended in MeOH (50 ml) and THF (10 ml). The suspension was stirred for 20 min at 50° C. to obtain a clear yellow solution. To the solution was added NaOH (2.0 M in water, 10 ml, 20.0 mmol) and the mixture was stirred for 16 h at 50° C. The mixture cooled to 0° C. To the mixture, was added a 1N aqueous solution of HCl to adjust to pH 7.0. The mixture was stirred for 2 h at 0° C. to obtain a yellow suspension. The solid was collected by filtration, washed with water and then dried in vacuo at 90° C. for 3 h to obtain 2-[4-(morpholin-4-yl)piperidin-1-yl]-3-phenylquinoxaline-6-carboxylic acid (1.120 g, 98%). $^1$H NMR (300 MHz, DMSO-d$_6$) δ 1.29-1.50 (m, 2H), 1.75 (d, J=12.5 Hz, 2H), 2.18-2.34 (m, 1H), 2.43 (m, J=4.2 Hz, 4H), 2.78 (t, J=11.9 Hz, 2H), 3.50-3.60 (m, 4H), 3.81 (d, J=13.2 Hz, 2H), 7.47-7.62 (m, 3H), 7.78 (d, J=8.7 Hz, 1H), 7.93 (m, J=1.3 Hz, 2H), 8.11 (dd, J=8.7, 1.9 Hz, 1H), 8.41 (d, J=1.6 Hz, 1H), 13.09 (br s, 1H).

Step 4: N-[3-(1H-imidazol-2-yl)propyl]-2-[4-(morpholin-4-yl)piperidin-1-yl]-3-phenylquinoxaline-6-carboxamide dihydrochloride 2-[4-(Morpholin-4-yl)piperidin-1-yl]-3-phenylquinoxaline-6-carboxylic acid (108.0 mg, 0.26 mmol) was dissolved in DMA (5 ml). To this solution was added 3-(1H-imidazol-2-yl)propan-1-amine dihydrochloride (94.2 mg, 0.48 mmol), TEA (200 µL, 1.43 mmol) and HATU (116 mg, 0.31 mmol). The mixture was stirred for 2 h at rt. The mixture was diluted with toluene (10 mL) and then concentrated under reduced pressure. The residue was diluted with toluene (10 mL) and then concentrated under reduced pressure again to remove DMA. The residue was purified by NH silica gel chromatography to give a yellow syrup. The residue was dissolved in MeOH (10 mL) and then treated with a 4 N HCl (5 mL). The resulting solution was stirred for 30 min at rt. The solution was concentrated under reduced pressure. The residue was dissolved in MeOH (2 mL) and then diluted with THF (5 mL) and diisopropyl ether (30 mL). The resulting suspension was sonicated and then concentrated under reduced pressure to obtain N-[3-(1H-imidazol-2-yl)propyl]-2-[4-(morpholin-4-yl)piperidin-1-yl]-3-phenylquinoxaline-6-carboxamide dihydrochloride (144 mg, 93%). $^1$H NMR (300 MHz, DMSO-d$_6$) δ 1.63-1.84 (m, 2H), 2.03 (m, J=7.1 Hz, 4H), 2.79 (t, J=12.5 Hz, 2H), 3.01 (t, J=7.6 Hz, 2H), 3.22-3.42 (m, 7H), 3.77-3.97 (m, 6H), 6.55 (s, 1H), 7.48-7.65 (m, 5H), 7.82 (d, J=8.7 Hz, 1H), 7.97 (dd, J=7.8, 1.7 Hz, 2H), 8.14 (dd, J=8.7, 2.0 Hz, 1H), 8.49 (d, J=1.9 Hz, 1H), 8.89 (t, J=5.6 Hz, 1H), 14.16 (br s, 1H).

The compounds listed in the table below were prepared in an analogous fashion to that described above starting from the appropriate starting materials:

| Starting Material Step 4 | Compound No. or Name | LCMS Data |
|---|---|---|
| 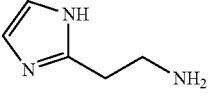 | I-71 | LCMS (ESI+): m/z = 512.2 (M + H) |

Example 8: 2,3-Bis(4-fluorophenyl)-N-[2-(1H-imidazol-2-yl)ethyl]quinoxaline-6-carboxamide (I-122)

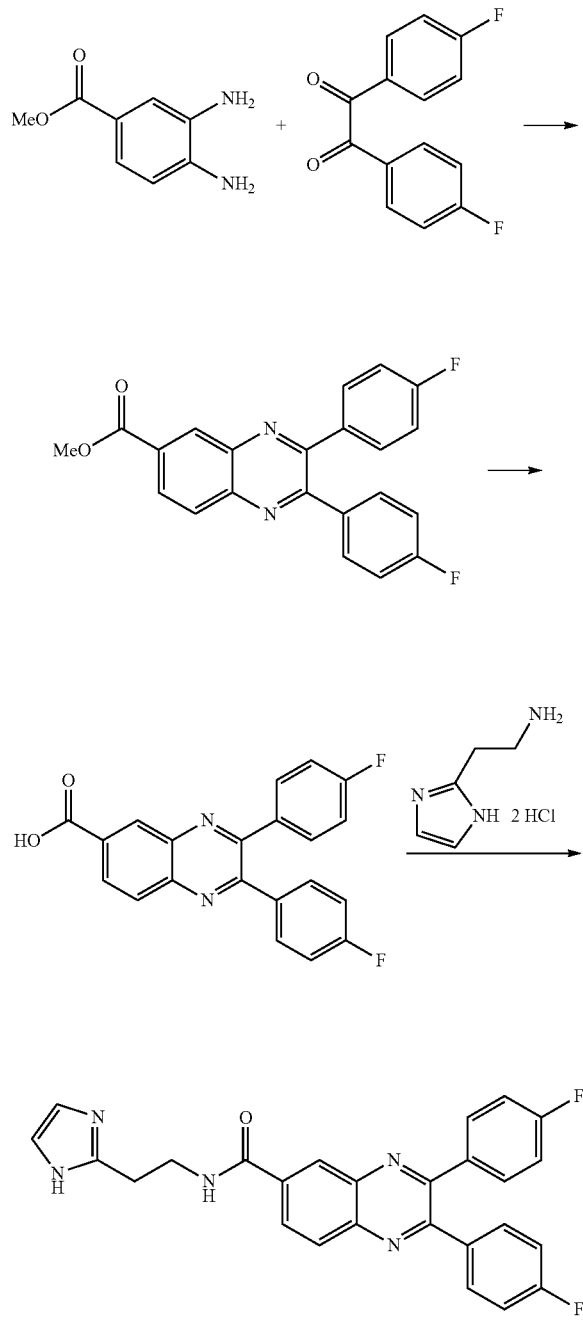

Step 1: Methyl 2,3-bis(4-fluorophenyl)quinoxaline-6-carboxylate

A solution of acetic acid (1.04 mL, 19.3 mmol) and methyl 3,4-diaminobenzoate (3.21 g, 19.3 mmol) and 1,2-bis(4-fluorophenyl)ethane-1,2-dione (5 g, 20.3 mmol) in toluene (40 mL) was refluxed for 2 h. The mixture was stirred at 90° C. overnight. The mixture was quenched with sat. NaHCO₃ aq. at rt and extracted with EtOAc. The organic layer was separated, washed with brine, dried over MgSO₄ and concentrated in vacuo. The residue was washed with EtOAc and dried in vacuo to give methyl 2,3-bis(4-fluorophenyl)quinoxaline-6-carboxylate (5.60 g, 77%) as an off-white solid. LCMS(ESI+): m/z=377.2 (M+H).

Step 2: 2,3-Bis(4-fluorophenyl)quinoxaline-6-carboxylic acid

To a solution of methyl 2,3-bis(4-fluorophenyl)quinoxaline-6-carboxylate (2.5 g, 6.64 mmol) in MeOH (20 mL) and THF (40 mL) was added NaOH (2 M in water, 6.64 mL, 13.3 mmol) at rt. The mixture was stirred at 50° C. for 1 h. The mixture was quenched with 1 N HCl aq. at 0° C. The resulting precipitate was collected by filtration and washed with water and dried in vacuo to give 2,3-bis(4-fluorophenyl)quinoxaline-6-carboxylic acid (2.34 g, 97%) as a white solid. LCMS (ESI+): m/z=363.2 (M+H).

Step 3: 2,3-Bis(4-fluorophenyl)-N-[2-(1H-imidazol-2-yl)ethyl]quinoxaline-6-carboxamide To a solution of 2,3-bis(4-fluorophenyl)quinoxaline-6-carboxylic acid (6.00 g, 16.6 mmol) and DIPEA (8.56 g, 66.4 mmol) in DMF (100 mL) was added HATU (9.46 g, 24.9 mmol) at 0° C. After it was stirred for 30 min at 0° C., [2-(1H-imidazol-2-yl)ethyl]amine dihydrochloride (3.34 g, 18.2 mmol) was added to the mixture. The mixture was stirred at 25-30° C. for 16 h. Then, NaOH (20% in water, 60 mL) was added to the reaction mixture and it was stirred for 0.5 h at 25° C. The mixture was diluted with H₂O (300 mL) and the suspension was filtered. The filter cake was washed with H₂O (100 mL×3) and dried in vacuo to give the crude product. It was washed with petroleum ether/EtOAc (2/1, 300 mL) and then recrystallized from DMSO/H₂O (80 mL/1600 mL) to give yellow solid. The obtained solid was dissolved in THF (100 mL), EtOAc (100 mL) and DMF (100 mL). The insoluble material was removed by filtration, and poured into sat. NaHCO₃ aq. and extracted with EtOAc. The organic layer was separated, washed with water and brine, dried over MgSO₄ and concentrated in vacuo. The resultant solid was washed with EtOH to give a white solid. A solution of obtained solid in DMSO (60 mL) was added dropwise to ice-cooled water (500 mL). The mixture was stirred at 0° C. for 30 min. The precipitate was collected by filtration, and washed with cold water and dried in vacuo to give 2,3-bis(4-fluorophenyl)-N-[2-(1H-imidazol-2-yl)ethyl]quinoxaline-6-carboxamide (3.35 g, 44%) as off-white solid. LCMS (ESI+): m/z=456.1 (M+H). $^1$H NMR (300 MHz, DMSO-$d_6$) δ 2.84-3.06 (m, 2H), 3.52-3.77 (m, 2H), 6.91 (s, 2H), 7.08-7.35 (m, 4H), 7.43-7.72 (m, 4H), 8.09-8.39 (m 2H), 8.66 (d, J=1.5 Hz, 1H), 9.03 (t, J=5.5 Hz, 1H), 11.85 (br s, 1H).

The compounds listed in the table below were prepared in an analogous fashion to that described above starting from the appropriate starting materials:

| Starting Material Step 1 | Starting Material Step 3 | Compound No. or Name | LCMS Data |
|---|---|---|---|
| 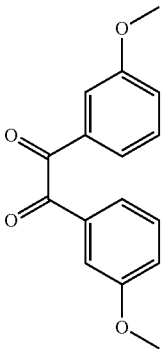 | 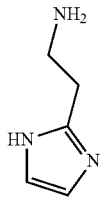 | I-134* | LCMS (ESI+): m/z = 480.2 (M + H) |
| 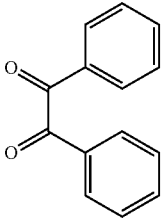 [SMILES: O=C(C(=O)c1ccccc1)c1ccccc1] | 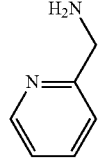 | I-76* | LCMS (ESI+): m/z = 417.1 (M + H) |
| 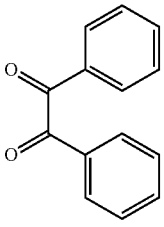 [SMILES: O=C(C(=O)c1ccccc1)c1ccccc1] | 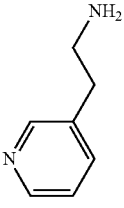 | I-93* | LCMS (ESI+): m/z = 431.1 (M + H) |
| 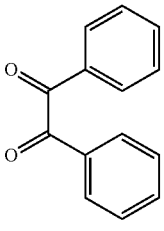 [SMILES: O=C(C(=O)c1ccccc1)c1ccccc1] | 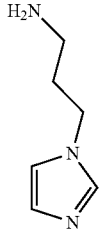 | I-261* | LCMS (ESI+): m/z = 434.1 (M + H) |
| 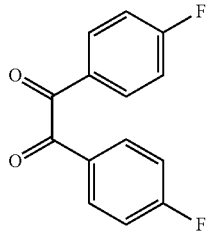 [SMILES: O=C(C(=O)c1ccc(F)cc1)c1ccc(F)cc1] | 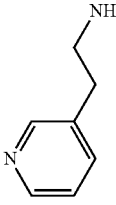 | I-269* | LCMS (ESI+): m/z = 467.1 (M + H) |
| 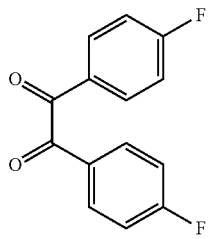 [SMILES: O=C(C(=O)c1ccc(F)cc1)c1ccc(F)cc1] | 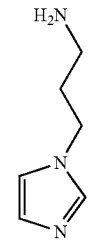 | I-19* | LCMS (ESI+): m/z = 470.1 (M + H) |

-continued
| Starting Material Step 1 | Starting Material Step 3 | Compound No. or Name | LCMS Data |
|---|---|---|---|
| 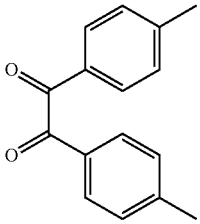 | 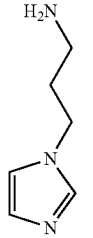 | I-214* | LCMS (ESI+): m/z = 462.2 (M + H) |
| 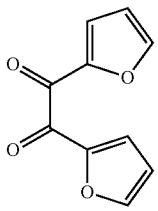 [SMILES: O=C(C(=O)c1ccco1)c1ccco1] | 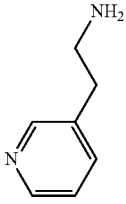 | I-117* | LCMS (ESI+): m/z = 411.1 (M + H) |
| 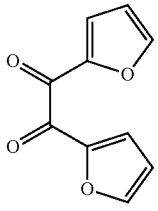 [SMILES: O=C(C(=O)c1ccco1)c1ccco1] |  | I-107* | LCMS (ESI+): m/z = 414.1 (M + H) |
| 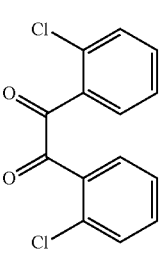 [SMILES: O=C(C(=O)c1ccccc1Cl)c1ccccc1Cl] | 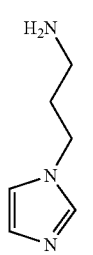 | I-260* | LCMS (ESI+): m/z = 502.1 (M + H) |
| 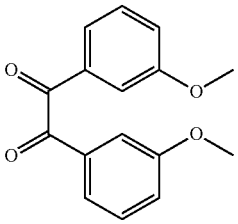 | 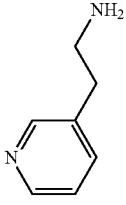 | I-181* | LCMS (ESI+): m/z = 491.2 (M + H) |
| 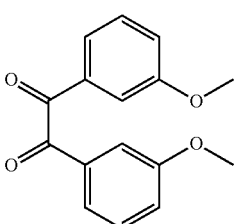 | 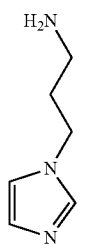 | I-52* | LCMS (ESI+): m/z = 494.2 (M + H) |

-continued

| Starting Material Step 1 | Starting Material Step 3 | Compound No. or Name | LCMS Data |
|---|---|---|---|
| benzil (1,2-diphenylethane-1,2-dione) | 2-(1H-imidazol-4-yl)ethan-1-amine | I-118 | LCMS (ESI+): m/z = 420.1 (M + H) |
| 1,2-bis(4-fluorophenyl)ethane-1,2-dione | 2-(1-methyl-1H-pyrazol-3-yl)ethan-1-amine | I-108 | LCMS (ESI+): m/z = 470.1 (M + H) |
| 1,2-bis(4-fluorophenyl)ethane-1,2-dione | 1-methyl-4,5,6,7-tetrahydro-1H-pyrrolo[3,2-c]pyridine | I-303 | LCMS (ESI+): m/z = 481.1 (M + H) |
| 1,2-bis(4-fluorophenyl)ethane-1,2-dione | 4-(piperidin-4-yl)pyridine | I-186 | LCMS (ESI+): m/z = 507.2 (M + H) |
| 1,2-bis(4-fluorophenyl)ethane-1,2-dione | N-methyl-1-(pyridin-2-yl)pyrrolidin-3-amine | I-163 | LCMS (ESI+): m/z = 493.2 (M + H) |
| 1,2-bis(4-fluorophenyl)ethane-1,2-dione | 3-(pyridazin-4-yl)propan-1-amine | I-229 | LCMS (ESI+): m/z = 481.2 (M + H) |

-continued
| Starting Material Step 1 | Starting Material Step 3 | Compound No. or Name | LCMS Data |
|---|---|---|---|
| 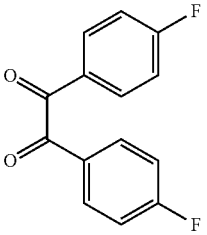 [SMILES: O=C(C(=O)c1ccc(F)cc1)c1ccc(F)cc1] | 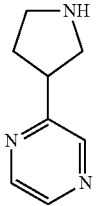 | I-40 | LCMS (ESI+): m/z = 494.0 (M + H) |
| 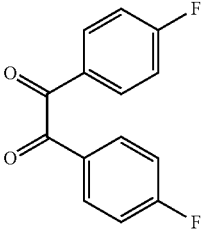 [SMILES: O=C(C(=O)c1ccc(F)cc1)c1ccc(F)cc1] | 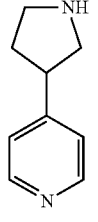 | I-98 | LCMS (ESI+): m/z = 493.2 (M + H) |
| 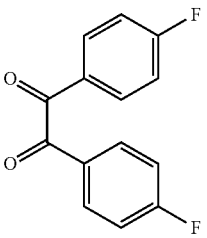 [SMILES: O=C(C(=O)c1ccc(F)cc1)c1ccc(F)cc1] | 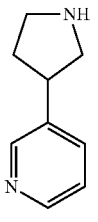 [SMILES: c1cncc(C2CCNC2)c1] | I-29 | LCMS (ESI+): m/z = 493.2 (M + H) |
|  | 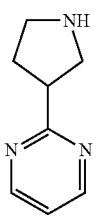 [SMILES: c1cnc(C2CCNC2)nc1] | I-294 | LCMS (ESI+): m/z = 494.1 (M + H) |
| 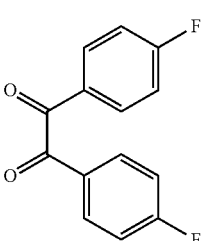 | 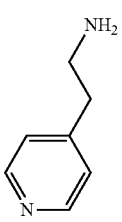 | I-212 | LCMS (ESI+): m/z = 467.1 (M + H) |
| 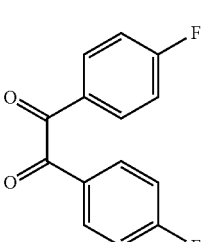 | 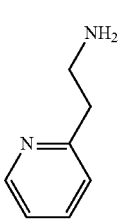 | I-169 | LCMS (ESI+): m/z = 467.1 (M + H) |

-continued
| Starting Material Step 1 | Starting Material Step 3 | Compound No. or Name | LCMS Data |
|---|---|---|---|
| 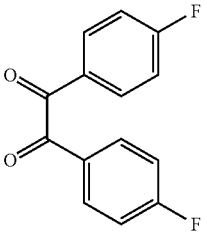 [SMILES: O=C(C(=O)c1ccc(F)cc1)c1ccc(F)cc1] | 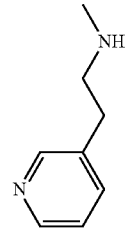 | I-84 | LCMS (ESI+): m/z = 481.1 (M + H) |
| 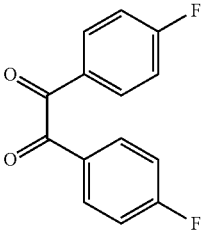 [SMILES: O=C(C(=O)c1ccc(F)cc1)c1ccc(F)cc1] | 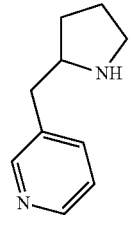 [SMILES: c1cncc(CC2CCCN2)c1] | I-246 | LCMS (ESI+): m/z = 507.2 (M + H) |
| 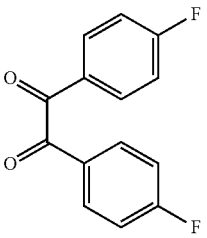 [SMILES: O=C(C(=O)c1ccc(F)cc1)c1ccc(F)cc1] | 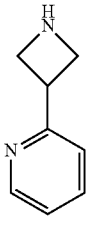 | I-110 | LCMS (ESI+): m/z = 479.1 (M + H) |
| 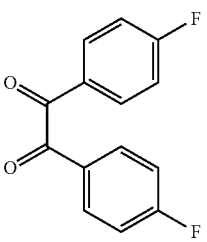 [SMILES: O=C(C(=O)c1ccc(F)cc1)c1ccc(F)cc1] |  | I-160 | LCMS (ESI+): m/z = 479.1 (M + H) |
| 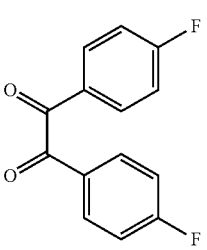 [SMILES: O=C(C(=O)c1ccc(F)cc1)c1ccc(F)cc1] | 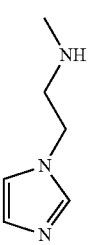 | I-279 | LCMS (ESI+): m/z = 470.1 (M + H) |
| 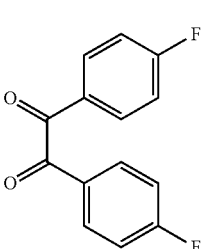 | 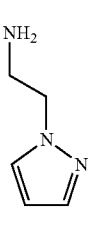 | I-83 | LCMS (ESI+): m/z = 456.1 (M + H) |

-continued
| Starting Material Step 1 | Starting Material Step 3 | Compound No. or Name | LCMS Data |
|---|---|---|---|
| 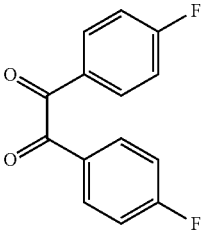 [SMILES: O=C(C(=O)c1ccc(F)cc1)c1ccc(F)cc1] | 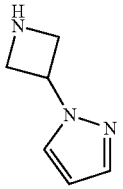 | I-249 | LCMS (ESI+): m/z = 468.1 (M + H) |
| 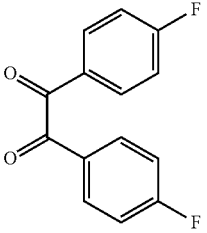 [SMILES: O=C(C(=O)c1ccc(F)cc1)c1ccc(F)cc1] | 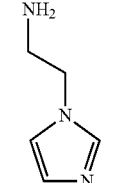 | I-270 | LCMS (ESI+): m/z = 456.1 (M + H) |
| 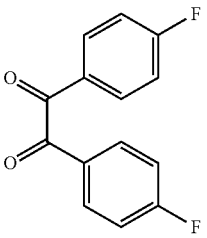 [SMILES: O=C(C(=O)c1ccc(F)cc1)c1ccc(F)cc1] | 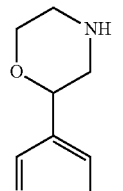 | I-155 | LCMS (ESI+): m/z = 509.2 (M + H) |
|  | 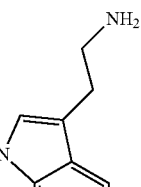 | I-293 | LCMS (ESI+): m/z = 505.1 (M + H) |
| 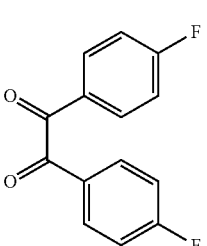 | 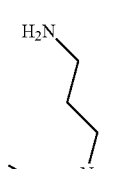 | I-57 | LCMS (ESI+): m/z = 484.2 (M + H) |
| 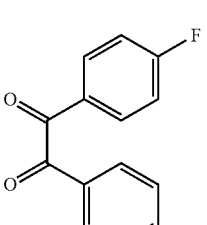 | 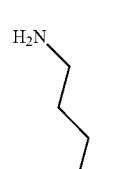 | I-178 | LCMS (ESI+): m/z = 470.2 (M + H) |

-continued
| Starting Material Step 1 | Starting Material Step 3 | Compound No. or Name | LCMS Data |
|---|---|---|---|
| 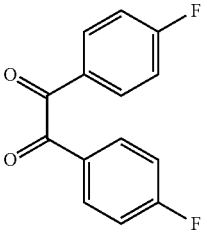 [SMILES: O=C(C(=O)c1ccc(F)cc1)c1ccc(F)cc1] | 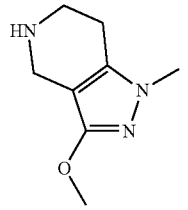 | I-304 | LCMS (ESI+): m/z = 512.1 (M + H) |
| 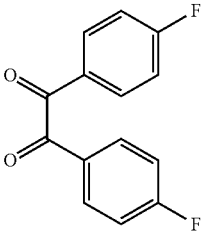 [SMILES: O=C(C(=O)c1ccc(F)cc1)c1ccc(F)cc1] | 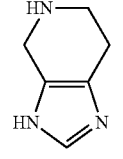 | I-121 | LCMS (ESI+): m/z = 468.2 (M + H) |
| 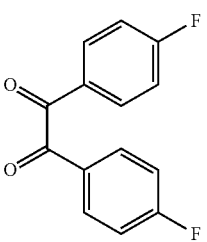 [SMILES: O=C(C(=O)c1ccc(F)cc1)c1ccc(F)cc1] | 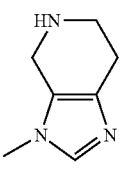 | I-33 | LCMS (ESI+): m/z = 482.2 (M + H) |
| 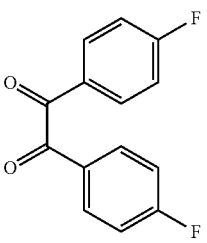 [SMILES: O=C(C(=O)c1ccc(F)cc1)c1ccc(F)cc1] | 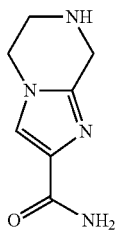 | I-123 | LCMS (ESI+): m/z = 511.1 (M + H) |
| 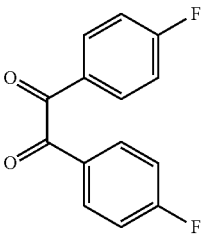 [SMILES: O=C(C(=O)c1ccc(F)cc1)c1ccc(F)cc1] | 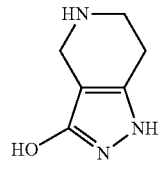 | I-285 | LCMS (ESI+): m/z = 484.2 (M + H) |
| 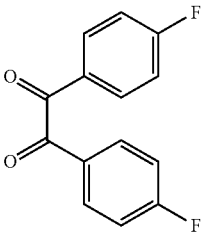 [SMILES: O=C(C(=O)c1ccc(F)cc1)c1ccc(F)cc1] | 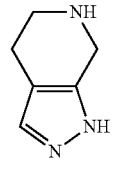 | I-244 | LCMS (ESI+): m/z = 468.2 (M + H) |

-continued
| Starting Material Step 1 | Starting Material Step 3 | Compound No. or Name | LCMS Data |
|---|---|---|---|
| 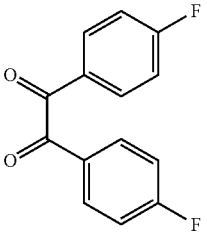 [SMILES: O=C(C(=O)c1ccc(F)cc1)c1ccc(F)cc1] | 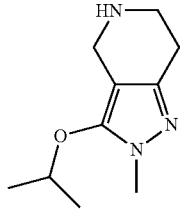 | I-284 | LCMS (ESI+): m/z = 540.3 (M + H) |
| 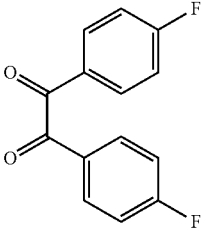 [SMILES: O=C(C(=O)c1ccc(F)cc1)c1ccc(F)cc1] | 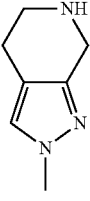 | I-22 | LCMS (ESI+): m/z = 482.1 (M + H) |
| 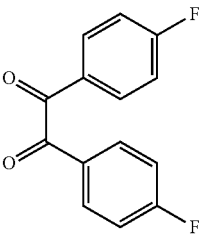 [SMILES: O=C(C(=O)c1ccc(F)cc1)c1ccc(F)cc1] | 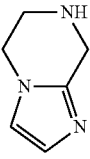 | I-56 | LCMS (ESI+): m/z = 468.2 (M + H) |
|  | 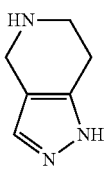 | I-225 | LCMS (ESI+): m/z = 468.2 (M + H) |
| 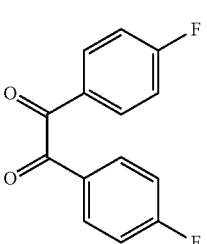 | 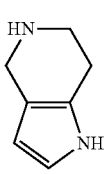 | I-75 | LCMS (ESI+): m/z = 467.1 (M + H) |
| 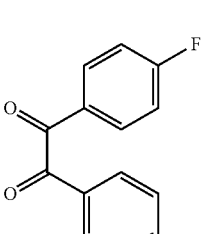 | 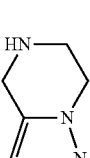 | I-28 | LCMS (ESI+): m/z = 469.2 (M + H) |

-continued
| Starting Material Step 1 | Starting Material Step 3 | Compound No. or Name | LCMS Data |
|---|---|---|---|
| 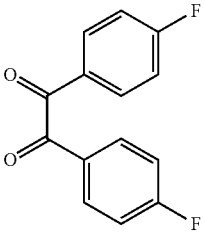 [SMILES: O=C(C(=O)c1ccc(F)cc1)c1ccc(F)cc1] | 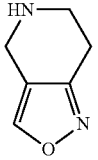 | I-266 | LCMS (ESI+): m/z = 469.2 (M + H) |
| 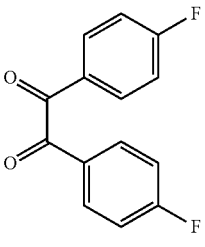 [SMILES: O=C(C(=O)c1ccc(F)cc1)c1ccc(F)cc1] | 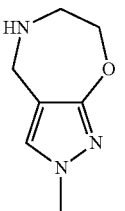 | I-68 | LCMS (ESI+): m/z = 498.2 (M + H) |
| 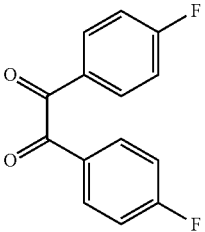 [SMILES: O=C(C(=O)c1ccc(F)cc1)c1ccc(F)cc1] | 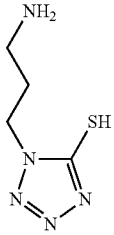 | I-8 | LCMS (ESI+): m/z = 504.1 (M + H) |
| 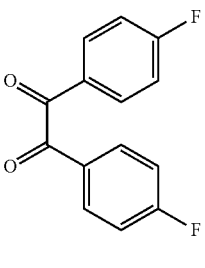 [SMILES: O=C(C(=O)c1ccc(F)cc1)c1ccc(F)cc1] | 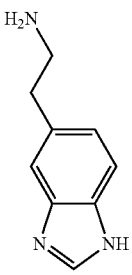 | I-43 | LCMS (ESI+): m/z = 506.2 (M + H) |
| 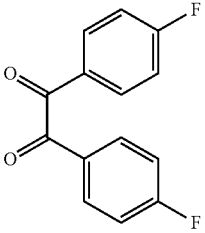 [SMILES: O=C(C(=O)c1ccc(F)cc1)c1ccc(F)cc1] | 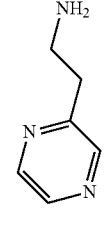 | I-184 | LCMS (ESI+): m/z = 468.2 (M + H) |
| 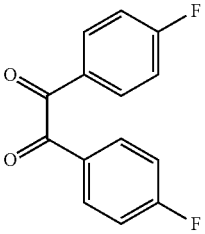 [SMILES: O=C(C(=O)c1ccc(F)cc1)c1ccc(F)cc1] | 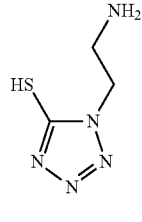 | I-139 | LCMS (ESI+): m/z = 490.1 (M + H) |

-continued
| Starting Material Step 1 | Starting Material Step 3 | Compound No. or Name | LCMS Data |
|---|---|---|---|
| 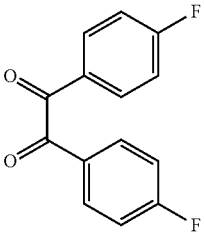 [SMILES: O=C(C(=O)c1ccc(F)cc1)c1ccc(F)cc1] | 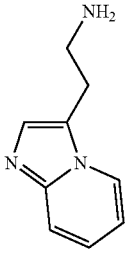 [SMILES: NCCc1cnc2ccccn12] | I-302 | LCMS (ESI+): m/z = 506.1 (M + H) |
| 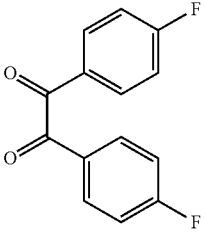 [SMILES: O=C(C(=O)c1ccc(F)cc1)c1ccc(F)cc1] | 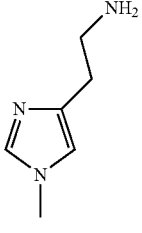 | I-276 | LCMS (ESI+): m/z = 470.1 (M + H) |
| 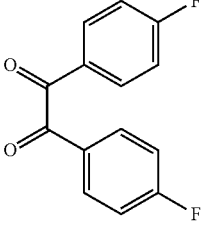 | 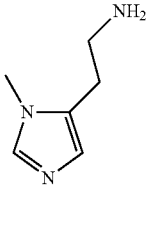 | I-53 | LCMS (ESI+): m/z = 470.1 (M + H) |
| 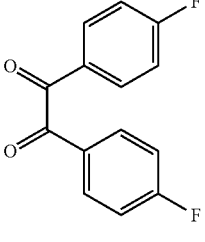 | 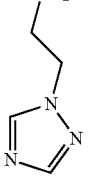 | I-237 | LCMS (ESI+): m/z = 457.2 (M + H) |
| 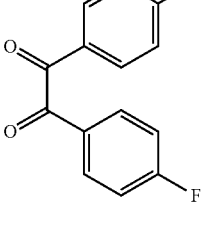 | 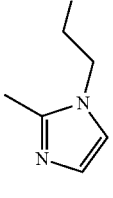 | I-26 | LCMS (ESI+): m/z = 470.1 (M + H) |
| 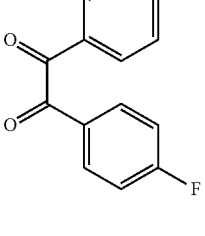 | 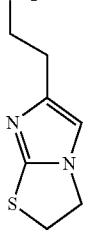 | I-238 | LCMS (ESI+): m/z = 514.1 (M + H) |

-continued

| Starting Material Step 1 | Starting Material Step 3 | Compound No. or Name | LCMS Data |
|---|---|---|---|
| 1,2-bis(4-fluorophenyl)ethane-1,2-dione | 2-(1H-imidazol-5-yl)ethan-1-amine | I-20 | LCMS (ESI+): m/z = 456.1 (M + H) |
| 1,2-bis(4-fluorophenyl)ethane-1,2-dione | 3-(1-methyl-1H-imidazol-2-yl)propan-1-amine | I-234 | LCMS (ESI+): m/z = 484.2 (M + H) |
| 1,2-bis(4-fluorophenyl)ethane-1,2-dione | 2-(pyridin-3-yloxy)ethan-1-amine | I-65 | LCMS (ESI+): m/z = 483.2 (M + H) |
| 1,2-bis(4-fluorophenyl)ethane-1,2-dione | imidazo[1,2-a]pyridin-6-ylmethanamine | I-299 | LCMS (ESI+): m/z = 492.2 (M + H) |

*EDCI and HOBT were used in place of HATU.

Step 1a: Alternative procedure for preparation of Methyl-2,3-bis(4-fluorophenyl)quinoxaline-6-carboxylate A mixture of methyl 3,4-diaminobenzoate (0.0702 g, 0.422 mmol) and 1,2-bis(4-fluorophenyl)ethane-1,2-dione (0.104 g, 0.422 mmol) and iodine (0.0107 g, 0.0422 mmol) in DMSO (0.5 mL) was stirred at rt for 4 h. The reaction mixture was poured into ice water and stirred for 10 min. The solid was collected by filtration and washed with 10% aqueous sodium thiosulfate solution followed by water, then dried under vacuum to give methyl 2,3-bis(4-fluorophenyl)quinoxaline-6-carboxylate (0.133 g, 84%) as a light brown solid. LCMS(ESI+): m/z=377.2 (M+H).

The compounds listed in the table below were prepared in an analogous fashion to that described in Example 8 starting from the appropriate starting materials:

| Starting Material Step 1 | Starting Material Step 3 | Compound No. or Name | LCMS Data |
|---|---|---|---|
| 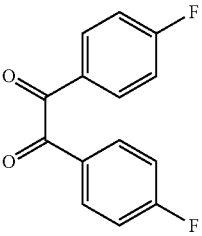 [SMILES: O=C(C(=O)c1ccc(F)cc1)c1ccc(F)cc1] | 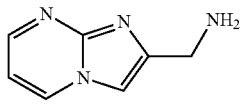 [SMILES: NCc1cn2cccnc2n1] | I-408*** | LCMS (ESI+): m/z = 493.2 (M + H) |
| 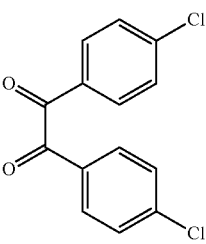 [SMILES: O=C(C(=O)c1ccc(Cl)cc1)c1ccc(Cl)cc1] | 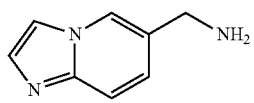 [SMILES: NCc1ccc2nccn2c1] | I-487, * | LCMS (ESI+): m/z = 524.1 (M + H) |
| 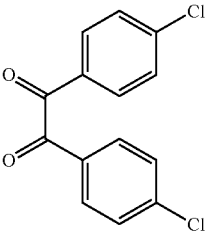 | 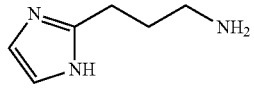 | I-315, * | LCMS (ESI+): m/z = 502.1 (M + H) |
| 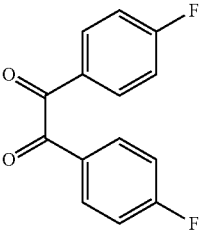 [SMILES: O=C(C(=O)c1ccc(F)cc1)c1ccc(F)cc1] | 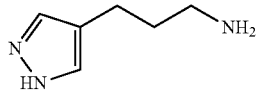 | I-508*** | LCMS (ESI+): m/z = 470 (M + H) |
| 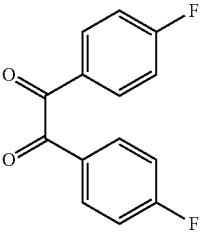 [SMILES: O=C(C(=O)c1ccc(F)cc1)c1ccc(F)cc1] | 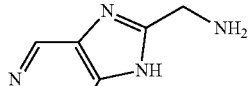 | I-464*** | LCMS (ESI+): m/z = 493.5 (M + H) |
*EDCI and HOBT were used in place of HATU
**Step 1a was used in synthetic sequence starting from the corresponding diketone
***DMA solvent and TEA base used as base in Step 3

Example 9: 3-[4-(Aminomethyl)phenyl]-2-phenyl-N-[2-(pyridin-3-yl)ethyl]quinoxaline-6-carboxamide (I-286)

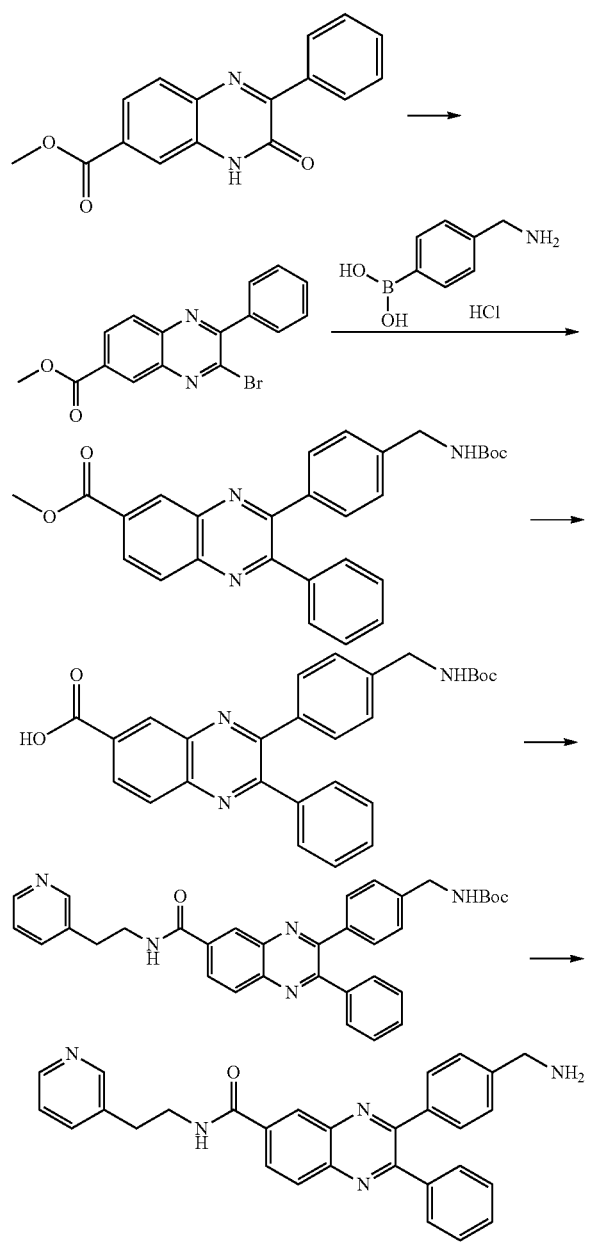

Step 1: Methyl 3-bromo-2-phenylquinoxaline-6-carboxylate

A solution of methyl 3-oxo-2-phenyl-3,4-dihydroquinoxaline-6-carboxylate (18.5 g, 66.1 mmol) (prepared according to Example 2, step 5) and POBr$_3$ (185 g, 645.3 mmol) in MeCN (400 mL) was heated under reflux for 18 h. After being cooled to rt, the resulting mixture was concentrated under reduced pressure. The residue was diluted with DCM and poured into ice-water. The resulting mixture was neutralized to a pH of 7-8 with saturated aqueous NaHCO$_3$ and then extracted with DCM. The combined organic layers were washed with brine, dried over Na$_2$SO$_4$, filtered and concentrated under reduced pressure. The resulting solid was washed with petroleum ether and dried in vacuum to give methyl 3-bromo-2-phenylquinoxaline-6-carboxylate (21.0 g, 92%) as off-white solid. $^1$H NMR (300 MHz, CDCl$_3$) δ 4.03 (s, 3H), 7.54-7.56 (m, 3H), 7.83-7.85 (m, 2H), 8.19 (d, J=8.8 Hz, 1H), 8.41 (dd, J=2.0, 8.8 Hz, 1H), 8.79 (d, J=1.6 Hz, 1H).

Step 2: Methyl 3-(4-(((tert-butoxycarbonyl)amino)methyl)phenyl)-2-phenylquinoxaline-6-carboxylate A mixture of cesium carbonate (1.42 g, 4.37 mmol), dichloro[1,1'-bis(diphenylphosphino)ferrocene]palladium dichloromethane adduct (119 mg, 0.15 mmol), methyl 3-bromo-2-phenylquinoxaline-6-carboxylate (500 mg, 1.46 mmol) and (4-(aminomethyl)phenyl)boronic acid hydrochloride (410 mg, 2.19 mmol) in DME (10 mL) and water (1.00 mL) was heated at 130° C. for 30 min under microwave irradiation. The mixture was cooled to rt and Boc$_2$O (0.507 mL, 2.19 mmol) was added. The mixture was stirred for 2 h. The mixture was quenched with sat. NaHCO$_3$ aq. and extracted with EtOAc. The organic layer was separated, washed with water and brine, dried over MgSO$_4$ and concentrated in vacuo. The residue was purified by NH silica gel chromatography to give methyl 3-(4-(((tert-butoxycarbonyl)amino)methyl)phenyl)-2-phenylquinoxaline-6-carboxylate (240 mg, 35%) as a white solid. LCMS (ESI+): m/z=470.2 (M+H).

Step 3: 3-(4-(((tert-Butoxycarbonyl)amino)methyl)phenyl)-2-phenylquinoxaline-6-carboxylic acid To a solution of methyl 3-(4-(((tert-butoxycarbonyl)amino)methyl)phenyl)-2-phenylquinoxaline-6-carboxylate (230 mg, 0.49 mmol) in MeOH (3.00 mL) and THF (3.00 mL) was added NaOH (2 M in water, 0.490 mL, 0.98 mmol) at rt. The mixture was stirred at rt overnight. 1 N HCl was added to bring the pH of the solution to 2-3. The precipitate solid was collected by filtration and washed with water and dried in vacuo to give 3-(4-(((tert-butoxycarbonyl)amino)methyl)phenyl)-2-phenylquinoxaline-6-carboxylic acid (195 mg, 88%) as an off-white solid. LCMS (ESI+): m/z=456.2 (M+H).

Step 4: tert-Butyl 4-(3-phenyl-7-((2-(pyridin-3-yl)ethyl)carbamoyl)quinoxalin-2-yl)benzylcarbamate HATU (87 mg, 0.23 mmol) was added to a solution of DIPEA (0.092 mL, 0.53 mmol), 2-(pyridin-3-yl)ethanamine (0.023 mL, 0.19 mmol) and 3-(4-(((tert-butoxycarbonyl)amino)methyl)phenyl)-2-phenylquinoxaline-6-carboxylic acid (80 mg, 0.18 mmol) in DMF (3 mL) at rt. The mixture was stirred at rt overnight. The mixture was quenched with sat. NaHCO$_3$ aq. and extracted with EtOAc. The organic layer was separated, washed with water and brine, dried over MgSO$_4$ and concentrated in vacuo. The resultant solid was washed with $^i$Pr$_2$O and dried in vacuo to give tert-butyl 4-(3-phenyl-7-((2-(pyridin-3-yl)ethyl)carbamoyl)quinoxalin-2-yl)benzylcarbamate (85 mg, 87%) as a white powder. LCMS (ESI+): m/z=560.3 (M+H).

Step 5: 3-(4-(Aminomethyl)phenyl)-2-phenyl-N-(2-(pyridin-3-yl)ethyl)quinoxaline-6-carboxamide To tert-butyl 4-(3-phenyl-7-((2-(pyridin-3-yl)ethyl)carbamoyl)quinoxalin-2-yl)benzylcarbamate (80 mg, 0.14 mmol) was added HCl (4 M in EtOAc, 5 mL, 20.00 mmol) at rt. The mixture was stirred at rt for 2 h. The solvent was removed. The resultant solid was dissolved in EtOAc, poured into sat. NaHCO₃ aq. and extracted with EtOAc. The organic layer was separated, washed with water and brine, dried over MgSO₄ and concentrated in vacuo to give 3-(4-(aminomethyl)phenyl)-2-phenyl-N-(2-(pyridin-3-yl)ethyl)quinoxaline-6-carboxamide (32.8 mg, 50%) as a white solid. LCMS (ESI+): m/z=460.2 (M+H). ¹H NMR (300 MHz, CDCl₃) δ 3.03 (t, J=7.0 Hz, 2H), 3.82 (q, J=6.8 Hz, 2H), 3.91 (s, 2H), 6.44 (br s, 1H), 7.27-7.32 (m, 3H), 7.33-7.44 (m, 3H), 7.44-7.58 (m, 4H), 7.59-7.67 (m, 1H), 8.09-8.29 (m, 2H), 8.40 (d, J=1.7 Hz, 1H), 8.47-8.64 (m, 2H).

Example 10: tert-Butyl [4-(7-{[3-(1H-imidazol-1-yl)propyl]carbamoyl}-3-phenylquinoxalin-2-yl)benzyl]carbamate (I-63)

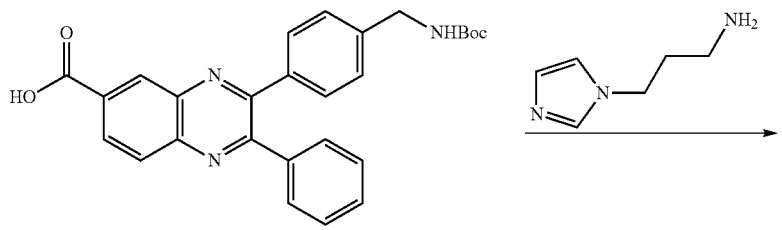

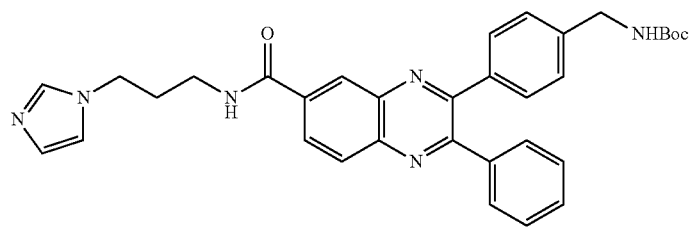

HATU (351 mg, 0.92 mmol) was added to a solution of DIPEA (0.403 mL, 2.31 mmol), N-(3-aminopropyl)imidazole (0.110 mL, 0.92 mmol) and 3-(4-(((tert-butoxycarbonyl)amino)methyl)phenyl)-2-phenylquinoxaline-6-carboxylic acid (350 mg, 0.77 mmol) (prepared according to Example 9, step 3) in DMF (4 mL) at rt. The mixture was stirred at rt for 30 min. The mixture was quenched with sat. NaHCO₃ aq. and extracted with EtOAc/THF. The organic layer was separated, washed with water and brine, dried over MgSO₄ and concentrated in vacuo. The residue was purified by NH silica gel to give tert-butyl 4-(7-((3-(1H-imidazol-1-yl)propyl)carbamoyl)-3-phenylquinoxalin-2-yl)benzylcarbamate (299 mg, 69%) as an off-white solid. LCMS (ESI+): m/z=563.3 (M+H). ¹H NMR (300 MHz, DMSO-d₆) δ 1.26-1.57 (m, 9H), 1.82-2.19 (m, 2H), 3.08-3.53 (m, 2H), 3.94-4.32 (m, 4H), 6.88-7.02 (m, 1H), 7.13-7.31 (m, 3H), 7.32-7.61 (m, 8H), 7.78 (s, 1H), 8.12-8.37 (m, 2H), 8.57-8.76 (m, 1H), 8.82-9.03 (m, 1H).

Example 11: tert-Butyl [4-(7-{[3-(1H-imidazol-1-yl)propyl]carbamoyl}-3-phenylquinoxalin-2-yl)benzyl]carbamate (I-85)

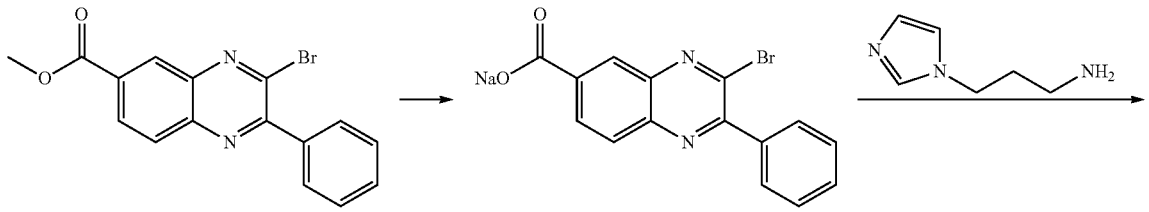

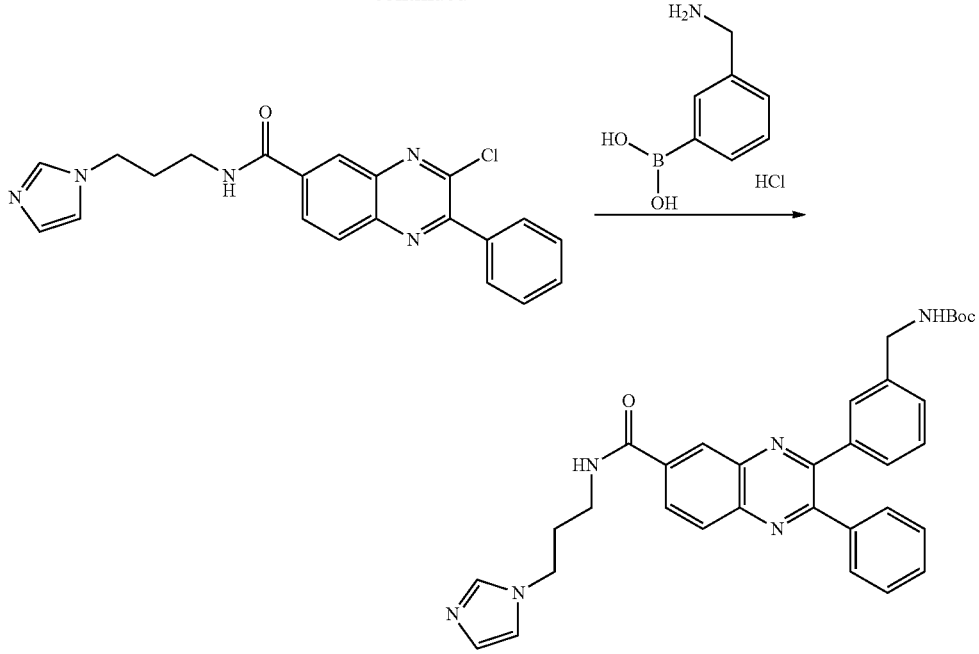

Step 1: Sodium 3-bromo-2-phenylquinoxaline-6-carboxylate

To a solution of methyl 3-bromo-2-phenylquinoxaline-6-carboxylate (5 g, 14.6 mmol) (prepared according to Example 9, step 1) in 2-propanol (70 mL) and THF (70 mL) was added NaOH (2 M in water, 14.6 mL, 29.1 mmol) at rt. The mixture was stirred at 60° C. for 2 h. The mixture was cooled to rt. The resulting precipitate was collected by filtration, and washed with $^{i}Pr_2O$ and dried in vacuo to give sodium 3-bromo-2-phenylquinoxaline-6-carboxylate (4.48 g, 88%) as an off-white solid. $^1$H NMR (300 MHz, DMSO-$d_6$) δ 7.37-7.67 (m, 3H), 7.70-7.88 (m, 2H), 8.00 (d, J=8.4 Hz, 1H), 8.25-8.54 (m, 2H).

Step 2: N-(3-(1H-imidazol-1-yl)propyl)-3-chloro-2-phenylquinoxaline-6-carboxamide To a solution of $SOCl_2$ (4.16 mL, 57.0 mmol) and sodium 3-bromo-2-phenylquinoxaline-6-carboxylate (4.0 g, 11.4 mmol) in THF (100 mL) was added 5 drops of DMF at rt. The mixture was stirred at 40° C. overnight. The mixture was concentrated in vacuo. The resulting off-white solid was dissolved in THF (200 mL), then TEA (4.76 mL, 34.2 mmol) and N-(3-aminopropyl)imidazole (1.63 mL, 13.7 mmol) were added to the mixture. The mixture was stirred at rt for 30 min. The mixture was quenched with sat. $NaHCO_3$ aq. and extracted with EtOAc. The organic layer was separated, washed with water and brine, dried over $MgSO_4$ and concentrated in vacuo. The resultant solid was washed with hexane/$^{i}Pr_2O$=1/1 (100 mL) and dried in vacuo to give N-(3-(1H-imidazol-1-yl)propyl)-3-chloro-2-phenylquinoxaline-6-carboxamide (2.75 g, 62%) as a light brown solid. LCMS (ESI+): m/z=392.2 (M+H).

Step 3: tert-Butyl [3-(7-{[3-(1H-imidazol-1-yl)propyl]carbamoyl}-3-phenylquinoxalin-2-yl)benzyl]carbamate A mixture of cesium carbonate (249 mg, 0.77 mmol), dichloro[1,1'-bis(diphenylphosphino)ferrocene]palladium dichloromethane adduct (20.8 mg, 0.03 mmol), N-(3-(1H-imidazol-1-yl)propyl)-3-chloro-2-phenylquinoxaline-6-carboxamide (100 mg, 0.26 mmol) and (3-(aminomethyl)phenyl)boronic acid hydrochloride (71.7 mg, 0.38 mmol) in DME (4 mL) and water (0.40 mL) was heated at 130° C. for 1 h under microwave irradiation. The mixture was cooled to rt and $Boc_2O$ (0.119 mL, 0.51 mmol) was added. The mixture was stirred overnight. The mixture was quenched with sat. $NaHCO_3$ aq. and extracted with EtOAc. The organic layer was separated, washed with water and brine, dried over $MgSO_4$ and concentrated in vacuo. The residue was purified by NH silica gel chromatography to give. tert-butyl [3-(7-{[3-(1H-imidazol-1-yl)propyl]carbamoyl}-3-phenylquinoxalin-2-yl)benzyl]carbamate (49.1 mg, 34%) as a light brown oil. LCMS (ESI+): m/z=563.3 (M+H). $^1$H NMR (300 MHz, DMSO-$d_6$) δ 1.27-1.51 (m, 9H), 2.00-2.11 (m, 2H), 3.33-3.40 (m, 2H), 4.04-4.21 (m, 4H), 6.90 (s, 1H), 7.12-7.31 (m, 4H), 7.32-7.44 (m, 4H), 7.45-7.54 (m, 2H), 7.58 (s, 1H), 7.69 (s, 1H), 8.14-8.37 (m, 2H), 8.70 (s, 1H), 8.92 (t, J=5.4 Hz, 1H).

The compounds listed in the table below were prepared in an analogous fashion to that described above starting from the appropriate starting materials:

| Starting Material Step 3 | Compound No. or Name | LCMS Data |
|---|---|---|
| ![2-(aminomethyl)phenylboronic acid pinacol ester] | I-217 | LCMS (ESI+): m/z = 563.2 (M + H) |

| Starting Material Step 3 | Compound No. or Name | LCMS Data |
|---|---|---|
| 2-methoxyphenylboronic acid | I-36* | LCMS (ESI+): m/z = 464.2 (M + H) |
| 3-methoxyphenylboronic acid | I-218* | LCMS (ESI+): m/z = 464.2 (M + H) |
| 4-methoxyphenylboronic acid | I-241* | LCMS (ESI+): m/z = 464.2 (M + H) |
| 2,3-dihydrobenzofuran-5-boronic acid | I-252* | LCMS (ESI+): m/z = 476.3 (M + H) |
| 3-(trifluoromethoxy)phenylboronic acid | I-95* | LCMS (ESI+): m/z = 518.1 (M + H) |
| 2-chlorophenylboronic acid | I-281* | LCMS (ESI+): m/z = 468.1 (M + H) |
| 3-chlorophenylboronic acid | I-224* | LCMS (ESI+): m/z = 468.1 (M + H) |
| 2-acetamidophenylboronic acid | I-135* | LCMS (ESI+): m/z = 491.2 (M + H) |
| 3-acetamidophenylboronic acid | I-248* | LCMS (ESI+): m/z = 491.3 (M + H) |

| Starting Material Step 3 | Compound No. or Name | LCMS Data |
|---|---|---|
| 4-acetamidophenyl pinacol boronate | I-223* | LCMS (ESI+): m/z = 491.3 (M + H) |
| thiophene-3-boronic acid | I-174* | LCMS (ESI+): m/z = 440.1 (M + H) |
| thiophene-2-boronic acid | I-236* | LCMS (ESI+): m/z = 440.0 (M + H) |
| 1-methyl-pyrrole-2-boronic acid pinacol ester | I-194* | LCMS (ESI+): m/z = 437.2 (M + H) |
| pyridine-3-boronic acid pinacol ester | I-176* | LCMS (ESI+): m/z = 435.1 (M + H) |
| pyridine-4-boronic acid pinacol ester | I-251* | LCMS (ESI+): m/z = 435.1 (M + H) |
| pyrimidine-5-boronic acid pinacol ester | I-41* | LCMS (ESI+): m/z = 436.2 (M + H) |

| Starting Material Step 3 | Compound No. or Name | LCMS Data |
|---|---|---|
| 3-(methanesulfonamido)phenylboronic acid pinacol ester | I-48* | LCMS (ESI+): m/z = 527.2 (M + H) |
| 3-cyanophenylboronic acid | I-157* | LCMS (ESI+): m/z = 459.2 (M + H) |
| 1-methylpyrazole-3-boronic acid pinacol ester | I-215* | LCMS (ESI+): m/z = 438.1 (M + H) |
| 1-methylpyrazole-4-boronic acid | I-167* | LCMS (ESI+): m/z = 438.1 (M + H) |
| 2,4-dimethylthiazole-5-boronic acid pinacol ester | I-9* | LCMS (ESI+): m/z = 469.2 (M + H) |
| 1-methylbenzimidazole-5-boronic acid | I-143* | LCMS (ESI+): m/z = 488.2 (M + H) |
| N-Boc-indole-5-boronic acid pinacol ester | I-97* | LCMS (ESI+): m/z = 473.2 (M + H) |
| 1H-indole-6-boronic acid | I-227* | LCMS (ESI+): m/z = 473.2 (M + H) |

| Starting Material Step 3 | Compound No. or Name | LCMS Data |
|---|---|---|
| imidazo[1,2-a]pyridine-6-boronic acid | I-69* | LCMS (ESI+): m/z = 474.2 (M + H) |
| 3-carbamoylphenylboronic acid | I-263* | LCMS (ESI+): m/z = 477.2 (M + H) |
| 4-carbamoylphenylboronic acid | I-6* | LCMS (ESI+): m/z = 477.2 (M + H) |
| ethyl 3-(4-boronophenyl)propanoate | I-171* | LCMS (ESI+): m/z = 534.2 (M + H) |
| 3,6-dihydro-2H-pyran-4-boronic acid pinacol ester | I-162* | LCMS (ESI+): m/z = 440.2 (M + H) |
| 1-methyl-1,2,3,6-tetrahydropyridine-4-boronic acid pinacol ester | I-3* | LCMS (ESI+): m/z = 453.2 (M + H) |
| 3,5-dimethoxyphenylboronic acid | I-245* | LCMS (ESI+): m/z = 494.2 (M + H) |
| 4-chlorophenylboronic acid | I-79* | LCMS (ESI+): m/z = 468.2 (M + H) |

*Step 3 conditions: PdCl(amphos), DME, 2M Cs$_2$CO$_3$, 130° C., 1 h microwave irradiation; no Boc protection before workup.
**Step 3 conditions: PdCl$_2$(dppf), DME, 2M K$_2$CO$_3$, 1 h microwave irradiation; no Boc protection before workup.
***Step 3: No Boc protection before workup.

Example 12: 3-[3-(Aminomethyl)phenyl]-N-[3-(1H-imidazol-1-yl)propyl]-2-phenylquinoxaline-6-carboxamide (I-120)

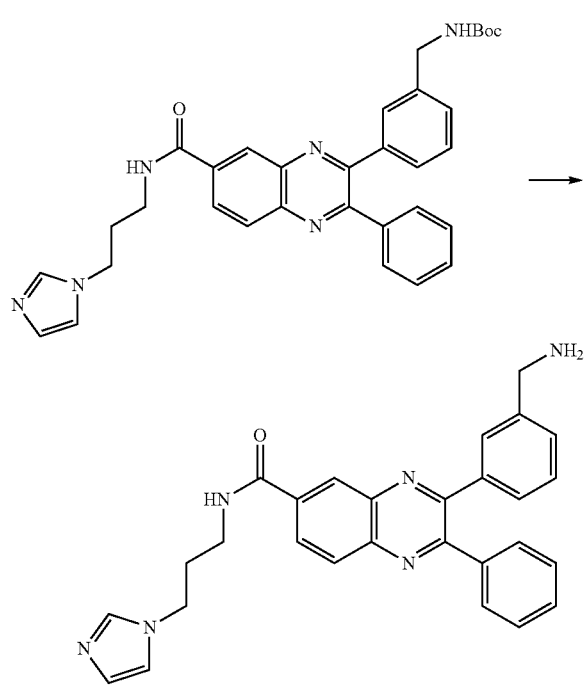

To a solution of tert-butyl 3-(7-((3-(1H-imidazol-1-yl)propyl)carbamoyl)-3-phenylquinoxalin-2-yl)benzylcarbamate (40.2 mg, 0.07 mmol) (prepared according to Example 11, step 3) in MeOH (2 mL) was added HCl (4 M in EtOAc, 5 mL, 0.07 mmol) at rt. The mixture was stirred at rt for 2 h. The mixture was concentrated in vacuo. The resultant solid was dissolved in EtOAc and added sat. $NaHCO_3$ aq. Then the mixture was extracted with EtOAc. The organic layer was separated, washed with brine, dried over $MgSO_4$ and concentrated in vacuo to give 3-[3-(aminomethyl)phenyl]-N-[3-(1H-imidazol-1-yl)propyl]-2-phenylquinoxaline-6-carboxamide (26.5 mg, 80%) as a brown oil. LCMS (ESI+): m/z=463.2 (M+H). $^1$H NMR (300 MHz, DMSO-$d_6$) δ 2.00-2.13 (m, 2H) 3.33-3.42 (m, 2H) 3.70 (s, 2H) 4.04-4.17 (m, 2H) 6.90 (t, J=0.99 Hz, 1H) 7.12-7.74 (m, 11H) 8.13-8.40 (m, 2H) 8.71 (d, J=1.51 Hz, 1H) 8.92 (t, J=5.62 Hz, 1H).

Example 13: 3-(4-Acetylpiperazin-1-yl)-N-[3-(1H-imidazol-1-yl)propyl]-2-phenylquinoxaline-6-carboxamide (I-168)

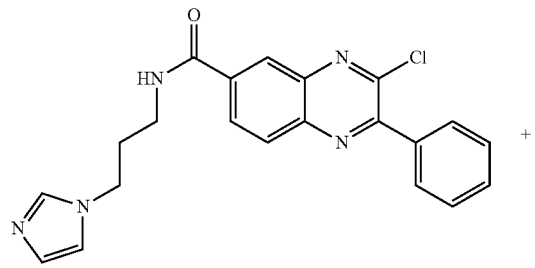

+

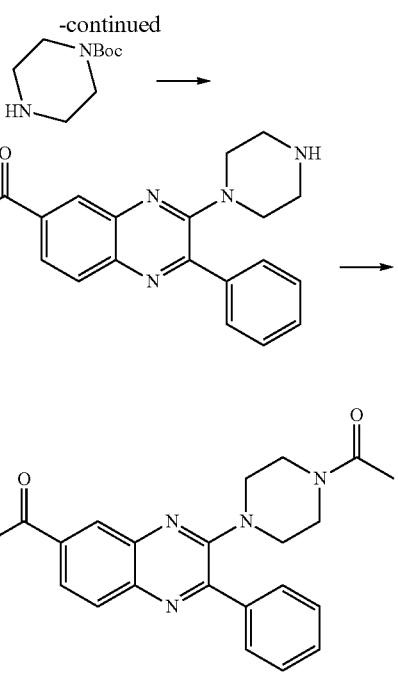

Step 1: N-(3-(1H-imidazol-1-yl)propyl)-2-phenyl-3-(piperazin-1-yl)quinoxaline-6-carboxamide A mixture of DIPEA (0.201 mL, 1.15 mmol), tert-butyl piperazine-1-carboxylate (356 mg, 1.91 mmol), N-(3-(1H-imidazol-1-yl)propyl)-3-chloro-2-phenylquinoxaline-6-carboxamide (150 mg, 0.38 mmol) (prepared according to Example 2, step 9) and 2-propanol (3 mL) was heated 170° C. for 5 h under microwave irradiation. The residual solvent was removed under high vacuum. To the mixture was added TFA (3 mL, 38.94 mmol). The mixture was stirred at rt for 1 h. The residue was directly purified by NH silica gel chromatography to give 3-(benzylamino)-N-[3-(1H-imidazol-1-yl)propyl]-2-phenylquinoxaline-6-carboxamide. (150 mg, 89%) as a yellow solid. LCMS (ESI+): m/z=442.1 (M+H).

Step 2: 3-(4-Acetylpiperazin-1-yl)-N-[3-(1H-imidazol-1-yl)propyl]-2-phenylquinoxaline-6-carboxamide To a solution of TEA (0.025 mL, 0.18 mmol) and N-(3-(1H-imidazol-1-yl)propyl)-2-phenyl-3-(piperazin-1-yl)quinoxaline-6-carboxamide (40 mg, 0.09 mmol) in THF (3 mL) was added AcCl (8.37 µL, 0.12 mmol) at room temperature. The mixture was stirred at room temperature for 20 min. The mixture was quenched with saturated aqueous solution of sat. $NaHCO_3$ aq. and extracted with EtOAc. The organic layer was separated, washed with water and brine, dried over $MgSO_4$ and concentrated in vacuo. The resultant solid was washed with $iPr_2O$ and dried in vacuo to give 3-(4-acetylpiperazin-1-yl)-N-[3-(1H-imidazol-1-yl)propyl]-2-phenylquinoxaline-6-carboxamide (35.7 mg, 81%) as a pale yellow solid. LCMS (ESI+): m/z=484.2 (M+H). $^1$H NMR (300 MHz, CDCl3) δ 2.09 (s, 3H), 2.13-2.25 (m, 2H), 3.19-3.29 (m, 2H), 3.30-3.39 (m, 2H), 3.42-3.69 (m, 6H), 3.91-4.35 (m, 2H), 6.66 (t, J=5.8 Hz, 1H), 7.01 (s, 1H), 7.10 (s, 1H), 7.42-7.66 (m, 4H), 7.84-8.08 (m, 4H), 8.17 (d, J=1.8 Hz, 1H).

Example 14: 2,3-Bis(4-fluorophenyl)-N-[3-(pyridin-2-yl)propyl]quinoxaline-6-carboxamide (I-180)

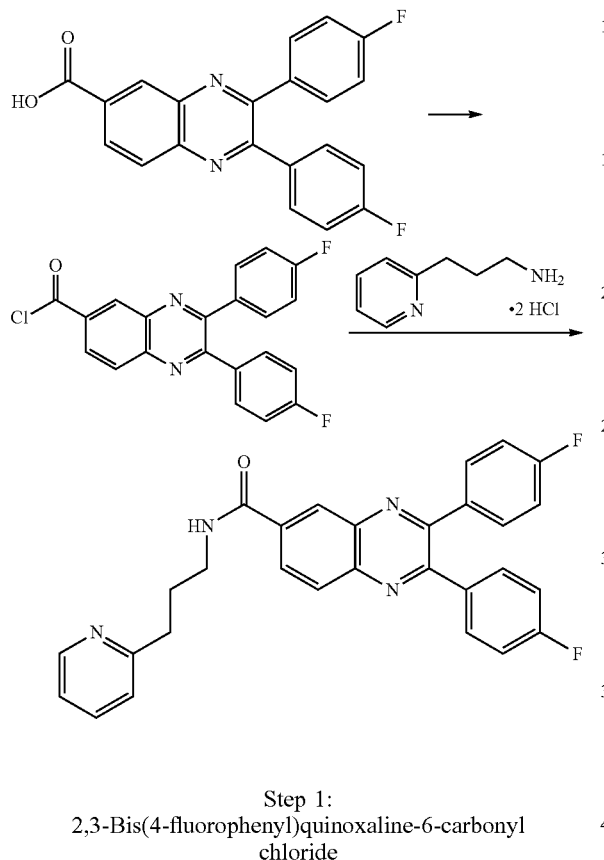

Step 1:
2,3-Bis(4-fluorophenyl)quinoxaline-6-carbonyl chloride

To a solution of SOCl$_2$ (0.435 mL, 5.96 mmol) and 2,3-bis(4-fluorophenyl)quinoxaline-6-carboxylic acid (720 mg, 1.99 mmol) (prepared according to Example 8, step 2) in THF (10 mL) was added 5 drops of DMF at rt. The mixture was stirred at 60° C. for 1 h. The mixture was concentrated in vacuo to give 2,3-bis(4-fluorophenyl)quinoxaline-6-carbonyl chloride (753 mg, 100%) as a pale yellow solid. $^1$H NMR (300 MHz, DMSO-d$_6$) δ 7.10-7.35 (m, 4H), 7.43-7.67 (m, 4H), 8.08-8.36 (m, 2H), 8.60-8.71 (m, 1H).

Step 2: 2,3-Bis(4-fluorophenyl)-N-[3-(pyridin-2-yl)propyl]quinoxaline-6-carboxamide 2,3-bis(4-fluorophenyl)quinoxaline-6-carbonyl chloride (100 mg, 0.26 mmol) was added to a solution of DIPEA (0.183 mL, 1.05 mmol) and 3-(pyridin-2-yl)propan-1-amine dihydrochloride (54.9 mg, 0.26 mmol) in THF (5 mL) at rt. The mixture was stirred at rt overnight. The mixture was poured into water and extracted with EtOAc. The organic layer was separated, washed with water and brine and passed through an NH silica gel pad with EtOAc. The filtrate was concentrated and the residue was triturated with $^i$Pr$_2$O and dried in vacuo to give 2,3-bis(4-fluorophenyl)-N-(3-(pyridin-2-yl)propyl)quinoxaline-6-carboxamide (71.4 mg, 56%) as white solid. LCMS (ESI+): m/z=481.2 (M+H). $^1$H NMR (300 MHz, DMSO-d$_6$) δ 1.92-2.10 (m, 2H), 2.77-2.92 (m, 2H), 3.35-3.50 (m, 2H), 7.06-7.37 (m, 6H), 7.42-7.63 (m, 4H), 7.64-7.81 (m, 1H), 8.06-8.35 (m, 2H), 8.40-8.55 (m, 1H), 8.68 (s, 1H), 8.93 (t, J=5.3 Hz, 1H).

The compounds listed in the table below were prepared in an analogous fashion to that described above starting from the appropriate starting materials:

| Starting Material Step 2 | Compound No. or Name | LCMS Data |
|---|---|---|
| ![pyridine-propylamine] | I-32 | LCMS (ESI+): m/z = 481.2 (M + H) |
| ![imidazole-propylamine] | I-192 | LCMS (ESI+): m/z = 470.2 (M + H) |

Example 15: 2,3-Bis(4-fluorophenyl)-N-[2-(1-methyl-1H-imidazol-2-yl)ethyl]quinoxaline-6-carboxamide (I-151)

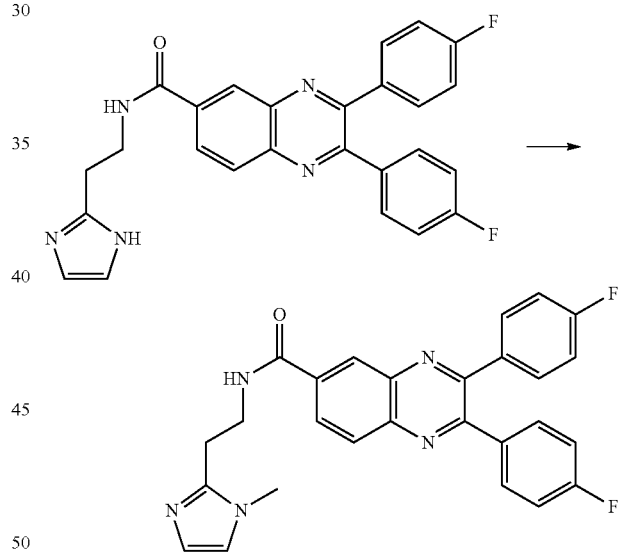

K$_2$CO$_3$ (25.5 mg, 0.18 mmol) was added to a solution of MeI (6.94 μL, 0.11 mmol) and N-(2-(1H-imidazol-2-yl)ethyl)-2,3-bis(4-fluorophenyl)quinoxaline-6-carboxamide (42.1 mg, 0.09 mmol) (prepared according to Example 8, step 3) in DMF (3 mL) at rt. The mixture was stirred at rt overnight. The mixture was poured into water and extracted with EtOAc. The organic layer was separated, washed with water and brine, dried over MgSO$_4$ and concentrated in vacuo. The residue was purified by NH silica gel chromatography to give a white solid. The obtained solid was further purified by preparative HPLC to give 2,3-bis(4-fluorophenyl)-N-(2-(1-methyl-1H-imidazol-2-yl)ethyl)quinoxaline-6-carboxamide (8.4 mg, 19%) as a white solid. LCMS (ESI+): m/z=470.1 (M+H). $^1$H NMR (300 MHz, DMSO-d$_6$) δ 2.81-3.07 (m, 2H), 3.49-3.80 (m, 5H), 6.78 (s, 1H), 7.05 (s, 1H), 7.14-7.37 (m, 4H), 7.44-7.70 (m, 4H), 8.11-8.40 (m, 2H), 8.65 (s, 1H), 8.91-9.23 (m, 1H).

Example 16: 2-Anilino-N-[3-(1H-imidazol-1-yl)propyl]-3-phenylquinoxaline-6-carboxamide (I-233)

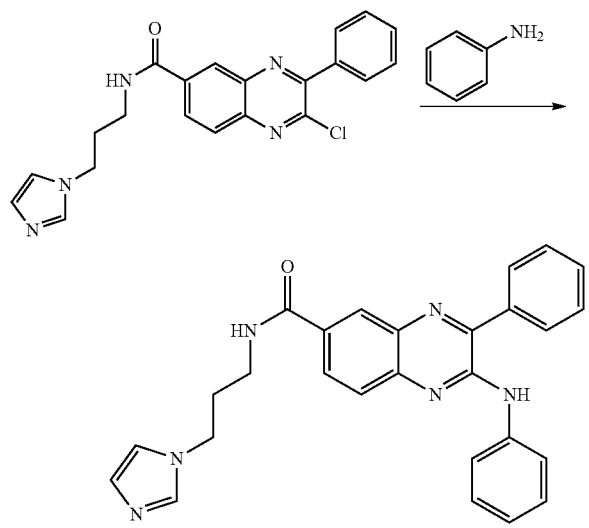

A mixture of aniline (0.052 mL, 0.57 mmol), N-(3-(1H-imidazol-1-yl)propyl)-2-chloro-3-phenylquinoxaline-6-carboxamide (150 mg, 0.38 mmol) (prepared according to Example 3, step 7), Xantphos (44.3 mg, 0.08 mmol), Pd$_2$(dba)$_3$ (35.1 mg, 0.04 mmol), sodium tert-butoxide (73.6 mg, 0.77 mmol) in toluene (3 mL) was heated at 100° C. for 1.5 h under microwave irradiation. After cooling, the mixture was diluted with sat. NaHCO$_3$ aq. and extracted with EtOAc. The organic layer was separated, washed with brine, dried over MgSO$_4$ and concentrated in vacuo. The residue was purified by NH silica gel chromatography to give an orange oil. The obtained oil was further purified by preparative HPLC to give 2-anilino-N-[3-(1H-imidazol-1-yl)propyl]-3-phenylquinoxaline-6-carboxamide (15.3 mg, 9%) as a pale yellow amorphous solid. LCMS (ESI+): m/z=449.1 (M+H). $^1$H NMR (300 MHz, DMSO-d$_6$) δ 1.75-2.17 (m, 2H), 3.02-3.52 (m, 2H), 4.05 (t, J=6.8 Hz, 2H), 6.90 (br s, 1H), 6.98-7.15 (m, 1H), 7.23 (br s, 1H), 7.30-7.43 (m, 2H), 7.48-7.78 (m, 5H), 7.78-7.96 (m, 4H), 8.01-8.21 (m, 1H), 8.45 (d, J=1.3 Hz, 1H), 8.59-8.81 (m, 2H).

Example 17: 2-Cyano-N-[3-(1H-imidazol-1-yl)propyl]-3-phenylquinoxaline-6-carboxamide (I-142)

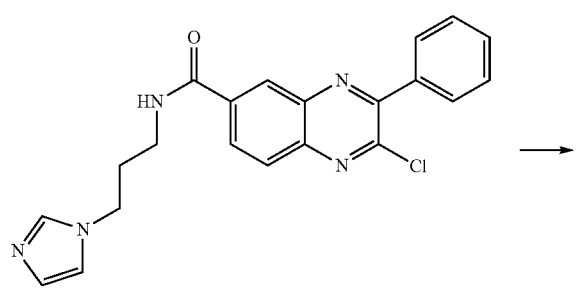

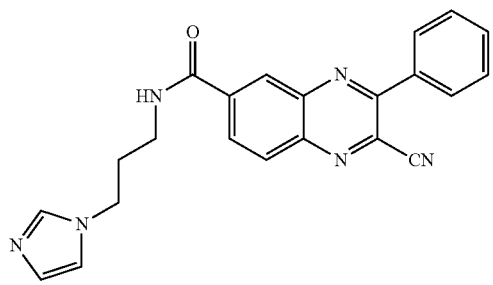

To a solution of sodium toluenesulfonate (44.6 mg, 0.23 mmol) and N-(3-(1H-imidazol-1-yl)propyl)-2-chloro-3-phenylquinoxaline-6-carboxamide (300 mg, 0.77 mmol) (prepared according to Example 3, step 7) in DMF (5 mL) was added KCN (60 mg, 0.92 mmol) at rt. The mixture was stirred at 80° C. under a N$_2$ atmosphere for 3 h. After cooling, the mixture was poured into sat. NaHCO$_3$ aq. and extracted with EtOAc. The organic layer was separated, washed with water and brine, passed through an NH silica gel pad with EtOAc. The filtrate was concentrated and the residue was triturated with $^i$Pr$_2$O and dried in vacuo to give 2-cyano-N-[3-(1H-imidazol-1-yl)propyl]-3-phenylquinoxaline-6-carboxamide. (215 mg, 73%). LCMS (ESI+): m/z=383.1 (M+H). $^1$H NMR (300 MHz, DMSO-d$_6$) δ 1.94-2.12 (m, 2H), 3.22-3.42 (m, 2H), 4.04-4.16 (m, 2H), 6.90 (t, J=0.9 Hz, 1H), 7.23 (t, J=0.9 Hz, 1H), 7.52-7.76 (m, 4H), 7.95-8.15 (m, 2H), 8.23-8.48 (m, 2H), 8.65-8.79 (m, 1H), 9.02 (t, J=5.5 Hz, 1H).

Example 18: N-[2,3-Bis(4-fluorophenyl)quinoxalin-6-yl]-4-(1H-imidazol-1-yl)butanamide (I-72)

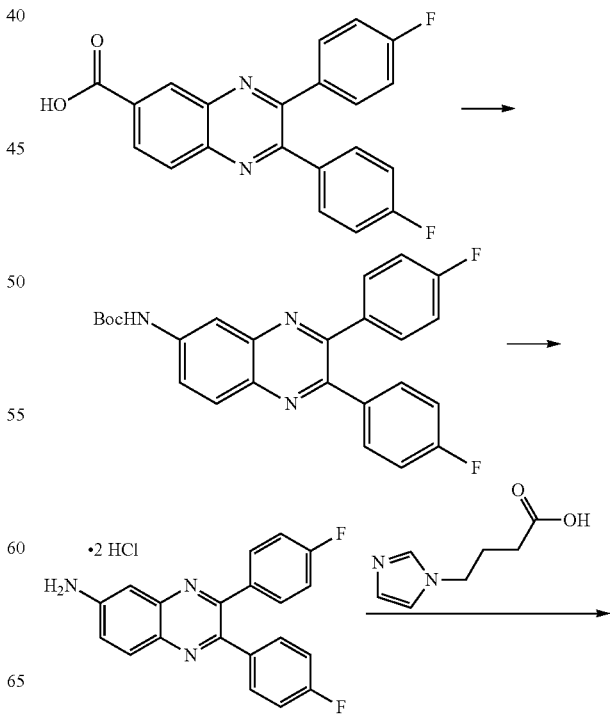

381

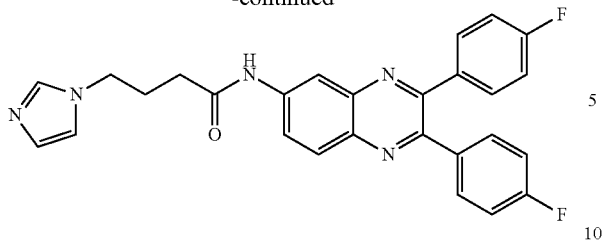

Step 1: tert-Butyl (2,3-bis(4-fluorophenyl)quinoxalin-6-yl)carbamate

To a solution of 2,3-bis(4-fluorophenyl)quinoxaline-6-carboxylic acid (4.00 g, 11.0 mmol) (prepared according to Example 8, step 2) and TEA (3.35 g, 33.1 mmol) in anhydrous tert-BuOH (40 mL) was added DPPA (4.57 g, 16.6 mmol). The reaction mixture was stirred at reflux under N$_2$ atmosphere for 16 h. After cooling to rt, the mixture was poured into water (100 mL) and extracted with DCM (100 mL×2). The extract was concentrated under reduced pressure. The crude product was purified by silica gel chromatography to afford tert-butyl (2,3-bis(4-fluorophenyl)quinoxalin-6-yl)carbamate (3.20 g, 67%) as an off-white solid. $^1$H NMR (400 MHz, DMSO-d$_6$) δ 1.52 (s, 9H), 7.16-7.22 (m, 4H), 7.42-7.52 (m, 4H), 7.89 (dd, J=9.2, 2.4 Hz, 1H), 8.02 (d, J=9.2 Hz, 1H), 8.28 (d, J=2.0 Hz, 1H), 9.98 (br s, 1H).

Step 2: 2,3-Bis(4-fluorophenyl)quinoxalin-6-amine dihydrochloride

A solution of tert-butyl (2,3-bis(4-fluorophenyl)quinoxalin-6-yl)carbamate (3.20 g, 7.39 mmol) in HCl (4 M in MeOH, 50 mL) was stirred at 25° C. for 16 h. The mixture was concentrated under reduced pressure to afford 2,3-bis(4-fluorophenyl)quinoxalin-6-amine (2.73 g, 91%) as the dihydrochloride salt. LCMS (ESI+): m/z=334.1 (M+H). $^1$H NMR (400 MHz, DMSO-d$_6$) δ 7.27-7.30 (m, 4H), 7.38 (d, J=2.0 Hz, 1H), 7.41-7.48 (m, 2H), 7.49-7.58 (m, 3H), 8.00 (d, J=8.8 Hz, 1H).

Step 3: N-[2,3-Bis(4-fluorophenyl)quinoxalin-6-yl]-4-(1H-imidazol-1-yl)butanamide dihydrochloride To a mixture of 2,3-bis(4-fluorophenyl)quinoxalin-6-amine dihydrochloride (240 mg, 0.591 mmol) and 4-(1H-imidazol-1-yl)butanoic acid (100 mg, 0.649 mmol) in pyridine (5 mL) was added EDCI (187 mg, 0.974 mmol). The resulting mixture was stirred at 25° C. for 3 h. The mixture was diluted with DCM and washed with water. The organic layer was concentrated under reduced pressure. The crude product was purified by prep-HPLC to afford N-[2,3-bis(4-fluorophenyl)quinoxalin-6-yl]-4-(1H-imidazol-1-yl)butanamide dihydrochloride (100 mg, 31%) as a red solid. LCMS (ESI+): m/z=470.1 (M+H). $^1$H NMR (400 MHz, DMSO-d$_6$) δ 2.16-2.27 (m, 2H), 2.45-2.58 (m, 2H), 4.31 (t, J=7.2 Hz, 2H), 7.14-7.28 (m, 4H), 7.46-7.57 (m, 4H), 7.71 (s, 1H),

382

7.85 (s, 1H), 7.96 (dd, J=9.2, 2.4 Hz, 1H), 8.09 (d, J=9.2 Hz, 1H), 8.58 (d, J=2.0 Hz, 1H). 9.23 (s, 1H), 10.76 (br s, 1H), 14.53 (br s, 1H).

Example 19: 2,3-Bis(4-fluorophenyl)-N-[2-(1,3-thiazol-2-yl)ethyl]quinoxaline-6-carboxamide (I-164)

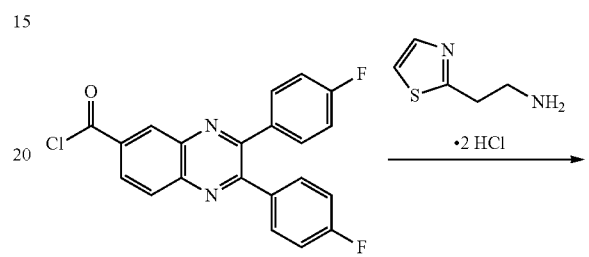

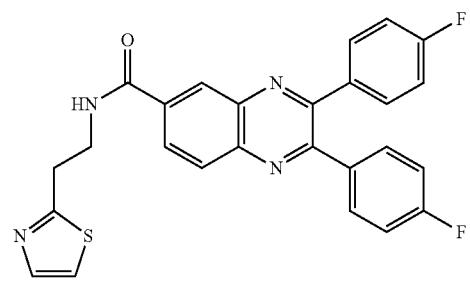

2,3-Bis(4-fluorophenyl)quinoxaline-6-carbonyl chloride (100 mg, 0.26 mmol) (prepared according to Example 14, step 1) was added to a solution of DIPEA (0.229 mL, 1.31 mmol) and 2-(thiazol-2-yl)ethanamine dihydrochloride (52.8 mg, 026 mmol) in THF (5 mL) at rt. The mixture was stirred at rt overnight. The mixture was poured into water and extracted with EtOAc. The organic layer was separated, washed with water and brine, dried over MgSO$_4$ and concentrated in vacuo. The residue was purified by NH silica gel chromatography to give 2,3-bis(4-fluorophenyl)-N-(2-(thiazol-2-yl)ethyl)quinoxaline-6-carboxamide (35.4 mg, 28%) as an off-white solid. LCMS (ESI+): m/z=473.1 (M+H). $^1$H NMR (300 MHz, DMSO-d$_6$) δ 3.12-3.26 (m, 2H), 3.49-3.71 (m, 2H), 7.15-7.36 (m, 4H), 7.45-7.63 (m, 4H), 7.75 (s, 1H), 8.15-8.34 (m, 2H), 8.66 (d, J=1.4 Hz, 1H), 8.95 (d, J=0.6 Hz, 1H), 9.06 (t, J=5.5 Hz, 1H).

Example 20: tert-Butyl [1'-(6-{[3-(1H-imidazol-1-yl)propyl]carbamoyl}-3-phenylquinoxalin-2-yl)-1,4'-bipiperidin-4-yl]carbamate (I-74)
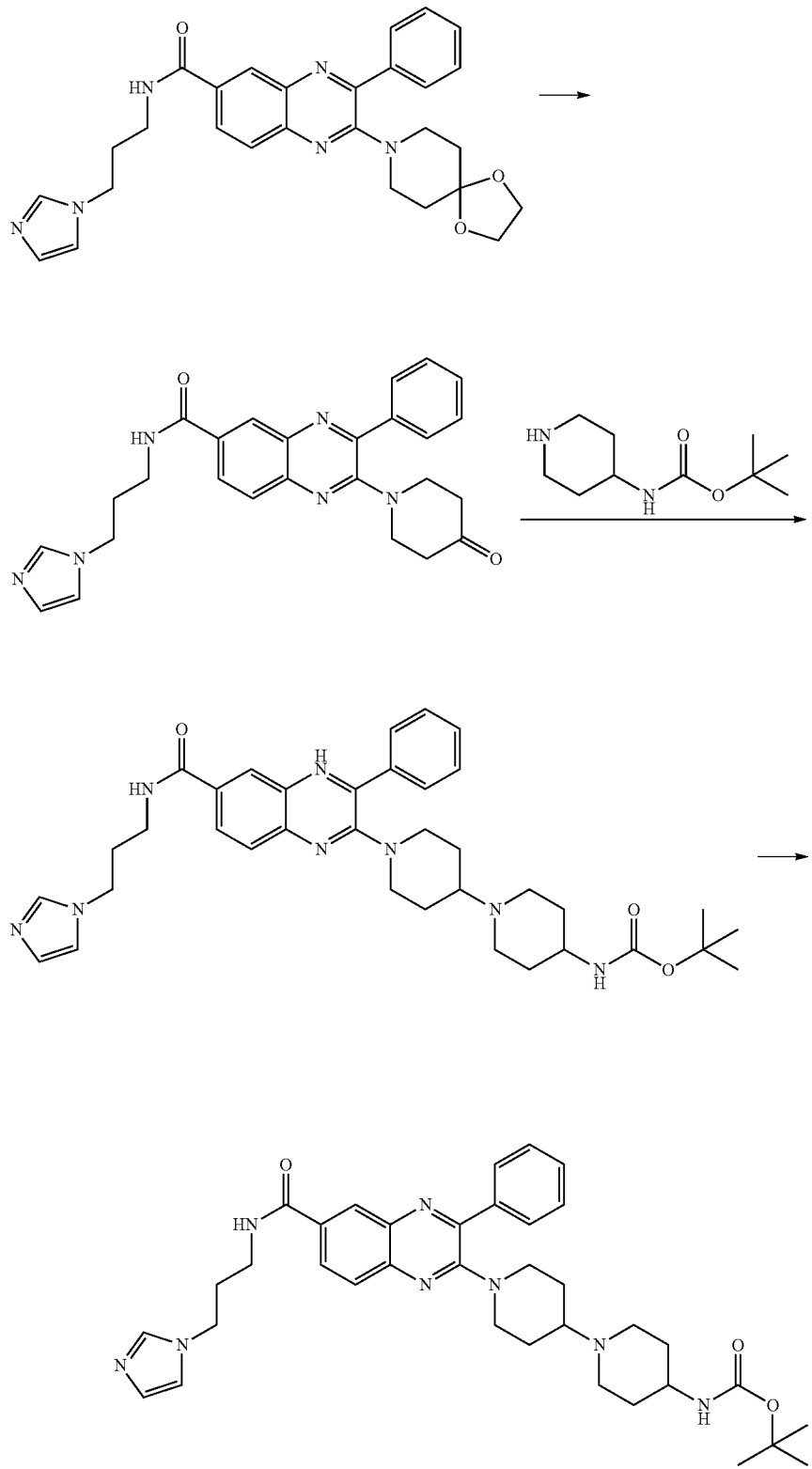

Step 1: N-[3-(1H-Imidazol-1-yl)propyl]-2-(4-oxopiperidin-1-yl)-3-phenylquinoxaline-6-carboxamide To a mixture of TFA (10 mL, 153 mmol) and water (0.5 mL, 27.8 mmol) was added 2-(1,4-dioxa-8-azaspiro[4.5]dec-8-yl)-N-[3-(1H-imidazol-1-yl)propyl]-3-phenylquinoxaline-6-carboxamide (624 mg, 1.25 mmol) (prepared according to Example 6, I-275) at rt. The mixture was stirred at rt for 3.5 h. The reaction mixture was basified to pH 8 with 2 M NaOH aq. and saturated $Na_2CO_3$ aq. at 0° C. and extracted with EtOAc/MeOH. The organic layer was separated, washed with water and brine, dried over $Na_2SO_4$ and concentrated in vacuo to give N-(3-(1H-imidazol-1-yl)propyl)-2-(4-oxopiperidin-1-yl)-3-phenylquinoxaline-6-carboxamide (1.22 g) as a hygroscopic yellow amorphous solid which was used in the next reaction without further purification. LCMS (ESI+): m/z=455.1 (M+H).

Step 2: tert-Butyl [1H'-(6-{[3-(1H-imidazol-1-yl)propyl]carbamoyl}-3-phenylquinoxalin-2-yl)-1,4'-bipiperidin-4-yl]carbamate To a solution of N-(3-(1H-imidazol-1-yl)propyl)-2-(4-oxopiperidin-1-yl)-3-phenylquinoxaline-6-carboxamide (130 mg, 0.066 mmol) in MeOH (2.7 mL) and AcOH (0.27 mL) were added tert-butyl piperidin-4-ylcarbamate (92 mg, 0.46 mmol) and 2-picoline borane complex (41 mg, 0.38 mmol) at rt. The resulting mixture was stirred at rt for 19 h. The reaction mixture was diluted with $H_2O$ (4 mL) at rt. To the mixture was added 2 M HCl (0.5 mL) at rt. The resulting mixture was stirred at rt for 5 min. The reaction mixture was diluted with EtOAc and saturated $NaHCO_3$ aq. The aqueous layer was extracted with EtOAc. The separated organic layers were combined, washed with brine, dried over $Na_2SO_4$ and concentrated in vacuo. The residue was purified by NH silica gel chromatography to give a colorless amorphous solid (21 mg). LCMS (ESI+): m/z=641.3 (M+H).

To a solution of the obtained solid (21 mg) in THF (3 mL) was added DDQ (14.9 mg, 0.07 mmol) at rt. The mixture was stirred at rt for 1.5 h. The reaction mixture was diluted with EtOAc and saturated $NaHCO_3$ aq. The aqueous layer was extracted with EtOAc. The separated organic layers were combined, washed with brine, dried over $Na_2SO_4$ and concentrated in vacuo. The residue was purified by NH silica gel chromatography to give tert-butyl [1'-(6-{[3-(1H-imidazol-1-yl)propyl]carbamoyl}-3-phenylquinoxalin-2-yl)-1,4'-bipiperidin-4-yl]carbamate (9.00 mg, 21%) as a yellow solid. LCMS (ESI+): m/z=639.4 (M+H). $^1$H NMR (300 MHz, CDCl$_3$) δ 1.34-1.51 (m, 13H), 1.82 (d, J=11.2 Hz, 2H), 1.95 (d, J=12.8 Hz, 2H), 2.10-2.25 (m, 4H), 2.29-2.40 (m, 1H), 2.76 (t, J=12.1 Hz, 2H), 2.90 (d, J=10.0 Hz, 2H), 3.38-3.48 (m, 1H), 3.53 (q, J=6.4 Hz, 2H), 3.93 (d, J=11.9 Hz, 2H), 4.06-4.12 (m, 2H), 4.39 (br s, 1H), 6.27 (t, J=5.9 Hz, 1H), 6.99 (s, 1H), 7.09 (s, 1H), 7.45-7.55 (m, 4H), 7.83 (d, J=8.7 Hz, 1H), 7.94 (dd, J=7.9, 1.6 Hz, 2H), 8.03 (dd, J=8.7, 2.1 Hz, 1H), 8.24 (d, J=1.9 Hz, 1H).

The compounds listed in the table below were prepared in an analogous fashion to that described above starting from the appropriate starting materials:

| Starting Material Step 2 | Compound No. or Name | LCMS Data |
|---|---|---|
| ![structure] | I-27 | LCMS (ESI+): m/z = 653.4 (M + H) |

Example 21: tert-Butyl {[4-hydroxy-1'-(6-{[3-(1H-imidazol-1-yl)propyl]carbamoyl}-3-phenylquinoxalin-2-yl)-1,4'-bipiperidin-4-yl]methyl}carbamate
I-231

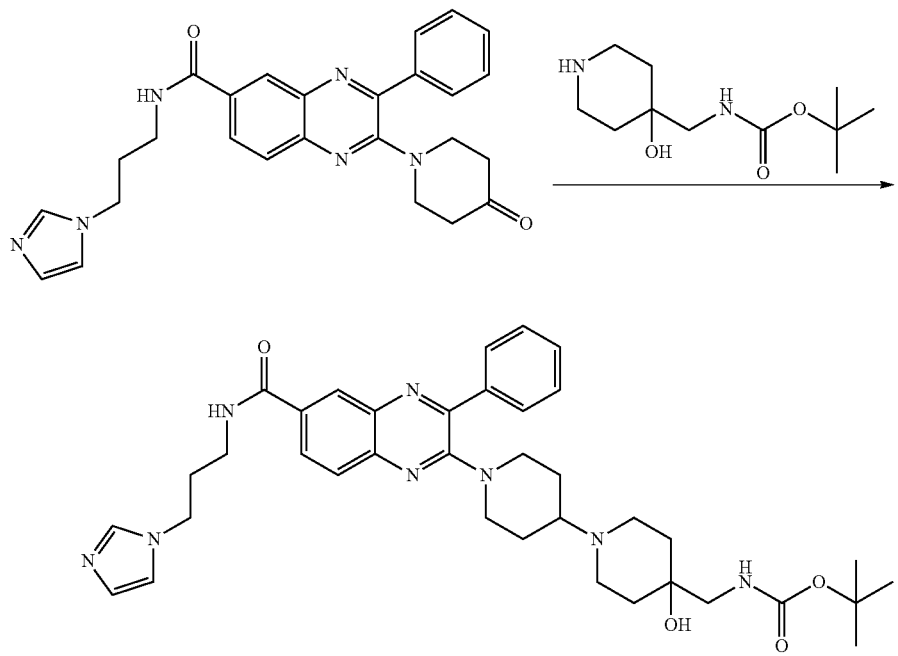

To a solution of N-(3-(1H-imidazol-1-yl)propyl)-2-(4-oxopiperidin-1-yl)-3-phenylquinoxaline-6-carboxamide (140 mg, 0.31 mmol) (prepared according to Example 20, step 1) in MeOH (2.7 mL) and AcOH (0.27 mL) were added tert-butyl((4-hydroxypiperidin-4-yl)methyl)carbamate (116 mg, 0.50 mmol) and 2-picoline borane complex (32.9 mg, 0.31 mmol) at rt. The resulting mixture was stirred at rt for 16 h. The reaction mixture was diluted with H₂O (4 mL) at rt. To the mixture was added 2 M HCl (0.5 mL) at rt. The reaction mixture was stirred at rt for 5 min. The reaction mixture was diluted with EtOAc and saturated NaHCO₃ aq. The aqueous layer was extracted with EtOAc. The separated organic layers were combined, washed with brine, dried over Na₂SO₄ and concentrated in vacuo. The residue was purified by NH silica gel chromatography to give tert-butyl {[4-hydroxy-1'-(6-{[3-(1H-imidazol-1-yl)propyl]carbamoyl}-3-phenylquinoxalin-2-yl)-1,4'-bipiperidin-4-yl]methyl}carbamate (11.0 mg, 5%) as a yellow amorphous solid. LCMS (ESI+): m/z=669.5 (M+H).
¹H NMR (300 MHz, CDCl₃) δ 1.44 (s, 9H), 1.58-1.65 (m, 6H), 1.80-1.85 (m, 2H), 2.09-2.21 (m, 2H), 2.27 (s, 1H), 2.32-2.83 (m, 7H), 3.13 (d, J=6.3 Hz, 2H), 3.53 (q, J=6.5 Hz, 2H), 3.88-3.98 (m, 2H), 4.08 (t, J=6.9 Hz, 2H), 4.86 (br s, 1H), 6.28 (t, J=6.1 Hz, 1H), 6.99 (t, J=1.2 Hz, 1H), 7.09 (s, 1H), 7.42-7.55 (m, 4H), 7.82 (d, J=8.8 Hz, 1H), 7.95 (dd, J=7.8, 1.6 Hz, 2H), 8.03 (dd, J=8.7, 2.1 Hz, 1H), 8.24 (d, J=2.0 Hz, 1H).

The compounds listed in the table below were prepared in an analogous fashion to that described above starting from the appropriate starting materials:

| Starting Material | Compound No. or Name | LCMS Data |
|---|---|---|
| 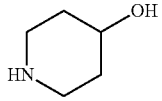 | I-210 | LCMS (ESI+): m/z = 540.3 (M + H) |

Example 22: 2-(4,4'-Bipiperidin-1-yl)-N-[3-(1H-imidazol-1-yl)propyl]-3-phenylquinoxaline-6-carboxamide (I-271)

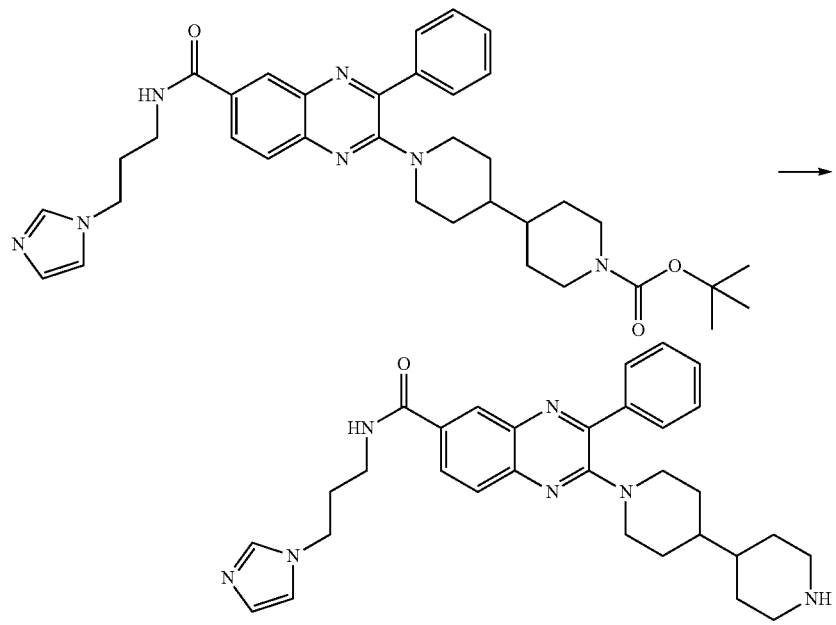

To a solution of tert-butyl 1'-(6-{[3-(1H-imidazol-1-yl)propyl]carbamoyl}-3-phenylquinoxalin-2-yl)-4,4'-bipiperidine-1-carboxylate (180 mg, 0.29 mmol) (prepared according to Example 6, I-275) in MeOH (2 mL) was added HCl (4 M in EtOAc, 2 mL, 8.00 mmol) at rt. The mixture was stirred at rt for 30 min. The reaction mixture was diluted with EtOAc (10 mL). The resulting mixture was neutralized with 2 M NaOH aq. at 0° C. and extracted with EtOAc. The organic layer was separated, washed with water and brine, dried over Na₂SO₄ and concentrated in vacuo. The obtained solid was triturated in THF/EtOAc (2/1), collected by filtration and washed with THF/EtOAc (2/1) and dried in vacuo to give 2-(4,4'-bipiperidin-1-yl)-N-[3-(1H-imidazol-1-yl)propyl]-3-phenylquinoxaline-6-carboxamide (143 mg, 95%) as a yellow solid. LCMS (ESI+): m/z=524.4 (M+H).
¹H NMR (300 MHz, DMSO-d₆) δ 1.17-1.34 (m, 5H), 1.58-1.66 (m, 2H), 1.76-1.81 (m, 2H), 1.97-2.03 (m, 2H), 2.65-2.81 (m, 4H), 3.17-3.32 (m, 6H), 3.81 (d, J=12.3 Hz, 2H), 4.01-4.09 (m, 2H), 6.89 (s, 1H), 7.22 (t, J=1.2 Hz, 1H), 7.48-7.60 (m, 3H), 7.67 (s, 1H), 7.78 (d, J=8.8 Hz, 1H), 7.94 (dd, J=7.7, 1.7 Hz, 2H), 8.10 (dd, J=8.7, 2.0 Hz, 1H), 8.47 (d, J=1.9 Hz, 1H), 8.73 (t, J=5.5 Hz, 1H).

The compounds listed in the table below were prepared in an analogous fashion to that described above starting from the appropriate starting materials:
| Starting Material | Compound No. or Name | LCMS Data |
|---|---|---|
| | I-112 | LCMS (ESI+): m/z = 525.3 (M + H) |
| | I-173 | LCMS (ESI+): m/z = 510.3 (M + H) |
Example 23: tert-Butyl 1'-(6-{[2-(1H-imidazol-1-yl)ethyl]carbamoyl}-3-phenylquinoxalin-2-yl)-4,4'-bipiperidine-1-carboxylate (I-239)
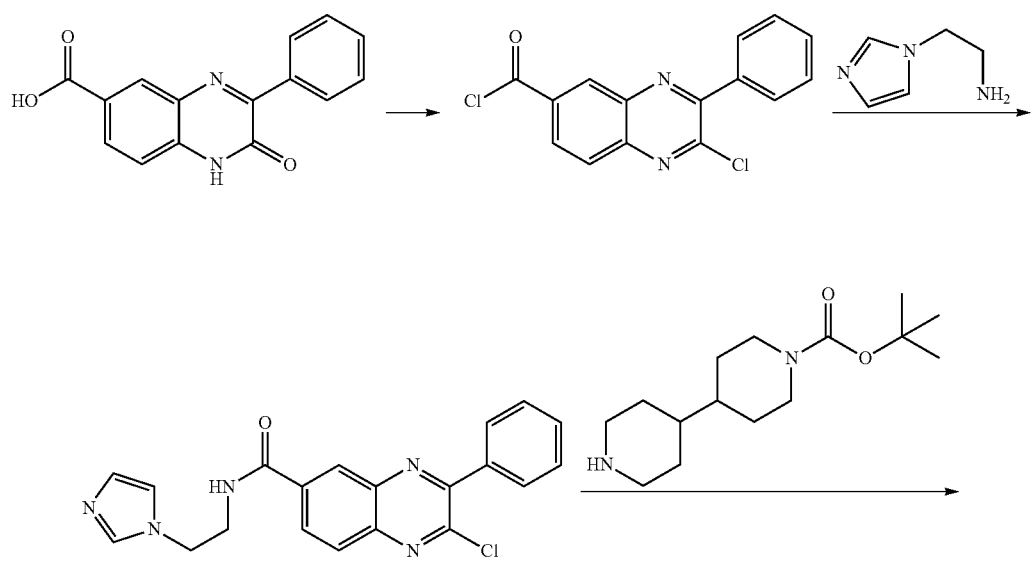

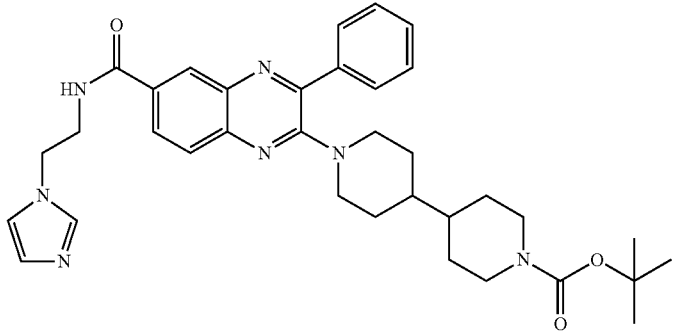 [SMILES: CC(C)(C)OC(=O)N1CCC(C2CCN(c3nc4ccc(C(=O)NCCn5ccnc5)cc4nc3-c3ccccc3)CC2)CC1]

Step 1: 2-Chloro-3-phenylquinoxaline-6-carbonyl chloride

2-Oxo-3-phenyl-1,2-dihydroquinoxaline-6-carboxylic acid (1.08 g, 4.06 mmol) (prepared according to Example 3, step 5) was suspended in toluene (50 mL). To the mixture were added $SOCl_2$ (6 mL, 82.2 mmol) and DMF (500 μL). The suspension was refluxed for 1.5 h with vigorous stirring. The reaction mixture was allowed to cool to rt and then concentrated under reduced pressure. The residue was suspended in toluene (50 mL) and then evaporated again to remove DMF to give 2-chloro-3-phenylquinoxaline-6-carbonyl chloride (1.22 g, 99%). $^1$H NMR (300 MHz, DMSO-$d_6$) δ 7.56-7.62 (m, 3H), 7.83-7.90 (m, 2H), 8.19 (d, J=8.7 Hz, 1H), 8.36 (dd, J=8.7, 1.8 Hz, 1H), 8.65 (d, J=1.5 Hz, 1H).

Step 2: N-(2-(1H-Imidazol-1-yl)ethyl)-2-chloro-3-phenylquinoxaline-6-carboxamide 2-Chloro-3-phenylquinoxaline-6-carbonyl chloride (660 mg, 2.18 mmol) was dissolved in THF (30 mL). To the solution were added a solution of 2-(1H-imidazol-1-yl)ethanamine (335 mg, 3.01 mmol) in THF (5 mL) and triethylamine (1.00 mL, 7.17 mmol). The mixture was stirred for 1 h at rt. To the reaction mixture were added saturated aqueous solution of $NaHCO_3$ (30 mL) and EtOAc (50 mL). The resulting biphasic mixture was vigorously stirred at rt for 15 min. The aqueous layer was separated and the organic layer was washed with brine, dried over anhydrous $MgSO_4$. Insoluble materials were removed by filtration and the filtrate was concentrated under reduced pressure. The resulting solid was triturated in n-hexane/EtOAc (1/1) containing 10% triethylamine and dried in vacuo to give N-(2-(1H-imidazol-1-yl)ethyl)-2-chloro-3-phenylquinoxaline-6-carboxamide (698 mg, 85%) as a yellow solid. LCMS (ESI+): m/z=378.1 (M+H).

Step 3: tert-Butyl 1'-(6-{[2-(1H-imidazol-1-yl)ethyl]carbamoyl}-3-phenylquinoxalin-2-yl)-4,4'-bipiperidine-1-carboxylate A mixture of N-(2-(1H-imidazol-1-yl)ethyl)-2-chloro-3-phenylquinoxaline-6-carboxamide (305 mg, 0.81 mmol), tert-butyl [4,4'-bipiperidine]-1-carboxylate (303 mg, 1.13 mmol) and DIPEA (0.423 mL, 2.42 mmol) in iPrOH (3.2 mL) was heated at 170° C. for 1.5 h under microwave irradiation. The reaction mixture was concentrated in vacuo. The residue was purified by NH silica gel chromatography. The resulting solid was triturated in n-hexane/EtOAc (1/1), collected by filtration and washed with n-hexane/EtOAc (1/1) and dried in vacuo to give tert-butyl 1'-(6-{[2-(1H-imidazol-1-yl)ethyl]carbamoyl}-3-phenylquinoxalin-2-yl)-4,4'-bipiperidine-1-carboxylate (325 mg, 66%) as a yellow solid. LCMS (ESI+): m/z=610.3 (M+H). $^1$H NMR (300 MHz, $CDCl_3$) δ 1.08-1.18 (m, 2H), 1.45 (s, 9H), 1.62-1.70 (m, 8H), 2.55-2.78 (m, 4H), 3.79 (q, J=5.8 Hz, 2H), 3.86-3.95 (m, 2H), 4.04-4.19 (m, 2H), 4.25 (t, J=5.7 Hz, 2H), 6.64 (t, J=5.9 Hz, 1H), 6.95 (t, J=1.2 Hz, 1H), 7.07 (s, 1H), 7.42-7.54 (m, 4H), 7.79 (d, J=8.6 Hz, 1H), 7.92 (dd, J=7.9, 1.7 Hz, 2H), 8.00 (dd, J=8.7, 2.1 Hz, 1H), 8.22 (d, J=1.9 Hz, 1H).

Example 24: 2-(4,4'-Bipiperidin-1-yl)-3-phenyl-N-[2-(pyridin-2-yl)ethyl]quinoxaline-6-carboxamide (I-130) trihydrochloride

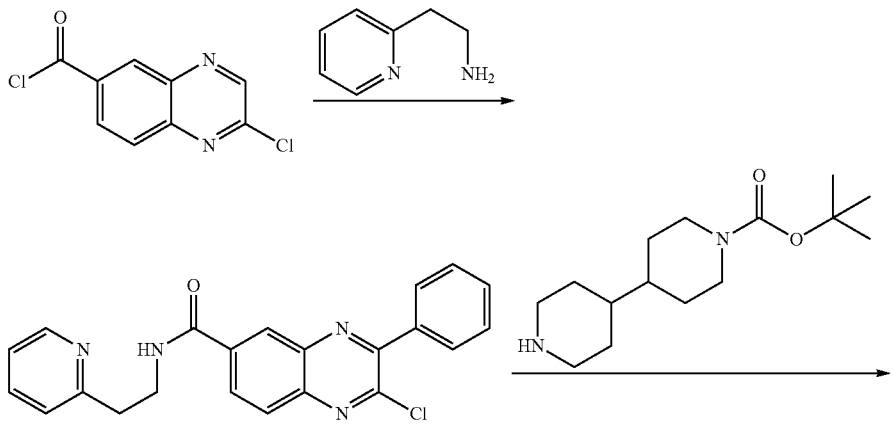

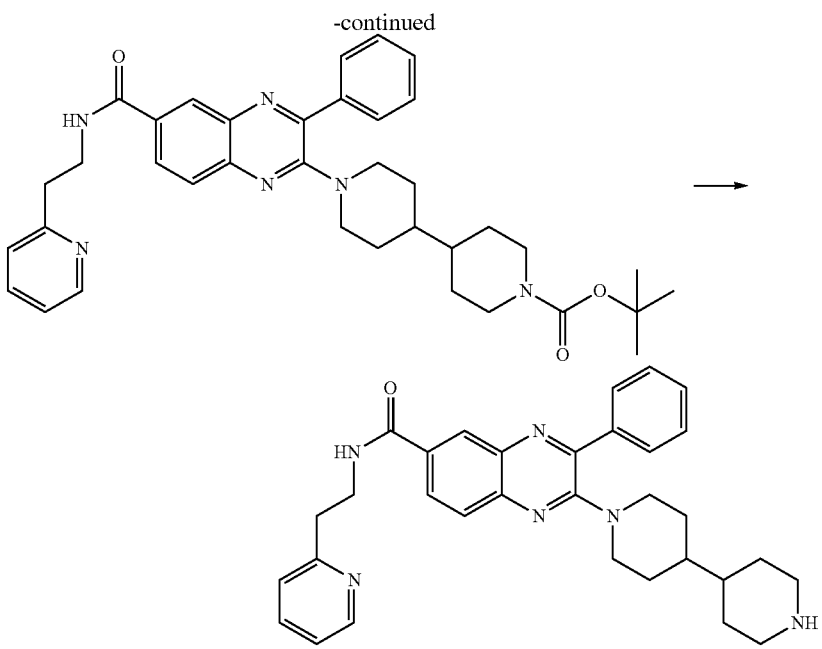

Step 1: 2-Chloro-3-phenyl-N-(2-(pyridin-2-yl)ethyl)quinoxaline-6-carboxamide 2-Chloro-3-phenylquinoxaline-6-carbonyl chloride (518 mg, 1.71 mmol) (prepared according to Example 3, step 6) was dissolved in THF (30 mL). To the solution were added 2-(pyridin-2-yl)ethanamine (250 μL, 2.09 mmol) and triethylamine (800 μL, 5.74 mmol), and the mixture was stirred at rt for 30 min. To the mixture were added saturated aqueous $NaHCO_3$ (30 mL) and EtOAc (50 mL). The resulting biphasic mixture was vigorously stirred at it for 15 min. The aqueous layer was separated and the organic layer was washed with brine and dried over anhydrous $MgSO_4$. Insoluble materials were removed by filtration and the filtrate was concentrated under reduced pressure. The resulting solid was triturated in n-hexane/EtOAc (1/1) and dried in vacuo to give 2-chloro-3-phenyl-N-(2-(pyridin-2-yl)ethyl)quinoxaline-6-carboxamide (464 mg, 69%) as brown solid. LCMS (ESI+): m/z=389.2 (M+H).

Step 2: tert-Butyl 1'-(3-phenyl-6-((2-(pyridin-2-yl)ethyl)carbamoyl)quinoxalin-2-yl)-[4,4'-bipiperidine]-1-carboxylate A mixture of 2-chloro-3-phenyl-N-(2-(pyridin-2-yl)ethyl)quinoxaline-6-carboxamide (299 mg, 0.77 mmol), tert-butyl [4,4'-bipiperidine]-1-carboxylate (268 mg, 1.00 mmol) and DIPEA (0.403 mL 2.31 mmol) in iPrOH (3.2 mL) was heated at 170° C. for 2 h under microwave irradiation. The mixture was concentrated in vacuo. The residue was purified by NH silica gel chromatography. The solid was triturated in n-hexane/EtOAc (1/1), collected by filtration and washed with n-hexane/EtOAc (1/1) and dried in vacuo to give tert-butyl 1'-(3-phenyl-6-((2-(pyridin-2-yl)ethyl)carbamoyl)quinoxalin-2-yl)-[4,4'-bipiperidine]-1-carboxylate (365 mg, 76%) as a yellow solid. LCMS (ESI+): m/z=621.4 (M+H).

$^1$H NMR (300 MHz, $CDCl_3$) δ 1.04-1.17 (m, 2H), 1.45 (s, 9H), 1.57-1.71 (m, 8H), 2.54-2.77 (m, 4H), 3.13 (t, J=6.1 Hz, 2H), 3.83-4.00 (m, 4H), 4.05-4.22 (m, 2H), 7.13-7.23 (m, 2H), 7.42-7.66 (m, 5H), 7.81 (d, J=8.7 Hz, 1H), 7.94 (dd, J=7.9, 1.6 Hz, 2H), 8.07 (dd, J=8.7, 2.1 Hz, 1H), 8.29 (d, J=1.9 Hz, 1H), 8.59 (dd, J=4.9, 0.9 Hz, 1H).

Step 3: 2-(4,4'-Bipiperidin-1-yl)-3-phenyl-N-[2-(pyridin-2-yl)ethyl]quinoxaline-6-carboxamide trihydrochloride To a solution of tert-butyl 1'-(3-phenyl-6-((2-(pyridin-2-yl)ethyl)carbamoyl)quinoxalin-2-yl)-[4,4'-bipiperidine]-1-carboxylate (351 mg, 0.57 mmol) in MeOH (3 mL) was added HCl (4 M in EtOAc, 3 mL, 12.0 mmol) at rt. The mixture was stirred at rt for 1 h. After removal of solvent under reduced pressure, the residue was dissolved in EtOAc (10 mL) and EtOH (2 mL) under sonication. The obtained solid was collected by filtration and washed with EtOAc under $N_2$ atmosphere and dried in vacuo to give 2-(4,4'-bipiperidin-1-yl)-3-phenyl-N-[2-(pyridin-2-yl)ethyl]quinoxaline-6-carboxamide trihydrochloride (352 mg, 99%) as a yellow solid. LCMS (ESI+): m/z=521.2 (M+H). $^1$H NMR (300 MHz, DMSO-$d_6$) δ 1.10-1.42 (m, 6H), 1.55-1.68 (m, 2H), 1.71-1.84 (m, 2H), 2.65-2.86 (m, 4H), 3.18-3.37 (m, 4H), 3.72-3.85 (m, 4H), 7.48-7.59 (m, 3H), 7.76 (d, J=8.7 Hz, 1H), 7.85-7.98 (m, 4H), 8.02 (dd, J=8.7, 1.9 Hz, 1H), 8.37 (d, J=1.9 Hz, 1H), 8.41-8.50 (m, 1H), 8.51-8.67 (m, 1H), 8.75-8.94 (m, 3H).

Example 25: 3-(4-Fluorophenyl)-N-[3-(1H-imidazol-2-yl)propyl]-2-isopropoxyquinoxaline-6-carboxamide (I-253)

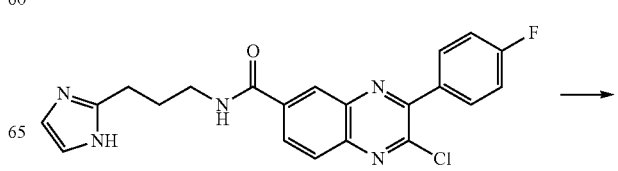

-continued

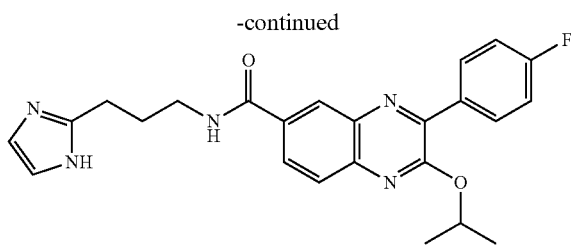

To a vial charged with NaH (60% in mineral oil, 11.7 mg, 0.293 mmol) was added isopropyl alcohol (134 uL, 1.76 mmol) and N-methylpyrrolidinone (1.00 mL, 10.4 mmol). The mixture was stirred at rt for 5 min until it formed a purple solution. To the mixture was added 2-chloro-3-(4-fluorophenyl)-N-[3-(1H-imidazol-2-yl)propyl]quinoxaline-6-carboxamide (60.0 mg, 0.146 mmol) (prepared according to Example 29, step 1). The resulting dark solution was stirred at rt for 30 min. The reaction mixture was distributed between water and EtOAc. The aqueous layer was extracted with EtOAc. The combined organic layer was washed with brine, dried, and concentrated. Purification by silica gel chromatography provided 3-(4-fluorophenyl)-N-[3-(1H-imidazol-2-yl)propyl]-2-isopropoxyquinoxaline-6-carboxamide as a white solid (36 mg, 57%). LCMS (ESI+): m/z=434.2 (M+H). $^1$H NMR (400 MHz, MeOD) δ 8.46 (d, J=1.9 Hz, 1H), 8.22-8.14 (m, 2H), 8.08 (dd, J=8.7, 2.0 Hz, 1H), 7.85 (d, J=8.7 Hz, 1H), 7.29-7.16 (m, 2H), 6.91 (s, 2H), 5.65 (hept, J=6.2 Hz, 1H), 3.46 (t, J=6.9 Hz, 2H), 2.80 (t, J=7.5 Hz, 2H), 2.03 (p, J=7.0 Hz, 2H), 1.46 (d, J=6.2 Hz, 6H).

The compounds listed in the table below were prepared in an analogous fashion to that described above starting from the appropriate starting materials:

| Starting Material 1 | Starting Material 2 | Compound No. or Name | LCMS Data |
|---|---|---|---|
| *(structure)* | Cl-phenyl, HO-iPr | I-222 | LCMS (ESI+, FA): m/z = 450.1, 452.1 (M + H) |
| *(structure)* | Cl-phenyl, HO-cyclohexyl | I-216 | LCMS (ESI+, FA): m/z = 490.2, 492.2 (M + H) |
| *(structure)* | Cl-phenyl, HO-tetrahydropyran | I-111 | LCMS (ESI+, FA): m/z = 492.1, 494.1 (M + H) |
| *(structure)* | Cl-phenyl, HO-Et | I-109 | LCMS (ESI+, FA): m/z = 422.1 (M + H) |
| *(structure)* | F-phenyl, (S)-3-hydroxytetrahydrofuran | I-372 | LCMS (ESI+, FA): m/z = 462.18 (M + H) |
| *(structure)* | Cl-phenyl, (S)-3-hydroxytetrahydrofuran | I-352 | LCMS (ESI+, FA): m/z = 478.2 (M + H) |

-continued

| Starting Material 1 | Starting Material 2 | Compound No. or Name | LCMS Data |
|---|---|---|---|
| (structure) | 3-hydroxyoxetane | I-318 | LCMS (ESI+, FA): m/z = 464.2 (M + H) |
| (structure) | ethanol (HOCH2CH3) | I-402 | LCMS (ESI+, FA): m/z = 436.1 (M + H) |
| (structure) | (S)-3-hydroxytetrahydrofuran | I-360 | LCMS (ESI+, FA): m/z = 478.2 (M + H) |
| (structure) | (S)-3-hydroxytetrahydrofuran | I-468 | LCMS (ESI+, FA): m/z = 462.16 (M + H) |
| (structure) | 3-(hydroxymethyl)pyridine | I-409 | LCMS (ESI+, FA): m/z = 483.1 (M + H) |
| (structure) | ethylene glycol | I-322 | LCMS (ESI+, FA): m/z = 436.2 (M + H) |
| (structure) | (3,5-dimethylisoxazol-4-yl)methanol | I-446 | LCMS (ESI+, FA): m/z = 501.3 (M + H) |
| (structure) | isobutanol | I-478 | LCMS (ESI+, FA): m/z = 448.2 (M + H) |

-continued

| Starting Material 1 | Starting Material 2 | Compound No. or Name | LCMS Data |
|---|---|---|---|
| ![SM1a] | ![SM2a] HO–CH₂–cyclopropyl | I-490 | LCMS (ESI+, FA): m/z = 446.2 (M + H) |
| ![SM1b] | ![SM2b] HO–cyclobutyl–OMe | (I-338)* | LCMS (ESI+, FA): m/z = 476.2 (M + H) |

*Reaction was run using KOtBu base in THF

Example 26: 3-(4-Fluorophenyl)-2-(4-hydroxypiperidin-1-yl)-N-[2-(pyridin-3-yloxy)ethyl]quinoxaline-6-carboxamide (I-114)

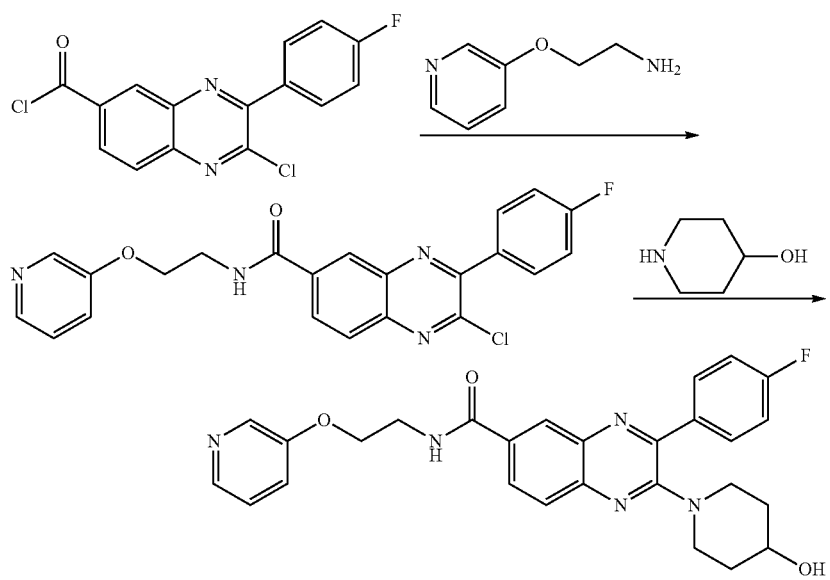

Step 1: 2-Chloro-3-(4-fluorophenyl)-N-[2-(pyridin-3-yloxy)ethyl]quinoxaline-6-carboxamide 2-chloro-3-(4-fluorophenyl)quinoxaline-6-carbonyl chloride (395 mg, 1.23 mmol) (prepared similarly to Example 3, step 6 or Example 27, step 6) was dissolved in DMA (26.8 mL). To the solution was added 3-(2-aminoethoxy)pyridine (204 mg, 1.48 mmol) and triethylamine (0.858 mL, 6.16 mmol), and the mixture was stirred at rt for 16 hours. To the mixture was added saturated aqueous NaHCO₃ (30 mL) and then stirred at rt for 15 minutes. Filtered, washed the solid with water and dried in vacuo to give 2-chloro-3-(4-fluorophenyl)-N-[2-(pyridin-3-yloxy)ethyl]quinoxaline-6-carboxamide (484 mg, 93%) as pale yellow solid. LCMS (ESI+): m/z=423.1 (M+H). ¹H NMR (400 MHz, DMSO-d₆) δ 9.15 (t, J=5.2 Hz, 1H), 8.69 (d, J=1.7 Hz, 1H), 8.40-8.28 (m, 2H), 8.18 (dd, J=4.9, 3.7 Hz, 2H), 8.01-7.89 (m, 2H), 7.53-7.40 (m, 3H), 7.34 (dd, J=8.3, 4.4 Hz, 1H), 4.28 (t, J=5.7 Hz, 2H), 3.75 (q, J=5.5 Hz, 2H).

Step 2: 3-(4-Fluorophenyl)-2-(4-hydroxypiperidin-1-yl)-N-[2-(pyridin-3-yloxy)ethyl]quinoxaline-6-carboxamide A mixture of 2-chloro-3-(4-fluorophenyl)-N-[2-(pyridin-3-yloxy)ethyl]quinoxaline-6-carboxamide (80.0 mg, 0.189 mmol), 4-hydroxypiperidine (95.7 mg, 0.946 mmol), DIPEA (0.099 mL, 0.568 mmol) and NMP (1.5 mL) was heated at 170° C. for 30 min under microwave irradiation. After cooling, the reaction mixture was poured into EtOAc and water. The layers were separated and the aqueous layer was extracted two more times with EtOAc. The combined organic layer was dried over anhydrous MgSO₄. Purified by silica gel chromatography to give 3-(4-fluorophenyl)-2-(4-hydroxypiperidin-1-yl)-N-[2-(pyridin-3-yloxy)ethyl]quinoxaline-6-carboxamide (72 mg, 78%) as a pale yellow solid. LCMS (ESI+): m/z=488.2 (M+H). $^1$H NMR (400 MHz, MeOD) δ 8.38 (d, J=1.8 Hz, 1H), 8.31 (d, J=2.7 Hz, 1H), 8.14 (d, J=4.3 Hz, 1H), 8.05 (ddd, J=14.2, 8.7, 3.7 Hz, 3H), 7.84 (d, J=8.7 Hz, 1H), 7.51 (dd, J=8.5, 1.8 Hz, 1H), 7.38 (dd, J=8.5, 4.7 Hz, 1H), 7.30 (t, J=8.7 Hz, 2H), 4.32 (t, J=5.5 Hz, 2H), 3.87 (t, J=5.5 Hz, 2H), 3.79 (m, 1H), 3.74-3.62 (m, 2H), 3.10-2.91 (m, 2H), 1.93-1.78 (m, 2H), 1.56 (m, 2H).

The compounds listed in the table below were prepared in an analogous fashion to that described above starting from the appropriate starting materials:

| Starting Material Step 2 | Compound No. or Name | LCMS Data |
|---|---|---|
| none | I-86 | LCMS (ESI+, FA): m/z = 423.1 (M + H) |
| 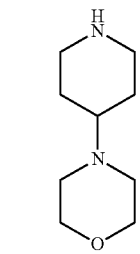 | I-221 | LCMS (ESI+, FA): m/z = 557.3 (M + H) |

Example 27: 3-(4-Fluorophenyl)-2-(morpholin-4-yl)-N-[3-(pyridazin-4-yl)propyl]quinoxaline-6-carboxamide (I-47)

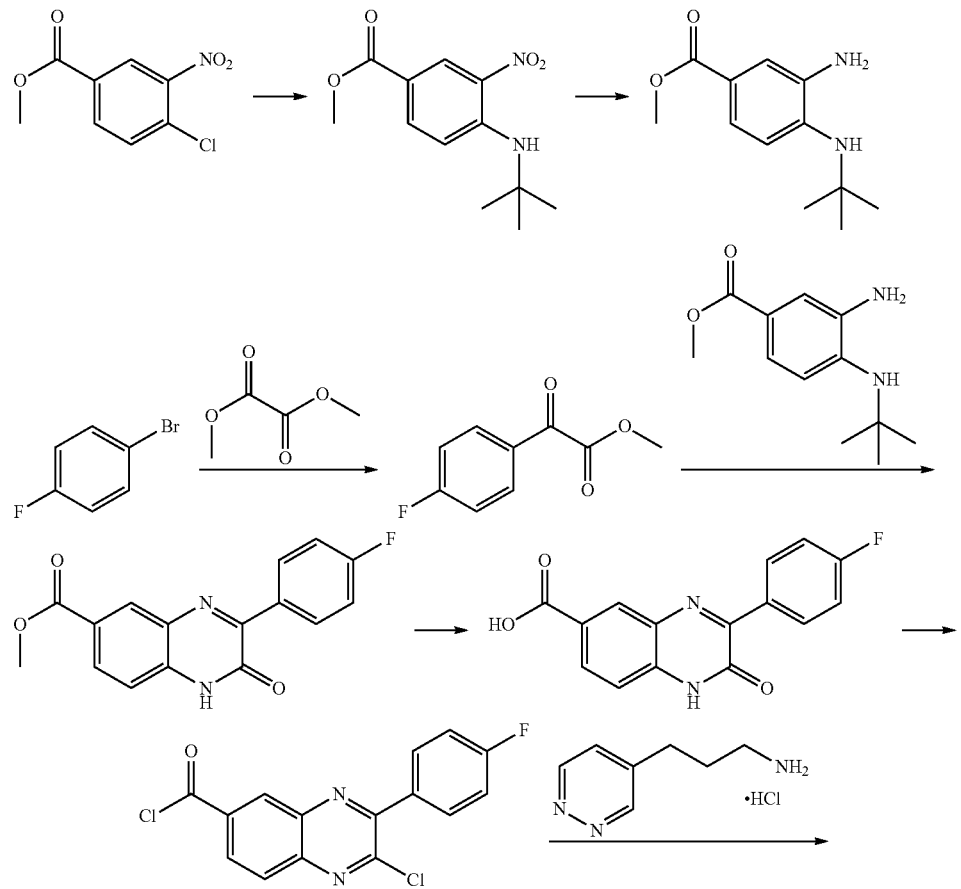

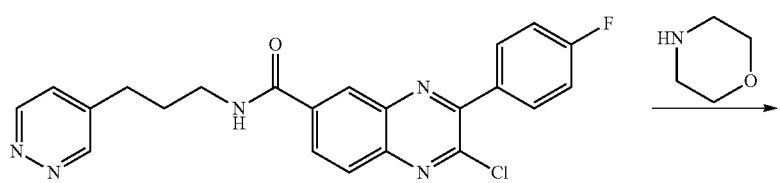

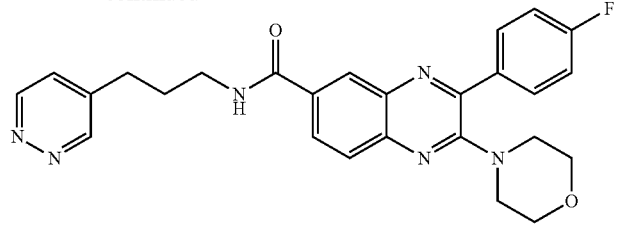

Step 1: Methyl 4-(tert-butylamino)-3-nitrobenzoate

To a solution of methyl 4-chloro-3-nitrobenzoate (250 g, 1.16 mol) in DMSO (1 L) was added t-butylamine (340 g, 4.64 mol) and the mixture was stirred at 80° C. for 13 h. The mixture was poured into water (8 L) and stirred at rt for 1 h. The solid was collected by filtration and dried in vacuum to give methyl 4-(tert-butylamino)-3-nitrobenzoate (277 g, 95%) as a yellow solid. $^1$H NMR (400 MHz, DMSO-$d_6$) δ 8.63 (br s, 1H), 8.52 (br s, 1H), 7.96 (br s, 1H), 7.38 (br s, 1H), 3.82 (s, 3H), 1.49 (s, 9H).

Step 2: Methyl 3-amino-4-(tert-butylamino)benzoate

Methyl 4-(tert-butylamino)-3-nitrobenzoate (92.3 g, 0.366 mol) was dissolved in methanol (1 L). 10% Pd/C (9.2 g) was added. The mixture was heated to 40° C. under $H_2$ at 35 psi for 18 hours. The mixture was cooled to rt, filtered and the cake was washed with EtOAc (200 mL). The filtrate was concentrated in vacuo to afford a crude product. Recrystallization from EtOAc/pet ether (1:1) gave methyl 3-amino-4-(tert-butylamino)benzoate (240 g, 77%) as a dark-grey solid. $^1$H NMR (400 MHz, DMSO-$d_6$) δ 7.20 (m, 2H), 6.72 (m, 1H), 4.76 (s, 2H), 4.52 (s, 1H), 3.72 (s, 3H), 1.36 (s, 9H).

Step 3: Methyl (4-fluorophenyl)(oxo)acetate

To a 2 L three neck round bottom flask were added magnesium (30.5 g, 1.25 mol), iodine (1.0 g, 0.004 mol) and 0.85 L of anhydrous THF. The mixture was degassed with $N_2$ and vacuum three times. With stirring the reaction mixture was heated by a heating gun to reflux until the yellow color disappeared. A solution of p-bromofluorobenzene (145 g, 0.85 mol) in 100 mL of THF was added dropwise at a speed to keep the reaction refluxing. After addition completed the reaction was kept stirring for 1 hour then cooled to rt.

In another flask a solution of dimethyl oxalate (110 g, 0.94 mol) in anhydrous THF (1.1 L) was cooled to −78° C. The Grignard solution obtained above was added dropwise to the dimethyl oxalate solution. The reaction mixture was stirred at −78° C. for 1 hour. The reaction mixture was added to saturated aqueous $NH_4Cl$ solution (2 L) and extracted with EtOAc (1 L×2). The combined organic layers were washed with brine (1 L), dried over anhydrous $Na_2SO_4$ and filtered. The filtrate was concentrated in vacuo to give a residue. Purification by silica gel chromatography afforded a crude product, which was recrystallization from pet ether (200 mL) to give the first crop of pure product (94 g). The mother liquid was concentrated and again purified by silica gel chromatography, recrystallized from 20 mL of pet ether to obtain the second crop of pure product (12 g). The two crops were combined to give methyl (4-fluorophenyl)(oxo)acetate (106 g, 34%). $^1$H NMR (400 MHz, CDCl3) δ 8.11-8.07 (m, 2H), 7.29-7.17 (m, 2H), 3.99 (s, 3H).

Step 4: Methyl 3-(4-fluorophenyl)-2-oxo-1,2-dihydroquinoxaline-6-carboxylate To a solution of methyl 3-amino-4-(tert-butylamino) benzoate (59 g, 0.265 mol), methyl (4-fluorophenyl)(oxo)acetate (53 g, 0.292 mol) in toluene (1.5 L), acetic acid (8.0 g, 0.13 mol) was added. The mixture was heated to reflux for 2 h. Another portion of acetic acid (50 g, 0.8 mol) was added. The mixture was stirred at 90° C. overnight. Additional portions of acetic acid were added every 4 hours (50 g×3), then the reaction was kept stirring at 90° C. overnight until TLC indicated the starting material methyl 3-amino-4-(tert-butylamino) benzoate was consumed completely. The reaction mixture was concentrated in vacuo to give a residue. The residue was dissolved in TFA (0.8 L) and stirred at it for 14 hours. The mixture was concentrated in vacuo, quenched with aqueous saturated $NaHCO_3$ (1 L) to pH 8~9. EtOAc (1.5 L) was added. The resulted bilayer suspension was filtered and the collected cake was washed with EtOAc (500 mL×3). The collected solid was dried in high vacuo to afford crude methyl 3-(4-fluorophenyl)-2-oxo-1,2-dihydroquinoxaline-6-carboxylate (85 g, 107%), which was used directly without further purification, $^1$H NMR (400 MHz, DMSO-$d_6$) δ 12.88 (s, 1H), 8.48-8.39 (m, 2H), 8.36 (d, J=1.8 Hz, 1H), 8.09 (dd, J=8.6, 1.9 Hz, 1H), 7.42 (d, J=8.6 Hz, 1H), 7.36 (t, J=9.0 Hz, 2H), 3.90 (s, 3H).

Step 5: 3-(4-Fluorophenyl)-2-oxo-1,2-dihydroquinoxaline-6-carboxylic acid

To a solution of methyl 3-(4-fluorophenyl)-2-oxo-1,2-dihydroquinoxaline-6-carboxylate in MeOH (800 mL) and THF (800 mL) was added NaOH (2.0 M in $H_2O$, 540 mL, 1.08 mol) at rt. The mixture was stirred at 60° C. for 12 h. After cooling, the mixture was quenched with 1N HCl aq. to bring the pH of the solution to 2-3. The precipitate was collected by filtration and washed with MeOH (200 mL), dried in vacuo to give 3-(4-fluorophenyl)-2-oxo-1,2-dihydroquinoxaline-6-carboxylic acid (67 g, 42% over three steps) as a yellow solid. LCMS (ESI+): m/z=285.1 (M+H). $^1$H NMR. (400 MHz, DMSO-$d_6$) δ 13.08 (s, 1H), 12.85 (s, 1H), 8.48-8.39 (m, 2H), 8.34 (d, J=1.7 Hz, 1H), 8.08 (dd, J=8.5, 1.8 Hz, 1H), 7.40 (d, J=8.5 Hz, 1H), 7.35 (t, J=8.9 Hz, 2H).

Step 6: 2-Chloro-3-(4-fluorophenyl)quinoxaline-6-carbonyl chloride 5 drops of DMF were added to a suspension of 3-(4-fluorophenyl)-2-oxo-1,2-dihydroquinoxaline-6-carboxylic acid (2.22 g, 7.81 mmol) and thionyl chloride (69.5 mL, 953 mmol) at rt. The mixture was refluxed for 2 h. After cooling, the mixture was concentrated in vacuo. The resulting off-white solid was used without further purification.

Step 7: 2-Chloro-3-(4-fluorophenyl)-N-[3-(pyridazin-4-yl)propyl]quinoxaline-6-carboxamide To a suspension of 2-chloro-3-(4-fluorophenyl)quinoxaline-6-carbonyl chloride (282 mg, 0.883 mmol) in N,N-dimethylacetamide (9.00 mL, 96.8 mmol) was added 3-(pyridazin-4-yl)propan-1-amine.2HCl (223 mg, 1.06 mmol) (prepared similarly to Example 31, step 2) and triethylamine (0.615 mL, 4.42 mmol). The resulting orange mixture was stirred at rt. After 24 h the mixture was distributed between NaHCO$_3$ (aq) saturated solution and EtOAc. The aqueous layer was extracted with EtOAc. The combined organic layer was washed with water and brine, dried, and concentrated. Purification by silica gel chromatography provided 2-chloro-3-(4-fluorophenyl)-N-[3-(pyridazin-4-yl)propyl]quinoxaline-6-carboxamide (101 mg, 27%) as a yellow solid. LCMS (ESI+): m/z=422.1, 424.1 (M+H). $^1$H NMR (400 MHz, CDCl$_3$) δ 9.19 (s, 1H), 9.12 (d, J=5.3 Hz, 1H), 8.47 (d, J=2.0 Hz, 1H), 8.25 (dd, J=8.7, 2.0 Hz, 1H), 8.20-8.07 (m, 1H), 7.96-7.86 (m, 2H), 7.49-7.39 (s, 1H), 7.27-7.24 (m, 2H), 6.56 (br s, 1H), 3.64 (q, J=6.8 Hz, 2H), 2.82 (t, J=7.7 Hz, 2H), 2.09 (dd, J=15.1, 7.1 Hz, 2H).

Step 8: 3-(4-Fluorophenyl)-2-(morpholin-4-yl)-N-[3-(pyridazin-4-yl)propyl]quinoxaline-6-carboxamide A mixture of 2-chloro-3-(4-fluorophenyl)-N-[3-(pyridazin-4-yl)propyl]quinoxaline-6-carboxamide (51.0 mg, 0.121 mmol), morpholine (52.7 uL, 0.604 mmol) and N,N-diisopropylethylamine (63.2 uL, 0.363 mmol) in N-methylpyrrolidinone (1.00 mL, 10.4 mmol) was heated at 170° C. in the microwave for 30 min. The reaction was distributed between water and EtOAc. The aqueous layer was extracted with EtOAc. The combined organic layer was washed with brine, dried, and concentrated. Purification by silica gel chromatography provided 3-(4-fluorophenyl)-2-(morpholin-4-yl)-N-[3-(pyridazin-4-yl)propyl]quinoxaline-6-carboxamide as a yellow solid (30 mg, 52%). LCMS m/z=473.2 (M+H). $^1$H NMR (400 MHz, MeOD) δ 9.14 (s, 1H), 9.02 (dd, J=5.3, 1.1 Hz, 1H), 8.35 (d, J=1.8 Hz, 1H), 8.05-8.03 (m, 3H), 7.85 (d, J=8.7 Hz, 1H), 7.65 (dd, J=5.3, 2.4 Hz, 1H), 7.35-7.16 (m, 2H), 3.40 (t, J=4.7 Hz, 4H), 3.50 (t, J=6.9 Hz, 2H), 2.83 (t, J=7.7 Hz, 2H), 2.04 (dt, J=14.5, 7.0 Hz, 2H).

The compounds listed in the table below were prepared in an analogous fashion to that described above starting from the appropriate starting materials:

| Starting Material Step 8 | Compound No. or Name | LCMS Data |
| --- | --- | --- |
| HN⟨piperidine⟩ | I-103 | LCMS (ESI+, FA): m/z = 471.2 (M + H) |

Example 28: 3-(4-Fluorophenyl)-N-(1H-indazol-5-ylmethyl)-2-(piperidin-1-yl)quinoxaline-6-carboxamide (I-220)

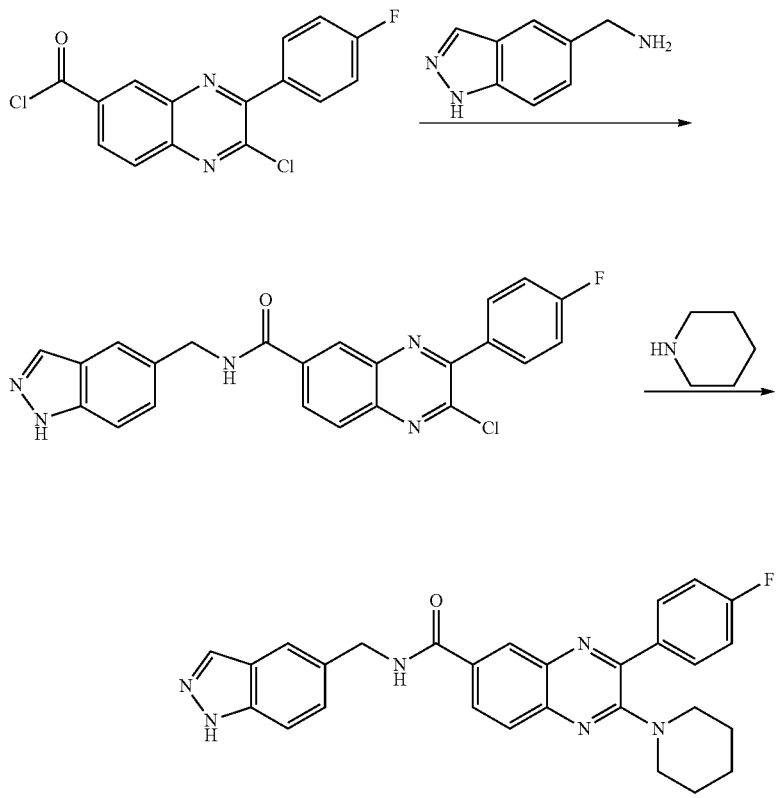

Step 1: 2-Chloro-3-(4-fluorophenyl)-N-(1H-indazol-5-ylmethyl)quinoxaline-6-carboxamide 2-Chloro-3-(4-fluorophenyl)quinoxaline-6-carbonyl chloride (275 mg, 0.856 mmol) (prepared similarly to Example 3, step 6, or Example 27, step 6) was dissolved in DMA (18.6 mL). To the solution was added 1-(1H-indazol-5-yl)methanamine (151 mg, 1.03 mmol) and triethylamine (0.597 mL, 4.28 mmol), and the mixture was stirred at it for 16 h. To the mixture was added saturated aqueous NaHCO$_3$ and EtOAc. The layers were separated and the aqueous layer was extracted two more times with EtOAc. The combined organic layer was washed with water then brine and dried over anhydrous MgSO$_4$. Purified by silica gel to give 2-chloro-3-(4-fluorophenyl)-N-(1H-indazol-5-ylmethyl)quinoxaline-6-carboxamide (184 mg, 50%) as a pale yellow solid. LCMS (ESI+): m/z=432.1 (M+H). $^1$H NMR (400 MHz, DMSO-d$_6$) δ 13.02 (s, 1H), 9.50 (t, J=5.9 Hz, 1H), 8.73 (d, J=1.5 Hz, 1H), 8.38 (dd, J=8.8, 1.9 Hz, 1H), 8.19 (d, J=8.7 Hz, 1H), 8.05 (s, 1H), 7.94 (dd, J=8.8, 5.5 Hz, 2H), 7.74 (s, 1H), 7.53 (d, J=8.6 Hz, 1H), 7.42 (dd, J=16.3, 7.5 Hz, 3H), 4.66 (d, J=5.8 Hz, 2H).

Step 2: 3-(4-Fluorophenyl)-N-(1H-indazol-5-ylmethyl)-2-(piperidin-1-yl)quinoxaline-6-carboxamide A mixture of 2-chloro-3-(4-fluorophenyl)-N-(1H-indazol-5-ylmethyl)quinoxaline-6-carboxamide (50.0 mg, 0.116 mmol), piperidine (0.057 mL, 0.579 mmol), DIPEA (0.061 mL, 0.347 mmol) and NMP (1.0 mL) was heated at 170° C. for 30 min under microwave irradiation. After cooling, the reaction mixture was poured into EtOAc and water. The layers were separated and the aqueous layer was extracted two more times with EtOAc. The combined organic layer was dried over anhydrous MgSO$_4$ and concentrated in vacuo. Purified by silica gel chromatography followed by prep HPLC to give 3-(4-fluorophenyl)-N-(1H-indazol-5-ylmethyl)-2-(piperidin-1-yl)quinoxaline-6-carboxamide (35 mg, 63%) as a pale yellow solid. LCMS (ESI+): m/z=481.2 (M+H). $^1$H NMR (400 MHz, MeOD) δ 8.41 (d, J=1.7 Hz, 1H), 8.11 (dd, J=8.7, 2.0 Hz, 1H), 8.03 (t, J=7.1 Hz, 3H), 7.85 (d, J=8.7 Hz, 1H), 7.80 (s, 1H), 7.52 (dd, J=23.3, 9.1 Hz, 2H), 7.29 (t, J=8.8 Hz, 2H), 4.75 (s, 2H), 3.30 (m, 4H), 1.60 (m, 6H).

The compounds listed in the table below were prepared in an analogous fashion to that described above starting from the appropriate starting materials:

| Starting Material-1 Step 1 | Starting Material-2 Step 2 | Compound No. or Name | LCMS Data |
|---|---|---|---|
| indazol-5-ylmethanamine | morpholine | I-16 | LCMS (ESI+, FA): m/z = 483.2 (M + H) |
| indazol-6-ylmethanamine | piperidine | I-133 | LCMS (ESI+, FA): m/z = 481.2 (M + H) |

Example 29: 3-(4-Fluorophenyl)-N-[3-(1H-imidazol-2-yl)propyl]-2-(2-oxa-7-azaspiro[3.5]non-7-yl)quinoxaline-6-carboxamide (I-277)

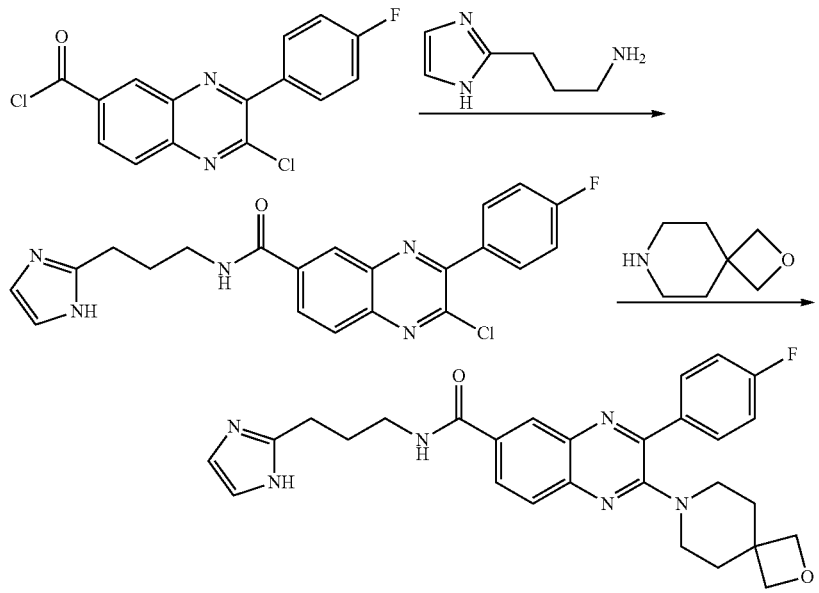

Step 1: 2-Chloro-3-(4-fluorophenyl)-N-[3-(1H-imidazol-2-yl)propyl]quinoxaline-6-carboxamide 2-Chloro-3-(4-fluorophenyl)quinoxaline-6-carbonyl chloride (1.35 g, 4.21 mmol) (prepared similarly to Example 3, step 6, or Example 27, step 6) was dissolved in DMA (91.5 mL). To the solution was added 3-(1H-imidazol-2-yl)-1-propanamine dihydrochloride (1.00 g, 5.05 mmol) and triethylamine (2.93 mL, 21.0 mmol), and the mixture was stirred at rt for 16 hours. To the mixture was added saturated aqueous NaHCO$_3$ (100 mL) and the mixture was stirred at rt for 30 minutes. Filtered and washed the solid with water and dried. Purified by silica gel chromatography to give 2-chloro-3-(4-fluorophenyl)-N-[3-(1H-imidazol-2-yl)propyl]quinoxaline-6-carboxamide (620 mg, 36%) as a pale yellow solid. LCMS (ESI+): m/z=410.1 (M+H). ¹H NMR (400 MHz, DMSO-d₆) δ 11.70 (s, 1H), 9.09 (t, J=5.3 Hz, 1H), 8.68 (d, J=1.6 Hz, 1H), 8.34 (dd, J=8.8, 1.9 Hz, 1H), 8.18 (d, J=8.7 Hz, 1H), 8.02-7.88 (m, 2H), 7.44 (t, J=8.9 Hz, 2H), 6.88 (s, 2H), 3.40 (dd, J=12.6, 6.7 Hz, 2H), 2.72 (t, J=7.5 Hz, 2H), 2.02-1.89 (m, 2H).

Step 2: 3-(4-Fluorophenyl)-N-[3-(1H-imidazol-2-yl)propyl]-2-(2-oxa-7-azaspiro[3.5]non-7-yl)quinoxaline-6-carboxamide A mixture of 2-chloro-3-(4-fluorophenyl)-N-[3-(1H-imidazol-2-yl)propyl]quinoxaline-6-carboxamide (55.0 mg, 0.134 mmol), 2-oxa-7-azaspiro[3,5]nonane hemioxalate (116 mg, 0.671 mmol), DIPEA (0.070 mL, 0.402 mmol) and NMP (1.1 mL) was heated at 170° C. for 30 min under microwave irradiation. After cooling, the reaction mixture was poured into EtOAc and water. The layers were separated and the aqueous layer was extracted two more times with EtOAc. The combined organic layer was dried over anhydrous MgSO₄ and concentrated in vacuo. Purified by silica gel chromatography to give 3-(4-fluorophenyl)-N-[3-(1H-imidazol-2-yl)propyl]-2-(2-oxa-7-azaspiro[3.5]non-7-yl)quinoxaline-6-carboxamide (27 mg, 40%) as a pale yellow solid. LCMS (ESI+): m/z=501.2 (M+H). ¹H NMR (400 MHz, MeOD) δ 8.39 (d, J=1.7 Hz, 1H), 8.07-8.01 (m, 2H), 7.84 (d, J=8.7 Hz, 1H), 7.81-7.71 (m, 1H), 7.30 (dd, J=12.2, 5.4 Hz, 2H), 6.95 (s, 2H), 4.47 (s, 4H), 3.48 (t, J=6.9 Hz, 2H), 3.30-3.20 (m, 4H), 2.83 (t, J=7.5 Hz, 2H), 2.05 (m, 2H), 1.91 (dd, J=11.1, 5.4 Hz, 4H).

The compounds listed in the table below were prepared in an analogous fashion to that described above starting from the appropriate starting materials:

| Starting Material Step 1 | Starting Material Step 2 | Compound No. or Name | LCMS Data |
|---|---|---|---|
| (structure) | (oxetane-azetidine) | I-154 | LCMS (ESI+, FA): m/z = 473.2 (M + H) |
| (structure) | (3-methoxyazetidine) | I-172 | LCMS (ESI+, FA): m/z = 461.2 (M + H) |
| (structure) | (2-azaspiro[3.5] tetrahydropyran) | I-288 | LCMS (ESI+, FA): m/z = 501.3 (M + H) |
| (structure) | (4-methoxypiperidine) | I-178 | LCMS (ESI+, FA): m/z = 489.2 (M + H) |
| (structure) | (morpholine) | I-39 | LCMS (ESI+, FA): m/z = 461.2 (M + H) |
| (structure) | none | I-211 | LCMS (ESI+, FA): m/z = 410.1 (M + H) |

-continued

| Starting Material Step 1 | Starting Material Step 2 | Compound No. or Name | LCMS Data |
|---|---|---|---|
| [structure: imidazole-propyl-NH-C(O)-quinoxaline with 4-F-phenyl and Cl] | thiomorpholine (HN-CH2CH2-S-CH2CH2) | I-256 | LCMS (ESI+, FA): m/z = 477.2 (M + H) |
| [structure: imidazole-propyl-NH-C(O)-quinoxaline with 4-F-phenyl and Cl] | thiomorpholine-1,1-dioxide | I-287 | LCMS (ESI+, FA): m/z = 509.2 (M + H) |
| [structure: imidazole-propyl-NH-C(O)-quinoxaline with 4-Cl-phenyl and Cl] | pyrrolidine | I-116 | LCMS (ESI+, FA): m/z = 461.2, 463.2 (M + H) |
| [structure: imidazole-propyl-NH-C(O)-quinoxaline with 3-methoxyphenyl and Cl] | piperidine | I-183 | LCMS (ESI+, FA): m/z = 471.2 (M + H) |
| [structure: imidazole-propyl-NH-C(O)-quinoxaline with 4-Cl-phenyl and Cl] | piperidine | I-198 | LCMS (ESI+, FA): m/z = 475.2, 477.2 (M + H) |
| [structure: imidazole-propyl-NH-C(O)-quinoxaline with thiophene and Cl] | 4-morpholinopiperidine | I-44 | LCMS (ESI−, FA): m/z = 530.3 (M − H) |
| [structure: imidazole-propyl-NH-C(O)-quinoxaline with thiophene and Cl] | piperidine | I-195 | LCMS (ESI+, FA): m/z = 447.2 (M + H) |

| Starting Material Step 1 | Starting Material Step 2 | Compound No. or Name | LCMS Data |
|---|---|---|---|
| (structure) | (4-morpholinopiperidine) | I-255 | LCMS (ESI+, FA): m/z = 560.3, 562.2 (M + H) |
| (structure) | (morpholine) | I-104 | LCMS (ESI+, FA): m/z = 477.2, 479.2 (M + H) |
| (structure) | (4-hydroxypiperidine) | I-298 | LCMS (ESI+, FA): m/z = 491.2, 493.2 (M + H) |
| (structure) | none | I-50 | LCMS (ESI+, FA): m/z = 426.1, 428.1 (M + H) |
| (structure) | (4-morpholinopiperidine) | I-91 | LCMS (ESI+, FA): m/z = 557.2 (M + H) |
| (structure) | (piperidine) | I-232 | LCMS (ESI+, FA): m/z = 459.2 (M + H) |
| (structure) | (4-hydroxypiperidine) | I-213 | LCMS (ESI+, FA): m/z = 475.2 (M + H) |

| Starting Material Step 1 | Starting Material Step 2 | Compound No. or Name | LCMS Data |
|---|---|---|---|
| | | I-23 | LCMS (ESI+, FA): m/z = 544.3 (M + H) |
| | | I-12 | LCMS (ESI+, FA): m/z = 487.3 (M + H) |
| | | I-465 | LCMS (ESI+, FA): m/z = 445.2 (M + H) |
| | | I-457 | LCMS (ESI+, FA): m/z = 475.2 (M + H) |
| | | I-383 | LCMS (ESI+, FA): m/z = 489.3 (M + H) |

Example 30: 3-(4-Fluorophenyl)-2-(morpholin-4-yl)-N-[3-(pyrimidin-5-yl)propyl]quinoxaline-6-carboxamide (I-193)

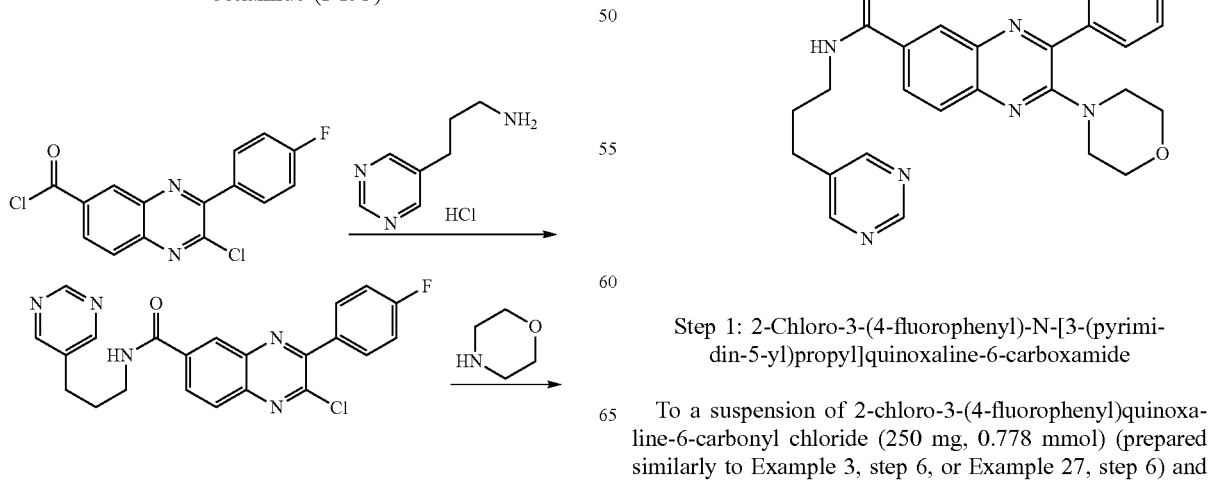

Step 1: 2-Chloro-3-(4-fluorophenyl)-N-[3-(pyrimidin-5-yl)propyl]quinoxaline-6-carboxamide To a suspension of 2-chloro-3-(4-fluorophenyl)quinoxaline-6-carbonyl chloride (250 mg, 0.778 mmol) (prepared similarly to Example 3, step 6, or Example 27, step 6) and 3-(pyrimidin-5-yl)propan-1-amine hydrochloride (162 mg, 0.934 mmol) (prepared similarly to Example 31, step 2) in DMA (17 mL) was added triethylamine (542 µL, 3.89 mmol). The mixture was stirred at rt overnight. To the mixture was added saturated aqueous NaHCO₃ (30 mL), and a solid precipitated. The obtained solid was collected by filtration and washed with water to give 2-chloro-3-(4-fluorophenyl)-N-[3-(pyrimidin-5-yl)propyl]quinoxaline-6-carboxamide (320 mg, 97%). LCMS (ESI+): m/z=422.1 (M+H).

Step 2: 3-(4-Fluorophenyl)-2-(morpholin-4-yl)-N-[3-(pyrimidin-5-yl)propyl]quinoxaline-6-carboxamide A mixture of 2-chloro-3-(4-fluorophenyl)-N-[3-(pyrimidin-5-yl)propyl]quinoxaline-6-carboxamide (80 mg, 0.2 mmol), morpholine (82.7 uL, 0.948 mmol) and DIPEA (99.1 uL, 0.569 mmol) in NMP (1.25 mL) was heated at 170° C. for 30 min under microwave irradiation. The reaction mixture was distributed between water and EtOAc. The aqueous layer was extracted with EtOAc. The combined organic layers were washed with brine, dried and concentrated. The crude product was purified by silica gel chromatography to give 3-(4-fluorophenyl)-2-(morpholin-4-yl)-N-[3-(pyrimidin-5-yl)propyl]quinoxaline-6-carboxamide (54 mg, 60%) as yellow solid. LCMS (ESI+): m/z=473.2 (M+H).

¹H NMR (400 MHz, DMSO-d₆) δ 9.02 (s, 1H), 8.79-8.69 (m, 3H), 8.48 (d, J=1.8 Hz, 1H), 8.12 (dd, J=8.7, 2.0 Hz, 1H), 8.09-8.02 (m, 2H), 7.83 (d, J=8.7 Hz, 1H), 7.44-7.35 (m, 2H), 3.71-3.58 (m, 4H), 3.40-3.30 (m, 2H), 3.28-3.14 (m, 4H), 2.70 (m, 2H), 1.97-1.85 (m, 2H).

The compounds listed in the table below were prepared in an analogous fashion to that described above starting from the appropriate starting materials:

| Starting Material Step 2 | Compound No. or Name | LCMS Data |
|---|---|---|
| HN-cyclohexyl | I-138 | LCMS (ESI+, FA): m/z = 471.2 (M + H) |

Example 31: 3-(4-Fluorophenyl)-N-[3-(6-methylpyridin-3-yl)propyl]-2-(morpholin-4-yl)quinoxaline-6-carboxamide (I-21)

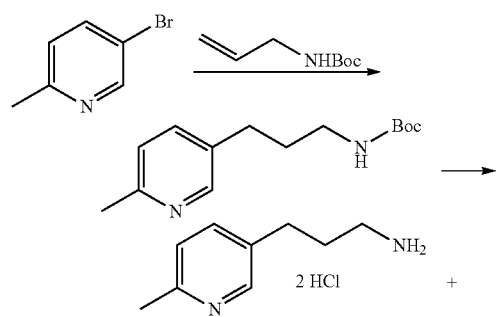

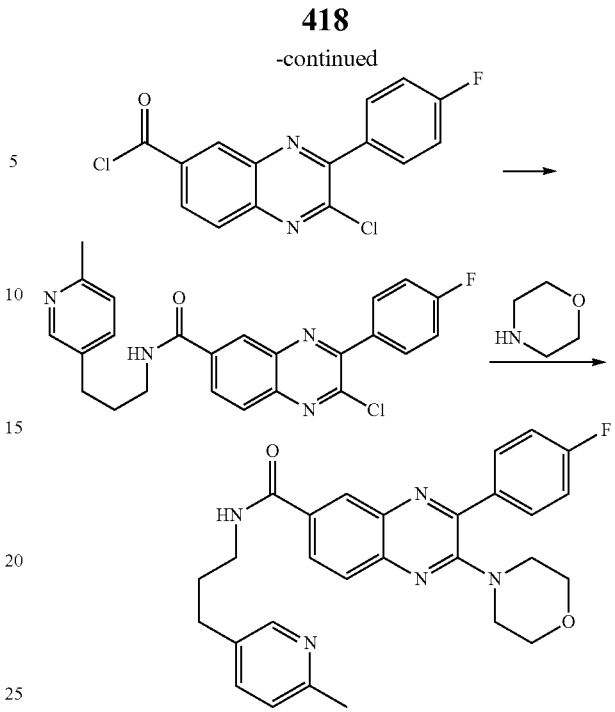

Step 1: tert-Butyl [3-(6-methylpyridin-3-yl)propyl]carbamate

3-N-tert-Butoxycarbonylamino-1-propene (1.90 g, 12.1 mmol) was dissolved in anhydrous tetrahydrofuran (20.0 mL) and cooled to 0° C. 9-BBN (0.5M in THF, 23.2 mL, 11.6 mmol) was added dropwise. The mixture was stirred under N₂ atmosphere at 0° C. then stirred at rt overnight. Additional 9-BBN (0.5 M in THF, 23.2 mL, 11.6 mmol) was added and the solution was stirred at rt for 3.5 hours. Sodium hydroxide (2.0 M in water, 16.0 mL, 32.0 mmol) was added and the mixture was stirred at rt for 4 hours. The alkylborane reagent solution generated above was degassed by low vacuum evacuation and flushing with N₂ for 3 times. A solution of 5-bromo-2-methylpyridine (1.00 g, 5.81 mmol) and tetrakis(triphenylphosphine)palladium (362 mg, 0.313 mmol) in anhydrous THF (20.0 mL, 246 mmol) was degassed and added to the boronic acid solution obtained above. The mixture was degassed two more times, heated under N₂ atmosphere at 80° C. for 17 hours. The brown solution was cooled to rt and concentrated in vacuo. The aqueous residue was extracted with EtOAc, washed with water, then brine, dried over anhydrous Na₂SO₄, filtered and concentrated in vacuo to give a crude residue. Purification by silica gel chromatography afforded tert-butyl [3-(6-methylpyridin-3-yl)propyl]carbamate (1.10 g, yield 73%) as an oil.

Step 2: 3-(6-methylpyridin-3-yl)propan-1-amine.2[HCl]

tert-Butyl [3-(6-methylpyridin-3-yl)propyl]carbamate was dissolved in THF (10.0 mL, 123 mmol). HCl (4.0 M in dioxane, 5.0 mL, 20.0 mmol) was added. The resulting solution was stirred at rt for 23 hrs. The resulting white suspension was filtered and the solid was washed with EtOAc then hexane, dried in air then in vacuo to give 3-(6-methylpyridin-3-yl)propan-1-amine.2[HCl] (0.861 g, yield 65%) as a white solid. LCMS (ESI+): m/z=151

(M+H). 1H NMR (400 MHz, MeOH-$d_4$) δ 8.67 (s, 1H), 8.44 (d, J=8.2 Hz, 1H), 7.89 (d, J=8.3 Hz, 1H), 3.03 (t, J=7.5 Hz, 2H), 2.98-2.90 (m, 2H), 2.78 (s, 3H), 2.11-2.00 (m, 2H).

Step 3: 2-Chloro-3-(4-fluorophenyl)-N-[3-(6-methylpyridin-3-yl)propyl]quinoxaline-6-carboxamide To a suspension of 2-chloro-3-(4-fluorophenyl)quinoxaline-6-carbonyl chloride (0.250 g, 0.778 mmol) (prepared similarly to Example 3, step 6, or Example 27, step 6) and 3-(6-methylpyridin-3-yl)propan-1-amine hydrochloride (174 mg, 0.934 mmol) in N,N-dimethylacetamide (16.9 mL, 182 mmol) was added triethylamine (0.542 mL, 3.89 mmol). The reaction mixture was stirred at rt overnight. To the mixture was added saturated aqueous $NaHCO_3$ (30 mL), a solid precipitated. The obtained solid was collected by filtration and washed with water to give 2-chloro-3-(4-fluorophenyl)-N-[3-(6-methylpyridin-3-yl)propyl]quinoxaline-6-carboxamide (340 mg, 97%). LCMS (ESI+): m/z=435.1 (M+H).

Step 4: 3-(4-Fluorophenyl)-N-[3-(6-methylpyridin-3-yl)propyl]-2-(morpholin-4-yl)quinoxaline-6-carboxamide A mixture of 2-chloro-3-(4-fluorophenyl)-N-[3-(6-methylpyridin-3-yl)propyl]quinoxaline-6-carboxamide (80 mg, 0.2 mmol), morpholine (82.7 uL, 0.948 mmol), DIPEA (99.1 uL, 0.569 mmol) in NMP (1.25 mL, 13.0 mmol) was heated at 170° C. for 30 min under microwave irradiation. The reaction mixture was distributed between water and EtOAc. The aqueous layer was extracted with EtOAc. The combined organic layers were washed with brine, dried, and concentrated. The crude product was purified by silica gel chromatography to give 3-(4-fluorophenyl)-N-[3-(6-methylpyridin-3-yl)propyl]-2-(morpholin-4-yl)quinoxaline-6-carboxamide (20 mg, 21%) as yellow solid. LCMS (ESI+): m/z=486.2 (M+H). $^1$H NMR (400 MHz, DMSO-$d_6$) δ 1.92-1.80 (m, 2H), 2.41 (s, 3H), 2.63 (m, 2H), 3.27-3.19 (m, 4H), 3.36-3.28 (m, 2H), 3.68-3.60 (m, 4H), 7.17 (d, J=7.9 Hz, 1H), 7.44-7.36 (m, 2H), 7.55 (dd, J=7.9, 2.3 Hz, 1H), 7.83 (d, J=8.7 Hz, 1H), 8.09-8.02 (m, 2H), 8.12 (dd, J=8.7, 2.0 Hz, 1H), 8.33 (d, J=2.0 Hz, 1H), 8.48 (d, J=1.8 Hz, 1H), 8.72 (m, 1H).

The compounds listed in the table below were prepared in an analogous fashion to that described above starting from the appropriate starting materials:

| Starting Material Step 4 | Starting Material Step 2 | Compound No. or Name | LCMS Data |
|---|---|---|---|
| | HN-piperidine | I-185 | LCMS (ESI+, FA): m/z = 484.3 (M + H) |
| | HN-4-hydroxypiperidine | I-25 | LCMS (ESI+, FA): m/z = 486.2 (M + H) |
| | HN-(4-morpholinyl)piperidine | I-70 | LCMS (ESI+, FA): m/z = 567.3 (M + H) |
| | HN-piperidine | I-197 | LCMS (ESI+, FA): m/z = 482.3 (M + H) |

| Starting Material Step 4 | Starting Material Step 2 | Compound No. or Name | LCMS Data |
|---|---|---|---|
| (structure) | (structure) | I-46 | LCMS (ESI−, FA): m/z = 496.2 (M − H) |

Example 32: N-(1H-Benzimidazol-5-ylmethyl)-3-(4-fluorophenyl)-2-(morpholin-4-yl)quinoxaline-6-carboxamide (I-132)

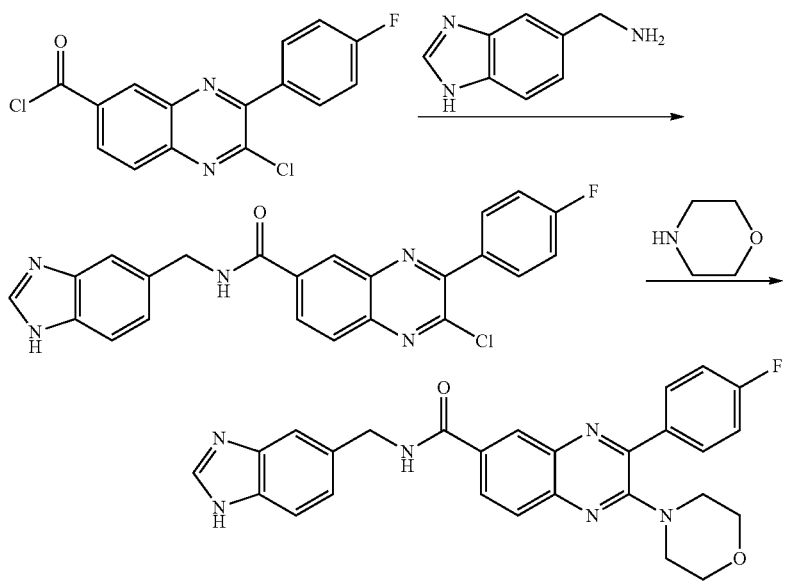

Step 1: N-(1H-Benzimidazol-5-ylmethyl)-2-chloro-3-(4-fluorophenyl)quinoxaline-6-carboxamide 2-Chloro-3-(4-fluorophenyl)quinoxaline-6-carbonyl chloride (275 mg, 0.856 mmol) (prepared similarly to Example 3, step 6, or Example 27, step 6) was dissolved in DMA (18.5 mL). To the solution was added (1H-benzimidazol-5-ylmethyl)amine dihydrochloride (226 mg, 1.03 mmol) and triethylamine (0.597 mL, 4.28 mmol), and the mixture was stirred at rt for 16 hours. To the mixture was added saturated aqueous NaHCO$_3$ (20 mL) and then stirred at rt for 15 minutes. Filtered, washed the solid with water and dried in vacuo to give N-(1H-benzimidazol-5-ylmethyl)-2-chloro-3-(4-fluorophenyl)quinoxaline-6-carboxamide (320 mg, 86%) as pale yellow solid. LCMS (ESI+): m/z=432.1 (M+H). $^1$H NMR (400 MHz, DMSO-d$_6$) δ 9.50 (s, 1H), 8.73 (d, J=1.5 Hz, 1H), 8.38 (dd, J=8.8, 1.8 Hz, 1H), 8.27-8.13 (m, 2H), 7.95 (dd, J=8.7, 5.5 Hz, 2H), 7.62 (m, 2H), 7.43 (t, J=8.9 Hz, 2H), 7.22 (d, J=8.5 Hz, 1H), 4.66 (d, J=5.7 Hz, 2H).

Step 2: N-(1H-Benzimidazol-5-ylmethyl)-3-(4-fluorophenyl)-2-(morpholin-4-yl)quinoxaline-6-carboxamide A mixture of N-(1H-benzimidazol-5-ylmethyl)-2-chloro-3-(4-fluorophenyl)quinoxaline-6-carboxamide (98.0 mg, 0.227 mmol), morpholine (0.099 mL, 1.13 mmol), DIPEA (0.118 mL, 0.681 mmol) and NMP (1.9 mL) was heated at 170° C. for 30 min under microwave irradiation. After cooling, the reaction mixture was poured into EtOAc and water. The layers were separated and the aqueous layer was extracted two more times with EtOAc. The combined organic layer was dried over anhydrous MgSO$_4$ and concentrated in vacuo. Purified by silica gel chromatography to give N-(1H-benzimidazol-5-ylmethyl)-3-(4-fluorophenyl)-2-(morpholin-4-yl)quinoxaline-6-carboxamide (30 mg, 27%) as a pale yellow solid. LCMS (ESI+): m/z=483.2 (M+H). $^1$H NMR (400 MHz, MeOD) δ 8.45 (d, J=1.8 Hz, 1H), 8.16 (s, 1H), 8.13 (dd, J=8.7, 2.0 Hz, 1H), 8.10-8.02 (m, 2H), 7.89 (dd, J=8.9, 6.1 Hz, 1H), 7.68 (s, 1H), 7.61 (d, J=8.3 Hz, 1H), 7.40-7.34 (m, 1H), 7.30 (t, J=8.8 Hz, 2H), 4.78 (s, 2H), 3.77-3.68 (m, 4H), 3.31 (in, 4H).

Example 33: 3-(4-Fluorophenyl)-N-[2-(1H-imidazol-2-yl)ethyl]-2-(piperidin-1-yl)quinoxaline-6-carboxamide (I-1)

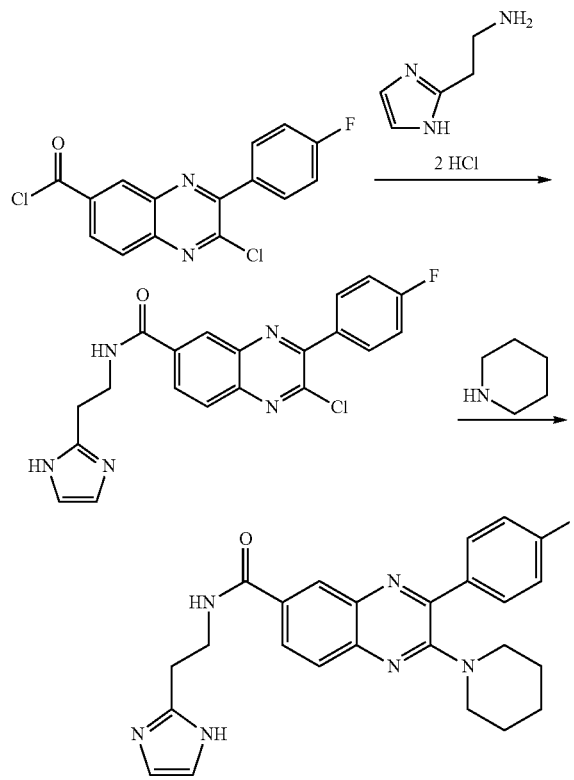

Step 1: 2-Chloro-3-(4-fluorophenyl)-N-[2-(1H-imidazol-2-yl)ethyl]quinoxaline-6-carboxamide To a suspension of 2-chloro-3-(4-fluorophenyl)quinoxaline-6-carbonyl chloride (0.250 g, 0.778 mmol) (prepared similarly to Example 3, step 6, or Example 27, step 6) and [2-(1H-imidazol-2-yl)ethyl]amine dihydrochloride (172 mg, 0.934 mmol) in DMA (16.9 mL, 182 mmol) was added triethylamine (0.542 mL, 3.89 mmol). The homogeneous reaction mixture was stirred at rt overnight. The reaction mixture was diluted with EtOAc and sat.NaHCO$_3$. The NaHCO$_3$ layer was extracted with EtOAc. The combined EtOAc layers were washed with water and evaporated to dryness, triturated with small amount of CH$_3$CN and water to give 2-chloro-3-(4-fluorophenyl)-N-[2-(1H-imidazol-2-yl)ethyl]quinoxaline-6-carboxamide (280 mg, 91%) as a white solid. LCMS (ESI+): m/z=396.1 (M+H).

Step 2: 3-(4-Fluorophenyl)-N-[2-(1H-imidazol-2-yl) ethyl]-2-(piperidin-1-yl)quinoxaline-6-carboxamide A mixture of 2-chloro-3-(4-fluorophenyl)-N-[2-(1H-imidazol-2-yl)ethyl]quinoxaline-6-carboxamide (80.0 mg, 0.202 mmol), piperidine (99.9 uL, 1.01 mmol) and DIPEA (106 uL, 0.606 mmol) in NMP (1.34 mL, 13.8 mmol) was heated at 170° C. for 30 min under microwave irradiation. Water was added to the reaction mixture, the precipitated solid was collected by filtration. The solid was washed with more water, then ether and dried to give 3-(4-fluorophenyl)-N-[2-(1H-imidazol-2-yl)ethyl]-2-(piperidin-1-yl)quinoxaline-6-carboxamide (50 mg, 60%). LCMS (ESI+): m/z=445.2 (M+H). $^1$H NMR (400 MHz, DMSO-d$_6$) δ 1.55 (s, 6H), 2.98-2.84 (m, 2H), 3.23 (m, 4H), 3.62 (m, 2H), 6.90 (m, 2H), 7.40 (m, 2H), 7.79 (d, J=8.7 Hz, 1H), 8.05 (m, 2H), 8.10 (dd, J=8.7, 2.0 Hz, 1H), 8.44 (d, J=1.8 Hz, 1H), 8.83 (m, 1H).

The compound listed in the table below was prepared in an analogous fashion to that described above starting from the appropriate starting materials:

| Starting Material Step 2 | Compound No. or Name | LCMS Data |
| --- | --- | --- |
| none | I-102 | LCMS (ESI+, FA): m/z = 396.1 (M + H) |

Example 34: 3-(4-Fluorophenyl)-N-[3-(1H-imidazol-4-yl)propyl]-2-(piperidin-1-yl)quinoxaline-6-carboxamide (I-301)

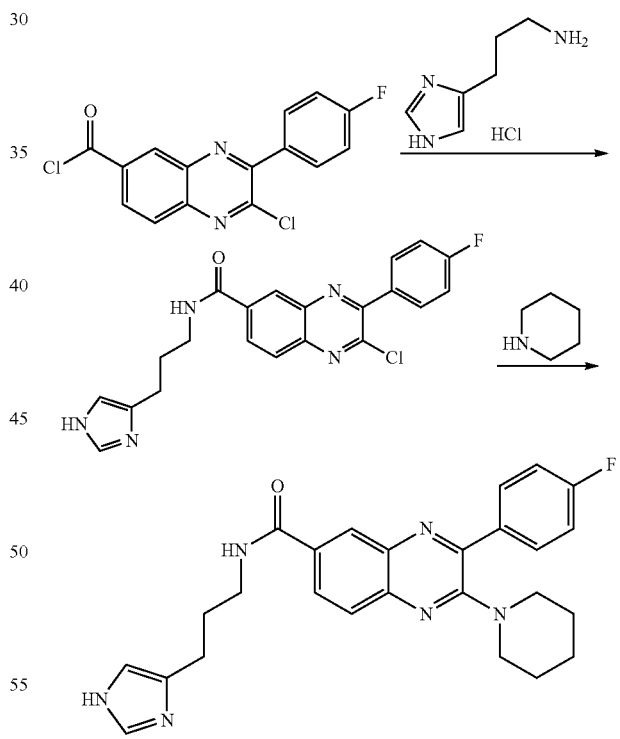

Step 1: 2-Chloro-3-(4-fluorophenyl)-N-[3-(1H-imidazol-4-yl)propyl]quinoxaline-6-carboxamide To a suspension of 2-chloro-3-(4-fluorophenyl)quinoxaline-6-carbonyl chloride (250 mg, 0.778 mmol) (prepared similarly to Example 3, step 6, or Example 27, step 6) in DMA (16.9 mL, 182 mmol), triethylamine (0.542 mL, 3.89 mmol) and 3-(1H-imidazol-4-yl)propan-1-amine HCl (0.151 g, 0.934 mmol) were added. The mixture was stirred at rt overnight. To the mixture was added saturated aqueous NaHCO$_3$ and a solid precipitated. The obtained solid was collected by filtration and washed with water to give 2-chloro-3-(4-fluorophenyl)-N-[3-(1H-imidazol-4-yl)propyl]quinoxaline-6-carboxamide (230 mg, 72%). LCMS (ESI+): m/z=410.1 (M+H).

Step 2: 3-(4-Fluorophenyl)-N-[3-(1H-imidazol-4-yl)propyl]-2-(piperidin-1-yl)quinoxaline-6-carboxamide A mixture of 2-chloro-3-(4-fluorophenyl)-N-[3-(1H-imidazol-4-yl)propyl]quinoxaline-6-carboxamide (70 mg, 0.2 mmol), piperidine (87.4 uL, 0.884 mmol) and DIPEA (92.4 uL, 0.530 mmol) in NMP (1.17 mL, 12.1 mmol) was heated at 170° C. for 30 min under microwave irradiation. The reaction mixture was distributed between water and EtOAc. The aqueous layer was extracted with EtOAc. The combined organic layers were washed with brine, dried, and concentrated. The crude product was purified by silica gel chromatography to give 3-(4-fluorophenyl)-N-[3-(1H-imidazol-4-yl)propyl]-2-(piperidin-1-yl)quinoxaline-6-carboxamide (24 mg, 30%). LCMS (ESI+): m/z=459.2 (M+H). $^1$H NMR (400 MHz, DMSO-d$_6$) δ 1.55 (m, 6H), 1.94-1.80 (m, 2H), 2.58 (m, 2H), 3.23 (m, 4H), 3.35 (m, 2H), 6.79 (s, 1H), 7.40 (m, 2H), 7.54 (d, J=0.9 Hz, 1H), 7.79 (d, J=8.7 Hz, 1H), 8.08-8.00 (m, 2H), 8.11 (dd, J=8.7, 2.0 Hz, 1H), 8.47 (d, J=1.9 Hz, 1H), 8.76 (m, 1H).

The compound listed in the table below was prepared in an analogous fashion to that described above starting from the appropriate starting materials:

| Starting Material Step 2 | Compound No. or Name | LCMS Data |
|---|---|---|
| 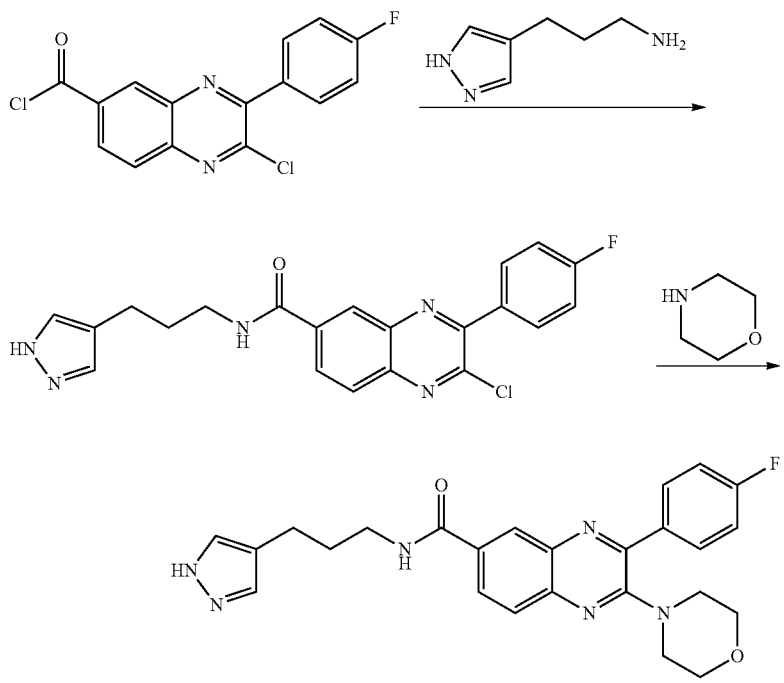 | I-35 | LCMS (ESI+, FA): m/z = 461.2 (M + H) |

Example 35: 3-(4-Fluorophenyl)-2-(morpholin-4-yl)-N-[3-(1H-pyrazol-4-yl)propyl]quinoxaline-6-carboxamide (I-297)

Step 1: 2-Chloro-3-(4-fluorophenyl)-N-[3-(1H-pyrazol-4-yl)propyl]quinoxaline-6-carboxamide To a suspension of 2-chloro-3-(4-fluorophenyl)quinoxaline-6-carbonyl chloride (534 mg, 1.67 mmol) (prepared similarly to Example 3, step 6, or Example 27, step 6) in N,N-dimethylacetamide (15.0 mL, 161 mmol) was added 3-(1H-pyrazol-4-yl)-propylamine (251 mg, 2.00 mmol) and triethylamine (1.16 mL, 8.36 mmol). The resulting orange solution was stirred at rt for 1 h. The mixture was distributed between NaHCO$_3$ (aq) saturated solution and EtOAc. The aqueous layer was extracted with EtOAc. The combined organic layer was washed with water and brine, dried, and concentrated. Purification by silica gel chromatography provided 2-chloro-3-(4-fluorophenyl)-N-[3-(1H-pyrazol-4-yl)propyl]quinoxaline-6-carboxamide (509 mg, 74%) as an off-white solid. LCMS (ESI+); m/z=410.1, 412.1 (M+H). $^1$H NMR (400 MHz, DMSO-d$_6$) δ 12.53 (br s, 1H), 8.91 (t, J=5.5 Hz, 1H), 8.68 (d, J=1.6 Hz, 1H), 8.33 (dd, J=8.7, 1.9 Hz, 1H), 8.18 (d, J=8.7 Hz, 1H), 7.95 (dd, J=8.8, 5.5 Hz, 2H), 7.55 (br s, 1H), 7.44 (t, J=8.9 Hz, 2H), 7.37 (br s, 1H), 3.44-3.36 (m, 2H), 2.57-2.51 (m, 2H), 1.84 (p, J=7.3 Hz, 2H).

Step 2: 3-(4-Fluorophenyl)-2-(morpholin-4-yl)-N-[3-(1H-pyrazol-4-yl)propyl]quinoxaline-6-carboxamide A mixture of 2-chloro-3-(4-fluorophenyl)-N-[3-(1H-pyrazol-4-yl)propyl]quinoxaline-6-carboxamide (62.0 mg, 0.151 mmol), morpholine (66.0 uL, 0.756 mmol), N,N-diisopropylethylamine (79.0 uL, 0.454 mmol) in N-methylpyrrolidinone (1.00 mL, 10.4 mmol) was heated at 170° C. under microwave irradiation for 30 min. The reaction was distributed between water and EtOAc. The aqueous layer was extracted with EtOAc. The combined organic layer was washed with brine, dried, and concentrated. Purification by silica gel chromatography provided 3-(4-fluorophenyl)-2-(morpholin-4-yl)-N-[3-(1H-pyrazol-4-yl)propyl]quinoxaline-6-carboxamide (60 mg, 86%) as a yellow solid. LCMS (ESI+): m/z=461.2 (M+H). $^1$H NMR (400 MHz, MeOD) δ 8.35 (d, J=1.8 Hz, 1H), 8.12-7.99 (m, 3H), 7.83 (d, J=8.7 Hz, 1H), 7.47 (br s, 2H), 7.27 (t, J=8.8 Hz, 2H), 3.69 (t, J=4.6 Hz, 4H), 3.45 (t, J=7.1 Hz, 2H), 3.29-3.27 (m, 4H), 2.61 (t, J=7.5 Hz, 2H), 1.92 (p, J=7.4 Hz, 2H).

The compound listed in the table below was prepared in an analogous fashion to that described above starting from the appropriate starting materials:

| Starting Material Step 2 | Compound No. or Name | LCMS Data |
|---|---|---|
| 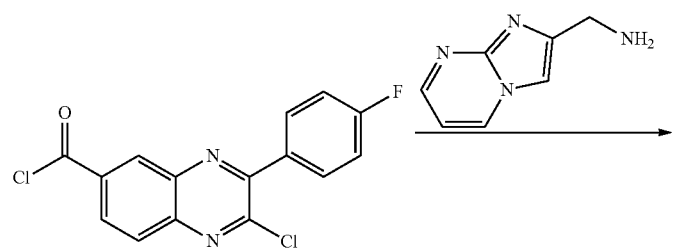 | I-94 | LCMS (ESI+, FA): m/z = 459.2 (M + H) |

Example 36: 3-(4-Fluorophenyl)-2-(4-hydroxypiperidin-1-yl)-N-(imidazo[1,2-a]pyrimidin-2-ylmethyl)quinoxaline-6-carboxamide (I-282)

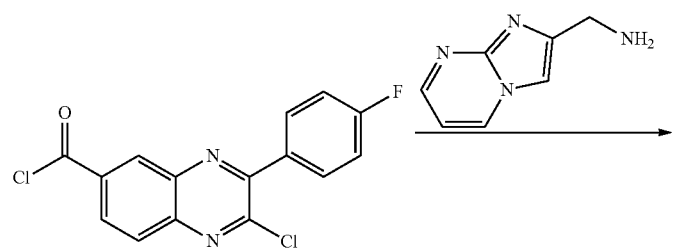

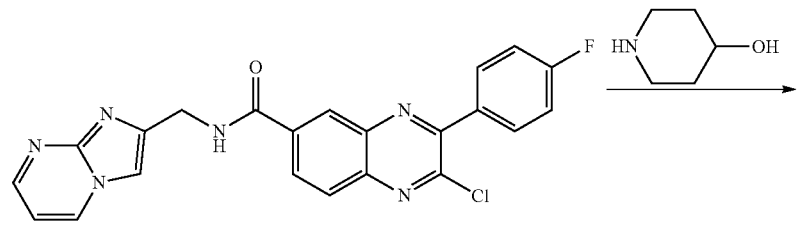

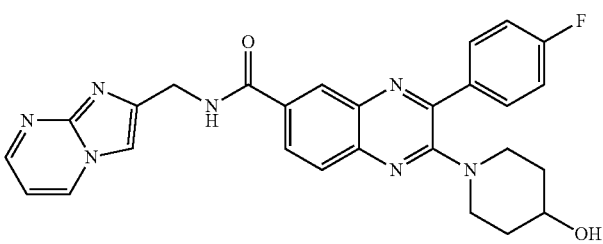

Step 1: 2-Chloro-3-(4-fluorophenyl)-N-(imidazo[1,2-a]pyrimidin-2-ylmethyl)quinoxaline-6-carboxamide 2-Chloro-3-(4-fluorophenyl)quinoxaline-6-carbonyl chloride (339 mg, 1.06 mmol) (prepared similarly to Example 3, step 6, or Example 27, step 6) was dissolved in DMA (23.0 mL). To the solution was added 1-imidazo[1,2-a]pyrimidin-2-ylmethanamine dihydrochloride (280 mg, 1.27 mmol) and triethylamine (0.736 mL, 5.28 mmol), and the mixture was stirred at rt for 16 hours. To the mixture was added saturated aqueous NaHCO$_3$ (25 mL) and then stirred at rt for 15 minutes. Filtered, washed the solid with water and dried in vacuo to give 2-chloro-3-(4-fluorophenyl)-N-(imidazo[1,2-a]pyrimidin-2-ylmethyl)quinoxaline-6-carboxamide (432 mg, 95%) as pale yellow solid. LCMS (ESI+): m/z=433.0 (M+H). $^1$H NMR (400 MHz, DMSO-d$_6$) δ 9.55 (s, 1H), 8.93 (dd, J=6.7, 2.0 Hz, 1H), 8.75 (d, J=1.5

Hz, 1H), 8.51 (dd, J=4.1, 2.0 Hz, 1H), 8.39 (dd, J=8.7, 1.8 Hz, 1H), 8.20 (d, J=8.8 Hz, 1H), 7.95 (dd, J=8.7, 5.5 Hz, 2H), 7.87 (s, 1H), 7.44 (t, J=8.9 Hz, 2H), 7.04 (dd, J=6.7, 4.1 Hz, 1H), 4.71 (d, J=5.3 Hz, 2H).

Step 2: 3-(4-Fluorophenyl)-2-(4-hydroxypiperidin-1-yl)-N-(imidazo[1,2-a]pyrimidin-2-ylmethyl)quinoxaline-6-carboxamide A mixture of 2-chloro-3-(4-fluorophenyl)-N-(imidazo[1,2-a]pyrimidin-2-ylmethyl)quinoxaline-6-carboxamide (81.0 mg, 0.187 mmol), 4-hydroxypiperidine (94.6 mg, 0.936 mmol), DIEA (0.098 mL, 0.561 mmol) and NMP (1.5 mL) was heated at 170° C. for 30 min under microwave irradiation. After cooling, the reaction mixture was poured into EtOAc and water. The layers were separated and the aqueous layer was extracted two more times with EtOAc. The combined organic layer was dried over anhydrous MgSO$_4$ and concentrated in vacuo. Purified by silica gel chromatography to give 3-(4-fluorophenyl)-2-(4-hydroxypiperidin-1-yl)-N-(imidazo[1,2-a]pyrimidin-2-ylmethyl)quinoxaline-6-carboxamide (60 mg, 64%) as a pale yellow solid. LCMS (ESI+): m/z=498.2 (M+H). $^1$H NMR (400 MHz, MeOD) δ 8.83 (dd, J=6.7, 1.7 Hz, 1H), 8.56 (dd, J=4.1, 1.8 Hz, 1H), 8.46 (d, J=1.5 Hz, 1H), 8.13 (dd, J=8.7, 1.8 Hz, 1H), 8.05 (dd, J=8.6, 5.5 Hz, 2H), 7.86 (d, J=8.7 Hz, 1H), 7.82 (s, 1H), 7.30 (t, J=8.7 Hz, 2H), 7.05 (dd, J=6.7, 4.2 Hz, 1H), 4.82 (s, 2H), 3.86-3.76 (m, 1H), 3.70 (m, 2H), 3.04 (t, J=10.4 Hz, 2H), 1.87 (m, 2H), 1.57 (dd, J=18.8, 9.2 Hz, 2H).

The compound listed in the table below was prepared in an analogous fashion to that described above starting from the appropriate starting materials:

| Starting Material Step 2 | Compound No. or Name | LCMS Data |
|---|---|---|
| 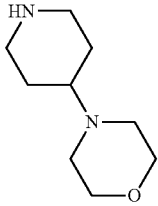 [SMILES: C1CC(N2CCOCC2)CCN1] | I-204 | LCMS (ESI+, FA): m/z = 567.3 (M + H) |

Example 37: 3-(4-Fluorophenyl)-N-[2-(1-methyl-1H-imidazol-5-yl)ethyl]-2-[4-(morpholin-4-yl)piperidin-1-yl]quinoxaline-6-carboxamide (I-82)

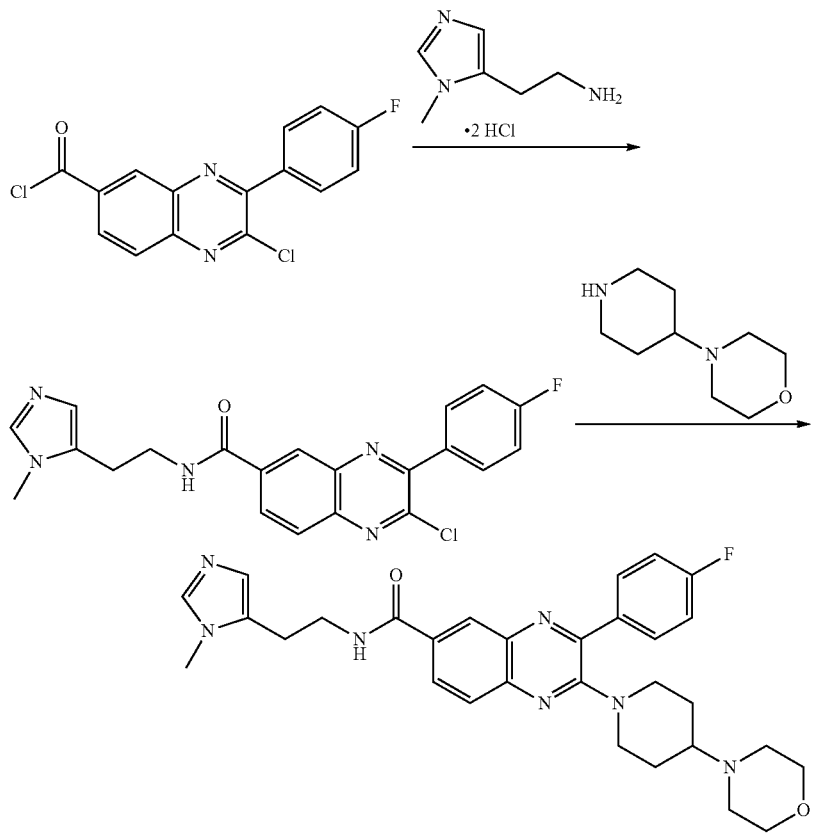

Step 1: 2-Chloro-3-(4-fluorophenyl)-N-[2-(1-methyl-1H-imidazol-5-yl)ethyl]quinoxaline-6-carboxamide 2-Chloro-3-(4-fluorophenyl) quinoxaline-6-carbonyl chloride (0.567 g, 1.77 mmol) was dissolved in N,N-dimethylacetamide (20.0 mL). N,N-diisopropylethylamine (1.60 mL, 9.18 mmol) was added, followed by 3-methylhistamine dihydrochloride (0.350 g, 1.77 mmol). The mixture was stirred at rt for 2 h. The mixture was evaporated in vacuo, azeotroped with toluene (~50 mL). The liquid residue was diluted with EtOAc and water. The organic layer was washed with water, then brine, dried over anhydrous Na₂SO₄, and filtered. The filtrate was concentrated and purified by silica gel chromatography to provide 2-chloro-3-(4-fluorophenyl)-N-[2-(1-methyl-1H-imidazol-5-yl)ethyl]quinoxaline-6-carboxamide as a yellow solid (494 mg, 67%). LCMS (ESI+, FA): m/z=410.2 (M+H). ¹H NMR (400 MHz, DMSO-d₆) δ 9.05 (t, J=5.5 Hz, 1H), 8.62 (d, J=1.6 Hz, 1H), 8.30 (dd, J=8.7, 1.9 Hz, 1H), 8.17 (d, J=8.7 Hz, 1H), 7.98-7.90 (m, 2H), 7.52 (s, 1H), 7.46-7.39 (m, 2H), 6.74 (s, 1H), 3.59 (s, 3H), 3.58-3.53 (m, 2H), 2.87 (t, J=7.2 Hz, 2H).

Step 2: 3-(4-Fluorophenyl)-N-[2-(1-methyl-1H-imidazol-5-yl)ethyl]-2-[4-(morpholin-4-yl)piperidin-1-yl]quinoxaline-6-carboxamide A mixture of 2-chloro-3-(4-fluorophenyl)-N-[2-(1-methyl-1H-imidazol-5-yl)ethyl]quinoxaline-6-carboxamide (0.101 g, 0.234 mmol), 4-(piperidin-4-yl)-morpholine (0.199 g, 1.17 mmol) and N,N-diisopropylethylamine (0.122 mL, 0.702 mmol) in N-methylpyrrolidinone (1.50 mL) was heated to 170° C. under microwave irradiation for 30 min. The mixture was cooled to rt, quenched with water (50 mL) and extracted with EtOAc. The combined EtOAc solution was washed with brine, dried over anhydrous Na₂SO₄, filtered, and concentrated in vacuo to give the crude product. Purification by silica gel chromatography afforded 3-(4-fluorophenyl)-N-[2-(1-methyl-1H-imidazol-5-yl)ethyl]-2-[4-(morpholin-4-yl)piperidin-1-yl]quinoxaline-6-carboxamide (108 mg, 82%) as a yellow solid. LCMS (ESI+, FA):

m/z=544.3 (M+H). ¹H NMR (400 MHz, DMSO-d₆) δ 8.84 (t, J=5.4 Hz, 1H), 8.44 (d, J=1.1 Hz, 1H), 8.10 (dd, J=8.7, 1.4 Hz, 1H), 8.04 (dd, J=8.3, 5.7 Hz, 2H), 7.80 (d, J=8.7 Hz, 1H), 7.51 (s, 1H), 7.41 (t, J=8.7 Hz, 2H), 6.73 (s, 1H), 3.77 (d, J=12.4 Hz, 2H), 3.59 (s, 3H), 3.58-3.47 (m, 6H), 2.85 (t, J=7.2 Hz, 2H), 2.78 (t, J=12.0 Hz, 2H), 2.45 (s, 4H), 2.28 (t, J=10.7 Hz, 1H), 1.78 (d, J=11.3 Hz, 2H), 1.42 (dd, J=21.0, 10.9 Hz, 2H).

The compounds listed in the table below were prepared in an analogous fashion to that described above starting from the appropriate starting materials:

| Starting Material Step 2 | Compound No. or Name | LCMS Data |
|---|---|---|
| H-N(CH₃)(CH₃) (methylamine structure) | I-58* | LCMS (ESI+, FA): m/z = 419.2 (M + H) |
| morpholine (O-CH₂CH₂-NH-CH₂CH₂) | I-177 | LCMS (ESI+, FA): m/z = 461.2 (M + H) |
| HN-piperidine-OH (4-hydroxypiperidine) | I-292 | LCMS (ESI+, FA): m/z = 475.2 (M + H) |
| HN-piperidine | I-4 | LCMS (ESI+, FA): m/z = 459.2 (M + H) |

*The temperature of the reaction was 120° C.

Example 38: 3-(4-Fluorophenyl)-2-(4-hydroxypiperidin-1-yl)-N-[3-(1,3-thiazol-2-yl)propyl]quinoxaline-6-carboxamide (I-77)

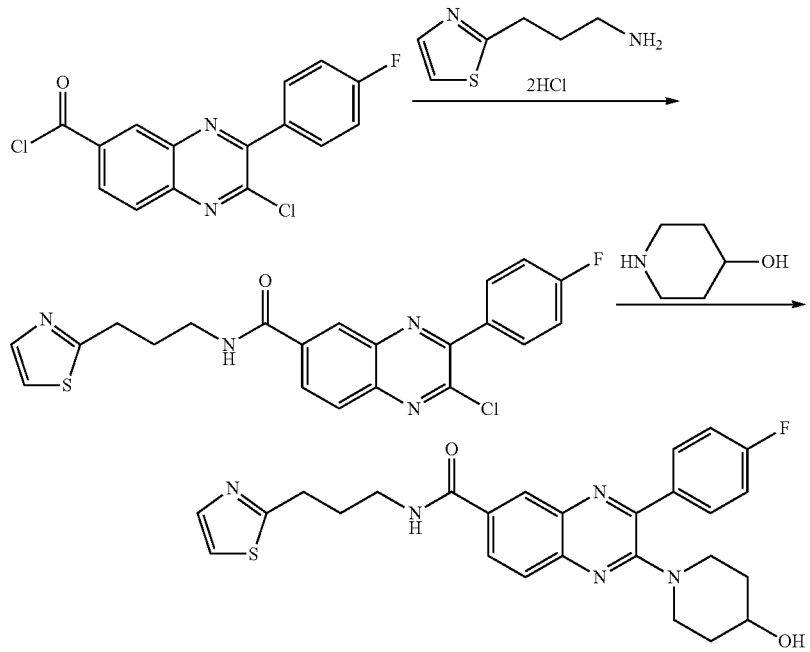

Step 1: 2-Chloro-3-(4-fluorophenyl)-N-[3-(1,3-thiazol-2-yl)propyl]quinoxaline-6-carboxamide 2-Chloro-3-(4-fluorophenyl)quinoxaline-6-carbonyl chloride (339 mg, 1.06 mmol) (prepared similarly to Example 3, step 6, or Example 27, step 6) was dissolved in DMA (23.0 mL). To the solution was added 3-(1,3-thiazol-2-yl)propan-1-amine dihydrochloride (272 mg, 1.27 mmol) and triethylamine (0.736 mL, 5.28 mmol), and the mixture was stirred at rt for 16 hours. To the mixture was added, saturated aqueous NaHCO₃ and EtOAc. The layers were separated and the aqueous layer was extracted two more times with EtOAc. The combined organic layer was washed with water, then brine, dried over anhydrous MgSO₄ and concentrated in vacuo. Purified by silica gel chromatography to give 2-chloro-3-(4-fluorophenyl)-N-[3-(1,3-thiazol-2-yl) propyl]quinoxaline-6-carboxamide (250 mg, 55%) as pale yellow solid. LCMS (ESI+): m/z=427.1 (M+H). $^1$H NMR (400 MHz, DMSO-d₆) δ 8.97 (t, J=5.4 Hz, 1H), 8.68 (d, J=1.5 Hz, 1H), 8.33 (dd, J=8.7, 1.9 Hz, 1H), 8.18 (d, J=8.8 Hz, 1H), 7.95 (dd, J=8.8, 5.5 Hz, 2H), 7.71 (d, J=3.3 Hz, 1H), 7.58 (d, J=3.3 Hz, 1H), 7.44 (t, J=8.9 Hz, 2H), 3.45 (dd, J=12.5, 6.7 Hz, 2H), 3.11 (t, J=7.6 Hz, 2H), 2.13-1.99 (m, 2H).

Step 2: 3-(4-fluorophenyl)-2-(4-hydroxypiperidin-1-yl)-N-[3-(1,3-thiazol-2-yl)propyl]quinoxaline-6-carboxamide A mixture of 2-chloro-3-(4-fluorophenyl)-N-[3-(1,3-thiazol-2-yl)propyl]quinoxaline-6-carboxamide (80.0 mg, 0.187 mmol), 4-hydroxypiperidine (94.8 mg, 0.937 mmol), DIPEA (0.098 mL, 0.562 mmol) and NMP (1.5 mL) was heated at 170° C. for 30 min under microwave irradiation. After cooling, the reaction mixture was poured into EtOAc and water. The layers were separated and the aqueous layer was extracted two more times with EtOAc. The combined organic layer was dried over anhydrous MgSO₄ and concentrated in vacuo. Purified by silica gel chromatography to give 3-(4-fluorophenyl)-2-(4-hydroxypiperidin-1-yl)-N-[3-(1,3-thiazol-2-yl)propyl]quinoxaline-6-carboxamide (67 mg, 73%) as a pale yellow solid. LCMS (ESI+): m/z=492.2 (M+H). $^1$H NMR (400 MHz, DMSO-d₆) δ 8.75 (s, 1H), 8.47 (s, 1H), 8.11 (d, J=8.6 Hz, 1H), 8.07-7.98 (m, 2H), 7.79 (d, J=8.7 Hz, 1H), 7.71 (d, J=2.5 Hz, 1H), 7.58 (d, J=2.6 Hz, 1H), 7.40 (t, J=8.5 Hz, 2H), 4.72 (d, J=3.3 Hz, 1H), 3.65 (s, 1H), 3.57 (d, J=12.9 Hz, 2H), 3.41 (d, J=5.7 Hz, 2H), 3.09 (t, J=7.5 Hz, 2H), 2.96 (t, J=10.6 Hz, 2H), 2.12-1.95 (m, 2H), 1.73 (m, 2H), 1.43 (m, 2H).

The compound listed in the table below was prepared in an analogous fashion to that described above starting from the appropriate starting materials:

| Starting Material Step 2 | Compound No. or Name | LCMS Data |
|---|---|---|
| 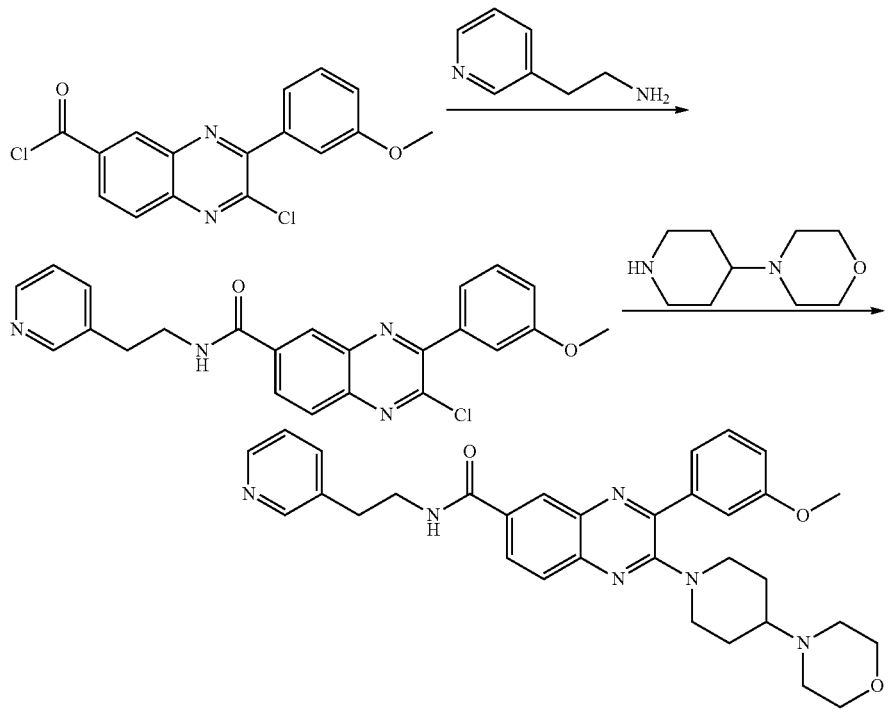 | I-42 | LCMS (ESI+, FA): m/z = 561.3 (M + H) |

Example 39: 3-(3-Methoxyphenyl)-2-[4-(morpholin-4-yl)piperidin-1-yl]-N-[2-(pyridin-3-yl)ethyl]quinoxaline-6-carboxamide I-291

Step 1: 2-Chloro-3-(3-methoxyphenyl)-N-[2-(pyridin-3-yl)ethyl]quinoxaline-6-carboxamide To a solution of 2-chloro-3-(3-methoxyphenyl)quinoxaline-6-carbonyl chloride (674 mg, 2.03 mmol) (prepared similarly to Example 3, step 6, or Example 27, step 6) in N,N-dimethylacetamide (25.0 mL, 269 mmol) was added triethylamine (1.41 mL, 10.1 mmol) and 2-pyridin-3-ylethanamine (0.297 g, 2.43 mmol). The resulting solution was stirred at rt for 1 h. The reaction was distributed between water and EtOAc. The aqueous layer was extracted with EtOAc. The combined organic layer was washed with brine, dried, and concentrated. Purification by silica gel chromatography provided 2-chloro-3-(3-methoxyphenyl)-N-[2-(pyridin-3-yl)ethyl]quinoxaline-6-carboxamide (601 mg, 70%) as a yellow solid. LCMS (ESI+): m/z=419.1, 421.1 (M+H). $^1$H NMR (400 MHz, CDCl$_3$) δ 8.51 (d, J=9.5 Hz, 2H), 8.38 (s, 1H), 8.18 (d, J=8.6 Hz, 1H), 8.08 (d, J=8.7 Hz, 1H), 7.61 (d, J=7.5 Hz, 1H), 7.51-7.40 (m, 2H), 7.36 (s, 1H), 7.30-7.26 (m, 1H), 7.08 (d, J=7.6 Hz, 1H), 6.61-6.43 (m, 1H), 3.89 (s, 3H), 3.80 (q, J=6.6 Hz, 2H), 3.01 (t, J=6.9 Hz, 2H).

Step 2: 3-(3-Methoxyphenyl)-2-[4-(morpholin-4-yl)piperidin-1-yl]-N-[2-(pyridin-3-yl)ethyl]quinoxaline-6-carboxamide A mixture of 2-chloro-3-(3-methoxyphenyl)-N-[2-(pyridin-3-yl)ethyl]quinoxaline-6-carboxamide (108 mg, 0.214 mmol), 4-(piperidin-4-yl)-morpholine (182 mg, 1.07 mmol), N,N-diisopropylethylamine (112 uL, 0.642 mmol) in N-methylpyrrolidinone (1.50 mL, 15.6 mmol) was heated at 170° C. under microwave irradiation for 30 min. The reaction was distributed between water and EtOAc. The aqueous layer was extracted with EtOAc. The combined organic layer was washed with brine, dried, and concentrated. The crude mixture was purified by HPLC to provide 3-(3-methoxyphenyl)-2-[4-(morpholin-4-yl)piperidin-1-yl]-N-[2-(pyridin-3-yl)ethyl]quinoxaline-6-carboxamide as a yellow solid (76.0 mg, 64%). LCMS (ESI+): m/z=553.3 (M+H). $^1$H NMR (400 MHz, CDCl$_3$) δ 8.52 (s, 1H), 8.48 (d, J=3.9 Hz, 1H), 8.26 (s, 1H), 8.21 (d, J=1.6 Hz, 1H), 8.02 (dd, J=8.7, 1.8 Hz, 1H), 7.80 (d, J=8.7 Hz, 1H), 7.62 (d, J=7.7

The compounds listed in the table below were prepared in an analogous fashion to that described above starting from the appropriate starting materials:

| Starting Material Step 2 | Compound No. or Name | LCMS Data |
|---|---|---|
| none | I-73 | LCMS (ESI+, FA): m/z = 419.1, 421.2 (M + H) |
| HN–⟨piperidine⟩ | I-196 | LCMS (ESI+, FA): m/z = 468.2 (M + H) |
| O⟨morpholine⟩NH | I-189 | LCMS (ESI+, FA): m/z = 470.2 (M + H) |
| HN–⟨4-hydroxypiperidine⟩OH | I-67 | LCMS (ESI+, FA): m/z = 484.2 (M + H) |

Example 40: 3-(4-Fluorophenyl)-2-(4-hydroxypiperidin-1-yl)-N-(imidazo[1,2-a]pyridin-6-ylmethyl)quinoxaline-6-carboxamide (I-156)

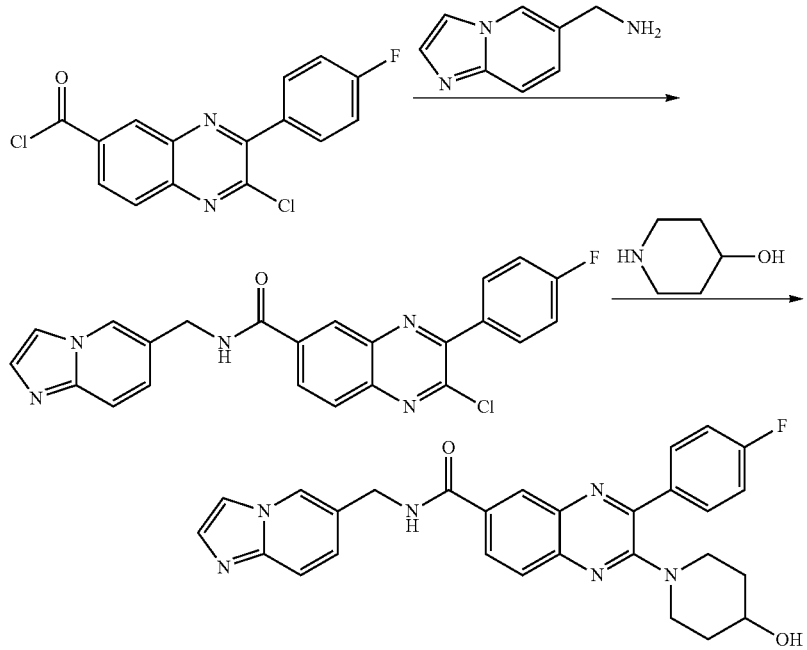

Hz, 1H), 7.48 (d, J=7.6 Hz, 1H), 7.44 (s, 1H), 7.39 (t, J=7.9 Hz, 1H), 7.30-7.27 (m, 1H), 7.00 (dd, J=8.1, 2.0 Hz, 1H), 6.49 (t, J=5.6 Hz, 1H), 3.95 (d, J=13.0 Hz, 2H), 3.88 (s, 3H), 3.83-3.67 (m, 6H), 2.99 (t, J=6.9 Hz, 2H), 2.82-2.66 (m, 6H), 2.57 (t, J=11.5 Hz, 1H), 1.89 (d, J=11.4 Hz, 2H), 1.68-1.47 (m, 2H).

Step 1: 2-Chloro-3-(4-fluorophenyl)-N-(imidazo[1,2-a]pyridin-6-ylmethyl)quinoxaline-6-carboxamide 2-Chloro-3-(4-fluorophenyl)quinoxaline-6-carbonyl chloride (445 mg, 1.39 mmol) (prepared similarly to Example 3, step 6, or Example 27, step 6) was dissolved in DMA (23.5 mL). To the solution was added imidazo[1,2-a]pyridine-6-ylmethylamine (245 mg, 1.66 mmol) and triethylamine (0.966 mL, 6.93 mmol), and the mixture was stirred at rt for 16 hours. To the mixture was added saturated aqueous NaHCO$_3$ and EtOAc. The layers were separated and the aqueous layer was extracted with EtOAc. The combined organic layer was washed with water then brine and dried over anhydrous MgSO$_4$ and concentrated in vacuo. Purified by silica gel chromatography to give 2-chloro-3-(4-fluorophenyl)-N-(imidazo[1,2-a]pyridin-6-ylmethyl)quinoxaline-6-carboxamide (365 mg, 61%) as pale yellow solid. LCMS (ESI+): m/z=432.1 (M+H). $^1$H NMR (400 MHz, DMSO-d$_6$) δ 9.49 (t, J=5.7 Hz, 1H), 8.73 (d, J=1.7 Hz, 1H), 8.56 (s, 1H), 8.37 (dd, J=8.8, 1.9 Hz, 1H), 8.19 (d, J=8.7 Hz, 1H), 8.01-7.87 (m, 3H), 7.62-7.51 (m, 2H), 7.43 (t, J=8.9 Hz, 2H), 7.29 (dd, J=9.3, 1.6 Hz, 1H), 4.58 (m, 2H).

Step 2: 3-(4-Fluorophenyl)-2-(4-hydroxypiperidin-1-yl)-N-(imidazo[1,2-a]pyridin-6-ylmethyl)quinoxaline-6-carboxamide A mixture of 2-chloro-3-(4-fluorophenyl)-N-(imidazo[1,2-a]pyridin-6-ylmethyl)quinoxaline-6-carboxamide (85.0 mg, 0.197 mmol), 4-hydroxypiperidine (99.5 mg, 0.984 mmol), DIPEA (0.103 mL, 0.590 mmol) and NMP (1.6 mL) was heated at 170° C. for 30 min under microwave irradiation. After cooling, the reaction mixture was poured into EtOAc and water. The layers were separated and the aqueous layer was extracted with EtOAc. The combined organic layer was dried over anhydrous MgSO$_4$ and concentrated in vacuo. Purified by silica gel chromatography to give 3-(4-fluorophenyl)-2-(4-hydroxypiperidin-1-yl)-N-(imidazo[1,2-a]pyridin-6-ylmethyl)quinoxaline-6-carboxamide (22 mg, 22%) as a pale yellow solid. LCMS (ESI+): m/z=497.2 (M+H). $^1$H NMR (400 MHz, DMSO-d$_6$) δ 9.28 (t, J=5.7 Hz, 1H), 8.56-8.50 (m, 2H), 8.14 (dd, J=8.7, 1.8 Hz, 1H), 8.03 (dd, J=8.6, 5.6 Hz, 2H), 7.97 (s, 1H), 7.80 (d, J=8.7 Hz, 1H), 7.55 (t, J=4.6 Hz, 2H), 7.40 (t, J=8.8 Hz, 2H), 7.28 (dd, J=9.3, 1.4 Hz, 1H), 4.72 (d, J=4.0 Hz, 1H), 4.52 (d, J=5.6 Hz, 2H), 3.72-3.61 (m, 1H), 3.57 (m, 2H), 2.96 (t, J=10.2 Hz, 2H), 1.74 (m, 2H), 1.43 (m, 2H).

The compounds listed in the table below were prepared in an analogous fashion to that described above starting from the appropriate starting materials:

| Starting Material Step 2 | Compound No. or Name | LCMS Data |
| --- | --- | --- |
| (morpholine) | I-147 | LCMS (ESI+, FA): m/z = 483.1 (M + H) |
| (4-morpholinopiperidine) | I-64 | LCMS (ESI+, FA): m/z = 566.3 (M + H) |
| (piperidine) | I-170 | LCMS (ESI+, FA): m/z = 481.2 (M + H) |

Example 41: 3-(4-Chlorophenyl)-N-[3-(1H-imidazol-2-yl)propyl]-2-phenoxyquinoxaline-6-carboxamide (I-273)

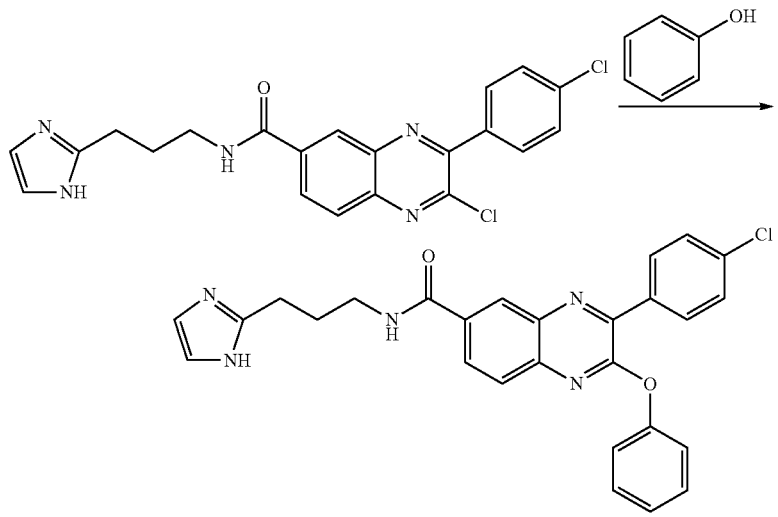

A mixture of 2-chloro-3-(4-chlorophenyl)-N-[3-(1H-imidazol-2-yl)propyl]quinoxaline-6-carboxamide (65.0 mg, 0.152 mmol) (prepared in Example 29, 1-50), phenol (40.0 mg, 0.425 mmol), and potassium carbonate (105 mg, 0.762 mmol) in N,N-dimethylformamide (1.00 mL, 12.9 mmol) was heated to 120° C. for 1.5 h. The mixture was distributed between water and EtOAc. The aqueous layer was extracted with EtOAc. The combined organic layer was washed with brine, dried, and concentrated. Purification by silica gel chromatography provided 3-(4-chlorophenyl)-N-[3-(1H- imidazol-2-yl)propyl]-2-phenoxyquinoxaline-6-carboxamide (30 mg, 41%) as a white solid. LCMS (ESI+): m/z=484.1, 486.1 (M+H). ¹H NMR (400 MHz, MeOD) δ 8.58 (s, 1H), 8.29 (d, J=8.7 Hz, 2H), 8.12 (d, J=6.7 Hz, 1H), 7.77 (d, J=8.7 Hz, 1H), 7.61 (d, J=8.6 Hz, 2H), 7.52 (t, J=7.6 Hz, 2H), 7.39-7.30 (m, 3H), 6.97 (s, 2H), 3.50 (t, J=6.7 Hz, 2H), 2.85 (t, J=7.5 Hz, 2H), 2.07 (t, J=7.3 Hz, 2H).

Example 42: 2-(4-Hydroxycyclohex-1-en-1-yl)-N-[3-(1H-imidazol-2-yl)propyl]-3-(2-thienyl)quinoxaline-6-carboxamide (I-202)

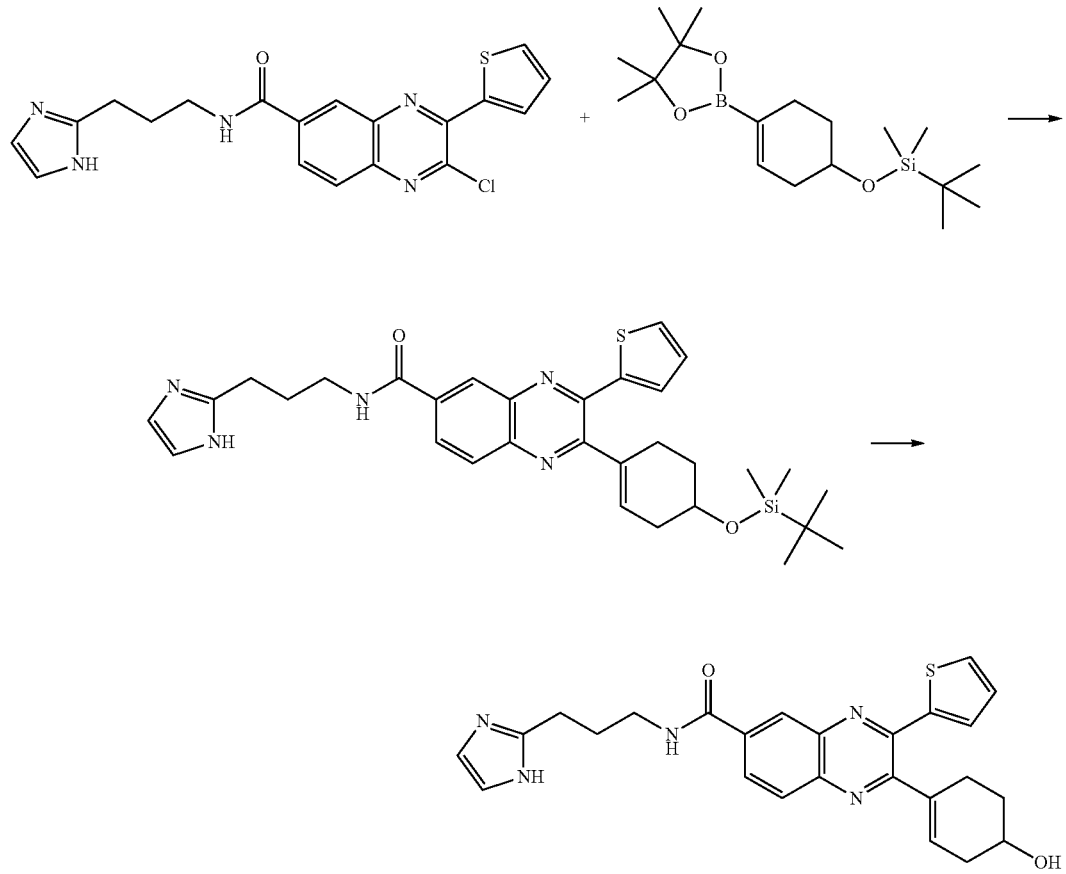

Step 1: 2-(4-{[tert-Butyl(dimethyl)silyl]oxy}cyclohex-1-en-1-yl)-N-[3-(1H-imidazol-2-yl)propyl]-3-(2-thienyl) quinoxaline-6-carboxamide To a solution of 2-chloro-N-[3-(1H-imidazol-2-yl)propyl]-3-(2-thienyl) quinoxaline-6-carboxamide (281 mg, 0.706 mmol) (prepared similarly to Example 29, step 1) in dioxane (15.8 mL) and water (1.59 mL) was added sodium carbonate (224 mg, 0.918 mmol), tert-butyl(dimethyl){[4-(4,4,5,5-tetramethyl-1,3,2-dioxaborolan-2-yl)cyclohex-3-en-1-yl]oxy}silane (311 mg, 0.918 mmol) (prepared according to: WO 2009/012125 A1) and PdCl₂(dppf) (58 mg, 0.071 mmol). The reaction mixture was degassed with argon for 5 minutes and then heated for 2 h at 105° C. After cooling, the mixture was filtered through celite and the filtrate was evaporated. The residue was purified by silica gel to give 2-(4-{[tert-butyl(dimethyl)silyl]oxy}cyclohex-1-en-1-yl)-N-[3-(1H-imidazol-2-yl)propyl]-3-(2-thienyl) quinoxaline-6-carboxamide (329 mg, 81%). LCMS (ESI+): m/z=574.3 (M+H).

Step 2: 2-(4-Hydroxycyclohex-1-en-1-yl)-N-[3-(1H-imidazol-2-yl)propyl]-3-(2-thienyl)quinoxaline-6-carboxamide To a solution of 2-(4-{[tert-butyl(dimethyl)silyl]oxy}cyclohex-1-en-1-yl)-N-[3-(1H-imidazol-2-yl)propyl]-3-(2-thienyl) quinoxaline-6-carboxamide (325 mg, 55.6 mmol) in DCM (7.0 mL) was added trifluoroacetic acid (1.00 mL, 13.0 mmol) and the resulting solution was stirred at rt overnight. 1 N NaOH was added until the reaction mixture was basic. The layers were separated and the aqueous layer was extracted with DCM. The combined organic layers were dried over MgSO₄ and concentrated in vacuo. The residue was purified by silica gel chromatography to give 2-(4-hydroxycyclohex-1-en-1-yl)-N-[3-(1H-imidazol-2-yl)propyl]-3-(2-thienyl)quinoxaline-6-carboxamide (131 mg, 50%). LCMS (ESI+): m/z=460.2 (M+H). ¹H NMR (400 MHz, DMSO-d₆) δ 1.54-1.63 (m, 1H), 1.74-1.86 (m, 3H), 1.94-2.02 (m, 1H), 2.19-2.35 (m, 3H), 2.57-2.60 (m, 2H), 3.23-3.28 (m, 2H), 3.83 (bs, 1H), 4.71 (s, 1H), 5.82 (s, 1H), 6.76 (s, 2H), 7.08 (dd, J=5.2, 3.6 Hz, 1H), 7.68 (dd, J=5.2, 1.2 Hz, 1H), 7.80 (dd, J=3.6, 1.2 Hz, 1H), 7.94 (d, J=8.8 Hz, 1H), 8.06 (dd, J=8.8, 2.0 Hz, 1H), 8.42 (d, J=1.2 Hz, 1H), 8.94 (t, J=5.2 Hz, 1H), 11.66 (bs, 1H).

The compound listed in the table below was prepared in an analogous fashion to that described above starting from the appropriate starting materials:

| Starting Material Step 1 | Compound No. or Name | LCMS Data |
|---|---|---|
| 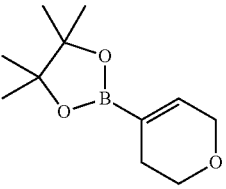 | I-300 | LCMS (ESI+, FA): m/z = 446.2 (M + H) |

Example 43: N-(3-(1H-imidazol-2-yl)propyl)-3-(3-chloro-4-fluorophenyl)-2-(4-fluorophenyl)quinoxaline-6-carboxamide (I-502)

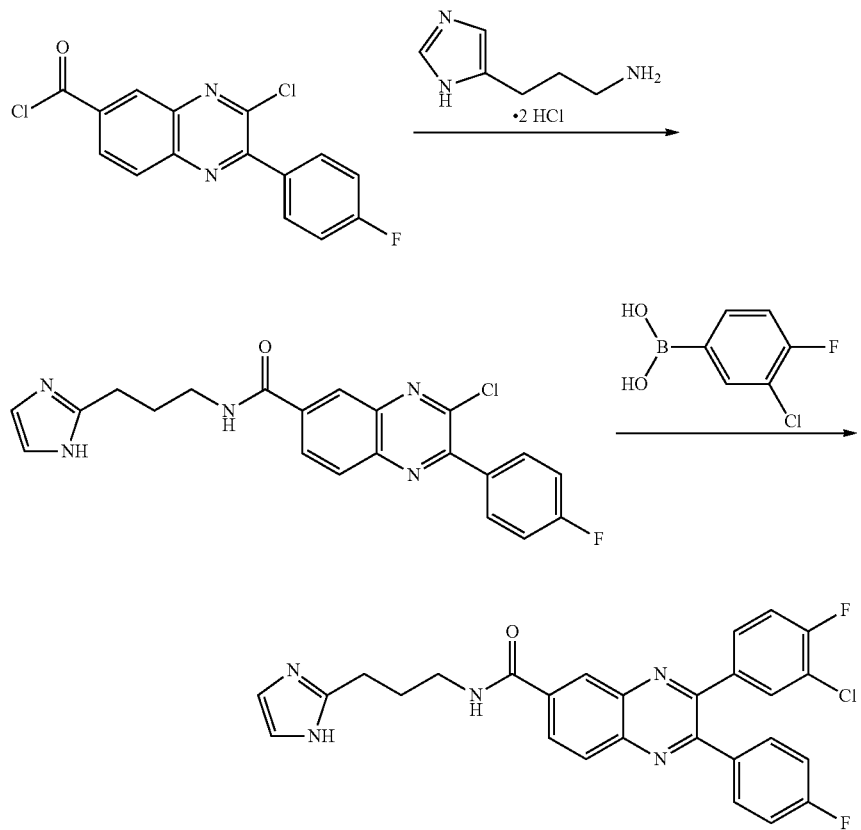

Step 1: N-(3-(1H-imidazol-2-yl)propyl)-3-chloro-2-(4-fluorophenyl)quinoxaline-6-carboxamide To a mixture of 3-chloro-2-(4-fluorophenyl)quinoxaline-6-carbonyl chloride (28.2 g, 87.8 mmol, prepared according to Example 44, Route 1, Step 3) in N,N-dimethylacetamide (650 mL) was added 3-(1H-imidazol-2-yl)propan-1-amine dihydrochloride (20.9 g, 106 mmol) and TEA (61 mL, 440 mmol) and the resulting mixture was stirred at room temperature for 3 days. The reaction was then pured into saturated sodium bicarbonate (500 mL) and stirred for 90 minutes. The solids were filtered and washed with water (400 mL) and ether (400 mL). The solids were then added to water (500 mL) and sonicated for 10 minutes. The solids were filtered to give N-(3-(1H-imidazol-2-yl)propyl)-3-chloro-2-(4-fluorophenyl)quinoxaline-6-carboxamide (29 g, 80%). LCMS (ESI+): m/z=410.1 (M+H). $^1$H NMR (400 MHz, DMSO-d$_6$) δ 11.73 (bs, 1H), 9.11 (bs, 1H), 8.59 (d, J=1.6 Hz, 1H), 8.32 (dd, J=8.8, 1.6 Hz, 1H), 8.23 (d, J=8.8 Hz, 1H), 7.96-7.93 (m, 2H), 7.45-7.40 (m, 2H), 6.98 (bs, 1H), 6.82 (bs, 1H), 3.42-3.38 (m, 2H), 2.74-2.70 (m, 2H), 2.00-1.93 (m, 2H).

Step 2: N-(3-(1H-imidazol-2-yl)propyl)-3-(3-chloro-4-fluorophenyl)-2-(4 fluorophenyl)quinoxaline-6-carboxamide N-(3-(1H-imidazol-2-yl)propyl)-3-chloro-2-(4-fluorophenyl)quinoxaline-6-carboxamide (20.0 mg, 0.0488 mmol) was dissolved in 1,4-dioxane (2.0 mL). To the solution was added (3-chloro-4-fluorophenyl)boronic acid (12.6 mg, 0.0732 mmol), sodium carbonate (15.5 mg, 0.146 mmol) and water (0.150 mL). The vial was purged with nitrogen for a few min and [1,1' bis(diphenylphosphino)ferrocene]palladium(II)dichloride (4.01 mg, 0.00488 mmol) was added to the vial. The reaction mixture was heated at 100° C. for 30 min under microwave irradiation. After cooling, the reaction mixture was dried down. To the dried solid was added DMSO (1.0 mL). The solids were filtered off and the remaining mixture was transferred into a clean vial and purified by prep HPLC to give N-(3-(1H-imidazol-2-yl)propyl)-3-(3-chloro-4-fluorophenyl)-2-(4 fluorophenyl)quinoxaline-6-carboxamide (4.9 mg, 20%). LCMS (ESI+): m/z=504.24 (M+H).

The compounds listed in the table below were prepared in an analogous fashion to that described in Example 43 starting from the appropriate starting materials:

| Starting Material | Compound No. or Name | LCMS Data |
|---|---|---|
| 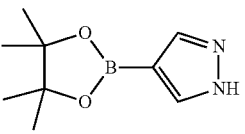 | I-429 | LCMS (ES+, FA): m/z = 442.38 (M + H) |
| 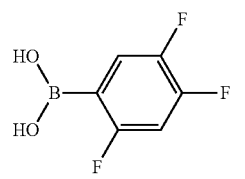 [SMILES: OB(O)c1cc(F)c(F)cc1F] | I-337 | LCMS (ES+, FA): m/z = 506.42 (M + H) |
| 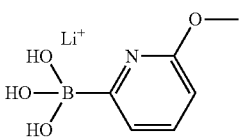 | I-495 | LCMS (ES+, FA): m/z = 483.39 (M + H) |
| 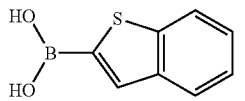 | I-412 | LCMS (ES+, FA): m/z = 508.41 (M + H) |
| 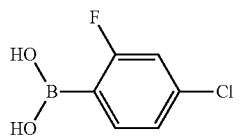 | I-455 | LCMS (ES+, FA): m/z = 504.37 (M + H) |
| 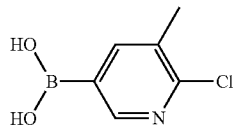 | I-309 | LCMS (ES+, FA): m/z = 501.24 (M + H) |
| 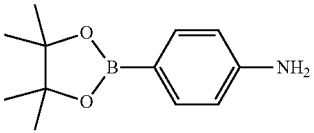 | I-479 | LCMS (ES+, FA): m/z = 467.41 (M + H) |
| 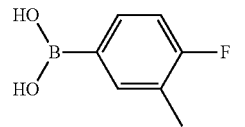 | I-471 | LCMS (ES+, FA): m/z = 484.41 (M + H) |
| 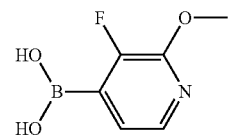 | I-391 | LCMS (ES+, FA): m/z = 501.42 (M + H) |
| 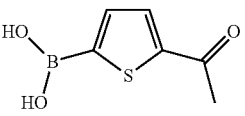 | I-370 | LCMS (ES+, FA): m/z = 500.39 (M + H) |
| 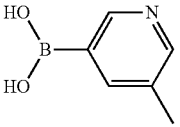 | I-394 | LCMS (ES+, FA): m/z = 467.41 (M + H) |

-continued
| Starting Material | Compound No. or Name | LCMS Data |
|---|---|---|
| 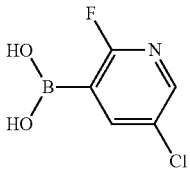 [SMILES: OB(O)c1cc(Cl)cnc1F] | I-410 | LCMS (ES+, FA): m/z = 505.4 (M + H) |
| 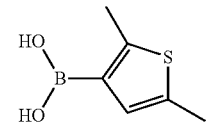 | I-422 | LCMS (ES+, FA): m/z = 486.4 (M + H) |
| 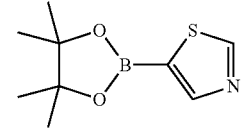 | I-325 | LCMS (ES+, FA): m/z = 459.38 (M + H) |
| 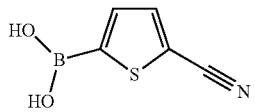 | I-363 | LCMS (ES+, FA): m/z = 483.39 (M + H) |
| 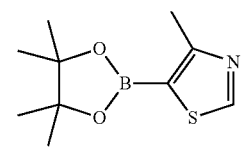 | I-494 | LCMS (ES+, FA): m/z = 473.37 (M + H) |
| 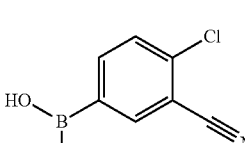 | I-377 | LCMS (ES+, FA): m/z = 511.36 (M + H) |
| 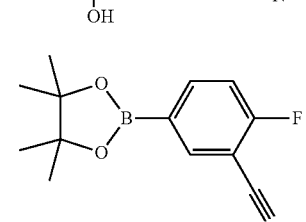 | I-388 | LCMS (ES+, FA): m/z = 495.39 (M + H) |
| 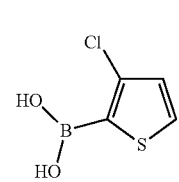 | I-504 | LCMS (ES+, FA): m/z = 492.31 (M + H) |
| 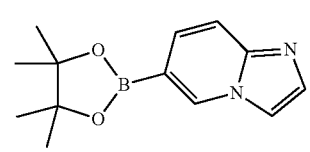 | I-417 | LCMS (ES+, FA): m/z = 492.43 (M + H) |
| 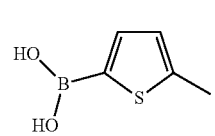 | I-473 | LCMS (ES+, FA): m/z = 472.41 (M + H) |

-continued
| Starting Material | Compound No. or Name | LCMS Data |
|---|---|---|
| 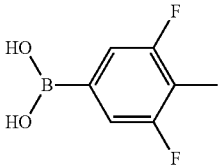 | I-306 | LCMS (ES+, FA): m/z = 502.44 (M + H) |
| 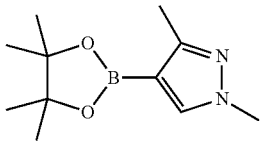 | I-475 | LCMS (ES+, FA): m/z = 470.42 (M + H) |
| 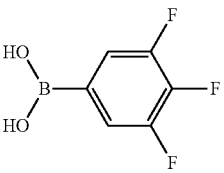 [SMILES: OB(O)c1cc(F)c(F)c(F)c1] | I-449 | LCMS (ES+, FA): m/z = 506.36 (M + H) |
| 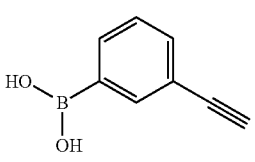 | I-425 | LCMS (ES+, FA): m/z = 476.39 (M + H) |
| 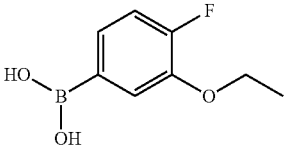 | I-355 | LCMS (ES+, FA): m/z = 514.44 (M + H) |
| 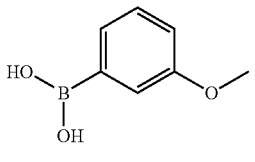 | I-484 | LCMS (ES+, FA): m/z = 482.42 (M + H) |
| 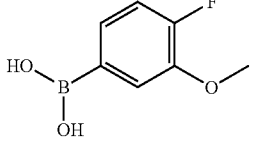 | I-488 | LCMS (ES+, FA): m/z = 500.46 (M + H) |
| 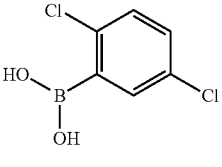 [SMILES: OB(O)c1cc(Cl)ccc1Cl] | I-353 | LCMS (ES+, FA): m/z = 520.35 (M + H) |
| 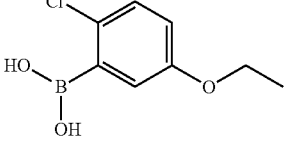 | I-437 | LCMS (ES+, FA): m/z = 530.42 (M + H) |

-continued
| Starting Material | Compound No. or Name | LCMS Data |
|---|---|---|
| 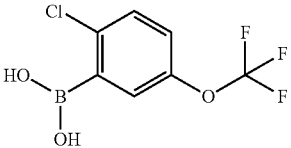 | I-432 | LCMS (ES+, FA): m/z = 570.34 (M + H) |
| 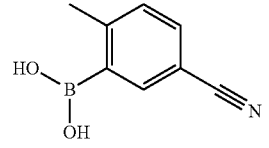 | I-472 | LCMS (ES+, FA): m/z = 491.47 (M + H) |
| 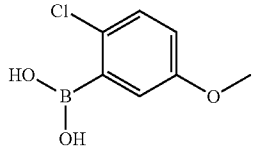 | I-354 | LCMS (ES+, FA): m/z = 516.37 (M + H) |
|  | I-467 | LCMS (ES+, FA): m/z = 496.48 (M + H) |
| 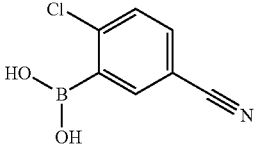 | I-393 | LCMS (ES+, FA): m/z = 511.36 (M + H) |
| 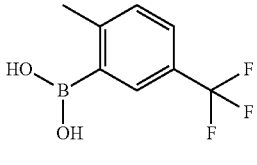 | I-445 | LCMS (ES+, FA): m/z = 534.47 (M + H) |
| 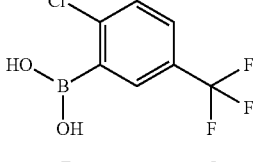 | I-381 | LCMS (ES+, FA): m/z = 554.36 (M + H) |
| 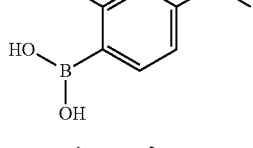 | I-415 | LCMS (ES+, FA): m/z = 500.46 (M + H) |
| 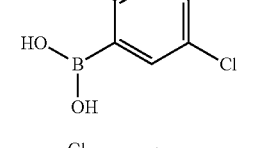 | I-493 | LCMS (ES+, FA): m/z = 500.46 (M + H) |
| 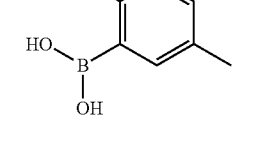 | I-365 | LCMS (ES+, FA): m/z = 500.39 (M + H) |

-continued
| Starting Material | Compound No. or Name | LCMS Data |
|---|---|---|
| 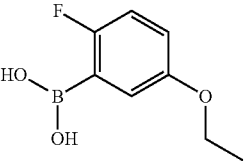 | I-343 | LCMS (ES+, FA): m/z = 514.44 (M + H) |
| 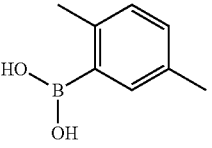 | I-450 | LCMS (ES+, FA): m/z = 480.43 (M + H) |
| 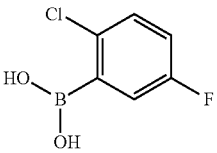 | I-399 | LCMS (ES+, FA): m/z = 504.37 (M + H) |
| 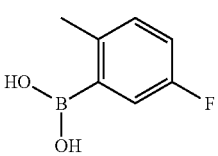 | I-336 | LCMS (ES+, FA): m/z = 484.41 (M + H) |
| 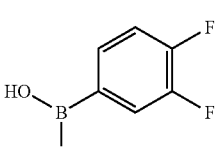 | I-474 | LCMS (ES+, FA): m/z = 488.26 (M + H) |
| 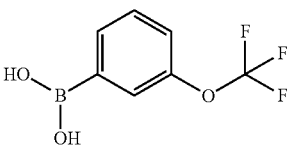 [SMILES: OB(O)c1cccc(OC(F)(F)F)c1] | I-350 | LCMS (ES+, FA): m/z = 536.26 (M + H) |
| 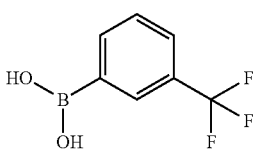 | I-328 | LCMS (ES+, FA): m/z = 520.22 (M + H) |
| 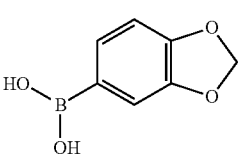 [SMILES: OB(O)c1ccc2c(c1)OCO2] | I-461 | LCMS (ES+, FA): m/z = 496.35 (M + H) |
| 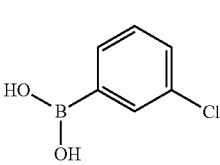 | I-463 | LCMS (ES+, FA]: m/z = 486.27 (M + H) |

-continued
| Starting Material | Compound No. or Name | LCMS Data |
|---|---|---|
| 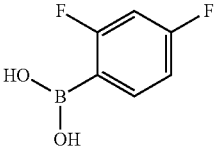 | I-373 | LCMS (ES+, FA): m/z = 488.20 (M + H) |
| 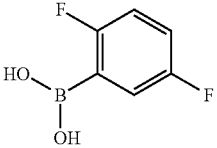 | I-319 | LCMS (ES+, FA): m/z = 488.26 (M + H) |
| 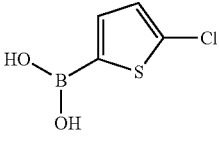 | I-499 | LCMS (ES+, FA): m/z = 492.18 (M + H) |
| 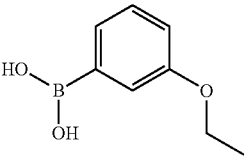 | I-447 | LCMS (ES+, FA): m/z = 496.28 (M + H) |
| 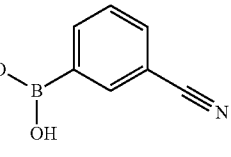 | I-458 | LCMS (ES+, FA): m/z = 477.29 (M + H) |
| 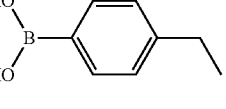 | I-382 | LCMS (ES+, FA): m/z = 480.31 (M + H) |
| 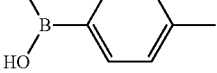 | I-497 | LCMS (ES+, FA): m/z = 466.32 (M + H) |
| 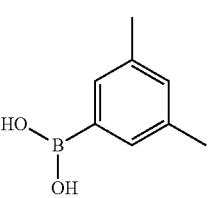 | I-335 | LCMS (ES+, FA): m/z = 480.31 (M + H) |
| 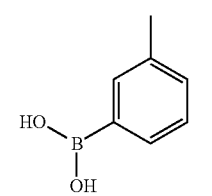 | I-395 | LCMS (ES+, FA): m/z = 466.32 (M + H) |
| 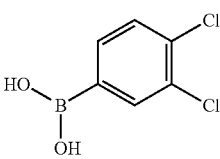 [SMILES: OB(O)c1ccc(Cl)c(Cl)c1] | I-397 | LCMS (ES+, FA): m/z = 520.39 (M + H) |

| Starting Material | Compound No. or Name | LCMS Data |
|---|---|---|
| 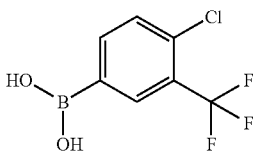 [SMILES: OB(O)c1ccc(Cl)c(C(F)(F)F)c1] | I-369 | LCMS (ES+, FA): m/z = 554.23 (M + H) |
| 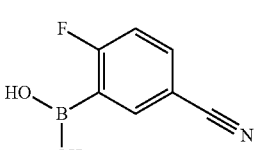 | I-501 | LCMS (ES+, FA): m/z = 495.26 (M + H) |
| 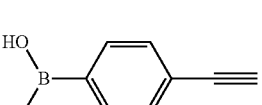 | I-416 | LCMS (ES+, FA): m/z = 476.26 (M + H) |
| 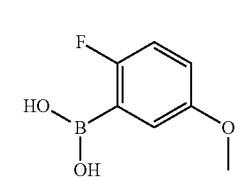 | I-481 | LCMS (ES+, FA): m/z = 500.33 (M + H) |
| 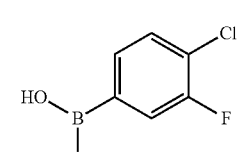 | I-431 | LCMS (ES+, FA): m/z = 504.24 (M + H) |
| 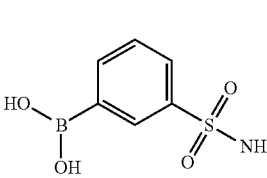 | I-308 | LCMS (ES+, FA): m/z = 531.26 (M + H) |
| 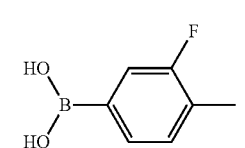 | I-311 | LCMS (ES+, FA): m/z = 484.28 (M + H) |
| 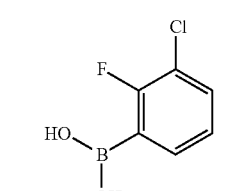 | I-312 | LCMS (ES+, FA): m/z = 504.24 (M + H) |
| 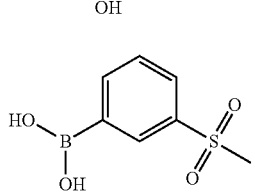 | I-384 | LCMS (ES+, FA): m/z = 530.23 (M + H) |

| Starting Material | Compound No. or Name | LCMS Data |
|---|---|---|
| 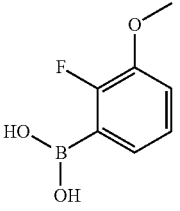 | I-398 | LCMS (ES+, FA): m/z = 500.26 (M + H) |
| 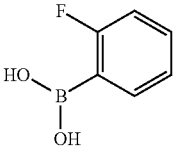 | I-313 | LCMS (ES+, FA): m/z = 470.29 (M + H) |
| 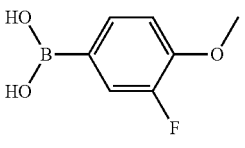 | I-470 | LCMS (ES+, FA): m/z = 500.26 (M + H) |
| 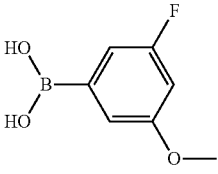 | I-512 | LCMS (ES+, FA): m/z = 500.26 (M + H) |
| 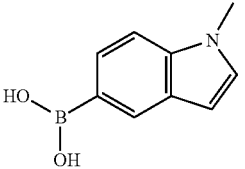 | I-386 | LCMS (ES+, FA): m/z = 505.33 (M + H) |
| 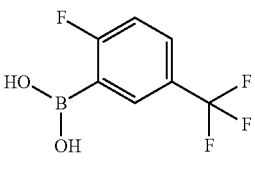 [SMILES: OB(O)c1cc(C(F)(F)F)ccc1F] | I-451 | LCMS (ES+, FA): m/z = 538.25 (M + H) |
| 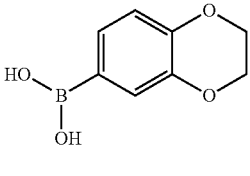 [SMILES: OB(O)c1ccc2c(c1)OCCO2] | I-320 | LCMS (ES+, FA): m/z = 510.27 (M + H) |
| 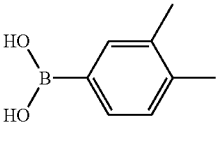 | I-433 | LCMS (ES+, FA): m/z = 480.31 (M + H) |
| 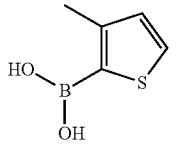 | I-342 | LCMS (ES+, FA): m/z = 472.22 (M + H) |

-continued
| Starting Material | Compound No. or Name | LCMS Data |
|---|---|---|
| 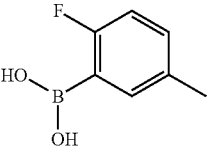 | I-507 | LCMS (ES+, FA): m/z = 484.41 (M + H) |
| 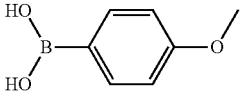 | I-448 | LCMS (ES+, FA): m/z = 482.23 (M + H) |
| 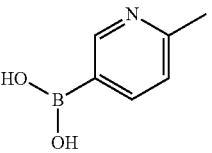 | I-486 | LCMS (ES+, FA): m/z = 467.21 (M + H) |
| 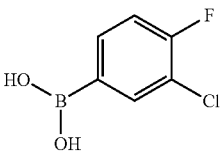 [SMILES: OB(O)c1ccc(F)c(Cl)c1] | I-502 | LCMS (ES+, FA): m/z = 504.24 (M + H) |
| 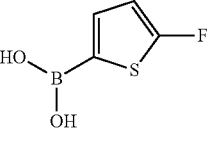 | I-368* | LCMS (ES+, FA): m/z = 476.1 (M + H) |
| 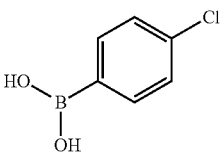 | I-361** | LCMS (ES+, FA): m/z = 486.1 (M + H) |
*X-Phos and K2CO3 used in Step 2
**Cs$_2$CO$_3$ used in Step 2
Example 44: 3-(5-fluoro-2-methoxy-4-pyridyl)-2-(4-fluorophenyl)-N-[3-(1H-imidazol-2-yl)propyl]quinoxaline-6-carboxamide (I-466)
Route 1:
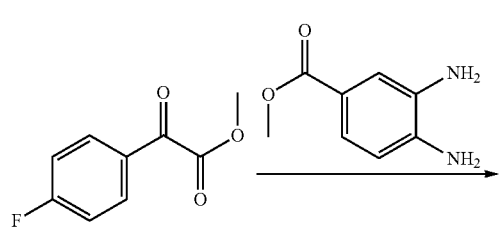
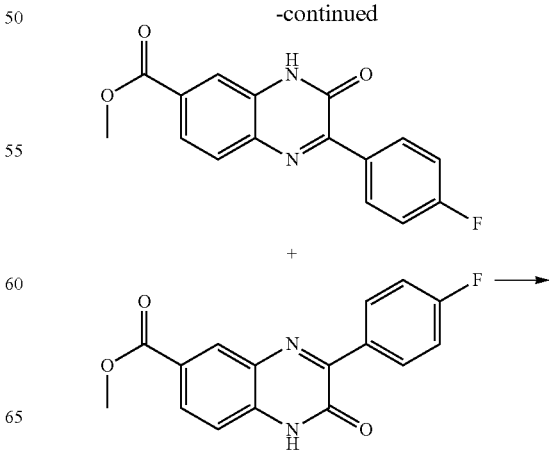

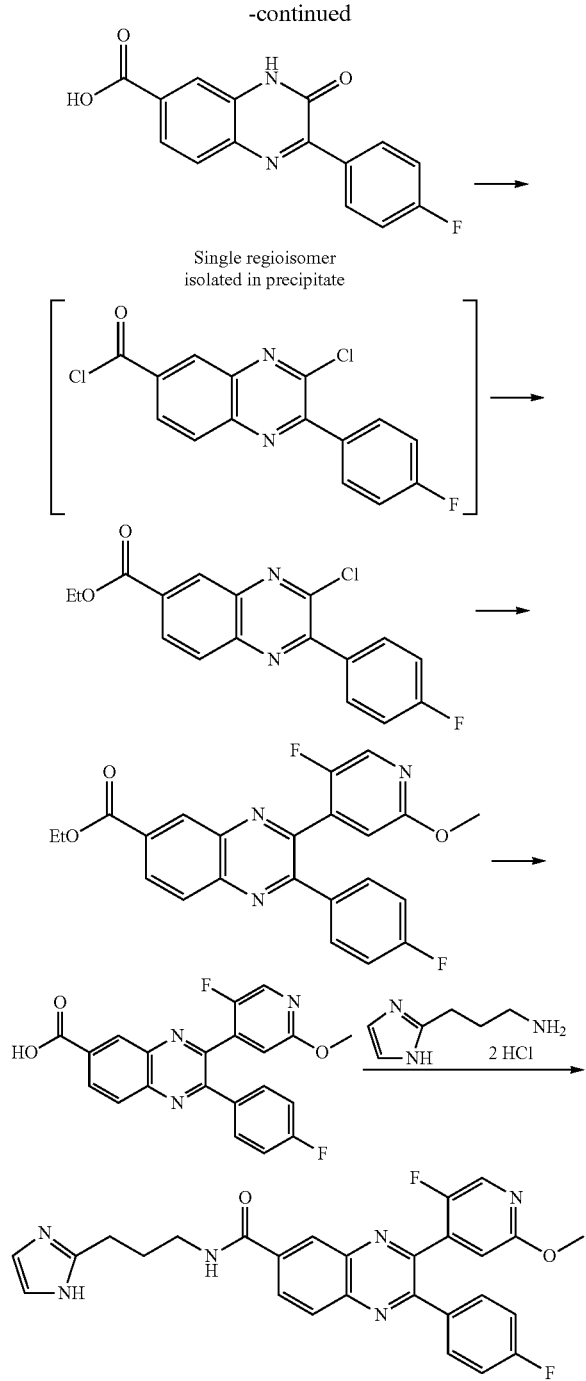

Step 1: Methyl 2-(4-fluorophenyl)-3-oxo-3,4-dihydroquinoxaline-6-carboxylate A solution of methyl (4-fluorophenyl)(oxo)acetate (50.0 g, 275 mmol) and methyl 3,4-diaminobenzoate (46.9 g, 282 mmol) in ethanol (2.5 L) was heated to reflux for 2 d. The mixture was cooled to rt and most of the ethanol was removed in vacuo to form a thick paste. 0.5 L of THF was added to get a stirrable slurry and the slurry was stirred for 1 h, diluted further with 1 L of ether and solid was collected by filtration (50.0 g, 76.3%) as a mixture of regioisomers.

Step 2: 2-(4-Fluorophenyl)-3-oxo-3,4-dihydroquinoxaline-6-carboxylate acid

To a solution of methyl 2-(4-fluorophenyl)-3-oxo-3,4-dihydroquinoxaline-6-carboxylate (50.0 g, 168 mmol) (mixture of regioisomers) in THF (0.9 L) and methanol (0.9 L) at it was added 2.0 M of sodium hydroxide in water (300 mL). The reaction mixture was stirred at 70° C. for 2 h. The mixture was allowed to cool slightly and some solids formed. The reaction mixture was filtered while warm to afford a clear orange solution. The filtrate was stirred with mechanic stirring. 1N HCl aqueous solution (~450 mL) was slowly added (over 15 min) to pH=8. The suspension was stirred for 5 min, filtered, washed with 100 mL of 1:1 MeOH:THF, dried to give a light yellow solid. [In some cases, there is still some undesired isomer present at this point. If so, the material was redissolved in methanol/THF mixture (14 mL per gram of each solvent) and 1 N NaOH (4.2 equivalents), and then reprecipitated to pH=8 using 1 N HCl. This dissolution/reprecipitation procedure can be repeated until the pure desired regioisomer is obtained.] To the solid was added 300 mL of methanol, 300 mL of THF, and 250 mL of 1N NaOH and the resulting solution was stirred by mechanical stirring until dissolved. The resulting solution was adjusted to pH=2.5 by adding 1N HCl. The precipitate was collected by filtration, transferred to a round bottom flask using MeOH, evaporated in vacuo, and azeotroped with MeCN. The resulting solid was dried in vacuum pump to give a pure acid product (26.3 g, 55.2%) as a beige powder. LCMS (ESI+): m/z=285.0 (M+H). $^1$H NMR (400 MHz, DMSO-$d_6$) δ 13.34 (s, 1H), 12.76 (s, 1H), 8.44 (dd, J=9.1, 5.8 Hz, 2H), 7.96-7.89 (m, 2H), 7.83 (dd, J=8.4, 1.8 Hz, 1H), 7.35 (t, J=9.0 Hz, 2H).

Step 3: Ethyl 3-chloro-2-(4-fluorophenyl)quinoxaline-6-carboxylate

To a suspension of 2-(4-fluorophenyl)-3-oxo-3,4-dihydroquinoxaline-6-carboxylic acid (16.2 g, 57.0 mmol) in thionyl chloride (80 equiv., 4560 mmol) was added ~10 drops of DMF, then stirred at 80° C. (oil bath temp) for 2 h. The reaction mixture was concentrated in vacuo and azeotroped with toluene, dried under vacuum pump to give a pale yellow solid intermediate. The intermediate acid chloride was suspended in ethanol (844 mL), sonicated for 5 min, then added DCM (650 mL), sonicated another 5 min to give a clear solution, and stirred at rt overnight. The solution was evaporated in vacuo, azeotroped with MeCN and dried in high vacuum pump to give a powder product ethyl 3-chloro-2-(4-fluorophenyl)quinoxaline-6-carboxylate (18.8 g, 90.7%). LCMS (ESI+): m/z=331.1 (M+H). 1H NMR (400 MHz, Chloroform-d) δ 8.77 (d, J=1.5 Hz, 1H), 8.40 (dd, J=8.7, 1.9 Hz, 1H), 8.18 (d, J=8.7 Hz, 1H), 7.97-7.89 (m, 2H), 7.28-7.20 (m, 2H), 4.48 (q, J=7.1 Hz, 2H), 1.47 (t, J=7.1 Hz, 3H).

Step 4: Ethyl 3-(5-fluoro-2-methoxypyridin-4-yl)-2-(4-fluorophenyl)quinoxaline-6-carboxylate To a mixture of ethyl 3-chloro-2-(4-fluorophenyl)quinoxaline-6-carboxylate (1.21 g, 3.4 mmol), (5-fluoro-2-methoxypyridin-4-yl)boronic acid (1.18 g, 6.88 mmol) and cesium carbonate (2.24 g, 6.88 mmol) was added 1,4-dioxane (77 mL), degassed with argon 3×, then added 1,1'-Bis(diphenylphosphino)ferrocenedichloropalladium(II) (281 mg, 0.344 mmol), then stirred under nitrogen at 100° C. overnight. The mixture was cooled to rt, diluted with DCM (10 mL), and filtered. The filtrate was concentrated in vacuo to give a crude residue. The residue was purified by chromatography in an 80 g silica column using EtOAc/hexane (0/100 to 10/90) and afforded a white foamy solid product (1.29 gr, 89%). LCMS (ESI+): m/z=422.1. 1H NMR (400 MHz, Chloroform-d) δ 8.90 (d, J=1.6 Hz, 1H), 8.45 (dd, J=8.8, 1.9 Hz, 1H), 8.24 (d, J=8.8 Hz, 1H), 7.92 (d, J=1.1 Hz, 1H), 7.62-7.55 (m, 2H), 7.11-7.05 (m, 3H), 4.49 (q, J=7.1 Hz, 2H), 3.98 (s, 3H), 1.47 (t, J=7.1 Hz, 3H).

Step 5: 3-(5-Fluoro-2-methoxypyridin-4-yl)-2-(4-fluorophenyl)quinoxaline-6-carboxylic acid Ethyl 3-(5-fluoro-2-methoxypyridin-4-yl)-2-(4-fluorophenyl)quinoxaline-6-carboxylate (1.29 g, 3.06 mmol) was dissolved in THF (34 mL) and then water (8.5 mL) was added, followed by 1.00 M of sodium hydroxide in water (8.5 mL, 8.5 mmol, 1.00 mol/L). The mixture was stirred at rt overnight. The mixture was concentrated in vacuo to give an aqueous residue. 1N HCl was added until the pH was ~7. The mixture was sonicated for ~10 min, then filtered and the solid was dried to give a white solid (0.800 g, 66%). LCMS (ESI+): m/z=394.1. 1H NMR (400 MHz, Chloroform-d) δ 8.98 (s, 1H), 8.48 (d, J=8.3 Hz, 1H), 8.27 (d, J=8.7 Hz, 1H), 7.92 (s, 1H), 7.59 (dd, J=8.4, 5.3 Hz, 2H), 7.08 (t, J=7.3 Hz, 3H), 3.98 (d, J=4.4 Hz, 3H).

Step 6: 3-(5-Fluoro-2-methoxy-4-pyridyl)-2-(4-fluorophenyl)-N-[3-(1H-imidazol-2-yl)propyl]quinoxaline-6-carboxamide (I-466)

To a solution of 3-(5-fluoro-2-methoxy-4-pyridyl)-2-(4-fluorophenyl)quinoxaline-6-carboxylic acid (150 mg, 0.381 mmol) and 3-(1H-imidazol-2-yl)-1-propanamine 2HCl (113 mg, 0.572 mmol) in DMF (2.4 mL) and TEA (0.532 mL, 3.81 mmol) was added 2,4,6-tripropyl-1,3,5,2,4,6-trioxatriphosphorinane-2,4,6-trioxide (1.67 mol/L) in EtOAc (0.457 mL, 0.763 mmol, 1.67 mol/L). The solution was stirred at rt overnight. The reaction mixture was diluted with EtOAc and water. The organic layer was washed with 10% LiCl, then water 2× then brine, dried over anhydrous Na$_2$SO$_4$, and filtered. The filtrate was concentrated in vacuo to give a crude residue and then purified in a silica column using 0-8% MeOH in DCM to afford a white solid product (146 mg, 76.5%). LCMS (ESI+): m/z=501.2. 1H NMR (400 MHz, Methanol-d$_4$) δ 8.65 (d, J=1.6 Hz, 1H), 8.33 (dd, J=8.8, 1.9 Hz, 1H), 8.27 (d, J=8.7 Hz, 1H), 7.95 (s, 1H), 7.63 (dd, J=8.8, 5.3 Hz, 2H), 7.20-7.09 (m, 3H), 6.95 (s, 2H), 3.95 (s, 3H), 3.51 (t, J=6.9 Hz, 2H), 2.85 (t, J=7.5 Hz, 2H), 2.07 (m, 2H).

The compounds listed in the table below were prepared in an analogous fashion to that described in Example 44, Route 1 starting from the appropriate starting materials:

| Starting Material Step 6 | Compound No. or Name | LCMS Data |
|---|---|---|
| ![triazole-propylamine structure] | I-515* | LCMS (ES+, FA): m/z = 502.17 (M + H) |
| ![imidazopyridine-methylamine structure] | I-516* | LCMS (ES+, FA): m/z = 524.20 (M + H) |

*HATU coupling reagent and THF solvent were used in Step 6

Route 2:

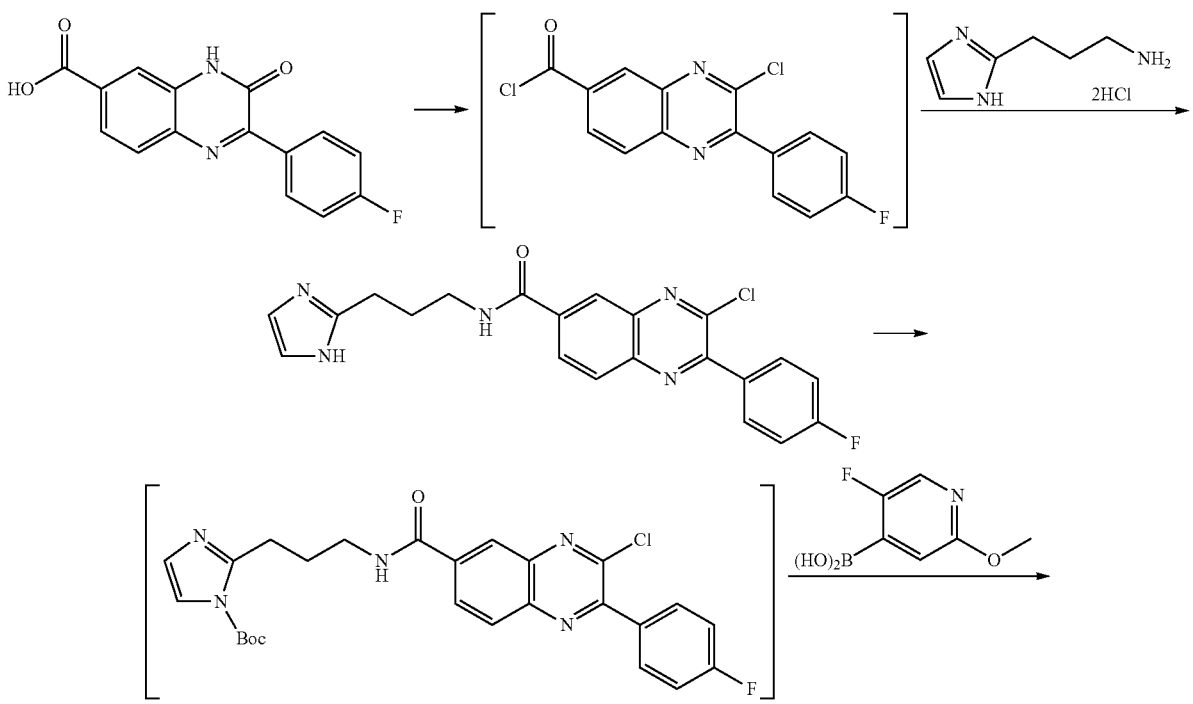

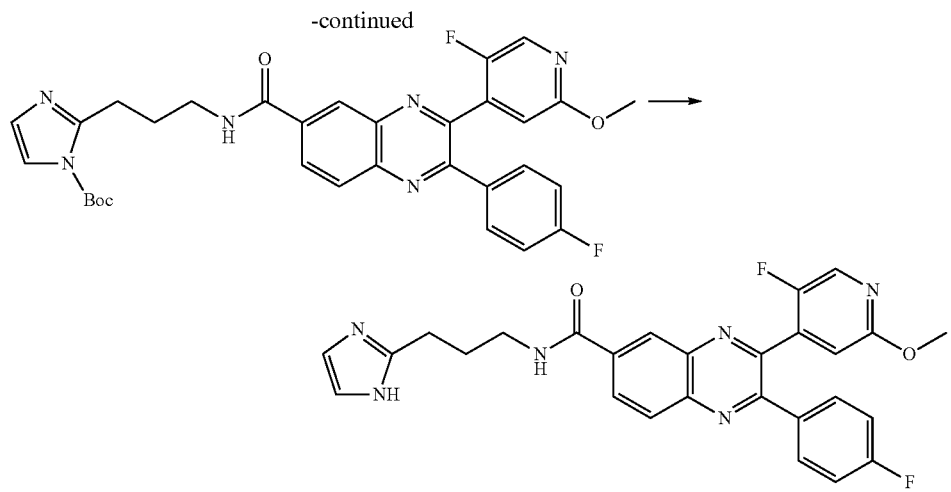

Step 1: 3-Chloro-2-(4-fluorophenyl)-N-[3-(1H-imidazol-2-yl)propyl]quinoxaline-6-carboxamide To a solution of 2-(4-fluorophenyl)-3-oxo-4H-quinoxaline-6-carboxylic acid (25.0 g, 88.0 mmol, prepared using procedure described in Example 44, Route 1) in thionyl chloride (510 mL, 7040 mmol) was added ~10 drops DMF. The resulting mixture was then stirred at 80° C. for 2 h, cooled to rt and then the solvent was evaporated. The residue was azeotroped with ~100 mL of toluene, then left on hi-vac for 2 h. The intermediate was then suspended in DMA (890 mL). 3-(1H-imidazol-2-yl)propan-1-amine dihydrochloride (20.9, 106 mmol) and TEA (61.1 mL, 440 mmol) were added. The mixture was stirred at rt overnight. The reaction mixture was poured into saturated sodium bicarbonate in water (500 mL, 570 mmol, 1.14 mol/L) and stirred at rt for 90 min. The solid was collected by filtration and washed with water (400 mL), then diethyl ether (400 mL), transferred to a flask, water (500 mL) was added and the suspension was sonicated for ~10 min. The suspension was filtered and the solid was washed with water (400 mL), transferred to a round bottom flask and azeotroped with MeCN. The solid was dried under house vacuum to give the final product (27.2 g, 75.5%). 1H NMR (400 MHz, DMF-d7) δ 12.16 (s, 1H), 9.54 (s, 1H), 9.00 (d, J=1.7 Hz, 1H), 8.74 (dd, J=8.7, 1.9 Hz, 1H), 8.65 (d, J=8.7 Hz, 1H), 8.40-8.31 (m, 2H), 7.90-7.78 (m, 2H), 7.30 (s, 2H), 3.82 (t, J=6.9 Hz, 2H), 3.14 (t, J=7.5 Hz, 2H), 2.39 (m, 2H).

Step 2: tert-Butyl 2-[3-({[3-(5-fluoro-2-methoxypyridin-4-yl)-2-(4-fluorophenyl)quinoxalin-6-yl]carbonyl}amino)propyl]-1H-imidazole-1-carboxylate In a 40 mL vial a mixture of 3-chloro-2-(4-fluorophenyl)-N-[3-(1H-imidazol-2-yl)propyl]quinoxaline-6-carboxamide (400 mg, 0.976 mmol), cesium carbonate (1.27 g, 3.90 mmol) and di-tert-butyldicarbonate (640 mg, 2.93 mmol) in anhydrous 1,4-dioxane (16 mL) was stirred under nitrogen atmosphere at rt for 18 h. (5-fluoro-2-methoxypyridin-4-yl) boronic acid (500 mg, 2.93 mmol) and 1,1' bis(diphenylphosphino) ferrocenedichloropalladium(II) (79.7 mg, 0.0976 mmol) were added. The mixture was degassed by vacuum evacuation and refilled with nitrogen 4 times. The mixture was heated under nitrogen atmosphere to 105° C. for 2 h. The mixture was cooled to rt, diluted with DCM (15 mL), and filtered. The filtrate was concentrated in vacuo to give a crude oil. The crude oil was chromatographed in an 80 g silica column using EtOAc/DCM (0/100 to 100/0) to give a solid product (509 mg, 86%). LCMS (ESI+): m/z=601.3. 1H NMR (400 MHz, Methanol-d₄) δ 8.67 (d, J=1.6 Hz, 1H), 8.33 (dd, J=8.8, 1.9 Hz, 1H), 8.26 (d, J=8.8 Hz, 1H), 7.95 (s, 1H), 7.63 (dd, J=8.8, 5.3 Hz, 2H), 7.45 (d, J=1.8 Hz, 1H), 7.20-7.08 (m, 3H), 6.87 (d, J=1.7 Hz, 1H), 3.96 (s, 3H), 3.55 (t, J=6.7 Hz, 2H), 3.20-3.13 (m, 2H), 2.09 (p, J=6.9 Hz, 2H), 1.61 (s, 9H).

Step 3: 3-(5-Fluoro-2-methoxy-4-pyridyl)-2-(4-fluorophenyl)-N-[3-(1H-imidazol-2-yl)propyl]quinoxaline-6-carboxamide (I-466)

tert-Butyl 2-[3-({[3-(5-fluoro-2-methoxypyridin-4-yl)-2-(4-fluorophenyl)quinoxalin-6-yl]carbonyl}amino)propyl]-1H-imidazole-1-carboxylate (126 mg, 0.207 mmol) was dissolved in THF (1.0 mL). 1.00 M of hydrochloric acid in water (1.0 mL, 1.0 mmol) was added. The single layer solution was stirred at rt for 3 h. The mixture was diluted with 2.0 mL of water, evaporated in vacuo to remove most of the THF. The resulting aqueous layer was made basic with saturated NaHCO₃ aqueous solution to pH ~8.5, extracted with DCM (8 mL, 1 mL×2). The combined DCM cloudy solution was washed with brine, dried over anhydrous Na₂SO₄, filtered. The filtrate was concentrated in vacuo to give a crude solid product. The crude was dissolved in 10% MeOH/DCM (10 mL), filtered through a 2 g silica pad with low vacuum, the pad was washed with another 10 mL of 10% MeOH/DCM until the filtrate drip showed no strong UV spot on TLC plate. The filtrate solution was evaporated in vacuo. The oily residue was diluted with DCM (10 mL), and concentrated in vacuo until solid appeared. The concentration was paused for 15 min to allow more solid to form. The suspension then was evaporated in vacuo, dried in vacuum pump to give an off-white solid product (105 mg, 97%). LCMS (ESI+): m/z=501.2. 1H NMR (400 MHz, Methanol-d₄) δ 8.65 (d, J=1.9 Hz, 1H), 8.33 (dd, J=8.8, 1.9 Hz, 1H), 8.27 (d, J=8.8 Hz, 1H), 7.95 (d, J=1.3 Hz, 1H), 7.67-7.60 (m, 2H), 7.20-7.10 (m, 3H), 6.98 (s, 2H), 3.96 (s, 3H), 3.51 (t, J=6.9 Hz, 2H), 2.87 (t, J=7.5 Hz, 2H), 2.08 (m, 2H).

The compounds listed in the table below were prepared in an analogous fashion to that described in Example 44, Route 2 starting from the appropriate starting materials:

| Starting Material Step 2 | Compound No. or Name | LCMS Data |
|---|---|---|
| (structure: 5-fluoro-2-ethoxy-4-pyridinylboronic acid) | I-517 | LCMS (ES+, FA): m/z = 515.20 (M + H) |
| (structure: 5-fluoro-2-isopropoxy-4-pyridinylboronic acid) | I-518 | LCMS (ES+, FA): m/z = 529.20 (M + H) |

Example 45: 3-(5-Chloro-2-fluoro-phenyl)-2-(4-fluorophenyl)-N-[3-(1H-imidazol-2-yl)propyl]quinoxaline-6-carboxamide (I-480)

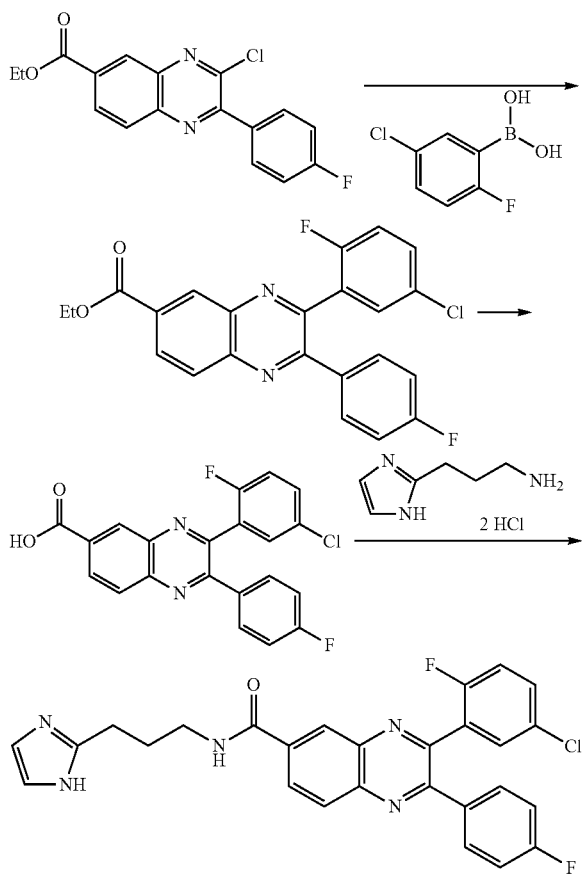

Step 1: Ethyl 3-(5-chloro-2-fluoro-phenyl)-2-(4-fluorophenyl)quinoxaline-6-carboxylate To a mixture of ethyl 3-chloro-2-(4-fluorophenyl)quinoxaline-6-carboxylate (3.24 g, 9.2 mmol; prepared in Example 44, step 3), 5-chloro-2-fluorophenylboronic acid (2.00 g, 12.0 mmol) and cesium carbonate (6.00 g, 18.4 mmol) was added 1,4-dioxane (205 mL), degassed with argon 3×, then added 1,1'-bis(diphenylphosphino)ferrocenedichloropalladium(II) (380 mg, 0.460 mmol), then stirred under nitrogen at 100° C. overnight. The mixture was cooled to rt, diluted with DCM (30 mL) and filtered. The filtrate was concentrated in vacuo to give a crude residue. Purification by silica gel chromatography afforded a white foamy solid product (3.23 g, 83%). LCMS (ESI+): m/z=425.1. 1H NMR (400 MHz, Methanol-d4) δ 8.83 (s, 1H), 8.45 (d, J=8.7 Hz, 1H), 8.27 (d, J=8.8 Hz, 1H), 7.88-7.78 (m, 1H), 7.62 (dd, J=8.0, 5.6 Hz, 2H), 7.57-7.48 (m, 1H), 7.13 (t, J=8.6 Hz, 2H), 7.07 (t, J=9.1 Hz, 1H), 4.51 (q, J=7.1 Hz, 2H), 1.49 (t, J=7.1 Hz, 3H).

Step 2: 3-(5-Chloro-2-fluoro-phenyl)-2-(4-fluorophenyl)quinoxaline-6-carboxylic acid Ethyl 3-(5-chloro-2-fluoro-phenyl)-2-(4-fluorophenyl)quinoxaline-6-carboxylate (3.23 g, 7.60 mmol) was dissolved in THF (84 mL) and then water (21 mL) was added, followed by 1.00 M of sodium hydroxide in water (21 mL, 21 mmol). The mixture was stirred at rt overnight. The mixture was concentrated in vacuo to give an aqueous residue. 1N HCl was added until the pH was ~2. The mixture was filtered and the solid was dried to give the product as a white solid (2.85 g, 94%). LCMS (ESI+): m/z=397.1. 1H NMR (400 MHz, Methanol-d4) δ 8.86 (s, 1H), 8.47 (d, J=8.8 Hz, 1H), 8.27 (d, J=8.7 Hz, 1H), 7.83 (d, J=5.9 Hz, 1H), 7.69-7.58 (m, 2H), 7.53 (d, J=8.7 Hz, 1H), 7.14 (t, J=8.6 Hz, 2H), 7.07 (t, J=9.2 Hz, 1H).

Step 3: 3-(5-Chloro-2-fluoro-phenyl)-2-(4-fluorophenyl)-N-[3-(1H-imidazol-2-yl)propyl]quinoxaline-6-carboxamide (I-480)

To a solution of 3-(5-chloro-2-fluoro-phenyl)-2-(4-fluorophenyl)quinoxaline-6-carboxylic acid (2.85 g, 7.18 mmol) and 3-(1H-imidazol-2-yl)-1-propanamine 2HCl (2.13 g, 10.8 mmol) in DMF (45 mL) and TEA (5.01 mL, 35.9 mmol) was added 2,4,6-tripropyl-1,3,5,2,4,6-trioxatriphosphorinane-2,4,6-trioxide (1.67 mol/L) in EtOAc (8.60 mL, 14.4 mmol). The solution was stirred at rt overnight. The reaction mixture was diluted with EtOAc and water. The organic layer was washed with 10% LiCl, then water twice then brine, dried over anhydrous $Na_2SO_4$, filtered. The filtrate was concentrated in vacuo to give a crude residue. Purification by silica gel chromatography afforded a white solid product (2.90 g, 80%). LCMS (ESI+): m/z=504.1. 1H NMR (400 MHz, Methanol-$d_4$) δ 8.66 (s, 1H), 8.38-8.23 (m, 2H), 7.82 (d, J=3.5 Hz, 1H), 7.61 (d, J=6.9 Hz, 2H), 7.52 (s, 1H), 7.14 (t, J=8.6 Hz, 2H), 7.08 (t, J=9.0 Hz, 1H), 6.96 (s, 2H), 3.53 (t, J=6.8 Hz, 2H), 2.87 (t, J=7.5 Hz, 2H), 2.16-2.05 (m, 2H).

The compound listed in the table below was prepared in an analogous fashion to that described in Example 45 starting from the appropriate starting materials:

| Starting Material Step 3 | Compound No. or Name | LCMS Data |
|---|---|---|
| (structure: 3-(1H-1,2,4-triazol-3-yl)propan-1-amine) | I-520 | LCMS (ES+, FA): m/z = 505.10 (M + H) |

Example 47: 3-(4-Fluorophenyl)-2-(4-hydroxypiperidin-1-yl)-N-[2-(pyridin-3-yloxy)ethyl]quinoxaline-6-carboxamide (I-367)

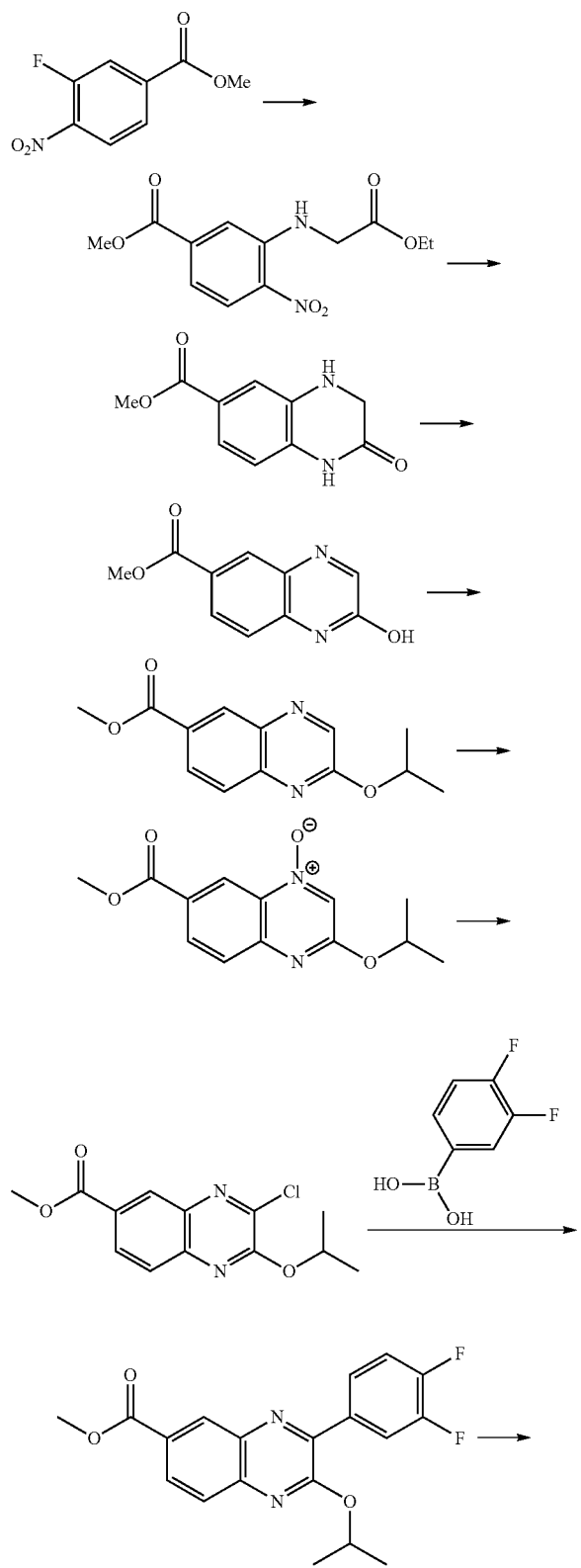

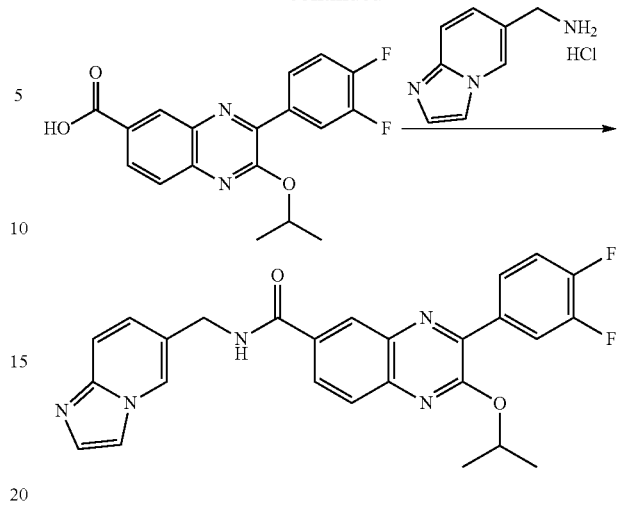

Step 1: Methyl 3-((2-ethoxy-2-oxoethyl)amino)-4-nitrobenzoate

A mixture of 3-fluoro-4-nitrobenzoicacidmethylester (4.0 g, 2.0 mmol), glycine ethyl ester hydrochloride (3.36 g, 24.1 mmol) and potassium carbonate (5.55 g, 40.2 mmol) in MeCN (100 mL) was heated to 70° C. for 36 h. To the mixture was added water. The aqueous layer was extracted with EtOAc. The combined organic layer was washed with brine, dried over anhydrous $Na_2SO_4$ and concentrated in vacuo to give methyl 3-((2-ethoxy-2-oxoethyl)amino)-4-nitrobenzoate (5.28 g, 93%) as yellow syrup. LCMS (ESI+): m/z=283.1 (M+H). 1H NMR (400 MHz, DMSO-$d_6$) δ 8.41 (m, 1H), 8.22 (d, J=8.8 Hz, 1H), 7.39 (d, J=1.6 Hz, 1H), 7.23 (dd, J=8.8, 1.7 Hz, 1H), 4.34 (d, J=5.8 Hz, 2H), 4.20 (q, J=7.1 Hz, 2H), 3.89 (s, 3H), 1.24 (t, J=7.1 Hz, 3H).

Step 2: Methyl 2-oxo-1,2,3,4-tetrahydroquinoxaline-6-carboxylate

A mixture of methyl 3-((2-ethoxy-2-oxoethyl)amino)-4-nitrobenzoate and iron (13.0 g, 234 mmol) in acetic acid (232 mL, 4080 mmol) and water (38.7 mL, 2150 mmol) was heated to 70° C. for 1.5 h. At high temp the mixture turned to a dark homogeneous solution. The reaction mixture was cooled to rt. 50 mL of water was added and the mixture was further cooled to 0° C. The mixture was filtered over a fritted funnel. The filtered purple solid was washed with water and dried under air to give methyl 2-oxo-1,2,3,4-tetrahydroquinoxaline-6-carboxylate (14.2 g, 88%), LCMS (ESI+): m/z=207.1 (M+H). 1H NMR (400 MHz, DMSO-d6) δ 10.57 (s, 1H), 7.29 (s, 1H), 7.24 (m, 1H), 6.80 (d, J=8.1 Hz, 1H), 6.25 (s, 1H), 3.79 (s, 3H).

Step 3: Methyl 2-hydroxyquinoxaline-6-carboxylate

To a suspension of methyl 2-oxo-1,2,3,4-tetrahydroquinoxaline-6-carboxylate (3.09 g, 15.0 mmol) in THF (75 mL) was added manganese(IV) oxide (6.51 g, 74.9 mmol). The suspension was stirred at rt overnight. The mixture was filtered over a celite pad, the celite pad was washed using EtOAc (20 mL) and then methanol (2×20 mL). The filtrate was concentrated in vacuo to give methyl 2-hydroxyquinoxaline-6-carboxylate (1.13 g, 36.9%). LCMS (ESI+):

m/z=205.1 (M+H). 1H NMR (400 MHz, DMSO-d$_6$) δ 12.73 (s, 1H), 8.29 (m, 1H), 8.26 (s, 1H), 8.10 (m, 1H), 3.89 (s, 3H).

Step 4: Methyl 2-isopropoxyquinoxaline-6-carboxylate

A round bottom flask was charged with a mixture of methyl 2-hydroxyquinoxaline-6-carboxylate (2.91 g, 14.25 mmol), diisopropyl azodicarboxylate (3.09 mL, 15.7 mmol), triphenylphosphine (4.11 g, 15.7 mmol) and isopropyl alcohol (2.73 mL, 35.6 mmol) in THF (73 mL). The flask was sealed, evacuated and purged with nitrogen. The mixture was heated at 70° C. overnight. The reaction mixture was diluted with water and extracted with EtOAc twice. The combined EtOAc layer was washed with brine and then dried over anhydrous Na$_2$SO$_4$ and concentrated in vacuo to give crude. Chromatography in silica column using EtOAc/hexane (0/100 to 20/80) gave methyl 2-isopropoxyquinoxaline-6-carboxylate (1.67 g, 48%). LCMS (ESI+): m/z=247.1 (M+H). 1H NMR (400 MHz, Chloroform-d) δ 8.63 (d, J=1.8 Hz, 1H), 8.38 (s, 1H), 8.19 (dd, J=8.7, 1.9 Hz, 1H), 7.75 (d, J=8.7 Hz, 1H), 5.48 (m, 1H), 3.92 (s, 3H), 1.38 (d, J=6.2 Hz, 6H).

Step 5: Methyl 2-isopropoxyquinoxaline-6-carboxylate 4-oxide

To a solution of methyl 2-isopropoxyquinoxaline-6-carboxylate (1.26 g, 5.11 mmol) in DCM (26.0 mL) was added m-chloroperbenzoic acid (2.29 g, 10.2 mmol). The reaction mixture was stirred at rt overnight. The reaction mixture was distributed between NaHCO$_3$(aqueous) saturated solution and DCM. The aqueous layer was extracted with DCM twice. The combined organic layer was washed with 1M NaOH solution three times, dried over anhydrous Na$_2$SO$_4$ and dried in vacuo to give methyl 2-isopropoxyquinoxaline-6-carboxylate 4-oxide (1.3 g, 97%). LCMS (ESI+): m/z=263.1 (M+H). 1H NMR (400 MHz, DMSO-d6) δ 8.92 (d, J=1.9 Hz, 1H), 8.51 (s, 1H), 8.32 (dd, J=8.7, 2.0 Hz, 1H), 8.01 (d, J=8.7 Hz, 1H), 5.55 (m, 1H), 4.00 (s, 3H), 1.46 (d, J=6.2 Hz, 6H).

Step 6: Methyl 3-chloro-2-isopropoxyquinoxaline-6-carboxylate

A solution of methyl 2-isopropoxyquinoxaline-6-carboxylate 4-oxide (1.75 g, 6.67 mmol) in DMF (27.7 mL) was cooled under ice/brine bath, oxalyl chloride (0.736 mL, 8.70 mmol) was added dropwise, then allowed to warm up to rt for about 30 mins. The reaction mixture was quenched with water, then extracted with DCM 3 times. Combined organic layers were washed with water 3 times, then brine and dried over anhydrous Na$_2$SO$_4$ and concentrated in vacuo to give methyl 3-chloro-2-isopropoxyquinoxaline-6-carboxylate 1.79 g (95%). LCMS (ESI+): m/z=281.0 (M+H). 1H NMR (400 MHz, DMSO-d6) δ 8.50 (d, J=1.8 Hz, 1H), 8.29 (dd, J=8.7, 1.9 Hz, 1H), 8.01 (s, 1H), 5.57 (m, 1H), 3.99 (s, 3H), 1.50 (d, J=62 Hz, 6H).

Step 7: Methyl 3-(3,4-difluorophenyl)-2-isopropoxyquinoxaline-6-carboxylate

Methyl 3-chloro-2-isopropoxyquinoxaline-6-carboxylate (243.0 mg, 0.8657 mmol) and (3,4-difluorophenyl)boranediol (271 mg, 1.72 mmol), cesium carbonate (846 mg, 2.60 mmol) and SiliaCat® DPP-Pd (0.260 mmol/g loading; 666 mg, 0.173 mmol) were weighed into a microwave vial purged with nitrogen then added 1,4-dioxane (14.1 mL) and water (3.53 mL). Sealed the vial and heated it in microwave at 125° C. for 30 min. Filtered to remove resin, then evaporated to remove solvent. The crude reaction mixture was purified by chromatography in silica column using 0 to 30% EtOAc % hexane to give methyl 3-(3,4-difluorophenyl)-2-isopropoxyquinoxaline-6-carboxylate (193 mg, 62%). LCMS (ESI+): m/z=359.1. (M+H).

Step 8: 3-(3,4-Difluorophenyl)-2-isopropoxyquinoxaline-6-carboxylic acid

To a solution of methyl 3-(3,4-difluorophenyl)-2-isopropoxyquinoxaline-6-carboxylate (193 mg, 0.538 mmol) in THF (3.2 mL) and methanol (3.2 mL) was added 1.0 M of sodium hydroxide in water (1.6 mL, 1.6 mmol) and water (1.6 mL, 88 mmol). The resulting suspension was stirred at rt overnight until a clear solution was obtained. The solution was diluted with water, then adjusted with 1N NaOH until the pH reached around 3. The resulting precipitate was filtered and collected. The solid was washed with water and then dried under vacuo to give 3-(3,4-difluorophenyl)-2-isopropoxyquinoxaline-6-carboxylic acid (185 mg, 99%). LCMS (ESI+): m/z=345.2 (M+H).

Step 9: 3-(3,4-Difluorophenyl)-N-(imidazo[1,2-a]pyridin-6-ylmethyl)-2-isopropoxyquinoxaline-6-carboxamide (I-367)

To a solution of 3-(3,4-difluorophenyl)-2-isopropoxyquinoxaline-6-carboxylic acid (40.5 mg, 0.118 mmol) in THF (0.59 mL), (imidazo[1,2-a]pyridin-6-yl)methylamine hydrochloride (32.4 mg, 0.176 mmol), N,N,N',N'-tetramethyl-O-(7-azabenzotriazol-1-yl)uronium hexafluorophosphate (49.2 mg, 0.129 mmol) and TEA (81.9 uL, 0.588 mmol) was added at rt. The reaction mixture was allowed to stir at rt for about 1 h. To the reaction mixture was added 10 ml of water. The resulting precipitate was filtered and collected. The crude solid was purified by HPLC to give 3-(3,4-difluorophenyl)-N-(imidazo[1,2-a]pyridin-6-ylmethyl)-2-isopropoxyquinoxaline-6-carboxamide (56 mg, 92%, isolated as formic acid salt). LCMS (ESI+): m/z=474.2 (M+H). 1H NMR (400 MHz, DMSO-d6) δ 9.36 (m, 1H), 8.64 (s, 1H), 8.55 (s, 1H), 8.24 (dd, J=8.7, 1.7 Hz, 1H), 8.21-8.09 (m, 1H), 8.02 (m, 1H), 7.97 (s, 1H), 7.92 (d, J=8.7 Hz, 1H), 7.64 (m, 1H), 7.56 (m, 2H), 7.29 (d, J=9.3 Hz, 1H), 5.59 (m, 1H), 4.54 (d, J=5.6 Hz, 2H), 1.46 (d, J=6.2 Hz, 6H).

The compounds listed in the table below were prepared in an analogous fashion to that described in Example 47 starting from the appropriate starting materials:

| Material Step 7 | Material Step 9 | Compound No. or Name | LCMS Data |
|---|---|---|---|
| 2-thienyl boronic acid | 2-(3-aminopropyl)-1H-imidazole | I-385 | LCMS (ESI+): m/z = 493.2 (M + H) |
| 3-methoxyphenyl boronic acid | 2-(3-aminopropyl)-1H-imidazole | I-511 | LCMS (ESI+): m/z = 446.2 (M + H) |
| 2-fluoro-5-methoxyphenyl boronic acid | 2-(3-aminopropyl)-1H-imidazole | I-492 | LCMS (ESI+): m/z = 464.2 (M + H) |
| 5-cyano-2-fluorophenyl boronic acid | 2-(3-aminopropyl)-1H-imidazole | I-414 | LCMS (ESI+): m/z = 459.2 (M + H) |
| 4-fluoro-3-methoxyphenyl boronic acid | 2-(3-aminopropyl)-1H-imidazole | I-344 | LCMS (ESI+): m/z = 464.2 (M + H) |
| 3,4-difluorophenyl boronic acid | 2-(3-aminopropyl)-1H-imidazole | I-339 | LCMS (ESI+): m/z = 452.2 (M + H) |
| 3-(trifluoromethylthio)phenyl boronic acid | 2-(3-aminopropyl)-1H-imidazole | I-421 | LCMS (ESI+): m/z = 516.2 (M + H) |

-continued
| Material Step 7 | Material Step 9 | Compound No. or Name | LCMS Data |
|---|---|---|---|
| | | I-392 | LCMS (ESI+): m/z = 465.2 (M + H) |
| | | I-435 | LCMS (ESI+): m/z = 468.2 (M + H) |
| | | I-403 | LCMS (ESI+): m/z = 478.1 (M + H) |
| | | I-334 | LCMS (ESI+): m/z = 456.1 (M + H) |
| | | I-317 | LCMS (ESI+): m/z = 478.1 (M + H) |
Example 48: N-(3-(1H-imidazol-2-yl)propyl)-2-(tert-butoxymethyl)-3-(4-fluorophenyl)quinoxaline-6-carboxamide (I-341)
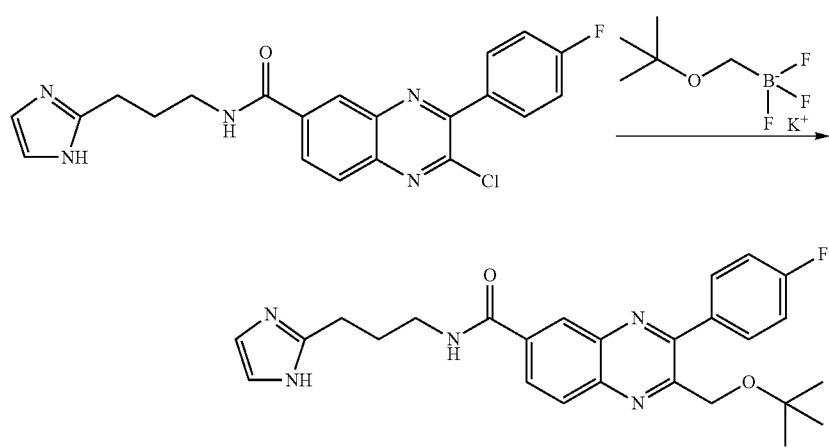

A mixture of 2-chloro-3-(4-fluorophenyl)-N-[3-(1H-imidazol-2-yl)propyl]quinoxaline-6-carboxamide (300 mg, 0.7 mmol, prepared according to Example 29, step 1), potassium tert-butoxymethyltrifluoroborate (568 mg, 2.93 mmol), cesium carbonate (715 mg, 2.20 mmol) and SiliaCat® DPP-Pd (0.260 mmol/g loading; 469 mg, 0.122 mmol) was weighed into a 2-5 mL microwave vial and purged with nitrogen 5 min. To the vial was added 1,4-dioxane (9.95 mL, 127 mmol) and water (2.20 mL, 122 mmol). The mixture was heated at 150° C. for 4 h under microwave irradiation. After cooling, the reaction mixture was poured into EtOAc and water. The layers were separated and the aqueous layer was extracted two more times with EtOAc. The combined organic layer was dried over anhydrous MgSO$_4$ and concentrated in vacuo. Purification by HPLC provided N-(3-(1H-imidazol-2-yl)propyl)-2-(tert-butoxymethyl)-3-(4-fluorophenyl)quinoxaline-6-carboxamide (100 mg, 30%) as a white solid. LCMS (ESI+): m/z=462 (M+H). 1H NMR (400 MHz, DMSO-d6) δ 9.05 (t, J=5.0 Hz, 1H), 8.63 (s, 1H), 8.28 (d, J=8.7 Hz, 1H), 8.18 (d, J=5.2 Hz, 2H), 7.93-7.83 (m, 2H), 7.40 (t, J=8.3 Hz, 2H), 6.98 (s, 2H), 4.61 (s, 2H), 3.45-3.33 (m, 2H), 2.76 (t, J=7.4 Hz, 2H), 1.97 (q, J=6.9 Hz, 2H), 1.09 (s, 9H).

Example 49: N-(2-(1H-imidazol-2-yl)ethyl)-3-(5-chlorothiophen-2-yl)-2-(4-fluorophenyl)quinoxaline-6-carboxamide (I-443)

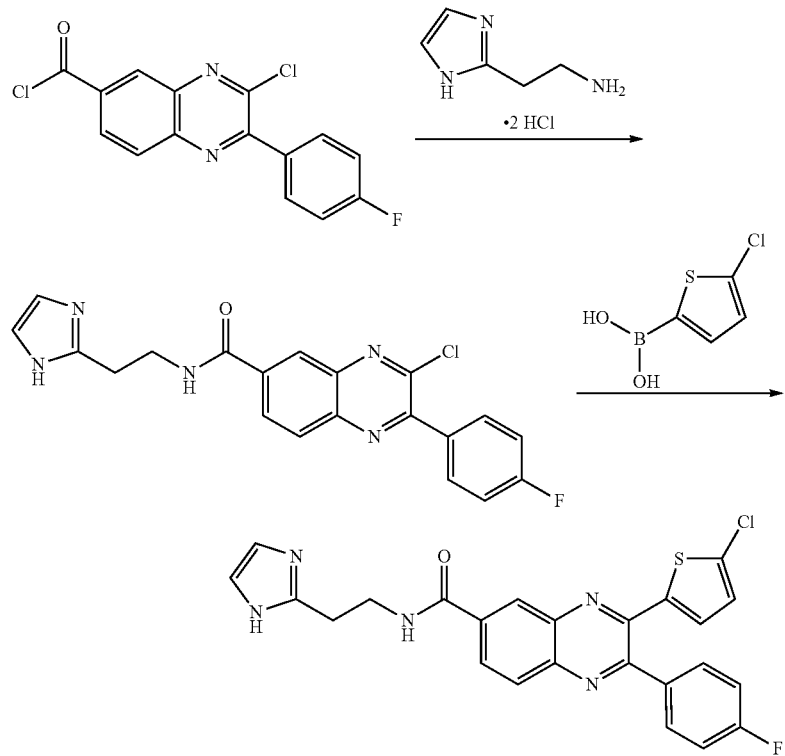

Step 1: N-(2-(-1H-imidazol-2-yl)ethyl)-3-chloro-2-(4-fluorophenyl)quinoxaline-6-carboxamide To a mixture of 3-chloro-2-(4-fluorophenyl)quinoxaline-6-carbonyl chloride (1.03 g, 3.21 mmol, prepared according to Example 44, Route 1, Step 3) in N,N-dimethylacetamide (45 mL) was added 2-(1H-imidazol-2-yl)ethanamine dihydrochloride (709 mg, 3.85 mmol) and TEA (2.24 mL, 16.1 mmol) and the resulting mixture was stirred at room temperature overnight. The reaction was then poured into saturated sodium bicarbonate (50 mL). Water (50 mL) and ethyl acetate (200 mL) were added. The layers were separated and the aqueous layer was extracted with ethyl acetate (100 mL). The combined organic layers were washed with water (5×50 mL), dried, filtered and concentrated in vacuo. Silica gel chromatography gave N-(2-(1H-imidazol-2-yl)ethyl)-3-chloro-2-(4-fluorophenyl)quinoxaline-6-carboxamide (541 mg, 42%). LCMS (ESI+): m/z=396.1 (M+H). $^1$H NMR (400 MHz, DMSO-d$_6$) δ 11.86 (bs, 1H), 9.06 (t, J=5.6 Hz, 1H), 8.55 (d, J=1.6 Hz, 1H), 8.30 (dd, J=8.8, 1.6 Hz, 1H), 8.27 (d, J=8.8 Hz, 1H), 7.96-7.93 (m, 2H), 7.45-7.40 (m, 2H), 6.92 (bs, 2H), 3.68-3.62 (m, 2H), 2.97-2.93 (m, 2H).

Step 2: N-(2-(1H-imidazol-2-yl)ethyl)-3-(5-chlorothiophen-2-yl)-2-(4-fluorophenyl)quinoxaline-6-carboxamide (I-443)

To a solution of N-(2-(1H-imidazol-2-yl)ethyl)-3-chloro-2-(4-fluorophenyl)quinoxaline-6-carboxamide (20.0 mg, 0.0505 mmol) in 1,4-dioxane (2.0 mL) was added (5-chlorothiophen-2-yl)boronic acid (11.89 mg, 0.073 mmol), sodium carbonate (15.5 mg, 0.146 mmol) and water (0.150 mL). After purging the vial with nitrogen for a few min SiliaCat® DPP-Pd (29.0 mg, 0.260 mmol/gm) was added. The reaction mixture was heated at 120° C. for 30 min under microwave irradiation. After cooling, the reaction mixture was concentrated and then suspended in DMSO (1.0 mL). After filtration the mixture was purified by preparative HPLC to give N-(2-(1H-imidazol-2-yl)ethyl)-3-(5-chlorothiophen-2-yl)-2-(4-fluorophenyl)quinoxaline-6-carboxamide (3.1 mg, 7.7%). LCMS (ESI+): m/z=478.38 (M+H).

The compounds listed in the table below were prepared in an analogous fashion to that described in Example 49 starting from the appropriate starting materials:

| Starting Material | Compound No. or Name | LCMS Data |
|---|---|---|
| (3-chlorophenyl)boronic acid | I-376 | LCMS (ES+, FA): m/z = 472.41 (M + H) |

Example 50: N-(3-(1H-imidazol-2-yl)propyl)-7-fluoro-3-(4-fluorophenyl)-2-isopropoxyquinoxaline-6-carboxamide (I-491)

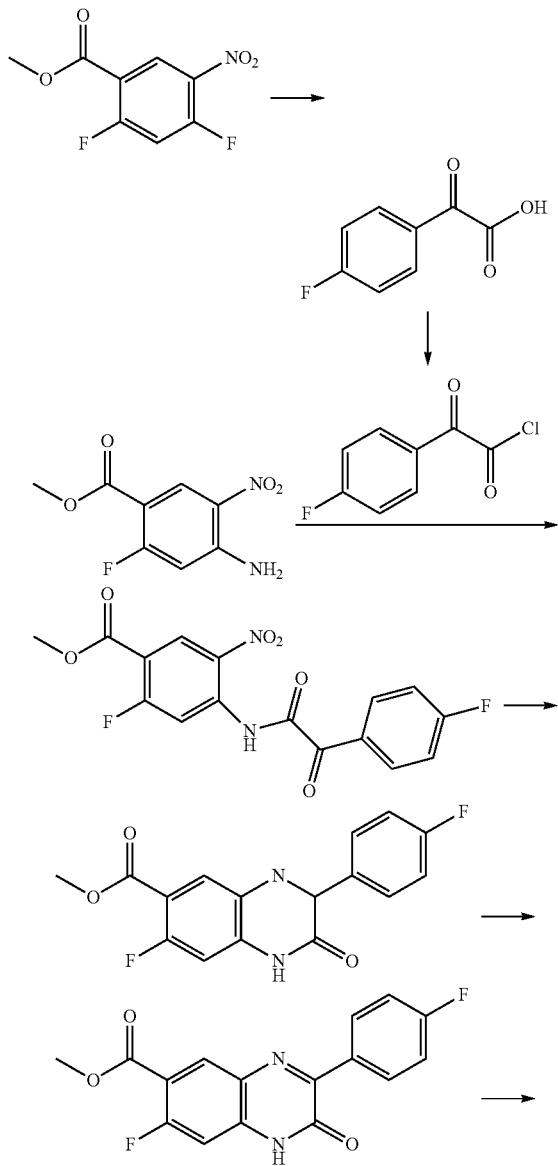

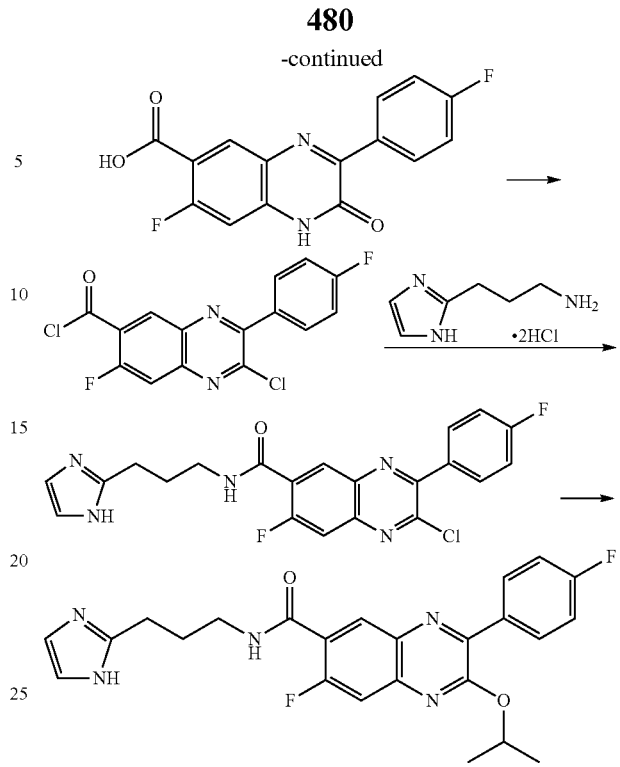

Step 1: Methyl 4-amino-2-fluoro-5-nitrobenzoate

To a solution of methyl 2,4-difluoro-5-nitrobenzoate (6.00 g, 27.6 mmol) in THF (25 mL) in an ice bath was added concentrated aqueous ammonia (5.20 mL, 78.0 mmol). After stirring for 30 min, THF (25 ml) was added to thin the very thick mixture, which was then allowed to warm to rt overnight. Solvent was removed and the residue was suspended in water (100 mL). The mixture was stirred for 30 min. The solids were filtered and washed with water to give methyl 4-amino-2-fluoro-5-nitrobenzoate (4.85 g, 82%). LCMS (ESI+): m/z=215.0 (M+H). 1H NMR (400 MHz, DMSO-d6) δ 8.60 (d, J=7.6 Hz, 1H), 8.07 (bs, 2H), 6.80 (d, J=13.2 Hz, 1H), 3.81 (s, 3H).

Step 2: Methyl 2-fluoro-4-(2-(4-fluorophenyl)-2-oxoacetamido)-5-nitrobenzoate

To a solution of 4-fluorobenzoylformic acid (981 mg, 5.84 mmol) (prepared as in Boyce, Christopher W. et al., "Preparation of Quinoxaline Derivatives for use as CRTH2 Receptor Modulators", PCT Int. Appl. (2012), WO2012087861 A1, Jun. 28, 2012) in THF (13.2 mL) in an ice bath was added DMF (23 uL, 0.29 mmol) followed by oxalyl chloride (0.513 mL, 6.07 mmol). The solution was allowed to warm to rt over 2 h. The resulting solution was added to a solution of methyl 4-amino-2-fluoro-5-nitrobenzoate (1.14 g, 5.34 mmol) and TEA (1.46 mL, 10.4 mmol) in THF (39.5 mL). The mixture was stirred at rt overnight. The reaction mixture was distributed between EtOAc and saturated aqueous sodium bicarbonate. The organic layer was washed with brine, dried, filtered, and concentrated in vacuo. Purification by silica gel chromatography gave methyl 2-fluoro-4-(2-(4-fluorophenyl)-2-oxoacetamido)-5-nitrobenzoate (931 mg, 48%). LCMS (ESI−): m/z=363.1 (M−H). 1H NMR (400 MHz, DMSO-d6) δ 11.80 (s, 1H), 8.67 (d, J=7.2 Hz, 1H), 8.33-8.28 (m, 3H), 7.49-7.45 (m, 2H), 3.92 (s, 3H).

Step 3: Methyl 7-fluoro-3-(4-fluorophenyl)-2-oxo-1,2,3,4-tetrahydroquinoxaline-6-carboxylate A mixture of methyl 2-fluoro-4-(2-(4-fluorophenyl)-2-oxoacetamido)-5-nitrobenzoate (931 mg, 2.56 mmol) and 10% Pd/C (250 mg) in THF (25 mL) and methanol (25 mL) was transferred into a Parr shaker. The container was filled with 35 psi of hydrogen and shaken overnight. The catalyst was filtered and the filtrate was concentrated in vacuo. Silica gel chromatography gave methyl 7-fluoro-3-(4-fluorophenyl)-2-oxo-1,2,3,4-tetrahydroquinoxaline-6-carboxylate (211 mg, 26%). LCMS (ESI+): m/z=319.0 (M+H). 1H NMR (400 MHz, DMSO-$d_6$) δ 10.90 (s, 1H), 7.37 (dd, J=8.4, 5.6 Hz, 2H), 7.30 (d, J=6.8 Hz, 1H), 7.19 (t, J=8.4 Hz, 2H), 6.89 (s, 1H), 6.64 (d, J=11.2 Hz, 1H), 5.05 (s, 1H), 3.80 (s, 3H).

Step 4: Methyl 7-fluoro-3-(4-fluorophenyl)-2-oxo-1,2-dihydroquinoxaline-6-carboxylate To a solution of methyl 7-fluoro-3-(4-fluorophenyl)-2-oxo-1,2,3,4-tetrahydroquinoxaline-6-carboxylate (210 mg, 0.660 mmol) in 1,4-dioxane (4.0 mL) was added dichlorodicyanoquinone (392 mg, 1.73 mmol) and the mixture was stirred overnight at rt. The reaction mixture was concentrated in vacuo. The crude product was purified by silica gel chromatography to give methyl 7-fluoro-3-(4-fluorophenyl)-2-oxo-1,2-dihydroquinoxaline-6-carboxylate (61 mg, 29%). LCMS (ESI+): m/z=317.0 (M+H). 1H NMR (400 MHz, $CDCl_3$) δ 10.45 (s, 1H), 8.50 (d, J=8.8 Hz, 1H), 8.42-8.38 (m, 2H), 7.13 (t, J=8.8 Hz, 2H), 6.91 (d, J=10.4 Hz, 1H), 3.91 (s, 3H).

Step 5: 7-Fluoro-3-(4-fluorophenyl)-2-oxo-1,2-dihydroquinoxaline-6-carboxylic acid A solution of methyl 7-fluoro-3-(4-fluorophenyl)-2-oxo-1,2-dihydroquinoxaline-6-carboxylate (131 mg, 0.414 mmol) in THF (3.9 mL), methanol (3.9 mL) and 1M aqueous sodium hydroxide (1.76 mL, 1.76 mmol) was stirred at 65° C. overnight. The reaction mixture was cooled and acidified to pH=2 with 1N HCl. The mixture was concentrated in vacuo and azeotroped with MeCN. To the residue was added methanol (10 mL) and the mixture was stirred for 1 h. The solids were filtered and washed with methanol to give 7-fluoro-3-(4-fluorophenyl)-2-oxo-1,2-dihydroquinoxaline-6-carboxylic acid (99 mg, 79%). LCMS (ESI+): m/z=303.1 (M+H). 1H NMR (400 MHz, DMSO-$d_6$) δ 13.35 (s, 1H), 12.85 (s, 1H), 8.40-8.36 (m, 2H), 8.28 (d, J=7.6 Hz, 1H), 7.37-7.32 (m, 2H), 7.08 (d, J=10.2 Hz, 1H).

Step 6: 2-Chloro-7-fluoro-3-(4-fluorophenyl)quinoxaline-6-carbonyl chloride

To a suspension of 7-fluoro-3-(4-fluorophenyl)-2-oxo-1,2-dihydroquinoxaline-6-carboxylic acid (91.0 mg, 0.301 mmol) in thionyl chloride (2.7 mL, 27 mmol) was added 5 drops of DMF. The mixture was refluxed for 2 h, cooled and concentrated in vacuo. The resulting solid was used without further purification.

Step 7: N-(3-(1H-imidazol-2-yl)propyl)-2-chloro-7-fluoro-3-(4-fluorophenyl)quinoxaline-6-carboxamide To a suspension of 2-chloro-7-fluoro-3-(4-fluorophenyl)quinoxaline-6-carbonyl chloride (102 mg, 0.301 mmol) in DMA (4.3 mL)) was added 3-(1H-imidazol-2-yl)-1-propanamine.2HCl (72 mg, 0.36 mmol) and TEA (0.210 mL, 1.50 mmol). The resulting mixture was stirred at rt overnight. The mixture was distributed between aqueous saturated sodium bicarbonate and EtOAc. The aqueous layer was extracted with EtOAc. The combined organic layer was washed with water five times, dried, and concentrated. Purification by silica gel chromatography provided N-(3-(1H-imidazol-2-yl)propyl)-2-chloro-7-fluoro-3-(4-fluorophenyl)quinoxaline-6-carboxamide (46 mg, 36%). LCMS (ESI+): m/z=428.1 (M+H). 1H NMR (400 MHz, $CD_3OD$) δ 8.43 (d, J=7.2 Hz, 1H), 7.97-7.92 (m, 2H), 7.84 (d, J=10.8 Hz, 1H), 7.34-7.28 (m, 2H), 6.95 (s, 2H), 3.52-3.48 (m, 2H), 2.88-2.84 (m, 2H), 2.10-2.03 (m, 2H).

Step 8: N-(3-(1H-imidazol-2-yl)propyl)-7-fluoro-3-(4-fluorophenyl)-2-isopropoxyquinoxaline-6-carboxamide (I-491)

To a vial charged with NaH (60% in mineral oil, 8.60 mg, 0.215 mmol) was added isopropyl alcohol (123 uL, 1.61 mmol) and N-methylpyrrolidinone (0.631 mL, 6.54 mmol). The mixture was stirred at rt for 5 min until it formed a purple solution. To the mixture was added N-(3-(1H-imidazol-2-yl)propyl)-2-chloro-7-fluoro-3-(4-fluorophenyl)quinoxaline-6-carboxamide (46.0 mg, 9.108 mmol). The resulting dark solution was stirred at rt for 45 min. The reaction mixture was distributed between water and EtOAc. The aqueous layer was extracted with EtOAc. The combined organic layer was washed with water three times then with brine, dried, and concentrated in vacuo. Purification by HPLC provided N-(3-(1H-imidazol-2-yl)propyl)-7-fluoro-3-(4-fluorophenyl)-2-isopropoxyquinoxaline-6-carboxamide (3.0 mg, 5%, isolated as a formic acid salt). LCMS (ESI+): m/z=452.2 (M+H). 1H NMR (400 MHz, $CD_3OD$) δ 8.54 (bs, 2H), 8.36 (d, J=7.6 Hz, 1H), 8.21-8.17 (m, 2H), 7.60 (d, J=11.2 Hz, 1H), 7.29-7.24 (m, 2H), 7.07 (bs, 2H), 5.71-5.65 (m, 1H), 3.53-3.49 (m, 2H), 2.93-2.89 (m, 2H), 2.11-2.07 (m, 2H), 1.50 (d, J=6.4 Hz, 6H).

Example 51: N-[3-(6-aminopyridin-3-yl)propyl]-3-(4-fluorophenyl)-2-isopropoxyquinoxaline-6-carboxamide (I-359)

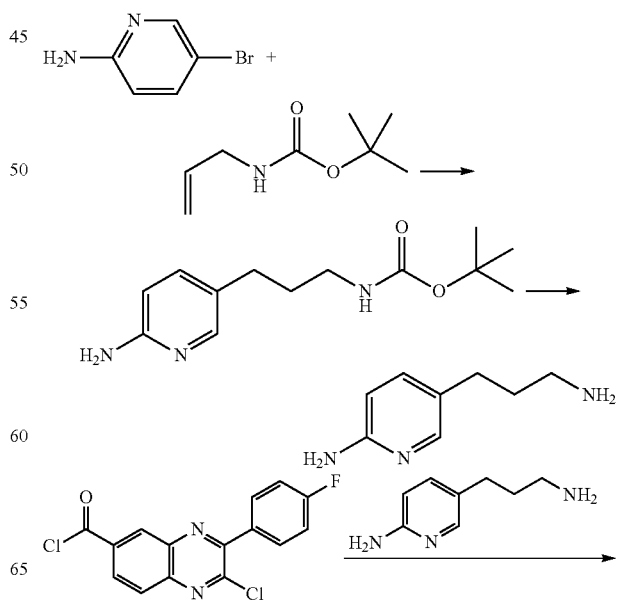

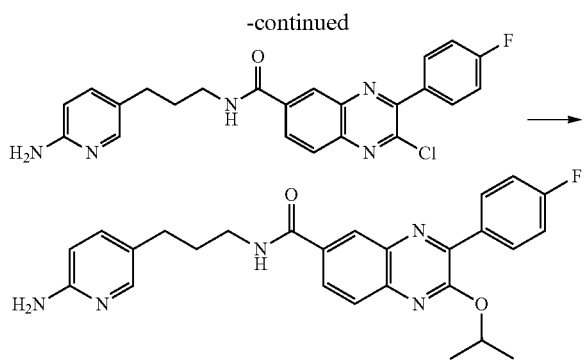

Step 1: tert-Butyl [3-(6-aminopyridin-3-yl)propyl]carbamate

3-N-t-Butoxycarbonylamino-1-propene (4.67 g, 29.7 mmol) was dissolved in anhydrous THF (50 mL, 600 mmol), and cooled with an ice bath. 0.5 M of 9-BBN in THF (57.0 mL, 28.5 mmol) was added dropwise. The mixture was stirred under nitrogen atmosphere with cooling then slowly brought to rt overnight. 0.5 M of 9-BBN in THF (57.0 mL, 28.5 mmol) was added and the solution was stirred at rt for another 3.5 h. 2.0 M of sodium hydroxide in water (39.3 mL, 78.5 mmol) was added and the mixture was stirred at rt for 2 h. The resulting solution was degassed by low vacuum evacuation and flushing with nitrogen 3 times. A solution of 2-amino-5-bromopyridine (2.50 g, 14.4 mmol) and tetrakis(triphenylphosphine)palladium(0) (760 mg, 0.657 mmol) in anhydrous THF (20 mL, 200 mmol) was added. The mixture was heated under nitrogen atmosphere to 80° C. for 20 h. The solution was then cooled to rt and the volatiles were removed. The aqueous residue was extracted with EtOAc. The organic layer was washed with water (3×) then with brine, dried over anhydrous $Na_2SO_4$, filtered and concentrated to give a crude mixture. Chromatography in a 150 g Agilent silica columns using MeOH/EtOAc (0/100 to 5/95) afforded tert-butyl [3-(6-aminopyridin-3-yl)propyl]carbamate (3.36 g, 13.4 mmol, 92.5%). LCMS (ESI+): m/z=252.2 (M+H). 1H NMR (400 MHz, $CDCl_3$) δ 7.91 (s, 1H), 7.31 (d, J=8.5 Hz, 1H), 6.48 (d, J=8.4 Hz, 1H), 4.60-4.55 (m, 3H), 3.21-3.11 (m, 2H), 2.57-2.47 (m, 2H), 1.82-1.70 (m, 2H), 1.47 (s, 9H).

Step 2: 5-(3-Aminopropyl)pyridin-2-amine.2[HCl]

tert-Butyl [3-(6-aminopyridin-3-yl)propyl]carbamate (3.36 g, 13.4 mmol) was dissolved in THF (30 mL, 400 mmol). 4M of hydrochloric acid in 1,4-dioxane (10.0 mL, 39.2 mmol) was added. The resulted solution was stirred at rt over 3 days. The suspension was filtered and the solid was washed with EtOAc then hexane, dried in air then under reduced pressure to give 5-(3-aminopropyl)pyridin-2-amine.2[HCl]. LCMS (ESI+): m/z=152.1 (M+H). 1H NMR (400 MHz, CD3OD) δ 7.93 (dd, J=9.2, 1.9 Hz, 1H), 7.77 (s, 1H), 7.04 (d, J=9.2 Hz, 1H), 3.00 (t, J=7.6 Hz, 2H), 2.73-2.64 (m, 2H), 2.03-1.92 (m, 2H).

Step 3: N-(3-(6-Aminopyridin-3-yl)propyl)-2-chloro-3-(4-fluorophenyl)quinoxaline-6-carboxamide To 2-chloro-3-(4-fluorophenyl)quinoxaline-6-carbonyl chloride (1.28 g, 4.00 mmol) was added DMA (25 mL, 270 mmol), DIPEA (3.62 mL, 20.8 mmol), and 5-(3-aminopropyl)pyridin-2-amine.2[HCl] (1.16 g, 5.20 mmol). The resulting mixture was stirred at rt for 17 h. Most of DMA was removed by evaporation and the liquid residue was diluted with EtOAc and water. The organic layer was washed with water (×3) and brine, dried over anhydrous $Na_2SO_4$ and concentrated. The crude mixture was purified on a 120 g silica column with 2-10% MeOH in DCM to provide N-(3-(6-aminopyridin-3-yl)propyl)-2-chloro-3-(4-fluorophenyl)quinoxaline-6-carboxamide (847 mg, 1.87 mmol, 46.7%). LCMS (ESI+): m/z=436.1 (M+H). 1H NMR (400 MHz, $CD_3OD$) δ 8.57 (d, J=1.5 Hz, 1H), 8.26 (dd, J=8.8, 1.8 Hz, 1H), 8.12 (d, J=8.8 Hz, 1H), 7.97 (dd, J=8.8, 5.4 Hz, 2H), 7.79 (s, 1H), 7.44 (dd, J=8.5, 2.2 Hz, 1H), 7.32 (d, J=8.8 Hz, 2H), 6.58 (d, J=8.5 Hz, 11), 3.50 (t, J=7.1 Hz, 2H), 2.62 (t, J=7.6 Hz, 2H), 2.00-1.90 (m, 2H).

Step 4: N-[3-(6-Aminopyridin-3-yl)propyl]-3-(4-fluorophenyl)-2-isopropoxyquinoxaline-6-carboxamide (I-359)

A vial was charged with NaH 60% in mineral oil (13.6 mg, 0.341 mmol). To the vial was added N-methylpyrrolidinone (1.00 mL, 10.4 mmol) and isopropanol (196 µL, 2.56 mmol). The mixture was stirred at rt for 5 min (gas generation observed, the mixture turned purple) under nitrogen. To the mixture was added N-[3-(6-aminopyridin-3-yl)propyl]-2-chloro-3-(4-fluorophenyl)quinoxaline-6-carboxamide (74.3 mg, 0.170 mmol). The resulting dark orange solution was stirred at rt. After 3 h the mixture was distributed between water and EtOAc. The aqueous layer was extracted with EtOAc. The combined organic layer was washed with brine, dried, and concentrated. The crude mixture was purified on a 24 g silica gel column (continuous gradient from 0-15% MeOH/$CH_2Cl_2$ over 25 min). N-[3-(6-aminopyridin-3-yl)propyl]-2-chloro-3-(4-fluorophenyl)quinoxaline-6-carboxamide was provided as a white solid (59.0 mg, 0.128 mmol, 75.4%). LCMS (ESI+): m/z=460.2 (M+H). 1H NMR (400 MHz, CD3OD) δ 8.47 (s, 1H), 8.21 (dd, J=8.0, 5.8 Hz, 2H), 8.11 (d, J=8.2 Hz, 1H), 7.89 (d, J=8.6 Hz, 1H), 7.80 (s, 1H), 7.43 (d, J=7.6 Hz, 1H), 7.27 (t, J=8.6 Hz, 2H), 6.58 (d, J=8.5 Hz, 1H), 5.69 (hept, J=6.1 Hz, 1H), 3.48 (t, J=6.9 Hz, 2H), 2.61 (t, J=7.5 Hz, 2H), 1.94 (p, J=7.3 Hz, 2H), 1.50 (d, J=6.1 Hz, 6H).

Example 52: N-(3-(1H-imidazol-2-yl)propyl)-3-(4-fluorophenyl)-2-(2H-1,2,3-triazol-2-yl)quinoxaline 6-carboxamide (I-330)

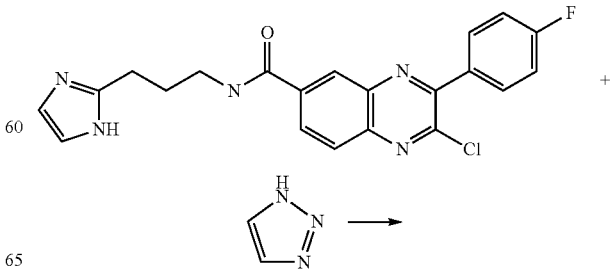

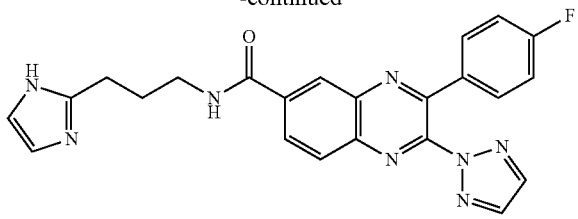

To a 2-dram vial pre-weighted with 1H-1,2,3-triazole (0.0252 g, 0.366 mmol) was added 2-chloro-3-(4-fluorophenyl)-N-[3-(1H-imidazol-2-yl)propyl]quinoxaline-6-carboxamide (0.0500 g, 0.122 mmol, prepared according to Example 29, step 1), cesium carbonate (0.119 g, 0.366 mmol) and DMF (1.00 mL). The mixture was shaken at rt for 4 h. Solvent was then evaporated. The residue was dissolved in DMSO (1.2 mL). After filtration, it was purified by prep-HPLC to give N-(3-(1H-imidazol-2-yl)propyl)-3-(4-fluorophenyl)-2-(2H-1,2,3-triazol-2-yl)quinoxaline-6-carboxamide (0.012 g, 22%). LCMS (ESI+): m/z=443 (M+H). 1H NMR (400 MHz, Methanol-$d_4$) δ 8.69 (d, J=1.6 Hz, 1H), 8.47 (s, 1H), 8.33 (dd, J=8.8, 1.9 Hz, 1H), 8.24 (d, J=8.8 Hz, 1H), 8.03 (s, 2H), 7.47-7.32 (m, 2H), 7.24 (s, 2H), 7.13 (t, J=8.8 Hz, 2H), 3.56 (t, J=6.7 Hz, 2H), 3.02 (t, J=7.6 Hz, 2H), 2.27-2.03 (m, 2H).

The compounds listed in the table below were prepared in an analogous fashion to that described in Example 52 starting from the appropriate starting materials:

| Starting Material | Compound No. or Name | LCMS Data |
|---|---|---|
| (pyrazole) | I-503 | LCMS (ESI+, FA): m/z = 456.4 (M + H) |
| (azaindole) | I-389 | LCMS (ESI+, FA): m/z = 492.4 (M + H) |
| (indazole) | I-305 | LCMS (ESI+, FA): m/z = 492.4 (M + H) |
| (benzimidazole) | I-453 | LCMS (ESI+, FA): m/z = 492.4 (M + H) |
| (imidazole) | I-324 | LCMS (ESI+, FA): m/z = 442.4 (M + H) |
| (triazole) | I-374 | LCMS (ESI+, FA): m/z = 443.3 (M + H) |
| (methylimidazole) | I-413 | LCMS (ESI+, FA): m/z = 456.4 (M + H) |
| (triazole) | I-418 | LCMS (ESI+, FA): m/z = 443.3 (M + H) |
| (dimethylpyrazole) | I-428 | LCMS (ESI+, FA): m/z = 470.4 (M + H) |
| (pyrazole) | I-434 | LCMS (ESI+, FA): m/z = 442.4 (M + H) |

Example 53: 3-(4-fluorophenyl)-2-isopropoxy-N-[3-(4H-1,2,4-triazol-3-yl)propyl]quinoxaline-6-carboxamide (I-310)

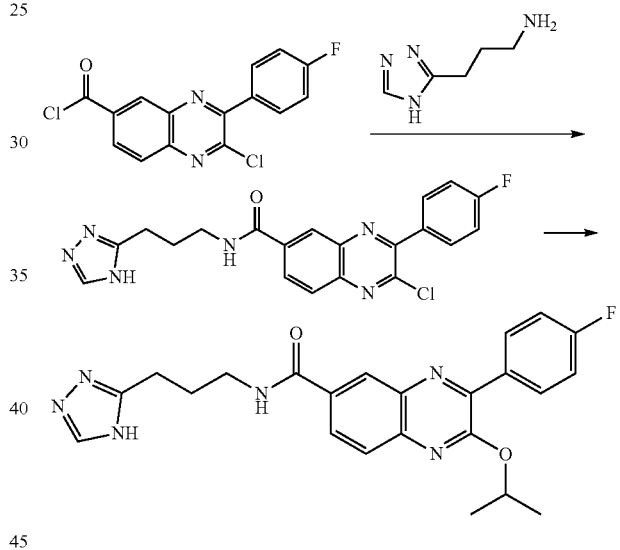

Step 1: 2-Chloro-3-(4-fluorophenyl)-N-[3-(4H-1,2,4-triazol-3-yl)propyl]quinoxaline-6-carboxamide To a suspension of 2-chloro-3-(4-fluorophenyl)quinoxaline-6-carbonyl chloride (397 mg, 1.23 mmol, prepared using analogous procedure as described in Example 23, Step 1) in DMA (6.00 mL, 64.5 mmol) was added 3-(4H-1,2,4-triazol-3-yl)propan-1-amine (208 mg, 1.48 mmol) and TEA (0.860 mL, 6.17 mmol). The resulting orange mixture was stirred at rt. After 4 h the mixture was distributed between NaHCO$_3$(aq) saturated solution and EtOAc. The aqueous layer was extracted with EtOAc. The combined organic layer was washed with water (×5) and brine, dried, and concentrated. The crude mixture was purified on a 40 g silica gel column (continuous gradient 0-15% MeOH/CH$_2$Cl$_2$) to provide 2-chloro-3-(4-fluorophenyl)-N-[3-(4H-1,2,4-triazol-3-yl)propyl]quinoxaline-6-carboxamide (338 mg, 0.823 mmol, 66.6%) LCMS (ESI+): m/z=411.1 (M+H). 1H NMR (400 MHz, CD3OD) δ 8.60 (d, J=1.5 Hz, 1H), 8.29 (dd, J=8.8, 2.0 Hz, 1H), 8.13 (d, J=8.8 Hz, 1H), 8.04-7.88

(m, 3H), 7.33 (t, J=8.8 Hz, 2H), 3.54 (t, J=6.9 Hz, 2H), 2.90 (m, 2H), 2.13 (p, J=7.1 Hz, 2H).

Step 2: 3-(4-Fluorophenyl)-2-isopropoxy-N-[3-(4H-1,2,4-triazol-3-yl)propyl]quinoxaline-6-carboxamide (I-310)

A vial was charged with NaH 60% in mineral oil (13.6 mg, 0.341 mmol). To the vial was added N-methylpyrrolidinone (1.00 mL, 10.4 mmol) and isopropanol (196 µL, 2.56 mmol). The mixture was stirred at rt for 5 min (gas generation observed, the mixture turned purple) under nitrogen. To the mixture was added 2-chloro-3-(4-fluorophenyl)-N-[3-(4H-1,2,4-triazol-3-yl)propyl]quinoxaline-6-carboxamide (70.0 mg, 0.170 mmol). The resulting orange solution was stirred at rt. LCMS showed complete conversion. The mixture was distributed between water and EtOAc. The aqueous layer was extracted with EtOAc. The combined organic layer was washed with brine, dried, and concentrated. The crude mixture was purified on a 24 g silica gel column (continuous gradient 0-15% MeOH/$CH_2Cl_2$ over 25 min) to provide 3-(4-fluorophenyl)-2-isopropoxy-N-[3-(4H-1,2,4-triazol-3-yl)propyl]quinoxaline-6-carboxamide (74.0 mg, 0.127 mmol, 74.3%) as a white solid. LCMS (ESI+): m/z=435.2 (M+H). 1H NMR (400 MHz, CD3OD) δ 8.50 (d, J=1.7 Hz, 1H), 8.22 (dd, J=8.7, 5.6 Hz, 2H), 8.13 (dd, J=8.6, 1.8 Hz, 1H), 7.90 (d, J=8.7 Hz, 1H), 7.27 (t, J=8.8 Hz, 2H), 5.70 (hept, J=6.2 Hz, 1H), 3.54 (t, J=6.8 Hz, 2H), 2.93 (d, J=7.3 Hz, 2H), 2.13 (p, J=7.1 Hz, 2H), 1.51 (d, J=6.2 Hz, 6H).

The compounds listed in the table below were prepared in an analogous fashion to that described in Example 53 starting from the appropriate starting materials:

| Starting Material Step 2 | Compound No. or Name | LCMS Data |
|---|---|---|
| HO∼∼ | I-358 | LCMS (ESI+, FA): m/z = 435.2 (M + H) |

Example 54: 3-(4-Fluorophenyl)-N-(imidazo[1,2-a]pyridin-6-ylmethyl)-2-isopropoxyquinoxaline-6-carboxamide (I-452)

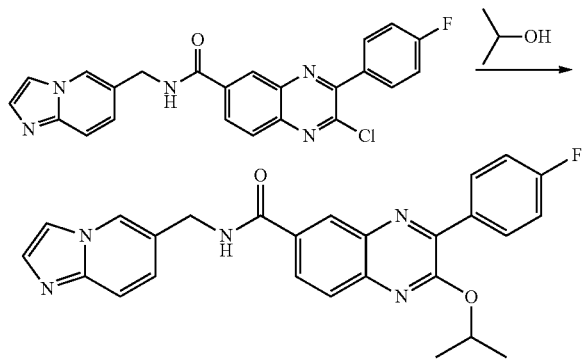

To a round bottomed flask was added sodium hydride (60:40 sodium hydride:mineral oil, 0.0139 g, 0.347 mmol) followed by isopropyl alcohol (0.160 mL, 2.08 mmol) and N-methylpyrrolidinone (1.19 mL, 12.3 mmol). The mixture was stirred at rt for 10 min, then 2-chloro-3-(4-fluorophenyl)-N-(imidazo[1,2-a]pyridin-6-ylmethyl)quinoxaline-6-carboxamide (0.0750 g, 0.174 mmol; prepared in example 40, step 1) was added. The resulting solution was stirred at rt for 30 min. The reaction mixture was poured into EtOAc and water. The layers were separated and the aqueous layer was extracted two more times with EtOAc. The combined organic layer was dried over anhydrous $MgSO_4$ and purified by silica gel chromatography to give 3-(4-fluorophenyl)-N-(imidazo[1,2-a]pyridin-6-ylmethyl)-2-isopropoxyquinoxaline-6-carboxamide (0.056 g, 71%) as a white solid. LCMS (ESI+): m/z=456.2 (M+H). 1H NMR (400 MHz, Methanol-d4) δ 8.55 (d, J=1.9 Hz, 1H), 8.51 (s, 1H), 8.26-8.14 (m, 3H), 7.91 (d, J=8.7 Hz, 1H), 7.86 (s, 1H), 7.61-7.53 (m, 2H), 7.42 (dd, J=9.3, 1.6 Hz, 1H), 7.27 (t, J=8.9 Hz, 2H), 5.70 (hept, J=6.2 Hz, 1H), 4.68 (s, 2H), 1.50 (d, J=6.2 Hz, 6H).

Example 55: 3-(4-Fluorophenyl)-N-(imidazo[1,2-a]pyrimidin-2-ylmethyl)-2-isopropoxyquinoxaline-6-carboxamide (I-506)

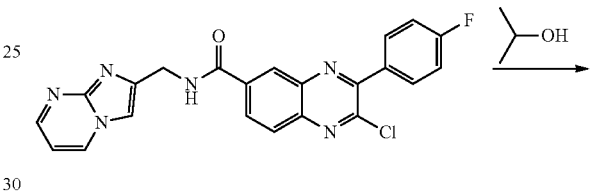

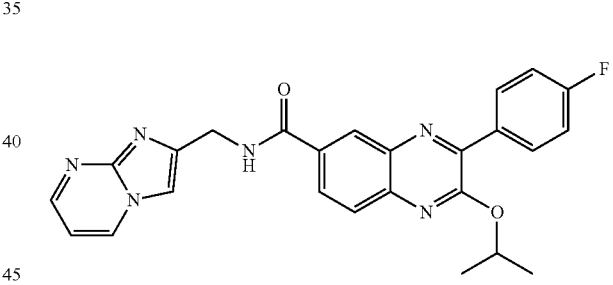

To a round bottomed flask was added sodium hydride (60:40 sodium hydride:mineral oil, 0.0139 g, 0.347 mmol) followed by isopropyl alcohol (0.160 mL, 2.08 mmol) and N-methylpyrrolidinone (1.19 mL, 12.3 mmol). The mixture was stirred at rt for 10 min, then 2-chloro-3-(4-fluorophenyl)-N-(imidazo[1,2-a]pyrimidin-2-ylmethyl)quinoxaline-6-carboxamide (0.0752 g, 0.174 mmol; prepared in Example 36, step 1) was added. The resulting solution was stirred at rt for 30 min. The reaction mixture was poured into EtOAc and water. The layers were separated and the aqueous layer was extracted two more times with EtOAc. The combined organic layer was dried over anhydrous $MgSO_4$ and purified by prep HPLC to give 3-(4-fluorophenyl)-N-(imidazo[1,2-a]pyrimidin-2-ylmethyl)-2-isopropoxyquinoxaline-6-carboxamide (0.032 g, 40%) as a white solid. LCMS (ESI+): m/z=457.2 (M+H). 1H NMR (400 MHz, Methanol-$d_4$) δ 8.90-8.80 (m, 1H), 8.63-8.52 (m, 2H), 8.29-8.14 (m, 3H), 7.92 (d, J=8.7 Hz, 1H), 7.84 (s, 1H), 7.27 (t, J=8.8 Hz, 2H), 7.06 (dd, J=6.7, 4.2 Hz, 1H), 5.70 (hept, J=6.2 Hz, 1H), 4.84 (s, 2H), 1.51 (d, J=6.2 Hz, 6H).

Example 56: 3-(4-Fluorophenyl)-N-[3-(1H-imidazol-2-yl)propyl]-2-(isopropylsulfanyl)quinoxaline-6-carboxamide (I-375)

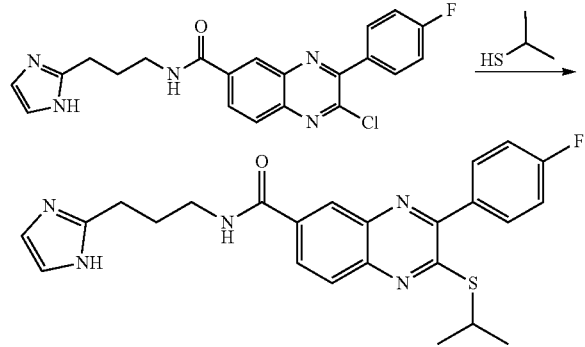

To a solution of 2-propanethiol (40.8 uL, 0.439 mmol) in THF (1.07 mL, 13.2 mmol) was added 1 M potassium tert-butoxide in THF (0.366 mL, 0.366 mmol). The mixture was stirred at rt for 30 min then added 2-chloro-3-(4-fluorophenyl)-N-[3-(1H-imidazol-2-yl)propyl]quinoxaline-6-carboxamide (60.0 mg, 0.146 mmol, prepared as described in Example 29, Step 1), and the mixture was stirred at rt for another 1 h. The mixture was distributed between water and EtOAc. The aqueous layer was extracted with EtOAc. The combined organic layer was washed with brine, dried, and concentrated. The crude mixture was purified by silica gel chromatography to give 3-(4-fluorophenyl)-N-[3-(1H-imidazol-2-yl)propyl]-2-(isopropylsulfanyl)quinoxaline-6-carboxamide (30 mg, 50%) as white solid. LCMS (ESI+): m/z=450.2 (M+H). 1H NMR (400 MHz, Chloroform-d) δ 8.60-8.48 (m, 2H), 8.21 (dd, J=8.7, 1.8 Hz, 1H), 7.94 (d, J=8.7 Hz, 1H), 7.77 (dd, J=8.7, 5.4 Hz, 2H), 7.20 (t, J=8.6 Hz, 2H), 7.04 (s, 2H), 4.20 (h, J=6.9 Hz, 1H), 3.59 (d, J=5.5 Hz, 2H), 3.13-3.02 (m, 2H), 2.13 (s, 2H), 1.47 (d, J=6.8 Hz, 6H).

Example 57: 3-(4-Fluorophenyl)-2-isopropoxy-N-[3-(1H-pyrazol-4-yl)propyl]quinoxaline-6-carboxamide (I-380)

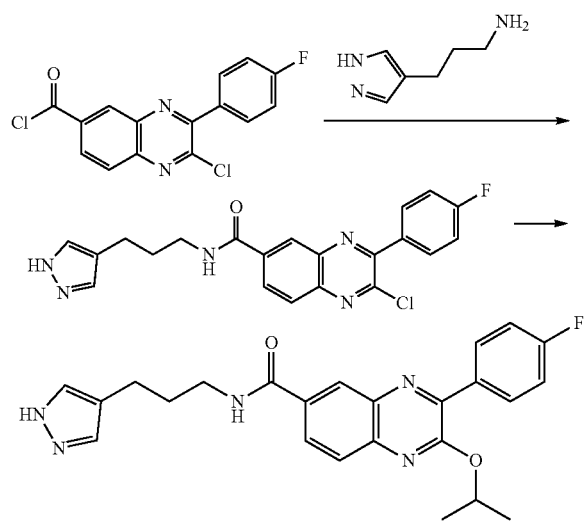

Step 1: 2-Chloro-3-(4-fluorophenyl)-N-[3-(1H-pyrazol-4-yl)propyl]quinoxaline-6-carboxamide To a suspension of 2-chloro-3-(4-fluorophenyl)quinoxaline-6-carbonyl chloride (537 mg, 1.67 mmol, prepared using analogous procedure as described in Example 23, Step 1) in DMA (15.0 mL, 161 mmol) was added 3-(1H-pyrazol-4-yl)-propylamine (251 mg, 2.00 mmol) and TEA (1.16 mL, 8.36 mmol). The resulting orange solution was stirred at rt. In 1 h, the mixture was distributed between NaHCO$_3$(aq) saturated solution and EtOAc. The aqueous layer was extracted with EtOAc. The combined organic layer was washed with water (×5) and brine, dried, and concentrated. The crude mixture was purified on a 40 g silica gel column (continuous gradient 0-10% MeOH/CH$_2$Cl$_2$) to provide 2-chloro-3-(4-fluorophenyl)-N-[3-(1H-pyrazol-4-yl)propyl]quinoxaline-6-carboxamide (685 mg, 1.24 mmol, 74.3%) as a white solid. LCMS (ESI+): m/z=410.1 (M+H). 1H NMR (400 MHz, DMSO-d6) δ 12.52 (s, 1H), 8.91 (t, J=5.5 Hz, 1H), 8.67 (d, J=1.6 Hz, 1H), 8.33 (dd, J=8.7, 1.9 Hz, 1H), 8.17 (d, J=8.7 Hz, 1H), 7.95 (dd, J=8.8, 5.5 Hz, 2H), 7.55 (s, 1H), 7.44 (t, J=8.9 Hz, 2H), 7.36 (s, 1H), 3.37 (q, J=6.6 Hz, 2H), 2.51 (m, 2H), 1.83 (p, J=7.3 Hz, 2H).

Step 2: 3-(4-Fluorophenyl)-2-isopropoxy-N-[3-(1H-pyrazol-4-yl)propyl]quinoxaline-6-carboxamide (I-380)

A vial was charged with NaH 60% in mineral oil (11.7 mg, 0.293 mmol). To the vial was added N-methylpyrrolidinone (1.00 mL, 10.4 mmol) and isopropanol (134 uL, 1.76 mmol). The mixture was stirred at rt for 5 min (gas generation observed, the mixture turned purple) under nitrogen. To the mixture was added 2-chloro-3-(4-fluorophenyl)-N-[3-(1H-pyrazol-4-yl)propyl]quinoxaline-6-carboxamide (60.0 mg, 0.146 mmol). The resulting orange solution was stirred at rt for 1 h. The mixture was distributed between water and EtOAc. The aqueous layer was extracted with EtOAc. The combined organic layer was washed with brine, dried, and concentrated. The crude mixture was purified on a 24 g silica gel column (continuous gradient 0-15% MeOH/CH$_2$Cl$_2$ over 25 min) to provide 3-(4-fluorophenyl)-2-isopropoxy-N-[3-(1H-pyrazol-4-yl)propyl]quinoxaline-6-carboxamide (63.5 mg, 0.0969 mmol, 66.2%) as a white solid. LCMS (ESI+): m/z=434.2 (M+H). 1H NMR (400 MHz, CD$_3$OD) δ 8.36 (d, J=1.7 Hz, 1H), 8.15-8.05 (m, 2H), 8.00 (dd, J=8.7, 2.0 Hz, 1H), 7.78 (d, J=8.7 Hz, 1H), 7.39 (s, 2H), 7.24-7.08 (m, 2H), 5.57 (hept, J=6.2 Hz, 1H), 3.38 (t, J=7.1 Hz, 2H), 2.54 (t, J=7.5 Hz, 2H), 1.86 (h, J=7.4 Hz, 2H), 1.38 (d, J=6.2 Hz, 6H).

Example 58: 3-(4-Fluorophenyl)-N-[3-(1H-imidazol-4-yl)propyl]-2-isopropoxyquinoxaline-6-carboxamide (I-482)

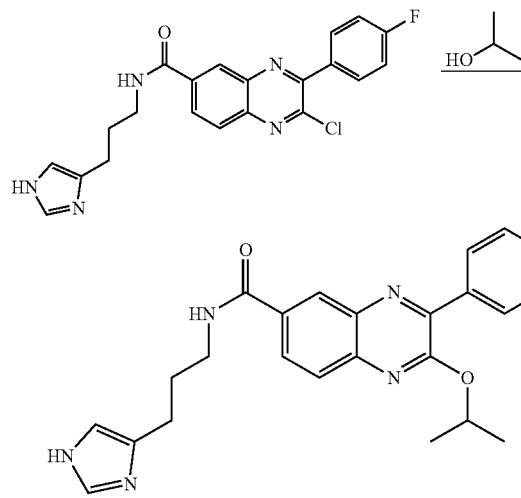

To an ice cold suspension of NaH 60% in mineral oil (18.0 mg, 0.450 mmol) in N-methylpyrrolidinone (0.967 mL, 10.0 mmol) was added isopropyl alcohol (54.2 uL, 0.708 mmol). The mixture was stirred at rt for 10-15 min. 2-Chloro-3-(4-fluorophenyl)-N-[3-(1H-imidazol-4-yl)propyl]quinoxaline-6-carboxamide (58.0 mg, 0.142 mmol, prepared as described in Example 34, Step 1) was added. The resulting dark solution was stirred at rt for 1 h. The reaction mixture was distributed between water and EtOAc. The aqueous layer was extracted with EtOAc. The combined organic layers were washed with brine, dried, and concentrated. The crude product was purified by silica gel chromatography to give 3-(4-fluorophenyl)-N-[3-(1H-imidazol-4-yl)propyl]-2-isopropoxyquinoxaline-6-carboxamide (33.4 mg; 54.4%). LCMS (ESI+): m/z=434.2 (M+H). 1H NMR (400 MHz, DMSO-d6) δ 11.83 (s, 1H), 8.84 (s, 1H), 8.58 (d, J=1.8 Hz, 1H), 8.23-8.15 (m, 3H), 7.90 (d, J=8.7 Hz, 1H), 7.52 (s, 1H), 7.40 (t, J=8.9 Hz, 2H), 5.59 (h, J=6.2 Hz, 1H), 3.43-3.34 (m, 3H), 2.59 (m, 2H), 1.88 (m, J=7.3 Hz, 2H), 1.45 (d, J=6.2 Hz, 6H).

Example 59: 2-(4-Fluorophenyl)-N-[3-(1H-imidazol-2-yl)propyl]-3-(2-thienyl)quinoxaline-6-carboxamide (I-340)

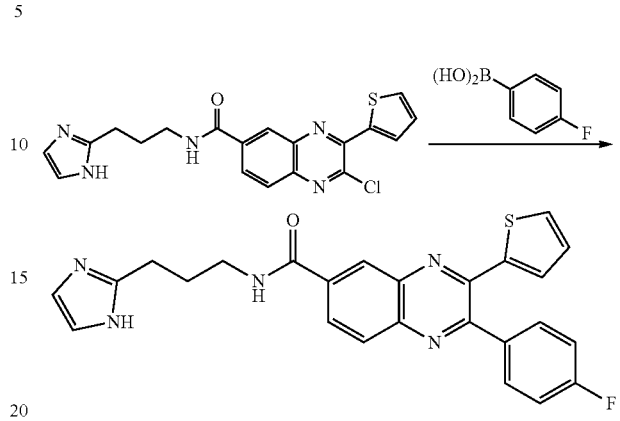

A mixture of 2-chloro-N-[3-(1H-imidazol-2-yl)propyl]-3-(2-thienyl)quinoxaline-6-carboxamide (112 mg, 0.281 mmol) (listed in Example 29; prepared from 2-oxo-3-(thiophen-2-yl)-1,2-dihydroquinoxaline-6-carboxylic acid similarly to Example 27, steps 6 and 7), 4-fluorobenzeneboronic acid (43.3 mg, 0.310 mmol), potassium carbonate (77.8 mg, 0.563 mmol) and tetrakis(triphenylphosphine)palladium(0) (16 mg, 0.014 mol) in dioxane (4.5 mL) and water (2.2 mL) was degassed with argon and heated at 80° C. for 5 h. After cooling, the reaction was concentrated in vacuo and the residue was purified by HPLC to give 2-(4-fluorophenyl)-N-[3-(1H-imidazol-2-yl)propyl]-3-(2-thienyl)quinoxaline-6-carboxamide (35 mg, 27%). LCMS (ESI+): m/z=458.1 (M+H). 1H NMR (400 MHz, DMSO-d6) δ 9.13 (t, J=5.2 Hz, 1H), 8.65 (d, J=1.6 Hz, 1H), 8.25 (dd, J=8.4, 1.6 Hz, 1H), 8.19 (s, 1H), 8.16 (d, J=8.4 Hz, 1H), 7.77 (dd, J=8.4, 1.2 Hz, 1H), 7.73-7.69 (m, 2H), 7.39 (t, J=8.8 Hz, 2H), 7.02 (dd, J=4.8, 3.6 Hz, 1H), 6.91 (s, 2H), 6.71 (dd, J=2.8, 1.2 Hz, 1H), 3.44-3.39 (m, 2H), 2.76-.272 (m, 2H), 2.01-1.95 (m, 2H).

The compounds listed in the table below were prepared in an analogous fashion to that described in Example 59 starting from the appropriate starting materials:

| Starting Material 1 | Starting Material 2 | Compound No. or Name | LCMS Data |
|---|---|---|---|
| 2-chloro-N-[3-(1H-imidazol-2-yl)propyl]-3-(2-thienyl)quinoxaline-6-carboxamide | (HO)₂B-phenyl | I-477 | LCMS (ESI+, FA): m/z = 440.2 (M + H) |
| 2-chloro-N-[3-(1H-imidazol-2-yl)propyl]-3-(4-fluorophenyl)quinoxaline-6-carboxamide | (HO)₂B-(5-chlorothiophen-2-yl) | I-483* | LCMS (ES+, FA): m/z = 458.8 (M + H) |

*SiliaCat DPP-Pd and Cs₂CO₃ used in Step 2

Example 60: 3-(4-fluorophenyl)-2-(piperidin-1-yl)-N-[3-(pyrazin-2-yl)propyl]quinoxaline-6-carboxamide (I-441)

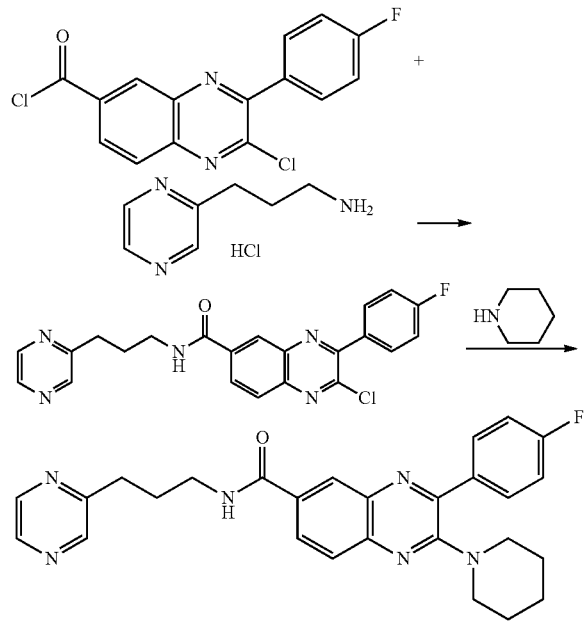

Step 1: 2-Chloro-3-(4-fluorophenyl)-N-[3-(pyrazin-2-yl)propyl]quinoxaline-6-carboxamide To a suspension of 2-chloro-3-(4-fluorophenyl)quinoxaline-6-carbonyl chloride (0.250 g, 0.778 mmol, prepared using analogous procedure as described in Example 23, Step 1) and 3-(pyrazin-2-yl)propan-1-amine hydrochloride (162 mg, 0.934 mmol) in DMA (17 mL) was added TEA (0.542 mL, 3.89 mmol. The resulting clear solution was stirred at rt overnight. The reaction mixture was diluted with sat-.NaHCO$_3$. A precipitate was formed, which was filtered and dried to give 2-chloro-3-(4-fluorophenyl)-N-[3-(pyrazin-2-yl)propyl]quinoxaline-6-carboxamide (266 mg, 81%). LCMS (ESI+): m/z=422.1 (M+H). 1H NMR (400 MHz, DMSO-d$_6$) δ 8.96 (m, 1H), 8.66 (d, J=1.6 Hz, 1H), 8.61 (s, 1H), 8.56 (m, 1H), 8.47 (d, J=2.5 Hz, 1H), 8.32 (dd, J=8.7, 1.8 Hz, 1H), 8.17 (d, J=8.7 Hz, 1H), 7.95 (m, 2H), 7.44 (m, 2H), 3.41 (m, 2H), 2.89 (m, 2H), 2.03 (m, 2H).

Step 2: 3-(4-Fluorophenyl)-2-(piperidin-1-yl)-N-[3-(pyrazin-2-yl)propyl]quinoxaline-6-carboxamide A mixture of 2-chloro-3-(4-fluorophenyl)-N-[3-(pyrazin-2-yl)propyl]quinoxaline-6-carboxamide (100 mg, 0.2 mmol), piperidine (117 uL, 1.18 mmol), DIPEA (124 uL, 0.711 mmol) in N-methylpyrrolidinone (1.6 mL) in a vial was heated at 170° C. in the microwave for 30 min. The reaction was distributed between water and EtOAc. The aqueous layer was extracted with EtOAc (×2). The combined organic layer was washed with brine, dried and concentrated. The crude material was purified by silica gel chromatography using 0-10% MeOH/CH$_2$Cl$_2$ gave 3-(4-fluorophenyl)-2-(piperidin-1-yl)-N-[3-(pyrazin-2-yl)propyl] quinoxaline-6-carboxamide (70 mg, 60%). LCMS (ESI+): m/z=471.2 (M+H). 1H NMR (400 MHz, DMSO-d$_6$) δ 8.74 (m, 1H), 8.61 (m, 1H), 8.56 (m, 1H), 8.47 (m, 2H), 8.10 (dd, J=8.7, 1.9 Hz, 1H), 8.05 (m, 2H), 7.79 (d, J=8.7 Hz, 1H), 7.40 (m, 2H), 3.38 (m, 2H), 3.23 (m, 4H), 2.88 (m, 2H), 2.01 (m, 2H), 1.55 (m, 6H).

Example 61: N-[3-(6-aminopyridin-3-yl)propyl]-3-(4-fluorophenyl)-2-(morpholin-4-yl)quinoxaline-6-carboxamide (I-362)

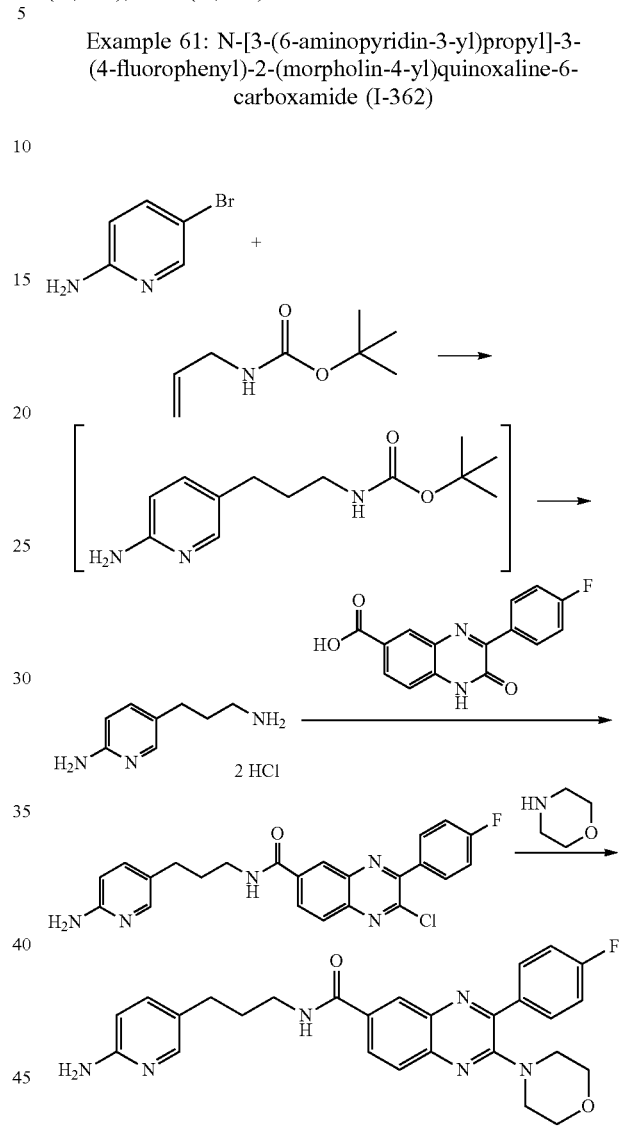

Step 1: 5-(3-Aminopropyl)pyridin-2-amine.2[HCl]

3-N-t-Butoxycarbonylamino-1-propene (4.67 g, 29.7 mmol) was dissolved in anhydrous THF (50 mL), cooled with an ice bath. 0.5 M of 9-BBN in THF (57.0 mL, 28.5 mmol) was added dropwise. The mixture was stirred under nitrogen atmosphere with cooling then brought to rt overnight. A second portion of 0.5 M of 9-BBN in THF (57.0 mL, 28.5 mmol) was added and the solution was stirred at rt for 3.5 h. 2.0 M of sodium hydroxide in water (39.3 mL, 78.5 mmol) was added and the mixture was stirred at rt for 2 h. The resulted boronic acid solution was degassed by evacuation and flushed with nitrogen 3 times. A solution of 2-amino-5-bromopyridine (2.50 g, 14.4 mmol) and tetrakis (triphenylphosphine)palladium(0) (760 mg, 0.657 mmol) in anhydrous THF (20 mL) was degassed and added to the boronic acid solution obtained above. The mixture was degassed two more times, then heated under nitrogen atmosphere to 80° C. for 20 h. The reaction mixture was cooled to rt and evaporated in vacuo. The aqueous residue was extracted with EtOAc, washed with water (3×) then brine, dried over anhydrous $Na_2SO_4$, filtered and evaporated in vacuo to give a crude residue. The resulting residue was purified by silica gel chromatography using MeOH/EtOAc (0/100 to 5/95) to afford a foamy solid intermediate. The intermediate tert-butyl [3-(6-aminopyridin-3-yl)propyl]carbamate (3.36 g) was dissolved in THF (30 mL). 4 M of hydrochloric acid in 1,4-dioxane (10.0 mL, 39.2 mmol) was added. The resulting solution was stirred at rt for 3 days. The reaction mixture was filtered and the solid was washed with EtOAc then hexane, dried in air then in vacuum to give a solid product (2.45 g). 1H NMR (400 MHz, MeOD) δ 7.93 (dd, J=9.2, 1.9 Hz, 1H), 7.77 (s, 1H), 7.04 (d, J=9.2 Hz, 1H), 3.00 (t, J=7.6 Hz, 2H), 2.73-2.64 (m, 2H), 2.03-1.92 (m, 2H).

Step 2: N-[3-(6-Aminopyridin-3-yl)propyl]-2-chloro-3-(4-fluorophenyl)quinoxaline-6-carboxamide To a suspension of 3-(4-fluorophenyl)-2-oxo-1,2-dihydroquinoxaline-6-carboxylic acid (1.14 g, 4.00 mmol, prepared as described in Example 27, Step 5) in thionyl chloride (12 mL, 160 mmol) at rt was added ~5 drops of DMF. The mixture was stirred at reflux under a nitrogen atmosphere for 1 h, then cooled to rt. The resulting white suspension was evaporated in vacuo, then azeotroped with anhydrous toluene to give a solid intermediate. To the solid intermediate was added DMA (25 mL), DIPEA (3.62 mL, 20.8 mmol), and 5-(3-aminopropyl)pyridin-2-amine.2[HCl] (1.16 g, 5.20 mmol). The mixture was stirred at rt for 17 h. The mixture was evaporated in vacuo and azeotroped with toluene (~50 mL). The liquid residue was diluted with EtOAc and water. The organic layer was washed with water (3×) then brine, dried over anhydrous $Na_2SO_4$, and filtered. The filtrate was concentrated in vacuo and purified on a 120 g silica column with 2-10% MeOH in DCM to afford N-[3-(6-aminopyridin-3-yl)propyl]-2-chloro-3-(4-fluorophenyl)quinoxaline-6-carboxamide as a solid. (0.847 g, 47%). LCMS (ESI+): m/z=436.1. 1H NMR (400 MHz, MeOD) δ 8.57 (d, J=1.5 Hz, 1H), 8.26 (dd, J=8.8, 1.8 Hz, 1H), 8.12 (d, J=8.8 Hz, 1H), 7.97 (dd, J=8.8, 5.4 Hz, 2H), 7.79 (s, 1H), 7.44 (dd, J=8.5, 2.2 Hz, 1H), 7.32 (t, J=8.8 Hz, 2H), 6.58 (d, J=8.5 Hz, 1H), 3.50 (t, J=7.1 Hz, 2H), 2.62 (t, J=7.6 Hz, 2H), 2.00-1.90 (m, 2H).

Step 3: N-[3-(6-Aminopyridin-3-yl)propyl]-3-(4-fluorophenyl)-2-(morpholin-4-yl)quinoxaline-6-carboxamide (I-362)

The mixture of N-[3-(6-aminopyridin-3-yl)propyl]-2-chloro-3-(4-fluorophenyl)quinoxaline-6-carboxamide (0.100 g, 0.229 mmol) and morpholine (0.100 mL, 1.15 mmol) in DMA (3.0 mL) was heated to 160° C. in microwave for 30 min, then cooled to rt. The reaction mixture was directly purified on an 80 g silica column using MeOH/DCM (0/100 to 10/90) to afford N-[3-(6-aminopyridin-3-yl)propyl]-3-(4-fluorophenyl)-2-(morpholin-4-yl)quinoxaline-6-carboxamide as a solid (0.101 g, 89%). LCMS (ESI+): m/z=487.2. 1H NMR (400 MHz, MeOD) δ 8.38 (d, J=1.7 Hz, 1H), 8.09-8.03 (m, 3H), 7.86 (d, J=8.7 Hz, 1H), 7.79 (d, J=1.5 Hz, 1H), 7.42 (dd, J=8.5, 2.3 Hz, 1H), 7.30 (t, J=8.8 Hz, 2H), 6.57 (d, J=8.5 Hz, 1H), 3.76-3.68 (m, 4H), 3.47 (t, J=7.1 Hz, 2H), 3.35-3.27 (m, 4H), 2.60 (t, J=7.6 Hz, 2H), 1.92 (dd, J=15.6, 6.4 Hz, 2H).

The compounds listed in the table below were prepared in an analogous fashion to that described in Example 61 starting from the appropriate starting materials:

| Starting Material Step 3 | Compound No. or Name | LCMS Data |
|---|---|---|
| ![morpholine structure] | I-485 | LCMS (ESI+, FA): m/z = 515.2 (M + H) |
| ![piperidine structure] | I-436 | LCMS (ESI+, FA): m/z = 485.2 (M + H) |

Example 62: 3-(4-fluorophenyl)-2-isopropoxy-N-[2-(1-methyl-1H-imidazol-5-yl)ethyl]quinoxaline-6-carboxamide (I-424)

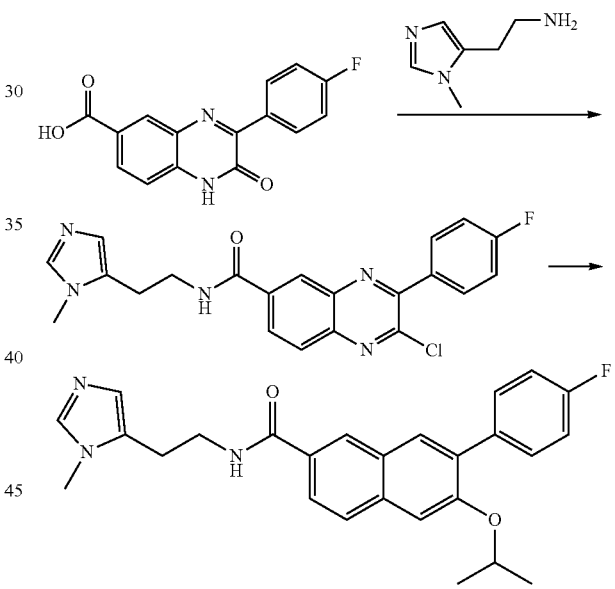

Step 1: 2-Chloro-3-(4-fluorophenyl)-N-[2-(1-methyl-1H-imidazol-5-yl)ethyl]quinoxaline-6-carboxamide Into a suspension of 3-(4-fluorophenyl)-2-oxo-1,2-dihydroquinoxaline-6-carboxylic acid (0.300 g, 1.06 mmol, prepared as described in Example 27, Step 5) in thionyl chloride (7.92 mL, 108 mmol) was added ~5 drops of DMF at rt. The mixture was then stirred at reflux for 1 h until the solid was completely dissolved. The reaction was cooled and concentrated. The residue was azeotroped with toluene and dried under high vacuum. Into a suspension of 2-chloro-3-(4-fluorophenyl)quinoxaline-6-carbonyl chloride in DMA (7.8 mL, 83 mmol) was added 3-methylhistamine dihydrochloride (0.100 g, 0.505 mmol) and TEA (0.736 mL, 5.28 mmol). The mixture was stirred at rt overnight. The reaction mixture was quenched with saturated Na₂HCO₃ and extracted into EtOAc. The organic layer was washed with water and brine, dried over Na₂SO₄, filtered and concentrated. The residue was purified by silica gel chromatography to afford 2-chloro-3-(4-fluorophenyl)-N-[2-(1-methyl-1H-imidazol-5-yl)ethyl]quinoxaline-6-carboxamide (41 mg, 20%) as a brown solid. LCMS (ESI=): m/z=410.1 (M+H). 1H NMR (400 MHz, Methanol-d4) δ 8.55 (d, J=1.5 Hz, 1H), 8.24 (dd, J=8.8, 1.9 Hz, 1H), 8.12 (d, J 8.8 Hz, 1H), 8.00-7.92 (m, 2H), 7.79 (s, 1H), 7.36-7.28 (m, 2H), 6.94 (s, 1H), 3.77 (s, 3H), 3.73 (t, J=7.1 Hz, 2H), 3.03 (t, J=7.0 Hz, 2H).

Step 2: 3-(4-Fluorophenyl)-2-isopropoxy-N-[2-(1-methyl-1H-imidazol-5-yl)ethyl]quinoxaline-6-carboxamide.CH₂O₂ (I-424)

Into a suspension of NaH (60% in mineral oil, 9.7 mg, 0.24 mmol) in N-methylpyrrolidinone (0.500 mL, 5.18 mmol) was added isopropyl alcohol (0.0919 mL, 1.20 mmol) dropwise. The mixture was stirred at rt for 15 min then added dropwise into a solution of 2-chloro-3-(4-fluorophenyl)-N-[2-(1-methyl-1H-imidazol-5-yl)ethyl]quinoxaline-6-carboxamide (0.041 g, 0.10 mmol) in N-methylpyrrolidinone (1.00 mL, 10.4 mmol). The resulting brown solution was stirred at rt for 1 h. The mixture was diluted with water and EtOAc and the aqueous layer was extracted again with EtOAc. The combined organic layer was washed with water and brine, dried over Na₂SO₄, filtered and concentrated in vacuo. The residue was purified by HPLC to give 3-(4-fluorophenyl)-2-isopropoxy-N-[2-(1-methyl-1H-imidazol-5-yl)ethyl]quinoxaline-6-carboxamide (18 mg, 38%, isolated as formic acid salt) as a white solid. LCMS (ESI+): m/z=434.2 (M+H). 1H NMR (400 MHz, DMSO-d6) δ 8.92 (t, J=5.5 Hz, 1H), 8.55 (d, J=1.8 Hz, 1H), 8.22-8.13 (m, 3H), 7.90 (d, J=8.6 Hz, 1H), 7.53 (s, 1H), 7.40 (t, J=8.9 Hz, 2H), 6.75 (s, 1H), 5.59 (p, J=6.2 Hz, 1H), 3.60 (s, 3H), 3.58-3.51 (m, 2H), 2.86 (t, J=7.2 Hz, 2H), 2.54-2.47 (m, 6H).

Example 63: 3-(4-fluorophenyl)-N-[3-(1H-imidazol-2-yl)propyl]-2-(tetrahydro-2H-pyran-4-yl)quinoxaline-6-carboxamide (I-366)

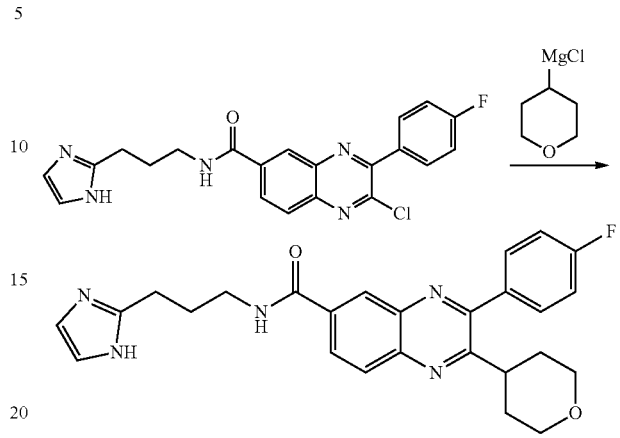

To a solution of 2-chloro-3-(4-fluorophenyl)-N-[3-(1H-imidazol-2-yl)propyl]quinoxaline-6-carboxamide (100 mg, 0.2 mmol, prepared according to Example 29, Step 1), acetylacetone iron (III) salt (8.4 mg, 0.024 mmol) in THF (2 mL, 30 mmol) at 0° C. was added 0.50 M of tetrahydropyran-4-ylmagnesium chloride in 2-methyltetrahydrofuran (2.4 mL, 1.2 mmol) dropwise. The mixture was stirred at rt overnight and then quenched with saturated NH₄Cl solution, and then extracted with EtOAc. The combined organic layer was washed with brine, dried, and concentrated. The crude mixture was purified by HPLC to give 3-(4-fluorophenyl)-N-[3-(1H-imidazol-2-yl)propyl]-2-(tetrahydro-2H-pyran-4-yl)quinoxaline-6-carboxamide (32 mg, 30%) as white solid. LCMS (ESI+): m/z=460.2 (M+H). 1H NMR (400 MHz, DMSO-d₆) δ 9.02 (t, J=5.4 Hz, 1H), 8.62 (d, J=1.8 Hz, 1H), 8.28 (dd, J=8.7, 1.9 Hz, 1H), 8.23-8.12 (m, 1H), 7.77 (dd, J=8.7, 5.5 Hz, 2H), 7.43 (t, J=8.9 Hz, 2H), 6.92 (s, 2H), 3.93 (dd, J=11.3, 3.2 Hz, 2H), 3.44-3.33 (m, 5H), 2.73 (t, J=7.5 Hz, 2H), 2.02-1.89 (m, 4H), 1.73 (d, J=11.1 Hz, 2H).

The compounds listed in the table below were prepared in an analogous fashion to that described in Example 63 starting from the appropriate starting materials:

| Starting Material 1 | Starting Material 2 | Compound No. | LCMS Data |
|---|---|---|---|
|  | MgCl (isopropyl) | I-444 | LCMS (ESI+, FA): m/z = 418.3 (M + H) |
|  | MgCl (ethyl) | I-307 | LCMS (ESI+, FA): m/z = 404.2 (M + H) |

| Starting Material 1 | Starting Material 2 | Compound No. | LCMS Data |
|---|---|---|---|
| (structure) | BrMg-cyclopropyl | I-357 | LCMS (ESI+, FA): m/z = 416.2 (M + H) |

Example 64: 3-(4-fluorophenyl)-N-[3-(1H-imidazol-2-yl)propyl]-2-(morpholin-4-ylmethyl)quinoxaline-6-carboxamide (I-405)

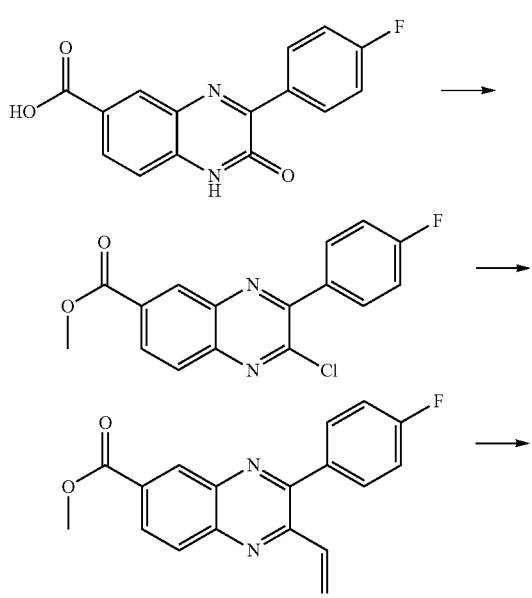

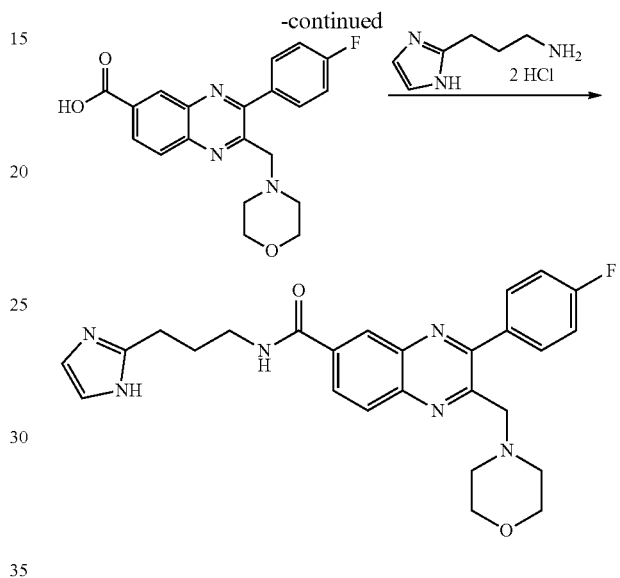

Step 1: Methyl 2-chloro-3-(4-fluorophenyl)quinoxaline-6-carboxylate 3-(4-fluorophenyl)-2-oxo-1,2-dihydroquinoxaline-6-carboxylic acid (11.0 g, 38.7 mmol, prepared as described in Example 27, Step 5) in Thionyl chloride (128 mL, 1760 mmol) (with 1 drop of DMF) was heated to reflux for 4 h. After cool to rt, remove all solvent under vacuum for 2 h. The solid was dissolved in Tetrahydrofuran (285 mL, 3520 mmol) and further added TEA (14.7 mL, 106 mmol) and Methanol (1.71 mL, 42.2 mmol). The mixture was stirred at RT for overnight. After evaporated all solvent, the residue was washed with 50 ml Ether, followed by 100 ml Hex and 20 ml water, the solid was dried under vacuum to get methyl 2-chloro-3-(4-fluorophenyl)quinoxaline-6-carboxylate as yellow solid (12.3 g, 100%) LCMS (ESI+): m/z=317.2 (M+H).

Step 2: Methyl 3-(4-fluorophenyl)-2-vinylquinoxaline-6-carboxylate

To a solution of methyl 2-chloro-3-(4-fluorophenyl)quinoxaline-6-carboxylate (500 mg, 2 mmol) in toluene (13.45 mL, 126.3 mmol) was added tributylethenylstannane (691.4 uL, 2.368 mmol) dropwise, and flushed with nitrogen for 10 min. Tetrakis(triphenylphosphine)palladium(0) (91.25 mg, 0.07897 mmol) was added and the reaction mixture was stirred at 85° C. overnight. After cooling, the reaction mixture was poured into EtOAc and water. The layers were separated and the aqueous layer was extracted two more times with EtOAc. The combined organic layer was dried over anhydrous MgSO$_4$ and concentrated in vacuo. The crude mixture was purified by silica gel chromatography to give methyl 3-(4-fluorophenyl)-2-vinylquinoxaline-6-carboxylate as a white solid (230 mg, 50%) LCMS (ESI+): m/z=309.5 (M+H). 1H NMR (400 MHz, Chloroform-d) δ 8.84 (d, J=1.5 Hz, 1H), 8.37 (dd, J=8.8, 1.9 Hz, 1H), 8.18 (d, J=8.7 Hz, 1H), 7.83-7.68 (m, 2H), 7.26 (d, J=8.7 Hz, 2H), 7.08 (dd, J=16.9, 10.6 Hz, 1H), 6.76 (dd, J=16.9, 1.8 Hz, 1H), 5.75 (dd, J=10.7, 1.8 Hz, 1H), 4.04 (s, 3H).

Step 3: Methyl 3-(4-fluorophenyl)-2-formylquinoxaline-6-carboxylate

To a solution of methyl 3-(4-fluorophenyl)-2-vinylquinoxaline-6-carboxylate (60 mg, 0.2 mmol) in 1,4-dioxane (2.30 mL) water (0.70 mL) was added 4% osmium tetroxide in water (5:95, 20.2 uL, 0.00584 mmol) and sodium metaperiodate (125 mg, 0.584 mmol). The mixture was stirred at rt overnight. The reaction mixture was quenched with water and extracted with EtOAc twice. The organic layer was washed with NaHSO$_3$, water and brine, dried over Na$_2$SO$_4$ and evaporated. The crude mixture was purified by silica gel chromatography to give methyl 3-(4-fluorophenyl)-2-formylquinoxaline-6-carboxylate as white solid (35 mg, 60%). 1H NMR (400 MHz, Chloroform-d) δ 10.35 (s, 1H), 8.93 (d, J=1.3 Hz, 1H), 8.48 (dd, J=8.8, 1.8 Hz, 1H), 8.37 (d, J=8.7 Hz, 1H), 7.82-7.70 (m, 2H), 7.36-7.22 (m, 2H), 4.07 (s, 3H).

Step 4: Methyl 3-(4-fluorophenyl)-2-(morpholin-4-ylmethyl) quinoxaline-6-carboxylate A solution of methyl 3-(4-fluorophenyl)-2-formylquinoxaline-6-carboxylate (100 mg, 0.3 mmol) and morpholine (30.9 uL, 0.355 mmol) in DCM (1 mL) was stirred at rt for 30 min, then sodium triacetoxyborohydride (102 mg, 0.484 mmol) was added and the mixture was stirred at rt overnight. The reaction mixture was quenched with saturated NaHCO$_3$ solution and was extracted with DCM twice and washed with brine and evaporated. The crude mixture was purified by silica gel chromatography to give methyl 3-(4-fluorophenyl)-2-(morpholin-4-ylmethyl) quinoxaline-6-carboxylate as solid (90 mg, 70%). LCMS (ESI+): m/z=382.2 (M+H).

Step 5: 3-(5-Fluoro-2-methoxypyridin-4-yl)-2-(4-fluorophenyl)quinoxaline-6-carboxylic acid To a solution of methyl 3-(4-fluorophenyl)-2-(morpholin-4-ylmethyl)quinoxaline-6-carboxylate (93 mg, 0.24 mmol) in THF (2 mL) was added 1.00 M of sodium hydroxide in water (0.366 mL, 0.366 mmol). The mixture was stirred at rt overnight. The mixture was concentrated in vacuo to give an aqueous residue. 1N HCl was added until the pH was ~6. The mixture was extracted with ether three times, and washed with brine, dried over Na$_2$SO$_4$ and evaporated to afford 3-(5-fluoro-2-methoxypyridin-4-yl)-2-(4-fluorophenyl)quinoxaline-6-carboxylic acid (93 mg, 100%) LCMS (ESI+): m/z=368.2 (M+H).

Step 6: 3-(4-Fluorophenyl)-N-[3-(1H-imidazol-2-yl)propyl]-2-(morpholin-4-ylmethyl)quinoxaline-6-carboxamide (I-405)

A mixture of 3-(4-fluorophenyl)-2-(morpholin-4-ylmethyl)quinoxaline-6-carboxylic acid (93 mg, 0.25 mmol), and 3-(1H-imidazol-2-yl)-1-propanamine 2HCl (60.2 mg, 0.304 mmol) and N,N,N',N'-Tetramethyl-O-(7-azabenzotriazol-1-yl)uronium Hexafluorophosphate (116 mg, 0.304 mmol) in THF (1 mL) was added TEA (176 uL, 1.26 mmol). The solution was stirred at rt overnight. The reaction mixture was diluted with EtOAc and water. The organic layer was washed with 10% LiCl, then water 2× then brine, dried over anhydrous Na$_2$SO$_4$ and filtered. The filtrate was concentrated in vacuo to give a crude residue. The crude residue was purified by HPLC to give 3-(4-fluorophenyl)-N-[3-(1H-imidazol-2-yl)propyl]-2-(morpholin-4-ylmethyl)quinoxaline-6-carboxamide as a formic acid salt (35 mg, 26%). (ESI+): m/z=475.2 (M+H). 1H NMR (400 MHz, Chloroform-d) δ 8.57-8.51 (m, 1H), 8.42 (s, 1H), 8.28-8.15 (m, 2H), 7.92 (dd, J=8.6, 5.4 Hz, 2H), 7.36 (s, 2H), 7.31 (t, J=8.7 Hz, 2H), 3.89 (s, 2H), 3.68-3.60 (m, 4H), 3.55 (s, 2H), 3.09 (s, 2H), 2.59 (d, J=4.1 Hz, 4H), 2.22-2.09 (m, 2H).

Example 65: 3-(4-fluorophenyl)-N-[3-(1H-imidazol-2-yl)propyl]-2-(tetrahydro-2H-pyran-4-yl)quinoxaline-6-carboxamide (I-476)

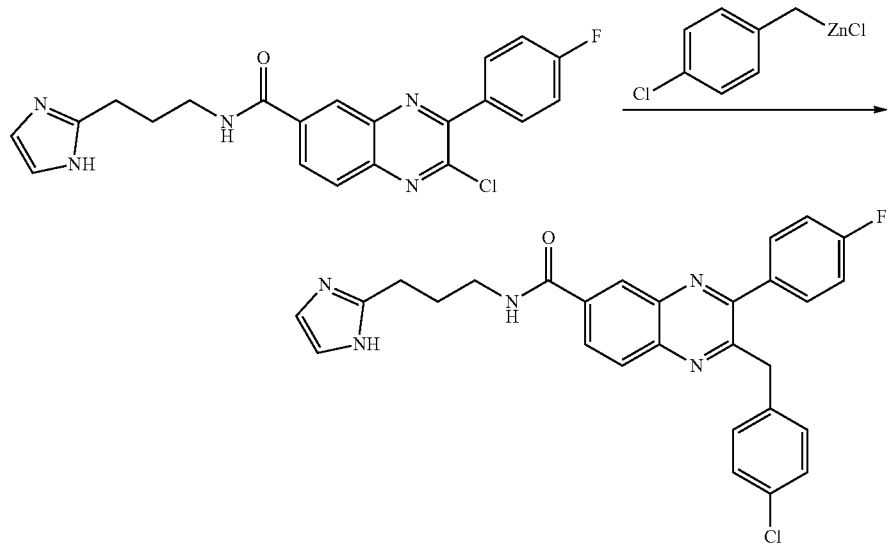

In a microwave vial was added 2-chloro-3-(4-fluorophenyl)-N-[3-(1H-imidazol-2-yl)propyl]quinoxaline-6-carboxamide (150 mg, 0.36 mmol, prepared according to Example 29, Step 1), 1,3-bis(diphenylphosphino)propane nickel (ii) chloride (0.040 g, 0.073 mmol) and 0.5 M of 4-chlorobenzylzinc chloride in THF (2.93 mL, 1.46 mmol) in 1,4-dioxane (2 mL). The mixture was degassed three times, and (further) heated in Biotage microwave at 110° C. for 2 h. The reaction mixture was quenched with MeOH and was extracted with EtOAc three times. The combined organic layer was washed with brine, dried, and concentrated. The crude mixture was purified by HPLC to give 3-(4-fluorophenyl)-N-[3-(1H-imidazol-2-yl)propyl]-2-(tetrahydro-2H-pyran-4-yl)quinoxaline-6-carboxamide (40 mg, 20%) as formic acid salt. LCMS (ESI+, FA): m/z=500.2 (M+H). 1H NMR (400 MHz, Methanol-d4) δ 8.56-8.52 (m, 1H), 8.42 (s, 1H), 8.30-8.14 (m, 2H), 7.56 (dd, J=8.9, 5.3 Hz, 2H), 7.27 (d, J=8.8 Hz, 2H), 7.24 (d, J=1.5 Hz, 2H), 7.21-7.15 (m, 2H), 6.95-6.89 (m, 2H), 4.46 (s, 2H), 3.54 (t, J=6.8 Hz, 2H), 3.00 (t, J=7.6 Hz, 2H), 2.20-2.04 (m, 2H).

Example 66: 3-(4-fluorophenyl)-N-[3-(1H-imidazol-2-yl)propyl]-2-(prop-2-yn-1-yloxy)quinoxaline-6-carboxamide (I-462)

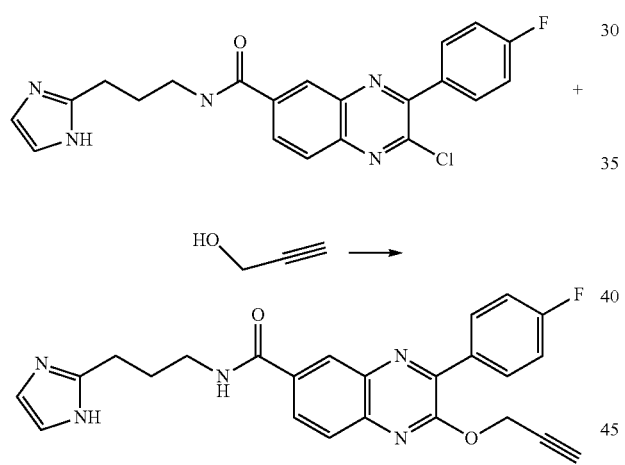

To a 2-dram vial was added 2-propyn-1-ol (0.0137 g, 0.244 mmol), THF (1.00 mL), and potassium tert-butoxide (0.244 mL, 0.244 mmol, 1.0 M in THF). The mixture was stirred at rt for 15 min, cooled to 0° C. then 2-chloro-3-(4-fluorophenyl)-N-[3-(1H-imidazol-2-yl)propyl]quinoxaline-6-carboxamide (0.040 g, 0.0976 mmol, prepared according to Example 29, Step 1) in DMF (1.00 mL) was added. The mixture was stirred at rt for 1 h. LCMS showed clean conversion to the desired product. Acetic acid was added to quench excess base. Solvent was then completely evaporated. The residue was dissolved in DMSO (1.2 mL). After filtration, the residue was purified by prep-HPLC to give 3-(4-fluorophenyl)-N-[3-(1H-imidazol-2-yl)propyl]-2-(prop-2-yn-1-yloxy)quinoxaline-6-carboxamide (0.0275 g, 60%). LCMS (ESI+, FA): m/z=430.2 (M+H).

The compounds listed in the table below were prepared in an analogous fashion to that described in Example 66 starting from the appropriate starting materials:

| Starting Material | Compound No. | LCMS Data |
|---|---|---|
| | I-505 | LCMS (ESI+, FA): m/z = 503.2 (M + H) |
| | I-349 | LCMS (ESI+, FA): m/z = 496 (M + H) |
| | I-439 | LCMS (ESI+, FA): m/z = 482.4 (M + H) |
| | I-346 | LCMS (ESI+, FA): m/z = 503.5 (M + H) |
| | I-326 | LCMS (ESI+, FA): m/z = 488.4 (M + H) |
| | I-401 | LCMS (ESI+, FA): m/z = 498.4 (M + H) |
| | I-323 | LCMS (ESI+, FA): m/z = 490.4 (M + H) |
| | I-379 | LCMS (ESI+, FA): m/z = 476.5 (M + H) |
| | I-489 | LCMS (ESI+, FA): m/z = 497.4 (M + H) |
| | I-396 | LCMS (ESI+, FA): m/z = 483.4 (M + H) |
| | I-371 | LCMS (ESI+, FA): m/z = 434.4 (M + H) |
| | I-496 | LCMS (ESI+, FA): m/z = 445.4 (M + H) |
| | I-420 | LCMS (ESI+, FA): m/z = 496.5 (M + H) |
| | I-351 | LCMS (ESI+, FA): m/z = 472.4 (M + H) |
| | I-500 | LCMS (ESI+, FA): m/z = 474.5 (M + H) |

-continued

| Starting Material | Compound No. | LCMS Data |
|---|---|---|
| HOCH2-cyclohexyl | I-314 | LCMS (ESI+, FA): m/z = 488.5 (M + H) |
| cyclobutyl-CH2OH | I-329 | LCMS (ESI+, FA): m/z = 460.4 (M + H) |
| HO-cyclopentyl | I-400 | LCMS (ESI+, FA): m/z = 460.4 (M + H) |
| HO-CH2-tetrahydrofuran-2-yl | I-438 | LCMS (ESI+, FA): m/z = 476.5 (M + H) |
| ethanol | I-440 | LCMS (ESI+, FA): m/z = 420.4 (M + H) |
| HO-CH2CH2-N(CH3)2 | I-509 | LCMS (ES+, FA): m/z = 463.49 (M + H) |
| HO-(1-methylpiperidin-4-yl) | I-345 | LCMS (ES+, FA): m/z = 489.48 (M + H) |
| HO-CH2-(1H-imidazol-2-yl) | I-459 | LCMS (ES+, FA): m/z = 472.41 (M + H) |
| HO-CH2-(4-chlorophenyl) | I-364 | LCMS (ES+, FA): m/z = 516.43 (M + H) |
| HO-(1-methylpiperidin-3-yl) | I-423 | LCMS (ES+, FA): m/z = 489.48 (M + H) |
| HO-CH2-(1-methylpyrrolidin-3-yl) | I-513 | LCMS (ES+, FA): m/z = 489.48 (M + H) |
| HO-CH2-(3-chlorophenyl) | I-498 | LCMS (ES+, FA): m/z = 516.43 (M + H) |
| HO-CH2-(1H-imidazol-4-yl) | I-356 | LCMS (ES+, FA): m/z = 472.41 (M + H) |
| HO-CH2-(1-methylpiperidin-3-yl) | I-510 | LCMS (ES+, FA): m/z = 503.54 (M + H) |
| HO-CH2-(2-chlorophenyl) | I-454 | LCMS (ES+, FA): m/z = 516.43 (M + H) |

-continued

| Starting Material | Compound No. | LCMS Data |
|---|---|---|
| HO-CH2-(1-methylpiperidin-4-yl) | I-327 | LCMS (ES+, FA): m/z = 503.54 (M + H) |
| HO-CH2-(tetrahydropyran-4-yl) | I-406 | LCMS (ES+, FA): m/z = 490.51 (M + H) |
| HO-CH2CH2-(1H-pyrazol-4-yl) | I-442 | LCMS (ES+, FA): m/z = 486.47 (M + H) |
| HO-CH2-(1-methyl-1H-pyrazol-3-yl) | I-460 | LCMS (ES+, FA): m/z = 486.47 (M + H) |
| HO-CH2-(1-methyl-1H-pyrazol-4-yl) | I-332 | LCMS (ES+, FA): m/z = 486.53 (M + H) |
| HO-CH2-(thiazol-2-yl) | I-469 | LCMS (ES+, FA): m/z = 489.42 (M + H) |
| HO-CH2CH2-(1-methyl-1H-pyrazol-4-yl) | I-321 | LCMS (ES+, FA): m/z = 500.46 (M + H) |
| HO-CH2-(1H-pyrazol-4-yl) | I-347 | LCMS (ES+, FA): m/z = 472.48 (M + H) |
| HO-CH2CH2-(isoxazol-4-yl) | I-390 | LCMS (ES+, FA): m/z = 487.43 (M + H) |
| HO-CH2-oxetan-3-yl | I-348 | LCMS (ES+, FA): m/z = 462.4 (M + H) |
| HO-piperidin-4-yl | I-514 | LCMS (ES+, FA): m/z = 475.43 (M + H) |
| HO-piperidin-3-yl | I-430 | LCMS (ES+, FA): m/z = 475.43 (M + H) |
| HO-(3-methoxycyclobutyl) | I-427 | LCMS (ES+, FA): m/z = 476.45 (M + H) |
| HO-CH2-(1-cyanocyclobutyl) | I-407 | LCMS (ES+, FA): m/z = 485.5 (M + H) |

507 -continued

| Starting Material | Compound No. | LCMS Data |
|---|---|---|
| (structure: 1,3-dimethoxy-2-propanol) | I-411 | LCMS (ES+, FA): m/z = 494.42 (M + H) |
| (structure: (2-oxaspiro[3.3]heptan-6-yl)methanol) | I-378 | LCMS (ES+, FA): m/z = 502.51 (M + H) |
| (structure: 4-(dimethylamino)cyclohexan-1-ol) | I-456 | LCMS (ES+, FA): m/z = 517.52 (M + H) |
| (structure: (3,3-difluorocyclobutyl)methanol) | I-316 | LCMS (ES+, FA): m/z = 496.48 (M + H) |

Example 67: 3-(4-fluorophenyl)-N-[3-(1H-imidazol-2-yl)propyl]-2-[3-(methylamino)cyclobutoxy]quinoxaline-6-carboxamide (I-331)

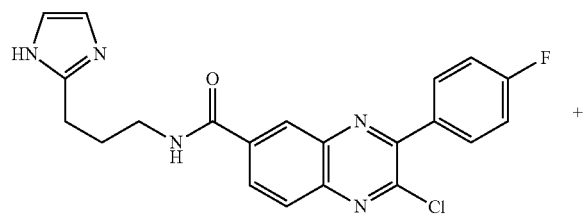

+

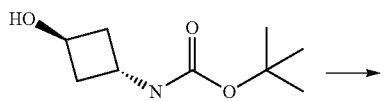

→

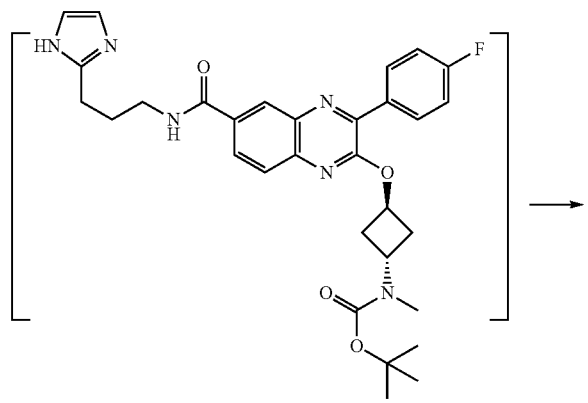

508 -continued

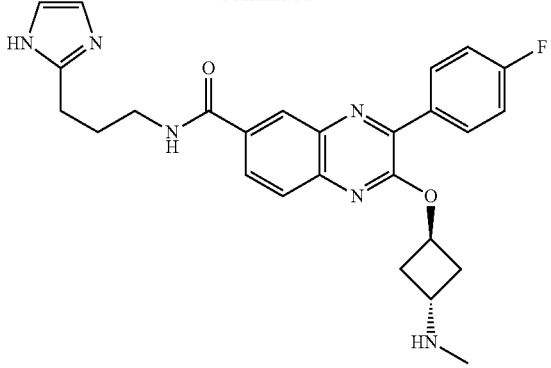

To a round bottom flask with tert-butyl N-(trans-3-hydroxycyclobutyl)-N-methylcarbamate (300.0 mg, 1.491 mmol) and THF (6.52 mL) was added 1M of potassium tert-butoxide in THF (2.23 mL, 2 mmol, 1 mol/L). The reaction mixture was stirred at rt for 30 min. Then 2-chloro-3-(4-fluorophenyl)-N-[3-(1H-imidazol-2-yl)propyl]quinoxaline-6-carboxamide (400.0 mg, 0.9761 mmol, prepared according to Example 29, Step 1) was added and the mixture was stirred for 30 min. LCMS showed complete conversion. The mixture was distributed between water and EtOAc. The aqueous layer was extracted with EtOAc. The combined organic layer was washed with brine, dried, and concentrated to give the crude intermediate. 5 mL of 4N HCl/dioxane was then added and stirred at rt for 2 h. Solvent was evaporated, and the crude product was separated using preparative HPLC purification to give 3-(4-fluorophenyl)-N-[3-(1H-imidazol-2-yl)propyl]-2-[3-(methylamino)cyclobutoxy]quinoxaline-6-carboxamide (102 mg, 22%). LCMS: (FA) ES+475.2 1H NMR (400 MHz, DMSO-d6) δ 11.71 (s, 1H), 8.96 (s, tH), 8.60 (s, 1H), 8.34-8.09 (m, 3H), 7.90 (m, 1H), 7.42 (m, 2H), 6.99 (s, 1H), 6.79 (s, 1H), 5.56 (m, 1H), 3.38 (m, 4H), 2.86 (m, 1H), 2.72 (m, 2H), 2.35 (m, 3H), 2.23 (m, 2H), 2.03-1.86 (m, 2H).

The compound listed in the table below was prepared in an analogous fashion to that described in Example 67 starting from the appropriate starting material:

| Starting Material | Compound No. | LCMS Data |
|---|---|---|
| (structure: 2-azaspiro[3.3]heptan-6-ol) | I-404 | LCMS (ES+, FA): m/z = 487.49 (M + H) |

Example 68: 3-(5-fluoro-2-methoxypyridin-4-yl)-2-(4-fluorophenyl)-N-(imidazo[1,2-a]pyridin-6-ylmethyl)quinoxaline-6-carboxamide (I-333)

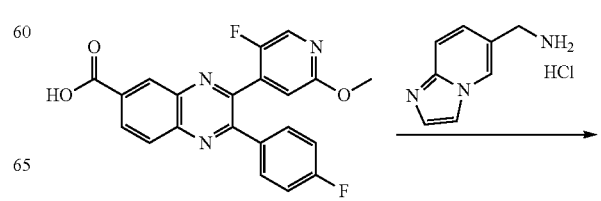

-continued

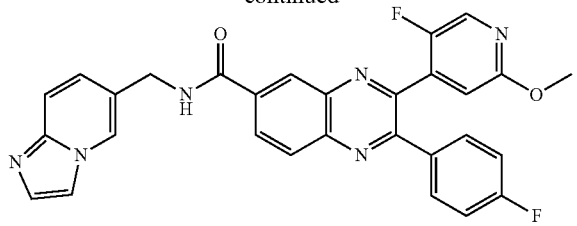

To a suspension of 3-(5-fluoro-2-methoxy-4-pyridyl)-2-(4-fluorophenyl)quinoxaline-6-carboxylic acid (113 mg, 0.289 mmol) in THF (1.8 mL), (imidazo[1,2-a]pyridin-6-yl)methylamine hydrochloride (120 mg, 0.818 mmol), N,N,N',N'-Tetramethyl-O-(7-azabenzotriazol-1-yl)uronium hexafluorophosphate (152 mg, 0.399 mmol) and TEA (253 uL, 1.81 mmol) were added at rt. The reaction mixture was stirred at rt overnight and was quenched with 2 mL of 1N NaOH and further diluted with 10 mL of water. The mixture was extracted with EtOAc (3×10 mL). Combined organic extracts were washed with brine (5 mL), dried with $Na_2SO_4$, filtered and evaporated. The residue was purified using ISCO chromatography on Silica gel (12 g), elution DCM to EtOAc to give 3-(5-fluoro-2-methoxypyridin-4-yl)-2-(4-fluorophenyl)-N-(imidazo[1,2-a]pyridin-6-ylmethyl)quinoxaline-6-carboxamide (110 mg, 65%). LCMS (ESI+): m/z=523.1 (M+H). 1H NMR (400 MHz, DMSO-$d_6$) δ 1H NMR (400 MHz, DMSO-d6) δ 9.53 (t, J=5.7 Hz, 1H), 8.78 (d, J=1.7 Hz, 1H), 8.60 (s, 1H), 8.42 (dd, J=8.8, 1.9 Hz, 1H), 8.32 (d, J=8.8 Hz, 1H), 8.15 (s, 1H), 8.00 (s, 1H), 7.70-7.54 (m, 3H), 7.39-7.24 (m, 3H), 7.22 (d, J=4.7 Hz, 1H), 4.58 (d, J=5.7 Hz, 2H), 3.90 (s, 3H).

Example 69: N-[3-(6-aminopyridin-3-yl)propyl]-2,3-bis(4-fluorophenyl)quinoxaline-6-carboxamide (I-419)

A Microwave tube was charged with N-[3-(6-aminopyridin-3-yl)propyl]-2-chloro-3-(4-fluorophenyl)quinoxaline-6-carboxamide (63.7 mg, 0.146 mmol, prepared according to Example 61, Step 2), 4-fluorobenzeneboronic acid (30.7 mg, 0.219 mmol), cesium carbonate (95.2 mg, 0.292 mmol), and tetrakis(triphenylphosphine)palladium(0) (8.44 mg, 0.00731 mmol) in 1,4-dioxane (1.20 mL, 15.4 mmol) and water (0.300 mL, 16.6 mmol). The tube was sealed, evacuated and purged with nitrogen (×3). The reaction was heated to 100° C. and stirred vigorously for 1 hour. The mixture was cooled to rt, distributed between $NaHCO_3$(aq) saturated solution and EtOAc. The aqueous layer was extracted with EtOAc. The combined org layer was washed with brine, dried, and concentrated. Purification on a silica gel column (continuous gradient from 0-15% MeOH/DCM) provided N-[3-(6-aminopyridin-3-yl)propyl]-2,3-bis(4-fluorophenyl)quinoxaline-6-carboxamide (I-419) as a white solid (51.0 mg, 70.4% yield). LCMS (ESI+): m/z=496.2 (M+H). $^1$H NMR (400 MHz, MeOD) δ 8.56 (d, J=1.51 Hz, 1H), 8.22 (dd, J=2.51, 9.54 Hz, 1H), 8.19 (d, J=8.03 Hz, 1H), 7.74-7.85 (m, 1H), 7.56 (dd, J=5.27, 8.53 Hz, 4H), 7.44 (dd, J=3.01, 9.29 Hz, 1H), 7.14 (t, J=8.78 Hz, 4H), 6.58 (d, J=8.53 Hz, 1H), 3.50 (t, J=7.03 Hz, 2H), 2.62 (t, J=7.65 Hz, 2H), 1.96 (quin, J=7.34 Hz, 2H).

The compound listed in the table below was prepared in an analogous fashion to that described in Example 69 starting from the appropriate starting material:

| Starting Material | Compound No. | LCMS Data |
|---|---|---|
| 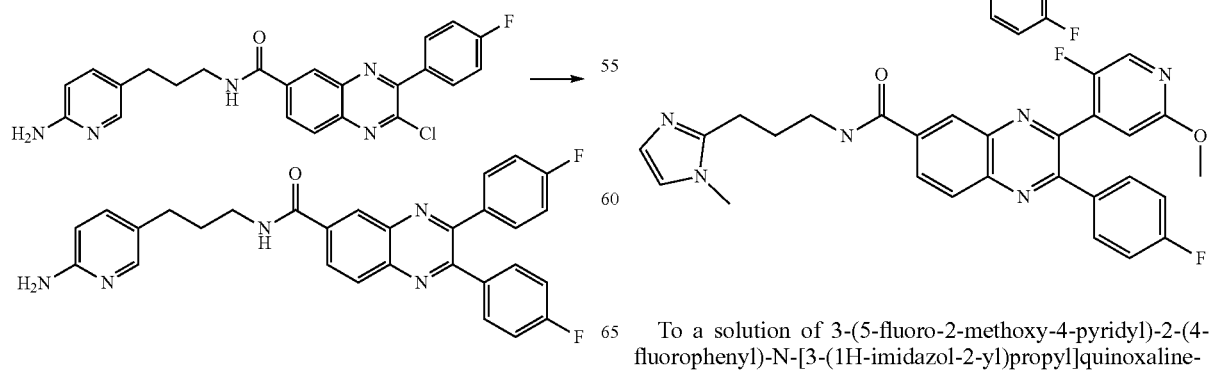 Prepared according to Example 53, Step 1 | I-387 | LCMS (ES+, FA): m/z = 471.2 (M + H) |

Example 70: 3-(5-fluoro-2-methoxypyridin-4-yl)-2-(4-fluorophenyl)-N-[3-(1-methyl-1H-imidazol-2-yl)propyl]quinoxaline-6-carboxamide (I-519)

To a solution of 3-(5-fluoro-2-methoxy-4-pyridyl)-2-(4-fluorophenyl)-N-[3-(1H-imidazol-2-yl)propyl]quinoxaline-6-carboxamide (347 mg, 0.693 mmol, compound I-466 in Example 44) in DMF (7.5 mL) was added cesium carbonate (293 mg, 0.900 mmol) followed by iodomethane (249 mg, 1.75 mmol) and the resulting solution was stirred at rt for 2 h. The reaction mixture was taken up in EtOAc (25 mL) and washed with water (5×5 mL). The organic layer was dried ($Na_2SO_4$), filtered and concentrated to give the crude product. Chromatography on silica gel (0-10% MeOH/DCM) gave 357 mg (33%) of 3-(5-fluoro-2-methoxy-4-pyridyl)-2-(4-fluorophenyl)-N-[3-(1-methylimidazol-2-yl)propyl]quinoxaline-6-carboxamide (I-519). LCMS (ESI+): m/z=515.2 (M+H). $^1$H NMR (400 MHz, DMSO-d6) δ 9.14-9.11 (m, 1H), 8.73 (d, J=1.5 Hz, 1H), 8.38 (dd, J=8.8, 1.5 Hz, 1H), 8.29 (d, J=8.8 Hz, 1H), 8.14 (d, J=1.0 Hz, 1H), 7.64-7.61 (m, 2H), 7.30-7.25 (m, 2H), 7.23 (d, J=4.8 Hz, 1H), 7.01 (d, J=1.0 Hz, 1H), 6.76 (d, J=1.0 Hz, 1H), 3.89 (s, 3H), 3.56 (3, 3 H), 3.47-3.42 (m, 2H), 2.74-2.71 (m, 2H), 2.04-1.96 (m, 2H).

Biological Data

Example 69: NAMPT Enzyme Assay

To measure the inhibition of NAMPT activity hNAMPT protein stock and anti 6His-Tb (Cisbio; Cat. No. 61HISTLB) is diluted to 3× final concentration with assay buffer (50 mM Tris-HCl (pH7.5), 1 mM DTT, 100 mM NaCl, 10 mM $MgCl_2$, 0.005% Tween 20). To this solution is added test compounds or vehicle control (DMSO) and BodiPY ligand (structure below). The plate is shaken for 1-2 min, sealed and incubated for 1 hour at rt in the dark. The TR-FRET signal is measured using BMG Pherastar (Lanthascreen protocol on BMG Pherastar). Excitation was carried out at 320 nm, and the ratio of emission of BodiPY (520 nm) to terbium (486 nm) was determined. Concentration response curves are generated by calculating the excitation increase in test compound-treated samples relative to DMSO-treated controls. For the assay method described above, test compound percent inhibition values at a single concentration are calculated relative to control (DMSO) treated samples. Compound concentration response curves are fitted to generate $IC_{50}$ values from those curves. One skilled in the art will appreciate that these values generated either as percentage inhibition at a single concentration or $IC_{50}$ values are subject to experimental variation.

Structure of BODIPY Ligand:

Compounds of the invention were assayed at a concentration of 1 μM with the % inhibition values as shown in the table below (Table 2). Data for one compound at 1 uM not available due to solubility limitations. Additionally, compounds of the invention inhibit NAMPT with the following IC50 ranges: (A)<100 nM; (B) 100 nM to <500 nM; (C) 500 nM to <1000 nM; (D) 1000 nM to <2000; or (E) 2000 nM to <10000 nM.

TABLE 2

NAMPT Inhibition of Compounds of the Invention

| Compound | Concentration (μM) | Percent Inhibition | IC50 |
|---|---|---|---|
| I-1 | 1 | 51 | C |
| I-2 | 1 | 77 | B |
| I-3 | 1 | 9 | E |
| I-4 | 1 | 93 | A |
| I-5 | 1 | 53 | C |
| I-6 | 1 | 20 | E |
| I-7 | 1 | 12 | E |
| I-8 | 1 | 43 | D |
| I-9 | 1 | 36 | D |
| I-10 | 1 | 23 | E |
| I-11 | 1 | 85 | B |
| I-12 | 1 | >99 | A |
| I-13 | 1 | 69 | B |
| I-14 | 1 | 17 | E |
| I-15 | 1 | 15 | E |
| I-16 | 1 | 84 | B |
| I-17 | 1 | 19 | E |
| I-18 | 1 | 100 | A |
| I-19 | 1 | 82 | B |
| I-20 | 1 | 42 | D |
| I-21 | 1 | 50 | C |
| I-22 | 1 | 41 | D |
| I-23 | 1 | 100 | A |
| I-24 | 1 | 88 | B |
| I-25 | 1 | 98 | A |
| I-26 | 1 | 37 | D |
| I-27 | 1 | 102 | A |
| I-28 | 1 | 19 | E |
| I-29 | 1 | 36 | E |
| I-30 | 1 | 83 | B |
| I-31 | 1 | 89 | A |
| I-32 | 1 | 78 | B |
| I-33 | 1 | 20 | E |
| I-34 | 1 | 47 | D |
| I-35 | 1 | 90 | A |
| I-36 | 1 | 51 | B |
| I-37 | 1 | 65 | C |
| I-38 | 1 | 94 | A |
| I-39 | 1 | 97 | A |
| I-40 | 1 | 33 | E |

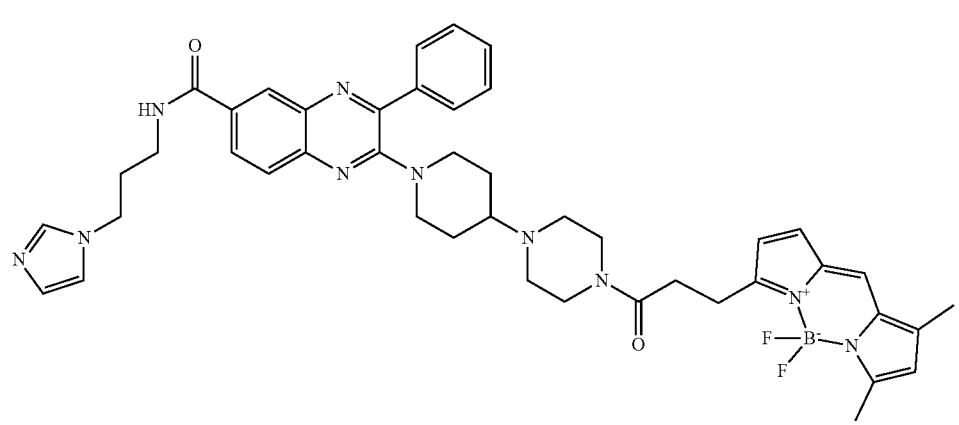 [SMILES: Cc1cc(C)n2c1C=C1C=CC(CCC(=O)N3CCN(C4CCN(c5nc6ccc(C(=O)NCCCn7ccnc7)cc6nc5-c5ccccc5)CC4)CC3)=[N+]1[B-]2(F)F]

TABLE 2-continued

NAMPT Inhibition of Compounds of the Invention

| Compound | Concentration (µM) | Percent Inhibition | IC50 |
|---|---|---|---|
| I-41 | 1 | 17 | E |
| I-42 | 1 | 96 | A |
| I-43 | 1 | 23 | E |
| I-44 | 1 | >99 | A |
| I-45 | 1 | 50 | B |
| I-46 | 1 | 98 | A |
| I-47 | 1 | 90 | A |
| I-48 | 1 | 87 | B |
| I-49 | 1 | 56 | C |
| I-50 | 1 | 87 | A |
| I-51 | 1 | 81 | B |
| I-52 | 1 | 103 | A |
| I-53 | 1 | 77 | B |
| I-54 | 1 | 50 | C |
| I-55 | 1 | 102 | A |
| I-56 | 1 | 33 | E |
| I-57 | 1 | 96 | A |
| I-58 | 1 | 64 | C |
| I-59 | 1 | 49 | D |
| I-60 | 1 | 51 | C |
| I-61 | 1 | 75 | B |
| I-62 | 1 | 24 | E |
| I-63 | 1 | 17 | E |
| I-64 | 1 | 98 | A |
| I-65 | 1 | 95 | A |
| I-66 | 1 | 102 | A |
| I-67 | 1 | 96 | A |
| I-68 | 1 | 16 | E |
| I-69 | 1 | 75 | B |
| I-70 | 1 | >99 | A |
| I-71 | 1 | 81 | B |
| I-72 | 1 | 46 | D |
| I-73 | 1 | 13 | D |
| I-74 | 1 | 100 | A |
| I-75 | 1 | 16 | E |
| I-76 | 1 | 29 | E |
| I-77 | 1 | 86 | B |
| I-78 | 1 | >99 | A |
| I-79 | 1 | 93 | A |
| I-80 | 1 | 65 | C |
| I-81 | 1 | 63 | C |
| I-82 | 1 | 98 | A |
| I-83 | 1 | 33 | E |
| I-84 | 1 | 17 | E |
| I-85 | 1 | 25 | E |
| I-86 | 1 | 62 | A |
| I-87 | 1 | 39 | D |
| I-88 | 1 | 41 | D |
| I-89 | 1 | 68 | B |
| I-90 | 1 | 54 | C |
| I-91 | 1 | 99 | A |
| I-92 | 1 | 48 | D |
| I-93 | 1 | 52 | C |
| I-94 | 1 | 92 | A |
| I-95 | 1 | 61 | C |
| I-96 | 1 | 82 | B |
| I-97 | 1 | 58 | C |
| I-98 | 1 | 41 | D |
| I-99 | 1 | 75 | B |
| I-100 | 1 | 85 | B |
| I-101 | 1 | 16 | E |
| I-102 | 1 | 38 | C |
| I-103 | 1 | 96 | A |
| I-104 | 1 | 100 | A |
| I-105 | 1 | 92 | A |
| I-106 | 1 | 60 | C |
| I-107 | 1 | 47 | D |
| I-108 | 1 | 44 | D |
| I-109 | 1 | 97 | A |
| I-110 | 1 | 66 | C |
| I-111 | 1 | 99 | A |
| I-112 | 1 | 100 | A |
| I-113 | 1 | 64 | C |
| I-114 | 1 | >99 | A |
| I-115 | 1 | 100 | A |
| I-116 | 1 | 98 | A |
| I-117 | 1 | 22 | E |
| I-118 | 1 | 29 | E |
| I-119 | 1 | 58 | C |
| I-120 | 1 | 47 | E |
| I-121 | 1 | 12 | E |
| I-122 | 1 | 60 | E |
| I-123 | 1 | 31 | E |
| I-124 | 1 | 38 | D |
| I-125 | 1 | 73 | B |
| I-126 | 1 | 12 | E |
| I-127 | 1 | 16 | E |
| I-128 | 1 | 60 | C |
| I-129 | 1 | 70 | B |
| I-130 | 1 | 81 | B |
| I-131 | 1 | 64 | C |
| I-132 | 1 | 56 | C |
| I-133 | 1 | 68 | B |
| I-134 | 1 | 65 | C |
| I-135 | 1 | 16 | E |
| I-136 | 1 | 83 | B |
| I-137 | 1 | 18 | E |
| I-138 | 1 | 86 | B |
| I-139 | 1 | 41 | D |
| I-140 | 1 | 79 | B |
| I-141 | 1 | 74 | B |
| I-142 | 1 | 24 | E |
| I-143 | 1 | 3 | E |
| I-144 | 1 | 43 | D |
| I-145 | 1 | 76 | B |
| I-146 | 1 | 76 | B |
| I-147 | 1 | 95 | A |
| I-148 | 1 | 85 | B |
| I-149 | 1 | 86 | B |
| I-150 | 1 | 75 | B |
| I-151 | 1 | 79 | B |
| I-152 | 1 | 62 | C |
| I-153 | 1 | 22 | E |
| I-154 | 1 | 98 | A |
| I-155 | 1 | 12 | E |
| I-156 | 1 | 97 | A |
| I-157 | 1 | 40 | D |
| I-158 | 1 | 42 | D |
| I-159 | 1 | 71 | B |
| I-160 | 1 | 45 | E |
| I-161 | 1 | 89 | A |
| I-162 | 1 | 44 | D |
| I-163 | 1 | 17 | E |
| I-164 | 1 | 83 | B |
| I-165 | 1 | 78 | B |
| I-166 | 1 | 31 | E |
| I-167 | 1 | 24 | E |
| I-168 | 1 | 84 | B |
| I-169 | 1 | 36 | D |
| I-170 | 1 | 98 | A |
| I-171 | 1 | 27 | E |
| I-172 | 1 | >99 | A |
| I-173 | 1 | 83 | B |
| I-174 | 1 | 89 | B |
| I-175 | 1 | 20 | E |
| I-176 | 1 | 46 | D |
| I-177 | 1 | 77 | B |
| I-178 | 1 | 97 | A |
| I-179 | 1 | 57 | C |
| I-180 | 1 | 27 | E |
| I-181 | 1 | 100 | A |
| I-182 | 1 | 83 | B |
| I-183 | 1 | >99 | A |
| I-184 | 1 | 39 | D |
| I-185 | 1 | 57 | C |
| I-186 | 1 | 19 | E |
| I-187 | 1 | 84 | B |
| I-188 | 1 | 83 | B |
| I-189 | 1 | 91 | A |
| I-190 | 1 | 74 | B |

TABLE 2-continued

NAMPT Inhibition of Compounds of the Invention

| Compound | Concentration (µM) | Percent Inhibition | IC50 |
|---|---|---|---|
| I-191 | 1 | 16 | E |
| I-192 | 1 | 78 | B |
| I-193 | 1 | 73 | B |
| I-194 | 1 | 30 | E |
| I-195 | 1 | >99 | A |
| I-196 | 1 | 98 | A |
| I-197 | 1 | >99 | A |
| I-198 | 1 | >99 | A |
| I-199 | 1 | 101 | A |
| I-200 | 1 | 85 | B |
| I-201 | 1 | 62 | C |
| I-202 | 1 | >99 | A |
| I-203 | 1 | 37 | D |
| I-204 | 1 | >99 | A |
| I-205 | 1 | 84 | B |
| I-206 | 1 | 75 | B |
| I-207 | 1 | 69 | B |
| I-208 | 1 | 55 | C |
| I-209 | 1 | 74 | B |
| I-210 | 1 | 95 | A |
| I-211 | 1 | 79 | B |
| I-212 | 1 | 95 | A |
| I-213 | 1 | 99 | A |
| I-214 | 1 | 40 | D |
| I-215 | 1 | 15 | E |
| I-216 | 1 | 91 | A |
| I-217 | 1 | 26 | E |
| I-218 | 1 | 100 | A |
| I-219 | 1 | 74 | B |
| I-220 | 1 | 68 | B |
| I-221 | 1 | >99 | A |
| I-222 | 1 | 92 | A |
| I-223 | 1 | 10 | E |
| I-224 | 1 | 74 | B |
| I-225 | 1 | 14 | E |
| I-226 | 1 | 70 | B |
| I-227 | 1 | 68 | C |
| I-228 | 1 | 80 | B |
| I-229 | 1 | 73 | B |
| I-230 | 1 | 62 | C |
| I-231 | 1 | 95 | A |
| I-232 | 1 | >99 | A |
| I-233 | 1 | 43 | E |
| I-234 | 1 | 100 | A |
| I-235 | 1 | 79 | B |
| I-236 | 1 | 99 | A |
| I-237 | 1 | 21 | E |
| I-238 | 1 | 19 | E |
| I-239 | 1 | 25 | E |
| I-240 | 1 | 83 | B |
| I-241 | 1 | 57 | C |
| I-242 | 1 | 45 | D |
| I-243 | 1 | 62 | C |
| I-244 | 1 | 33 | E |
| I-245 | 1 | 62 | C |
| I-246 | 1 | 30 | E |
| I-247 | 1 | 58 | C |
| I-248 | 1 | 29 | E |
| I-249 | 1 | 45 | D |
| I-250 | 1 | 86 | B |
| I-251 | 1 | 65 | B |
| I-252 | 1 | 53 | C |
| I-253 | 1 | 93 | A |
| I-254 | 1 | 84 | B |
| I-255 | 1 | >99 | A |
| I-256 | 1 | 97 | A |
| I-257 | 1 | 77 | B |
| I-258 | 1 | 67 | B |
| I-259 | 1 | 44 | D |
| I-260 | 1 | 19 | E |
| I-261 | 1 | 67 | B |
| I-262 | 1 | 91 | A |
| I-263 | 1 | 81 | B |
| I-264 | 1 | 41 | D |
| I-265 | 1 | 17 | E |
| I-266 | 1 | 15 | E |
| I-267 | 1 | 81 | B |
| I-268 | 1 | 63 | D |
| I-269 | 1 | 73 | B |
| I-270 | 1 | 47 | D |
| I-271 | 1 | 102 | A |
| I-272 | 1 | 72 | B |
| I-273 | 1 | 88 | A |
| I-274 | 1 | 25 | E |
| I-275 | 1 | 99 | A |
| I-276 | 1 | 38 | D |
| I-277 | 1 | 99 | A |
| I-278 | 1 | 15 | E |
| I-279 | 1 | 13 | E |
| I-280 | 1 | 83 | B |
| I-281 | 1 | 37 | D |
| I-282 | 1 | 91 | A |
| I-283 | 1 | 12 | E |
| I-284 | 1 | 14 | E |
| I-285 | 1 | 7 | E |
| I-286 | 1 | 13 | E |
| I-287 | 1 | 98 | A |
| I-288 | 1 | >99 | A |
| I-289 | 1 | 45 | D |
| I-290 | 1 | 81 | B |
| I-291 | 1 | 98 | A |
| I-292 | 1 | 90 | A |
| I-293 | 1 | 26 | E |
| I-294 | 1 | 22 | E |
| I-295 | 1 | 49 | D |
| I-296 | 1 | 67 | C |
| I-297 | 1 | 88 | B |
| I-298 | 1 | >99 | A |
| I-299 | 1 | 76 | B |
| I-300 | 1 | >99 | A |
| I-301 | 1 | 99 | A |
| I-302 | 1 | 63 | C |
| I-303 | 1 | 15 | E |
| I-304 | 1 | 17 | E |
| I-305 | 1 | 93 | A |
| I-306 | 1 | 60 | C |
| I-307 | 1 | 73 | B |
| I-308 | 1 | 89 | B |
| I-309 | 1 | 86 | B |
| I-310 | 1 | 62 | C |
| I-311 | 1 | 76 | B |
| I-312 | 1 | 94 | A |
| I-313 | 1 | 86 | B |
| I-314 | 1 | 91 | A |
| I-315 | 1 | 88 | B |
| I-316 | 1 | 98 | A |
| I-317 | 1 | 66 | B |
| I-318 | 1 | 97 | A |
| I-319 | 1 | 94 | A |
| I-320 | 1 | 63 | C |
| I-321 | 1 | >99 | A |
| I-322 | 1 | 96 | A |
| I-323 | 1 | 99 | A |
| I-324 | 1 | 57 | C |
| I-325 | 1 | >99 | A |
| I-326 | 1 | 92 | A |
| I-327 | 1 | >99 | A |
| I-328 | 1 | 84 | B |
| I-329 | 1 | 95 | A |
| I-330 | 1 | 79 | B |
| I-331 | 1 | >99 | A |
| I-332 | 1 | >99 | A |
| I-333 | 1 | 63 | B |
| I-334 | 1 | >99 | A |
| I-335 | 1 | 85 | B |
| I-336 | 1 | 88 | B |
| I-337 | 1 | 88 | B |
| I-338 | 1 | >99 | A |
| I-339 | 1 | 91 | A |
| I-340 | 1 | >99 | A |

TABLE 2-continued

NAMPT Inhibition of Compounds of the Invention

| Compound | Concentration (μM) | Percent Inhibition | IC50 |
|---|---|---|---|
| I-341 | 1 | 73 | B |
| I-342 | 1 | 89 | A |
| I-343 | 1 | 82 | B |
| I-344 | 1 | >99 | A |
| I-345 | 1 | 98 | A |
| I-346 | 1 | 98 | A |
| I-347 | 1 | 97 | A |
| I-348 | 1 | >99 | A |
| I-349 | 1 | 91 | A |
| I-350 | 1 | 86 | B |
| I-351 | 1 | 96 | A |
| I-352 | 1 | 99 | A |
| I-353 | 1 | 97 | A |
| I-354 | 1 | 97 | A |
| I-355 | 1 | >99 | A |
| I-356 | 1 | 63 | C |
| I-357 | 1 | 83 | B |
| I-358 | 1 | 78 | B |
| I-359 | 1 | 46 | C |
| I-360 | 1 | >99 | A |
| I-361 | 1 | 98 | A |
| I-362 | 1 | 74 | B |
| I-363 | 1 | 78 | B |
| I-364 | 1 | 73 | B |
| I-365 | 1 | 97 | A |
| I-366 | 1 | 53 | C |
| I-367 | 1 | 50 | C |
| I-368 | 1 | >99 | A |
| I-369 | 1 | 93 | A |
| I-370 | 1 | 64 | C |
| I-371 | 1 | 97 | A |
| I-372 | 1 | >99 | A |
| I-373 | 1 | 84 | B |
| I-374 | 1 | 75 | B |
| I-375 | 1 | 80 | B |
| I-376 | 1 | 30 | C |
| I-377 | 1 | 85 | B |
| I-378 | 1 | >99 | A |
| I-379 | 1 | 100 | A |
| I-380 | 1 | 55 | C |
| I-381 | 1 | 96 | A |
| I-382 | 1 | 55 | C |
| I-383 | 1 | 99 | A |
| I-384 | 1 | 84 | B |
| I-385 | 1 | >99 | A |
| I-386 | 1 | 90 | B |
| I-387 | 1 | 61 | C |
| I-388 | 1 | 81 | B |
| I-389 | 1 | 93 | A |
| I-390 | 1 | 99 | A |
| I-391 | 1 | 83 | B |
| I-392 | 1 | 91 | B |
| I-393 | 1 | 98 | A |
| I-394 | 1 | 74 | B |
| I-395 | 1 | 83 | B |
| I-396 | 1 | 98 | A |
| I-397 | 1 | 97 | A |
| I-398 | 1 | 93 | A |
| I-399 | 1 | 95 | A |
| I-400 | 1 | 97 | A |
| I-401 | 1 | 69 | B |
| I-402 | 1 | 97 | A |
| I-403 | 1 | 89 | B |
| I-404 | 1 | >99 | A |
| I-405 | 1 | 72 | B |
| I-406 | 1 | >99 | A |
| I-407 | 1 | >99 | A |
| I-408 | 1 | 85 | B |
| I-409 | 1 | 98 | A |
| I-410 | 1 | 98 | B |
| I-411 | 1 | 97 | B |
| I-412 | 1 | 96 | B |
| I-413 | 1 | 80 | B |
| I-414 | 1 | 95 | A |
| I-415 | 1 | 75 | B |
| I-416 | 1 | 76 | B |
| I-417 | 1 | 81 | B |
| I-418 | 1 | 60 | C |
| I-419 | 1 | 52 | C |
| I-420 | 1 | 97 | A |
| I-421 | 1 | 78 | B |
| I-422 | 1 | 92 | A |
| I-423 | 1 | 88 | B |
| I-424 | 1 | 76 | B |
| I-425 | 1 | 87 | B |
| I-426 | 1 | 99 | A |
| I-427 | 1 | 99 | A |
| I-428 | 1 | 71 | B |
| I-429 | 1 | 90 | B |
| I-430 | 1 | 98 | A |
| I-431 | 1 | 90 | B |
| I-432 | 1 | 79 | B |
| I-433 | 1 | 79 | B |
| I-434 | 1 | 76 | B |
| I-435 | 1 | 93 | A |
| I-436 | 1 | 83 | B |
| I-437 | 1 | 71 | B |
| I-438 | 1 | 99 | A |
| I-439 | 1 | 93 | A |
| I-440 | 1 | 94 | A |
| I-441 | 1 | 50 | C |
| I-442 | 1 | >99 | A |
| I-443 | 0.333* | 57 | B |
| I-444 | 1 | 77 | B |
| I-445 | 1 | 91 | A |
| I-446 | 1 | >99 | A |
| I-447 | 1 | 99 | A |
| I-448 | 1 | 67 | B |
| I-449 | 1 | 82 | B |
| I-450 | 1 | 93 | A |
| I-451 | 1 | 97 | A |
| I-452 | 1 | 75 | B |
| I-453 | 1 | 88 | B |
| I-454 | 1 | 95 | A |
| I-455 | 1 | 80 | B |
| I-456 | 1 | >99 | A |
| I-457 | 1 | 98 | A |
| I-458 | 1 | 81 | B |
| I-459 | 1 | 47 | C |
| I-460 | 1 | 99 | A |
| I-461 | 1 | 86 | B |
| I-462 | 1 | 95 | A |
| I-463 | 1 | 97 | A |
| I-464 | 1 | >99 | A |
| I-465 | 1 | 98 | A |
| I-466 | 1 | 95 | A |
| I-467 | 1 | 94 | A |
| I-468 | 1 | 99 | A |
| I-469 | 1 | 98 | A |
| I-470 | 1 | 81 | B |
| I-471 | 1 | >99 | A |
| I-472 | 1 | 98 | A |
| I-473 | 1 | 85 | B |
| I-474 | 1 | 95 | B |
| I-475 | 1 | 77 | B |
| I-476 | 1 | 88 | B |
| I-477 | 1 | >99 | A |
| I-478 | 1 | 96 | A |
| I-479 | 1 | 75 | B |
| I-480 | 1 | 100 | A |
| I-481 | 1 | 98 | A |
| I-482 | 1 | 72 | B |
| I-483 | 1 | 77 | B |
| I-484 | 1 | 99 | A |
| I-485 | 1 | 96 | A |
| I-486 | 1 | 78 | B |
| I-487 | 1 | 70 | B |
| I-488 | 1 | 98 | A |
| I-489 | 1 | >99 | A |
| I-490 | 1 | 95 | A |

TABLE 2-continued

NAMPT Inhibition of Compounds of the Invention

| Compound | Concentration (μM) | Percent Inhibition | IC50 |
|---|---|---|---|
| I-491 | 1 | 83 | B |
| I-492 | 1 | 94 | A |
| I-493 | 1 | 98 | A |
| I-494 | 1 | >99 | A |
| I-495 | 1 | 96 | A |
| I-496 | 1 | 70 | B |
| I-497 | 1 | 80 | B |
| I-498 | 1 | 84 | A |
| I-499 | 1 | 98 | A |
| I-500 | 1 | 93 | A |
| I-501 | 1 | 99 | A |
| I-502 | 1 | 97 | A |
| I-503 | 1 | 84 | B |
| I-504 | 1 | 93 | A |
| I-505 | 1 | >99 | A |
| I-506 | 1 | 78 | B |
| I-507 | 1 | 97 | A |
| I-508 | 1 | 73 | B |
| I-509 | 1 | 94 | A |
| I-510 | 1 | 98 | A |
| I-511 | 1 | >99 | A |
| I-512 | 1 | 92 | A |
| I-513 | 1 | 99 | A |
| I-514 | 1 | 97 | A |
| I-515 | 1 | 75 | B |
| I-516 | 1 | 93 | A |
| I-517 | 1 | 76 | B |
| I-518 | 1 | 86 | B |
| I-519 | 1 | 97 | A |
| I-520 | 1 | 89 | A |

*Data at 1 uM not available due to solubility limitations

Compounds of the invention were assayed to measure PC3 growth inhibition at a concentration of 1 μM or 1.667 μM (Table 3). To measure PC3 growth inhibition, PC3 cells that were maintained in PRMI1640 growth medium (Life Technologies; Cat. No. 11875) at 37° C. under 5% $CO_2$ are trypsinized and diluted at a density of $8 \times 10^4$ cells/ml, 25 ul per well of cells and plated in 384-well black tissue culture plate. The cells are incubated overnight at 37° C. under 5% $CO_2$. For each measurement, a test compounds or vehicle control (DMSO) are diluted with AIM serum free medium and added to the cell plate. Incubate for 72 hours at 37° C. under 5% $CO_2$. 25 μl Cell-titer glo solution (Promega; Cat. No. G8462) is added and the cell plates are incubated for 10 minutes protected from light. The luminescence is measured. Concentration response curves are generated by calculating the luminescence increase in test compound-treated samples relative to DMSO-treated controls. Percentage remaining viability values at a single concentration, growth inhibition ($GI_{50}$) or cell viability ($LD_{50}$) values are determined from those curves. One skilled in the art will appreciate that these values are subject to experimental variation.

TABLE 3

PC3 Growth Inhibition of Compounds of the Invention

| Compound | Concentration (μM) | Percent Inhibition |
|---|---|---|
| I-1 | 1.667 | 3 |
| I-2 | 1 | -7 |
| I-3 | 1 | 39 |
| I-4 | 1.667 | 2 |
| I-5 | 1 | -7 |
| I-6 | 1 | 91 |
| I-7 | 1 | 105 |
| I-8 | 1 | 103 |
| I-9 | 1 | 1 |
| I-10 | 1 | 99 |
| I-11 | 1 | -7 |
| I-12 | 1.667 | 2 |
| I-13 | 1 | -6 |
| I-14 | 1 | -3 |
| I-15 | 1 | -6 |
| I-16 | 1.667 | 39 |
| I-17 | 1 | 4 |
| I-18 | 1.667 | 2 |
| I-19 | 1 | -1 |
| I-20 | 1 | 111 |
| I-21 | — | — |
| I-22 | 1 | 96 |
| I-23 | 1.667 | 2 |
| I-24 | 1 | -8 |
| I-25 | 1.667 | 2 |
| I-26 | 1 | 99 |
| I-27 | 1 | -1 |
| I-28 | 1 | 94 |
| I-29 | 1 | 96 |
| I-30 | 1 | -7 |
| I-31 | 1 | -7 |
| I-32 | 1 | -5 |
| I-33 | 1 | 92 |
| I-34 | 1 | -6 |
| I-35 | 1.667 | 2 |
| I-36 | 1 | 1 |
| I-37 | 1 | -6 |
| I-38 | 1 | -8 |
| I-39 | 1.667 | 2 |
| I-40 | — | — |
| I-41 | 1 | 5 |
| I-42 | 1.667 | >99 |
| I-43 | 1 | 16 |
| I-44 | 1.667 | 33 |
| I-45 | 1 | -6 |
| I-46 | 1.852 | 2 |
| I-47 | 1.667 | 33 |
| I-48 | 1 | 1 |
| I-49 | 1 | 8 |
| I-50 | 1.667 | 96 |
| I-51 | 1 | -7 |
| I-52 | 1 | 0 |
| I-53 | 1 | -6 |
| I-54 | 1 | -7 |
| I-55 | 1 | -7 |
| I-56 | 1 | 104 |
| I-57 | 1 | 45 |
| I-58 | 1.667 | 50 |
| I-59 | 1 | -6 |
| I-60 | 1 | -4 |
| I-61 | 1 | -7 |
| I-62 | 1 | -4 |
| I-63 | 1 | 25 |
| I-64 | 1.852 | 2 |
| I-65 | 1.667 | 2 |
| I-66 | 1 | -1 |
| I-67 | 1.667 | 2 |
| I-68 | 1 | 101 |
| I-69 | 1 | 0 |
| I-70 | 1.667 | 2 |
| I-71 | — | — |
| I-72 | 1 | 2 |
| I-73 | 1.852 | >99 |
| I-74 | 1 | -2 |
| I-75 | 1 | 96 |
| I-76 | 1 | 92 |
| I-77 | 1.667 | >99 |
| I-78 | 1.667 | 2 |
| I-79 | 1 | -8 |
| I-80 | 1 | 1 |
| I-81 | 1 | -7 |
| I-82 | 1.667 | 2 |

TABLE 3-continued

PC3 Growth Inhibition of Compounds of the Invention

| Compound | Concentration (µM) | Percent Inhibition |
|---|---|---|
| I-83 | 1 | 96 |
| I-84 | 1 | 85 |
| I-85 | 1 | 8 |
| I-86 | 1.667 | 3 |
| I-87 | 1 | −7 |
| I-88 | 1 | −7 |
| I-89 | 1 | −7 |
| I-90 | 1 | −7 |
| I-91 | 1.667 | 2 |
| I-92 | 1 | −7 |
| I-93 | 1 | 15 |
| I-94 | 1.667 | 34 |
| I-95 | 1 | 1 |
| I-96 | 1 | 0 |
| I-97 | 1 | 1 |
| I-98 | — | — |
| I-99 | 1 | −8 |
| I-100 | 1 | −7 |
| I-101 | 1 | 7 |
| I-102 | 1.667 | >99 |
| I-103 | 1.667 | 58 |
| I-104 | 1.667 | 2 |
| I-105 | 1 | −7 |
| I-106 | 1 | −5 |
| I-107 | 1 | 102 |
| I-108 | 1 | 93 |
| I-109 | 1.667 | 36 |
| I-110 | — | — |
| I-111 | 1.667 | 2 |
| I-112 | 1 | −1 |
| I-113 | 1 | −8 |
| I-114 | 1.667 | 2 |
| I-115 | 1 | −8 |
| I-116 | 1.667 | 2 |
| I-117 | 1 | 97 |
| I-118 | 1 | 85 |
| I-119 | 1 | −8 |
| I-120 | 1 | 1 |
| I-121 | 1 | 99 |
| I-122 | 1.667 | 4 |
| I-123 | 1 | 96 |
| I-124 | 1 | 27 |
| I-125 | 1 | −7 |
| I-126 | 1 | 93 |
| I-127 | 1 | 95 |
| I-128 | 1 | −7 |
| I-129 | 1 | −6 |
| I-130 | 1 | 93 |
| I-131 | 1 | −8 |
| I-132 | 1.667 | 2 |
| I-133 | 1.667 | 3 |
| I-134 | 1 | −3 |
| I-135 | 1 | 101 |
| I-136 | 1 | −7 |
| I-137 | 1 | 6 |
| I-138 | 1.667 | >99 |
| I-139 | 1 | 99 |
| I-140 | 1 | −8 |
| I-141 | 1 | −8 |
| I-142 | 1 | 95 |
| I-143 | 1 | 103 |
| I-144 | 1 | 2 |
| I-145 | 1 | −7 |
| I-146 | 1 | −7 |
| I-147 | 1.667 | 2 |
| I-148 | 1 | 1 |
| I-149 | 1 | −8 |
| I-150 | 1 | −7 |
| I-151 | 1 | 96 |
| I-152 | 1 | 3 |
| I-153 | 1 | 14 |
| I-154 | 1.667 | 2 |
| I-155 | 1 | 103 |
| I-156 | 1.667 | 2 |
| I-157 | 1 | 2 |
| I-158 | 1 | 0 |
| I-159 | 1 | −6 |
| I-160 | — | — |
| I-161 | 1 | −7 |
| I-162 | 1 | 1 |
| I-163 | 1 | 86 |
| I-164 | 1 | 101 |
| I-165 | 1 | −7 |
| I-166 | 1 | 5 |
| I-167 | 1 | 1 |
| I-168 | 1 | 1 |
| I-169 | 1 | 93 |
| I-170 | 1.667 | 2 |
| I-171 | 1 | 95 |
| I-172 | 1.667 | 2 |
| I-173 | 1 | −1 |
| I-174 | 1 | 1 |
| I-175 | 1 | 95 |
| I-176 | 1 | 1 |
| I-177 | 1.667 | 2 |
| I-178 | 1.667 | 2 |
| I-179 | 1 | −7 |
| I-180 | 1 | 102 |
| I-181 | 1 | 0 |
| I-182 | 1 | −7 |
| I-183 | 1.667 | 2 |
| I-184 | 1 | 101 |
| I-185 | — | — |
| I-186 | — | — |
| I-187 | 1 | −8 |
| I-188 | 1 | −7 |
| I-189 | 1.667 | 2 |
| I-190 | 1 | −6 |
| I-191 | 1 | 24 |
| I-192 | 1 | −7 |
| I-193 | 1.667 | >99 |
| I-194 | 1 | 29 |
| I-195 | 1.667 | 2 |
| I-196 | 1.667 | 2 |
| I-197 | 1.667 | 2 |
| I-198 | 1.667 | 3 |
| I-199 | 1 | 0 |
| I-200 | 1 | −7 |
| I-201 | 1 | −7 |
| I-202 | 1.667 | 2 |
| I-203 | 1 | −8 |
| I-204 | 1.667 | 63 |
| I-205 | 1 | 104 |
| I-206 | 1 | −7 |
| I-207 | 1 | −7 |
| I-208 | 1 | −6 |
| I-209 | 1 | −7 |
| I-210 | 1 | −2 |
| I-211 | 1.667 | >99 |
| I-212 | 1 | 101 |
| I-213 | 1.667 | 2 |
| I-214 | 1 | 0 |
| I-215 | 1 | 19 |
| I-216 | 1.667 | 3 |
| I-217 | 1 | 95 |
| I-218 | 1 | 0 |
| I-219 | 1 | −7 |
| I-220 | 1.667 | 4 |
| I-221 | 1.667 | 2 |
| I-222 | 1.667 | 12 |
| I-223 | 1 | 103 |
| I-224 | 1 | 1 |
| I-225 | 1 | 91 |
| I-226 | 1 | −7 |
| I-227 | 1 | 1 |
| I-228 | 1 | −8 |
| I-229 | 1 | 95 |
| I-230 | 1 | −7 |
| I-231 | 1 | −2 |
| I-232 | 1.667 | 2 |

TABLE 3-continued

PC3 Growth Inhibition of Compounds of the Invention

| Compound | Concentration (µM) | Percent Inhibition |
|---|---|---|
| I-233 | 1 | −8 |
| I-234 | 1 | 41 |
| I-235 | 1 | −8 |
| I-236 | 1 | 1 |
| I-237 | 1 | 96 |
| I-238 | 1 | 96 |
| I-239 | 1 | 14 |
| I-240 | 1 | −8 |
| I-241 | 1 | 1 |
| I-242 | 1 | −7 |
| I-243 | 1 | −6 |
| I-244 | 1 | 96 |
| I-245 | 1 | −8 |
| I-246 | — | — |
| I-247 | 1 | −5 |
| I-248 | 1 | 2 |
| I-249 | — | — |
| I-250 | 1 | −6 |
| I-251 | 1 | 1 |
| I-252 | 1 | 2 |
| I-253 | 1.667 | 2 |
| I-254 | 1 | −8 |
| I-255 | 1.667 | 2 |
| I-256 | 1.667 | 2 |
| I-257 | 1 | −8 |
| I-258 | 1 | −8 |
| I-259 | 1 | −7 |
| I-261 | 1 | −1 |
| I-262 | 1 | −7 |
| I-263 | 1 | 1 |
| I-264 | 1 | −8 |
| I-265 | 1 | 11 |
| I-266 | 1 | 104 |
| I-267 | 1 | −7 |
| I-268 | 1 | −6 |
| I-269 | 1 | 0 |
| I-270 | 1 | 111 |
| I-271 | 1 | −2 |
| I-272 | 1 | −6 |
| I-273 | 1.667 | 2 |
| I-274 | 1 | −5 |
| I-275 | 1 | 0 |
| I-276 | 1 | 90 |
| I-277 | 1.667 | 2 |
| I-278 | 1 | 98 |
| I-279 | 1 | 89 |
| I-280 | 1 | −6 |
| I-281 | 1 | 6 |
| I-282 | 1.667 | 96 |
| I-283 | 1 | 100 |
| I-284 | 1 | 98 |
| I-285 | 1 | 97 |
| I-286 | 1 | 4 |
| I-287 | 1.667 | 2 |
| I-288 | 1.667 | 2 |
| I-289 | 1 | −7 |
| I-290 | 1 | −8 |
| I-291 | 1.667 | 2 |
| I-292 | 1.667 | 2 |
| I-293 | — | — |
| I-294 | — | — |
| I-295 | 1 | −6 |
| I-296 | 1 | −7 |
| I-297 | 1.667 | 2 |
| I-298 | 1.667 | 2 |
| I-299 | 1.667 | 2 |
| I-300 | 1.667 | 32 |
| I-301 | 1.667 | 2 |
| I-302 | 1 | 87 |
| I-303 | 1 | 95 |
| I-304 | 1 | 92 |
| I-305 | 1.667 | 3 |
| I-306 | 1.667 | 3 |
| I-307 | 1.667 | 4 |
| I-308 | 1.667 | 4 |
| I-309 | 1.667 | 3 |
| I-310 | 1.667 | 4 |
| I-311 | 1.667 | 2 |
| I-312 | 1.667 | 2 |
| I-313 | 1.667 | 2 |
| I-314 | 1.667 | 3 |
| I-315 | 1.667 | 1 |
| I-316 | 1.667 | 2 |
| I-317 | 1.667 | 1 |
| I-318 | 1.667 | 2 |
| I-319 | 1.667 | 3 |
| I-320 | 1.667 | 3 |
| I-321 | 1.667 | 2 |
| I-322 | 1.667 | 2 |
| I-323 | 1.667 | 3 |
| I-324 | 1.667 | 3 |
| I-325 | 1.667 | 4 |
| I-326 | 1.667 | 3 |
| I-327 | 1.667 | 2 |
| I-328 | 1.667 | 3 |
| I-329 | 1.667 | 3 |
| I-330 | 1.667 | 3 |
| I-331 | 1.667 | 2 |
| I-332 | 1.667 | 34 |
| I-333 | 1.667 | 0 |
| I-334 | 1.667 | 1 |
| I-335 | 1.667 | 2 |
| I-336 | 1.667 | 1 |
| I-337 | 1.667 | 3 |
| I-338 | 1.667 | 1 |
| I-339 | 1.667 | 1 |
| I-340 | 1.667 | 3 |
| I-341 | 1.667 | 1 |
| I-342 | 1.667 | 3 |
| I-343 | 1.667 | 1 |
| I-344 | 1.667 | 1 |
| I-345 | 1.667 | 2 |
| I-346 | 1.667 | 3 |
| I-347 | 1.667 | 33 |
| I-348 | 1.667 | 3 |
| I-349 | 1.667 | 3 |
| I-350 | 1.667 | 2 |
| I-351 | 1.667 | 3 |
| I-352 | 1.667 | 2 |
| I-353 | 1.667 | 2 |
| I-354 | 1.667 | 2 |
| I-355 | 1.667 | 2 |
| I-356 | 1.667 | 4 |
| I-357 | 1.667 | 1 |
| I-358 | 1.667 | 3 |
| I-359 | 1.667 | 3 |
| I-360 | 1.667 | 2 |
| I-361 | 1.667 | 1 |
| I-362 | 1.667 | 2 |
| I-363 | 1.667 | 3 |
| I-364 | 1.667 | 4 |
| I-365 | 1.667 | 1 |
| I-366 | 1.667 | 1 |
| I-367 | 1.667 | 0 |
| I-368 | 1.667 | 1 |
| I-369 | 1.667 | 2 |
| I-370 | 1.667 | 3 |
| I-371 | 1.667 | 3 |
| I-372 | 1.667 | 2 |
| I-373 | 1.667 | 2 |
| I-374 | 1.667 | 3 |
| I-375 | 1.667 | 2 |
| I-376 | 1.667 | 52 |
| I-377 | 1.667 | 2 |
| I-378 | 1.667 | 2 |
| I-379 | 1.667 | 2 |
| I-380 | 1.667 | 2 |
| I-381 | 1.667 | 2 |
| I-382 | 1.667 | 3 |
| I-383 | 1.667 | 2 |

TABLE 3-continued

PC3 Growth Inhibition of Compounds of the Invention

| Compound | Concentration (μM) | Percent Inhibition |
|---|---|---|
| I-384 | 1.667 | 2 |
| I-385 | 1.667 | 2 |
| I-386 | 1.667 | 2 |
| I-387 | 1.667 | 5 |
| I-388 | 1.667 | 3 |
| I-389 | 1.667 | 2 |
| I-390 | 1.667 | 2 |
| I-391 | 1.667 | 3 |
| I-392 | 1.667 | 1 |
| I-393 | 1.667 | 2 |
| I-394 | 1.667 | 3 |
| I-395 | 1.667 | 2 |
| I-396 | 1.667 | 2 |
| I-397 | 1.667 | 2 |
| I-398 | 1.667 | 2 |
| I-399 | 1.667 | 1 |
| I-400 | 1.667 | 2 |
| I-401 | 1.667 | 99 |
| I-402 | 1.667 | 2 |
| I-403 | 1.667 | 0 |
| I-404 | 1.667 | 1 |
| I-405 | 1.667 | 3 |
| I-406 | 1.667 | 2 |
| I-407 | 1.667 | 2 |
| I-408 | 1.667 | >99 |
| I-409 | 1.667 | 2 |
| I-410 | 1.667 | 2 |
| I-411 | 1.667 | 2 |
| I-412 | 1.667 | 6 |
| I-413 | 1.667 | 3 |
| I-414 | 1.667 | 1 |
| I-415 | 1.667 | 2 |
| I-416 | 1.667 | 2 |
| I-417 | 1.667 | 2 |
| I-418 | 1.667 | 3 |
| I-419 | 1.667 | 3 |
| I-420 | 1.667 | 2 |
| I-421 | 1.667 | 1 |
| I-422 | 1.667 | 3 |
| I-423 | 1.667 | 2 |
| I-424 | 1.667 | 1 |
| I-425 | 1.667 | 3 |
| I-426 | 1.667 | 0 |
| I-427 | 1.667 | 2 |
| I-428 | 1.667 | 2 |
| I-429 | 1.667 | 76 |
| I-430 | 1.667 | 3 |
| I-431 | 1.667 | 2 |
| I-432 | 1.667 | 2 |
| I-433 | 1.667 | 3 |
| I-434 | 1.667 | 3 |
| I-435 | 1.667 | 0 |
| I-436 | 1.667 | 2 |
| I-437 | 1.667 | 3 |
| I-438 | 1.667 | 2 |
| I-439 | 1.667 | 3 |
| I-440 | 1.667 | 3 |
| I-441 | 1.667 | >99 |
| I-442 | 1.667 | 3 |
| I-443 | 1.667 | 11 |
| I-444 | 1.667 | 1 |
| I-445 | 1.667 | 2 |
| I-446 | 1.667 | 2 |
| I-447 | 1.667 | 2 |
| I-448 | 1.667 | 2 |
| I-449 | 1.667 | 3 |
| I-450 | 1.667 | 1 |
| I-451 | 1.667 | 2 |
| I-452 | 1.667 | 3 |
| I-453 | 1.667 | 3 |
| I-454 | 1.667 | 2 |
| I-455 | 1.667 | 3 |
| I-456 | 1.667 | 2 |
| I-457 | 1.667 | 2 |
| I-458 | 1.667 | 2 |
| I-459 | 1.667 | >99 |
| I-460 | 1.667 | 2 |
| I-461 | 1.667 | 2 |
| I-462 | 1.667 | 2 |
| I-463 | 1.667 | 3 |
| I-464 | 1.667 | 0 |
| I-465 | 1.667 | 2 |
| I-466 | 1.667 | 2 |
| I-467 | 1.667 | 2 |
| I-468 | 1.667 | 2 |
| I-469 | 1.667 | 2 |
| I-470 | 1.667 | 2 |
| I-471 | 1.667 | 2 |
| I-472 | 1.667 | 2 |
| I-473 | 1.667 | 3 |
| I-474 | 1.667 | 3 |
| I-475 | 1.667 | 3 |
| I-476 | 1.667 | 3 |
| I-477 | 1.667 | 2 |
| I-478 | 1.667 | 2 |
| I-479 | 1.667 | 3 |
| I-480 | 1.667 | 1 |
| I-481 | 1.667 | 2 |
| I-482 | 1.667 | 2 |
| I-483 | 1.667 | 2 |
| I-484 | 1.667 | 2 |
| I-485 | 1.667 | 2 |
| I-486 | 1.667 | 2 |
| I-487 | 1.667 | 1 |
| I-488 | 1.667 | 2 |
| I-489 | 1.667 | 2 |
| I-490 | 1.667 | 2 |
| I-491 | 1.667 | 4 |
| I-492 | 1.667 | 3 |
| I-493 | 1.667 | 1 |
| I-494 | 1.667 | 3 |
| I-495 | — | — |
| I-496 | 1.667 | >99 |
| I-497 | 1.667 | 2 |
| I-498 | 1.667 | 3 |
| I-499 | 1.667 | 2 |
| I-500 | 1.667 | 3 |
| I-501 | 1.667 | 2 |
| I-502 | 1.667 | 2 |
| I-503 | 1.667 | 3 |
| I-504 | 1.667 | 3 |
| I-505 | 1.667 | 3 |
| I-506 | 1.667 | >99 |
| I-507 | 1.667 | 2 |
| I-508 | 1.667 | 3 |
| I-509 | 1.667 | 3 |
| I-510 | 1.667 | 2 |
| I-511 | 1.667 | 2 |
| I-512 | 1.667 | 2 |
| I-513 | 1.667 | 3 |
| I-514 | 1.667 | 3 |
| I-515 | 1.667 | 1 |
| I-516 | 1.667 | 1 |
| I-517 | 1.667 | 1 |
| I-518 | 1.667 | 1 |
| I-519 | 1.667 | 99 |
| I-520 | 1.667 | 1 |

As detailed above, compounds of the invention inhibit NAMPT. In certain embodiments, compounds of the invention inhibit NAMPT with the percent inhibition at the concentrations shown in the table below. In certain embodiments, compounds of the invention inhibit NAMPT with the $IC_{50}$ values shown in the table below.

While we have described a number of embodiments of this invention, it is apparent that our basic examples may be altered to provide other embodiments, which utilize the compounds and methods of this invention. Therefore, it will

What is claimed:
1. A compound of formula I:

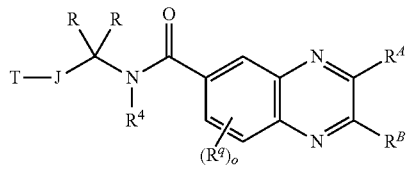

or a pharmaceutically acceptable salt thereof,
wherein:
$R^A$ and $R^B$ are each independently selected from

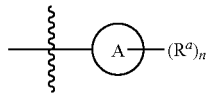

and $XR^1R^2R^3$, provided that one of $R^A$ and $R^B$ is

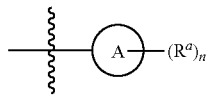

and the other is $XR^1R^2R^3$;
X is selected from CN, halogen, C, S, and N, provided that (1) when X is N, then one of $R^1$, $R^2$, and $R^3$ is absent, (2) when X is halogen or CN, then $R^1$, $R^2$, and $R^3$ are absent, and (3) when X is S, then two of $R^1$, $R^2$, and $R^3$ are absent;
$R^1$, $R^2$, and $R^3$ are each independently selected from hydrogen; $OR^{20}$; $N(R^{20})_2$; $C_{1-6}$ aliphatic, wherein 1 or 2 methylene units of the $C_{1-6}$ aliphatic are optionally and independently replaced by O, S, S(O), S(O)$_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl is optionally substituted with one or more $R^k$;
or wherein any two of $R^1$, $R^2$, and $R^3$ taken together with the atom X to which they are bound, when X is C or N, form a ring selected from a 4-10-membered heterocycle having 1-5 heteroatoms independently selected from nitrogen, oxygen and sulfur and a 3-10-membered cycloaliphatic, wherein the ring is optionally substituted with one or more $R^b$,
or wherein any two of $R^1$, $R^2$, and $R^3$ taken together with the atom X to which they are bound, when X is N, form a 5-10-membered heteroaryl having 1-5 heteroatoms independently selected from nitrogen, oxygen, and sulfur, wherein the heteroaryl is optionally substituted with one or more $R^b$,
or wherein $R^1$, $R^2$, and $R^3$ taken together with the atom X to which they are bound, when X is C, form a ring selected from a 5-10-membered heteroaryl having 1-4 heteroatoms independently selected from nitrogen, oxygen, and sulfur and a 6-10-membered aryl, wherein the ring is optionally substituted with one or more $R^b$;
or X is O, $R^2$ and $R^3$ are absent, and $R^1$ is $R^{1A}$;
wherein $R^{1A}$ is selected from $C_{1-6}$ aliphatic, $(CH_2)_s$-6-10-membered aryl, $(CH_2)_t$-3-10-membered cycloaliphatic, $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the aliphatic, aryl, cycloaliphatic, heterocycle, and heteroaryl are optionally substituted with one or more $R^k$,

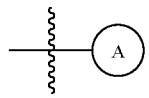

is a ring selected from a 3-7-membered saturated, partially unsaturated, and aromatic monocyclic ring having 0-3 heteroatoms independently selected from nitrogen, oxygen, and sulfur and an 8-10-membered saturated, partially unsaturated, and aromatic bicyclic ring having 0-5 heteroatoms independently selected from nitrogen, oxygen, and sulfur;
each occurrence of $R^a$ is independently selected from $C_{1-6}$ aliphatic and $Z_1$—$R^8$;
or wherein two $R^a$ taken together with the atom or atoms to which they are bound, form a ring selected from a 4-10-membered heterocycle having 1-5 heteroatoms independently selected from nitrogen, oxygen, and sulfur and a 3-6-membered cycloaliphatic, wherein the ring is optionally substituted with one or more $R^p$ each occurrence of $R^p$ is independently selected from CN, $CH_3$, $CF_3$, $CH_2F$, $CF_2H$, $NH_2$, $NH(C_{1-3}$ aliphatic), $N(C_{1-3}$ aliphatic)$_2$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;
each occurrence of $Z_1$ is independently selected from a direct bond, $C_{1-3}$ alkylene chain, O, $N(R^{16})$, S, S(O), $S(O)_2$, C(O), $CO_2$, $C(O)NR^{16}$, $N(R^{16})C(O)$, $N(R^{16})CO_2$, $S(O)_2NR^{16}$, $N(R^{16})S(O)_2$, $OC(O)N(R^{16})$, $N(R^{16})C(O)NR^{16}$, $N(R^{16})S(O)_2N(R^{16})$, and OC(O), wherein the alkylene chain is optionally substituted with one or more $R^h$;
each occurrence of $R^h$ is independently selected from CN, $CH_3$, $CF_3$, $CH_2F$, $CF_2H$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;
each occurrence of $R^b$ is independently selected from $C_{1-6}$ aliphatic and $Z_2$—$R^6$;
or wherein two $R^b$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein the ring is optionally substituted with one or more $R^c$;

each occurrence of $R^c$ is independently selected from $C_{1-6}$ aliphatic, $CF_3$, $CF_2H$, $CH_2F$, halogen, $OR^{12}$, $(CH_2)_v$—$C(O)R^9$, and $(CH_2)_w$—$NR^{10}C(O)R^{11}$;

each occurrence of $Z_2$ is independently selected from direct bond, $C_{1-3}$ alkylene chain, O, $N(R^{17})$, S, $S(O)$, $S(O)_2$, $C(O)$, $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2N(R^{17})$, and $OC(O)$, wherein the alkylene chain is optionally substituted with one or more $R^i$;

each occurrence of $R^i$ is independently selected from CN, $CH_3$, $CF_3$, $CH_2F$, $CF_2H$, halogen, OH, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^k$ is independently selected from $C_{1-6}$ aliphatic and $Z_3$—$R^{23}$;

or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 7-10-membered saturated, partially unsaturated, or aromatic bicyclic ring having 0-5 heteroatoms independently selected from nitrogen, oxygen, and sulfur, wherein the ring is optionally substituted with one or more $R^m$;

each occurrence of $R^m$ is independently selected from $C_{1-6}$ aliphatic, $CF_3$, CN, $CH_2F$, $CF_2H$, halogen, $OR^{25}$, $(CH_2)_q$—$C(O)R^{26}$, and $(CH_2)_r$—$NR^{27}C(O)R^{28}$;

each occurrence of $Z_3$ is independently selected from direct bond, $C_{1-3}$ alkylene chain, O, $N(R^{24})$, S, $S(O)$, $S(O)_2$, $C(O)$, $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and $OC(O)$, wherein the alkylene chain is optionally substituted with one or more $R^n$;

each occurrence of $R^n$ is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic), and $C_{2-3}$ aliphatic, wherein said $C_{2-3}$ aliphatic is optionally substituted with one or more F;

J is selected from a linear $C_{1-6}$aliphatic, wherein 1 or 2 methylene units of J are optionally and independently replaced by O, S, or $N(R^{13})$ and further wherein the $C_{1-6}$aliphatic is optionally substituted with one or more $R^j$;

each occurrence of $R^j$ is independently selected from fluorine, $CH_3$, $CF_3$, $CH_2F$, $CF_2H$, OH, $OCH_3$, $OCF_3$, $OCH_2F$, $OCF_2H$, $O(C_{2-3}$aliphatic), $NH_2$, $NH(C_{1-3}$aliphatic), $N(C_{1-3}$aliphatic$)_2$, and $C_{2-3}$ aliphatic, wherein said $C_{2-3}$ aliphatic is optionally substituted with one or more F;

or wherein two $R^j$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein the ring is optionally substituted with one or more $R^e$;

or wherein $R^j$ and one of R taken together with the atom or atoms to which they are bound form a ring selected from a 3-6-membered heterocycle having 1 heteroatom selected from nitrogen, oxygen, and sulfur and a 3-6-membered cycloaliphatic, wherein the ring is optionally substituted with one or more $R^e$;

each occurrence of R is independently selected from hydrogen and $C_{1-3}$ aliphatic, wherein the $C_{1-3}$ aliphatic is optionally substituted with one or more F;

$R^4$ is selected from hydrogen and $C_{1-6}$ aliphatic;

or wherein one of R and $R^4$ or $R^j$ and $R^4$ taken together with the atoms to which they are bound, form a 4-10-membered heterocycle having 1-5 heteroatoms independently selected from nitrogen, oxygen, and sulfur, wherein the heterocycle is optionally substituted with one or more $R^e$;

each occurrence of $R^e$ is independently selected from halogen, $CF_3$, $CF_2H$, $CH_2F$, $C_{1-6}$aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^{h'}$;

or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^{h'}$;

each occurrence of $R^{h'}$ is independently selected from halogen, $CF_3$, $CF_2H$, $CH_2F$, $C_{1-6}$ aliphatic, $C(O)N(R^{18})_2$, OH, and $OC_{1-6}$ aliphatic;

each occurrence of $R^5$ is independently selected from hydrogen, $CF_3$, $CF_2H$, $CH_2F$, and $C_{1-6}$ aliphatic;

each occurrence of $R^6$ is independently selected from CN, halogen, $OR^7$, $N(R^{19})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^c$;

each occurrence of $R^7$ is independently selected from hydrogen, $CF_3$, $CF_2H$, $CH_2F$, $C_{1-6}$ aliphatic, and 6-10-membered aryl;

each occurrence of $R^8$ is independently selected from CN, halogen, $OR^5$, $N(R^{21})_2$, $C_{1-6}$ aliphatic, 6-10-membered aryl, 3-10 membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein the aryl, cycloaliphatic, heteroaryl, and heterocycle is optionally substituted with one or more $R^g$;

each occurrence of $R^g$ is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^9$ is independently selected from OH, $OC_{1-6}$ aliphatic, $N(R^{15})_2$, and $C_{1-6}$ aliphatic;

each occurrence of $R^{10}$ is independently selected from hydrogen and $C_{1-6}$aliphatic;

each occurrence of $R^{11}$ is independently selected from OH, $OC_{1-6}$aliphatic, $N(R^{14})_2$, and $C_{1-6}$aliphatic;

each occurrence of $R^{12}$ is independently selected from hydrogen and $C_{1-6}$aliphatic;

each occurrence of $R^{13}$ is independently selected from hydrogen and $C_{1-6}$aliphatic;

each occurrence of $R^{14}$ is independently selected from hydrogen and $C_{1-6}$aliphatic;
each occurrence of $R^{15}$ is independently selected from hydrogen and $C_{1-6}$aliphatic;
each occurrence of $R^{16}$ is independently selected from hydrogen and $C_{1-6}$aliphatic;
each occurrence of $R^{17}$ is independently selected from hydrogen and $C_{1-6}$aliphatic;
each occurrence of $R^{18}$ is independently selected from hydrogen and $C_{1-6}$ aliphatic;
each occurrence of $R^{19}$ is independently selected from hydrogen and $C_{1-3}$ aliphatic;
each occurrence of $R^{20}$ is independently selected from hydrogen and $C_{1-6}$ aliphatic;
each occurrence of $R^{21}$ is independently selected from hydrogen and $C_{1-6}$aliphatic;
each occurrence of $R^{23}$ is independently selected from CN, halogen, $OR^{31}$, $N(R^{32})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^m$;
each occurrence of $R^{24}$ is independently selected from hydrogen and $C_{1-6}$aliphatic;
each occurrence of $R^{25}$ is independently selected from hydrogen and $C_{1-6}$aliphatic;
each occurrence of $R^{26}$ is independently selected from OH, $OC_{1-6}$ aliphatic, $N(R^{29})_2$, and $C_{1-6}$ aliphatic;
each occurrence of $R^{27}$ is independently selected from hydrogen and $C_{1-6}$aliphatic;
each occurrence of $R^{28}$ is independently selected from OH, $OC_{1-6}$aliphatic, $N(R^{30})_2$, and $C_{1-6}$aliphatic;
each occurrence of $R^{29}$ is independently selected from hydrogen and $C_{1-6}$aliphatic;
each occurrence of $R^{30}$ is independently selected from hydrogen and $C_{1-6}$aliphatic;
each occurrence of $R^{31}$ is independently selected from hydrogen, $CF_3$, $CF_2H$, $CH_2F$, $C_{1-6}$aliphatic, and 6-10-membered aryl;
each occurrence of $R^{32}$ is independently selected from hydrogen and $C_{1-3}$ aliphatic;
each occurrence of $R^{33}$ is independently selected from hydrogen and $C_{1-3}$ aliphatic;
T is $(CH_2)_z$-5-10-membered monocyclic or bicyclic heteroaryl having 1-5 heteroatoms independently selected from nitrogen, oxygen, and sulfur, wherein the heteroaryl is optionally substituted with one or more $R^d$;
each occurrence of $R^d$ is independently selected from halogen, $N(R^{33})_2$, and $C_{1-6}$aliphatic or wherein taken together two $R^d$ together with the atom or atoms to which they are bound, form a 4-10-membered heterocycle having 1-5 heteroatoms independently selected from nitrogen, oxygen, and sulfur;
each occurrence of $R^q$ is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic), and $C_{2-3}$ aliphatic, wherein said $C_{2-3}$ aliphatic is optionally substituted with one or more F;
n is 0, 1, 2, 3, 4, or 5;
o is 0, 1, 2, or 3;
p is 0, 1, 2, or 3;
q is 0, 1, 2, or 3;
r is 0, 1, 2, or 3;
s is 0, 1, 2, or 3;

t is 0, 1, 2, or 3;
u is 0, 1, 2, or 3;
v is 0, 1, 2, or 3;
w is 0, 1, 2, or 3;
x is 0, 1, 2, or 3; and
z is 0, 1, 2, or 3;
provided that:
1) when $R^A$ and $R^B$ are the same and selected from optionally substituted phenyl, unsubstituted 2-furan, unsubstituted 3-furan, unsubstituted 3-thiophene, optionally substituted 2-pyridine, and unsubstituted 2-thiophene;
o is 0;
R and $R^4$ are hydrogen;
J is unsubstituted $C_1$ aliphatic, then
T is other than

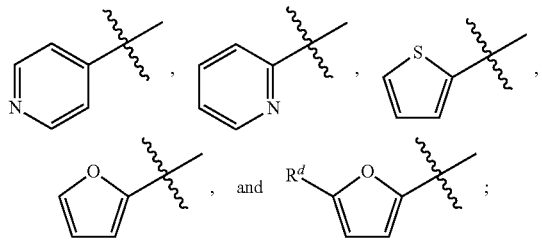

and
2) the compound is other than:

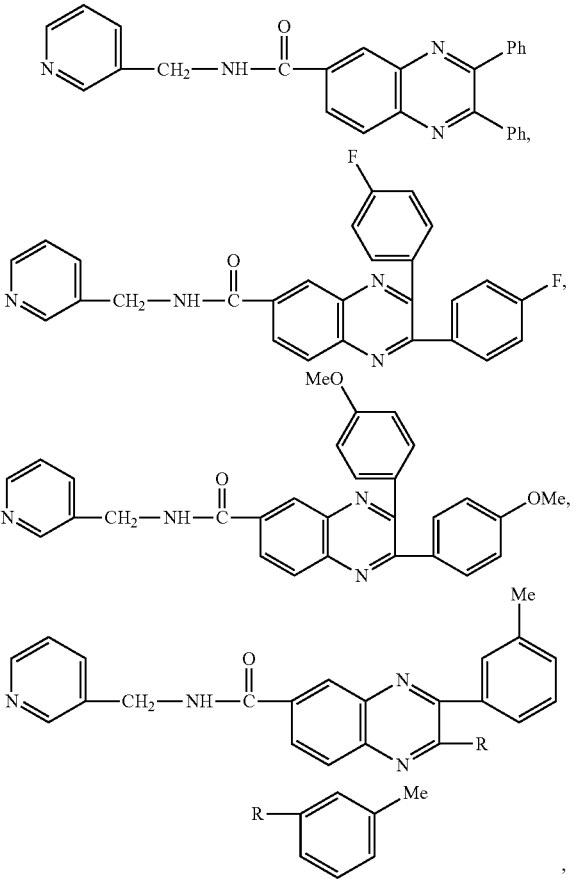

533
-continued

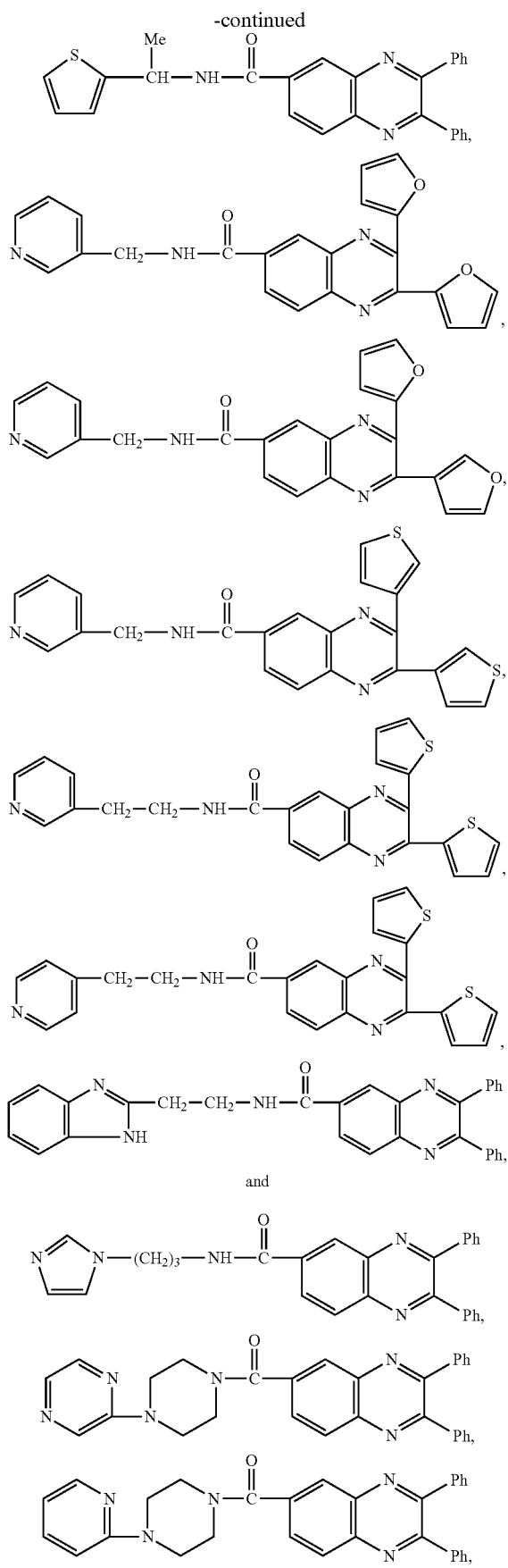

and

534
-continued

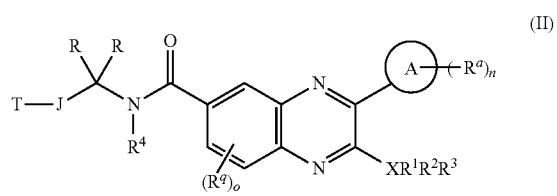

, and

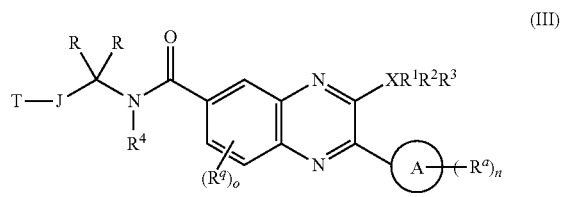

.

2. The compound of claim 1 of formula II:

$$\text{(II)}$$

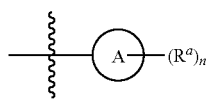

or a pharmaceutically acceptable salt thereof.

3. The compound of claim 1 of formula III:

$$\text{(III)}$$

or a pharmaceutically acceptable salt thereof.

4. The compound of claim 1 or a pharmaceutically acceptable salt thereof, wherein J is selected from $C_1$ aliphatic, and $C_2$ aliphatic.

5. The compound of claim 1 or a pharmaceutically acceptable salt thereof, wherein is selected from a 6 or 10-membered aryl and a 5-6 membered heteroaryl having 1-3 heteroatoms independently selected from nitrogen, oxygen, and sulfur, wherein the aryl and heteroaryl are optionally substituted with one or more $R^a$.

6. The compound of claim 1 or a pharmaceutically acceptable salt thereof, wherein X is N and one of $R^1$, $R^2$, and $R^3$ is absent.

7. The compound of claim 1 or a pharmaceutically acceptable salt thereof, wherein X is S and two of $R^1$, $R^2$, and $R^3$ are absent.

8. The compound of claim 1 or a pharmaceutically acceptable salt thereof, wherein X is C and $R^1$, $R^2$, and $R^3$ taken together with the carbon atom to which they are bound form a ring selected from a 5-10-membered heteroaryl having 1-5 heteroatoms independently selected from nitrogen, oxygen, and sulfur and a 6-10-membered aryl, wherein the ring is optionally substituted with one or more $R^b$.

9. The compound of claim 1 or a pharmaceutically acceptable salt thereof, wherein X is C and any two of $R^1$, $R^2$, and $R^3$ taken together with the carbon atom to which they are bound form a ring selected from 4-10-membered heterocycle having 1-5 heteroatoms independently selected from nitrogen, oxygen, and sulfur and a 3-10-membered cycloaliphatic, wherein the ring is optionally substituted with one or more $R^b$.

10. The compound of claim 1 or a pharmaceutically acceptable salt thereof, wherein X is halogen and $R^1$, $R^2$, and $R^3$ are absent.

11. A compound chosen from Table 1 or a pharmaceutically acceptable salt thereof.

12. A pharmaceutical composition comprising a pharmaceutically acceptable carrier and a compound of formula I:

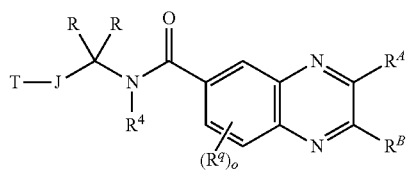

(I)

or a pharmaceutically acceptable salt thereof, wherein:

$R^A$ and $R^B$ are each independently selected from

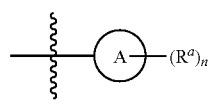

and $XR^1R^2R^3$, provided that one of $R^A$ and $R^B$ is

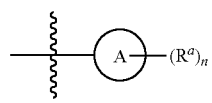

and the other is $XR^1R^2R^3$;

X is selected from CN, halogen, C, S, and N, provided that (1) when X is N, then one of $R^1$, $R^2$, and $R^3$ is absent, (2) when X is halogen or CN, then $R^1$, $R^2$, and $R^3$ are absent, and (3) when X is S, then two of $R^1$, $R^2$, and $R^3$ are absent;

$R^1$, $R^2$, and $R^3$ are each independently selected from hydrogen; $OR^{20}$; $N(R^{20})_2$; $C_{1-6}$aliphatic, wherein 1 or 2 methylene units of the $C_{1-6}$ aliphatic are optionally and independently replaced by O, S, S(O), S(O)$_2$, or N($R^{19}$); $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl is optionally substituted with one or more $R^k$;

or wherein any two of $R^1$, $R^2$, and $R^3$ taken together with the atom X to which they are bound, when X is C or N, form a ring selected from a 4-10-membered heterocycle having 1-5 heteroatoms independently selected from nitrogen, oxygen and sulfur and a 3-10-membered cycloaliphatic, wherein the ring is optionally substituted with one or more $R^b$, or wherein any two of $R^1$, $R^2$, and $R^3$ taken together with the atom X to which they are bound, when X is N, form a 5-10-membered heteroaryl having 1-5 heteroatoms independently selected from nitrogen, oxygen, and sulfur, wherein the heteroaryl is optionally substituted with one or more $R^b$, or wherein $R^1$, $R^2$, and $R^3$ taken together with the atom X to which they are bound, when X is C, form a ring selected from a 5-10-membered heteroaryl having 1-4 heteroatoms independently selected from nitrogen, oxygen, and sulfur and a 6-10-membered aryl, wherein the ring is optionally substituted with one or more $R^b$;

or X is O, $R^2$ and $R^3$ are absent, and $R^1$ is $R^{14}$;

wherein $R^{14}$ is selected from $C_{1-6}$ aliphatic, $(CH_2)_s$-6-10-membered aryl, $(CH_2)_t$-3-10-membered cycloaliphatic, $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the aliphatic, aryl, cycloaliphatic, heterocycle, and heteroaryl are optionally substituted with one or more $R^k$,

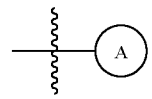

is a ring selected from a 3-7-membered saturated, partially unsaturated, and aromatic monocyclic ring having 0-3 heteroatoms independently selected from nitrogen, oxygen, and sulfur and an 8-10-membered saturated, partially unsaturated, and aromatic bicyclic ring having 0-5 heteroatoms independently selected from nitrogen, oxygen, and sulfur;

each occurrence of $R^a$ is independently selected from $C_{1-6}$ aliphatic and $Z_1$—$R^8$;

or wherein two $R^a$ taken together with the atom or atoms to which they are bound, form a ring selected from a 4-10-membered heterocycle having 1-5 heteroatoms independently selected from nitrogen, oxygen, and sulfur and a 3-6-membered cycloaliphatic, wherein the ring is optionally substituted with one or more $R^p$ each occurrence of $R^p$ is independently selected from CN, $CH_3$, $CF_3$, $CH_2F$, $CF_2H$, $NH_2$, $NH(C_{1-3}$ aliphatic), $N(C_{1-3}$ aliphatic)$_2$, OH, halogen, $OCH_3$, $OCF_3$, $OCH_2F$, OCF$_2$H, O(C$_{2-3}$ aliphatic) and C$_{2-3}$ aliphatic, wherein said C$_{2-3}$ aliphatic is optionally substituted with one or more F;

each occurrence of Z$_1$ is independently selected from a direct bond, C$_{1-3}$ alkylene chain, O, N(R$^{16}$), S, S(O), S(O)$_2$, C(O), CO$_2$, C(O)NR$^{16}$, N(R$^{16}$)C(O), N(R$^{16}$)CO$_2$, S(O)$_2$NR$^{16}$, N(R$^{16}$)S(O)$_2$, OC(O)N(R$^{16}$), N(R$^{16}$)C(O)NR$^{16}$, N(R$^{16}$)S(O)$_2$N(R$^{16}$), and OC(O), wherein the alkylene chain is optionally substituted with one or more R$^h$;

each occurrence of R$^h$ is independently selected from CN, CH$_3$, CF$_3$, CH$_2$F, CF$_2$H, OH, halogen, OCH$_3$, OCF$_3$, OCH$_2$F, OCF$_2$H, O(C$_{2-3}$ aliphatic) and C$_{2-3}$ aliphatic, wherein said C$_{2-3}$ aliphatic is optionally substituted with one or more F;

each occurrence of R$^b$ is independently selected from C$_{1-6}$ aliphatic and Z$_2$—R$^6$;

or wherein two R$^b$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein the ring is optionally substituted with one or more R$^c$;

each occurrence of R$^c$ is independently selected from C$_{1-6}$ aliphatic, CF$_3$, CF$_2$H, CH$_2$F, halogen, OR$^{12}$, (CH$_2$)$_v$—C(O)R$^9$, and (CH$_2$)$_w$—NR$^{10}$C(O)R$^{11}$;

each occurrence of Z$_2$ is independently selected from direct bond, C$_{1-3}$ alkylene chain, O, N(R$^{17}$), S, S(O), S(O)$_2$, C(O), CO$_2$, C(O)NR$^{17}$, N(R$^{17}$)C(O), N(R$^{17}$)CO$_2$, S(O)$_2$NR$^{17}$, N(R$^{17}$)S(O)$_2$, OC(O)N(R$^{17}$), N(R$^{17}$)C(O)NR$^{17}$, N(R$^{17}$)S(O)$_2$N(R$^{17}$), and OC(O), wherein the alkylene chain is optionally substituted with one or more R$^i$;

each occurrence of R$^i$ is independently selected from CN, CH$_3$, CF$_3$, CH$_2$F, CF$_2$H, halogen, OH, OCH$_3$, OCF$_3$, OCH$_2$F, OCF$_2$H, O(C$_{2-3}$ aliphatic) and C$_{2-3}$ aliphatic, wherein said C$_{2-3}$ aliphatic is optionally substituted with one or more F;

each occurrence of R$^k$ is independently selected from C$_{1-6}$ aliphatic and Z$_3$—R$^{23}$;

or wherein two R$^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 7-10-membered saturated, partially unsaturated, or aromatic bicyclic ring having 0-5 heteroatoms independently selected from nitrogen, oxygen, and sulfur, wherein the ring is optionally substituted with one or more R$^m$;

each occurrence of R$^m$ is independently selected from C$_{1-6}$ aliphatic, CF$_3$, CN, CH$_2$F, CF$_2$H, halogen, OR$^{25}$, (CH$_2$)$_q$—C(O)R$^{26}$, and (CH$_2$)$_r$—NR$^{27}$C(O)R$^{28}$;

each occurrence of Z$_3$ is independently selected from direct bond, C$_{1-3}$ alkylene chain, O, N(R$^{24}$), S, S(O), S(O)$_2$, C(O), CO$_2$, C(O)NR$^{24}$, N(R$^{24}$)C(O), N(R$^{24}$)CO$_2$, S(O)$_2$NR$^{24}$, N(R$^{24}$)S(O)$_2$, OC(O)N(R$^{24}$), N(R$^{24}$)C(O)NR$^{24}$, N(R$^{24}$)S(O)$_2$N(R$^{24}$), and OC(O), wherein the alkylene chain is optionally substituted with one or more R$^n$;

each occurrence of R$^n$ is independently selected from CN, CH$_3$, CF$_3$, CF$_2$H, CH$_2$F, halogen, OH, OCH$_3$, OCF$_3$, OCH$_2$F, OCF$_2$H, O(C$_{2-3}$ aliphatic), and C$_{2-3}$ aliphatic, wherein said C$_{2-3}$ aliphatic is optionally substituted with one or more F;

J is selected from; a linear C$_{1-6}$aliphatic, wherein 1 or 2 methylene units of J are optionally and independently replaced by O, S, or N(R$^{13}$) and further wherein the C$_{1-6}$aliphatic is optionally substituted with one or more R$^j$;

each occurrence of R$^j$ is independently selected from fluorine, CH$_3$, CF$_3$, CH$_2$F, CF$_2$H, OH, OCH$_3$, OCF$_3$, OCH$_2$F, OCF$_2$H, O(C$_{2-3}$aliphatic), NH$_2$, NH(C$_{1-3}$aliphatic), N(C$_{1-3}$aliphatic)$_2$, and C$_{2-3}$ aliphatic, wherein said C$_{2-3}$ aliphatic is optionally substituted with one or more F;

or wherein two R$^j$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein the ring is optionally substituted with one or more R$^e$;

or wherein R$^j$ and one of R taken together with the atom or atoms to which they are bound form a ring selected from a 3-6-membered heterocycle having 1 heteroatom selected from nitrogen, oxygen, and sulfur and a 3-6-membered cycloaliphatic, wherein the ring is optionally substituted with one or more R$^e$;

each occurrence of R is independently selected from hydrogen and C$_{1-3}$ aliphatic, wherein the C$_{1-3}$ aliphatic is optionally substituted with one or more F;

R$^4$ is selected from hydrogen and C$_{1-6}$ aliphatic;

or wherein one of R and R$^4$ or R and R$^4$ taken together with the atoms to which they are bound, form a 4-10-membered heterocycle having 1-5 heteroatoms independently selected from nitrogen, oxygen, and sulfur, wherein the heterocycle is optionally substituted with one or more R$^e$;

each occurrence of R$^e$ is independently selected from halogen, CF$_3$, CF$_2$H, CH$_2$F, C$_{1-6}$aliphatic, and (CH$_2$)$_x$-[3-7-membered saturated, partially unsaturated, or aromatic monocyclic ring having 1-3 heteroatoms independently selected from nitrogen, oxygen, and sulfur], wherein the ring is optionally substituted with one or more R$^{h'}$;

or wherein two R$^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more R$^{h'}$;

each occurrence of R$^{h'}$ is independently selected from halogen, CF$_3$, CF$_2$H, CH$_2$F, C$_{1-6}$ aliphatic, C(O)N(R$^{18}$)$_2$, OH, and OC$_{1-6}$ aliphatic;

each occurrence of R$^5$ is independently selected from hydrogen, CF$_3$, CF$_2$H, CH$_2$F, and C$_{1-6}$ aliphatic;

each occurrence of R$^6$ is independently selected from CN, halogen, OR$^7$, N(R$^{19}$)$_2$, C$_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more R$^c$;

each occurrence of R$^7$ is independently selected from hydrogen, CF$_3$, CF$_2$H, CH$_2$F, C$_{1-6}$ aliphatic, and 6-10-membered aryl;

each occurrence of $R^8$ is independently selected from CN, halogen, $OR^5$, $N(R^{21})_2$, $C_{1-6}$ aliphatic, 6-10-membered aryl, 3-10 membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein the aryl, cycloaliphatic, heteroaryl, and heterocycle is optionally substituted with one or more $R^g$;

each occurrence of $R^g$ is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^9$ is independently selected from OH, $OC_{1-6}$ aliphatic, $N(R^{15})_2$, and $C_{1-6}$ aliphatic;

each occurrence of $R^{10}$ is independently selected from hydrogen and $C_{1-6}$ aliphatic;

each occurrence of $R^{11}$ is independently selected from OH, $OC_{1-6}$ aliphatic, $N(R^{14})_2$, and $C_{1-6}$ aliphatic;

each occurrence of $R^{12}$ is independently selected from hydrogen and $C_{1-6}$ aliphatic;

each occurrence of $R^{13}$ is independently selected from hydrogen and $C_{1-6}$ aliphatic;

each occurrence of $R^{14}$ is independently selected from hydrogen and $C_{1-6}$ aliphatic;

each occurrence of $R^{15}$ is independently selected from hydrogen and $C_{1-6}$ aliphatic;

each occurrence of $R^{16}$ is independently selected from hydrogen and $C_{1-6}$ aliphatic;

each occurrence of $R^{17}$ is independently selected from hydrogen and $C_{1-6}$ aliphatic;

each occurrence of $R^{18}$ is independently selected from hydrogen and $C_{1-6}$ aliphatic;

each occurrence of $R^{19}$ is independently selected from hydrogen and $C_{1-3}$ aliphatic;

each occurrence of $R^{20}$ is independently selected from hydrogen and $C_{1-6}$ aliphatic;

each occurrence of $R^{21}$ is independently selected from hydrogen and $C_{1-6}$ aliphatic;

each occurrence of $R^{23}$ is independently selected from CN, halogen, $OR^{31}$, $N(R^{32})_2$, $C_{1-6}$ aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^m$;

each occurrence of $R^{24}$ is independently selected from hydrogen and $C_{1-6}$ aliphatic;

each occurrence of $R^{25}$ is independently selected from hydrogen and $C_{1-6}$ aliphatic;

each occurrence of $R^{26}$ is independently selected from OH, $OC_{1-6}$ aliphatic, $N(R^{29})_2$, and $C_{1-6}$ aliphatic;

each occurrence of $R^{27}$ is independently selected from hydrogen and $C_{1-6}$ aliphatic;

each occurrence of $R^{28}$ is independently selected from OH, $OC_{1-6}$ aliphatic, $N(R^{30})_2$, and $C_{1-6}$ aliphatic;

each occurrence of $R^{29}$ is independently selected from hydrogen and $C_{1-6}$ aliphatic;

each occurrence of $R^{30}$ is independently selected from hydrogen and $C_{1-6}$ aliphatic;

each occurrence of $R^{31}$ is independently selected from hydrogen, $CF_3$, $CF_2H$, $CH_2F$, $C_{1-6}$ aliphatic, and 6-10-membered aryl;

each occurrence of $R^{32}$ is independently selected from hydrogen and $C_{1-3}$ aliphatic;

each occurrence of $R^{33}$ is independently selected from hydrogen and $C_{1-3}$ aliphatic;

T is $(CH_2)_z$-5-10-membered monocyclic or bicyclic heteroaryl having 1-5 heteroatoms independently selected from nitrogen, oxygen, and sulfur, wherein the heteroaryl is optionally substituted with one or more $R^d$;

each occurrence of $R^d$ is independently selected from halogen, $N(R^{33})_2$, and $C_{1-6}$ aliphatic or wherein taken together two $R^d$ together with the atom or atoms to which they are bound, form a 4-10-membered heterocycle having 1-5 heteroatoms independently selected from nitrogen, oxygen, and sulfur;

each occurrence of $R^q$ is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic), and $C_{2-3}$ aliphatic, wherein said $C_{2-3}$ aliphatic is optionally substituted with one or more F;

n is 0, 1, 2, 3, 4, or 5;
o is 0, 1, 2, or 3;
p is 0, 1, 2, or 3;
q is 0, 1, 2, or 3;
r is 0, 1, 2, or 3;
s is 0, 1, 2, or 3;
t is 0, 1, 2, or 3;
u is 0, 1, 2, or 3;
v is 0, 1, 2, or 3;
w is 0, 1, 2, or 3;
x is 0, 1, 2, or 3; and
z is 0, 1, 2, or 3;
provided that:
3) when $R^A$ and $R^B$ are the same and selected from optionally substituted phenyl, unsubstituted 2-furan, unsubstituted 3-furan, unsubstituted 3-thiophene, optionally unsubstituted 2-pyridine, and unsubstituted 2-thiophene;
o is 0;
R and $R^4$ are hydrogen;
J is unsubstituted $C_1$ aliphatic, then
T is other than

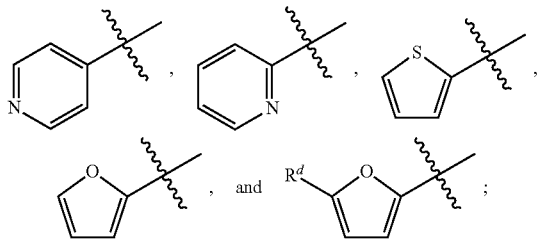

and
4) the compound is other than:

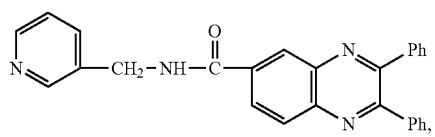

541
-continued
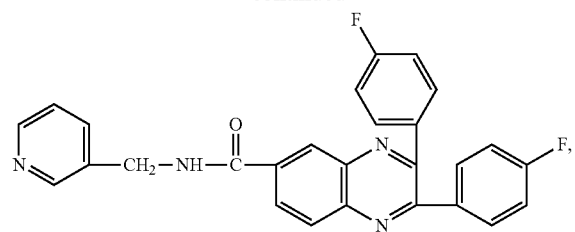
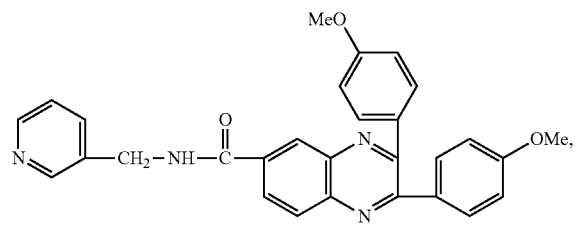
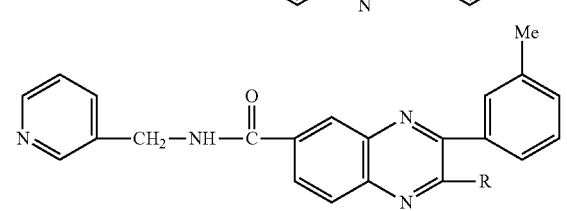
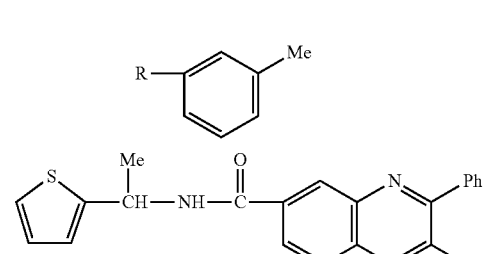
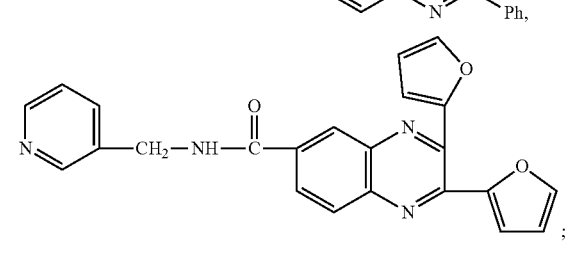
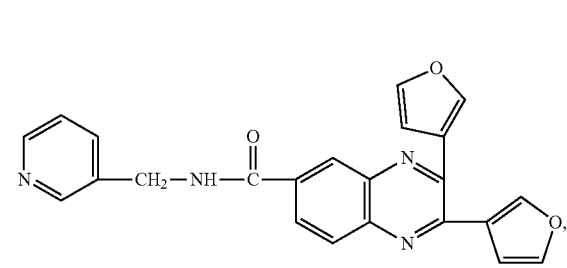
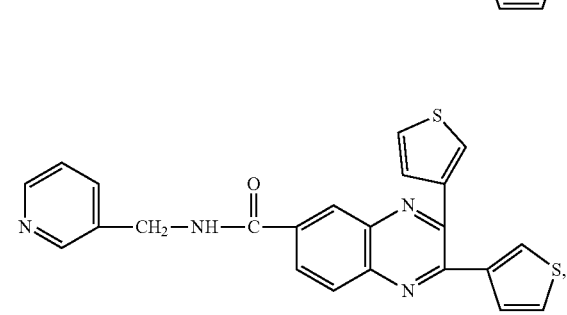
542
-continued
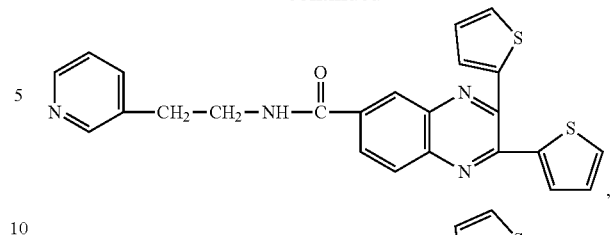
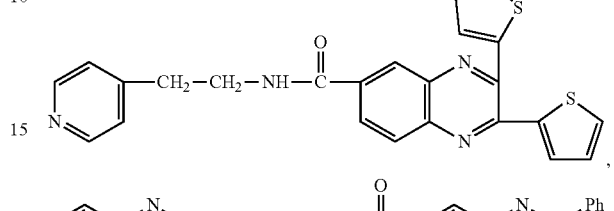
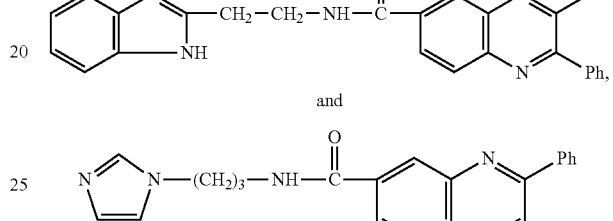
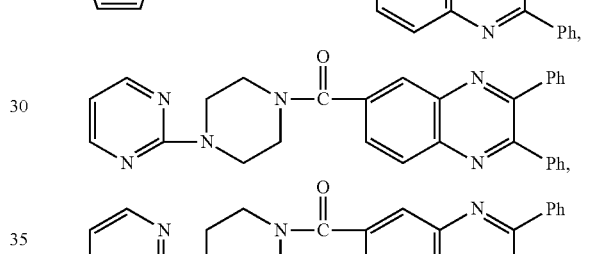

13. The pharmaceutical composition of claim 12, further comprising at least one additional therapeutic agent.

14. A method for inhibiting nicotinamide phosphoribosyltransferase (NAMPT) in a cell comprising contacting the cell with an amount of a compound of formula I:

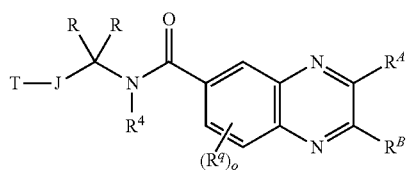
(I)

or a pharmaceutically acceptable salt thereof, wherein:

$R^A$ and $R^B$ are each independently selected from

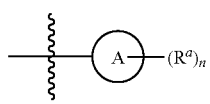

and $XR^1R^2R^3$, provided that one of $R^A$ and $R^B$ is

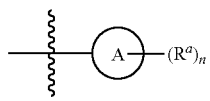

and the other is $XR^1R^2R^3$;

X is selected from CN, halogen, C, S, and N, provided that (1) when X is N, then one of $R^1$, $R^2$, and $R^3$ is absent, (2) when X is halogen or CN, then $R^1$, $R^2$, and $R^3$ are absent, and (3) when X is S, then two of $R^1$, $R^2$, and $R^3$ are absent;

$R^1$, $R^2$, and $R^3$ are each independently selected from hydrogen; $OR^{20}$; $N(R^{20})_2$; $C_{1-6}$aliphatic, wherein 1 or 2 methylene units of the $C_{1-6}$ aliphatic are optionally and independently replaced by O, S, S(O), S(O)$_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl is optionally substituted with one or more $R^k$;

or wherein any two of $R^1$, $R^2$, and $R^3$ taken together with the atom X to which they are bound, when X is C or N, form a ring selected from a 4-10-membered heterocycle having 1-5 heteroatoms independently selected from nitrogen, oxygen and sulfur and a 3-10-membered cycloaliphatic, wherein the ring is optionally substituted with one or more $R^b$, or wherein any two of $R^1$, $R^2$, and $R^3$ taken together with the atom X to which they are bound, when X is N, form a 5-10-membered heteroaryl having 1-5 heteroatoms independently selected from nitrogen, oxygen, and sulfur, wherein the heteroaryl is optionally substituted with one or more $R^b$, or wherein $R^1$, $R^2$, and $R^3$ taken together with the atom X to which they are bound, when X is C, form a ring selected from a 5-10-membered heteroaryl having 1-4 heteroatoms independently selected from nitrogen, oxygen, and sulfur and a 6-10-membered aryl, wherein the ring is optionally substituted with one or more $R^b$;

or X is O, $R^2$ and $R^3$ are absent, and $R^1$ is $R^{1A}$;

wherein $R^{1A}$ is selected from $C_{1-6}$ aliphatic, $(CH_2)_s$-6-10-membered aryl, $(CH_2)_t$-3-10-membered cycloaliphatic, $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the aliphatic, aryl, cycloaliphatic, heterocycle, and heteroaryl are optionally substituted with one or more $R^k$,

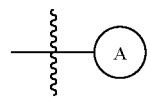

is a ring selected from a 3-7-membered saturated, partially unsaturated, and aromatic monocyclic ring having 0-3 heteroatoms independently selected from nitrogen, oxygen, and sulfur and an 8-10-membered saturated, partially unsaturated, and aromatic bicyclic ring having 0-5 heteroatoms independently selected from nitrogen, oxygen, and sulfur;

each occurrence of $R^a$ is independently selected from $C_{1-6}$ aliphatic and $Z_1$—$R^8$;

or wherein two $R^a$ taken together with the atom or atoms to which they are bound, form a ring selected from a 4-10-membered heterocycle having 1-5 heteroatoms independently selected from nitrogen, oxygen, and sulfur and a 3-6-membered cycloaliphatic, wherein the ring is optionally substituted with one or more $R^p$ each occurrence of $R^p$ is independently selected from CN, $CH_3$, $CF_3$, $CH_2F$, $CF_2H$, $NH_2$, $NH(C_{1-3}$ aliphatic), $N(C_{1-3}$ aliphatic)$_2$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $Z_1$ is independently selected from a direct bond, $C_{1-3}$ alkylene chain, O, $N(R^{16})$, S, S(O), S(O)$_2$, C(O), CO$_2$, C(O)NR$^{16}$, N(R$^{16}$)C(O), N(R$^{16}$)CO$_2$, S(O)$_2$NR$^{16}$, N(R$^{16}$)S(O)$_2$, OC(O)N(R$^{16}$), N(R$^{16}$)C(O)NR$^{16}$, N(R$^{16}$)S(O)$_2$N(R$^{16}$), and OC(O), wherein the alkylene chain is optionally substituted with one or more $R^h$;

each occurrence of $R^h$ is independently selected from CN, $CH_3$, $CF_3$, $CH_2F$, $CF_2H$, OH, halogen, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^b$ is independently selected from $C_{1-6}$ aliphatic and $Z_2$—$R^6$;

or wherein two $R^b$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 8-10-membered saturated, partially unsaturated, or aromatic bicyclic ring having 0-5 heteroatoms independently selected from nitrogen, oxygen, and sulfur, wherein the ring is optionally substituted with one or more $R^c$;

each occurrence of $R^c$ is independently selected from $C_{1-6}$ aliphatic, $CF_3$, $CF_2H$, $CH_2F$, halogen, $OR^{12}$, $(CH_2)_v-C(O)R^9$, and $(CH_2)_w-NR^{10}C(O)R^{11}$;

each occurrence of $Z_2$ is independently selected from direct bond, $C_{1-3}$ alkylene chain, O, $N(R^{17})$, S, $S(O)$, $S(O)_2$, $C(O)$, $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2N(R^{17})$, and $OC(O)$, wherein the alkylene chain is optionally substituted with one or more $R^i$;

each occurrence of $R^i$ is independently selected from CN, $CH_3$, $CF_3$, $CH_2F$, $CF_2H$, halogen, OH, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^k$ is independently selected from $C_{1-6}$ aliphatic and $Z_3-R^{23}$;

or wherein two $R^k$ taken together with the atom or atoms to which they are bound, form a ring selected from a 3-7-membered saturated, partially unsaturated, or aromatic monocyclic ring having 0-3 heteroatoms independently selected from nitrogen, oxygen, and sulfur and an 7-10-membered saturated, partially unsaturated, or aromatic bicyclic ring having 0-5 heteroatoms independently selected from nitrogen, oxygen, and sulfur, wherein the ring is optionally substituted with one or more $R^m$;

each occurrence of $R^m$ is independently selected from $C_{1-6}$ aliphatic, $CF_3$, CN, $CH_2F$, $CF_2H$, halogen, $OR^{25}$, $(CH_2)_q-C(O)R^{26}$, and $(CH_2)_r-NR^{27}C(O)R^{28}$;

each occurrence of $Z_3$ is independently selected from direct bond, $C_{1-3}$ alkylene chain, O, $N(R^{24})$, S, $S(O)$, $S(O)_2$, $C(O)$, $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and $OC(O)$, wherein the alkylene chain is optionally substituted with one or more $R^n$;

each occurrence of $R^n$ is independently selected from CN, $CH_3$, $CF_3$, $CH_2F$, $CF_2H$, halogen, OH, $OCH_3$, $OCF_3$, $OCH_2F$, $OCF_2H$, $O(C_{2-3}$ aliphatic), and $C_{2-3}$ aliphatic, wherein said $C_{2-3}$ aliphatic is optionally substituted with one or more F;

J is selected from a linear $C_{1-6}$ aliphatic, wherein 1 or 2 methylene units of J are optionally and independently replaced by O, S, or $N(R^{13})$ and further wherein the $C_{1-6}$ aliphatic is optionally substituted with one or more $R^j$;

each occurrence of $R^j$ is independently selected from fluorine, $CH_3$, $CF_3$, $CH_2F$, $CF_2H$, OH, $OCH_3$, $OCF_3$, $OCH_2F$, $OCF_2H$, $O(C_{2-3}$ aliphatic), $NH_2$, $NH(C_{1-3}$ aliphatic), $N(C_{1-3}$ aliphatic$)_2$, and $C_{2-3}$ aliphatic, wherein said $C_{2-3}$ aliphatic is optionally substituted with one or more F;

or wherein two $R^j$ taken together with the atom or atoms to which they are bound form a ring selected from a 3-6-membered heterocycle having 1 heteroatom selected from nitrogen, oxygen, and sulfur and a 3-6-membered cycloaliphatic ring, wherein the ring is optionally substituted with one or more $R^e$;

or wherein $R^j$ and one of R taken together with the atom or atoms to which they are bound form a ring selected from a 3-6-membered heterocycle having 1 heteroatom selected from nitrogen, oxygen, and sulfur and a 3-6-membered cycloaliphatic, wherein the ring is optionally substituted with one or more $R^e$;

each occurrence of R is independently selected from hydrogen and $C_{1-3}$ aliphatic, wherein the $C_{1-3}$ aliphatic is optionally substituted with one or more F;

$R^4$ is selected from hydrogen and $C_{1-6}$ aliphatic;

or wherein one of R and $R^4$ or R and $R^4$ taken together with the atoms to which they are bound, form a 4-10-membered heterocycle having 1-5 heteroatoms independently selected from nitrogen, oxygen, and sulfur, wherein the heterocycle is optionally substituted with one or more $R^e$;

each occurrence of $R^e$ is independently selected from halogen, $CF_3$, $CF_2H$, $CH_2F$, $C_{1-6}$ aliphatic, and $(CH_2)_x$-[3-7-membered saturated, partially unsaturated, or aromatic monocyclic ring having 1-3 heteroatoms independently selected from nitrogen, oxygen, and sulfur], wherein the ring is optionally substituted with one or more $R^{h'}$;

or wherein two $R^e$ taken together with the atom or atoms to which they are bound, for a ring selected from a 3-7-membered saturated, partially unsaturated, or aromatic monocyclic ring having 1-3 heteroatoms independently selected from nitrogen, oxygen, and sulfur, wherein the ring is optionally substituted with one or more $R^{h'}$;

each occurrence of $R^{h'}$ is independently selected from halogen, $CF_3$, $CF_2H$, $CH_2F$, $C_{1-6}$ aliphatic, $C(O)N(R^{18})_2$, OH, and $OC_{1-6}$ aliphatic;

each occurrence of $R^5$ is independently selected from hydrogen, $CF_3$, $CF_2H$, $CH_2F$, and $C_{1-6}$ aliphatic;

each occurrence of $R^6$ is independently selected from CN, halogen, $OR^7$, $N(R^{19})_2$, $C_{1-6}$ aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^c$;

each occurrence of $R^7$ is independently selected from hydrogen, $CF_3$, $CF_2H$, $CH_2F$, $C_{1-6}$ aliphatic, and 6-10-membered aryl;

each occurrence of $R^8$ is independently selected from CN, halogen, $OR^5$, $N(R^{21})_2$, $C_{1-6}$ aliphatic, 6-10-membered aryl, 3-10 membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein the aryl, cycloaliphatic, heteroaryl, and heterocycle is optionally substituted with one or more $R^g$;

each occurrence of $R^g$ is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic) and $C_{2-3}$ aliphatic, wherein said $C_{2-3}$ aliphatic is optionally substituted with one or more F;

each occurrence of $R^9$ is independently selected from OH, $OC_{1-6}$ aliphatic, $N(R^{15})_2$, and $C_{1-6}$ aliphatic;

each occurrence of $R^{10}$ is independently selected from hydrogen and $C_{1-6}$ aliphatic;

each occurrence of $R^{11}$ is independently selected from OH, $OC_{1-6}$ aliphatic, $N(R^{14})_2$, and $C_{1-6}$ aliphatic;

each occurrence of $R^{12}$ is independently selected from hydrogen and $C_{1-6}$ aliphatic;

each occurrence of $R^{13}$ is independently selected from hydrogen and $C_{1-6}$ aliphatic;

each occurrence of $R^{14}$ is independently selected from hydrogen and $C_{1-6}$aliphatic;
each occurrence of $R^{15}$ is independently selected from hydrogen and $C_{1-6}$aliphatic;
each occurrence of $R^{16}$ is independently selected from hydrogen and $C_{1-6}$aliphatic;
each occurrence of $R^{17}$ is independently selected from hydrogen and $C_{1-6}$aliphatic;
each occurrence of $R^{18}$ is independently selected from hydrogen and $C_{1-6}$ aliphatic;
each occurrence of $R^{19}$ is independently selected from hydrogen and $C_{1-3}$ aliphatic;
each occurrence of $R^{20}$ is independently selected from hydrogen and $C_{1-6}$ aliphatic;
each occurrence of $R^{21}$ is independently selected from hydrogen and $C_{1-6}$aliphatic;
each occurrence of $R^{23}$ is independently selected from CN, halogen, $OR^{31}$, $N(R^{32})_2$, $C_{1-6}$aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the is aryl, heteroaryl, heterocycle, and cycloaliphatic is optionally substituted with one or more $R^m$;
each occurrence of $R^{24}$ is independently selected from hydrogen and $C_{1-6}$aliphatic;
each occurrence of $R^{25}$ is independently selected from hydrogen and $C_{1-6}$aliphatic;
each occurrence of $R^{26}$ is independently selected from OH, $OC_{1-6}$ aliphatic, $N(R^{29})_2$, and $C_{1-6}$ aliphatic;
each occurrence of $R^{27}$ is independently selected from hydrogen and $C_{1-6}$aliphatic;
each occurrence of $R^{28}$ is independently selected from OH, $OC_{1-6}$aliphatic, $N(R^{30})_2$, and $C_{1-6}$aliphatic;
each occurrence of $R^{29}$ is independently selected from hydrogen and $C_{1-6}$aliphatic;
each occurrence of $R^{30}$ is independently selected from hydrogen and $C_{1-6}$aliphatic;
each occurrence of $R^{31}$ is independently selected from hydrogen, $CF_3$, $CF_2H$, $CH_2F$, $C_{1-6}$aliphatic, and 6-10-membered aryl;
each occurrence of $R^{32}$ is independently selected from hydrogen and $C_{1-3}$ aliphatic;
each occurrence of $R^{33}$ is independently selected from hydrogen and $C_{1-3}$ aliphatic;
T is $(CH_2)_z$-5-10-membered monocyclic or bicyclic heteroaryl having 1-5 heteroatoms independently selected from nitrogen, oxygen, and sulfur, wherein the heteroaryl is optionally substituted with one or more $R^d$;
each occurrence of $R^d$ is independently selected from halogen, $N(R^{33})_2$, and $C_{1-6}$aliphatic or wherein taken together two $R^d$ together with the atom or atoms to which they are bound, form a 4-10-membered heterocycle having 1-5 heteroatoms independently selected from nitrogen, oxygen, and sulfur;
each occurrence of R is independently selected from CN, $CH_3$, $CF_3$, $CF_2H$, $CH_2F$, halogen, OH, $OCH_3$, $OCF_3$, $OCH_2F$, $OCF_2H$, $O(C_{2-3}$ aliphatic), and $C_{2-3}$ aliphatic, wherein said $C_{2-3}$ aliphatic is optionally substituted with one or more F;
n is 0, 1, 2, 3, 4, or 5;
o is 0, 1, 2, or 3;
p is 0, 1, 2, or 3;
q is 0, 1, 2, or 3;
r is 0, 1, 2, or 3;
s is 0, 1, 2, or 3;
t is 0, 1, 2, or 3;
u is 0, 1, 2, or 3;
v is 0, 1, 2, or 3;
w is 0, 1, 2, or 3;
x is 0, 1, 2, or 3; and
z is 0, 1, 2, or 3;
provided that:
5) when $R^A$ and $R^B$ are the same and selected from optionally substituted phenyl, unsubstituted 2-furan, unsubstituted 3-furan, unsubstituted 3-thiophene, optionally substituted 2-pyridine, and unsubstituted 2-thiophene;
o is 0;
R and $R^4$ are hydrogen;
J is unsubstituted $C_1$ aliphatic, then
T is other than

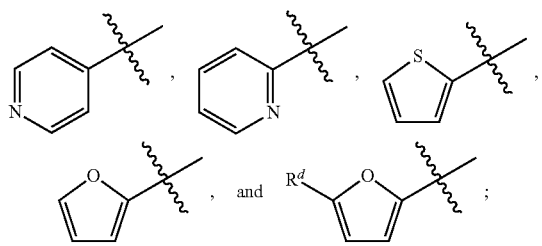

and
6) the compound is other than:

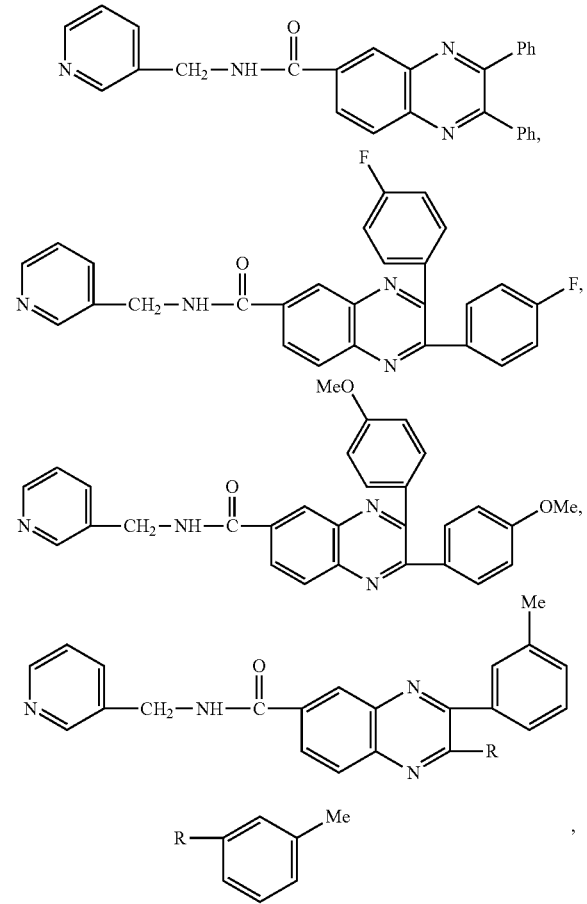

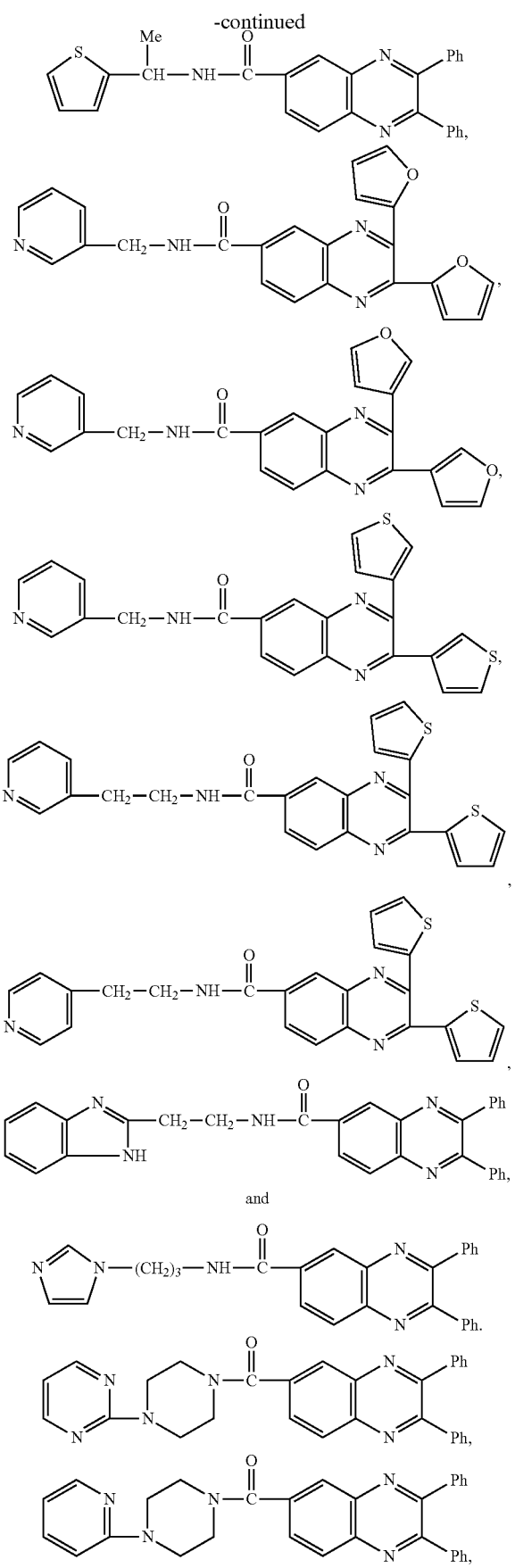

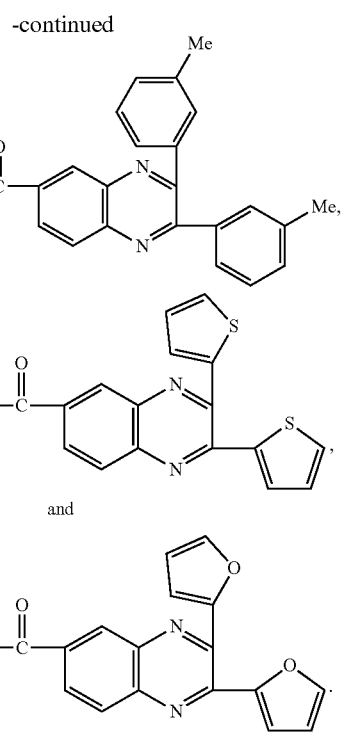

15. The compound of claim 1 or a pharmaceutically acceptable salt thereof, wherein T is a 5-10-membered heteroaryl having 1-5 heteroatoms independently selected from nitrogen, oxygen, and sulfur, wherein said heteroaryl is optionally substituted with one or more $R^d$.

16. The compound of claim 1 or a pharmaceutically acceptable salt thereof, wherein T is a 5-9-membered heteroaryl having 1-2 heteroatoms independently selected from nitrogen and sulfur, wherein said heteroaryl is optionally substituted with one or more $R^d$.

17. The compound of claim 1 or a pharmaceutically acceptable salt thereof, wherein

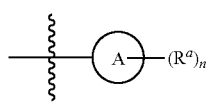

is

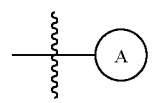

selected from phenyl, thiophene, pyrazole, furan, pyrrole, pyrazine, thiazole, imidazole, imidazopyridine, indole, and benzoimidazole, wherein said

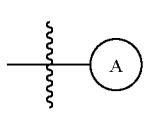

is optionally substituted with $R^a$ and n is 0, 1, 2, 3, 4, or 5.

* * * * *

UNITED STATES PATENT AND TRADEMARK OFFICE
CERTIFICATE OF CORRECTION

PATENT NO. : 10,144,742 B2
APPLICATION NO. : 15/304947
DATED : December 4, 2018
INVENTOR(S) : Kenneth M. Gigstad et al.

Page 1 of 1

It is certified that error appears in the above-identified patent and that said Letters Patent is hereby corrected as shown below:

In Claim 1, Column 532, Line 31 should read "2) the compound is other than:

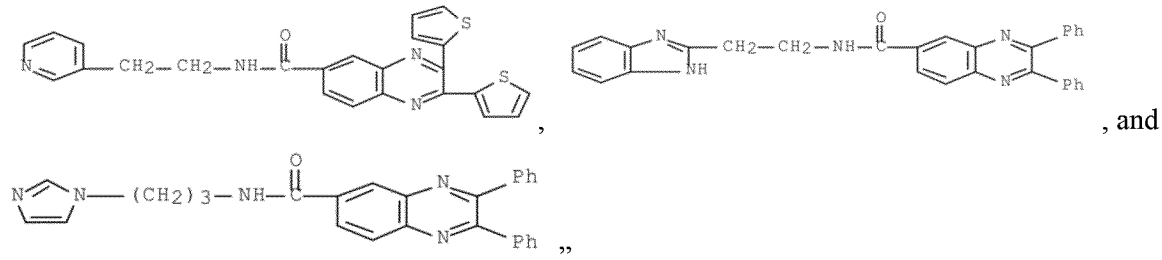

In Claim 12, Column 538, Line 31 should read "or wherein one of R and $R^4$ or $R^j$ and $R^4$ taken together"

In Claim 12, Column 540, Line 59 should read "4) the compound is other than:

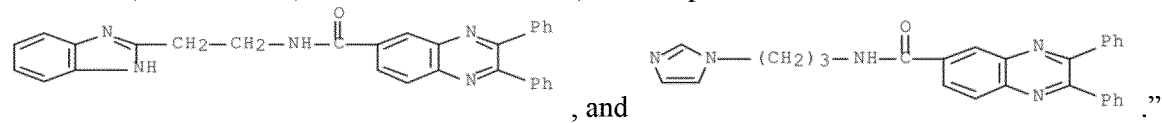

In Claim 14, Column 547, Line 57 should read "each occurrence of $R^q$ is independently selected from CN,"

In Claim 14, Column 548, Line 30 should read "6) the compound is other than:

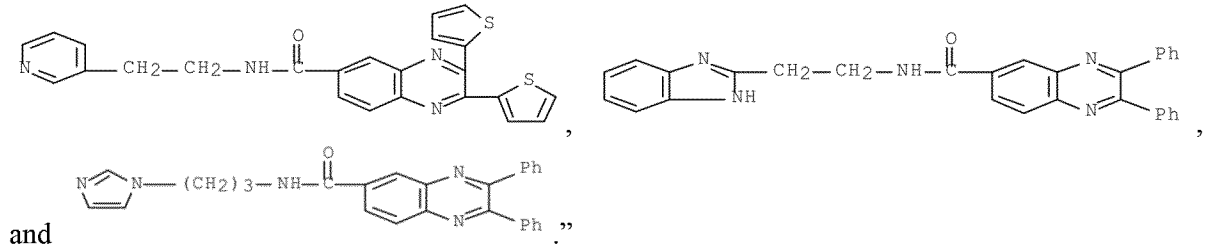

Signed and Sealed this
Thirtieth Day of April, 2019

Andrei Iancu
*Director of the United States Patent and Trademark Office*